(12) United States Patent
Kim et al.

(10) Patent No.: US 11,950,505 B2
(45) Date of Patent: Apr. 2, 2024

(54) CARBAZOLE-BASED COMPOUND AND ORGANIC LIGHT EMITTING DIODE COMPRISING SAME

(71) Applicant: LG CHEM, LTD., Seoul (KR)

(72) Inventors: Minjun Kim, Daejeon (KR); Kongkyeom Kim, Daejeon (KR); Min Woo Lee, Daejeon (KR); Donghee Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 828 days.

(21) Appl. No.: 16/981,429

(22) PCT Filed: Apr. 4, 2019

(86) PCT No.: PCT/KR2019/003998
§ 371 (c)(1),
(2) Date: Sep. 16, 2020

(87) PCT Pub. No.: WO2019/194599
PCT Pub. Date: Oct. 10, 2019

(65) Prior Publication Data
US 2021/0013425 A1  Jan. 14, 2021

(30) Foreign Application Priority Data
Apr. 5, 2018 (KR) .................. 10-2018-0039621

(51) Int. Cl.
*H10K 85/60* (2023.01)
*C07D 403/14* (2006.01)
(Continued)

(52) U.S. Cl.
CPC ....... *H10K 85/6572* (2023.02); *C07D 403/14* (2013.01); *C09K 11/06* (2013.01);
(Continued)

(58) Field of Classification Search
CPC ............. H10K 85/6572; H10K 85/615; H10K 85/626; H10K 85/654; H10K 50/11;
(Continued)

(56) References Cited

U.S. PATENT DOCUMENTS

2004/0251816 A1  12/2004  Leo et al.
2011/0240983 A1  10/2011  Sekiguchi et al.
(Continued)

FOREIGN PATENT DOCUMENTS

CN   105980521 A   9/2016
JP   2010-138121   6/2010
(Continued)

OTHER PUBLICATIONS

Translation of KR 1020160029721 (publication date Mar. 2016). (Year: 2016).*
(Continued)

*Primary Examiner* — Dawn L Garrett
(74) *Attorney, Agent, or Firm* — Bryan Cave Leighton Paisner LLP

(57) ABSTRACT

Provided is a compound of Chemical Formula 1:

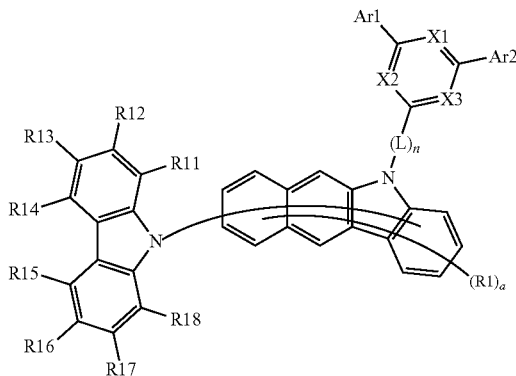

wherein:

X1 is N or CR, X2 is N or CR', and X3 is N or CR";

two or more of X1 to X3 are N;

R, R', R" and R1 each independently is hydrogen or deuterium, a is an integer of 0 to 9, and when a is 2 or greater, the R1s are the same as or different from each other;

Ar1 and Ar2 each independently is a substituted or unsubstituted aryl group;

L is a direct bond or a substituted or unsubstituted arylene group, n is an integer of 1 to 3, and when n is 2 or 3, the Ls are the same as or different from each other; and R11 to R18 each independently is hydrogen, deuterium, a nitrile group, or a substituted or unsubstituted: alkyl group, cycloalkyl group, alkoxy group, aryloxy group, aryl group, or heteroaryl group, or bond to adjacent groups to form a substituted or unsubstituted ring, and an organic light emitting device comprising same.

6 Claims, 2 Drawing Sheets

(51) Int. Cl.
| | | |
|---|---|---|
| *C09K 11/06* | (2006.01) | |
| *H10K 50/11* | (2023.01) | |
| *H10K 101/10* | (2023.01) | |

(52) U.S. Cl.
CPC ......... *H10K 85/615* (2023.02); *H10K 85/626* (2023.02); *H10K 85/654* (2023.02); *C09K 2211/1018* (2013.01); *H10K 50/11* (2023.02); *H10K 2101/10* (2023.02)

(58) Field of Classification Search
CPC .... H10K 2101/10; H10K 50/00; H10K 99/00; C07D 403/14; C07D 209/56; C09K 11/06; C09K 2211/1018; C09K 2211/1029

See application file for complete search history.

(56) References Cited

U.S. PATENT DOCUMENTS

| | | |
|---|---|---|
| 2014/0191208 A1 | 7/2014 | Kim et al. |
| 2015/0053934 A1 | 2/2015 | Lee et al. |
| 2016/0336518 A1 | 11/2016 | Chun et al. |
| 2017/0294590 A1 | 10/2017 | Moon et al. |

FOREIGN PATENT DOCUMENTS

| | | | |
|---|---|---|---|
| KR | 10-2014-0083897 | | 7/2014 |
| KR | 10-2014-0089259 | | 7/2014 |
| KR | 10-2015-0022268 | | 3/2015 |
| KR | 10-2015-0141179 | | 12/2015 |
| KR | 10-2016-0029721 | | 3/2016 |
| KR | 10-1603070 | | 3/2016 |
| KR | 20160029721 A | * | 3/2016 |
| KR | 10-2016-0037107 | | 4/2016 |
| KR | 10-2017-0058177 | | 5/2017 |
| WO | 2010-114264 | | 10/2010 |

OTHER PUBLICATIONS

Suh, M. C. et al., (2016). Synthesis of soluble host materials for highly efficient red phosphorescent organic light-emitting diodes. ACS applied materials & interfaces, 8(28), 18256-18265. (Year: 2016).*

* cited by examiner

【FIG. 1】
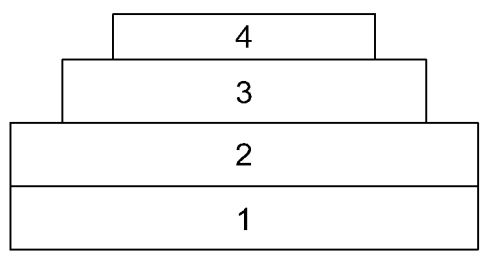
【FIG. 2】
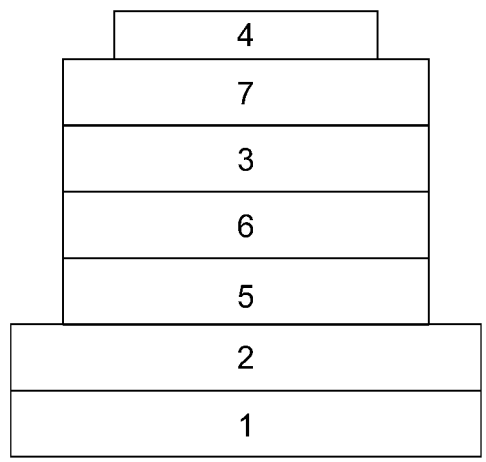

【FIG. 3】
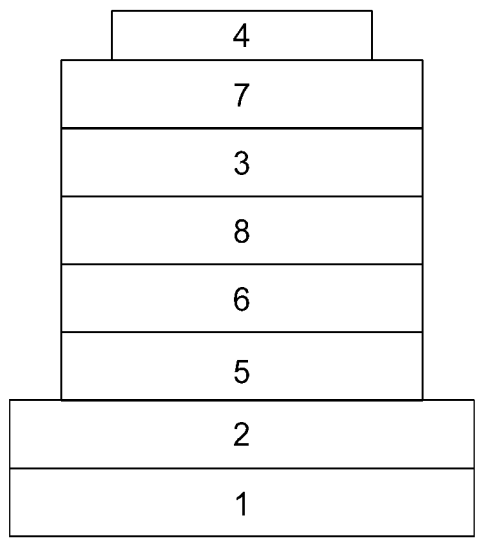
【FIG. 4】
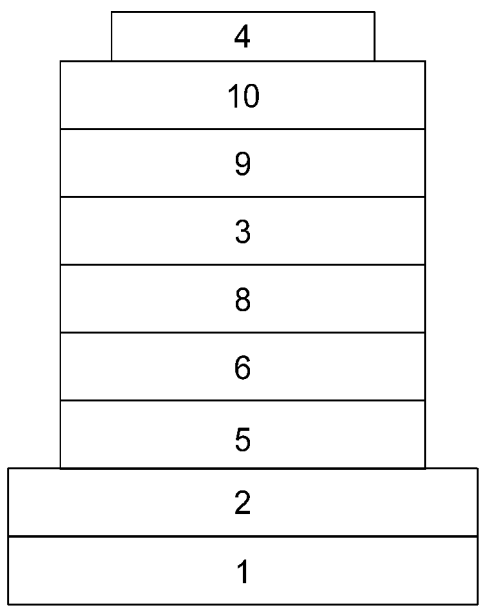

CARBAZOLE-BASED COMPOUND AND ORGANIC LIGHT EMITTING DIODE COMPRISING SAME

CROSS-REFERENCE TO RELATED APPLICATIONS

This application is a National Stage Application of International Application No. PCT/KR2019/003998 filed on Apr. 4, 2019, which claims priority to and the benefits of Korean Patent Application No. 10-2018-0039621, filed with the Korean Intellectual Property Office on Apr. 5, 2018, the entire contents of which are incorporated herein by reference.

TECHNICAL FIELD

The present specification relates to a carbazole-based compound, and an organic light emitting device comprising same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification is directed to providing a carbazole-based compound, and an organic light emitting device comprising same.

Technical Solution

One embodiment of the present specification provides a compound of Chemical Formula 1.

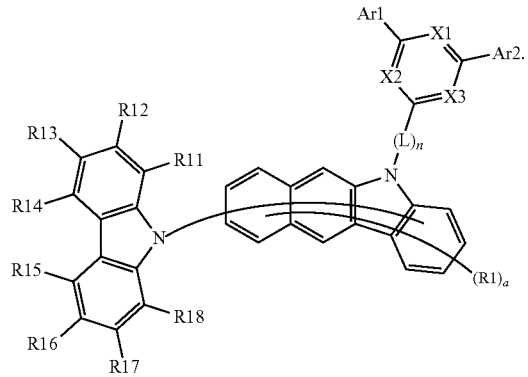

Chemical Formula 1

In Chemical Formula 1:
X1 is N or CR, X2 is N or CR', and X3 is N or CR";
two or more of X1 to X3 are N;
R, R', R" and R1 are the same as or different from each other, and each independently is hydrogen or deuterium, a is an integer of 0 to 9, and when a is 2 or greater, R1s are the same as or different from each other;
Ar1 and Ar2 are the same as or different from each other, and each independently is a substituted or unsubstituted aryl group;
L is a direct bond; or a substituted or unsubstituted arylene group, n is an integer of 1 to 3, and when n is 2 or 3, Ls are the same as or different from each other; and
R11 to R18 are the same as or different from each other, and each independently is hydrogen, deuterium, a nitrile group, a substituted or unsubstituted alkyl group, a substituted or unsubstituted cycloalkyl group, a substituted or unsubstituted alkoxy group, a substituted or unsubstituted aryloxy group, a substituted or unsubstituted aryl group, or a substituted or unsubstituted heteroaryl group, or bond to adjacent groups to form a substituted or unsubstituted ring.

Another embodiment of the present specification provides an organic light emitting device comprising a first electrode; a second electrode provided opposite to the first electrode; and one, two or more organic material layers provided between the first electrode and the second electrode, wherein one or more layers of the organic material layers comprise the compound of Chemical Formula 1.

Advantageous Effects

A compound according to one embodiment of the present specification can be used as a material of an organic material layer of an organic light emitting device, and by using the same, enhanced efficiency, low driving voltage and/or enhanced lifetime properties can be obtained in the organic light emitting device.

DESCRIPTION OF DRAWINGS

FIGS. 1 to 4 illustrate organic light emitting devices according to embodiments of the present specification.

DETAILED DESCRIPTION

Hereinafter, the present specification will be described in more detail.

One embodiment of the present specification provides a compound of Chemical Formula 1.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of substituents in the present specification are described below, however, the substituents are not limited thereto.

The term "substitution" means a hydrogen atom bonding to a carbon atom of a compound is changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium, a halogen group, a nitrile group, a silyl group, an alkyl group, a cycloalkyl group, an alkoxy group, an aryloxy group, an aryl group, and a heterocyclic group, or being substituted with a substituent linking two or more substituents among the substituents selected from the group, or having no substituents. For example, "a substituent linking two or more substituents" can include an aryl group substituted with an aryl group, an aryl group substituted with a heteroaryl group, a heterocyclic group substituted with an aryl group, an aryl group substituted with an alkyl group, and the like.

In the present specification, the halogen group can be F, Cl, I or the like, and is preferably F.

In the present specification, the silyl group can be an alkylsilyl group or an arylsilyl group. The silyl group can be SiRaRbRc, and Ra to Rc are the same as or different from each other and can be each independently hydrogen, an alkyl group or an aryl group.

In the present specification, the alkyl group can be linear or branched, and although not particularly limited thereto, the number of carbon atoms is preferably from 1 to 30. Specific examples thereof include a methyl group, an ethyl group, a propyl group, an n-propyl group, an isopropyl group, a butyl group, an n-butyl group, an isobutyl group, a tert-butyl group, a sec-butyl group, a 1-methylbutyl group, a 1-ethylbutyl group, a pentyl group, an n-pentyl group, an isopentyl group, a neopentyl group, a tert-pentyl group, a hexyl group, an n-hexyl group, a 1-methylpentyl group, a 2-methylpentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethylpropyl group, a 1,1-dimethylpropyl group, an isohexyl group, a 2-methylpentyl group, a 4-methylhexyl group, a 5-methylhexyl group and the like, but are not limited thereto.

In the present specification, the cycloalkyl group is not particularly limited, but preferably has 3 to 30 carbon atoms. Specific examples thereof include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the alkoxy group can be linear, branched or cyclic. The number of carbon atoms of the alkoxy group is not particularly limited, but is preferably from 1 to 30. Specific examples thereof can include a methoxy group, an ethoxy group, an n-propoxy group, an isopropoxy group, an i-propyloxy group, an n-butoxy group, an isobutoxy group, a tert-butoxy group, a sec-butoxy group, an n-pentyloxy group, a neopentyloxy group, an isopentyloxy group, an n-hexyloxy group, a 3,3-dimethylbutyloxy group, a 2-ethylbutyloxy group, an n-octyloxy group, an n-nonyloxy group, an n-decyloxy group, a benzyloxy group, a p-methylbenzyloxy group and the like, but are not limited thereto.

In the present specification, the aryl group is not particularly limited, but preferably has 6 to 30 carbon atoms, and the aryl group can be monocyclic or polycyclic.

When the aryl group is a monocyclic aryl group, the number of carbon atoms is not particularly limited, but is preferably from 6 to 30. Examples of the monocyclic aryl group can include a phenyl group, a biphenyl group, a terphenyl group and the like, but are not limited thereto.

When the aryl group is a polycyclic aryl group, the number of carbon atoms is not particularly limited, but is preferably from 10 to 30. Example of the polycyclic aryl group can include a naphthyl group, an anthracenyl group, a phenanthrenyl group, a triphenylenyl group, a pyrenyl group, a phenalenyl group, a perylenyl group, a chrysenyl group, a fluorenyl group and the like, but are not limited thereto.

In the present specification, the fluorenyl group can be substituted, and adjacent groups can bond to each other to form a ring.

When the fluorenyl group is substituted,

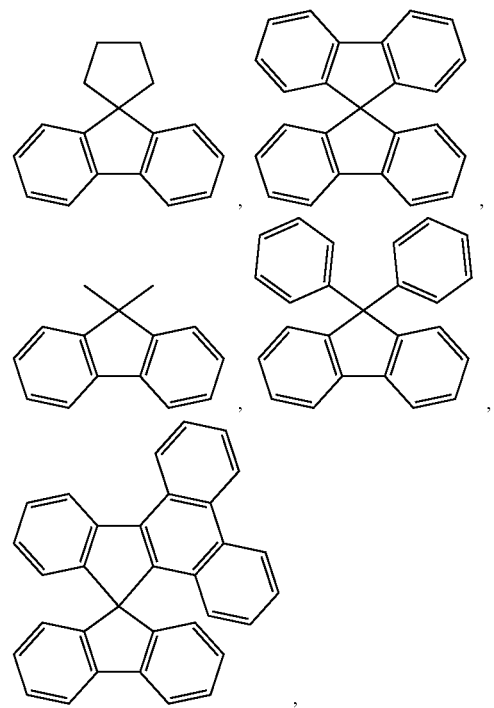

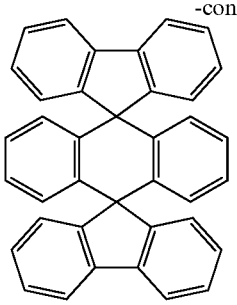

and the like can be included. However, the structure is not limited thereto.

In the present specification, the aryl group in the aryloxy group is the same as the examples of the aryl group described above. Specific examples of the aryloxy group include a phenoxy group, a p-tolyloxy group, an m-tolyloxy group, a 3,5-dimethylphenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthracenyloxy group, a 2-anthracenyloxy group, a 9-anthracenyloxy group, a 1-phenanthrenyloxy group, a 3-phenanthrenyloxy group, a 9-phenanthrenyloxy group and the like.

In the present specification, the heterocyclic group includes one or more atoms that are not carbon, that is, heteroatoms, and specifically, the heteroatom can include one or more atoms selected from the group consisting of O, N, Se and S. The number of carbon atoms is not particularly limited, but is preferably from 2 to 30, and the heterocyclic group can be monocyclic or polycyclic. Examples of the heterocyclic group can include a thiophenyl group, a furanyl group, a pyrrolyl group, an imidazolyl group, a thiazolyl group, an oxazolyl group, an oxadiazolyl group, a pyridinyl group, a bipyridinyl group, a pyrimidinyl group, a triazinyl group, a triazolyl group, an acridinyl group, a pyridazinyl group, a pyrazinyl group, a quinolinyl group, a quinazolinyl group, a quinoxalinyl group, a phthalazinyl group, a pyridopyrimidinyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a dibenzopyrrolyl group, an indolyl group, a benzothiophenyl group, a dibenzothiophenyl group, a benzofuranyl group, a benzoquinolyl group, a benzonaphthothiophenyl group, a benzonaphthofuranyl group, a phenanthrolinyl group, a thiazolyl group, an isoxazolyl group, an oxadiazolyl group, a thiadiazolyl group, a benzothiazolyl group, a phenoxazinyl group, a phenothiazinyl group, a dibenzofuranyl group and the like, but are not limited thereto.

In the present specification, examples of the aryl group described above can be applied to the arylene group except for being divalent.

In the present specification, the heteroaryl group means an aromatic heterocyclic group.

According to one embodiment of the present specification, L is a direct bond, a phenylene group, a biphenylene group, a terphenylene group, a quaterphenylene group, a divalent naphthyl group, a divalent anthracenyl group, a divalent fluorenyl group unsubstituted or substituted with alkyl or aryl, a divalent phenanthrenyl group, a divalent pyrenyl group, or a divalent triphenylenyl group.

According to one embodiment of the present specification, L is a direct bond, or any one selected from among the following structural formulae:

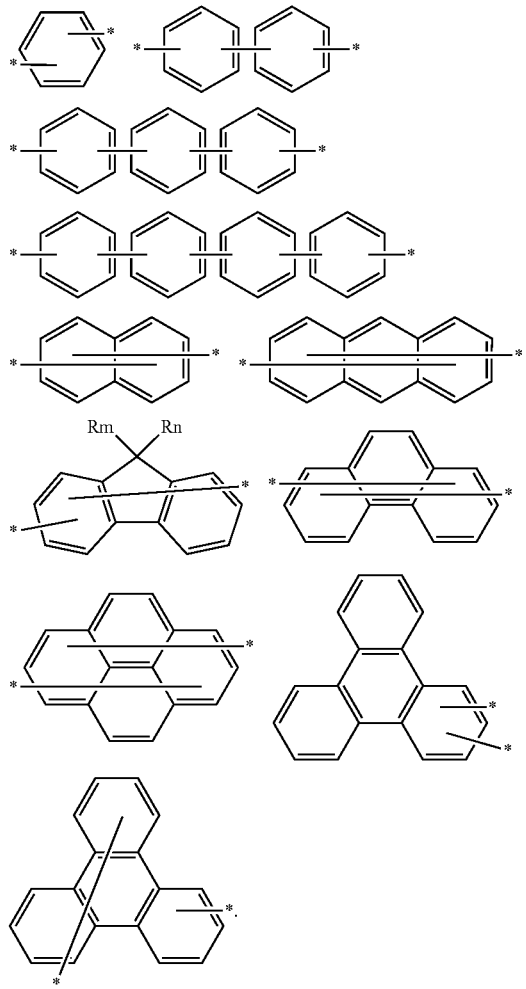

In the structural formulae, any one * is a site linking to N, and another * is a site linking to C, Rm and Rn are the same as or different from each other, and each independently is an alkyl group or an aryl group.

According to one embodiment of the present specification, Rm and Rn are the same as or different from each other, and each independently is a methyl group or a phenyl group.

According to one embodiment of the present specification, L is a direct bond, a substituted or unsubstituted phenylene group, or a substituted or unsubstituted divalent naphthyl group.

According to one embodiment of the present specification, L is a direct bond, a phenylene group, or a divalent naphthyl group.

According to one embodiment of the present specification, L is a direct bond, a phenylene group, or a divalent naphthyl group.

According to one embodiment of the present specification, L is a direct bond,

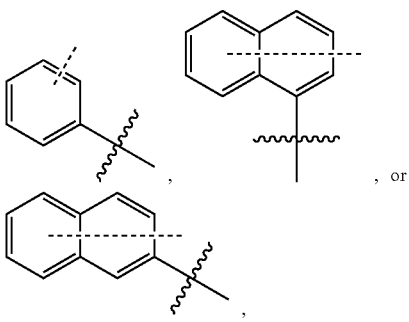

and herein,

is a site linking to N, and ---- is a site linking to C.

According to one embodiment of the present specification, L is a direct bond, or any one selected from among the following structural formulae;

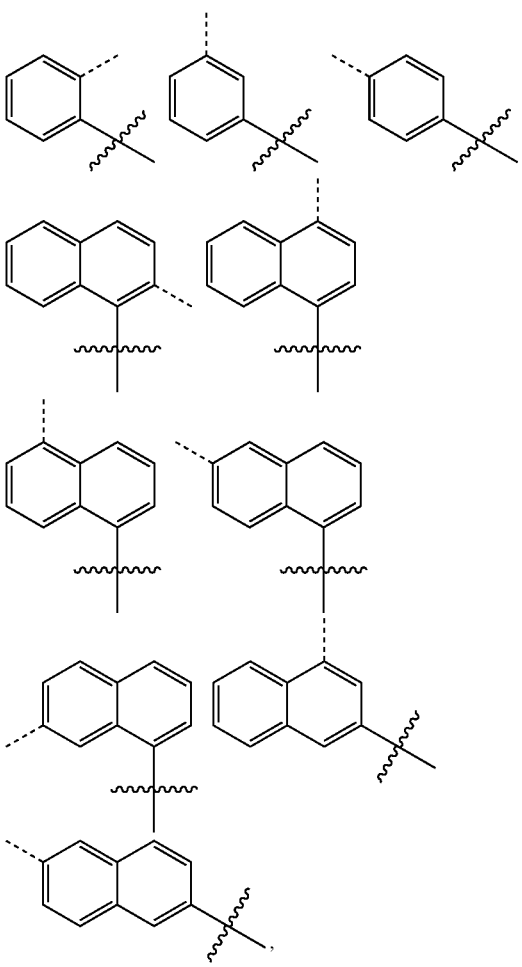

and in the structural formulae,

is a site linking to N, and ---- is a site linking to C.

According to one embodiment of the present specification, X1 and X2 are N, and X3 is CH.

According to one embodiment of the present specification, X2 and X3 are N, and X1 is CH.

According to one embodiment of the present specification, X1 to X3 are N.

According to one embodiment of the present specification, R1 and R11 to R18 are hydrogen.

According to one embodiment of the present specification, Chemical Formula 1 is any one of the following Chemical Formulae 2 to 5.

Chemical Formula 2

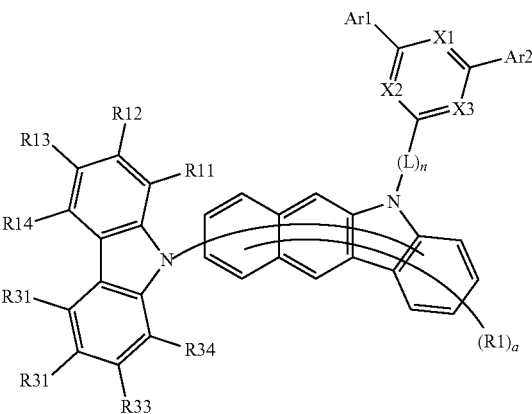

Chemical Formula 3

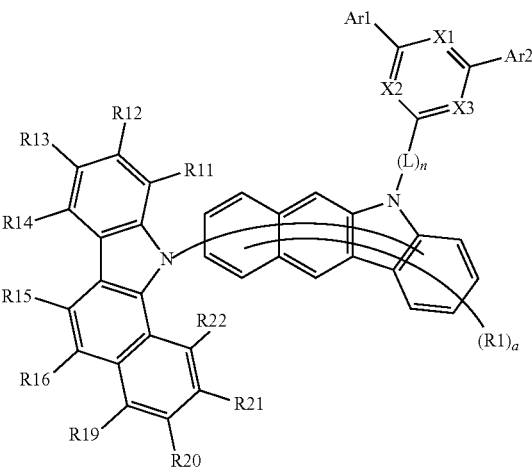

-continued

Chemical Formula 4

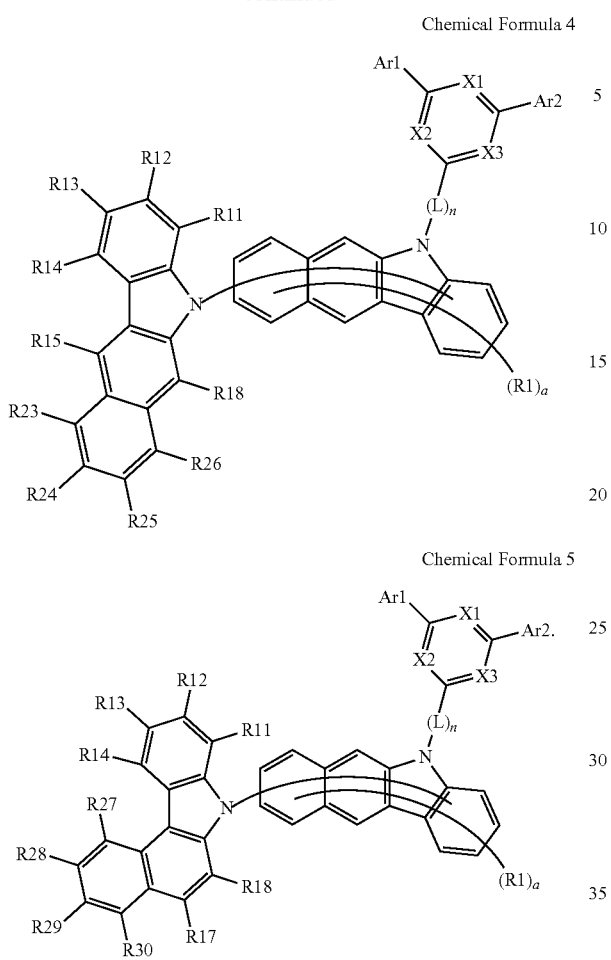

Chemical Formula 5

-continued

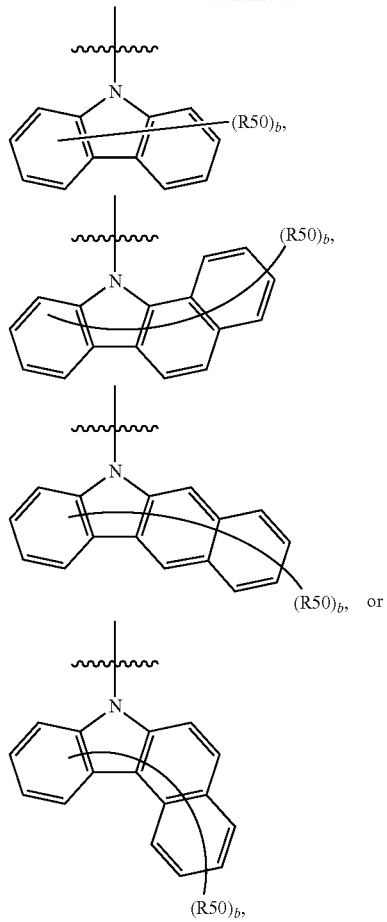

and herein,

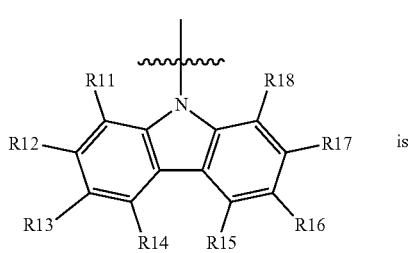

is a linking site, R50 is hydrogen, deuterium, an alkyl group, a cycloalkyl group, or an aryl group, b is an integer of 0 to 10, and when b is 2 or greater, the R50s are the same as or different from each other.

According to one embodiment of the present specification, R50 is hydrogen.

According to one embodiment of the present specification, b is 0.

According to one embodiment of the present specification, R1 and R11 to R34 are hydrogen.

According to one embodiment of the present specification, Ar1 and Ar2 are the same as or different from each other, and each independently is a substituted or unsubstituted C6-C30 aryl group.

According to one embodiment of the present specification, Ar1 and Ar2 are the same as or different from each other, and each independently is a substituted or unsubstituted C6-C22 aryl group.

According to one embodiment of the present specification, Ar1 and Ar2 are the same as or different from each other, and each independently is a substituted or unsubstituted C6-C18 aryl group.

In Chemical Formulae 2 to 5:

R19 to R34 are the same as or different from each other, and each independently is hydrogen, deuterium, a nitrile group, a substituted or unsubstituted alkyl group, a substituted or unsubstituted cycloalkyl group, a substituted or unsubstituted alkoxy group, a substituted or unsubstituted aryloxy group, a substituted or unsubstituted aryl group, or a substituted or unsubstituted heteroaryl group; and the remaining substituents have the same definitions as above.

According to one embodiment of the present specification,

According to one embodiment of the present specification, Ar1 and Ar2 are the same as or different from each other, and each independently is a substituted or unsubstituted C6-C14 aryl group.

According to one embodiment of the present specification, Ar1 and Ar2 are the same as or different from each other, and each independently is an aryl group unsubstituted or substituted with deuterium, a nitrile group, an aryl group or a heteroaryl group.

According to one embodiment of the present specification, Ar1 and Ar2 are the same as or different from each other, and each independently is a C6-C14 aryl group.

According to one embodiment of the present specification, Ar1 and Ar2 are the same as or different from each other, and each independently is a phenyl group, a biphenyl group, a naphthyl group, or a phenanthrenyl group.

According to one embodiment of the present specification, Ar1 and Ar2 are the same as or different from each other, and each independently is a phenyl group, a 1-naphthyl group, a 2-naphthyl group, a biphenyl group, a [1,1'-biphenyl]-4-yl group, a [1,1'-biphenyl]-3-yl group, a [1,1'-biphenyl]-2-yl group, a phenanthren-1-yl group, a phenanthren-2-yl group, a phenanthren-3-yl group, or a phenanthren-9-yl group.

According to one embodiment of the present specification, at least one of Ar1 and Ar2 is a substituted phenyl group or a polycyclic aryl group.

According to one embodiment of the present specification, at least one of Ar1 and Ar2 is a phenyl group substituted with an aryl group; or a polycyclic aryl group.

According to one embodiment of the present specification, Chemical Formula 1 is any one of Chemical Formulae 6-1 to 6-3:

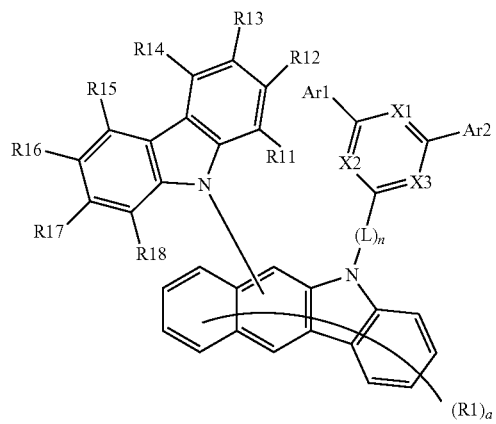

Chemical Formula 6-1

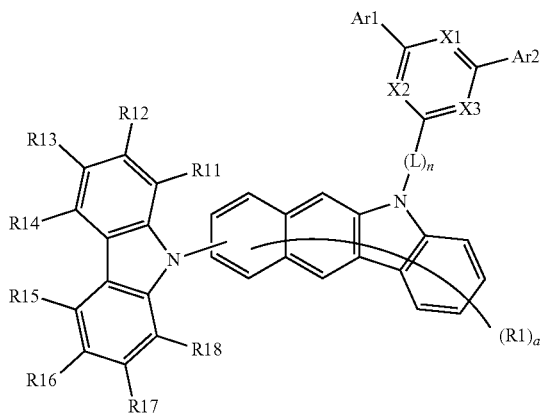

Chemical Formula 6-2

Chemical Formula 6-3

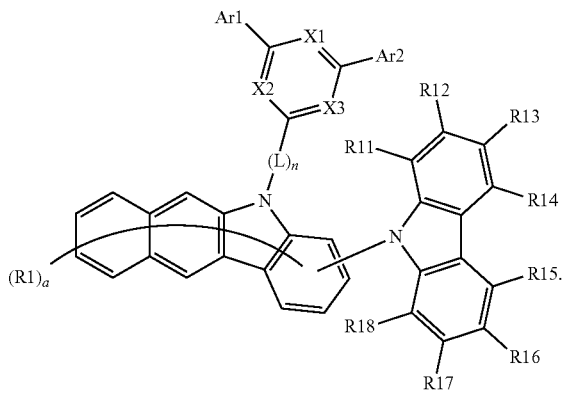

In Chemical Formulae 6-1 to 6-3, X1 to X3, L, n, Ar1, Ar2, R1, a, and R11 to R18 have the same definitions as in Chemical Formula 1.

According to one embodiment of the present specification, Chemical Formula 1 is any one of the following Chemical Formulae 7-1 to 7-10:

Chemical Formula 7-1

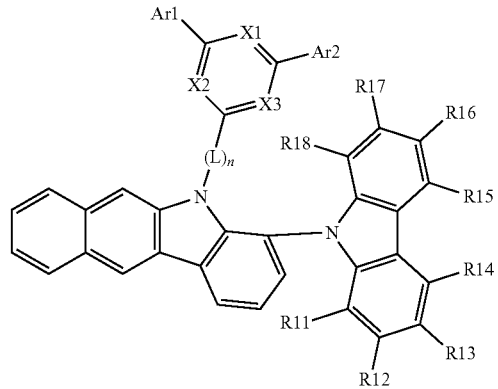

Chemical Formula 7-2
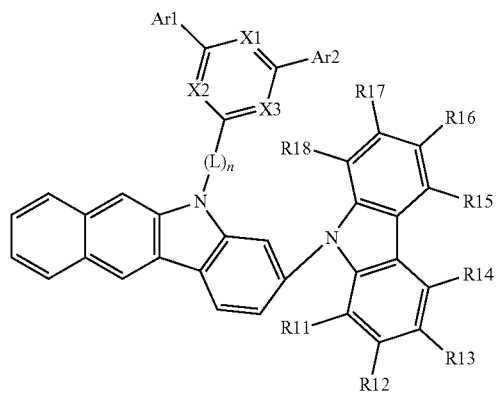
Chemical Formula 7-3
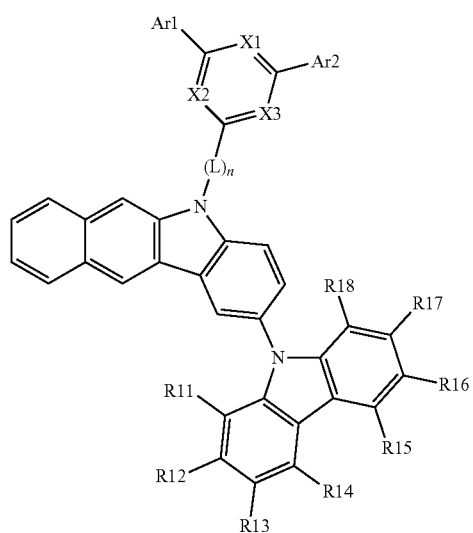
Chemical Formula 7-4
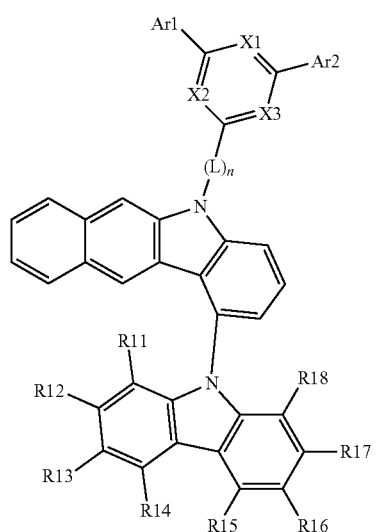
Chemical Formula 7-5
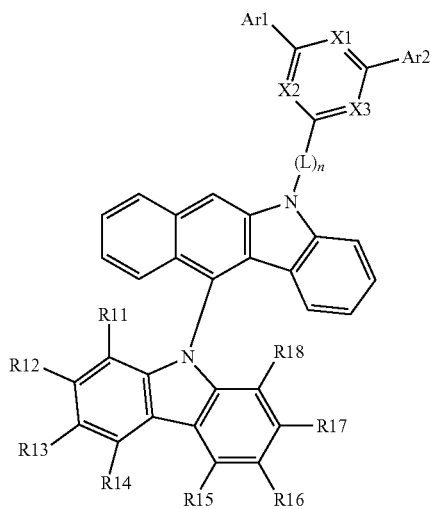
Chemical Formula 7-6
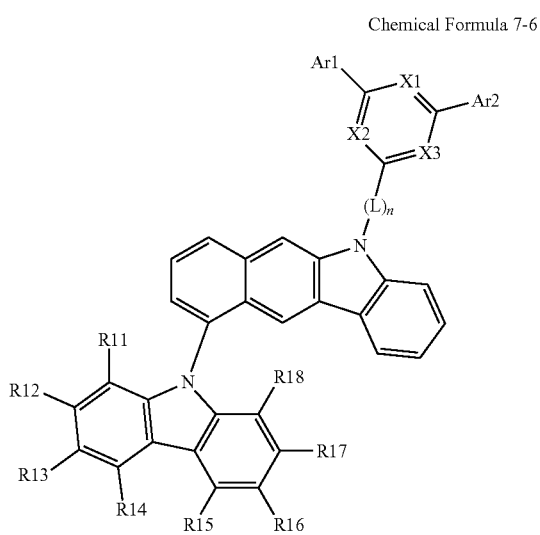
Chemical Formula 7-7
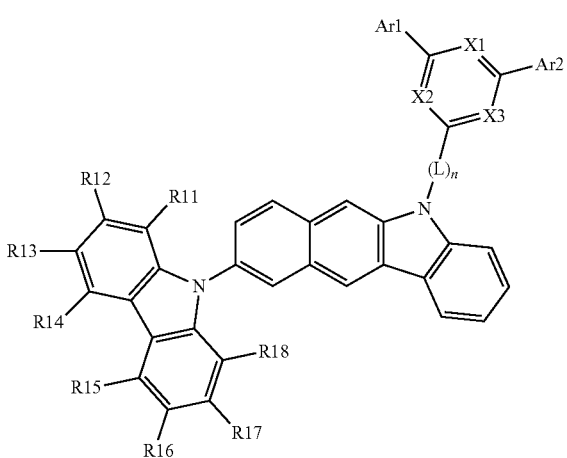

Chemical Formula 7-8
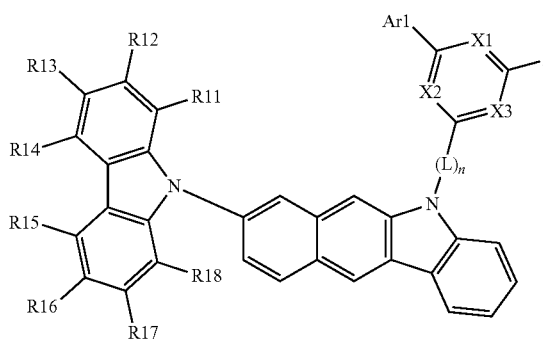
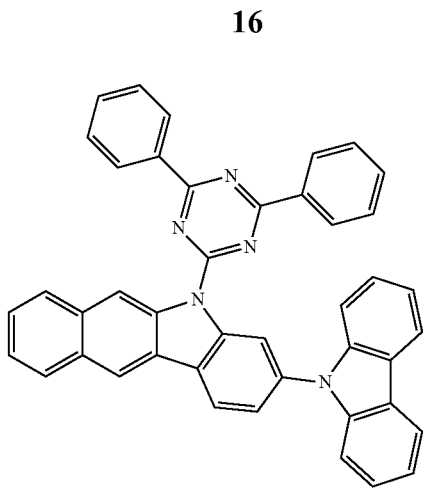
Chemical Formula 7-9
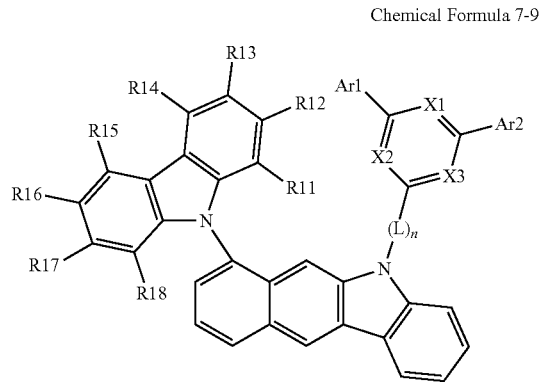
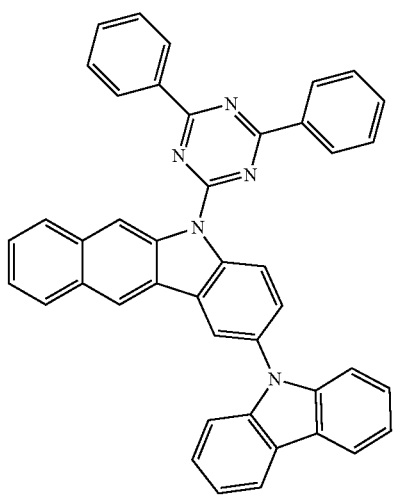
Chemical Formula 7-10
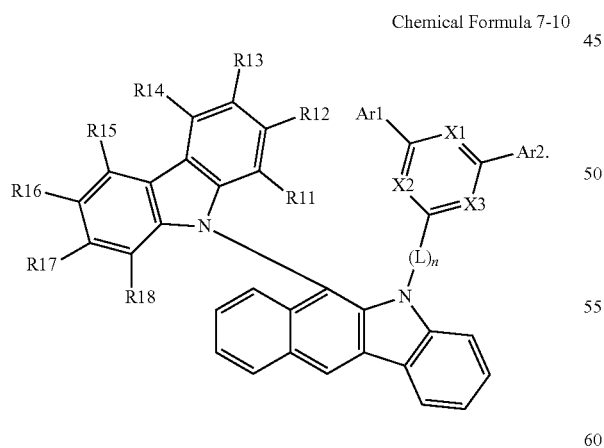
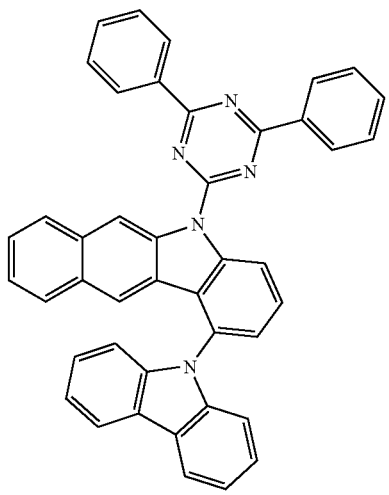
In Chemical Formulae 7-1 to 7-10, X1 to X3, L, n, Ar1, Ar2 and R11 to R18 have the same definitions as in Chemical Formula 1.
According to one embodiment of the present specification, Chemical Formula 1 is any one compound selected from among the following compounds:

-continued
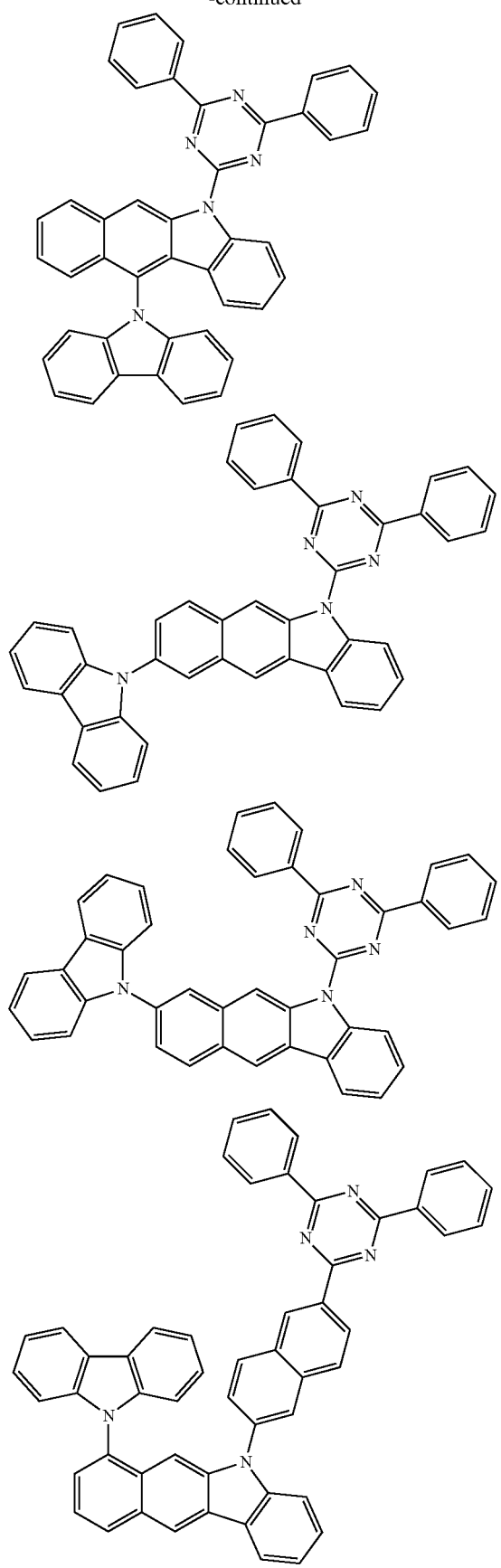
-continued
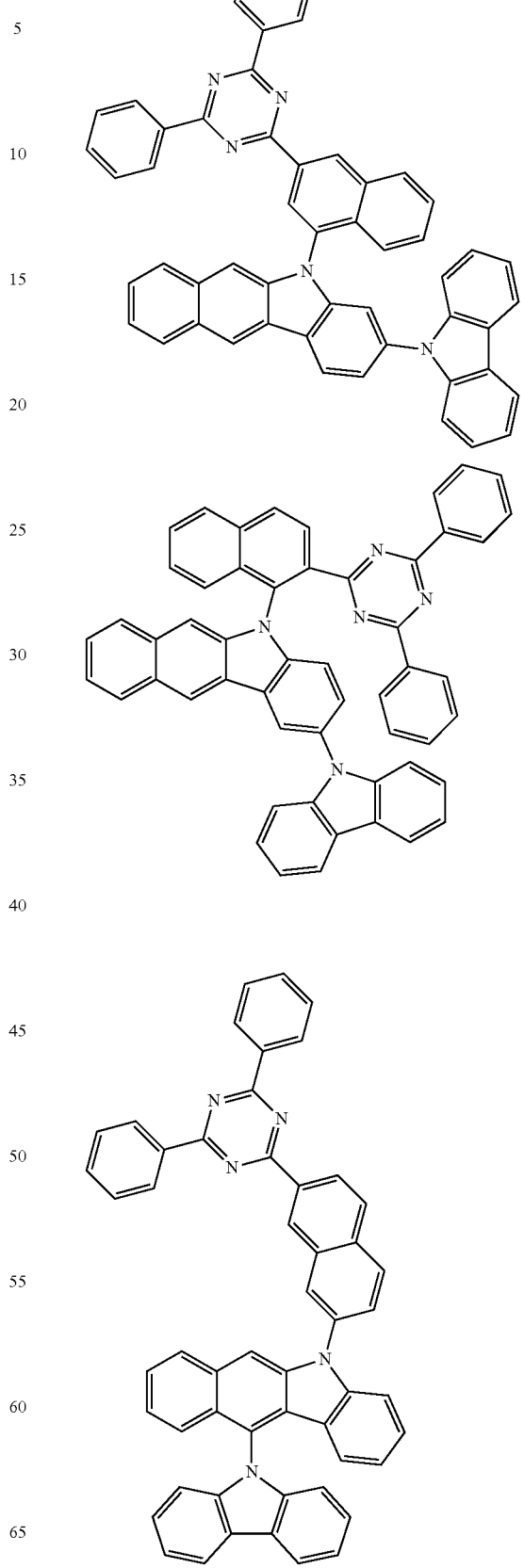

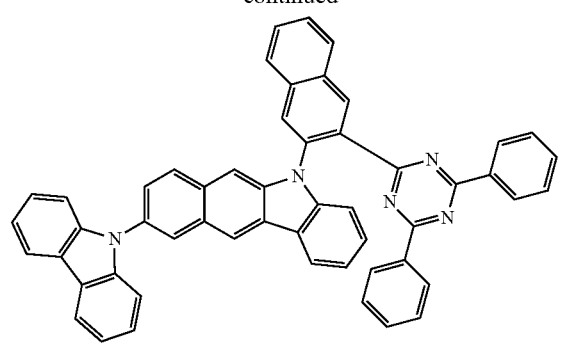
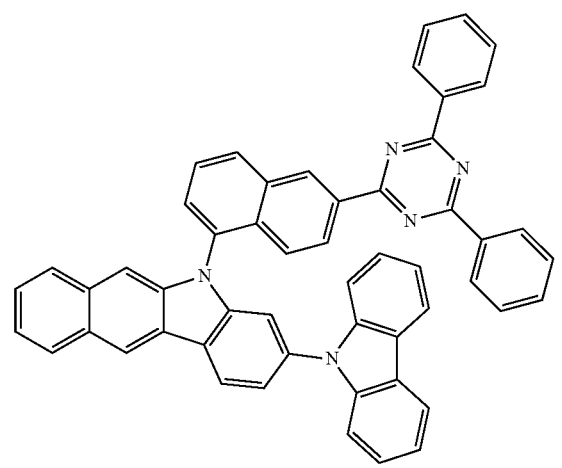
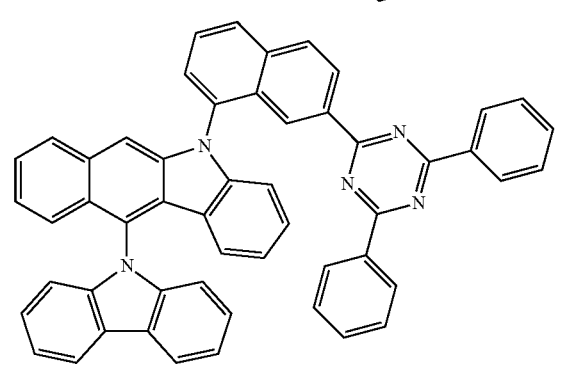
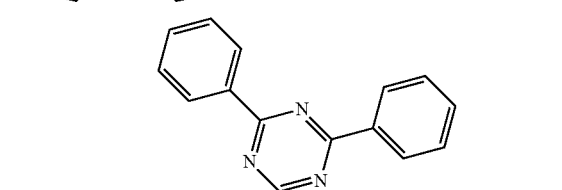
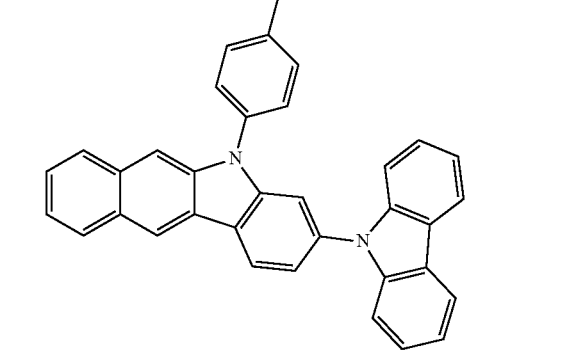
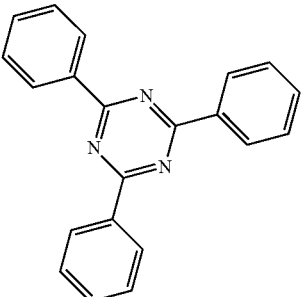
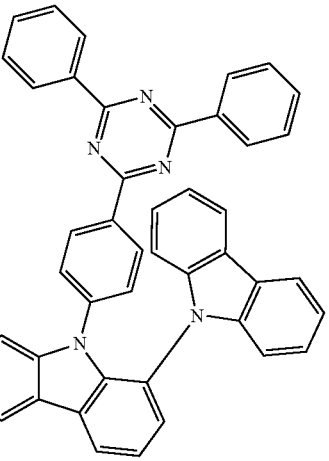
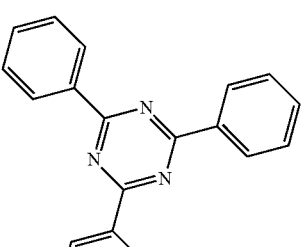
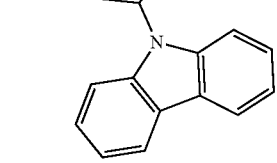

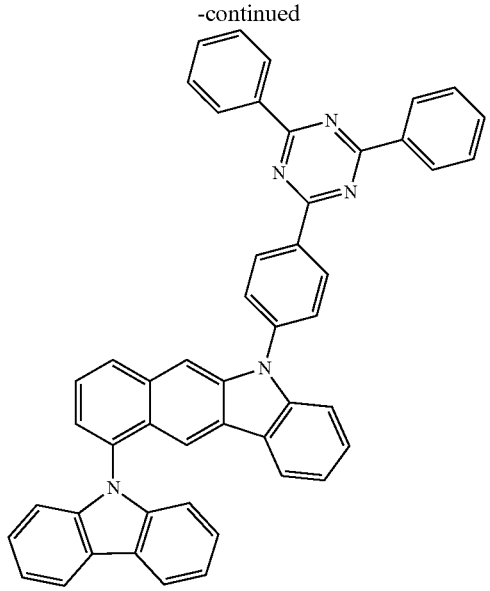
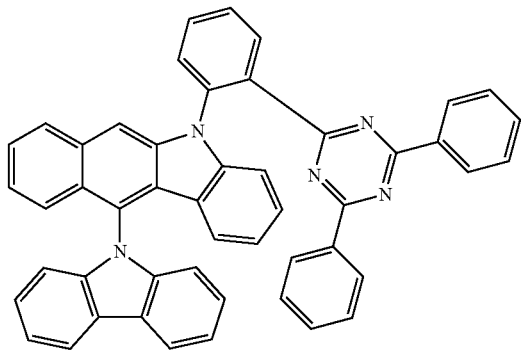
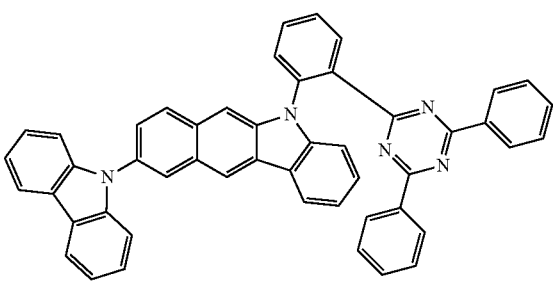
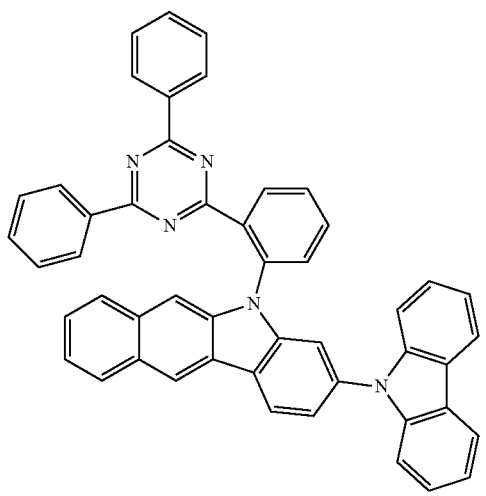
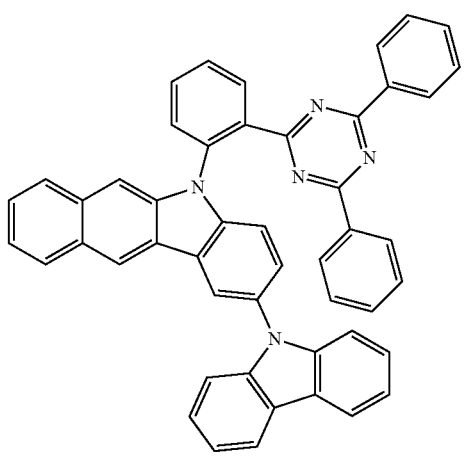
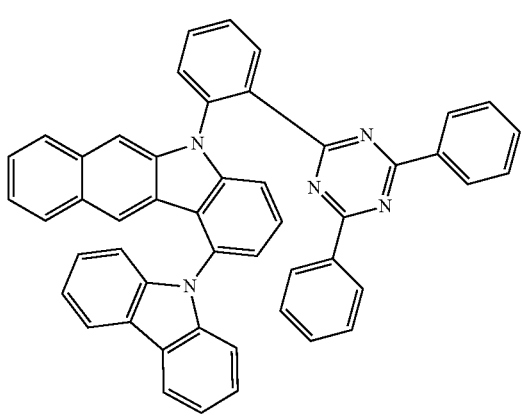
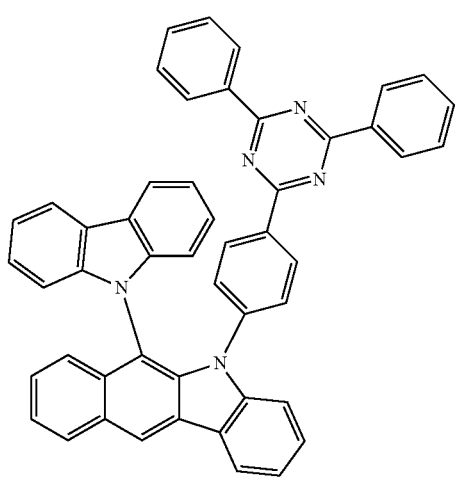

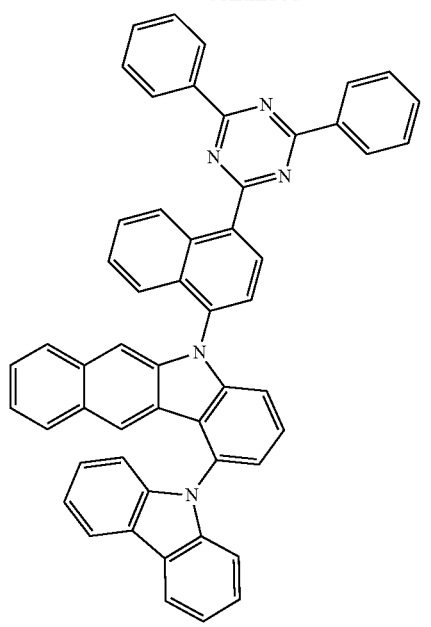
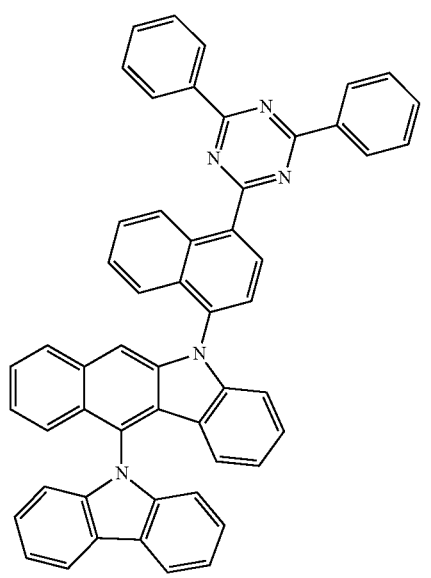
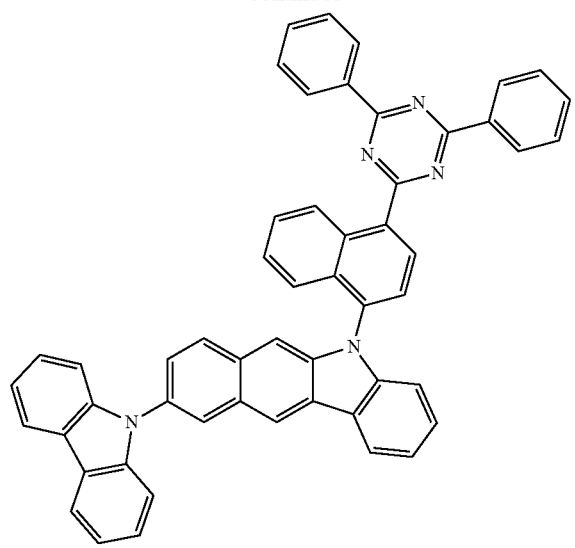
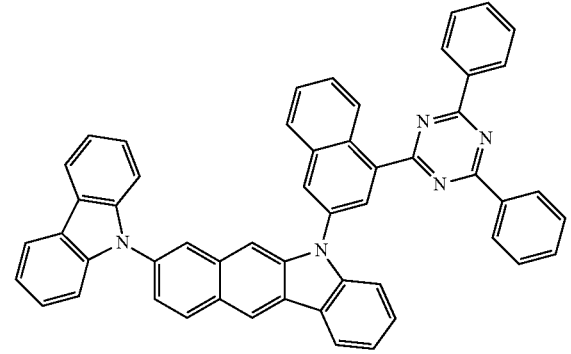
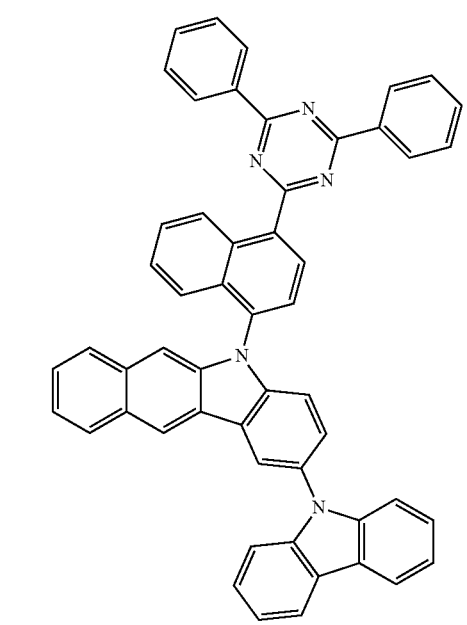

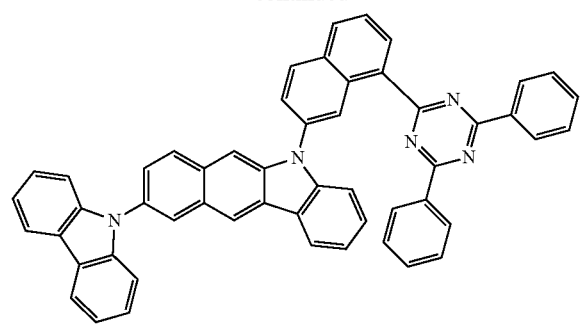
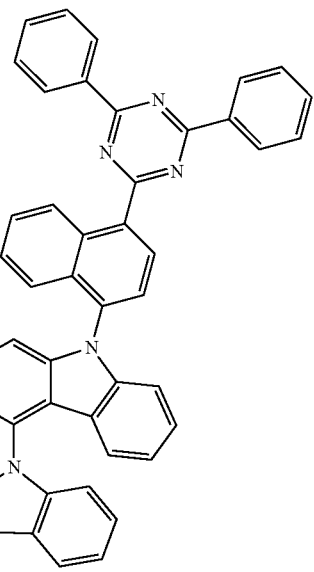
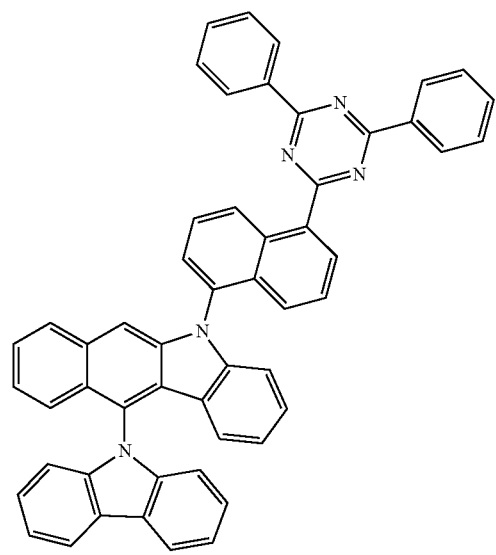
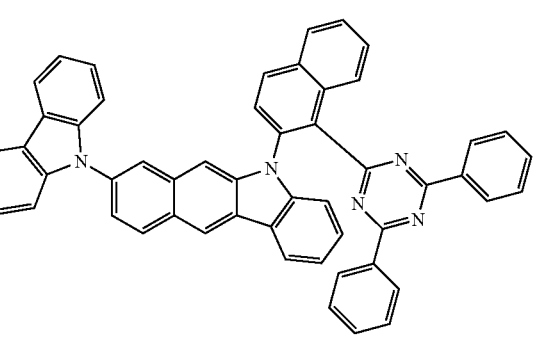
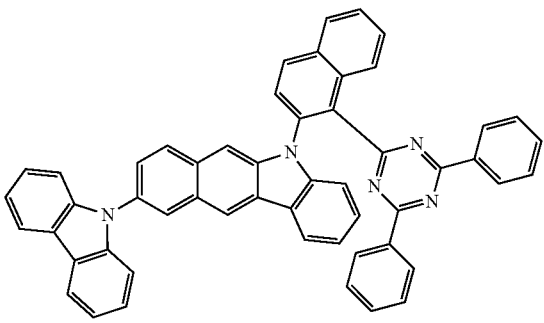
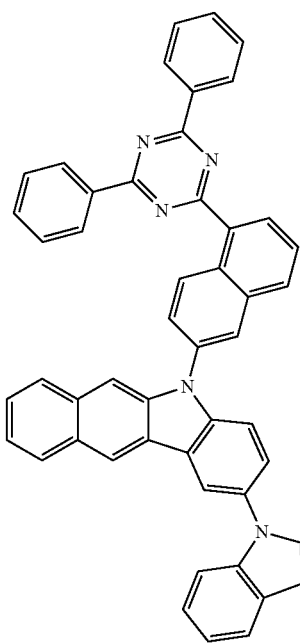

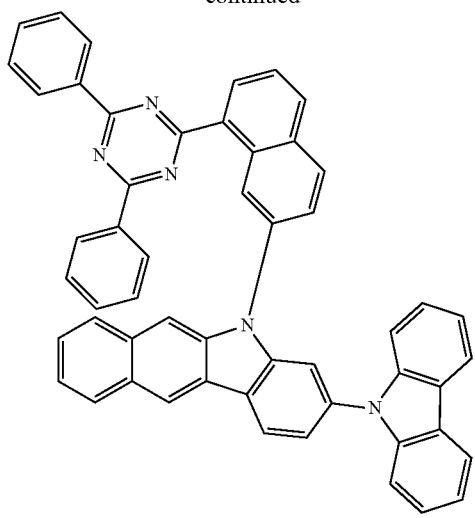
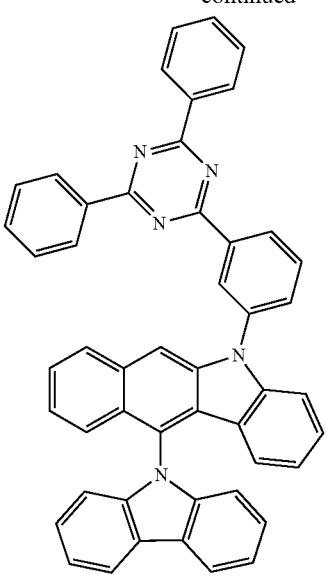
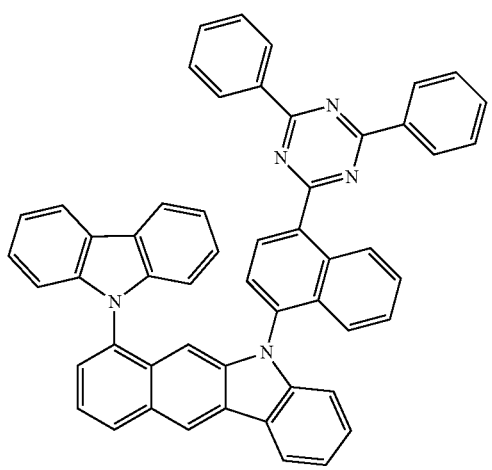
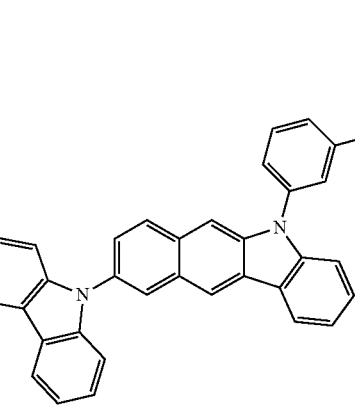
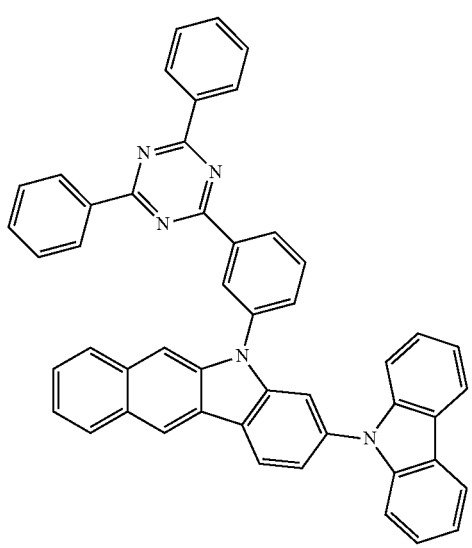
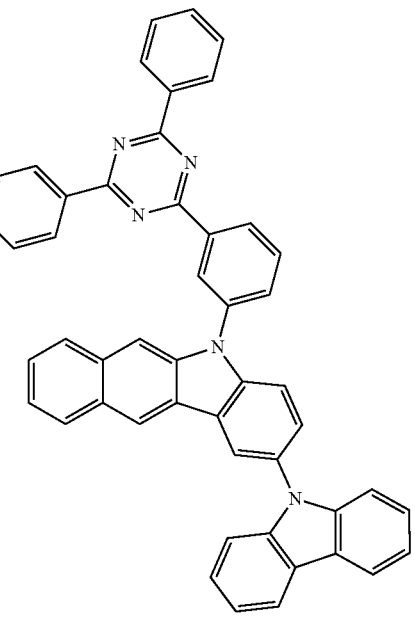

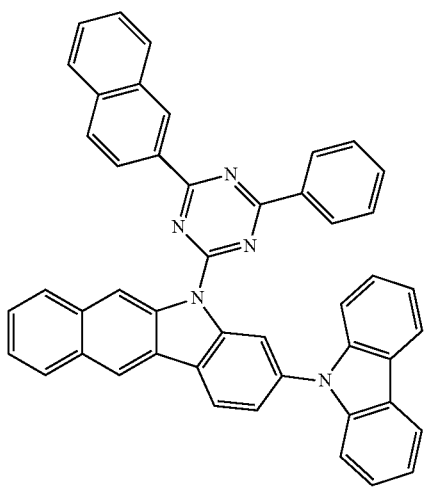
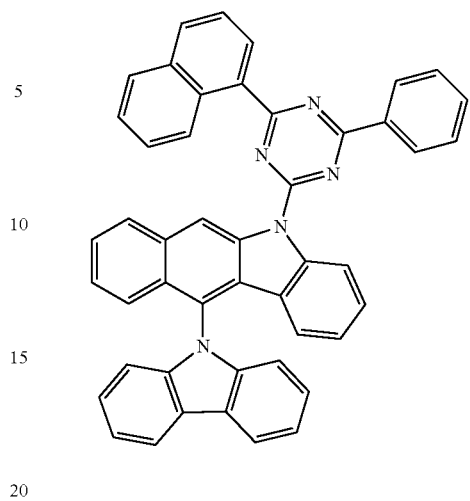
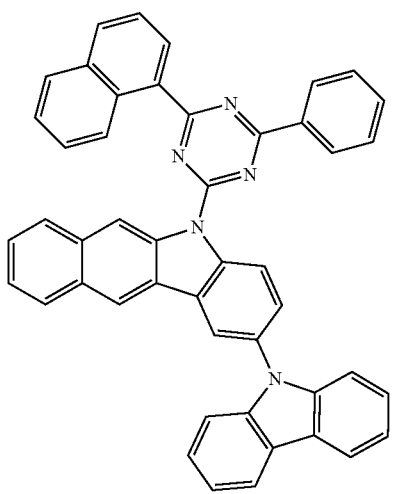
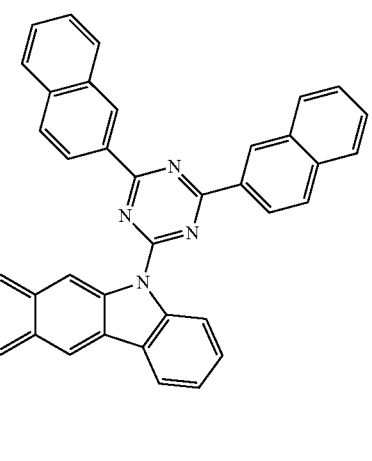
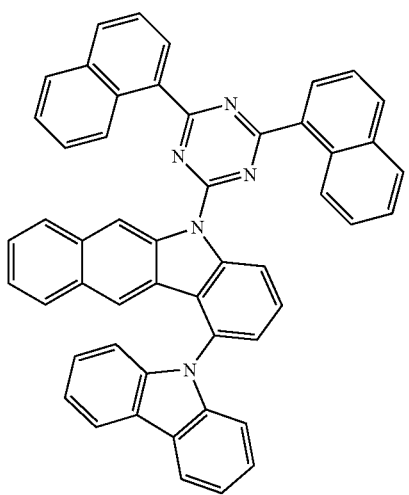
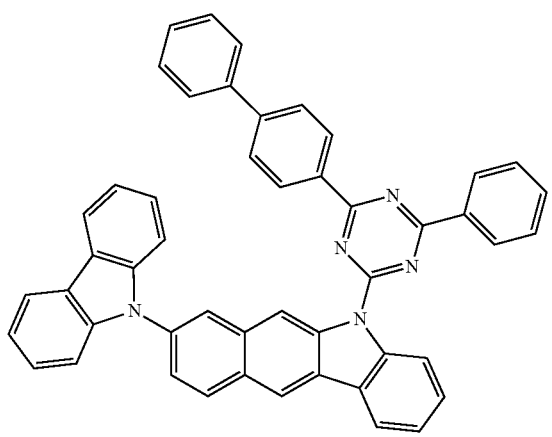

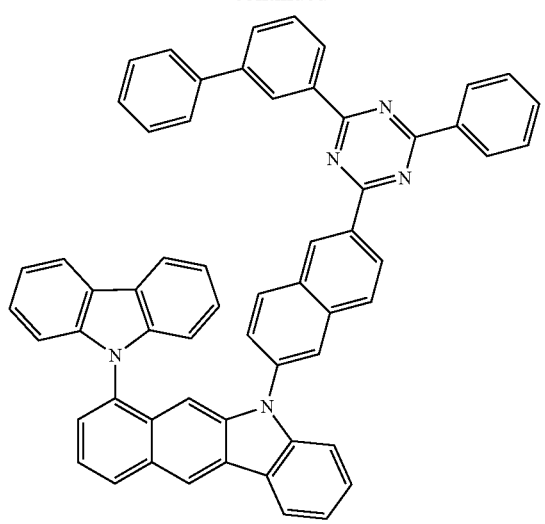
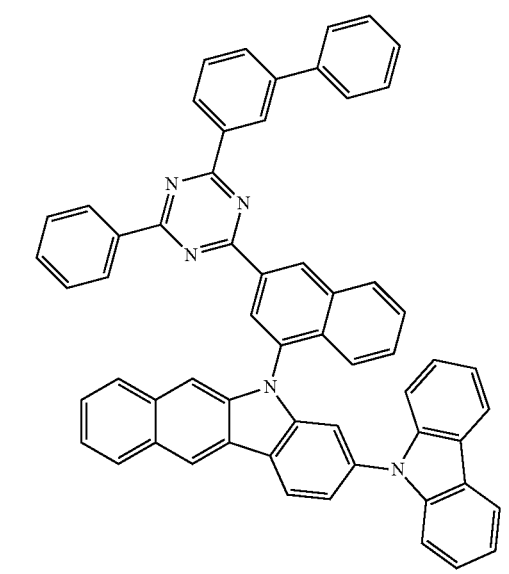
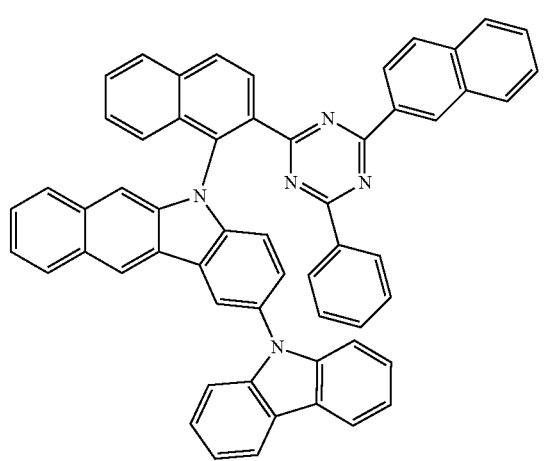
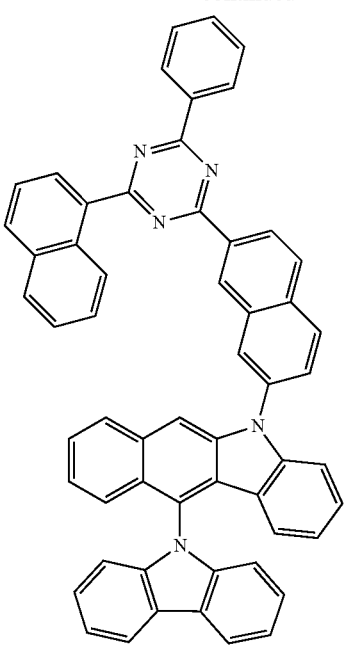
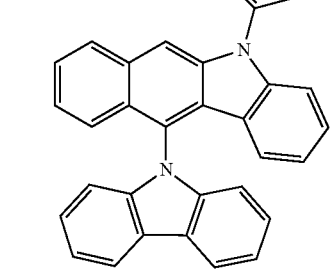
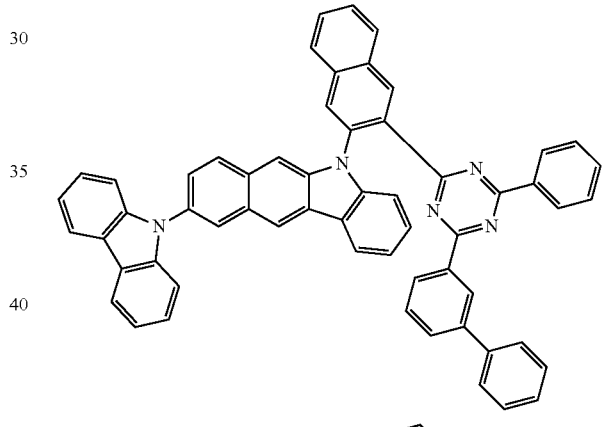
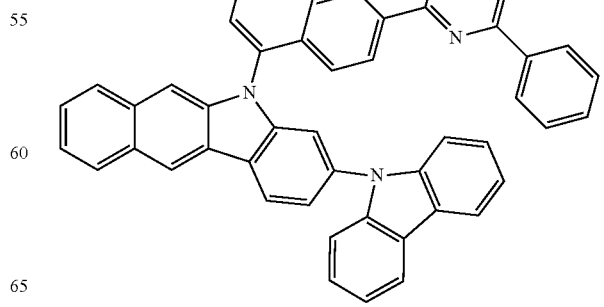

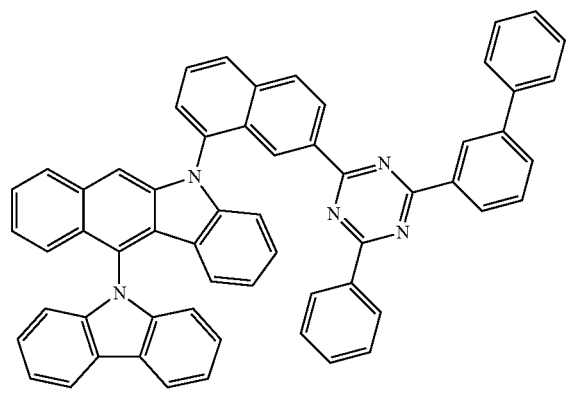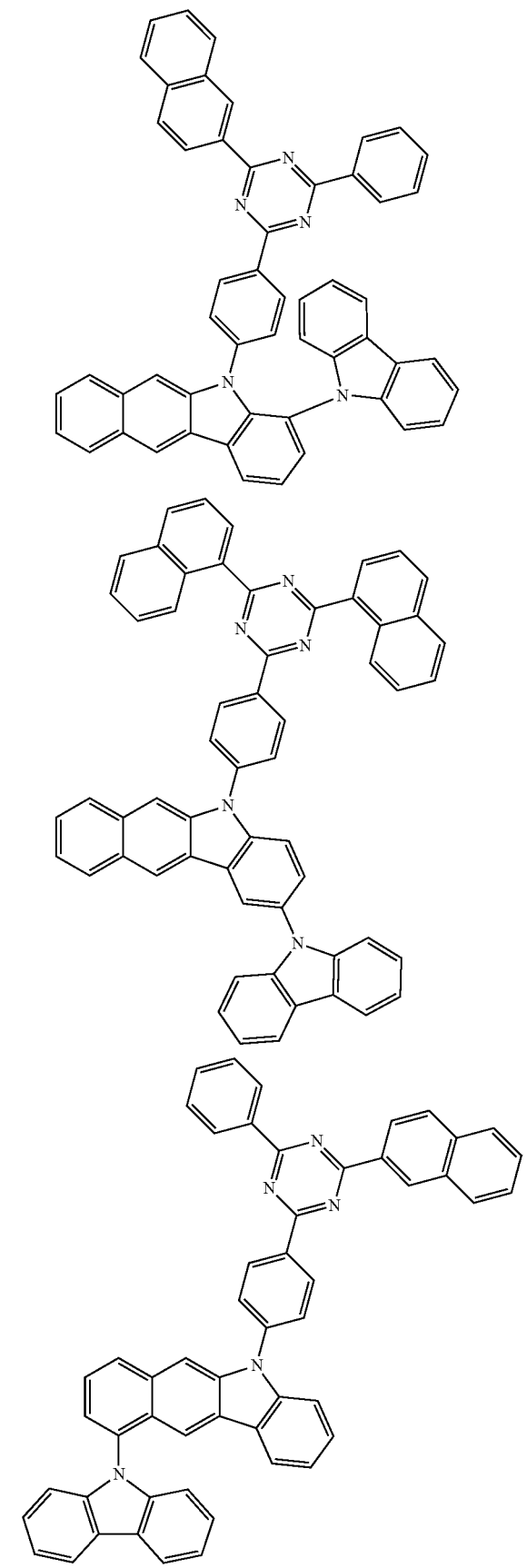

-continued
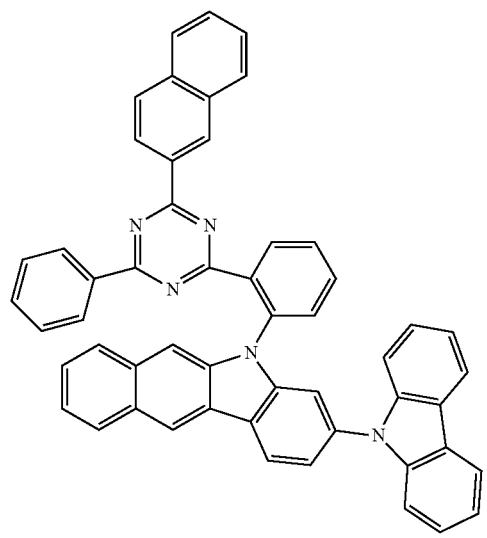
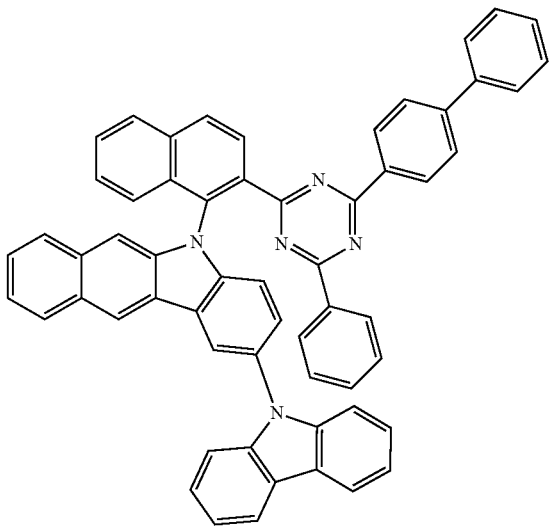
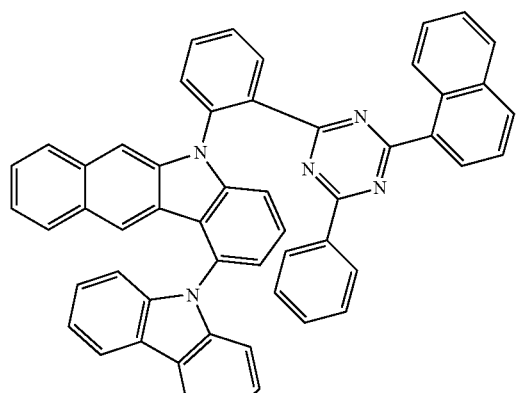
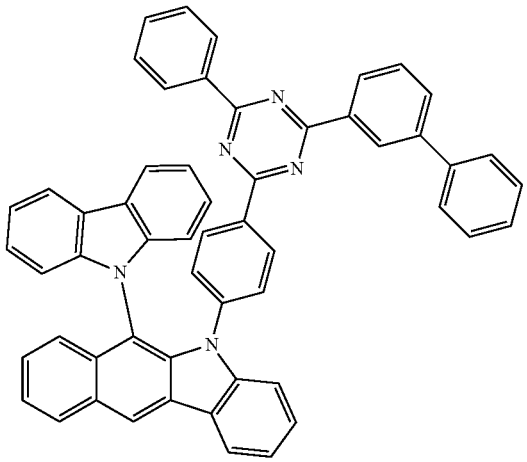
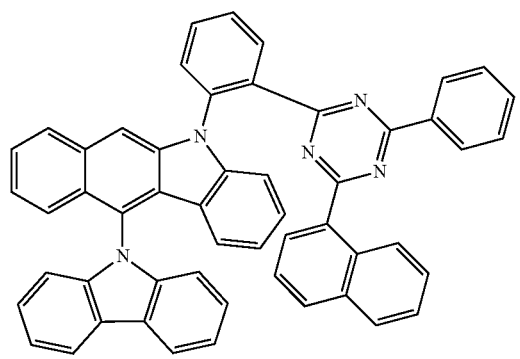
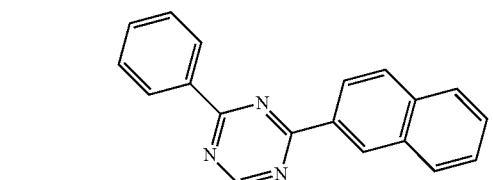
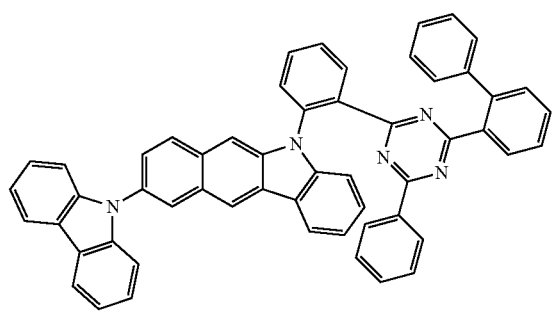
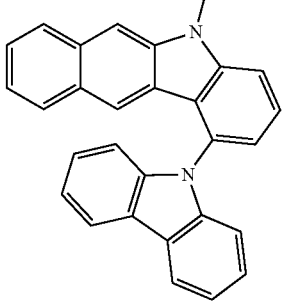

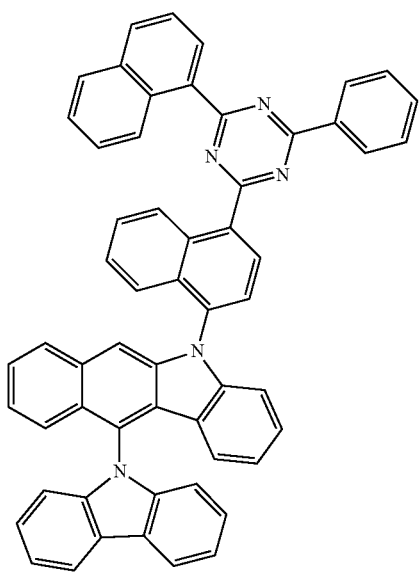
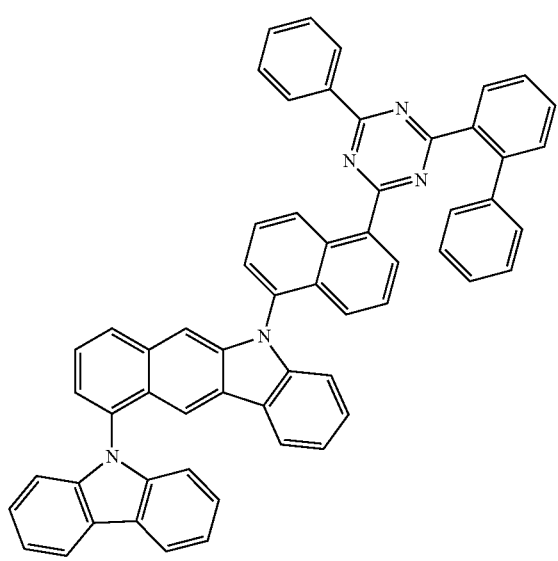
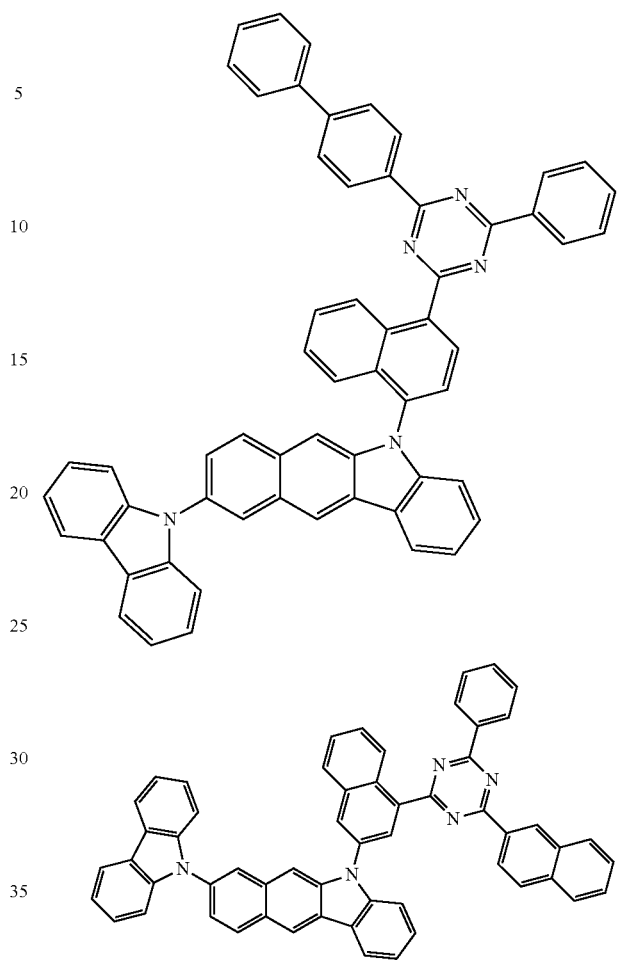
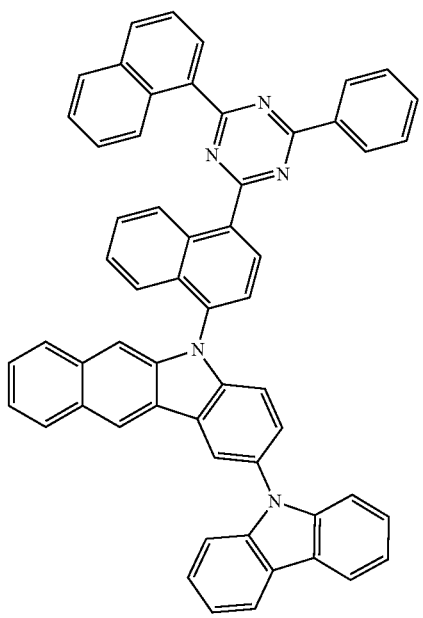

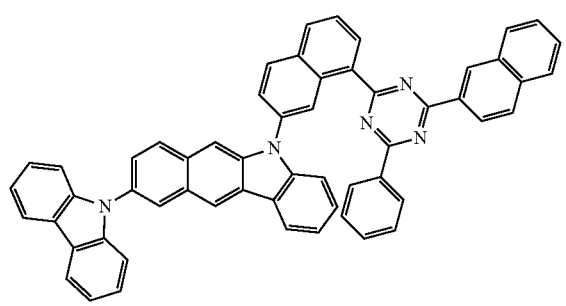
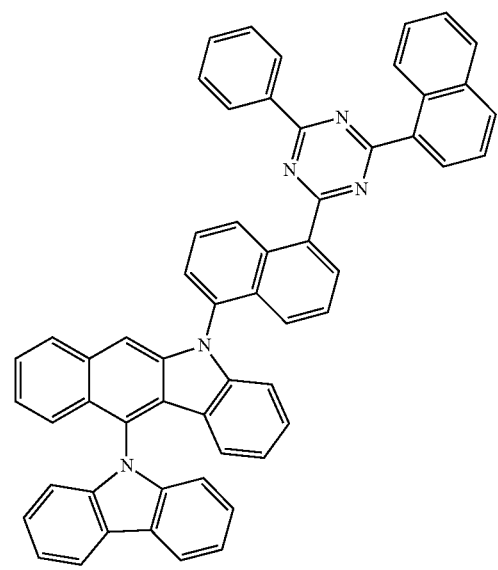
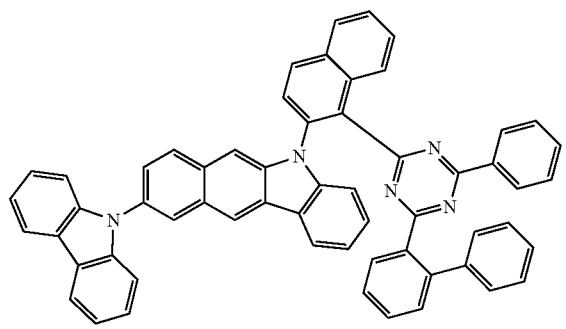
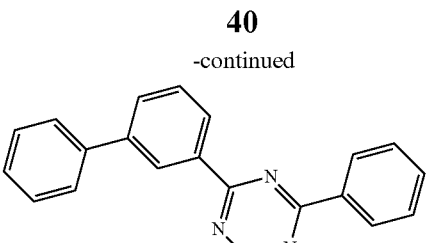
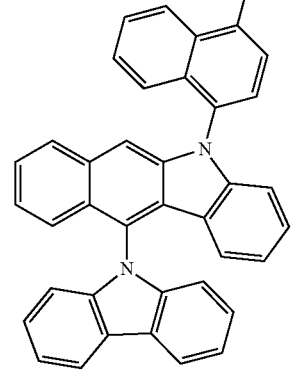
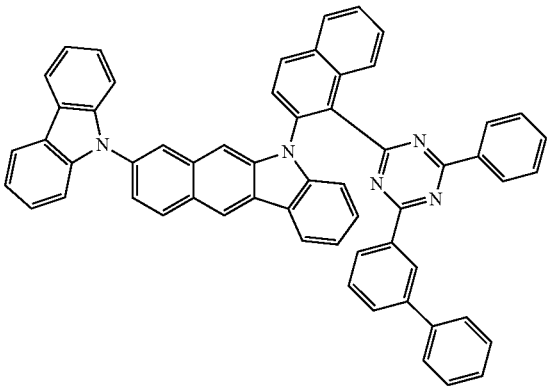
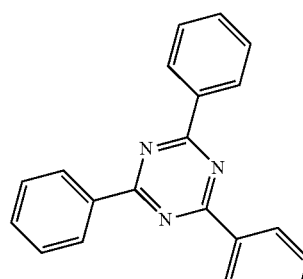
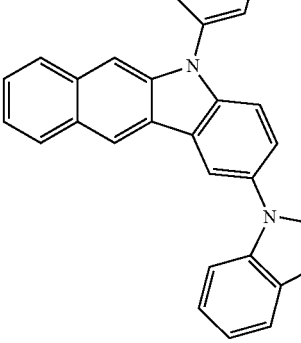

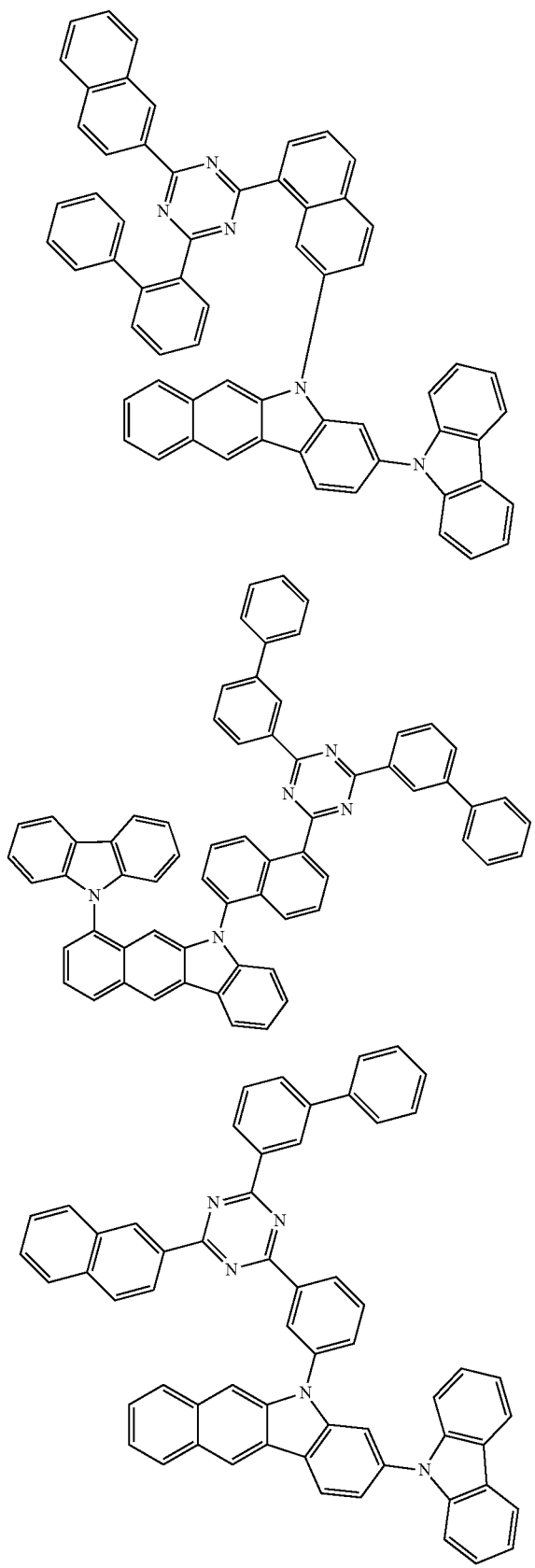
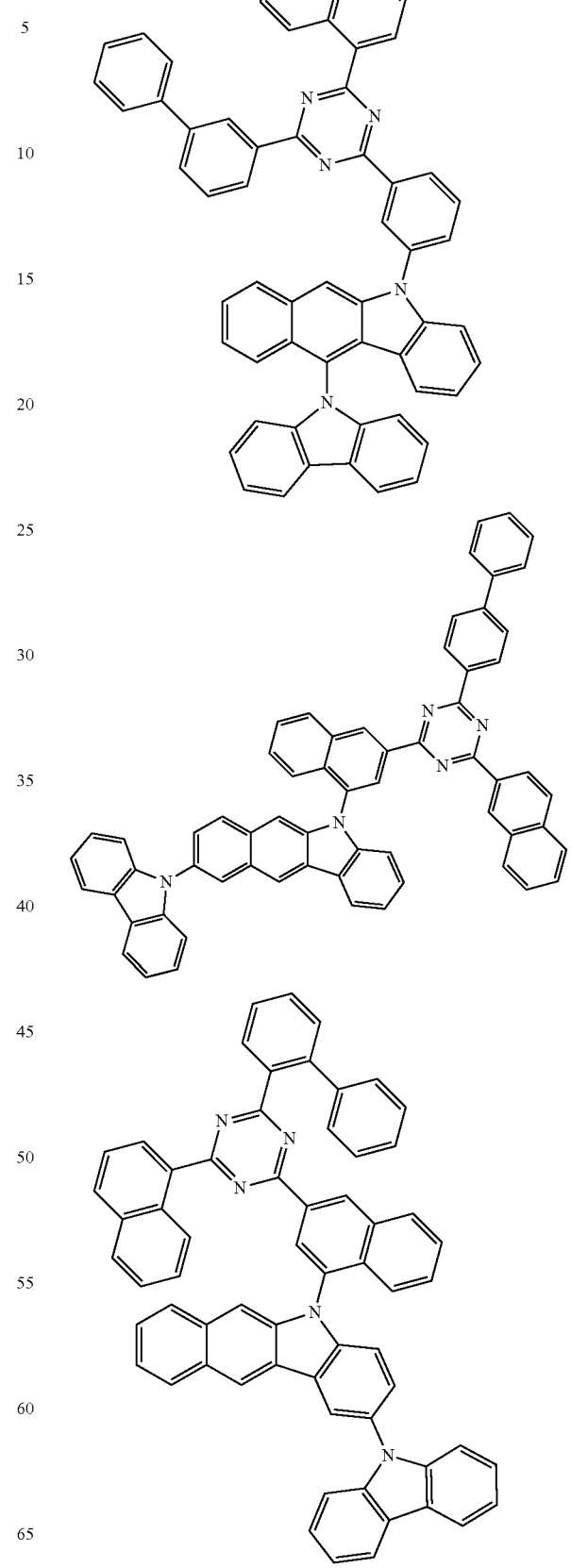

-continued
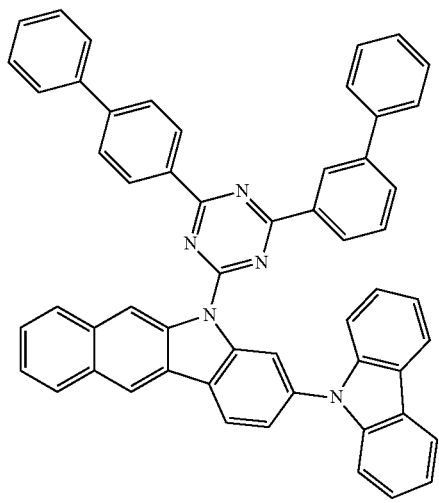
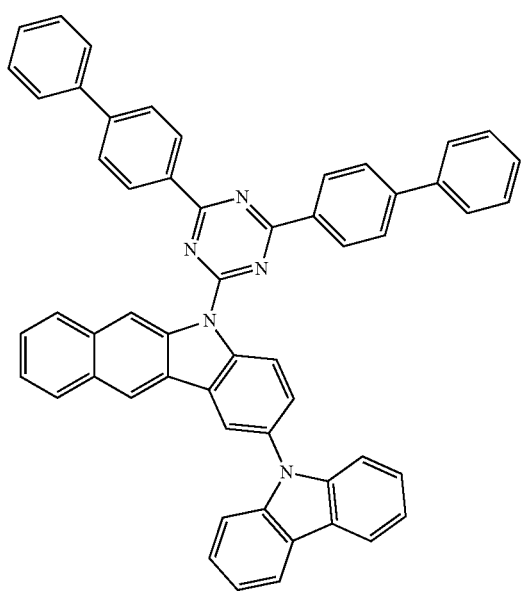
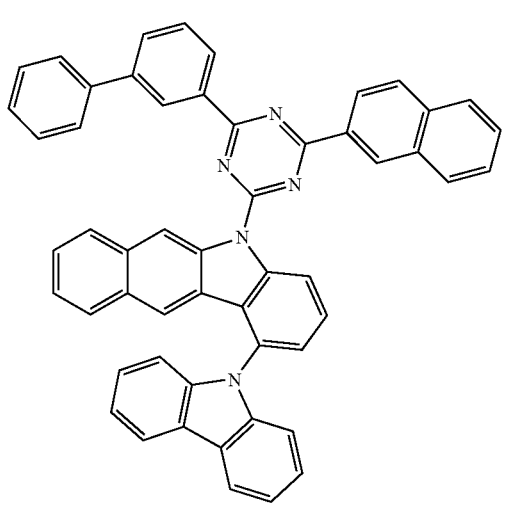
-continued
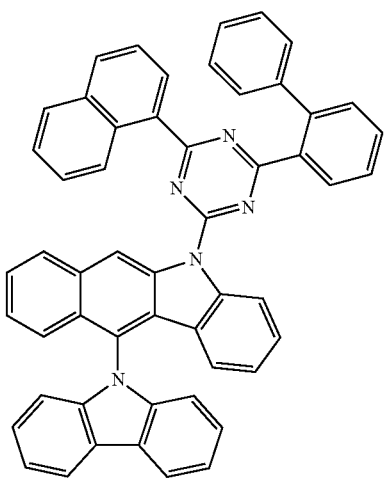
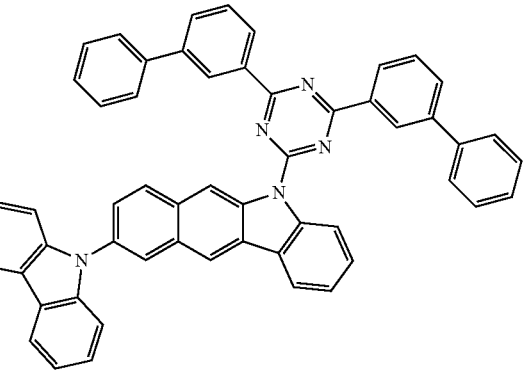
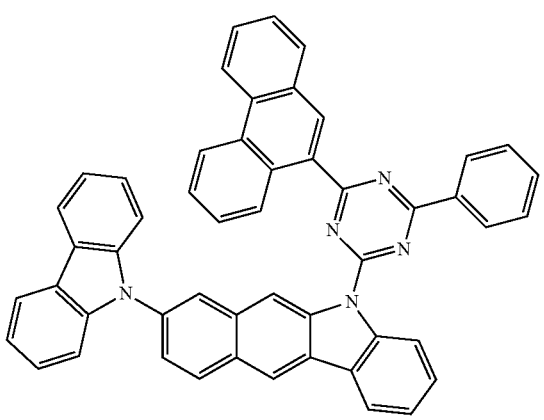

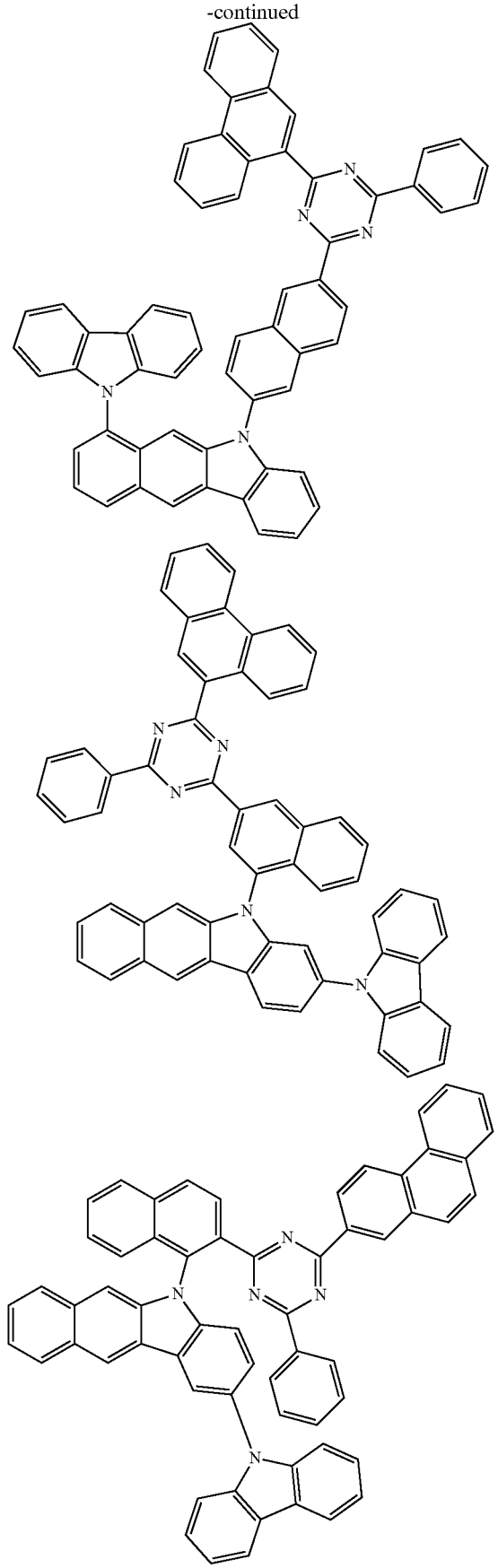
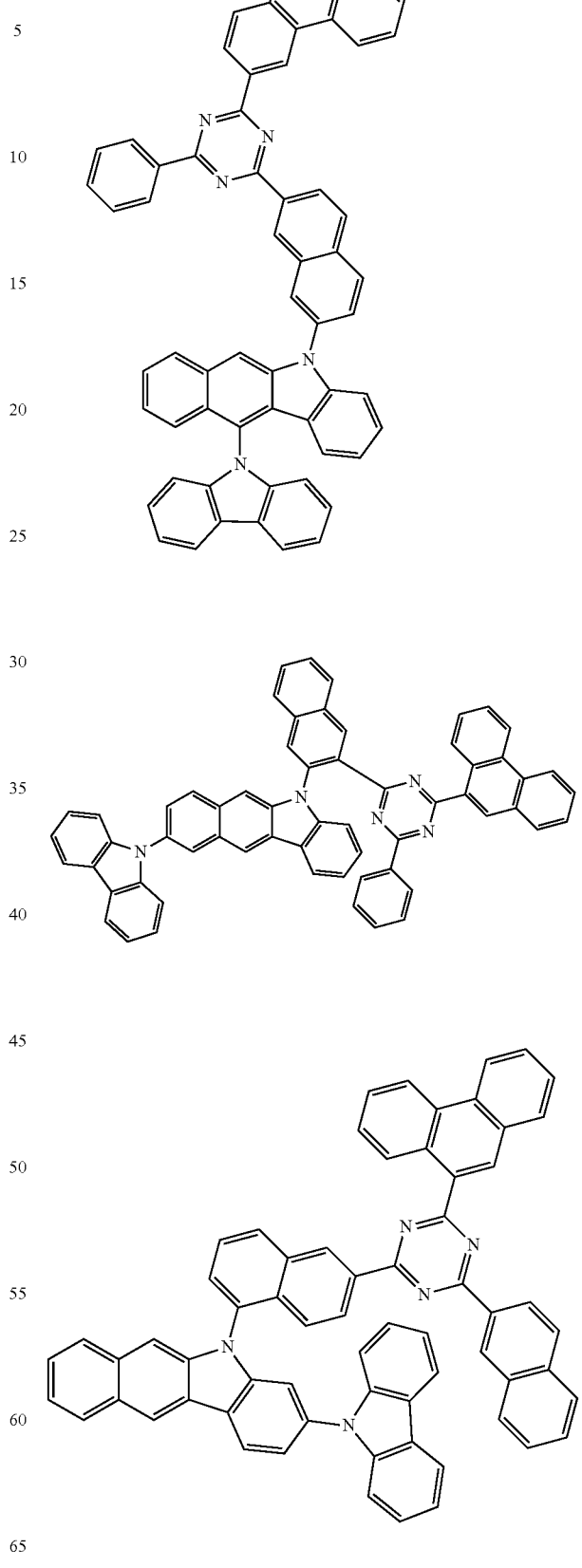

47
-continued
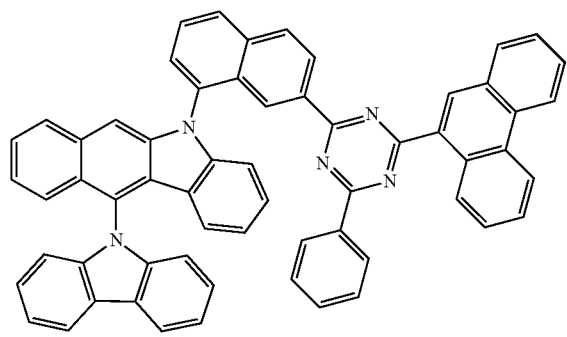
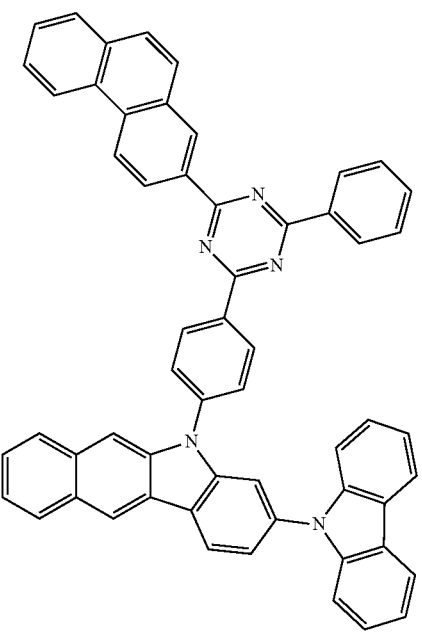
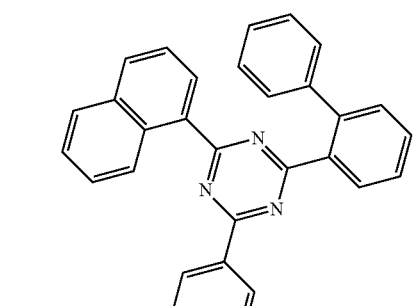
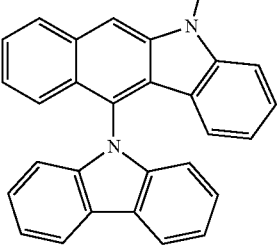
48
-continued
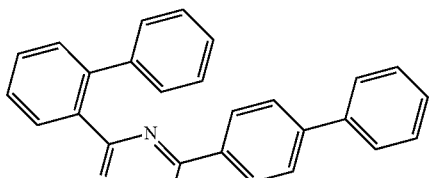
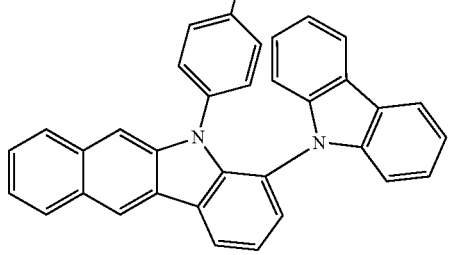
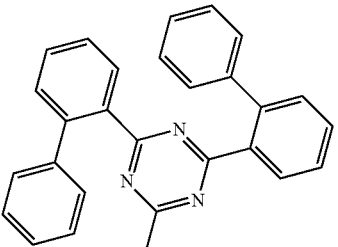
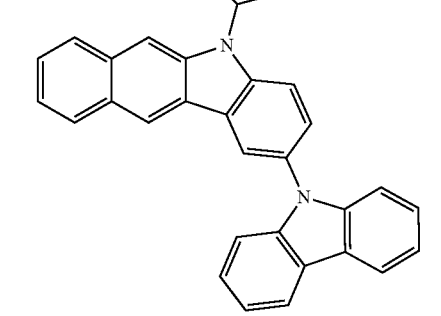
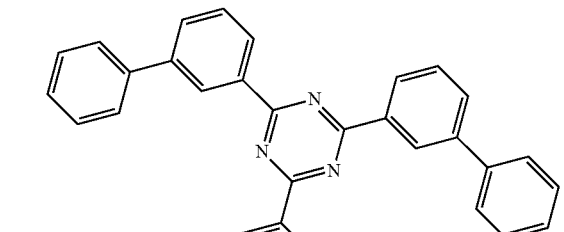
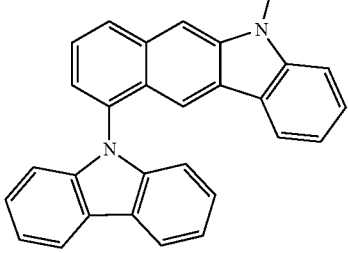

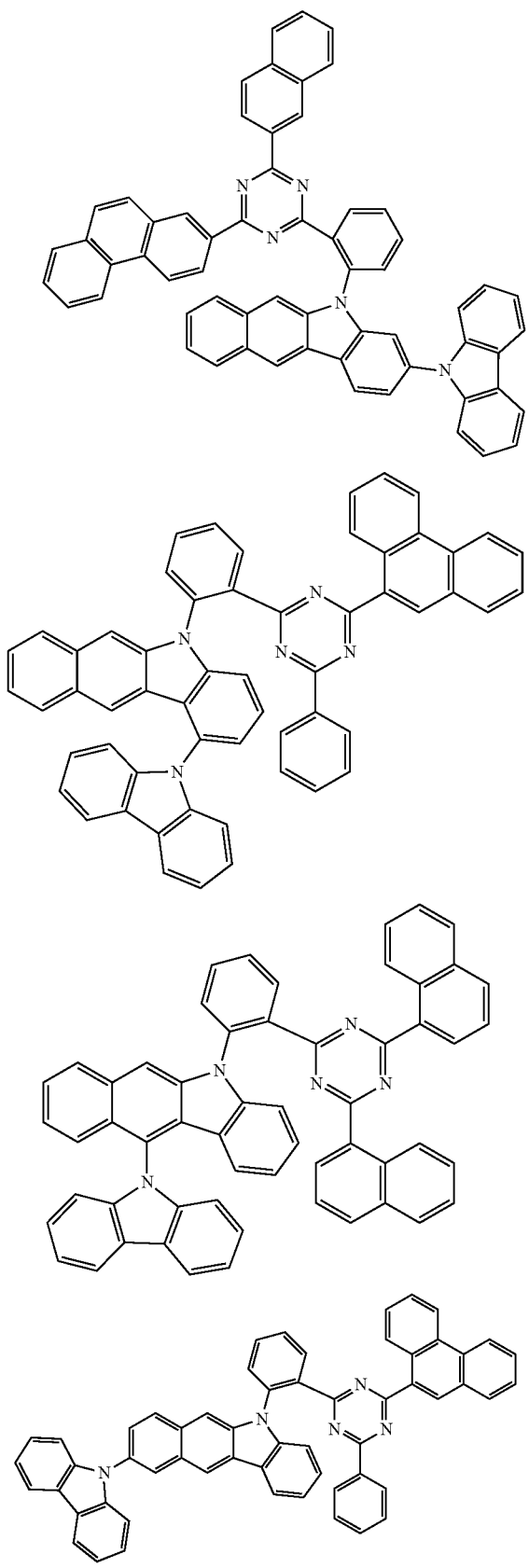
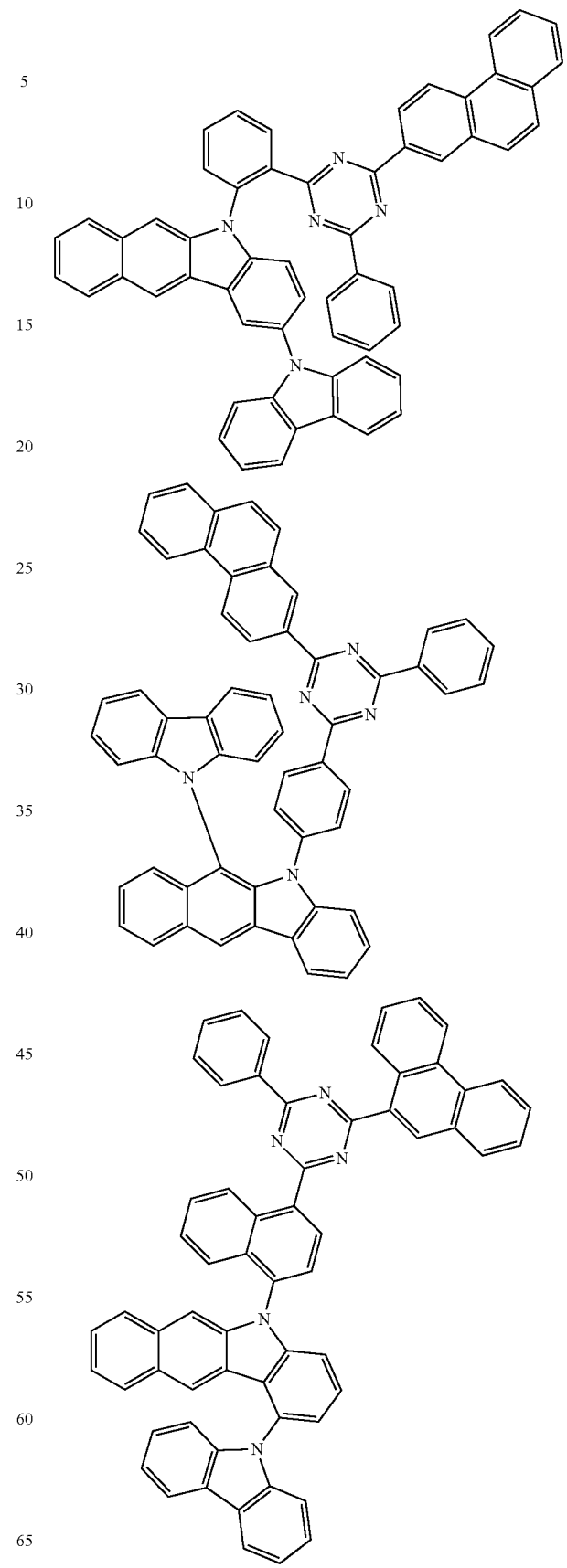

51
-continued
52
-continued
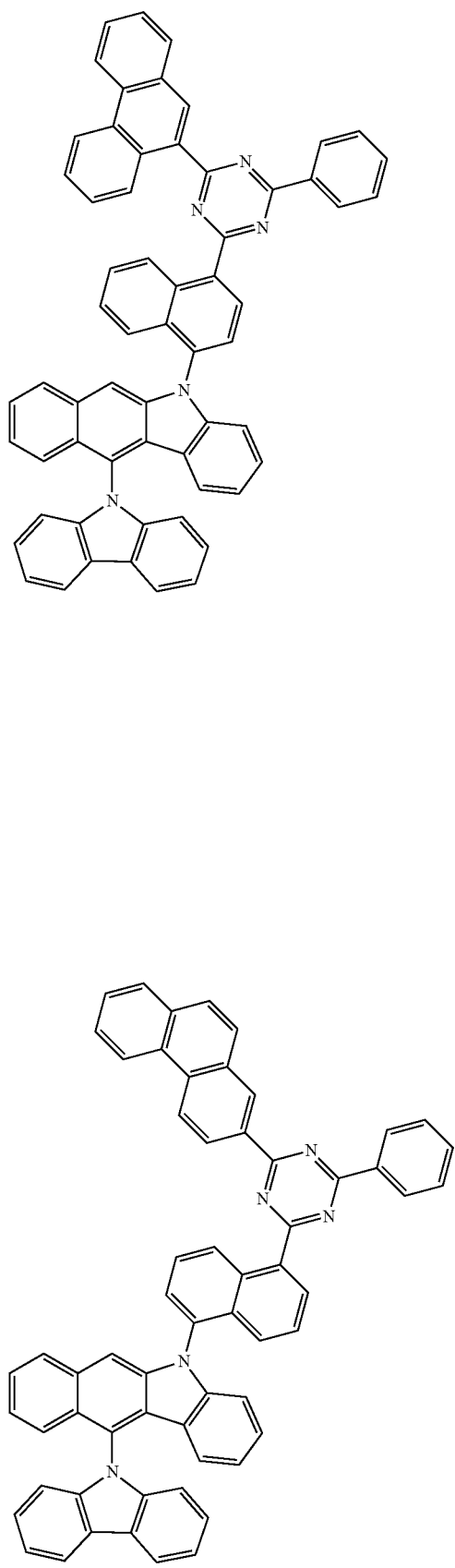
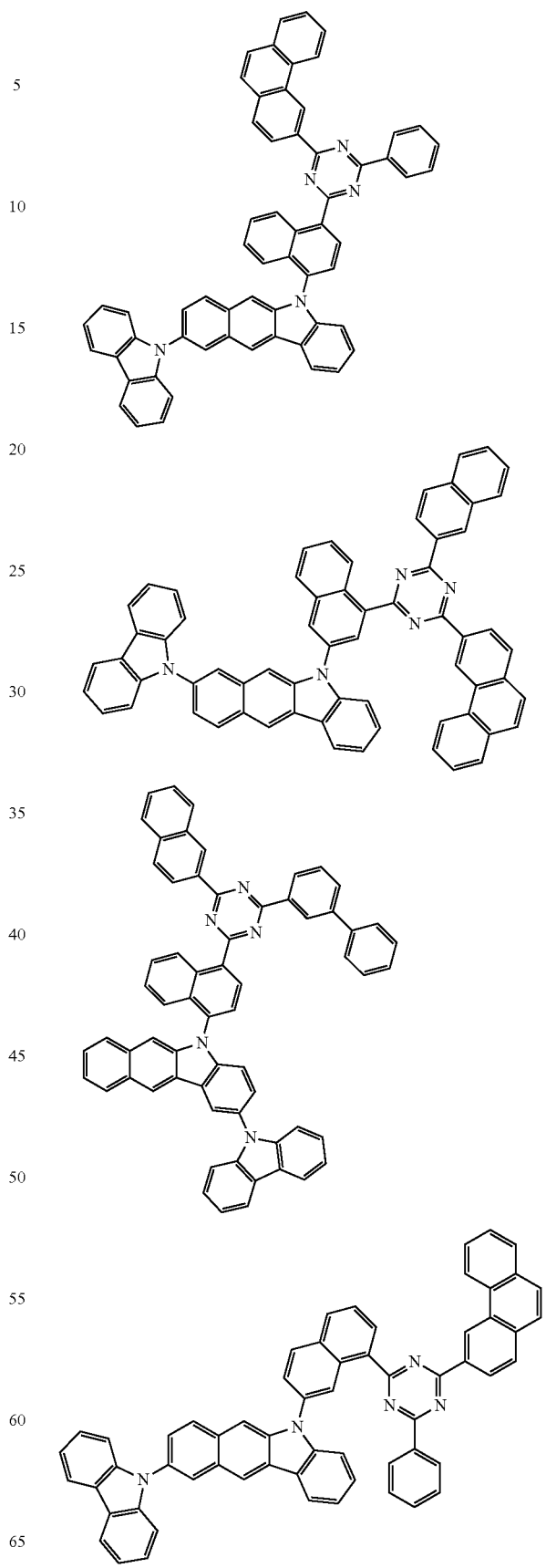

53
-continued
54
-continued
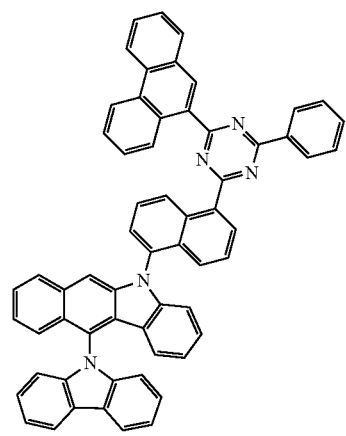
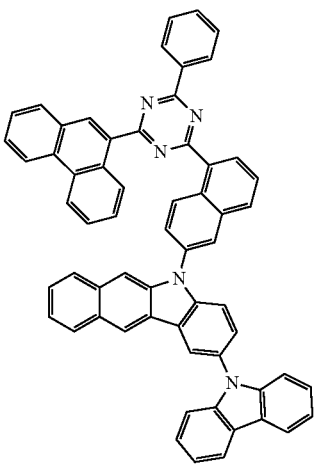
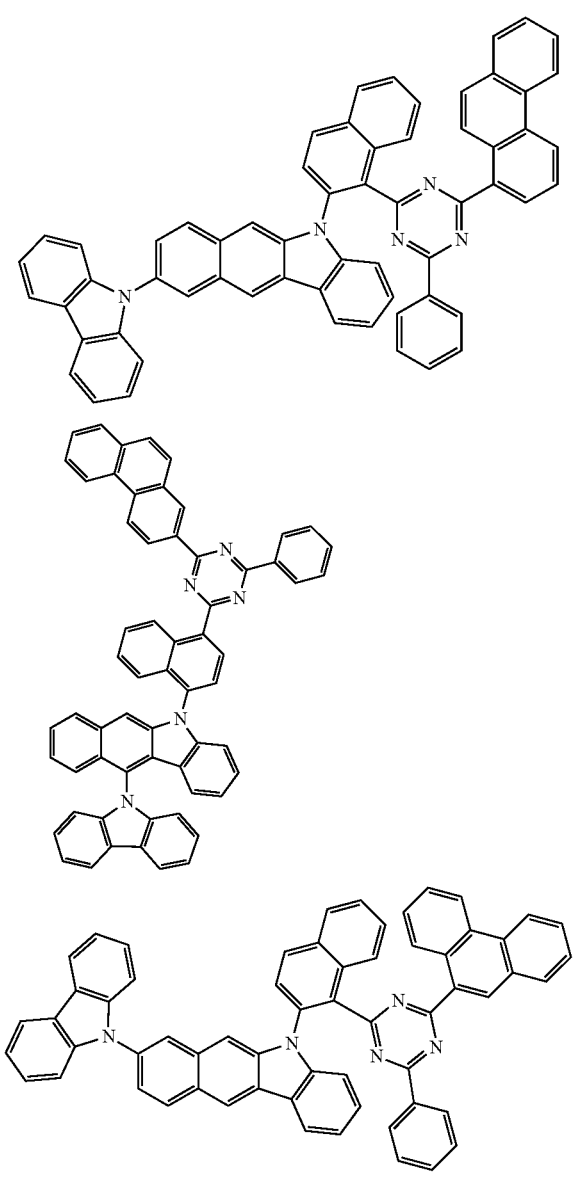
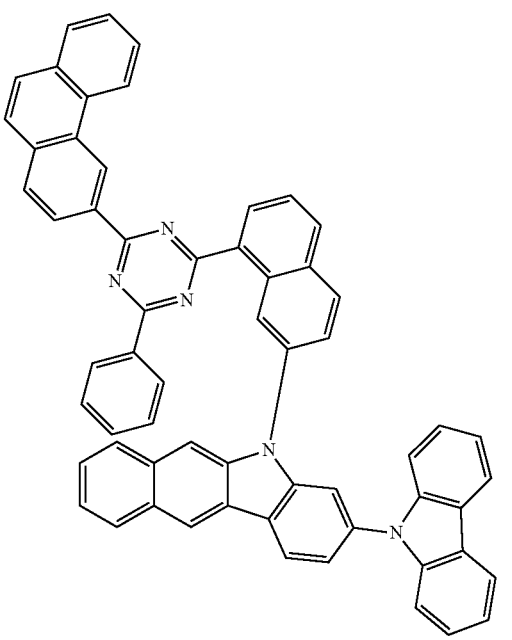

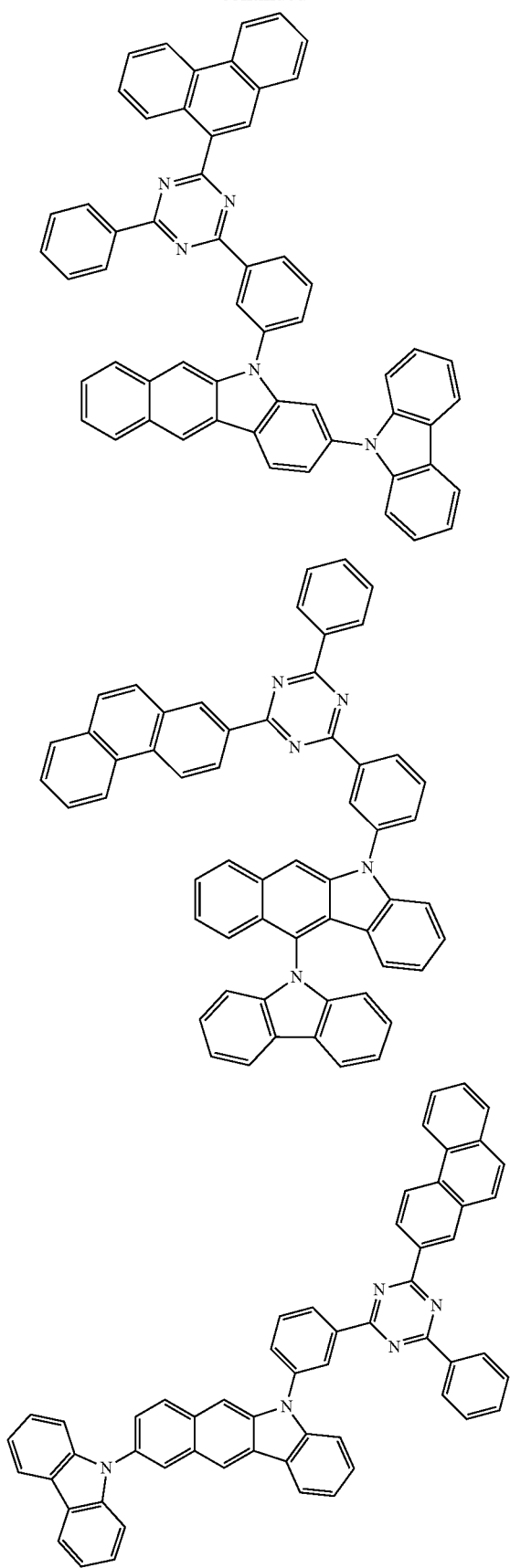
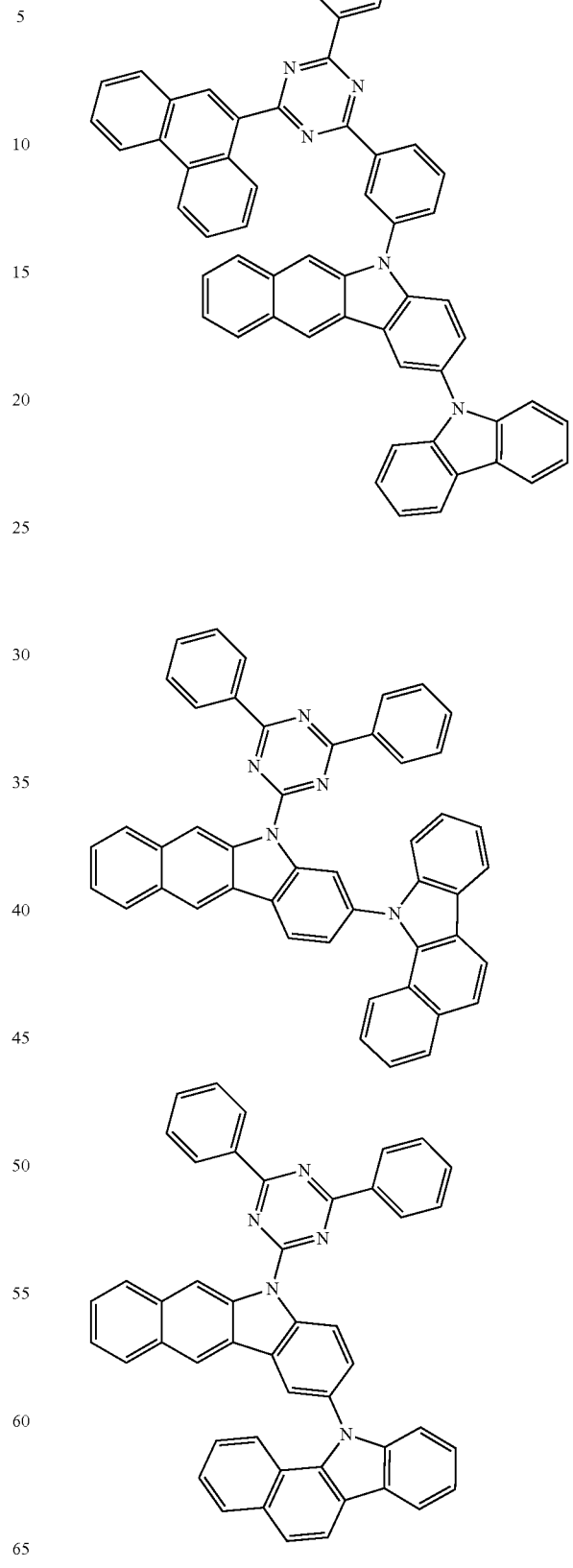

-continued
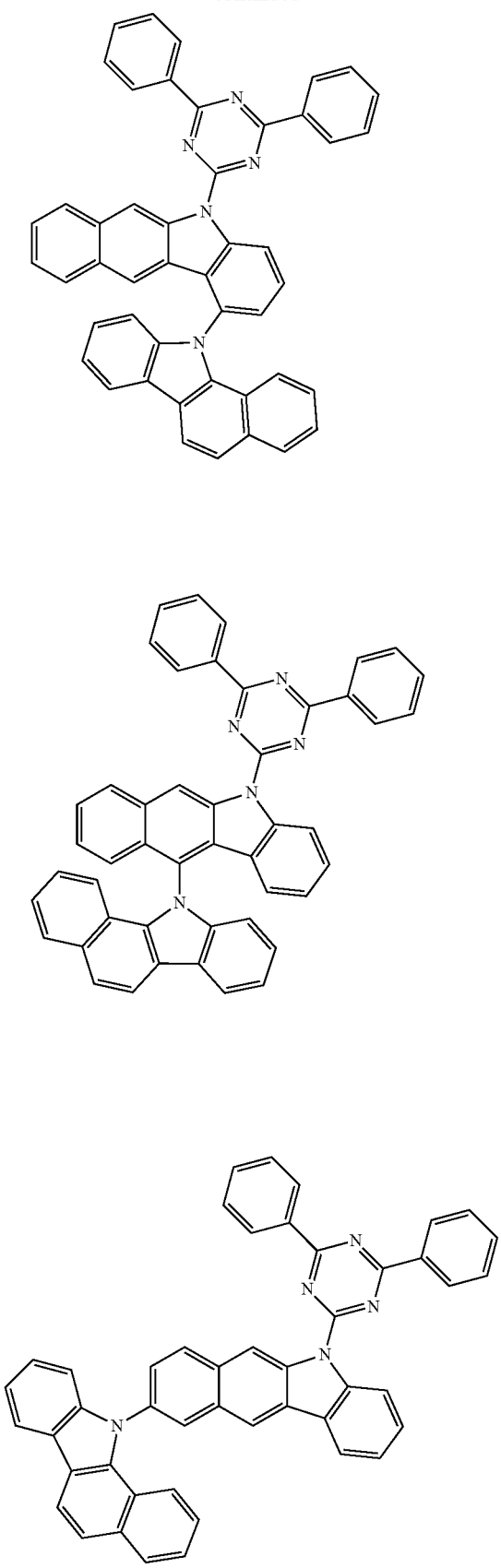
-continued
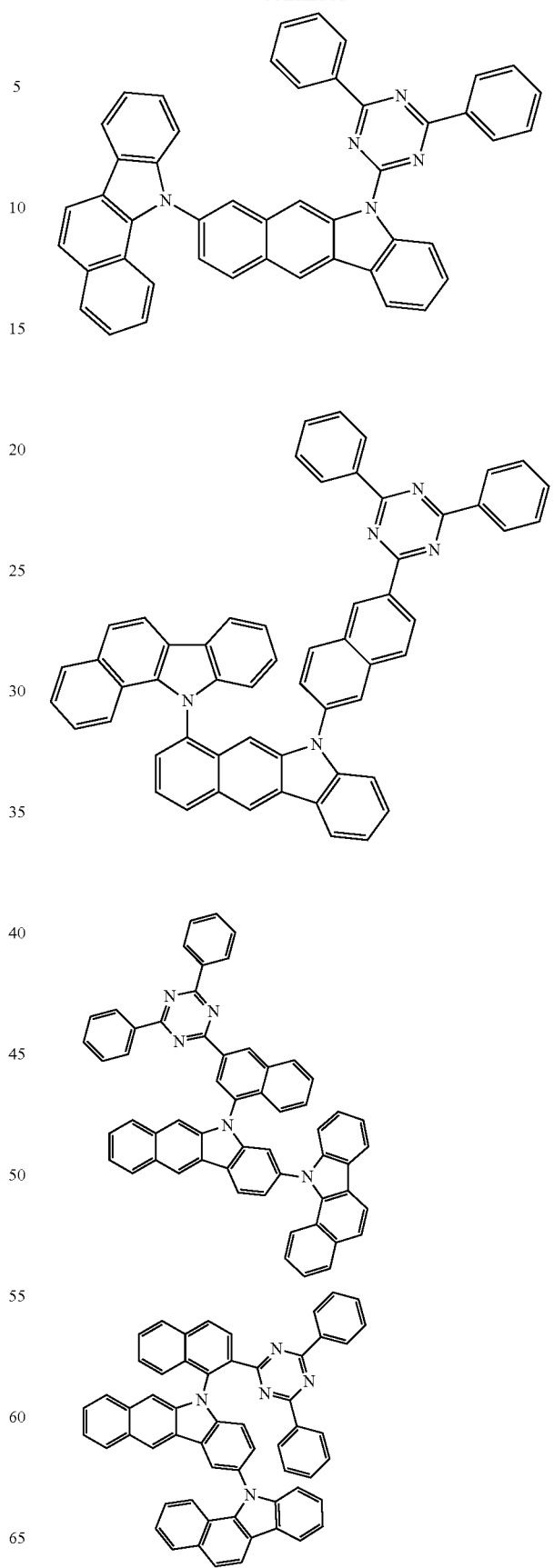

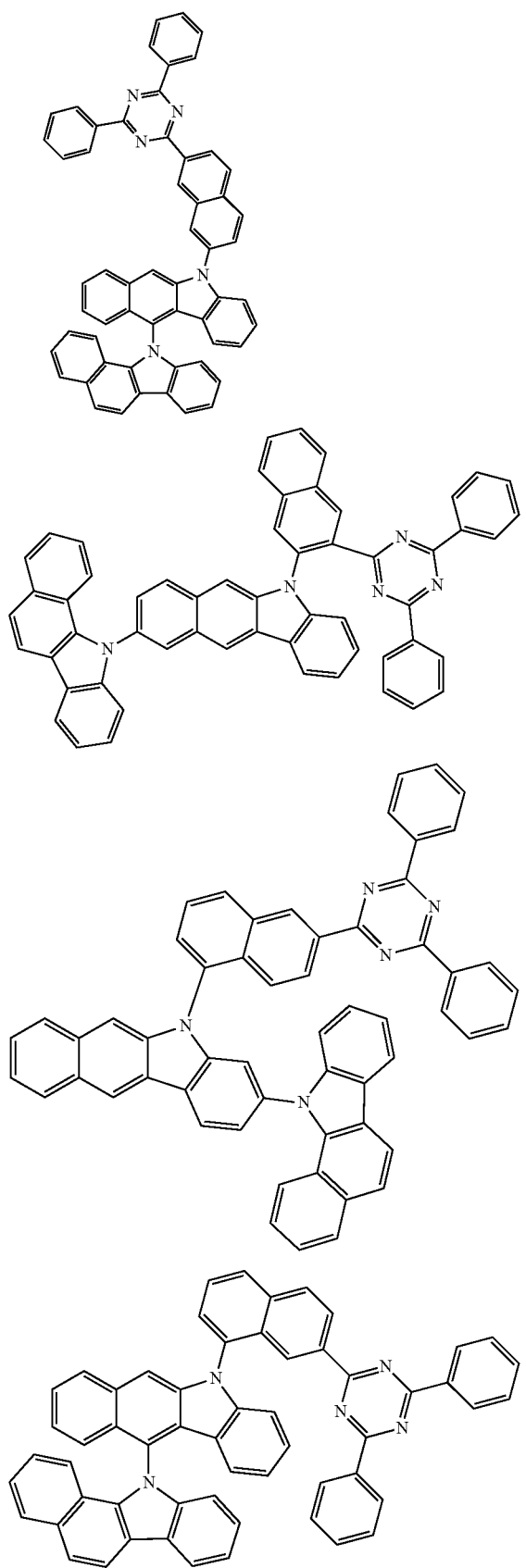
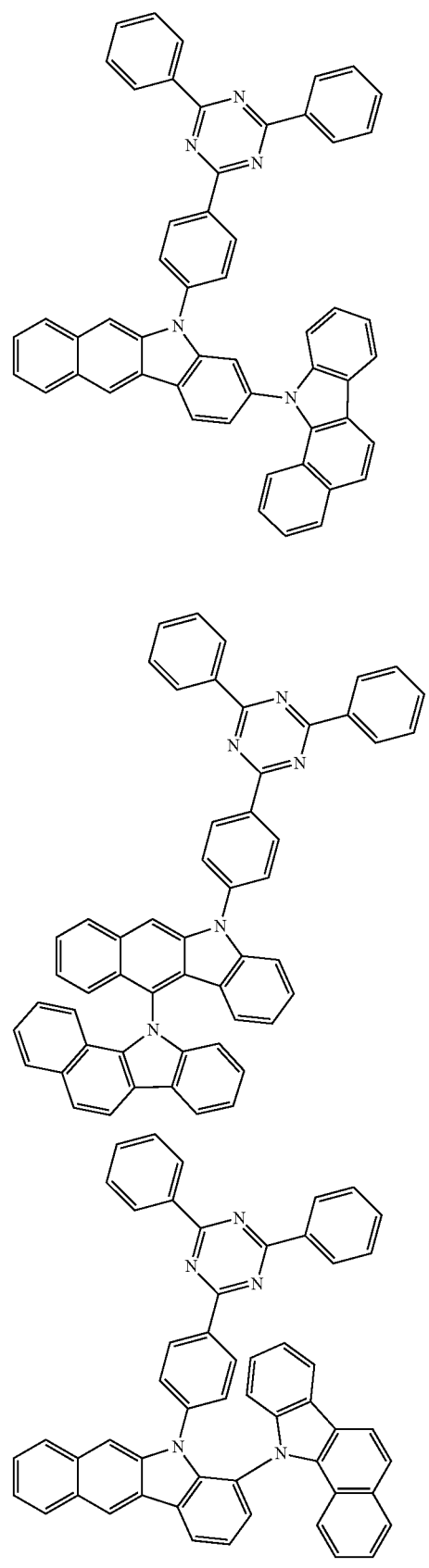

61
-continued
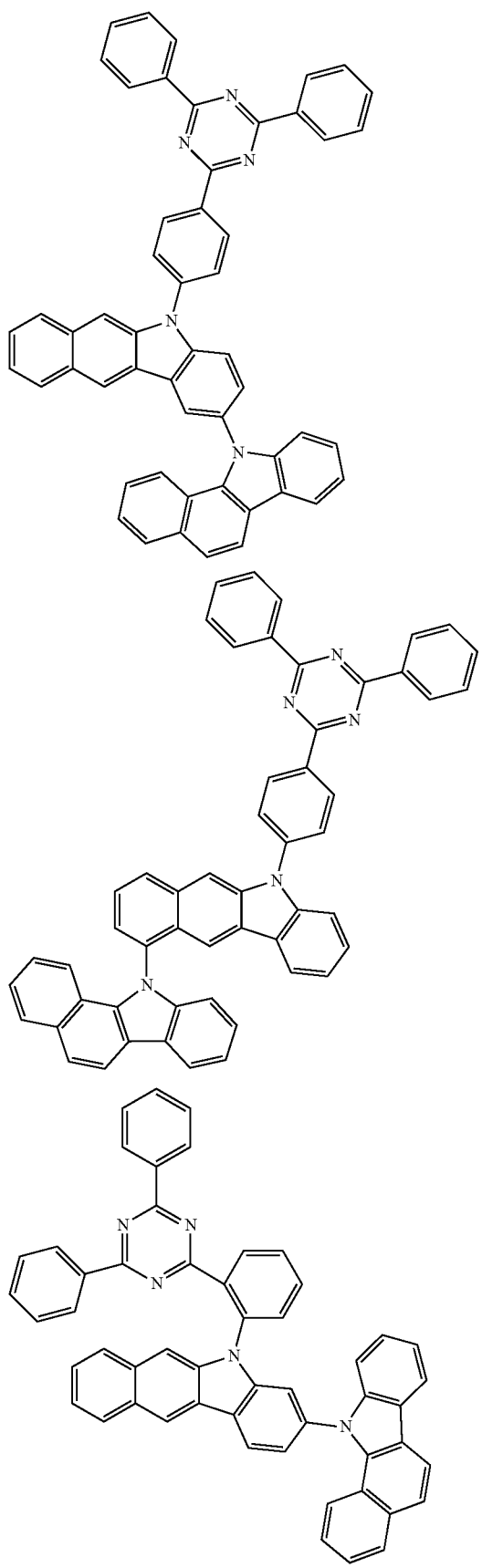
62
-continued
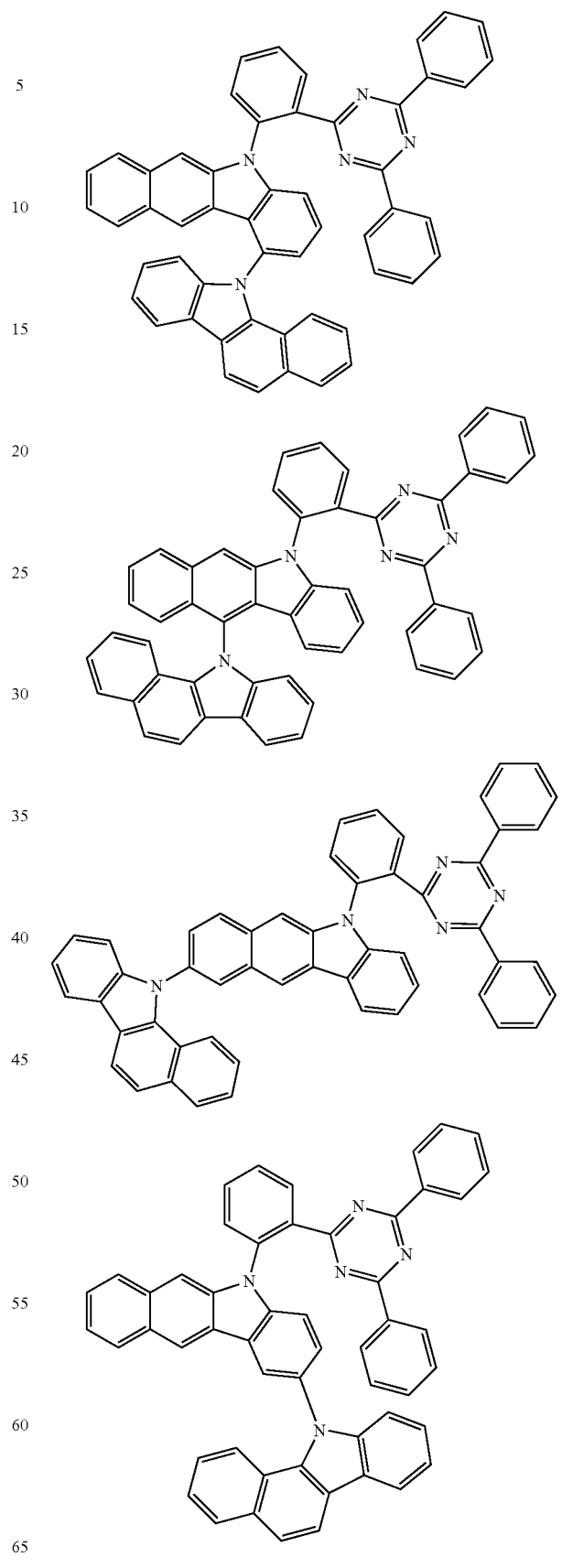

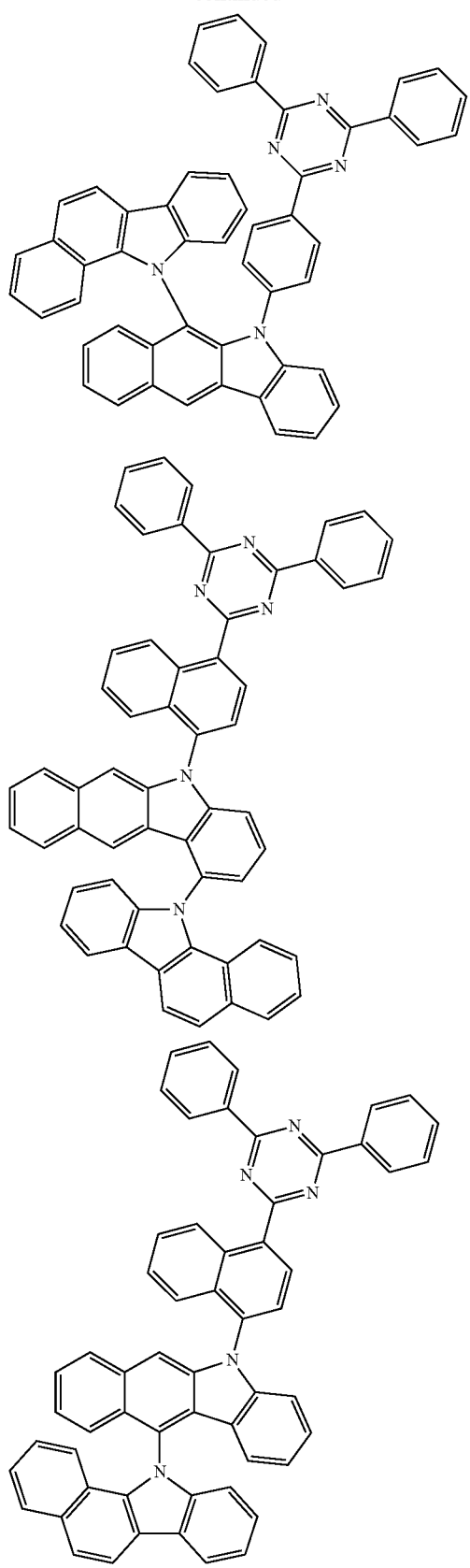
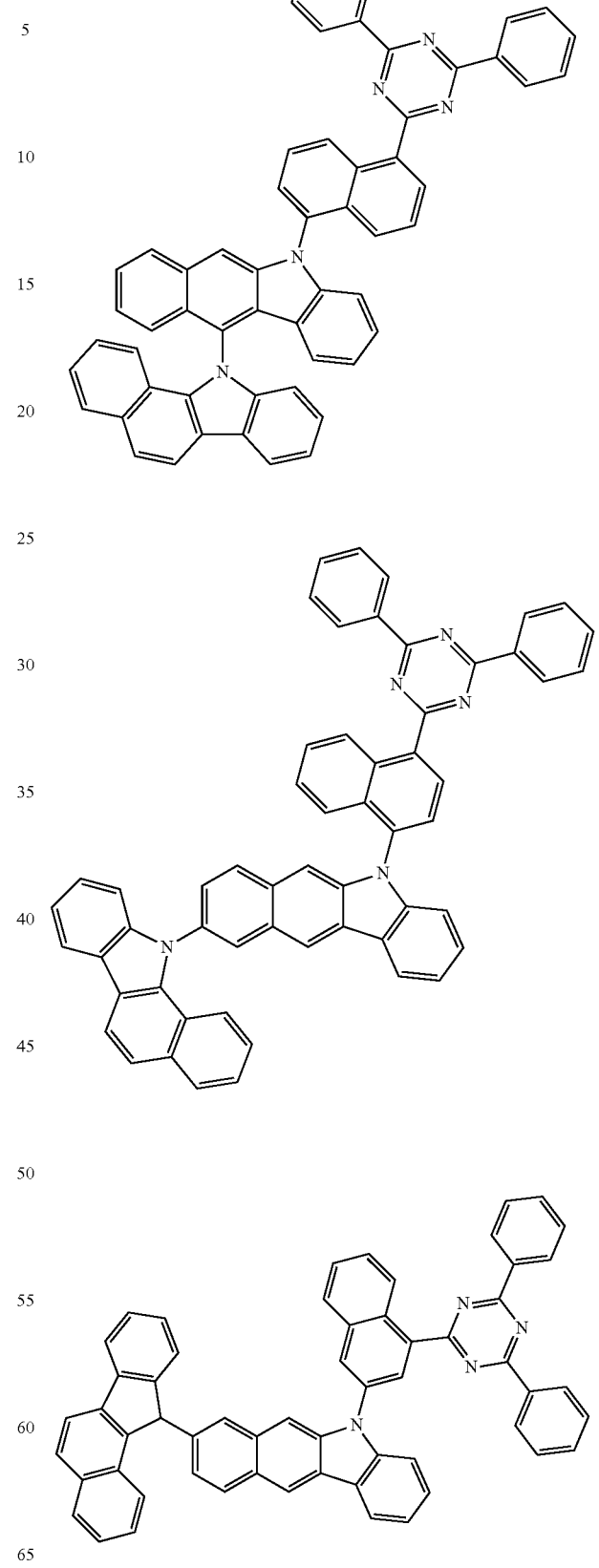

65 -continued
66 -continued
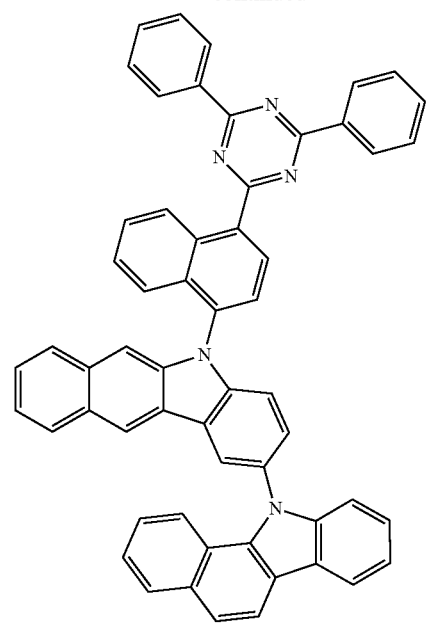
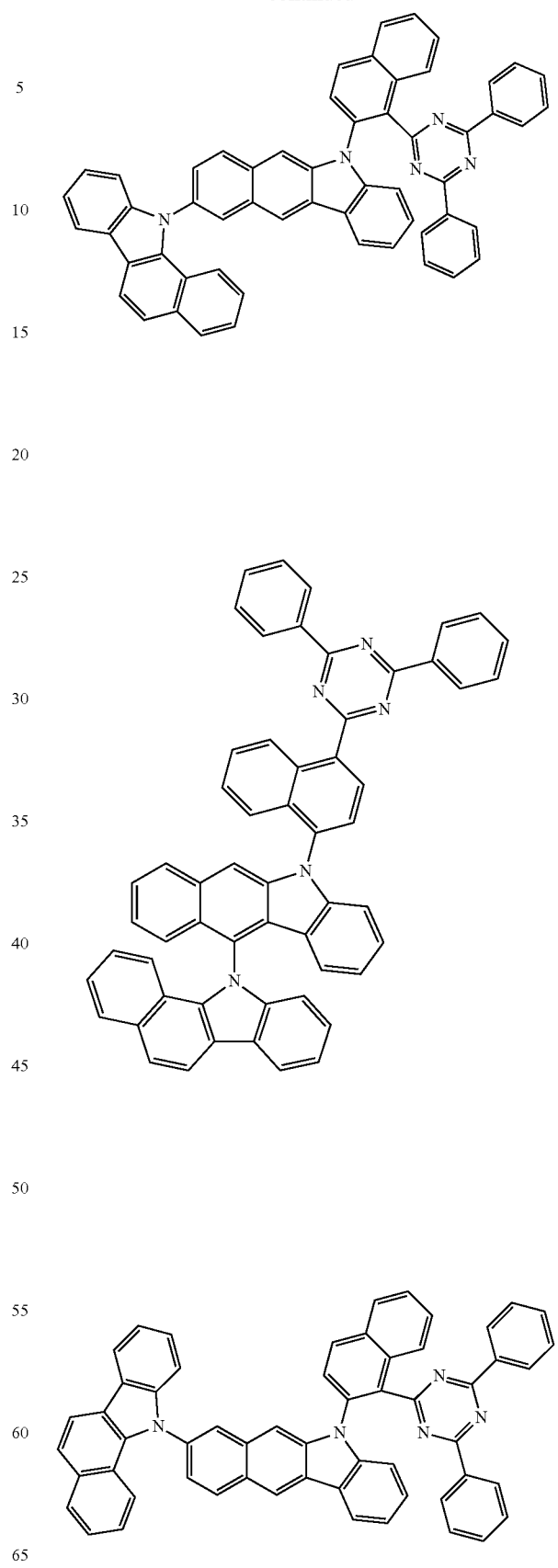

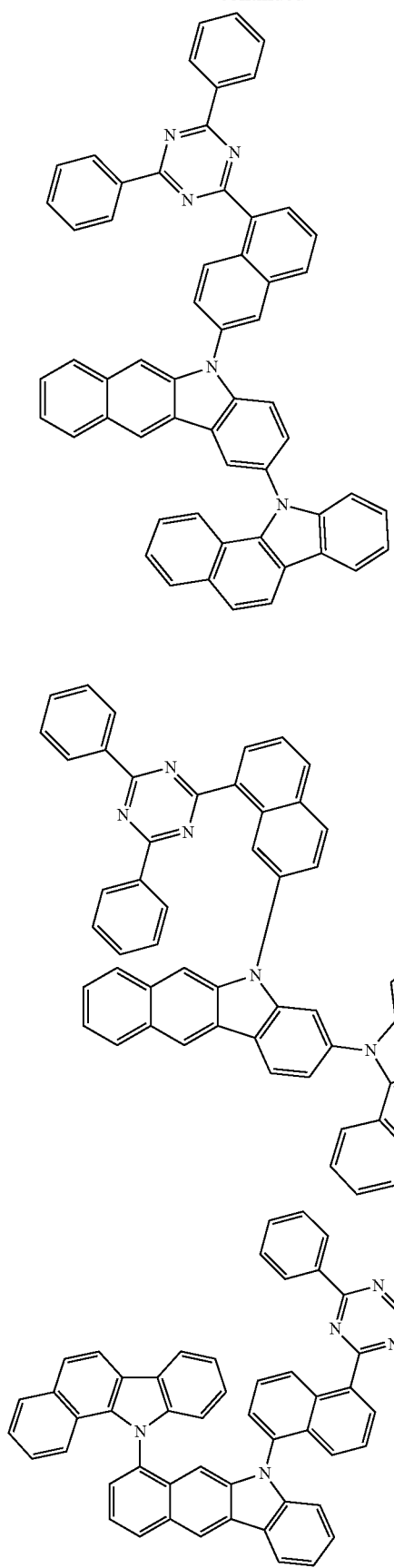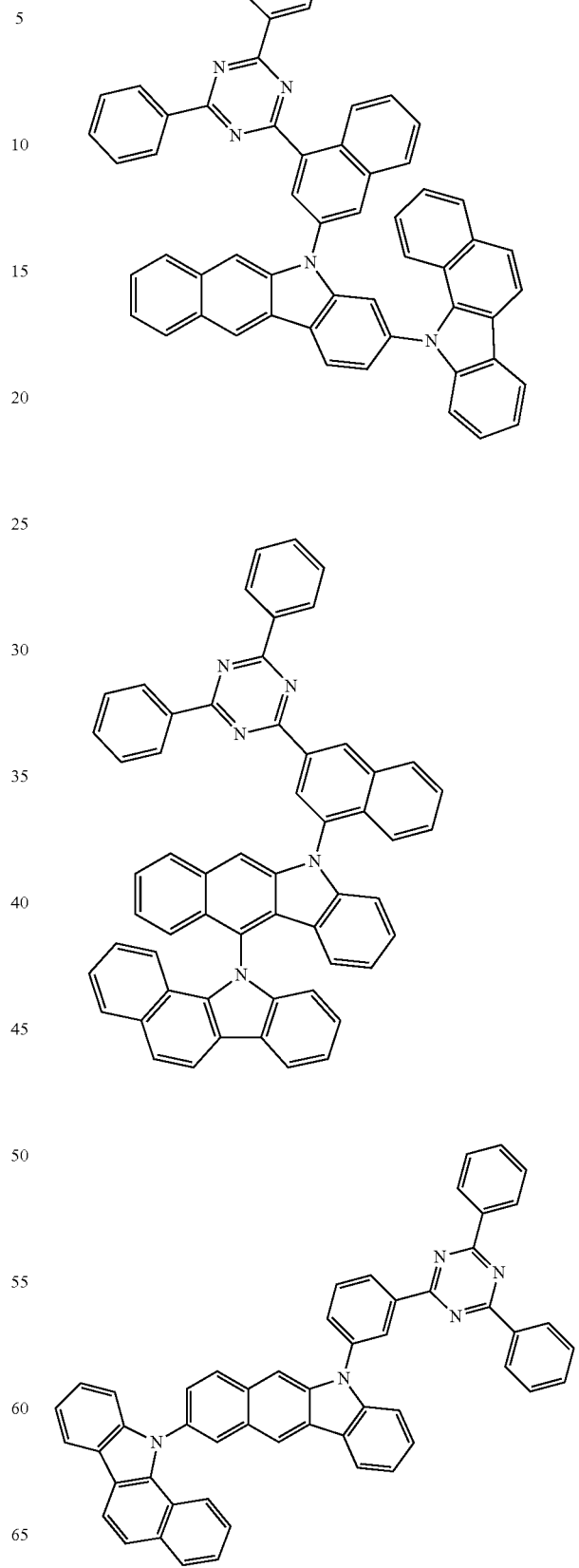

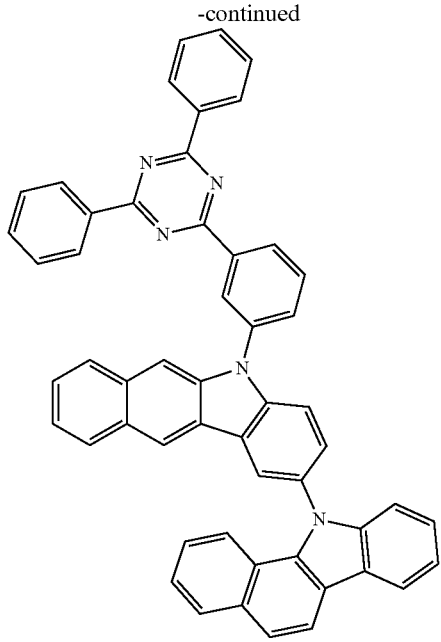
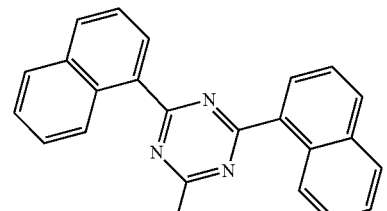
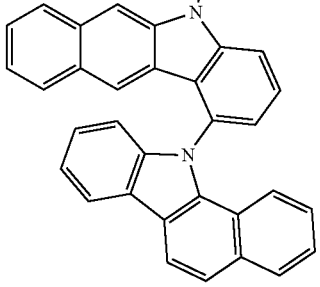
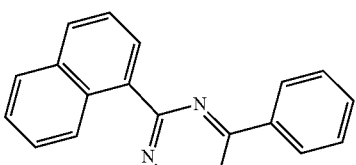
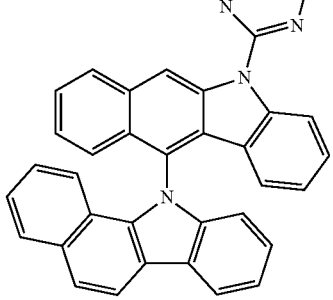
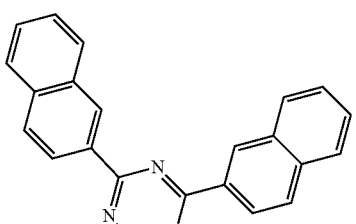
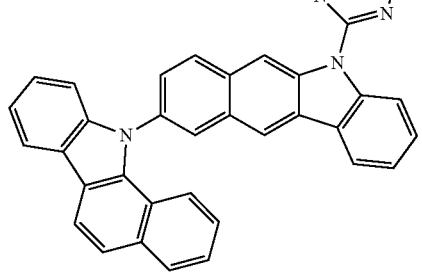

71
-continued
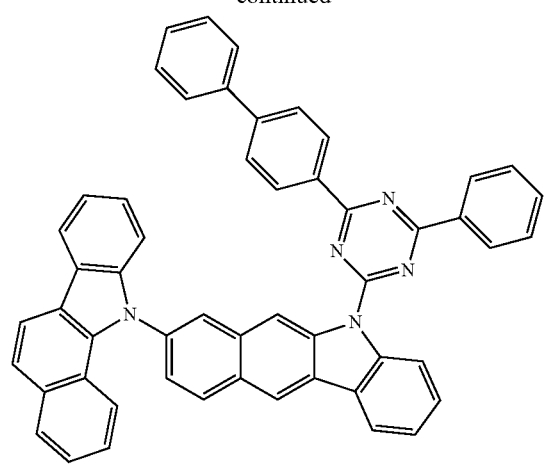
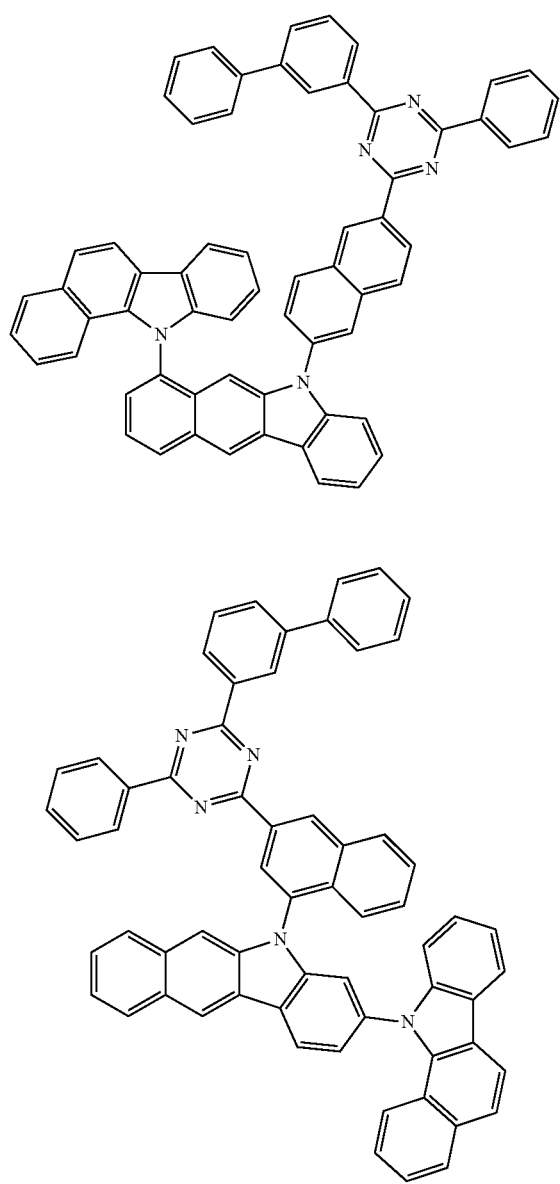
72
-continued
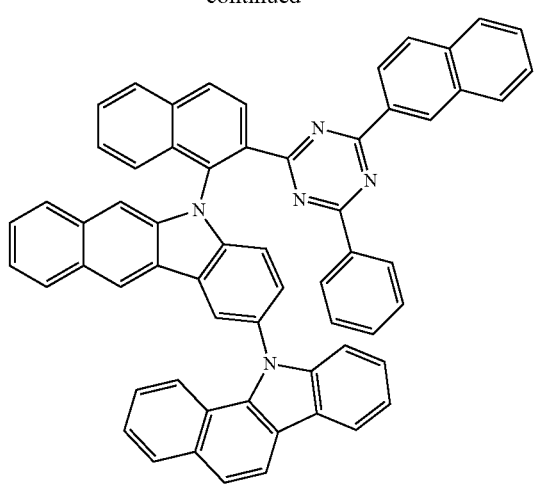
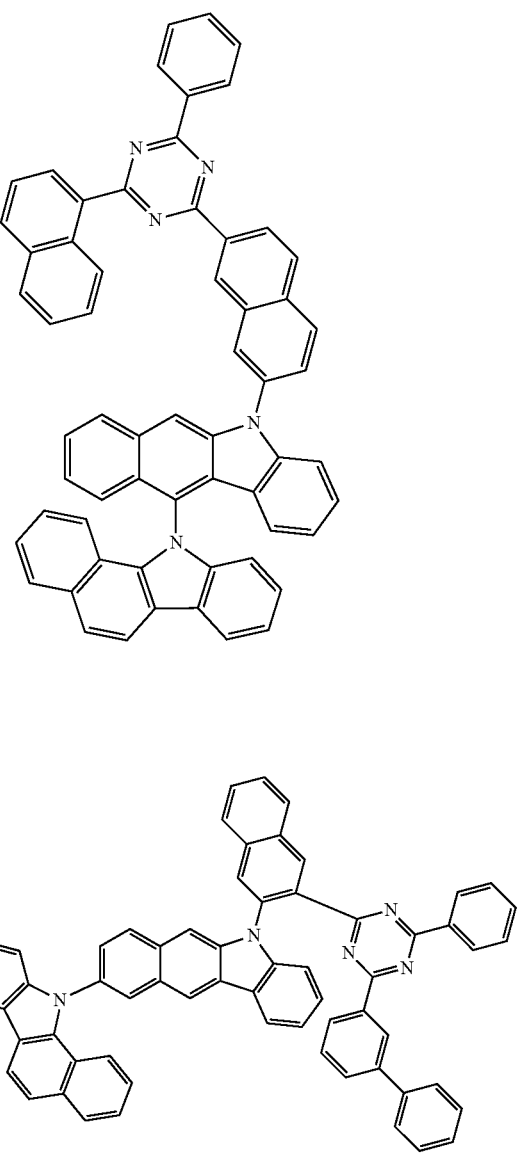

73
-continued
74
-continued
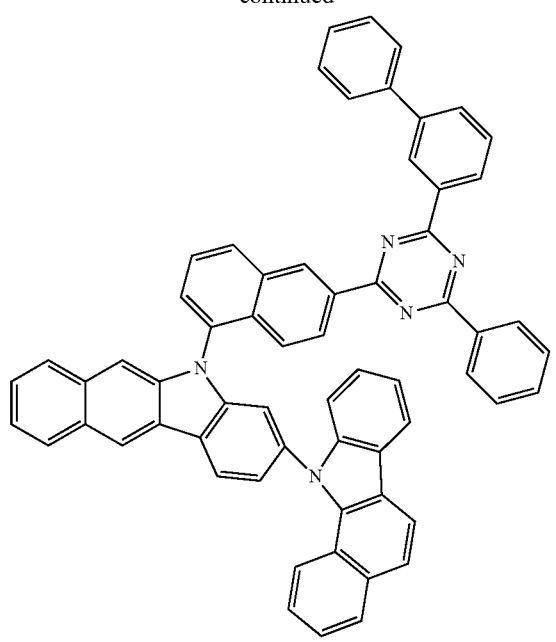
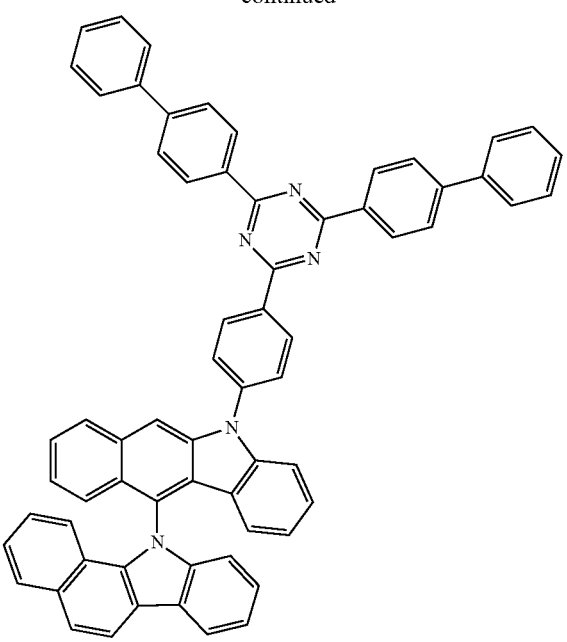
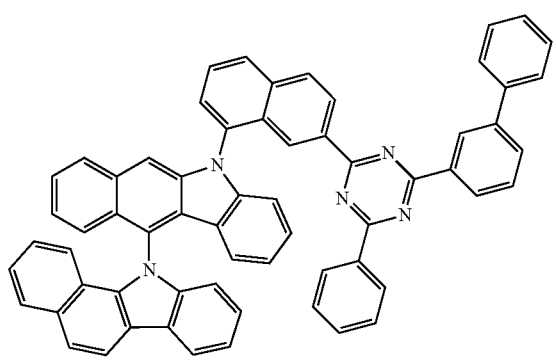
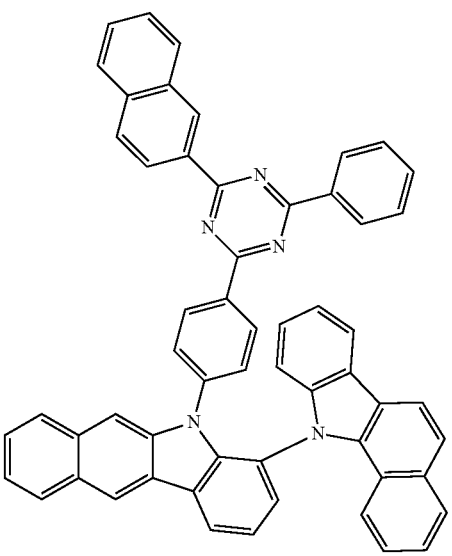

75
-continued
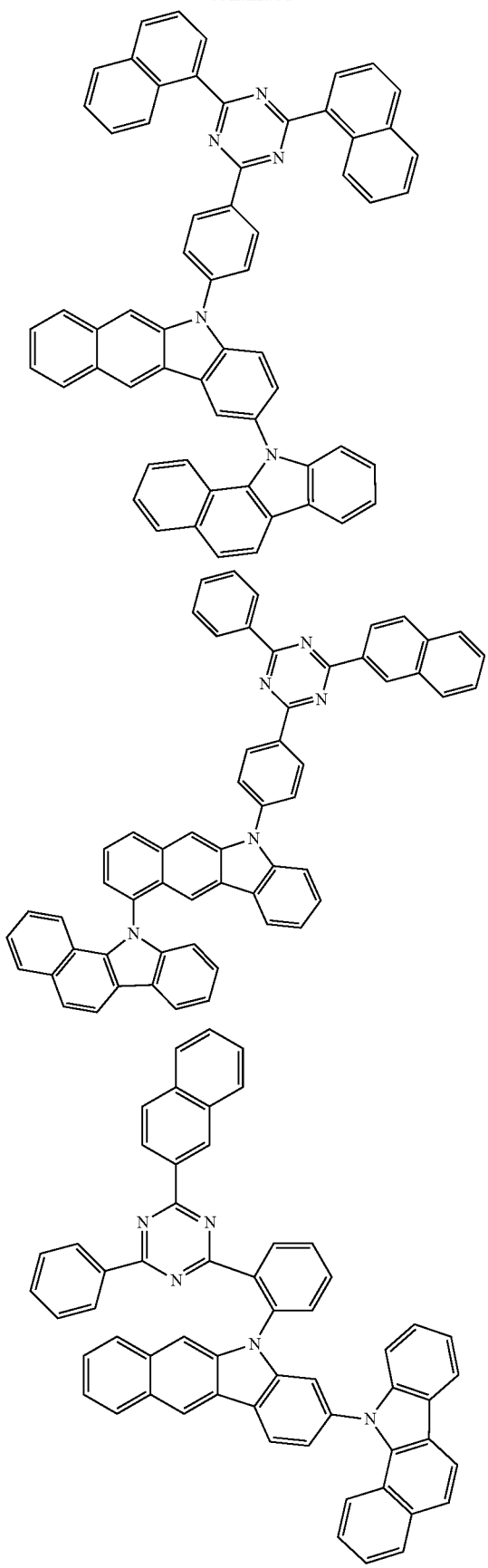
76
-continued
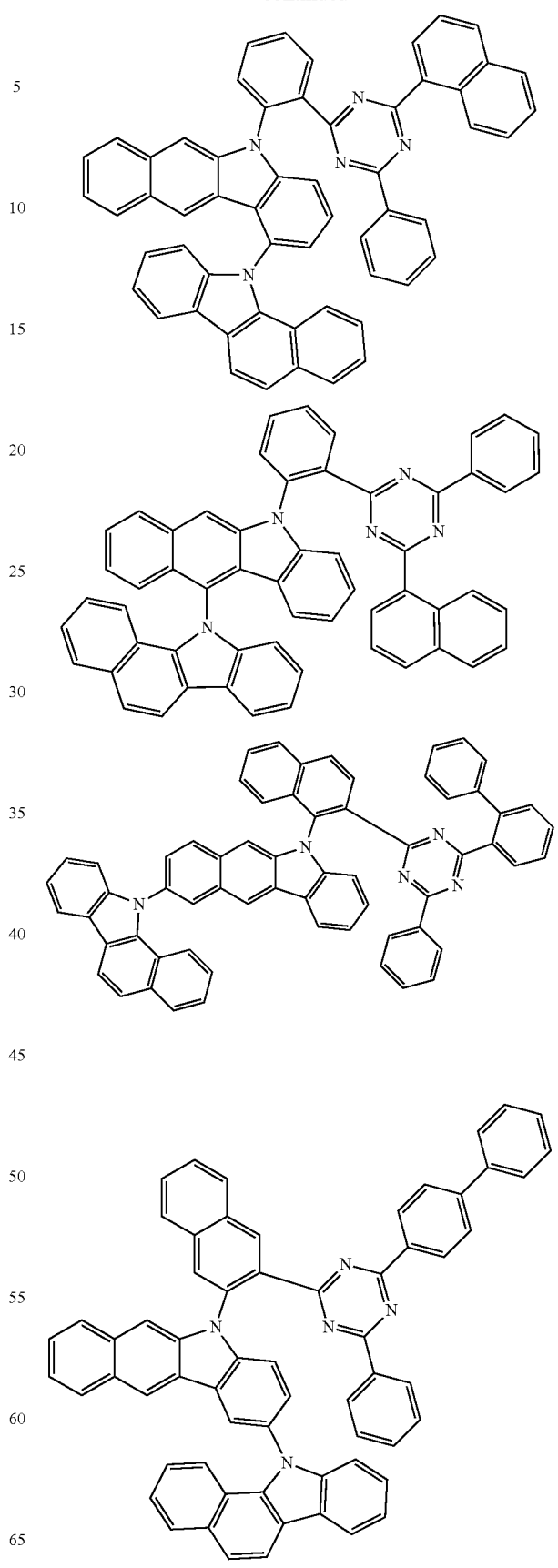

77
-continued
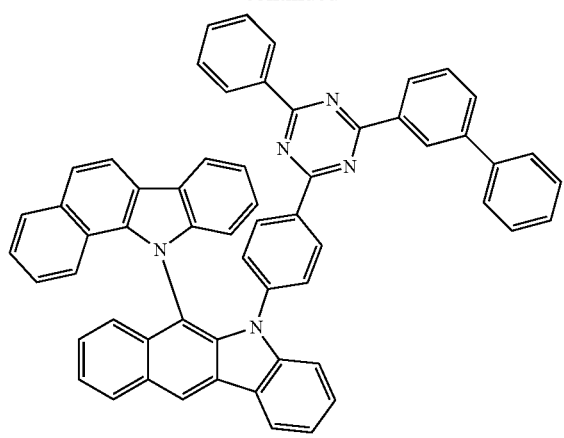
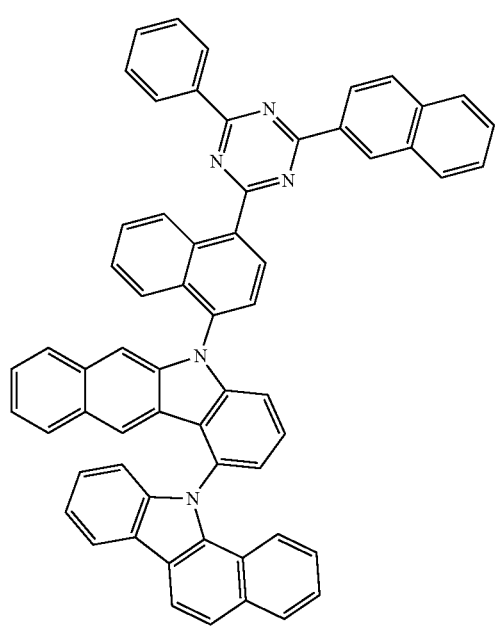
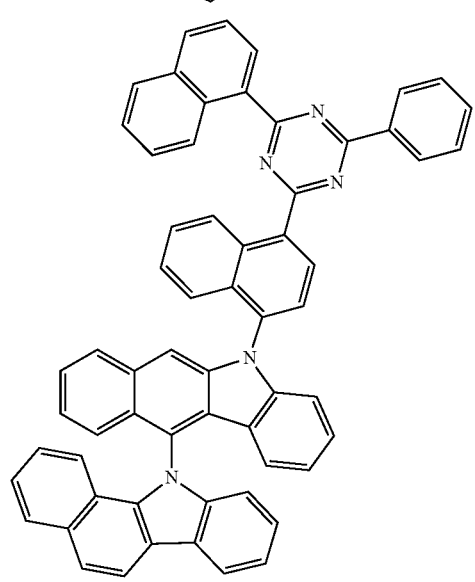
78
-continued
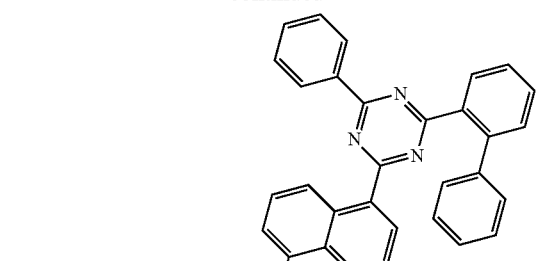
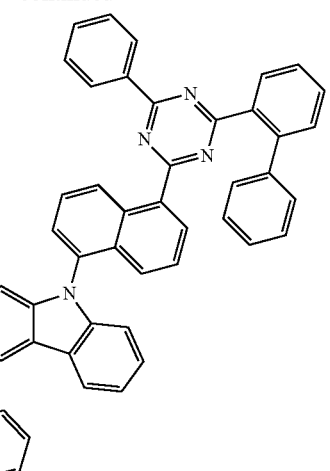
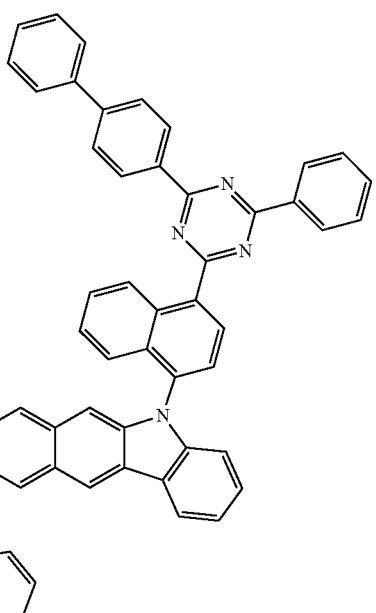
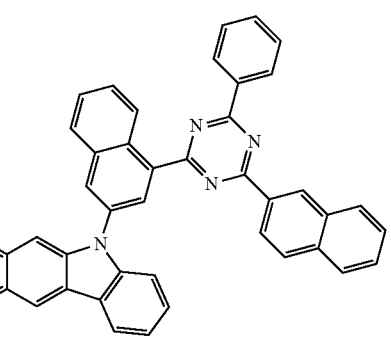

79
-continued
80
-continued
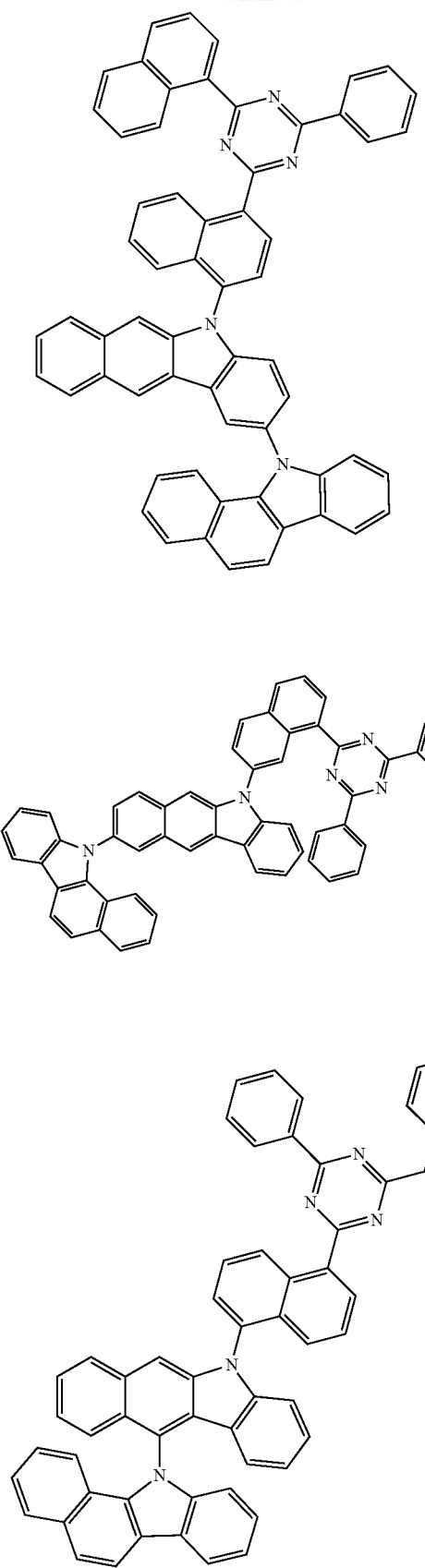
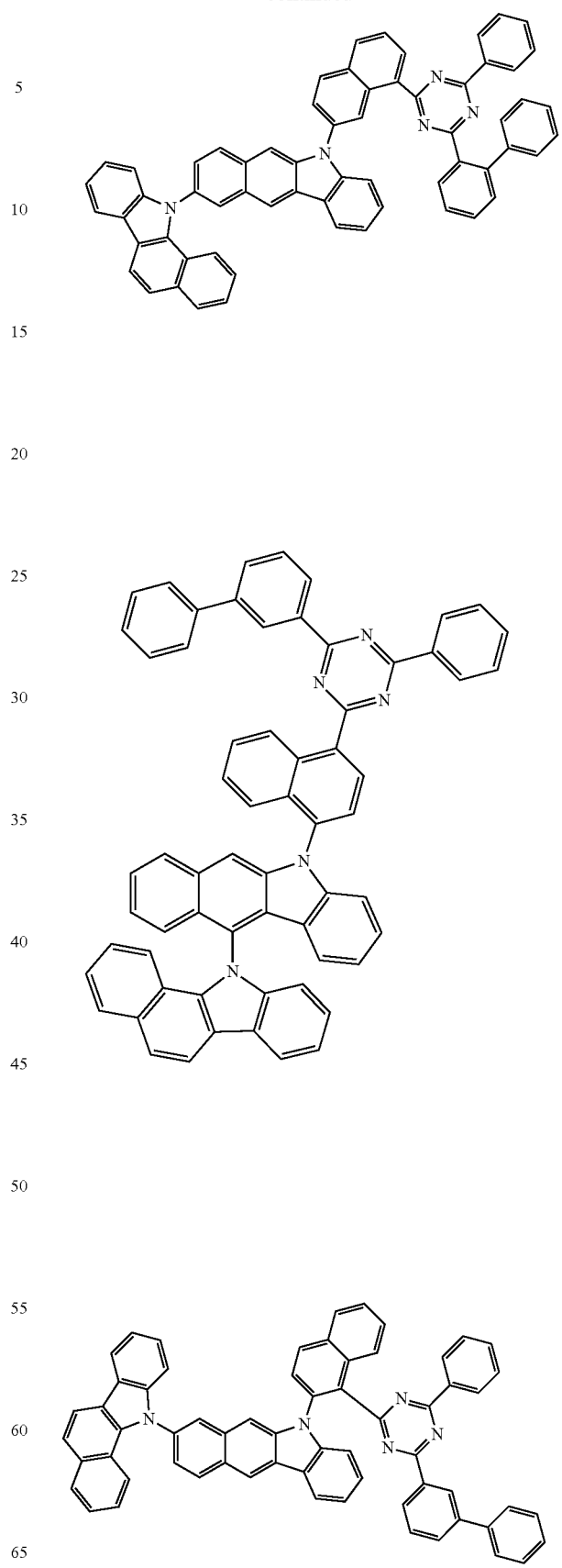

81
-continued
82
-continued
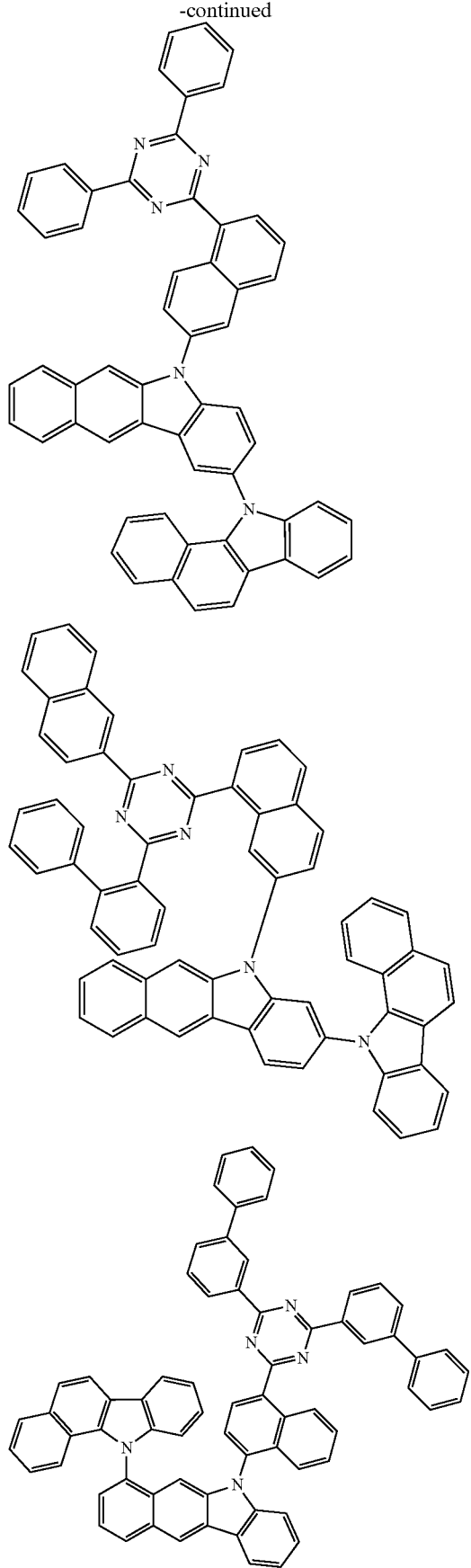
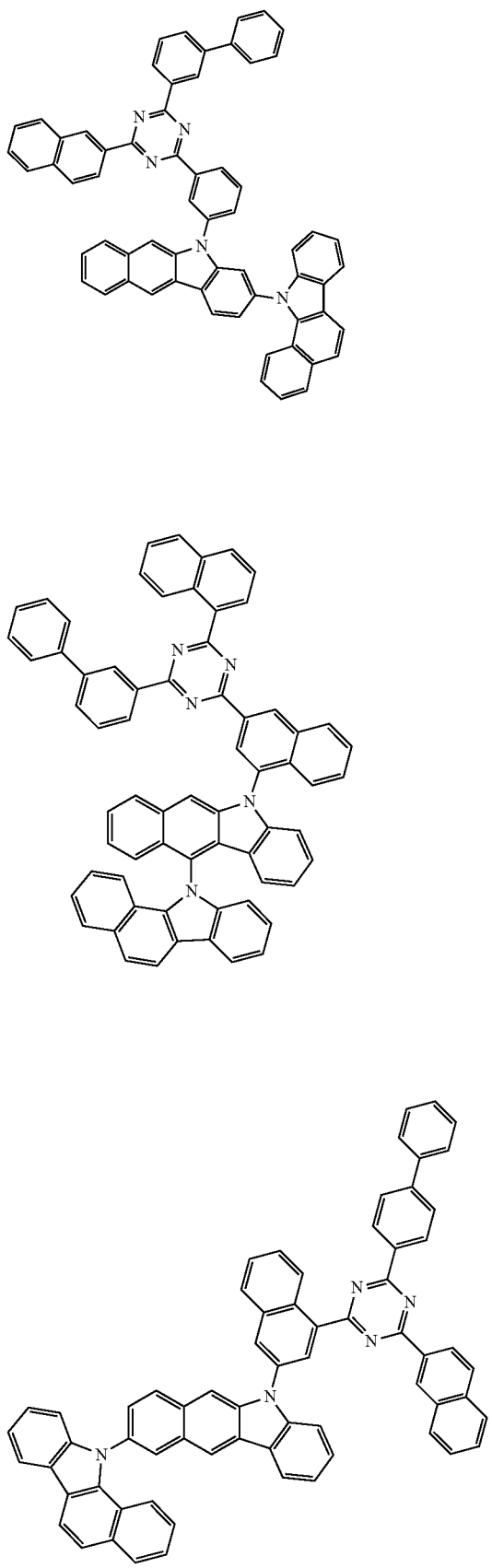

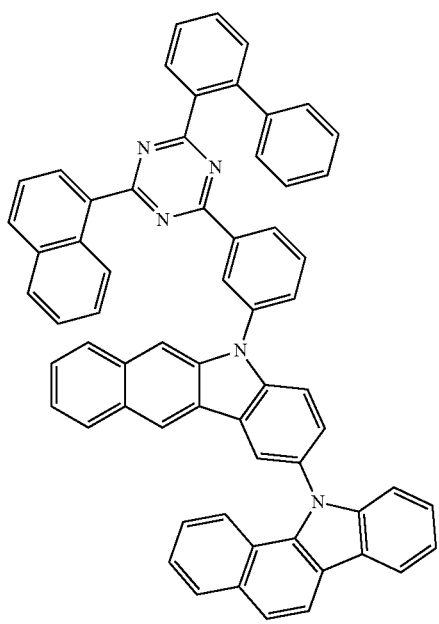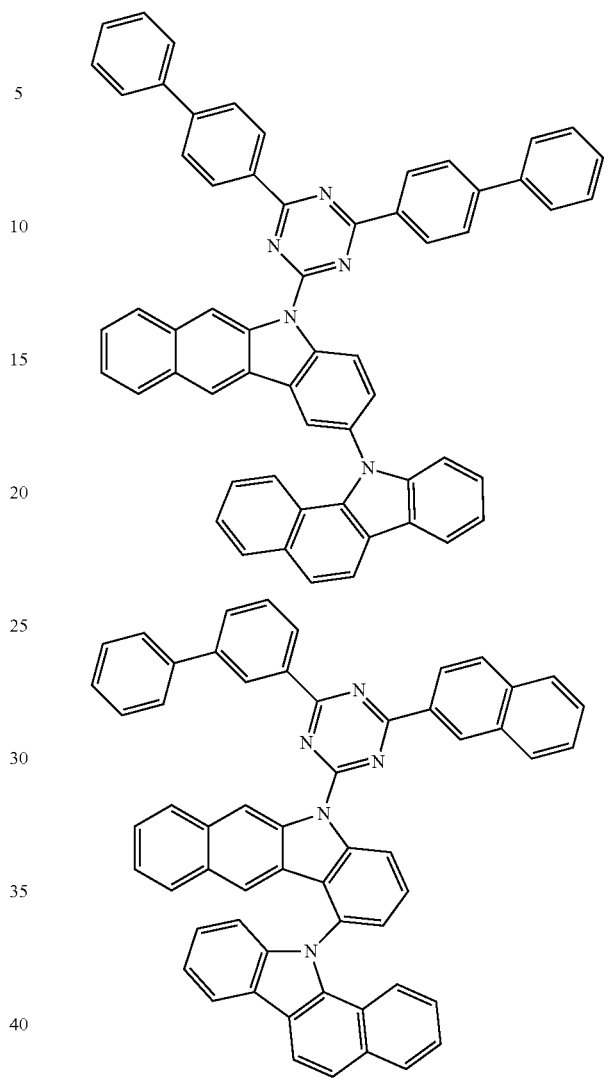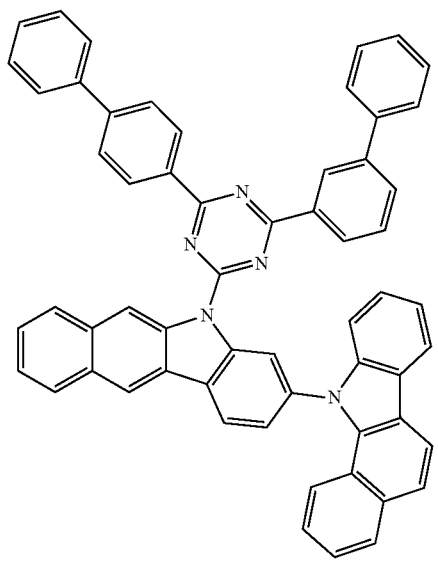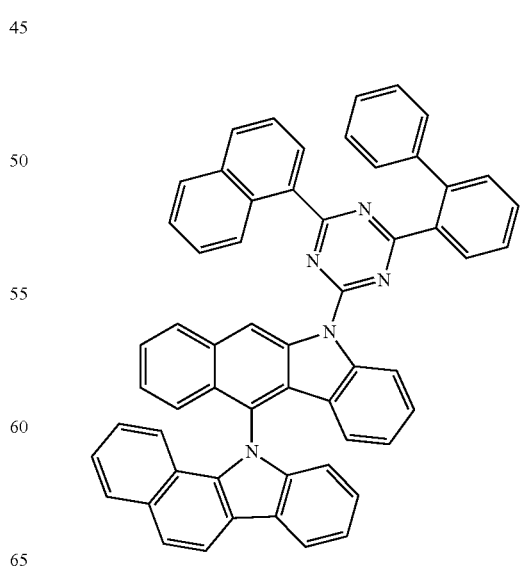

85
-continued
86
-continued
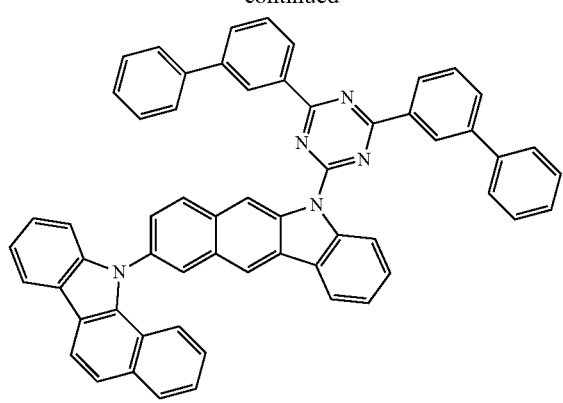
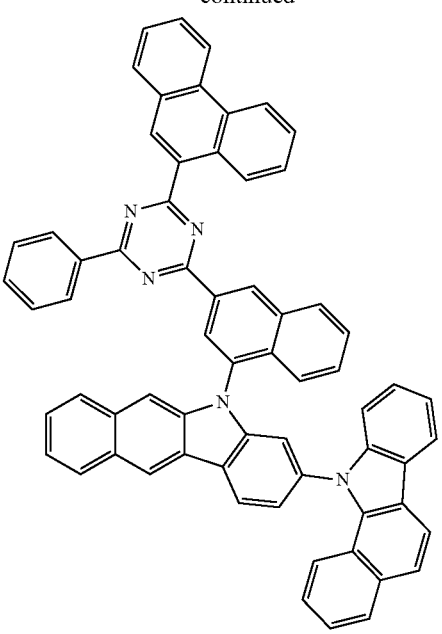
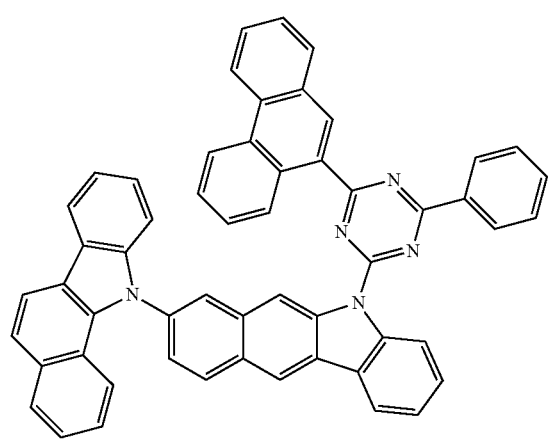
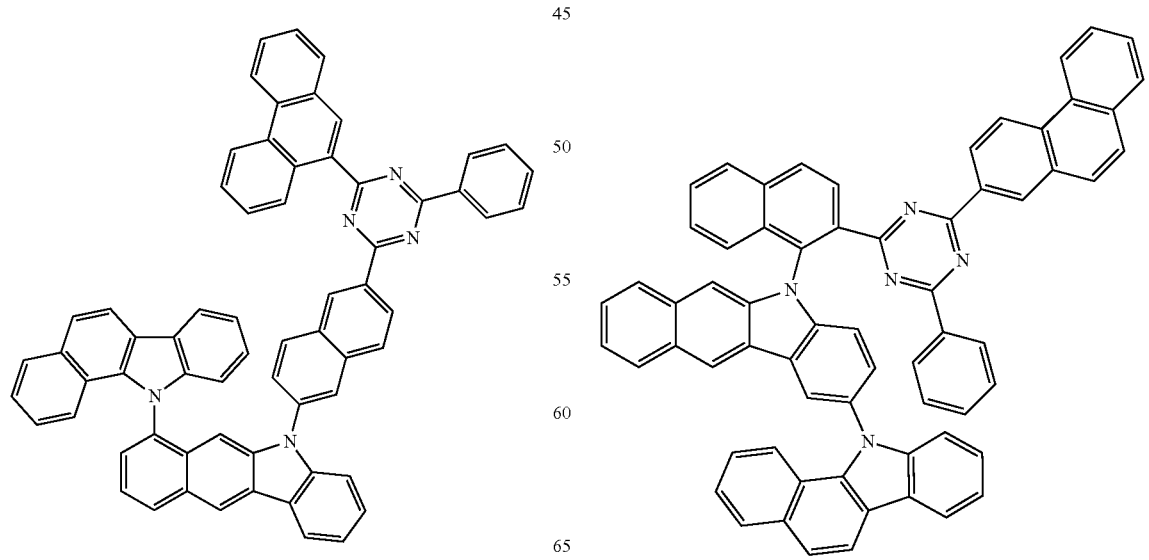

87
-continued
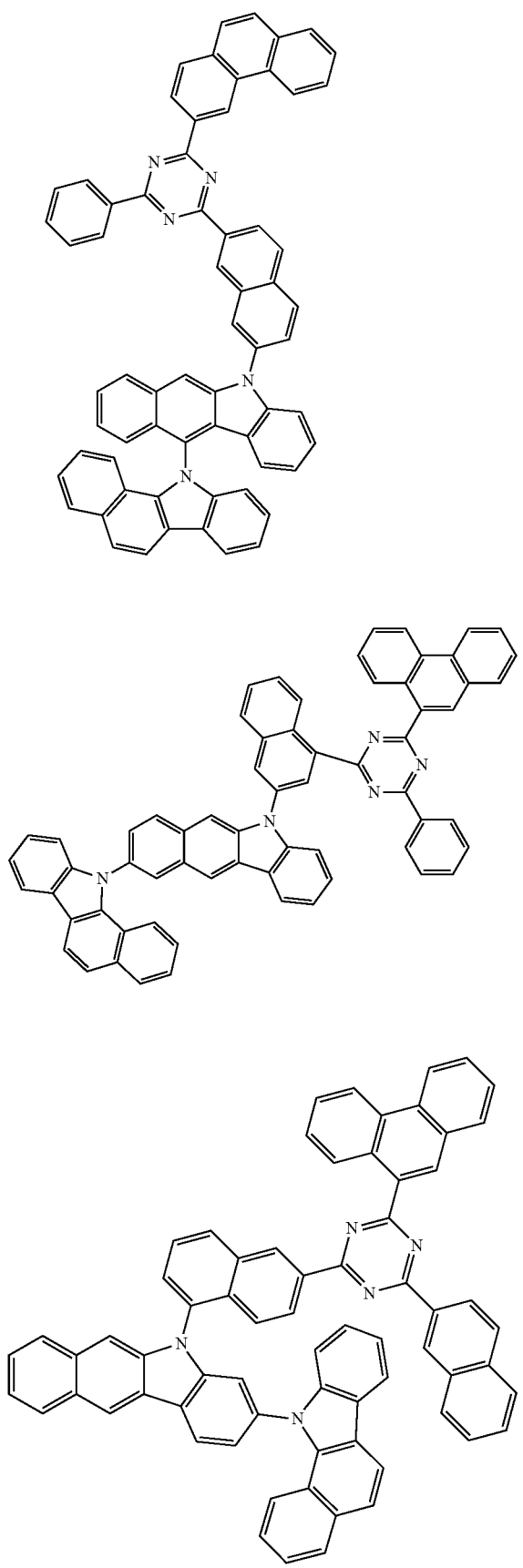 [SMILES: c1ccc(-c2nc(-c3ccc4ccc(-n5c6ccccc6c6c(-n7c8ccccc8c8ccc9ccccc9c87)c7ccccc7cc65)cc4c3)nc(-c3ccc4ccc5ccccc5c4c3)n2)cc1 ; c1ccc(-c2nc(-c3cc(-n4c5ccccc5c5cc6cc(-n7c8ccccc8c8ccc9ccccc9c87)ccc6cc54)cc4ccccc34)nc(-c3cc4ccccc4c4ccccc34)n2)cc1 ; c1ccc2cc(-c3nc(-c4ccc5c(-n6c7cc(-n8c9ccccc9c9ccc%10ccccc%10c98)ccc7c7cc8ccccc8cc76)cccc5c4)nc(-c4cc5ccccc5c5ccccc45)n3)ccc2c1]
88
-continued
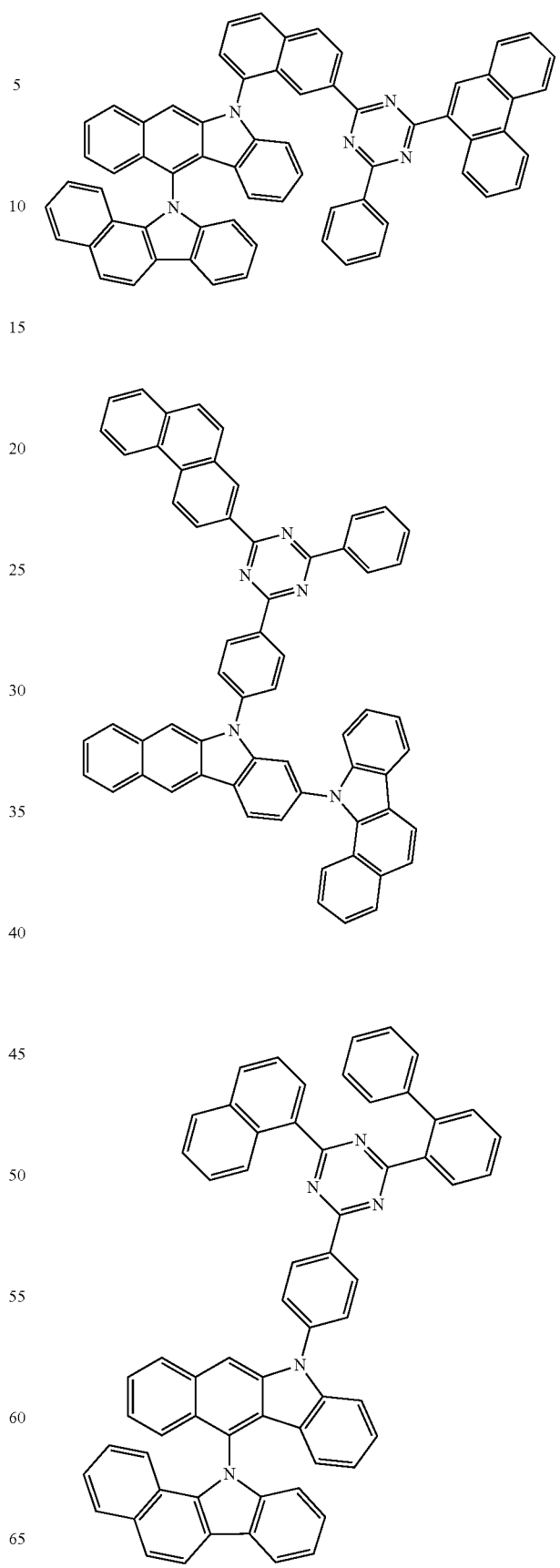

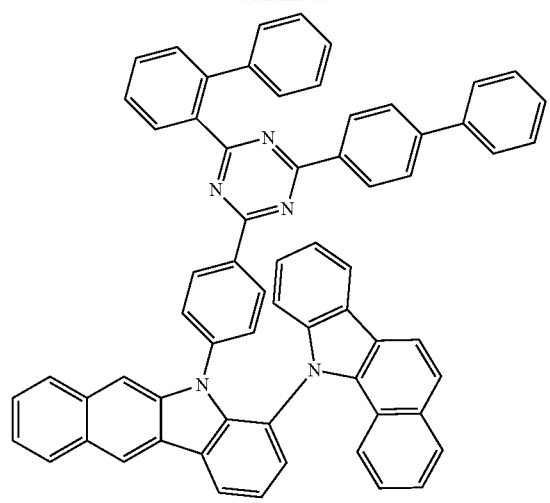
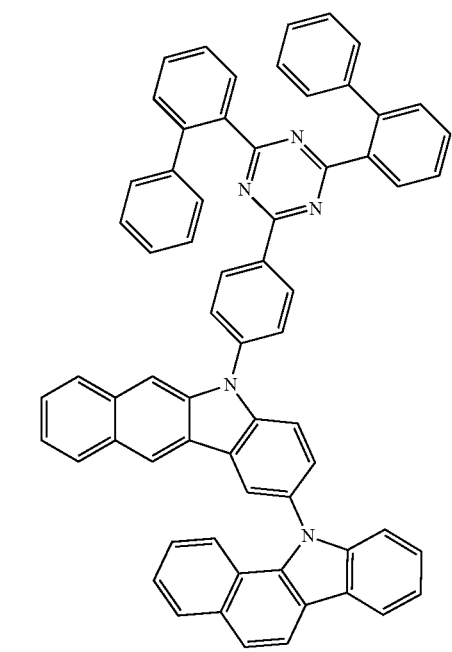
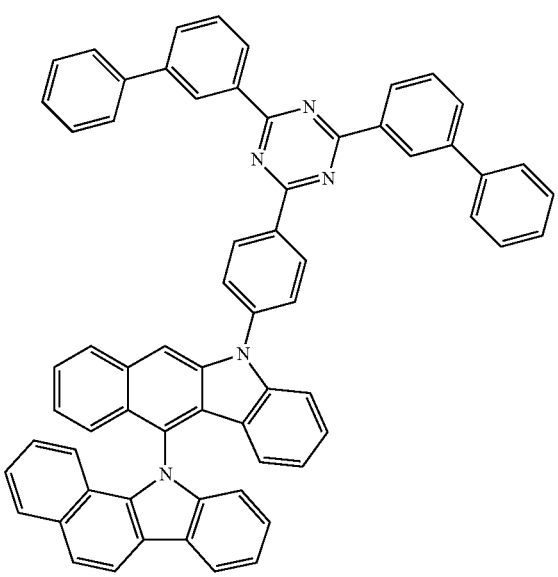
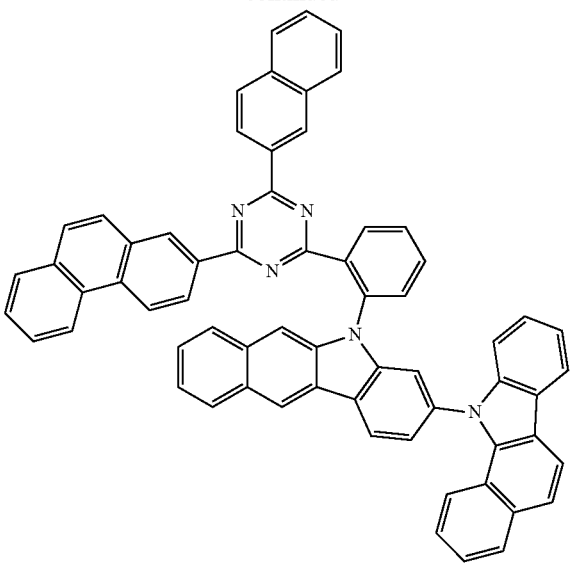
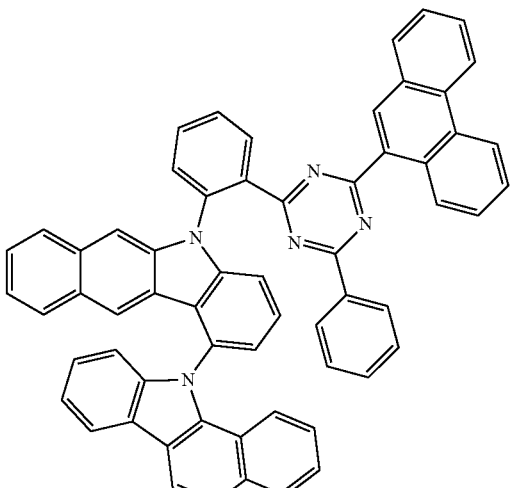
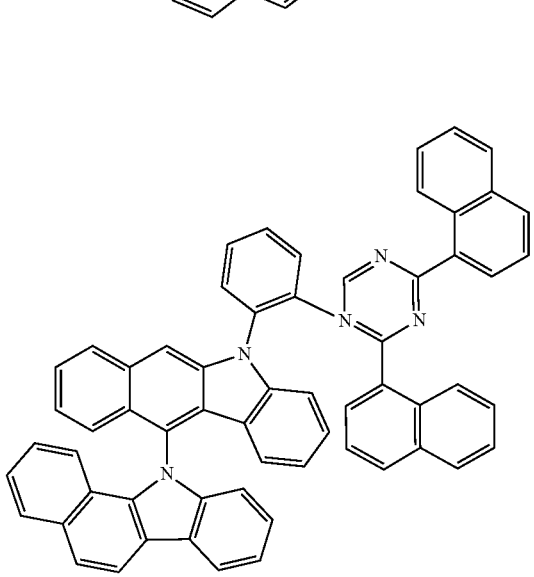

91
-continued
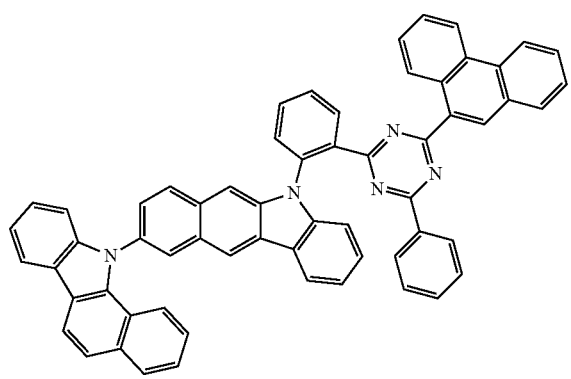
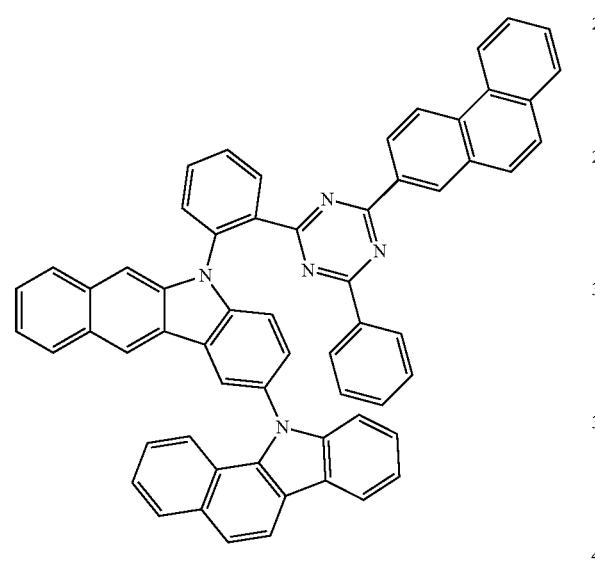
92
-continued
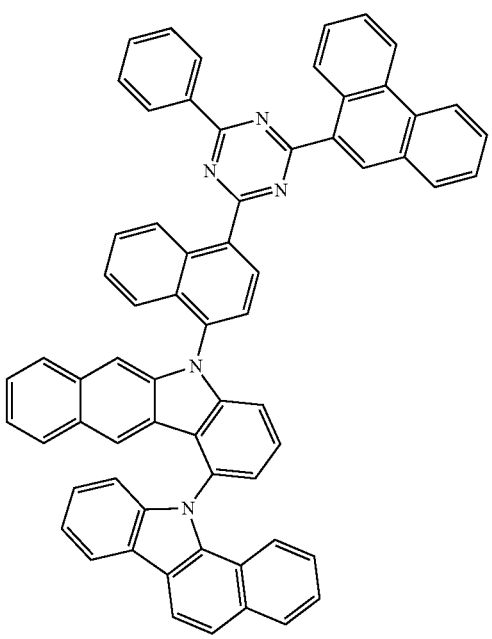
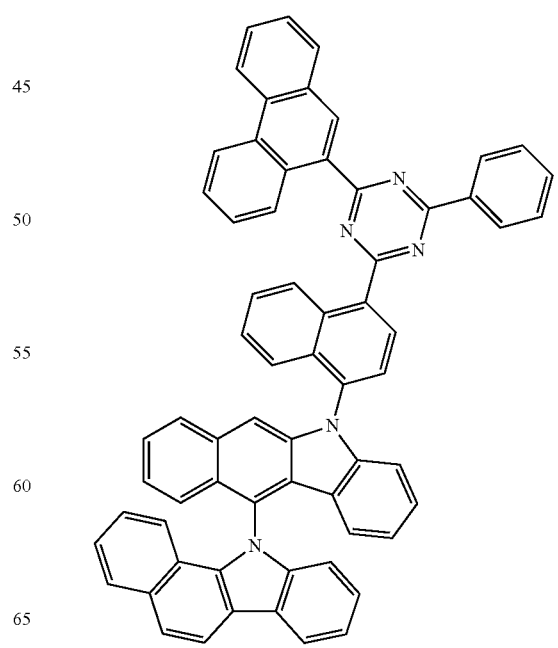

-continued
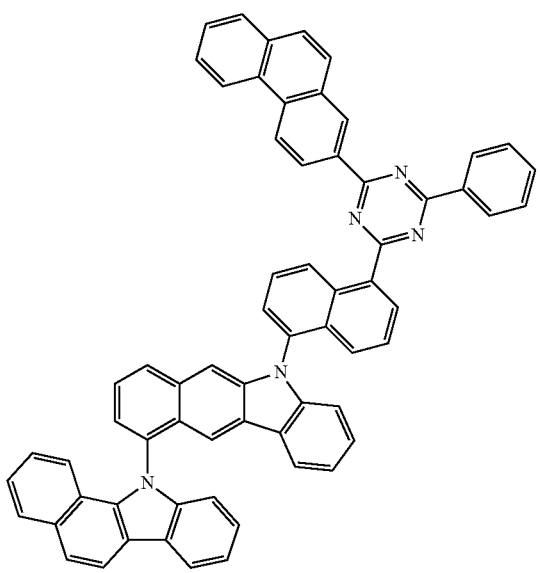
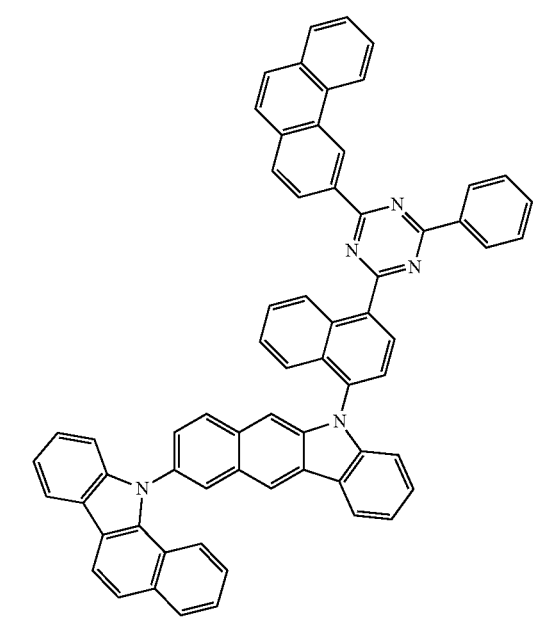
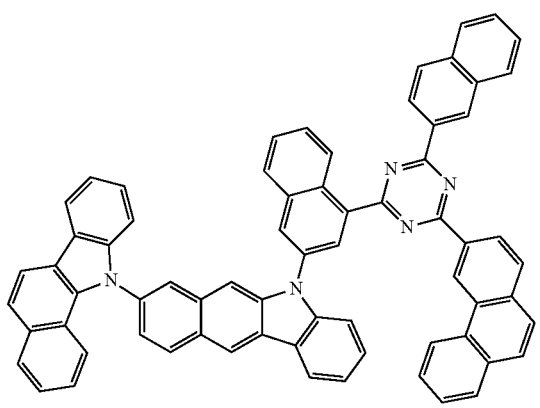
-continued
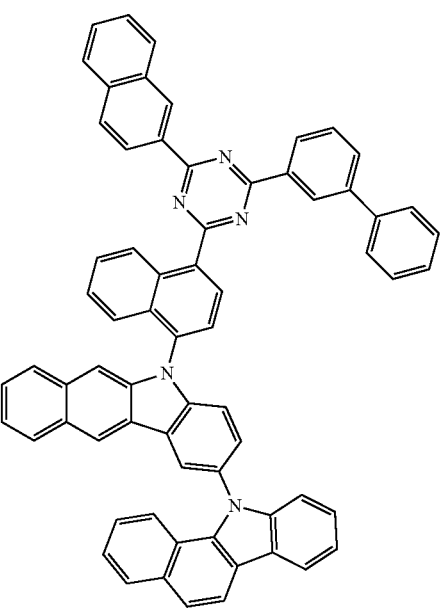
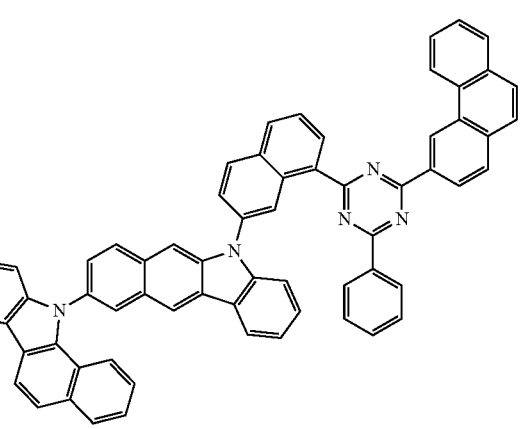
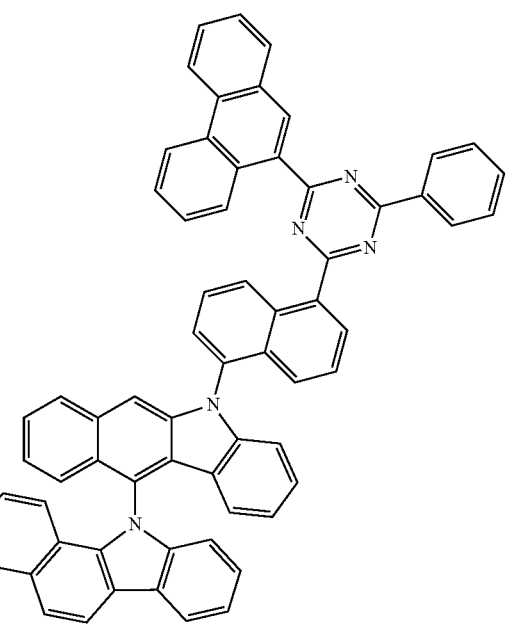

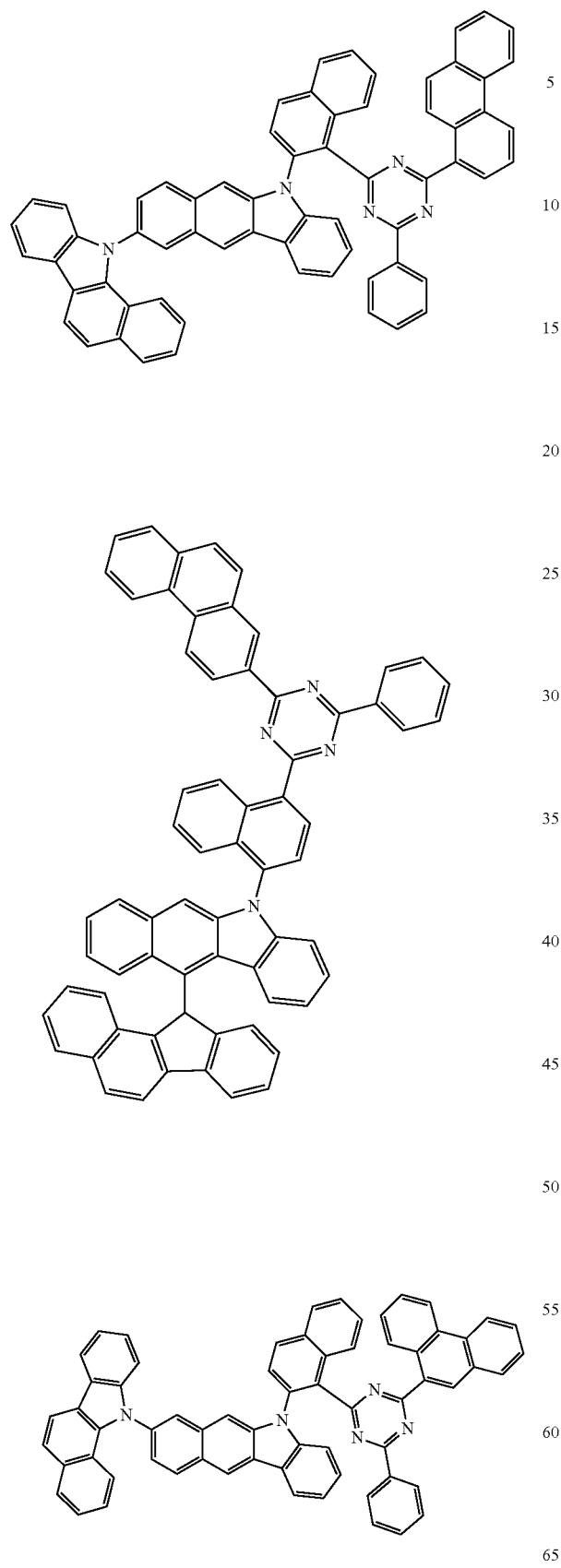
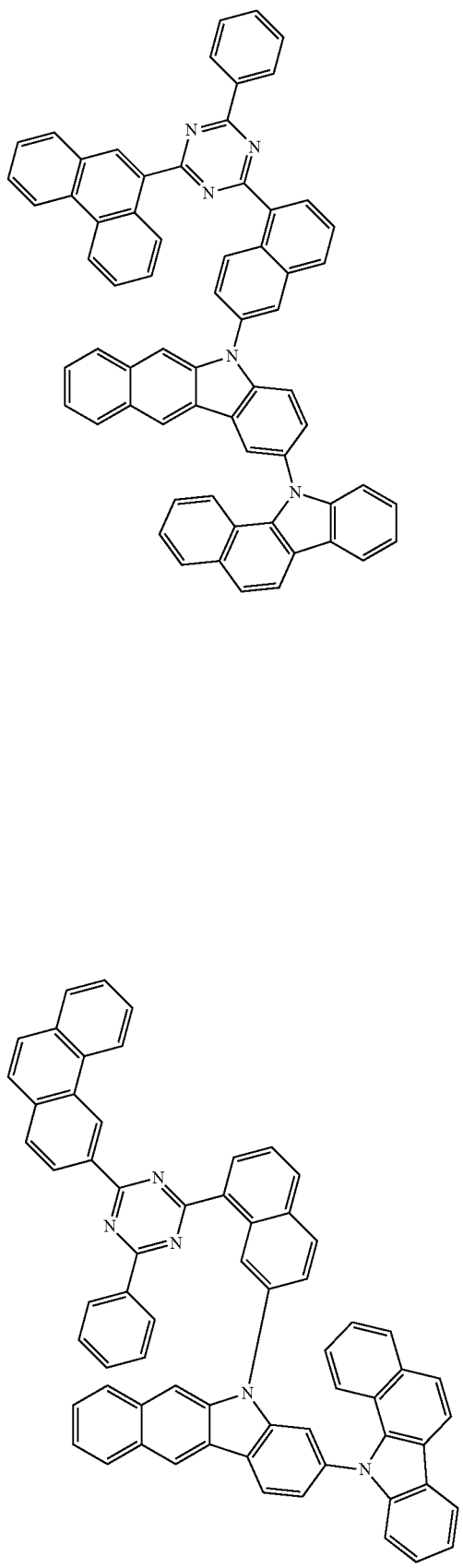

97
-continued
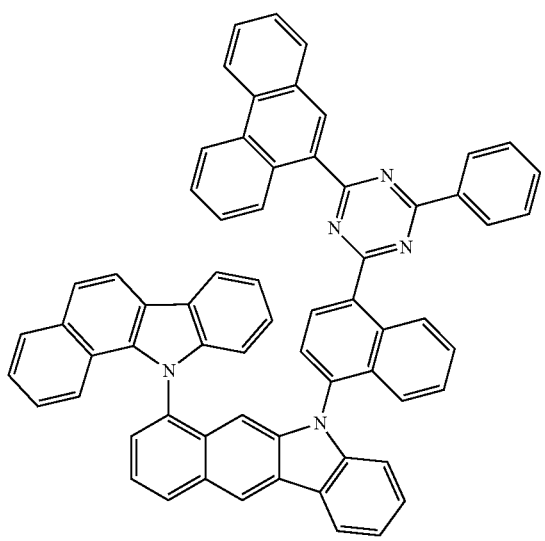
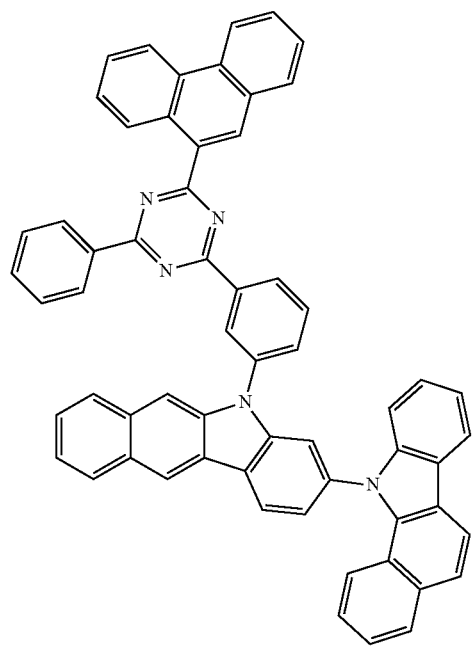
98
-continued
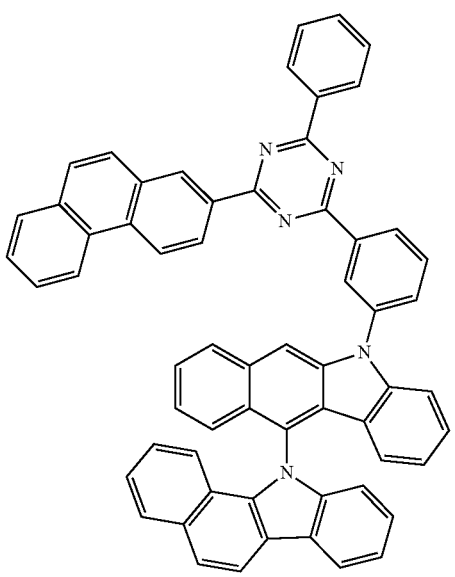
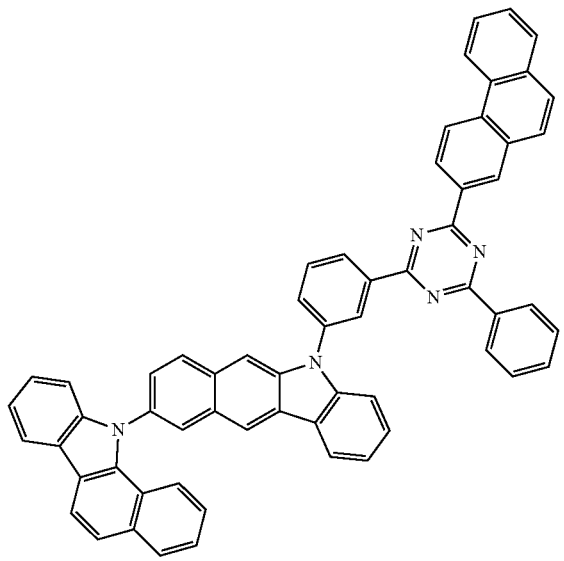

99
-continued
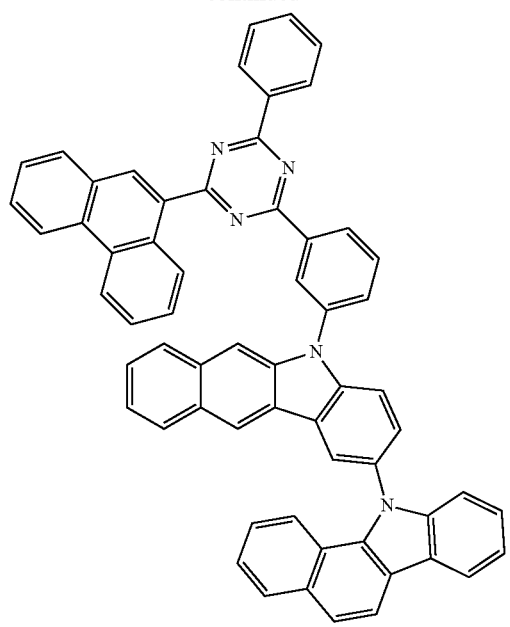
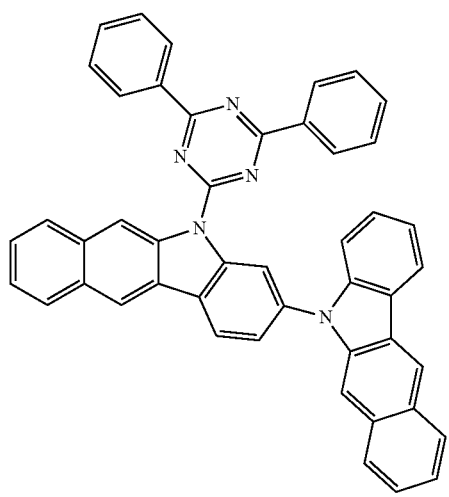
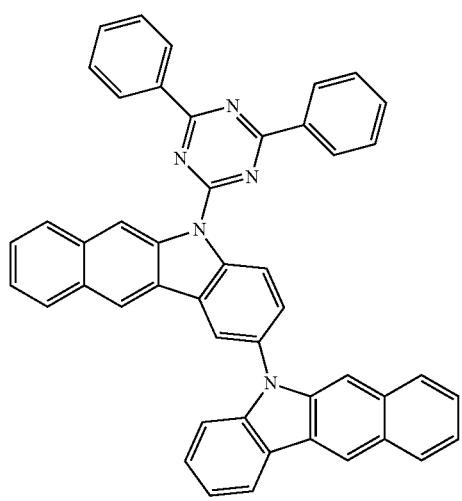
100
-continued
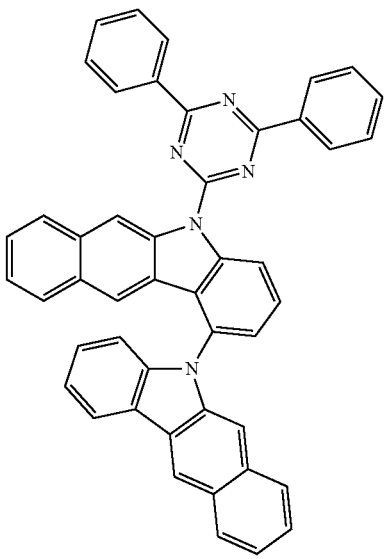
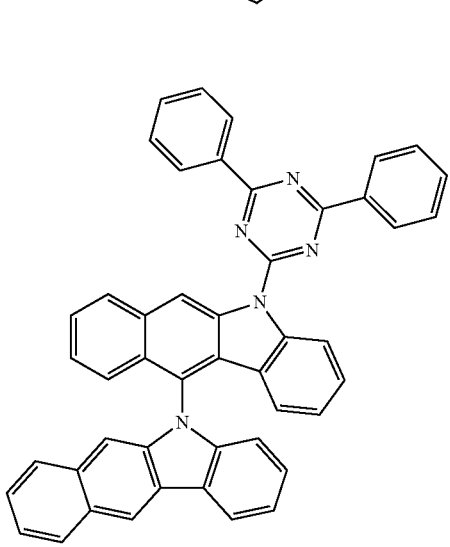
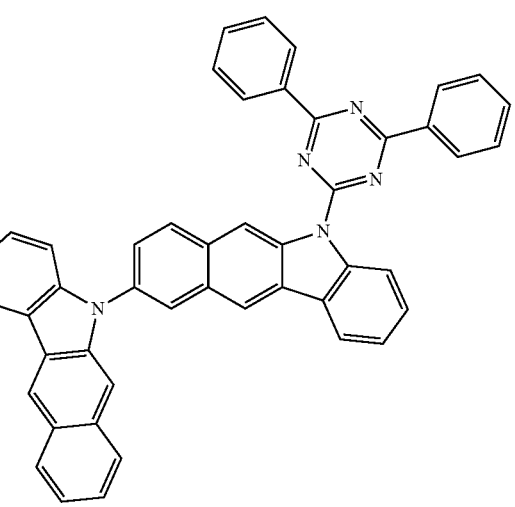

101
-continued
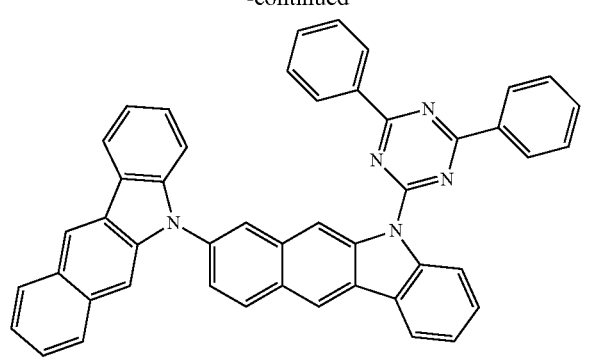
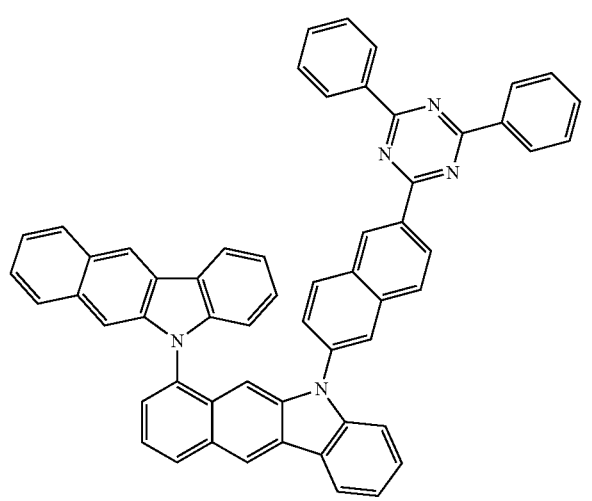
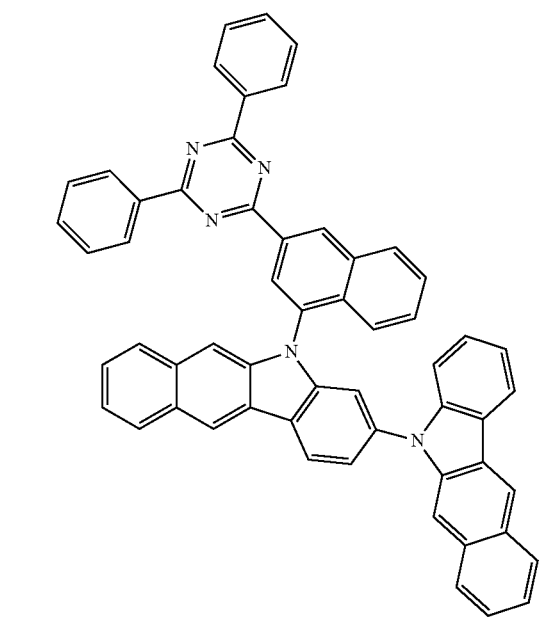
102
-continued
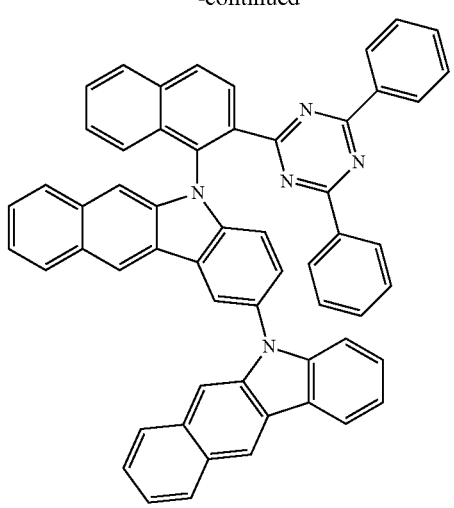
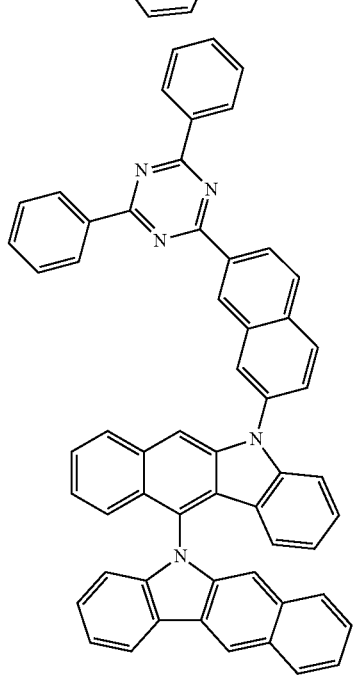
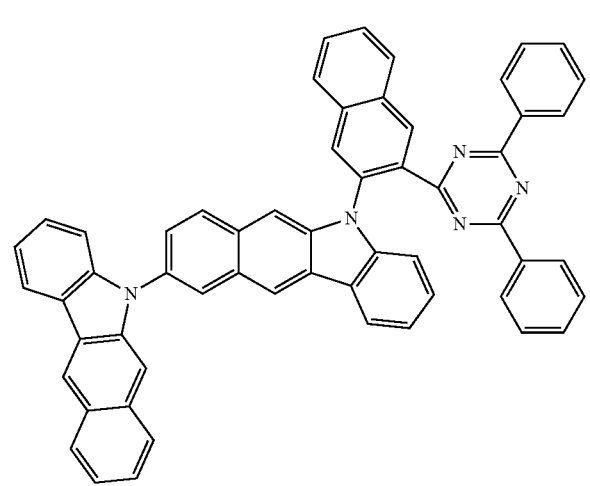

103
-continued
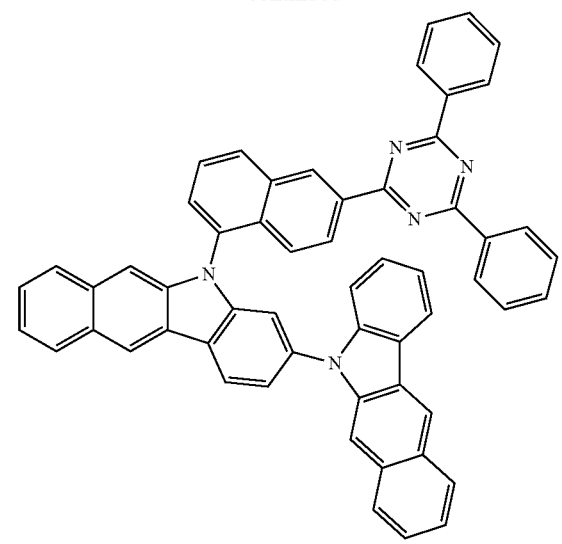
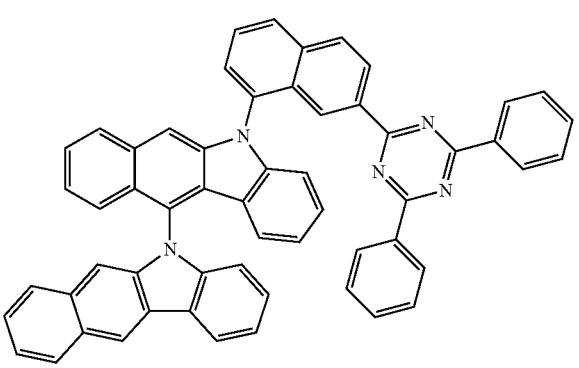
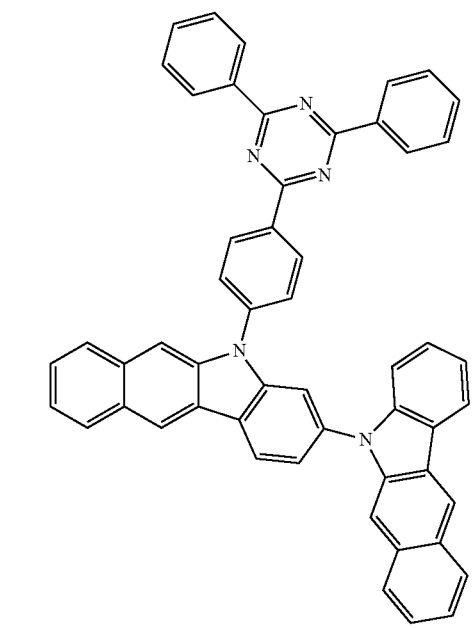
104
-continued
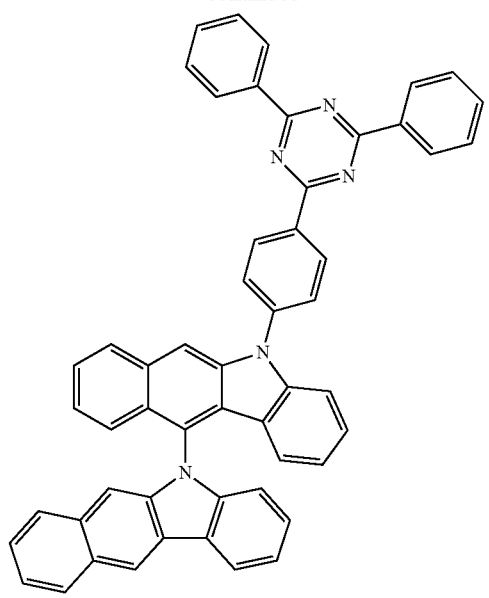
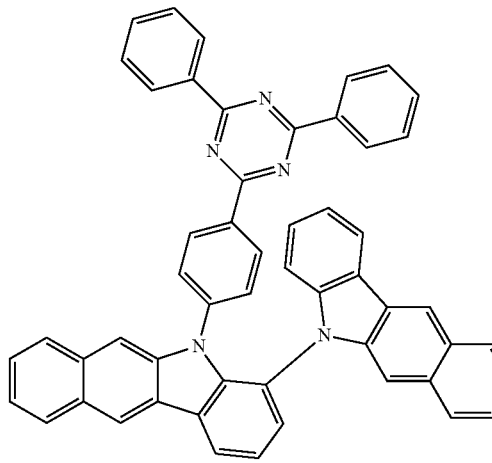
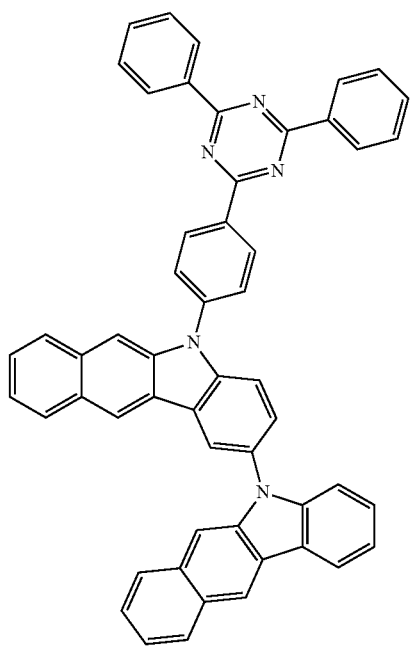

105
-continued
106
-continued
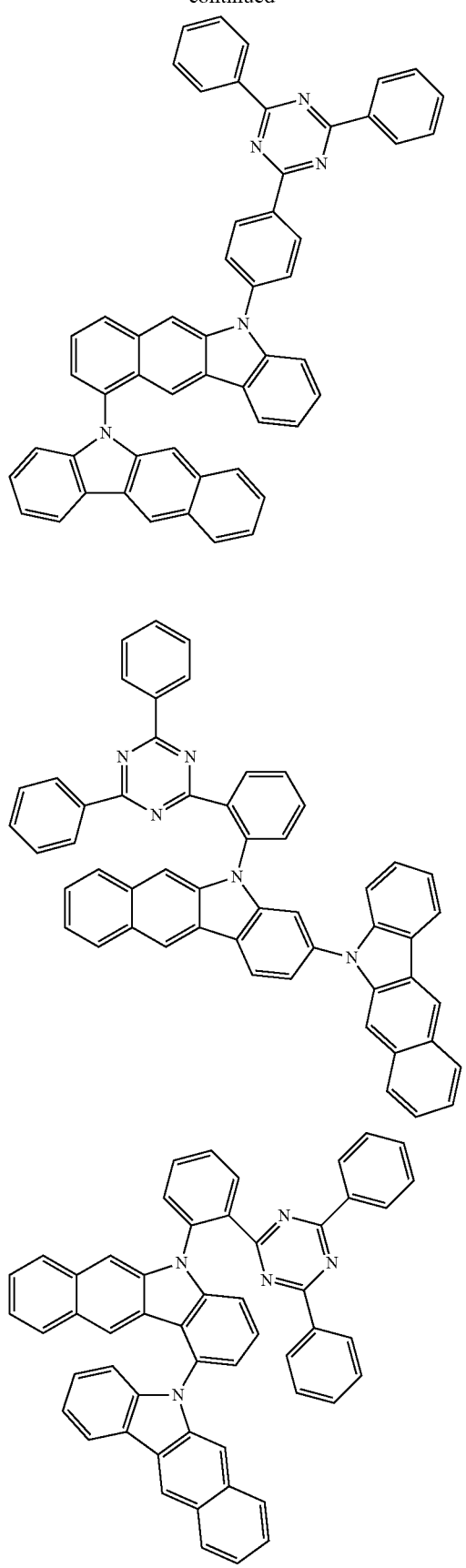
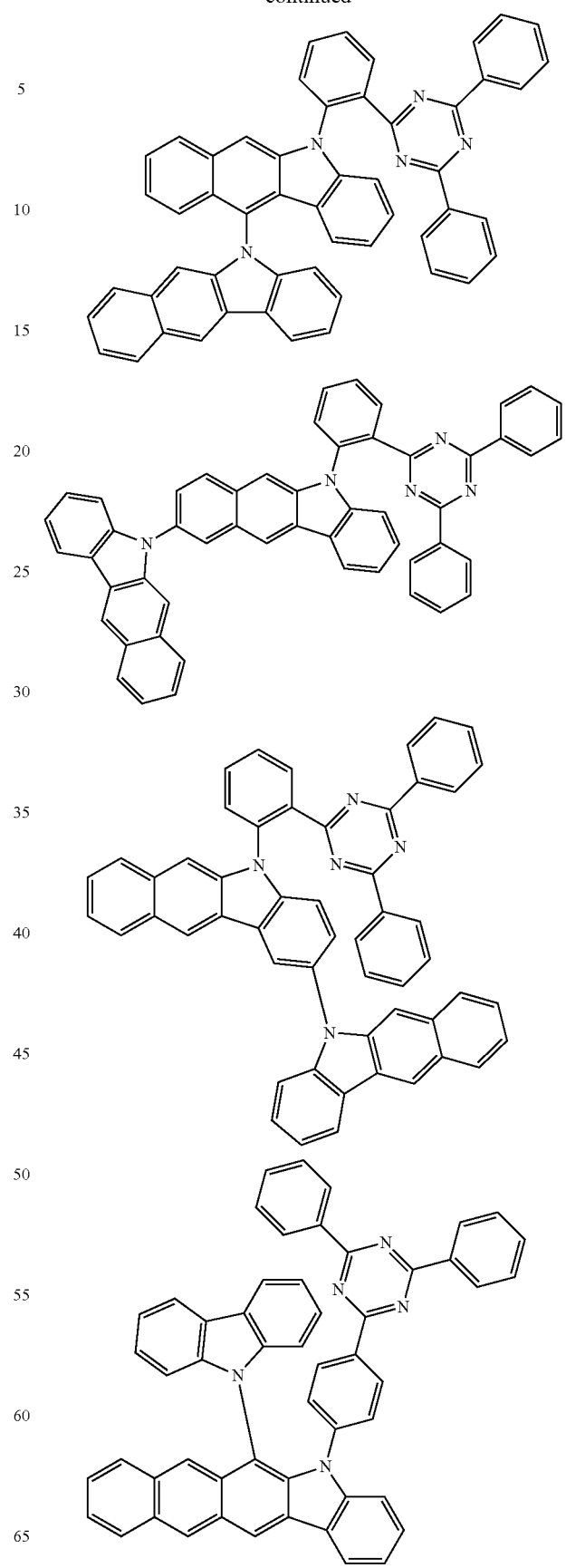

107
-continued
108
-continued
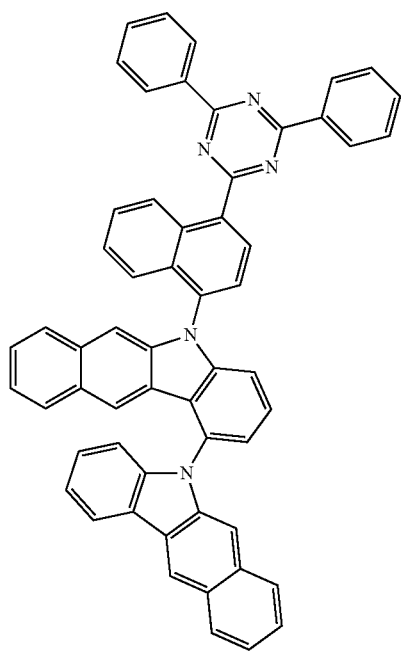
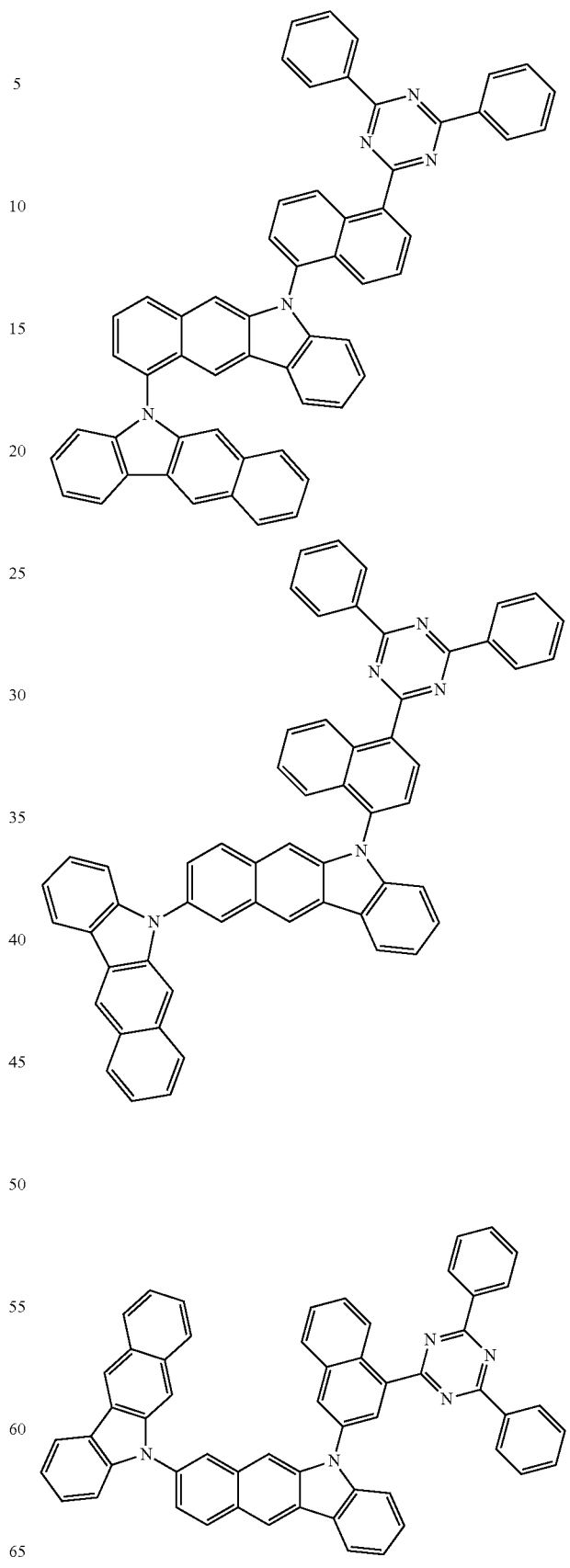

109
-continued
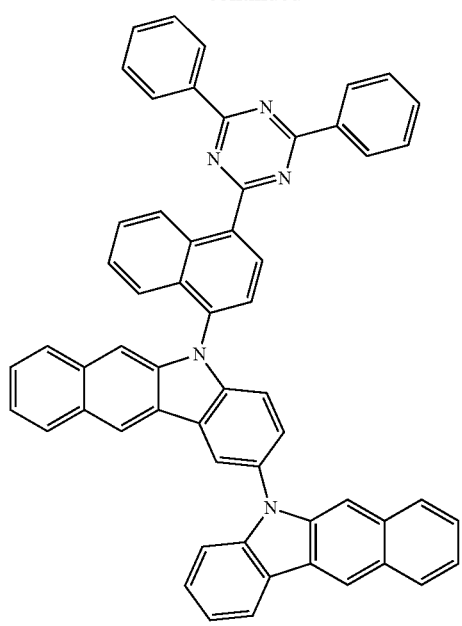
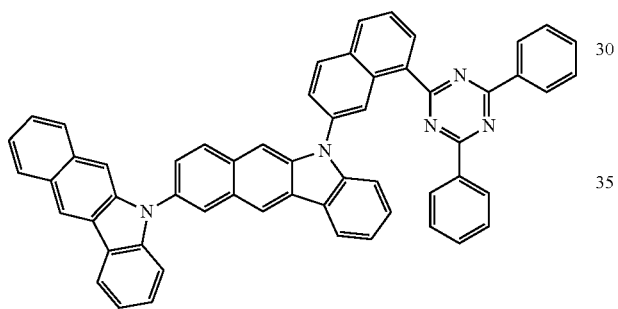
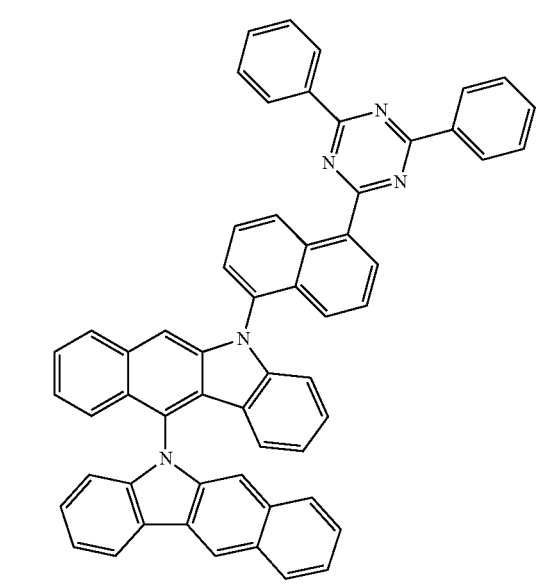
110
-continued
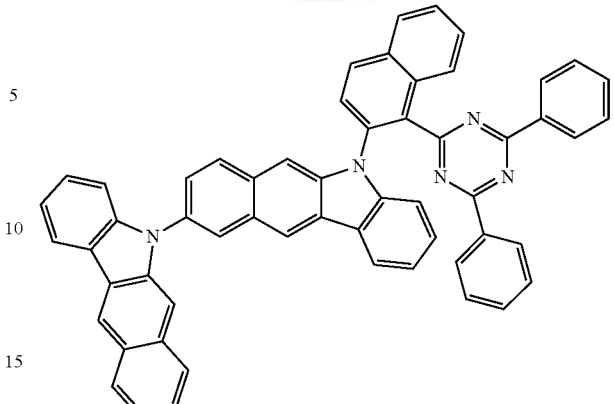
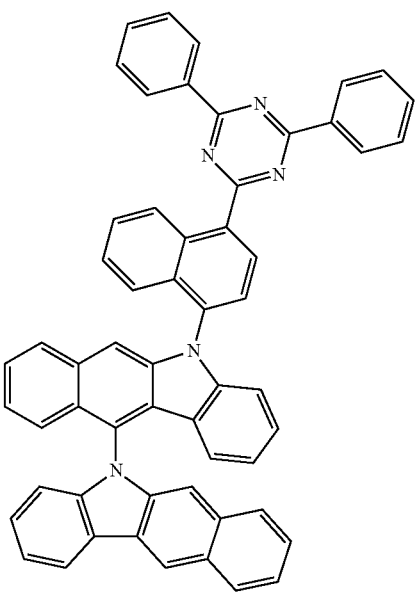
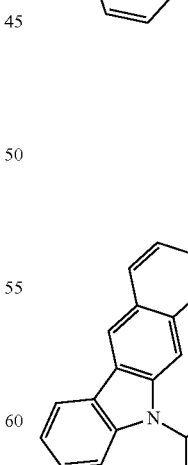
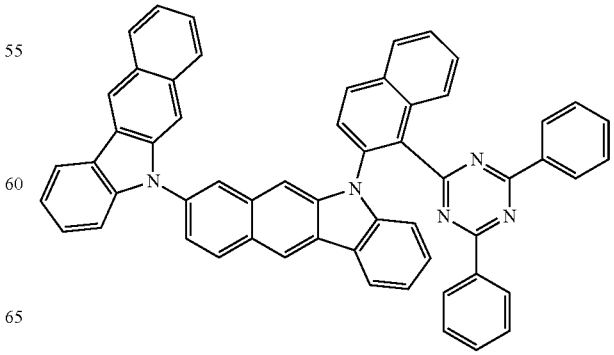

111
-continued
112
-continued
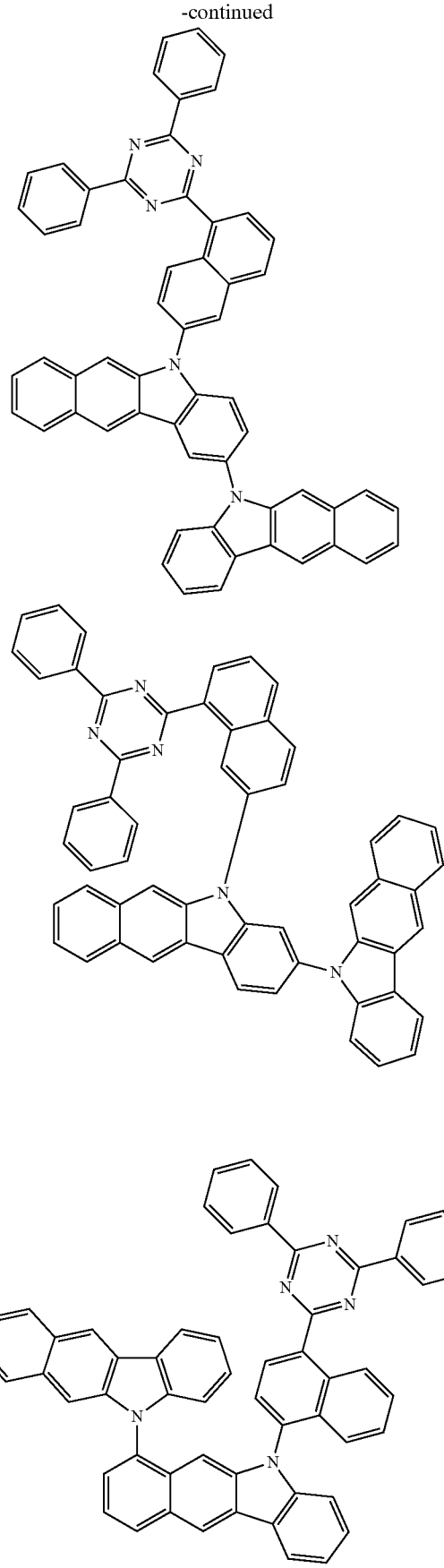
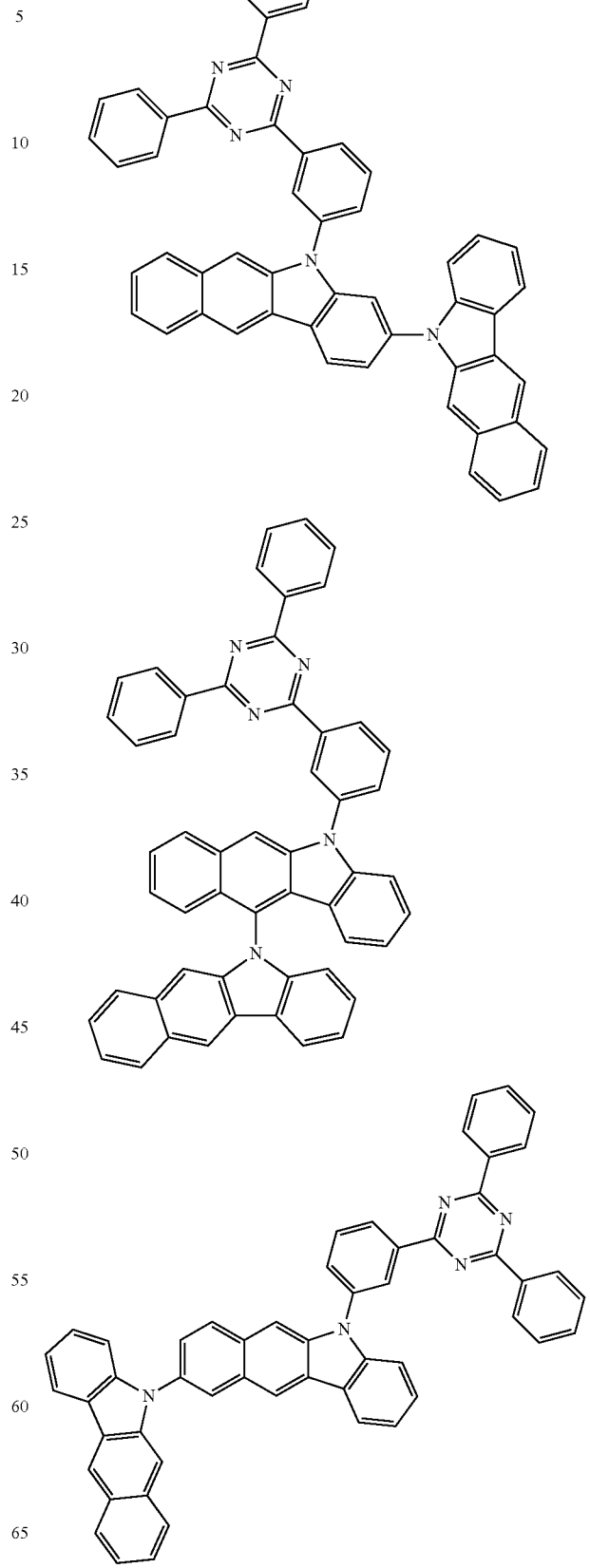

113
-continued
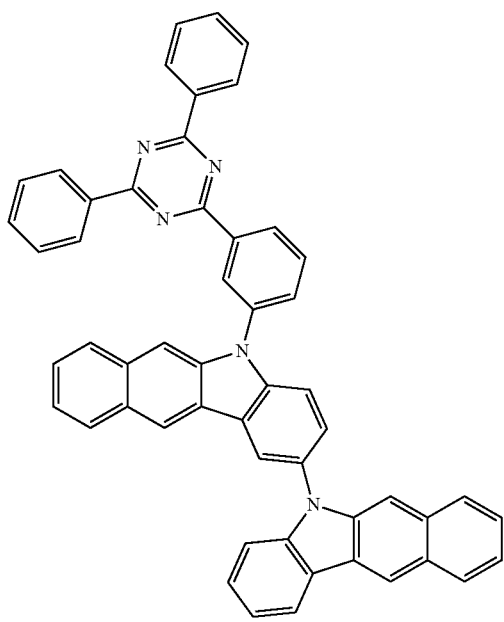
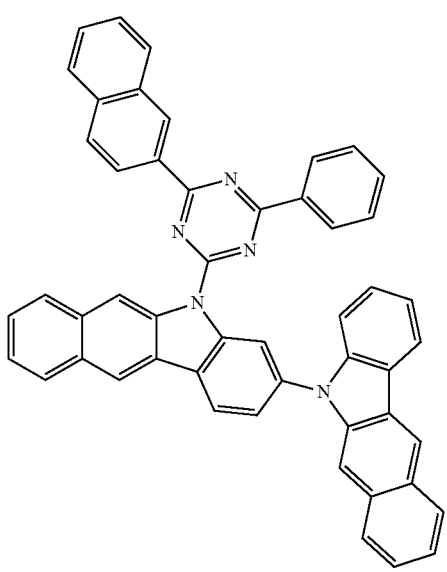
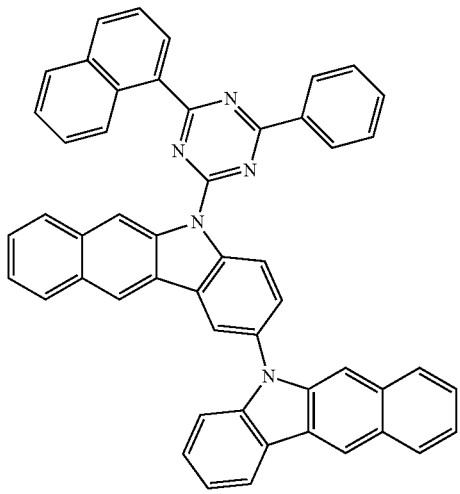
114
-continued
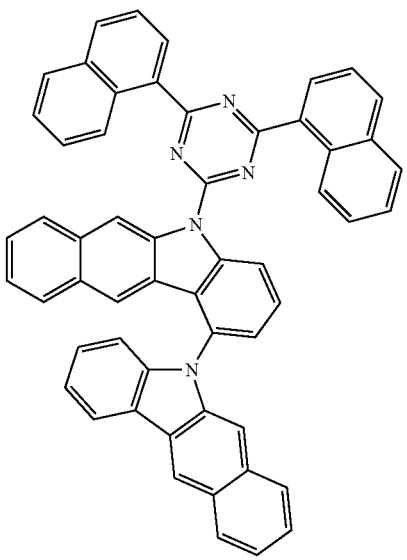
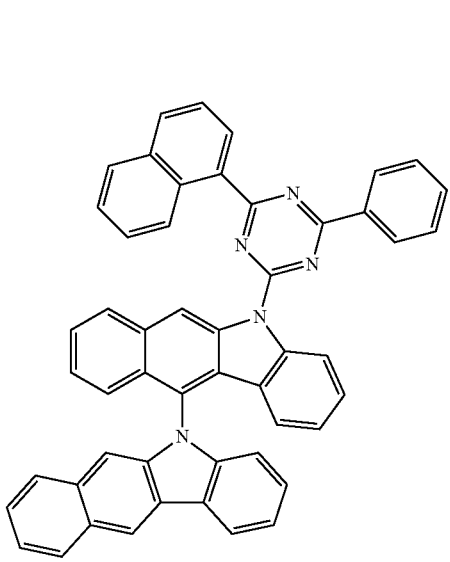
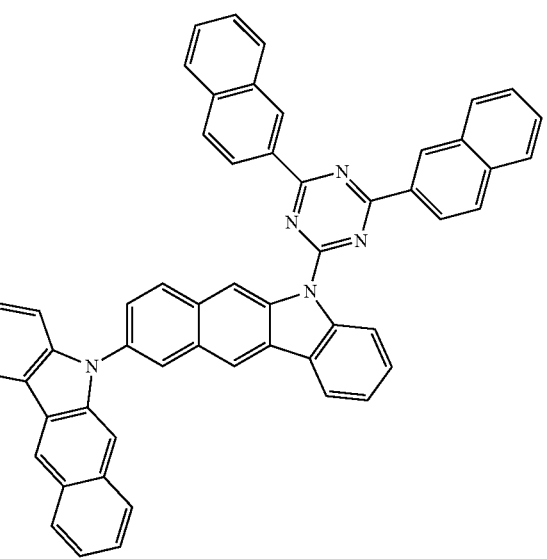

115
-continued
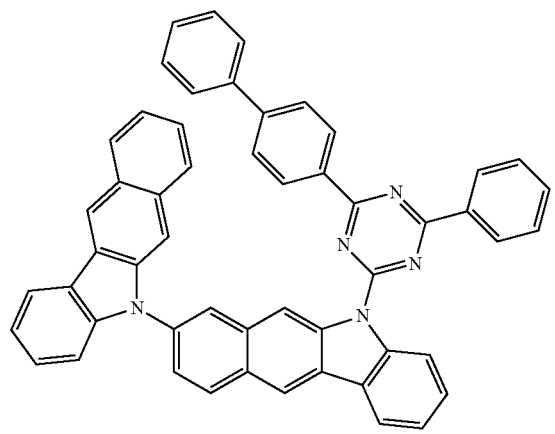
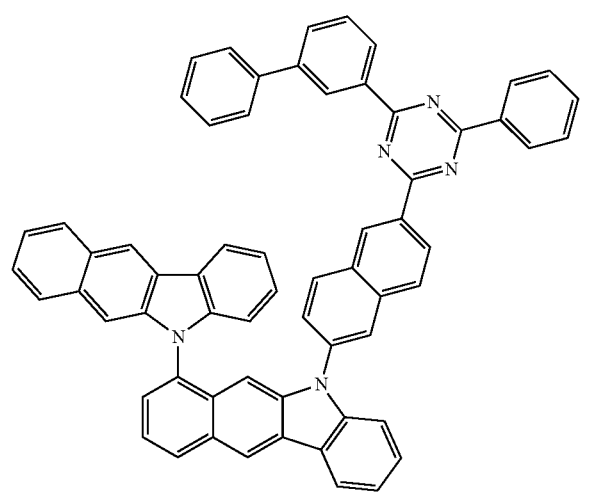
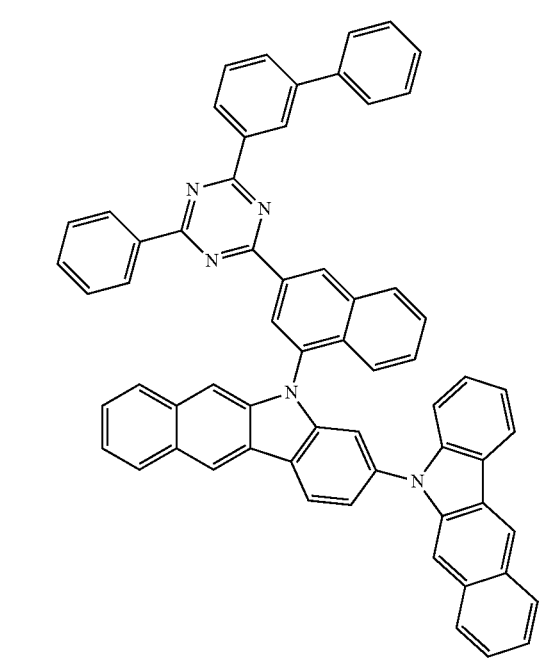
116
-continued
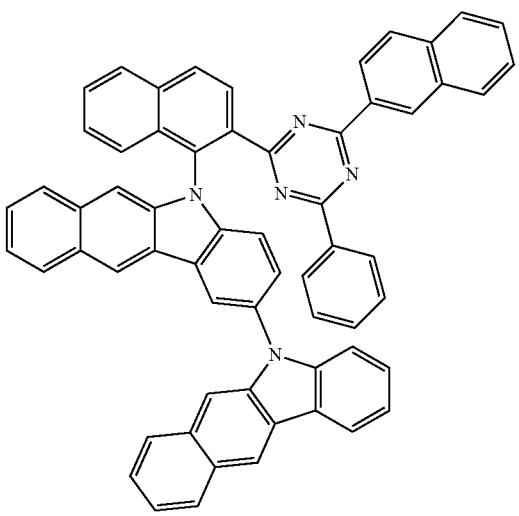
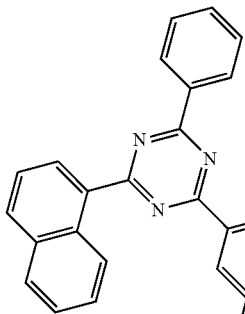
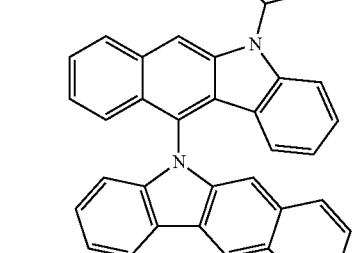
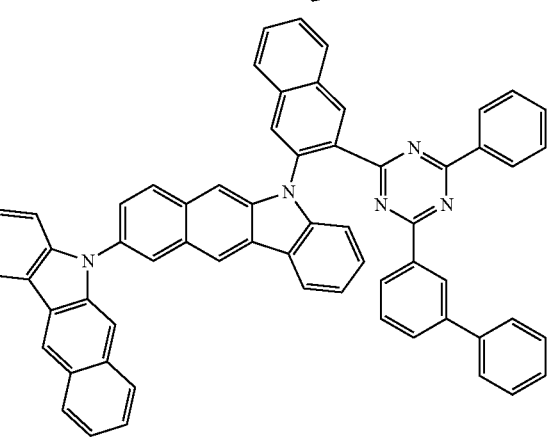

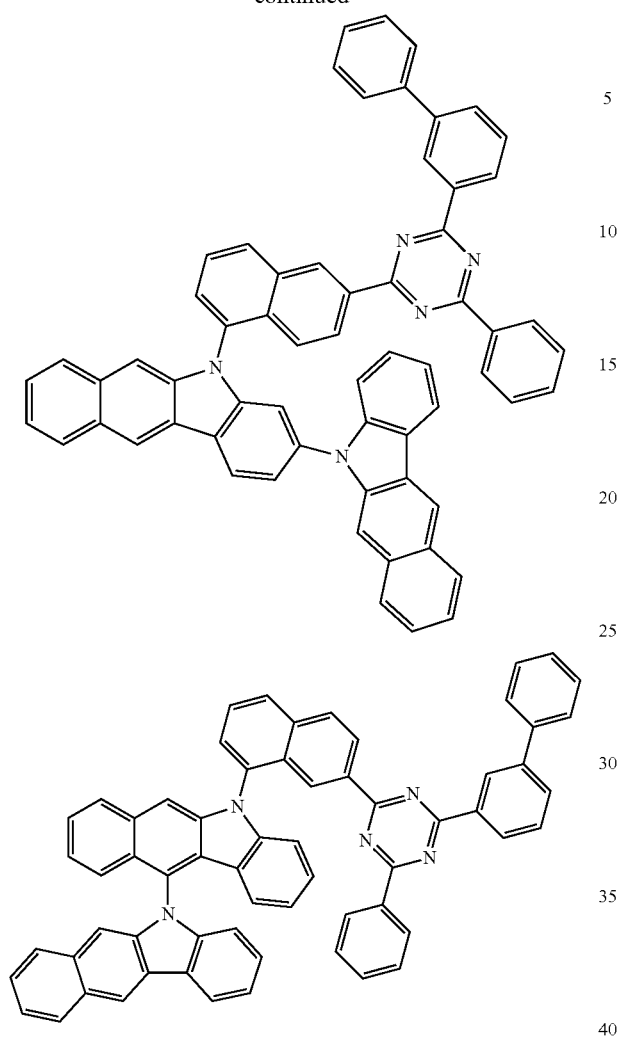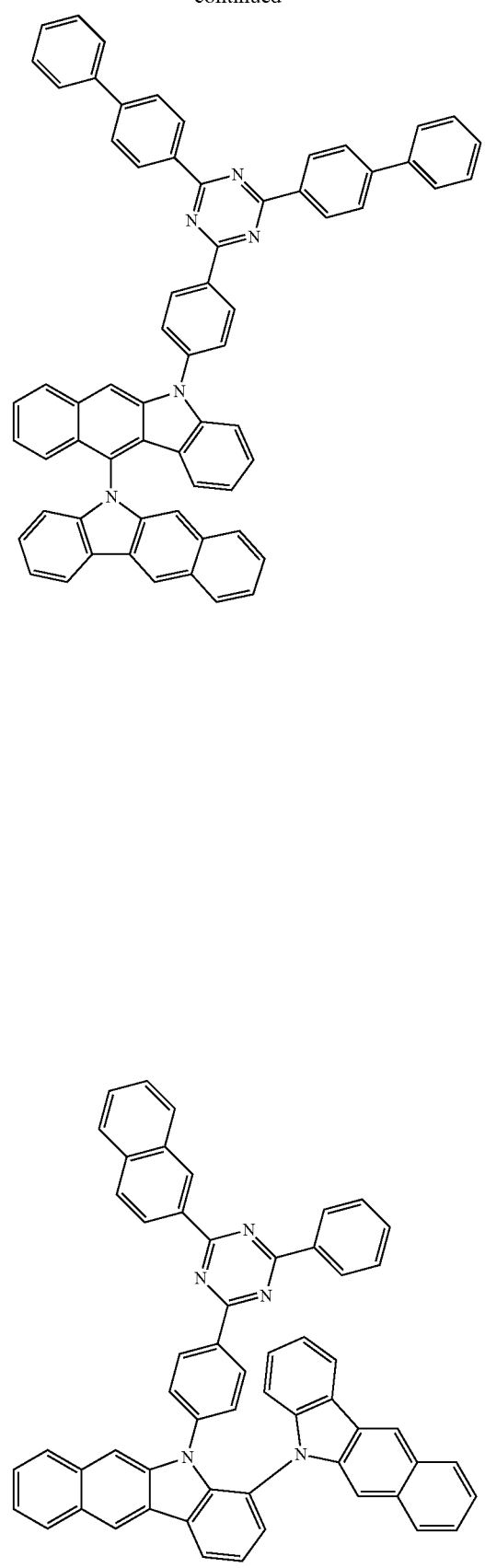

119
-continued
120
-continued
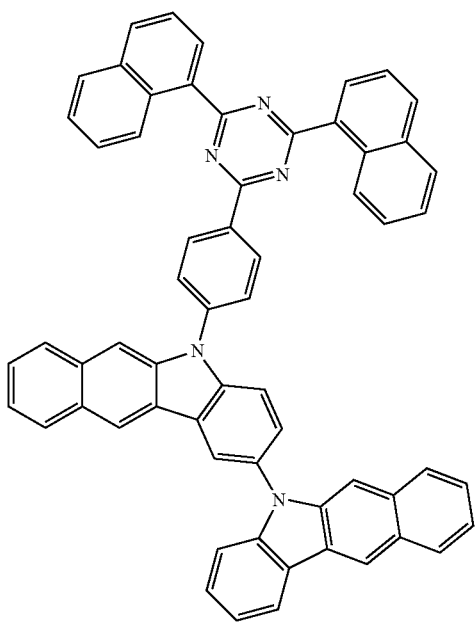
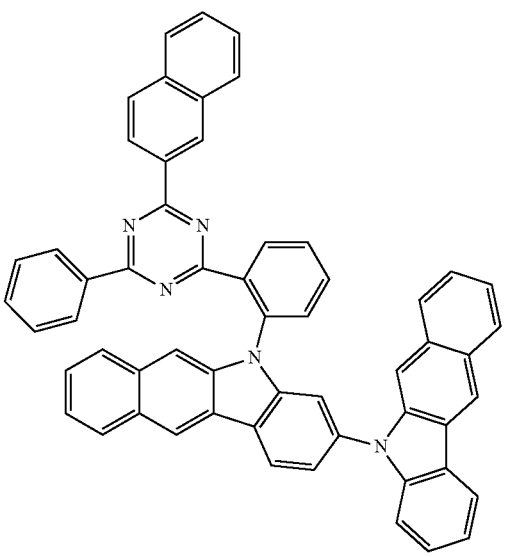
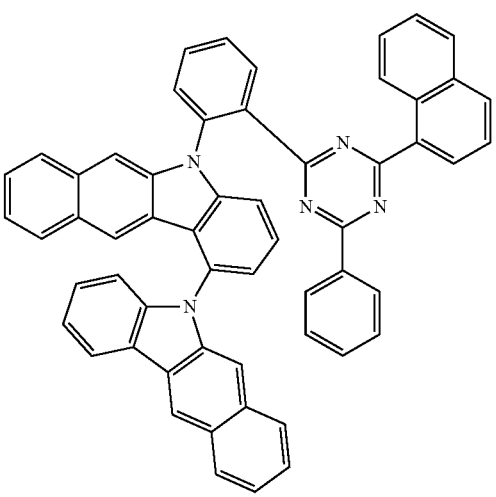
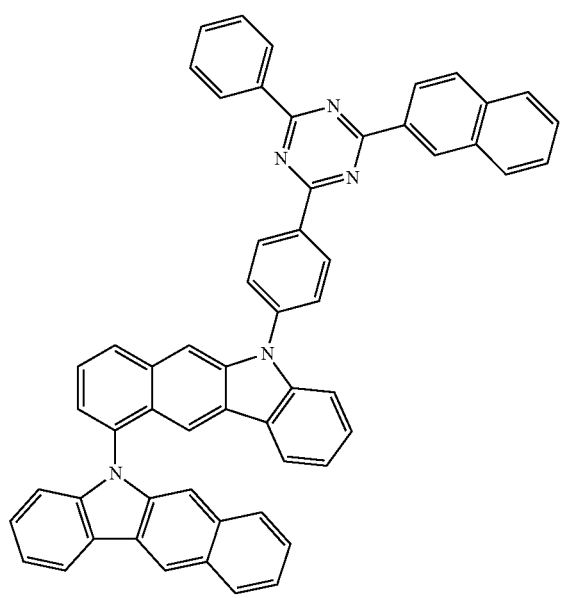
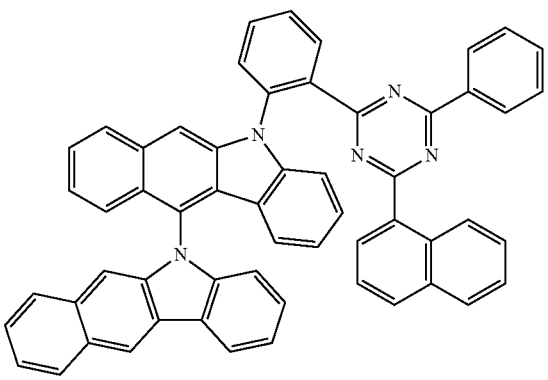

121
-continued
122
-continued
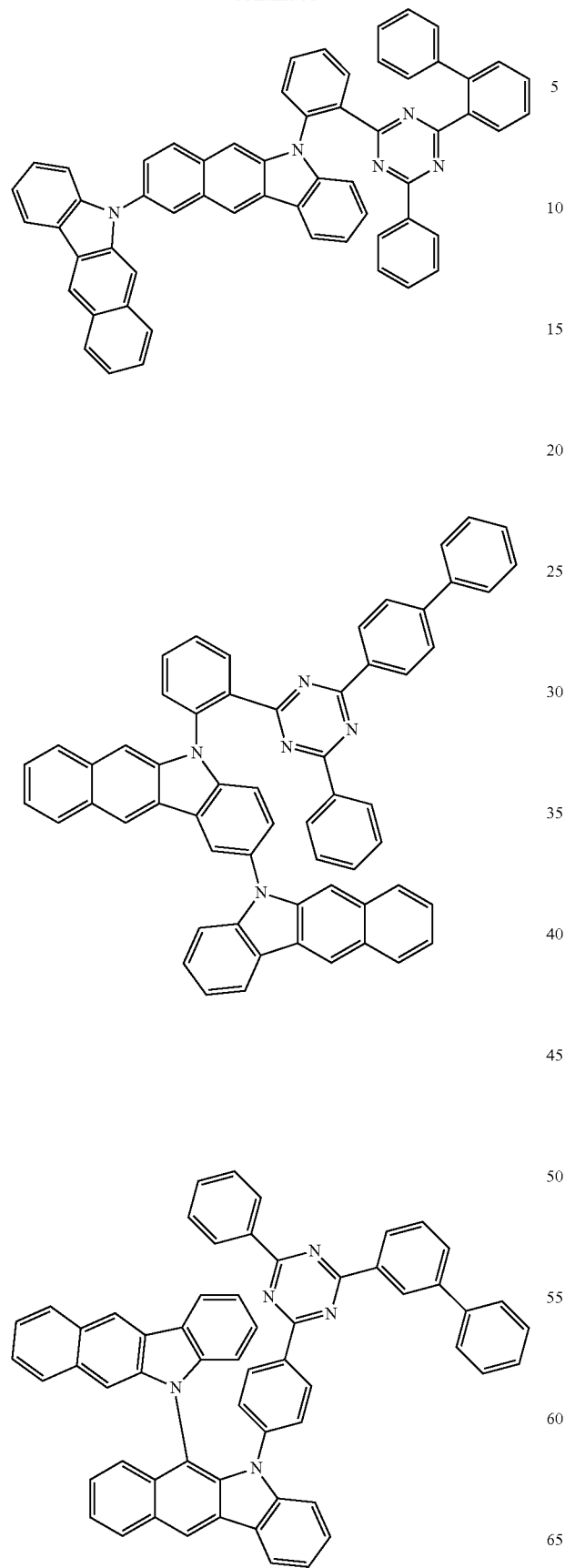
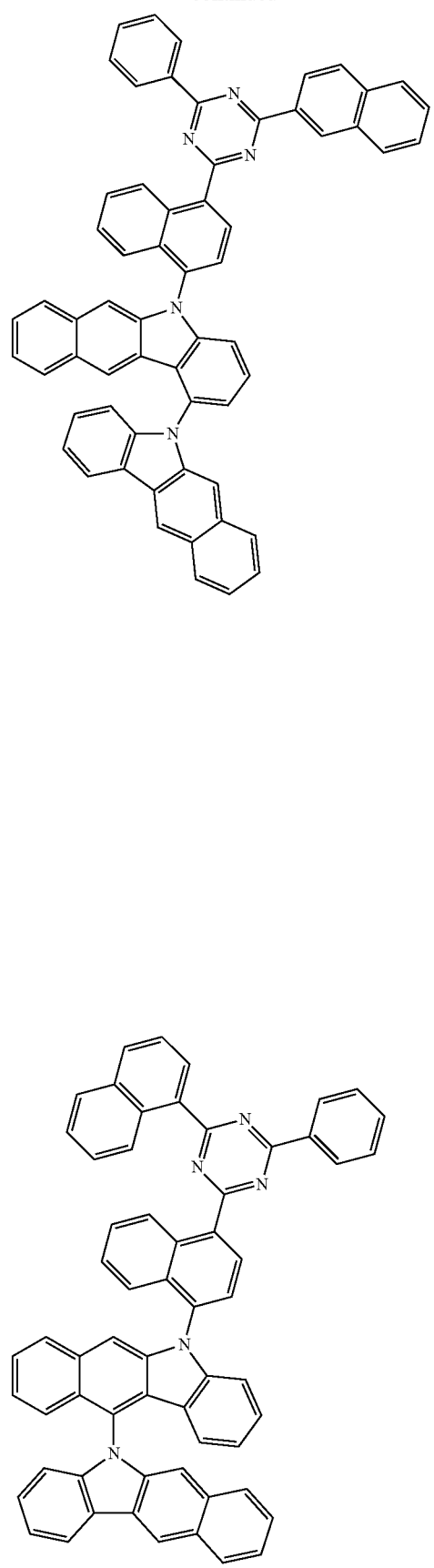

123
-continued
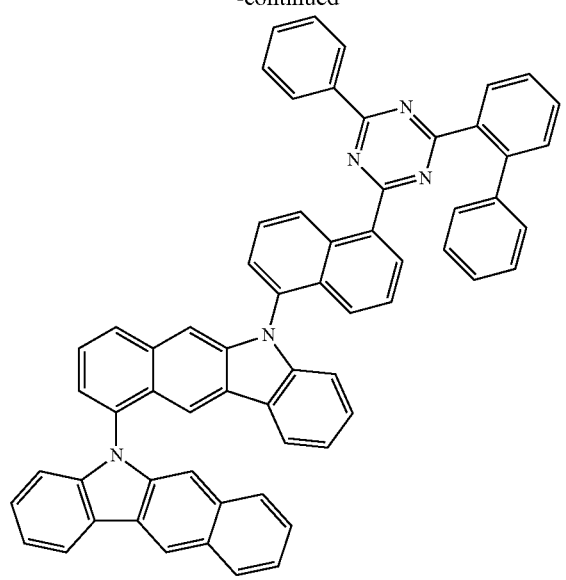
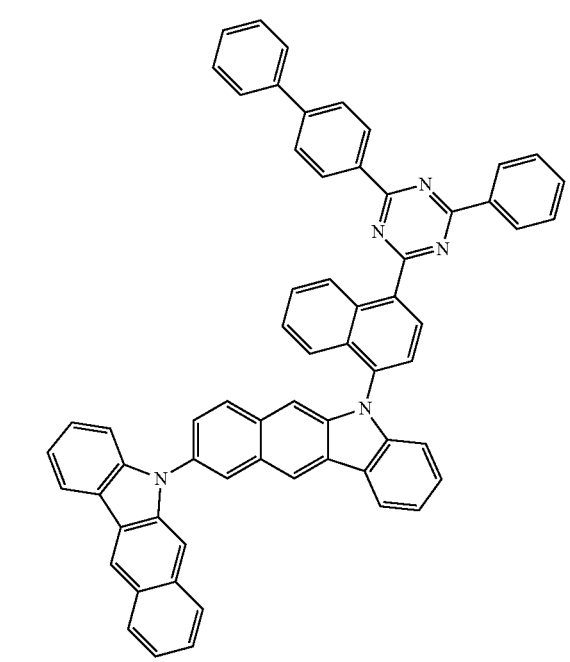
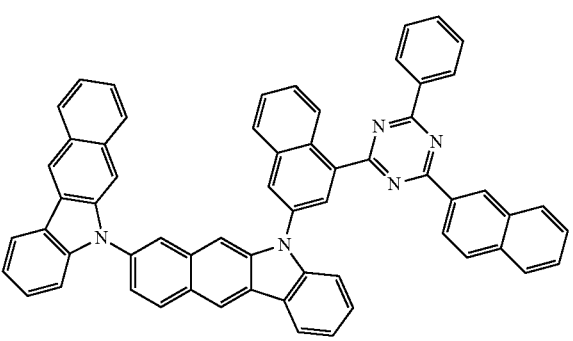
124
-continued
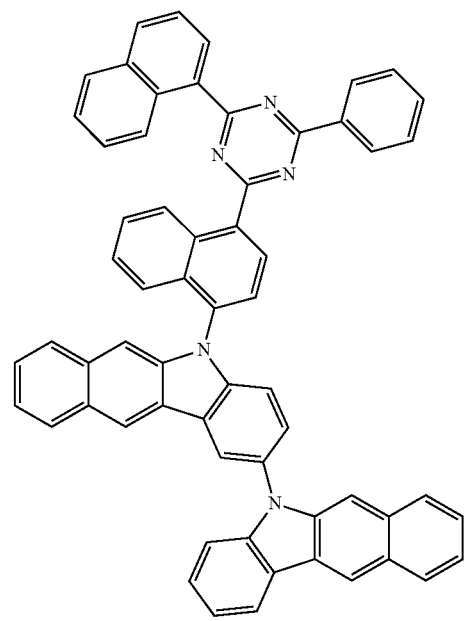
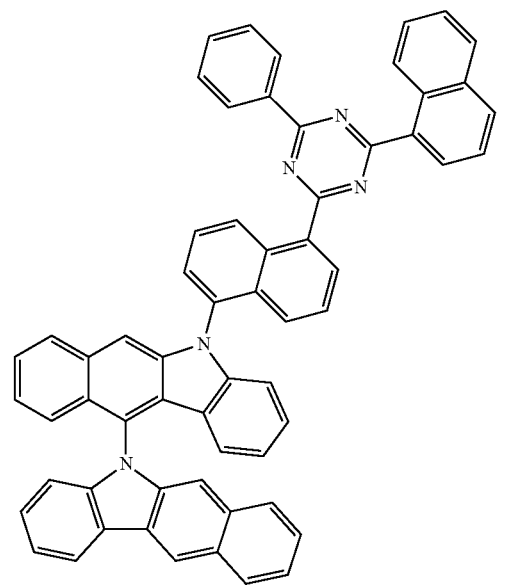

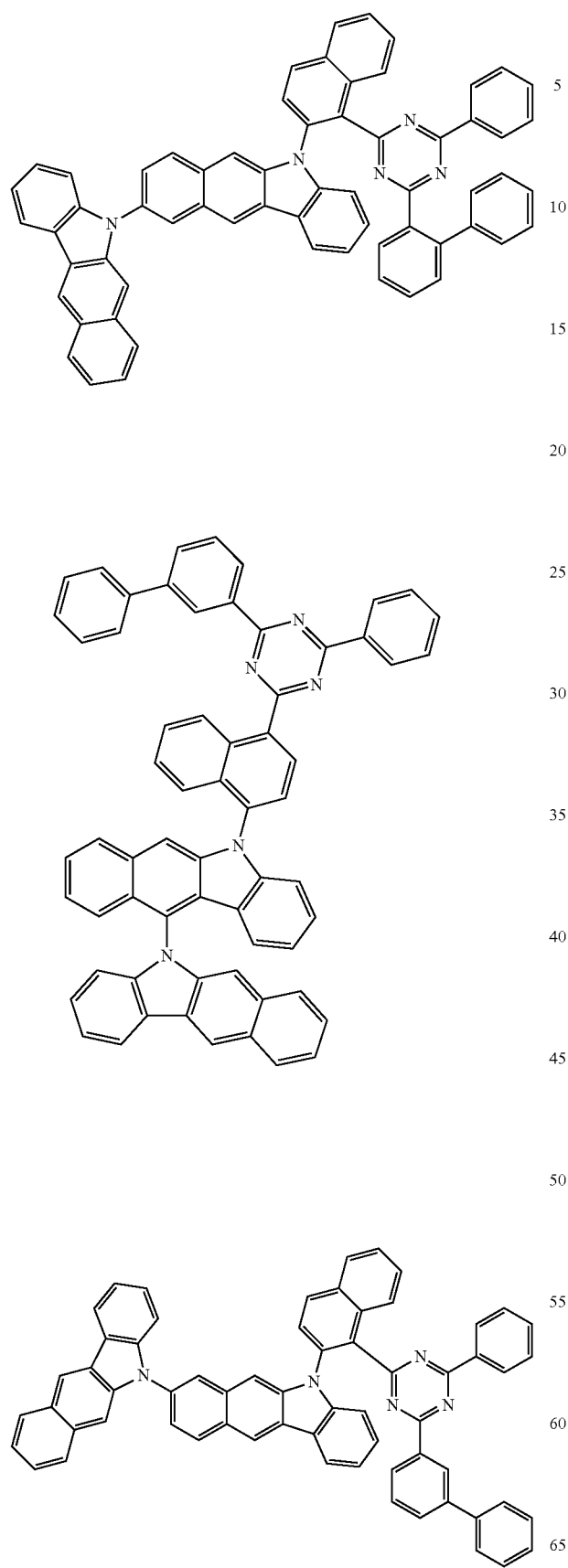
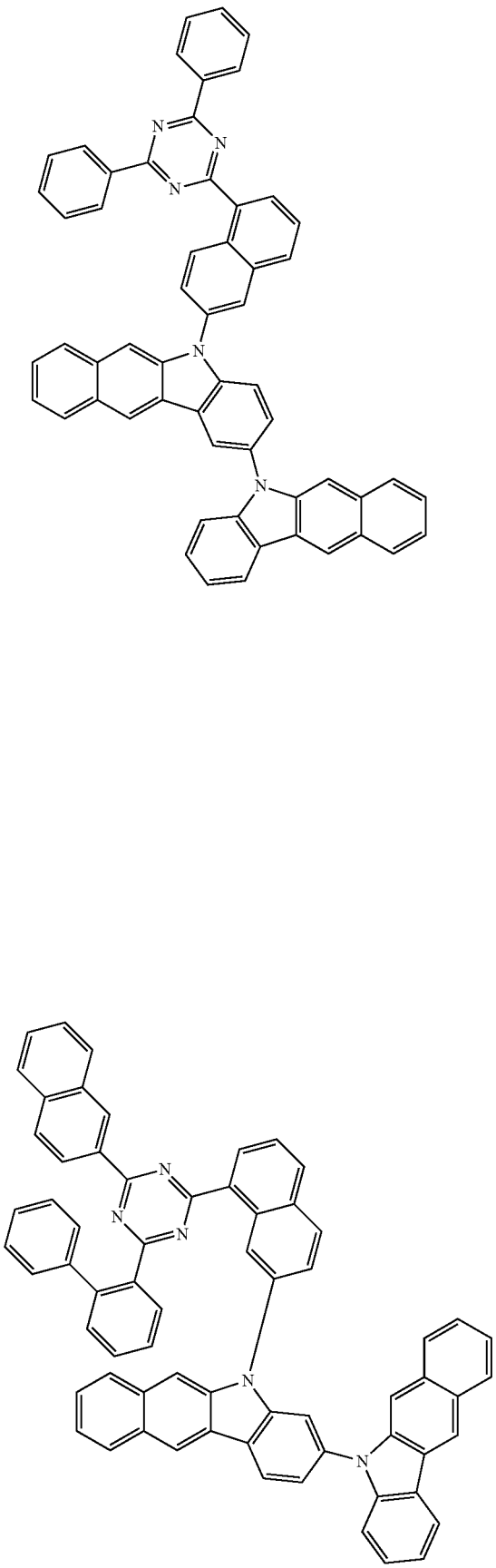

127
-continued
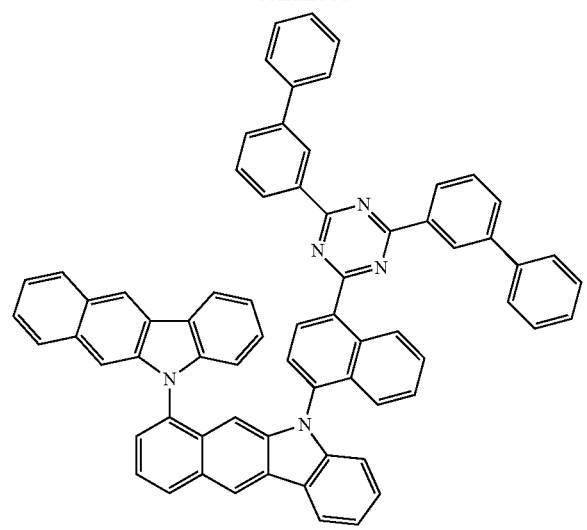
128
-continued
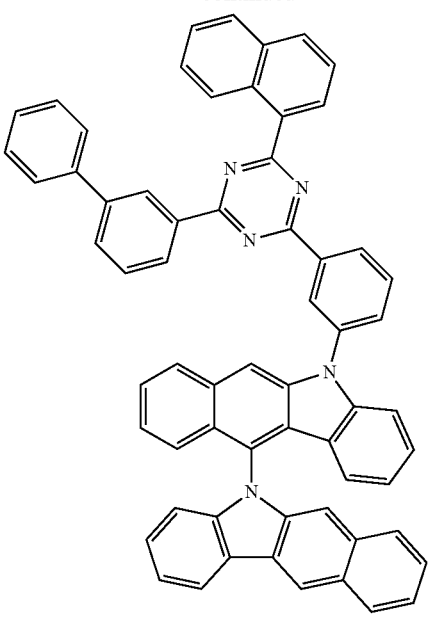
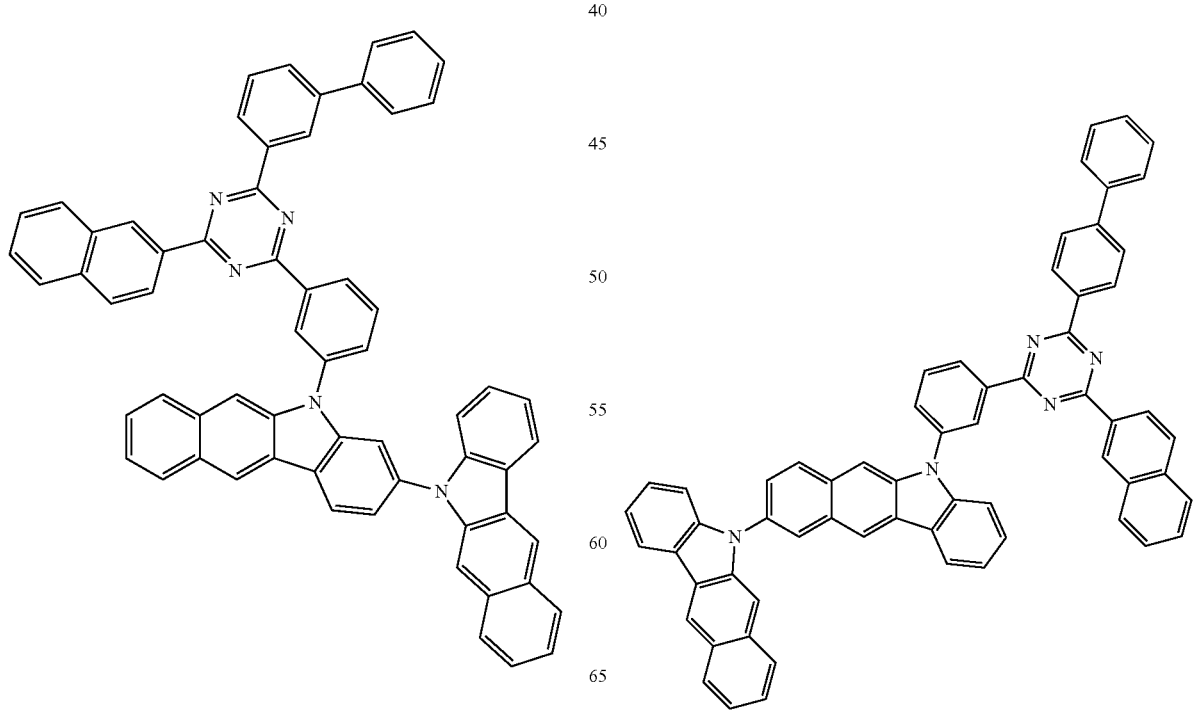

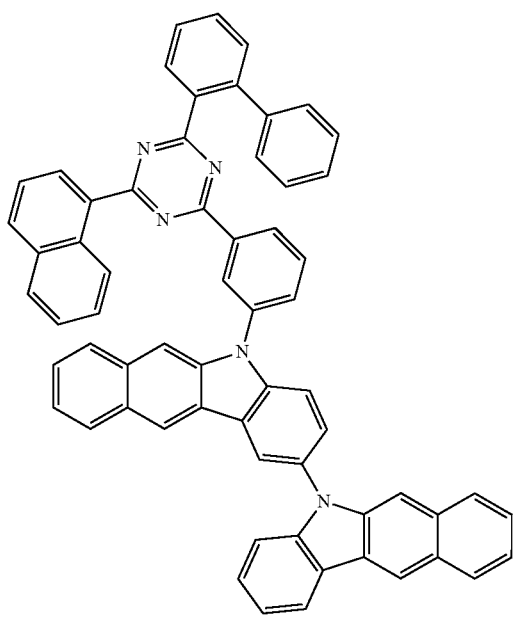
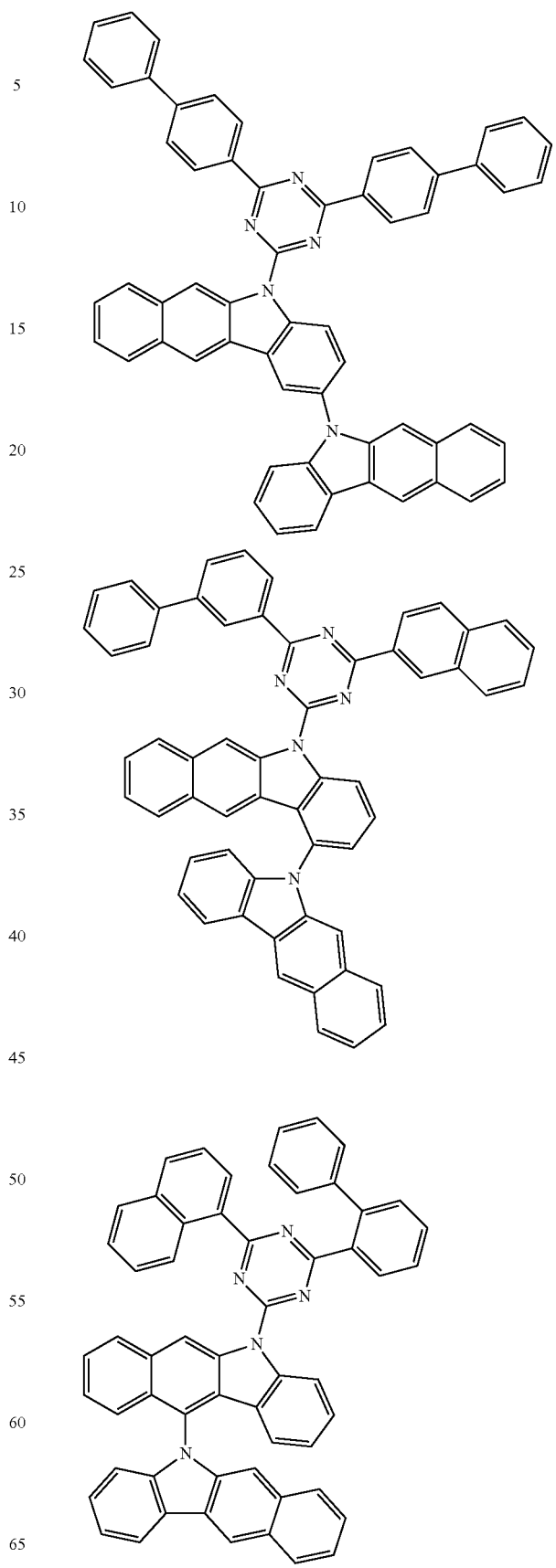

131
-continued
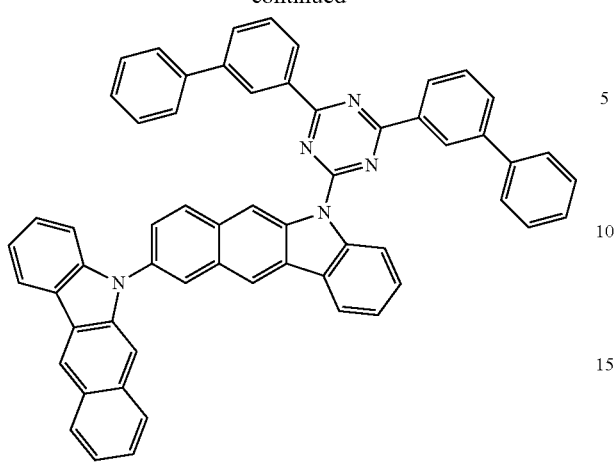
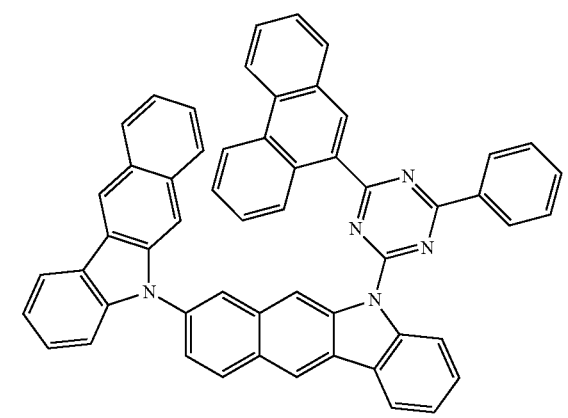
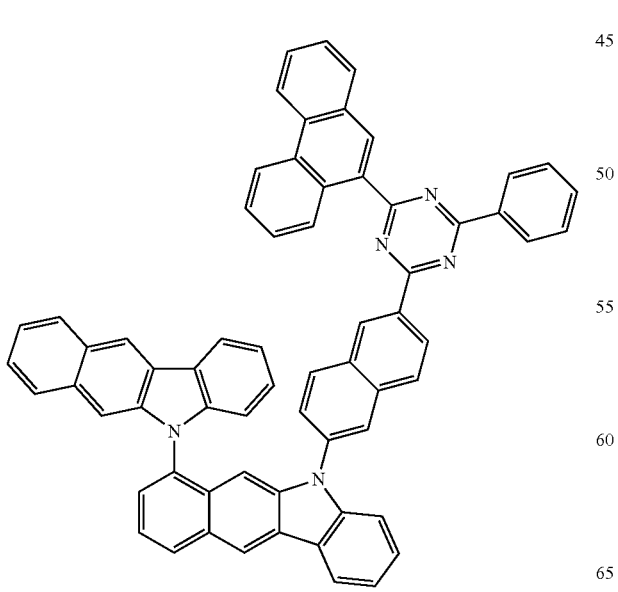
132
-continued
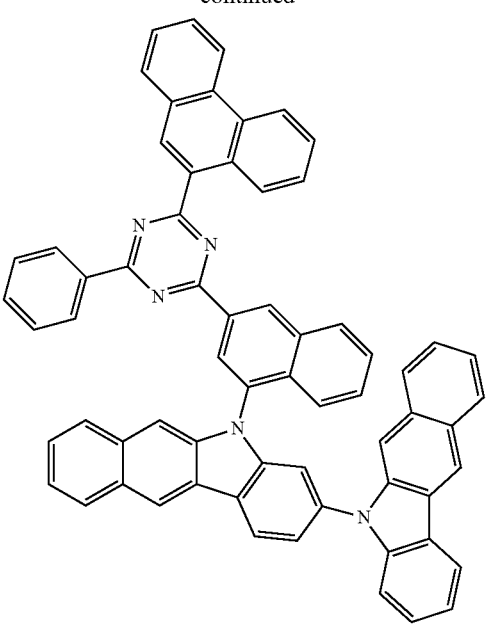
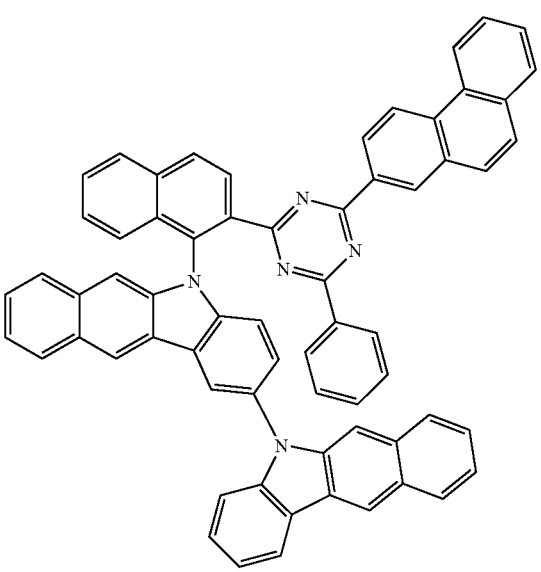

133
-continued
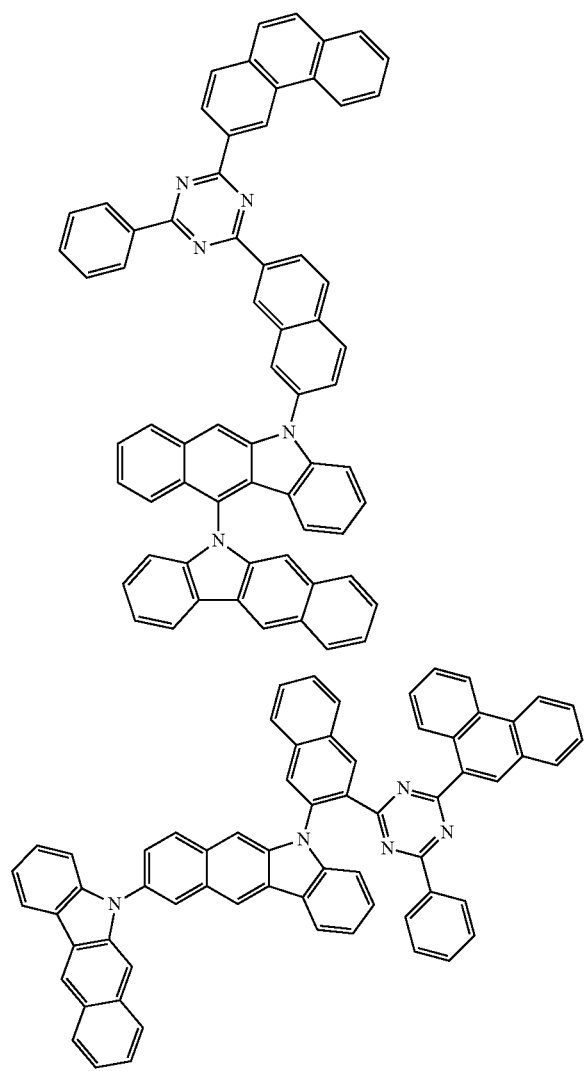
134
-continued
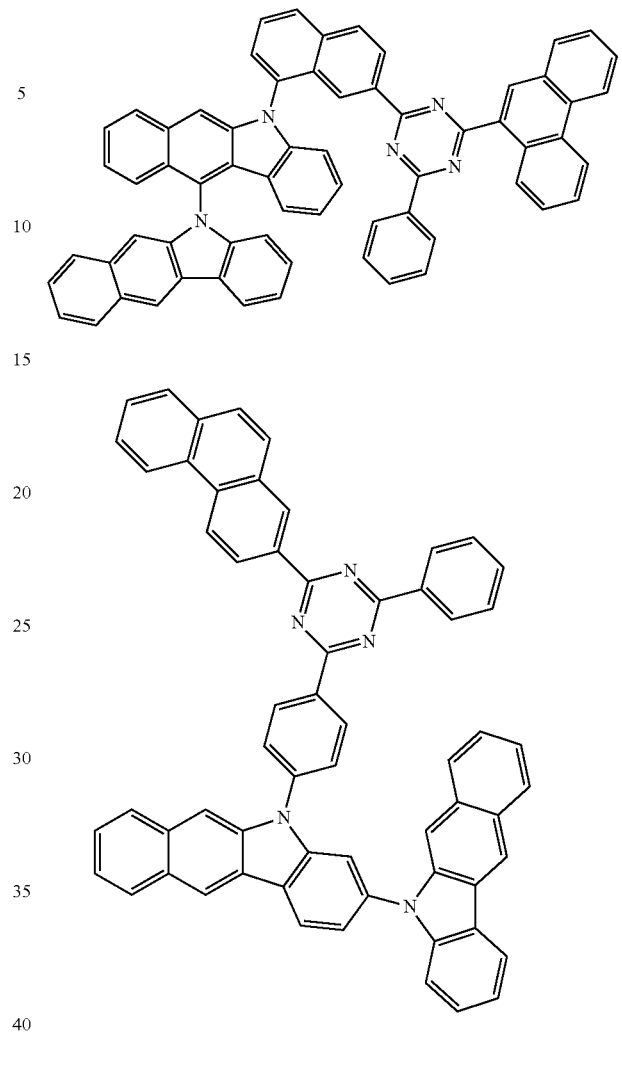
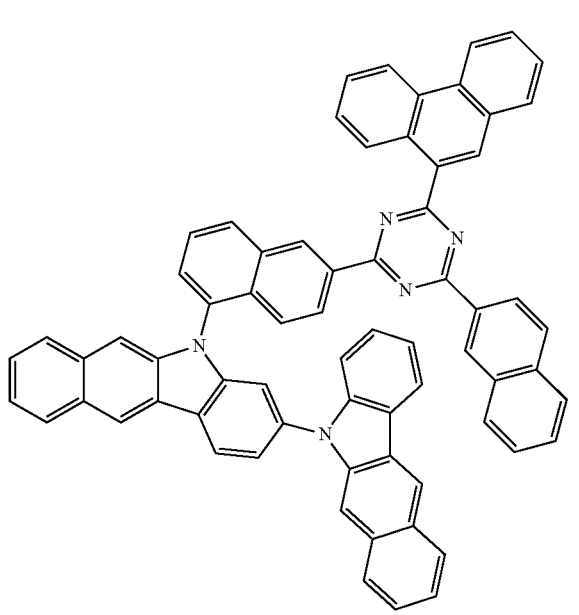
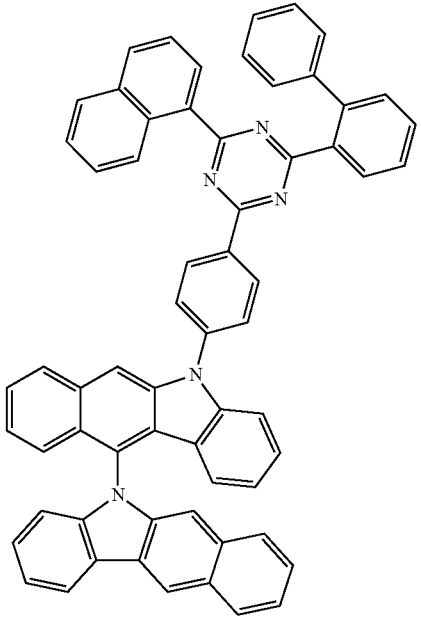

135
-continued
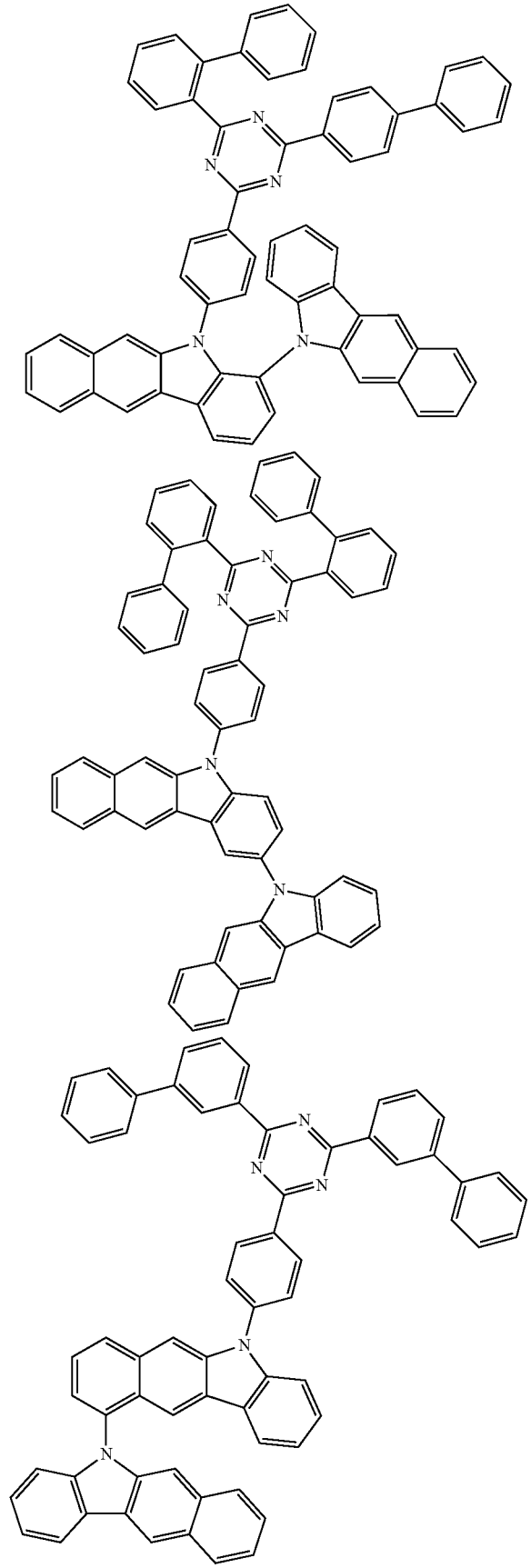
136
-continued
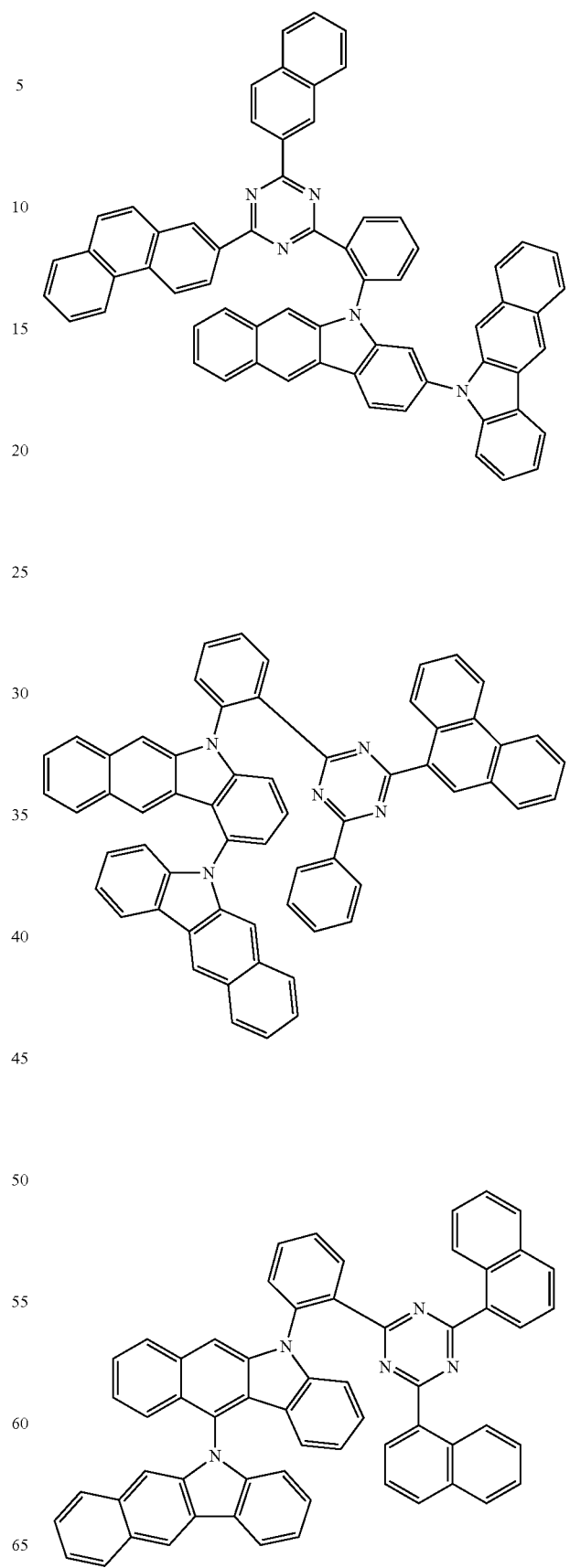

137
-continued
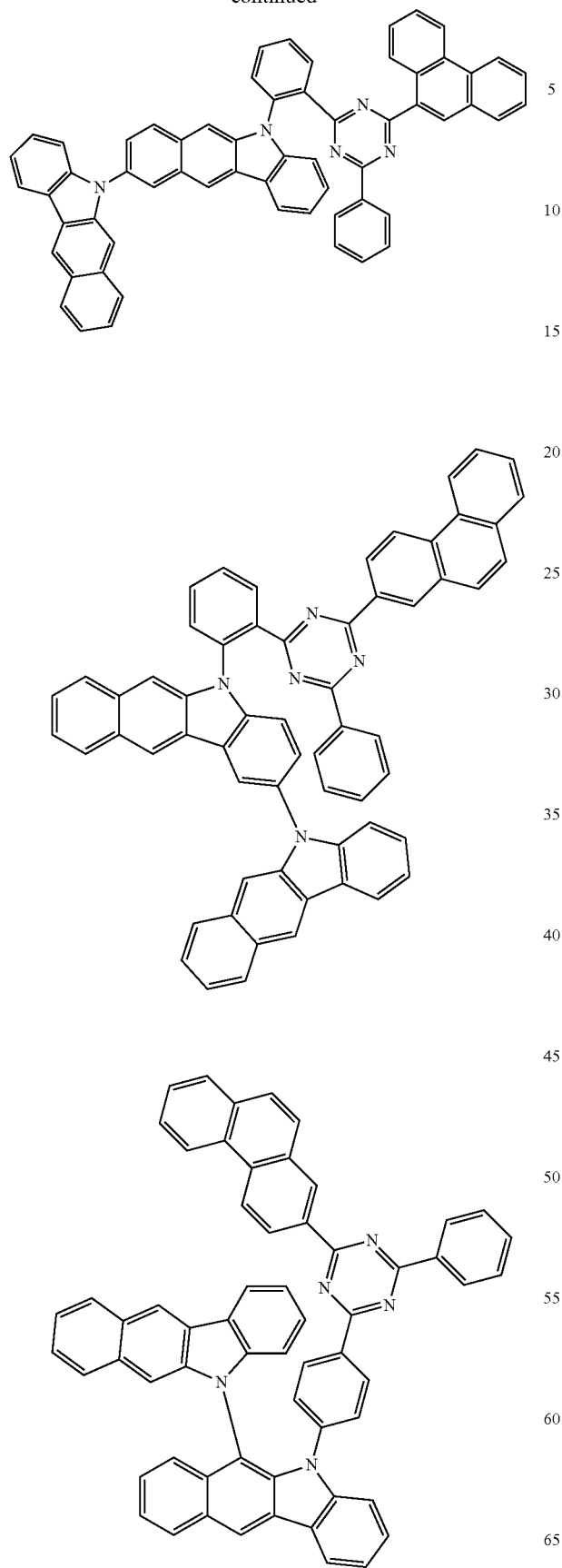
138
-continued
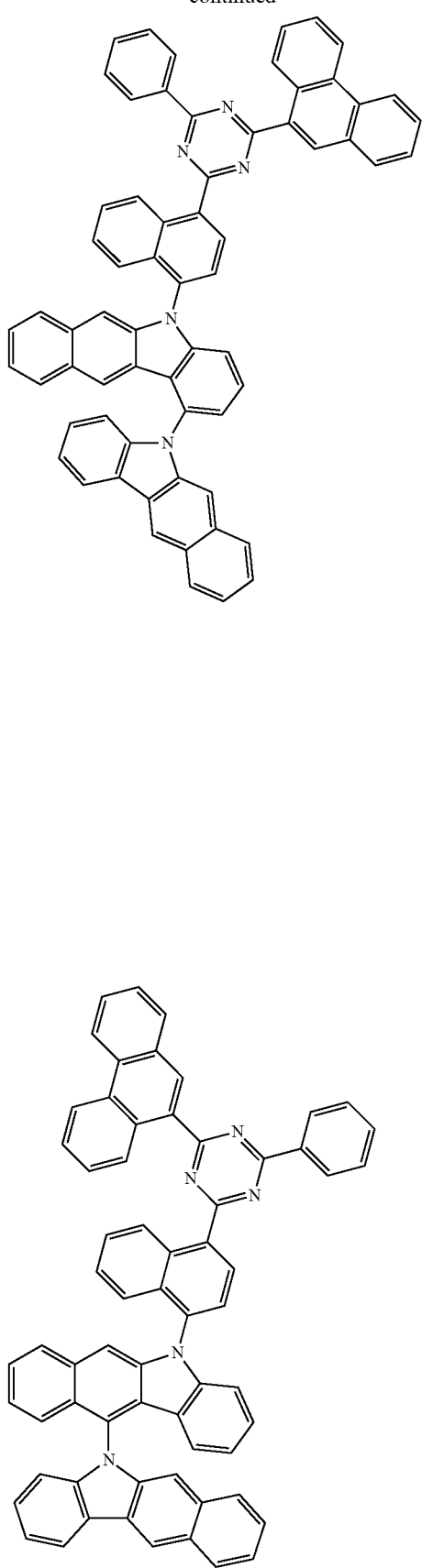

139
-continued
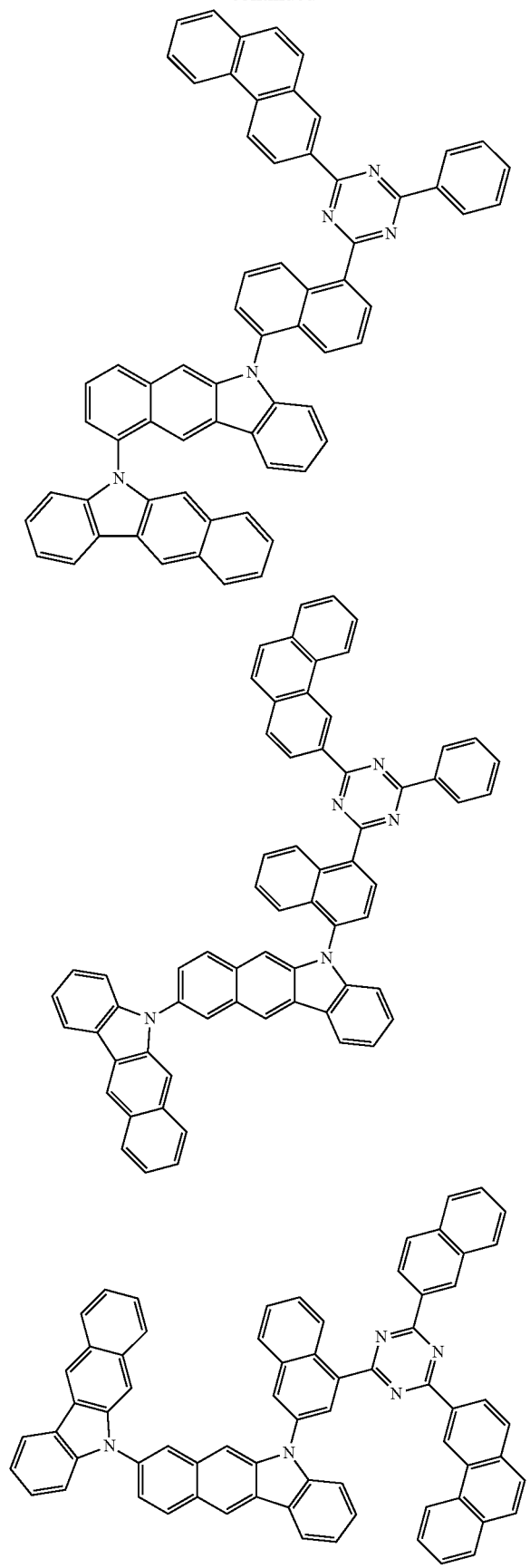
140
-continued
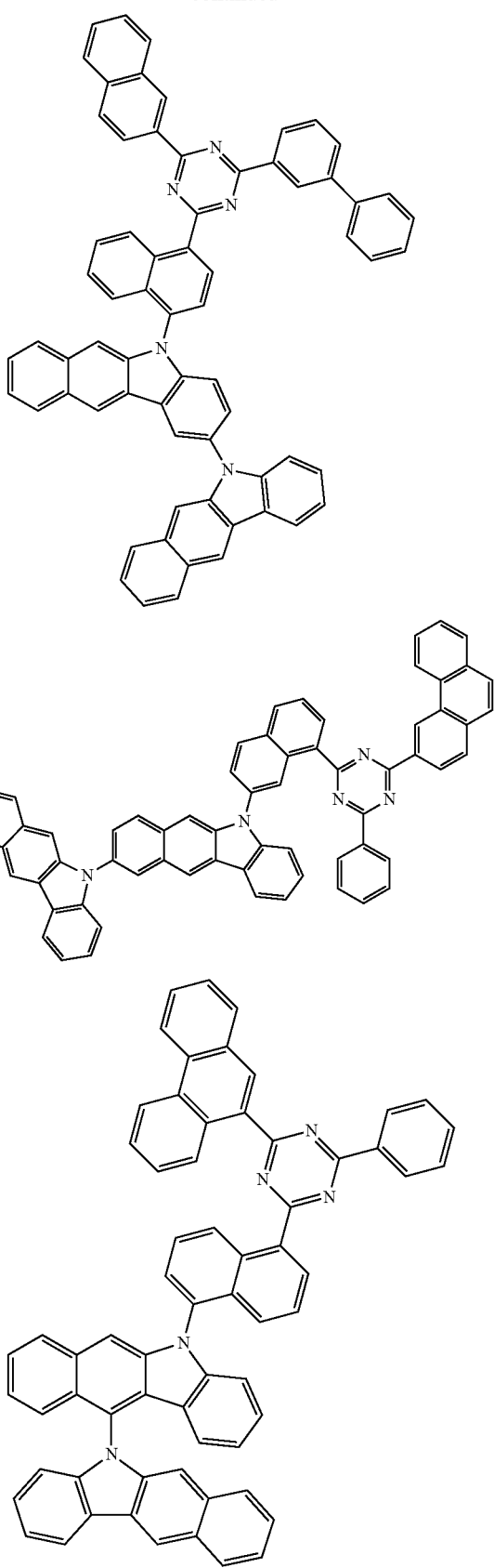

141
-continued
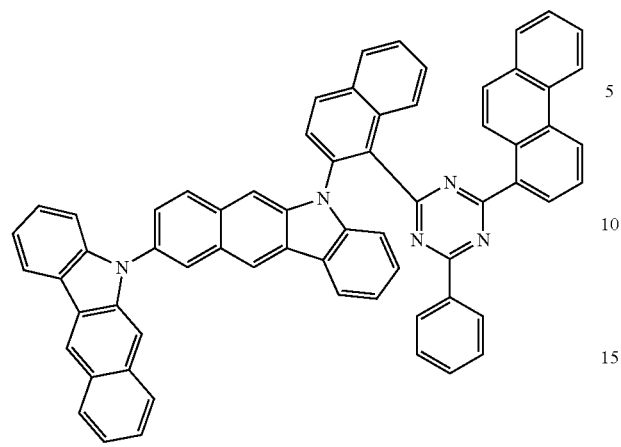
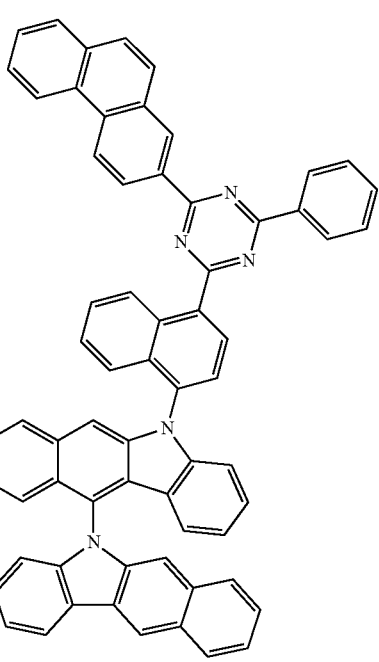
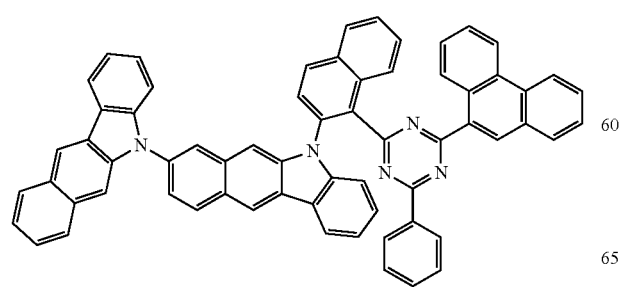
142
-continued
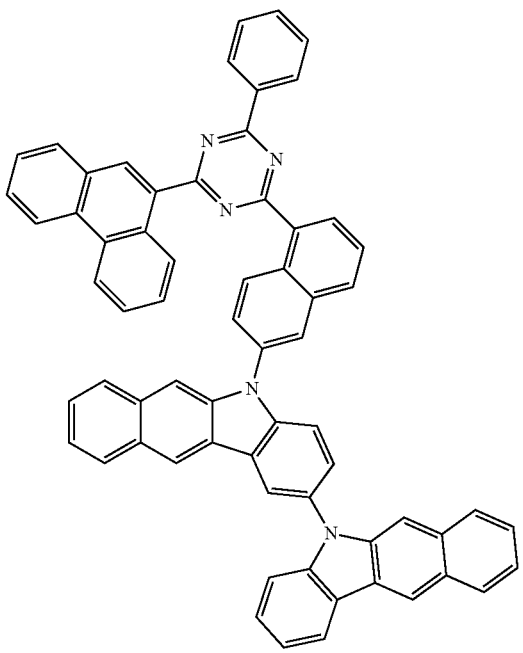
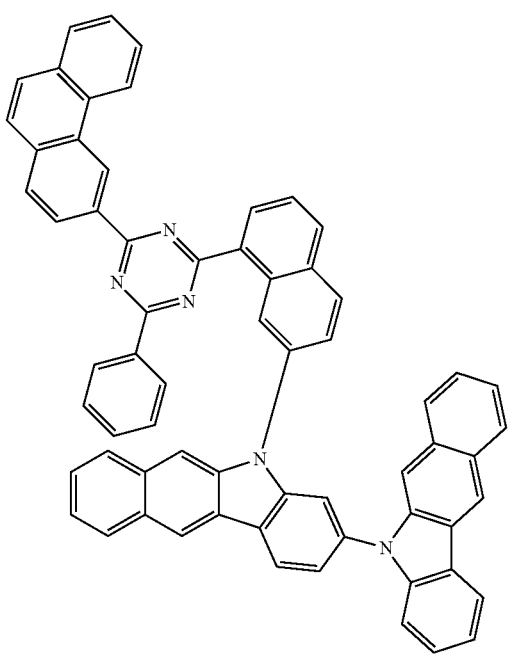

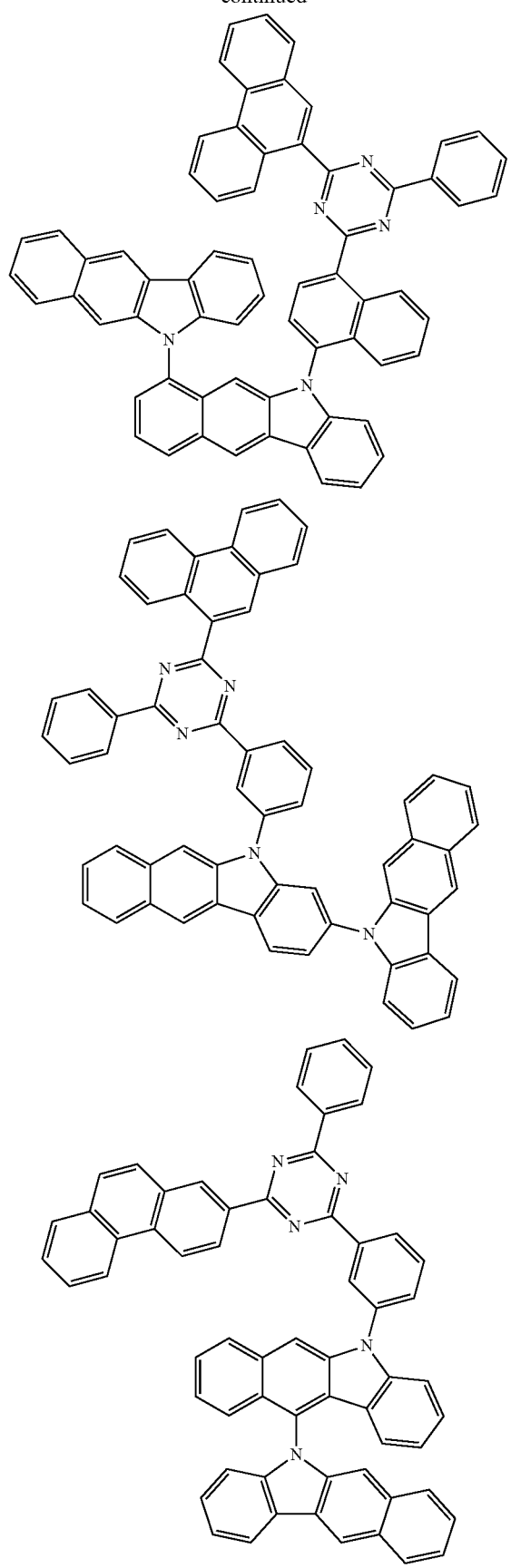
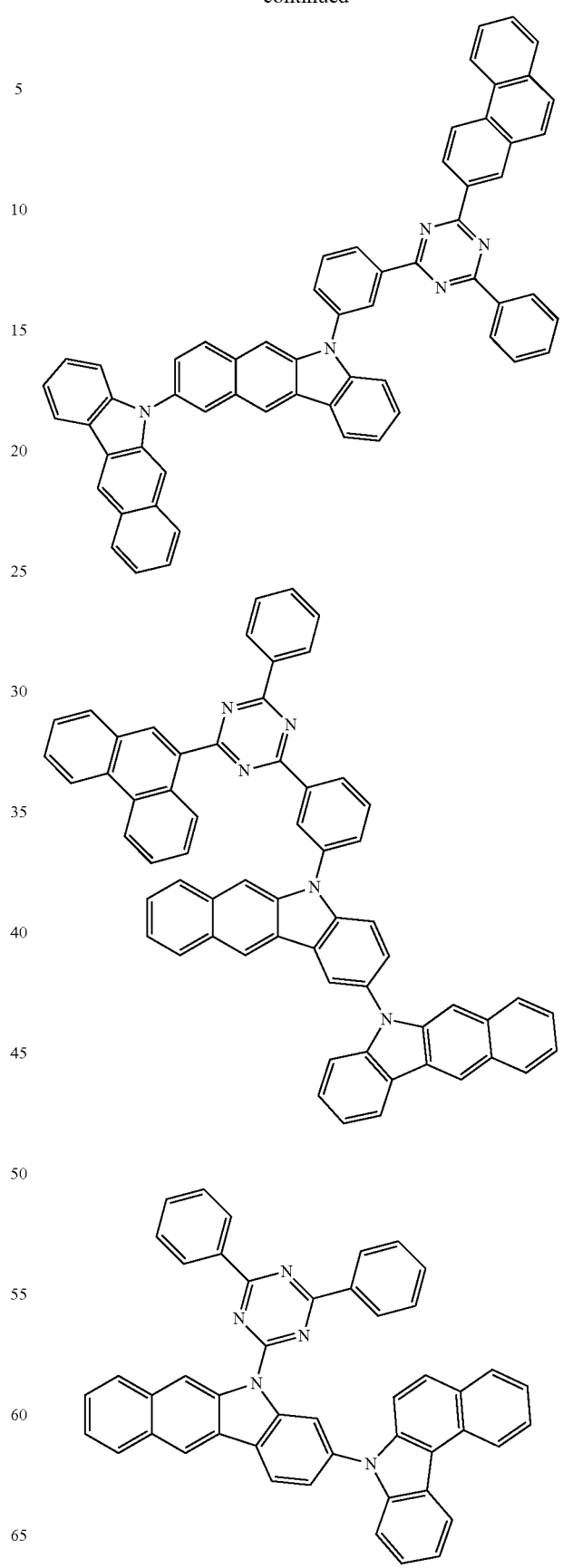

145
-continued
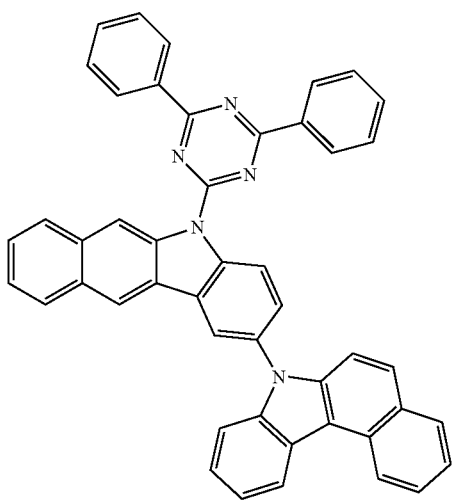
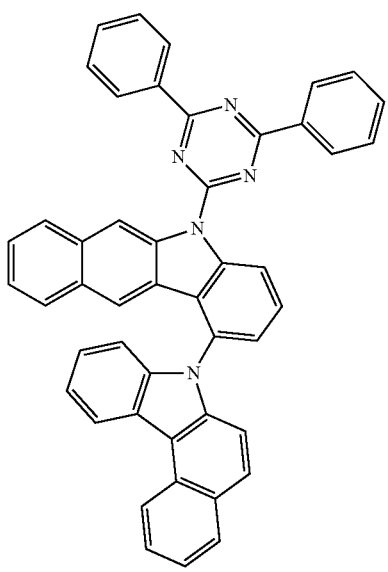
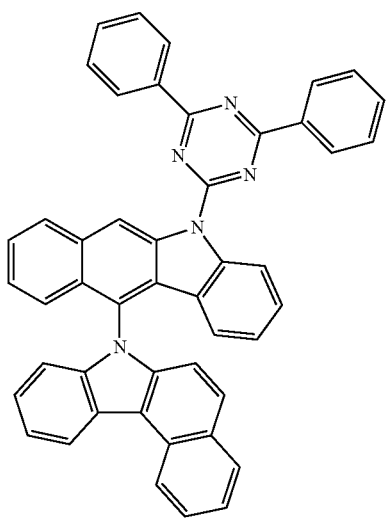
146
-continued
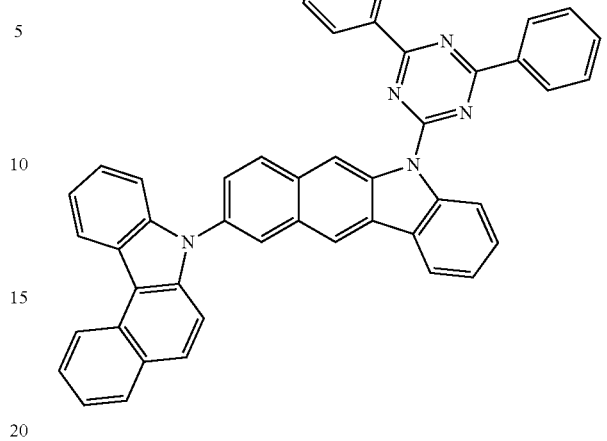
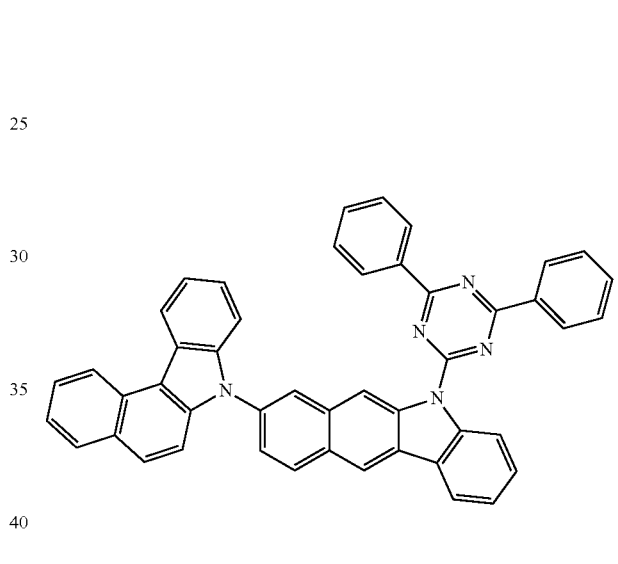
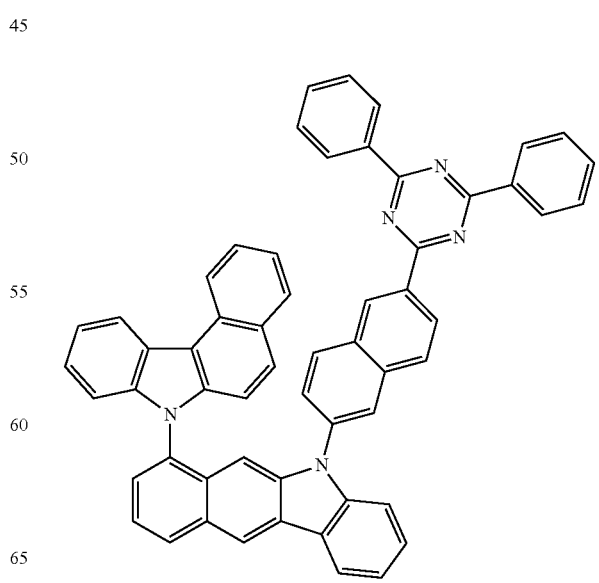

147
-continued
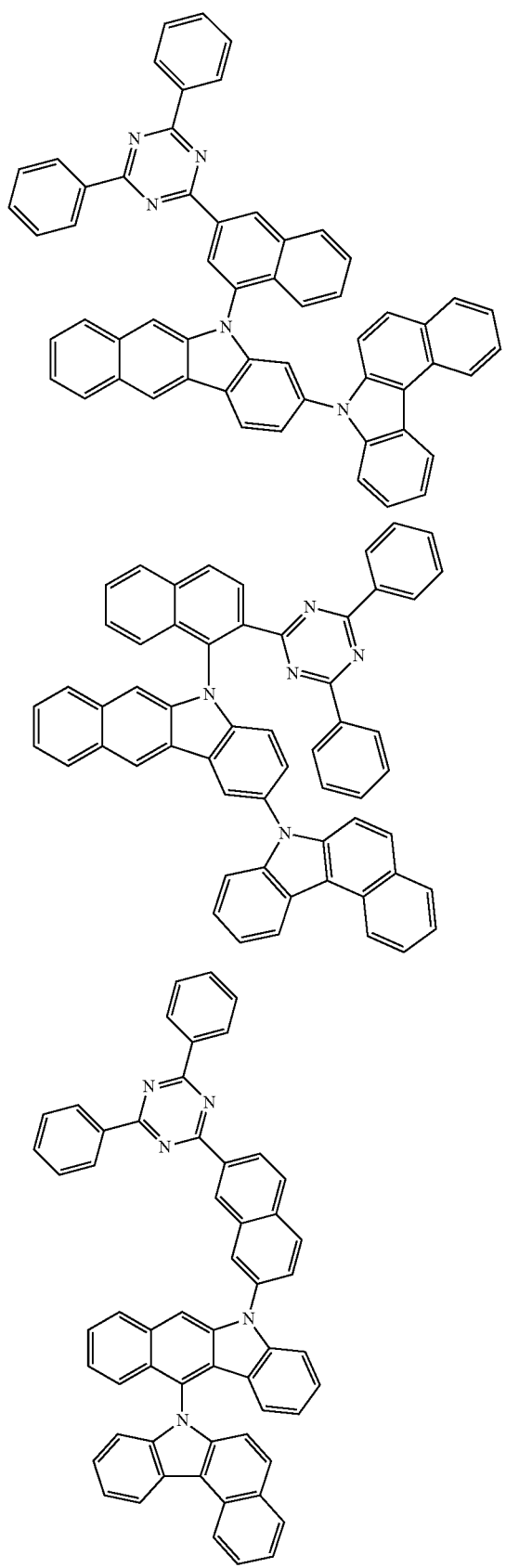
148
-continued
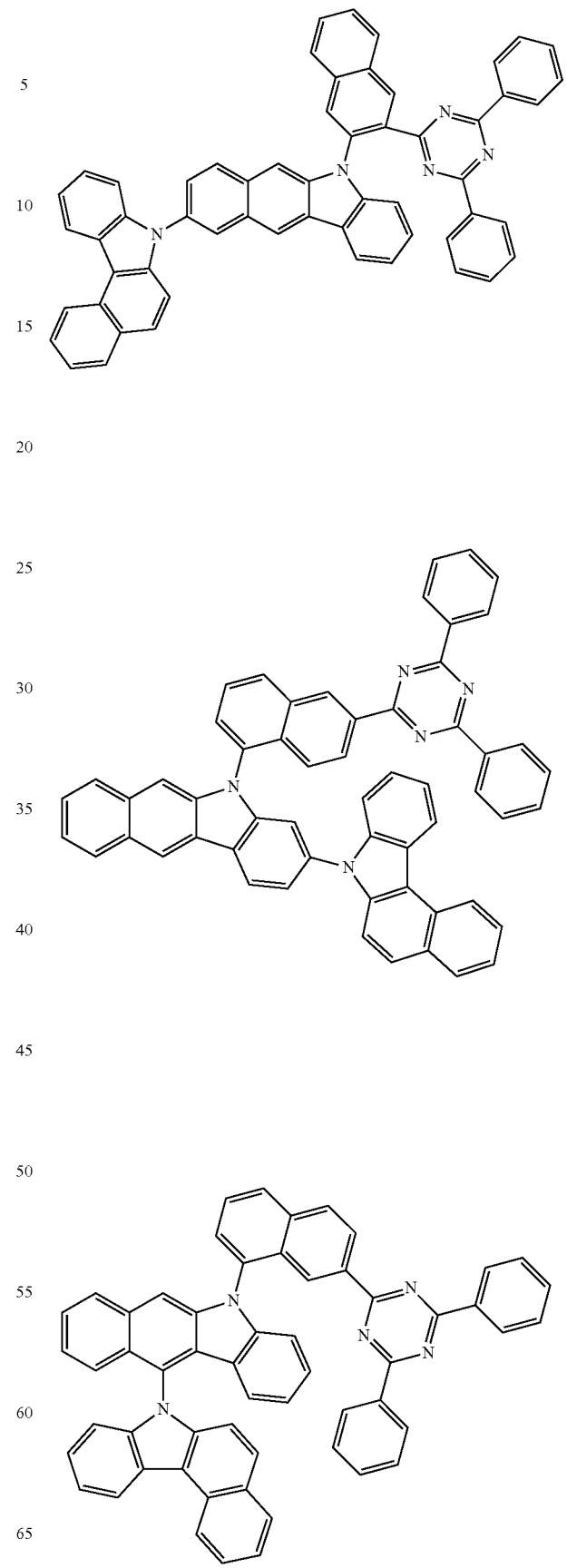

149
-continued
150
-continued
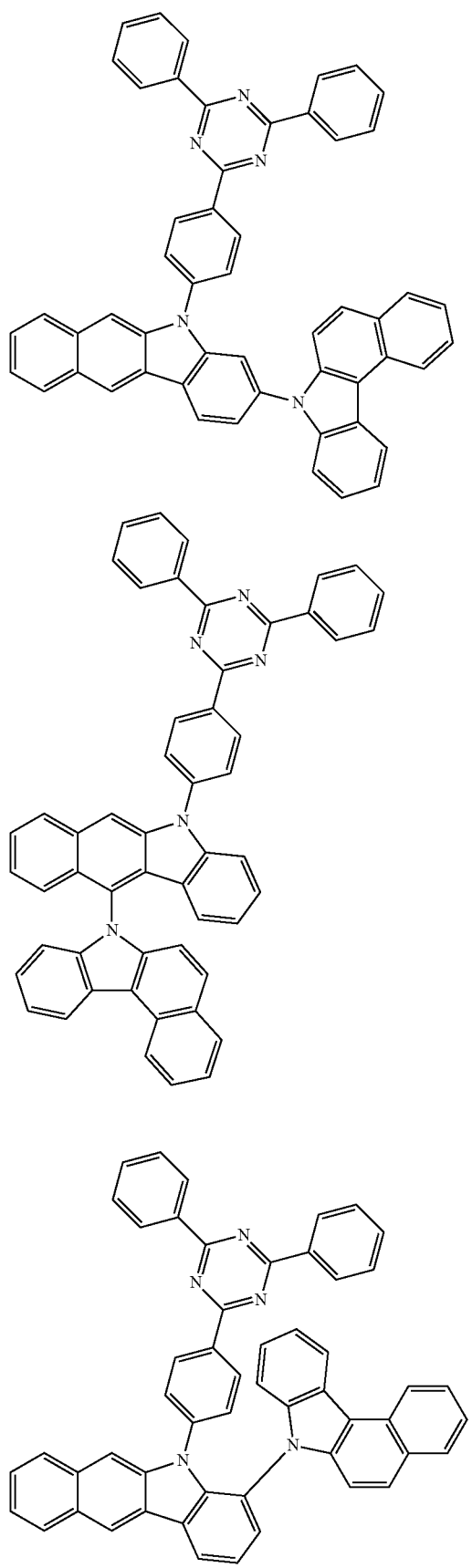
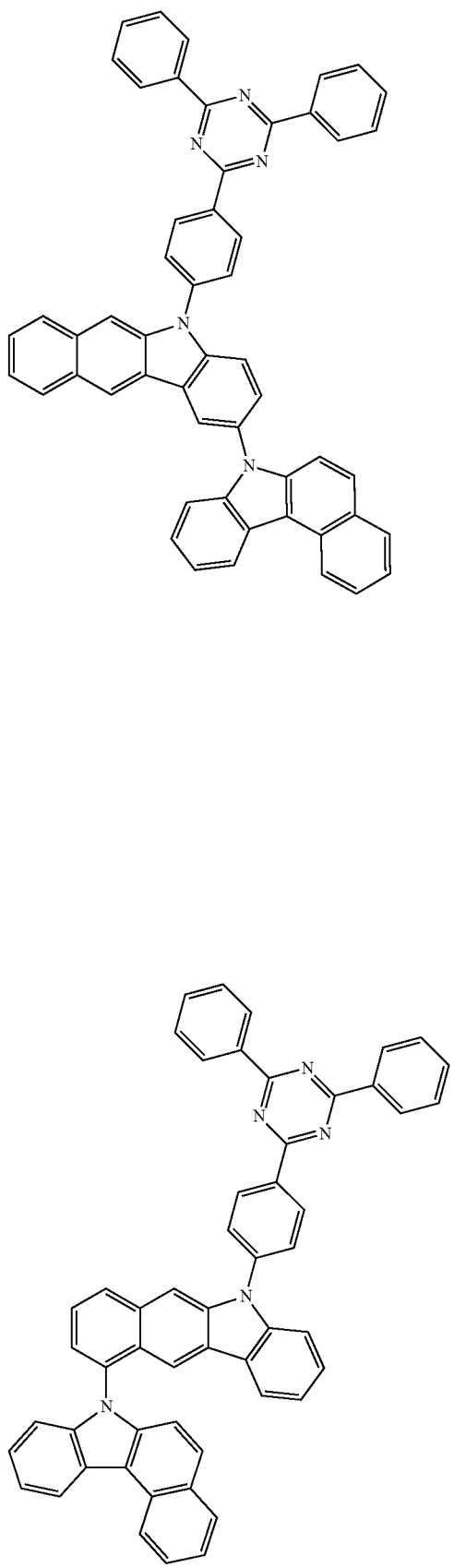

151
-continued
152
-continued
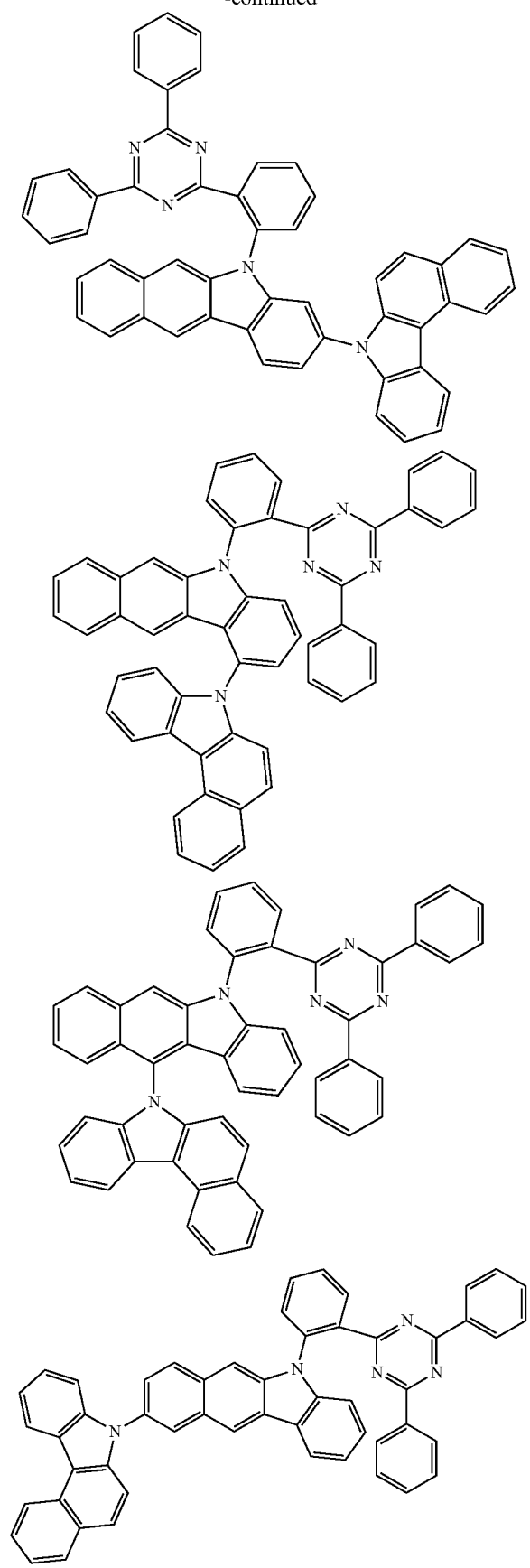
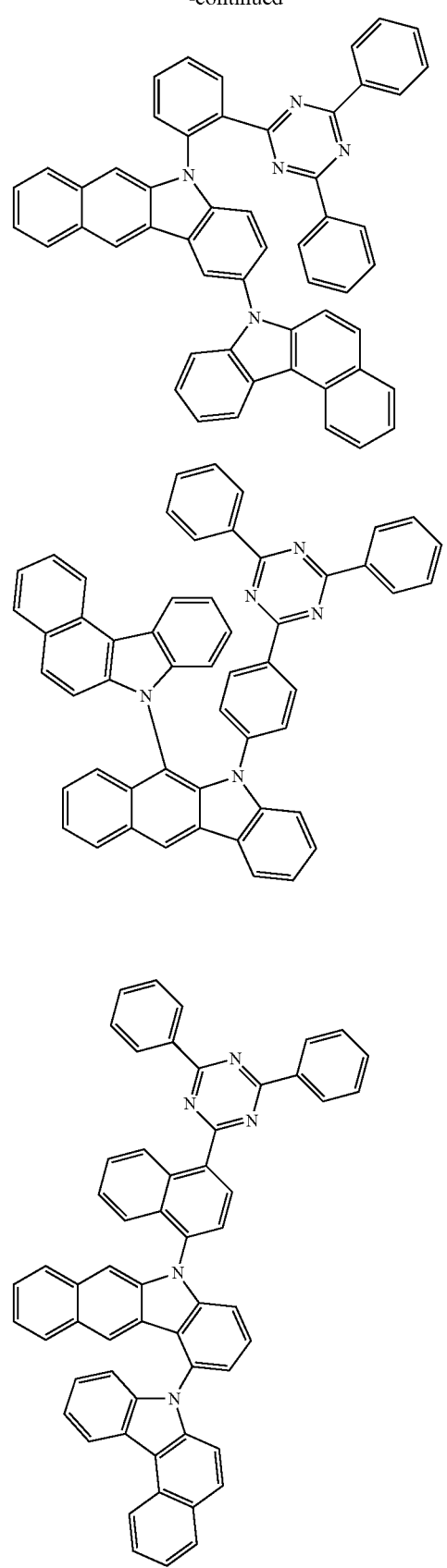

153
-continued
154
-continued
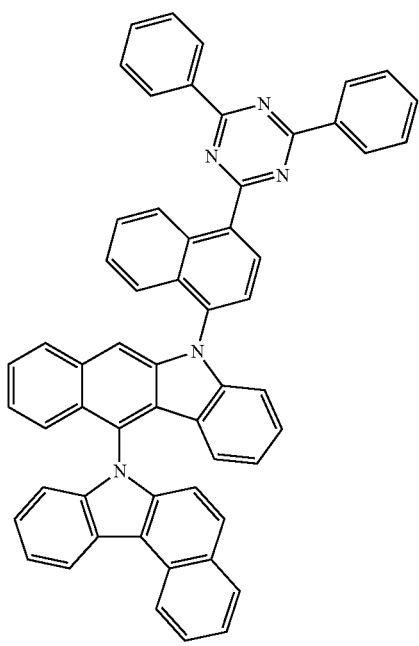
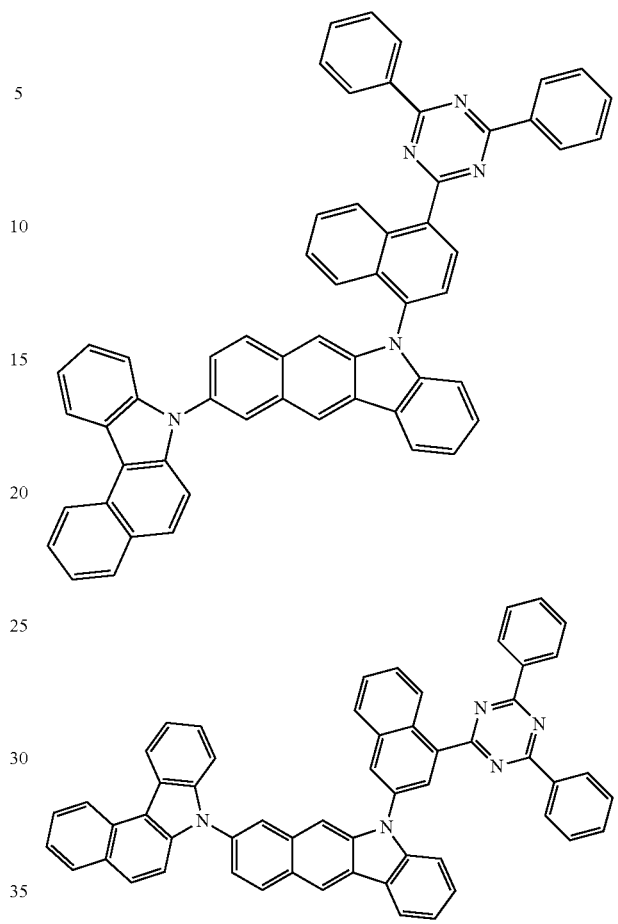
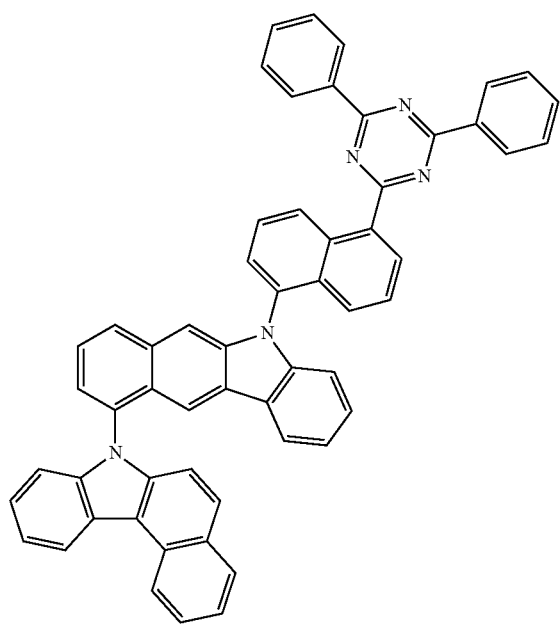

-continued
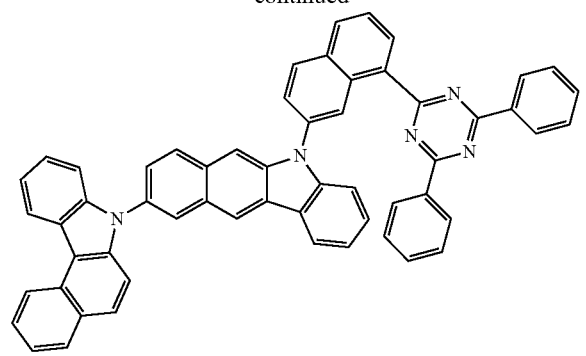
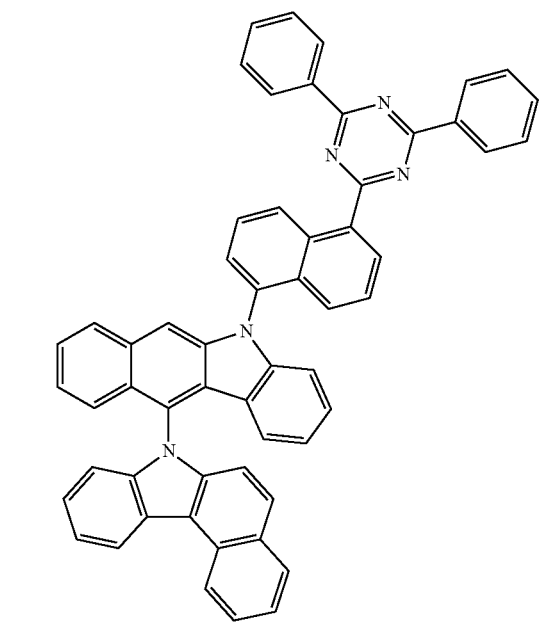
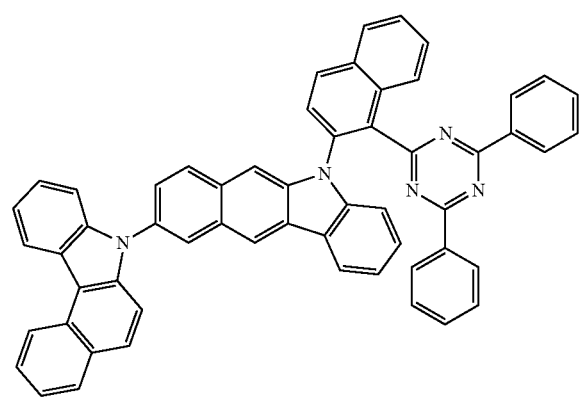
-continued
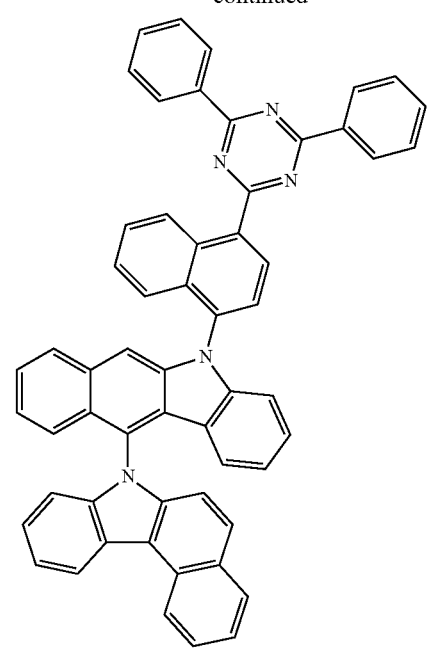
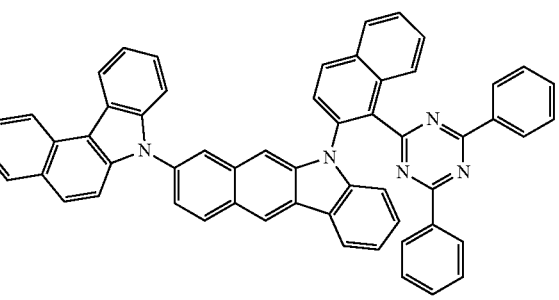
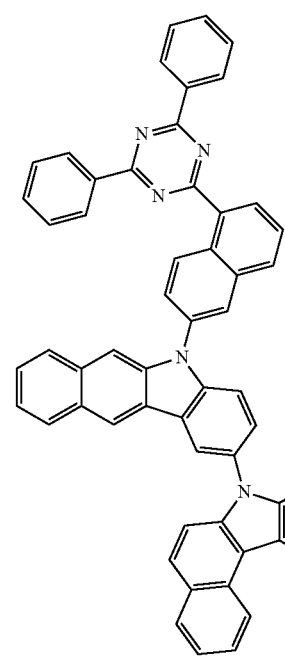

157
-continued
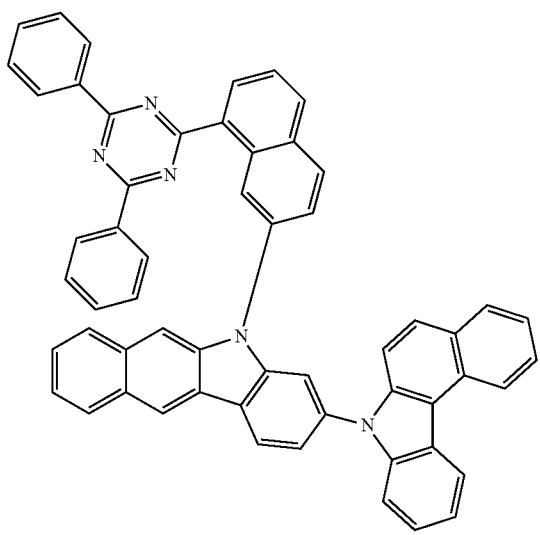
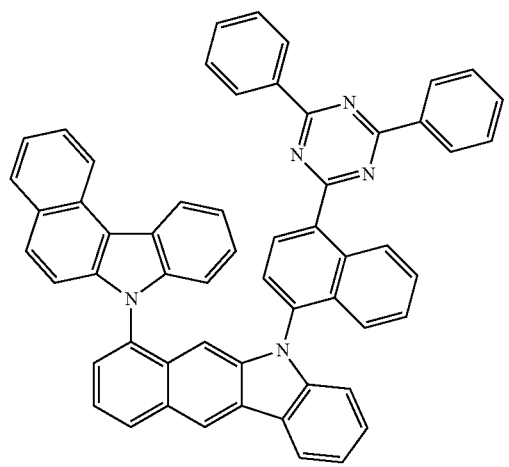
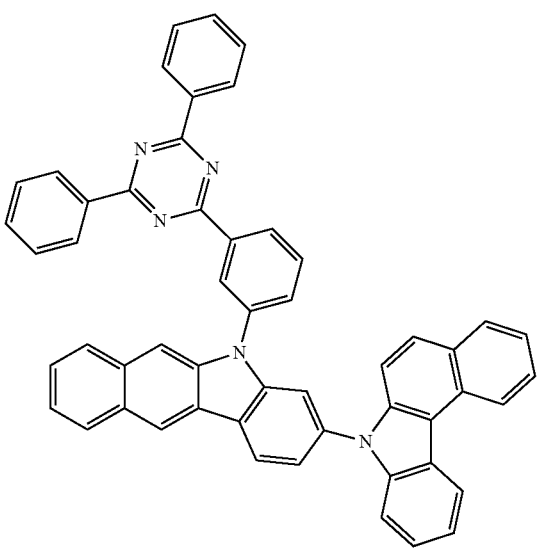
158
-continued
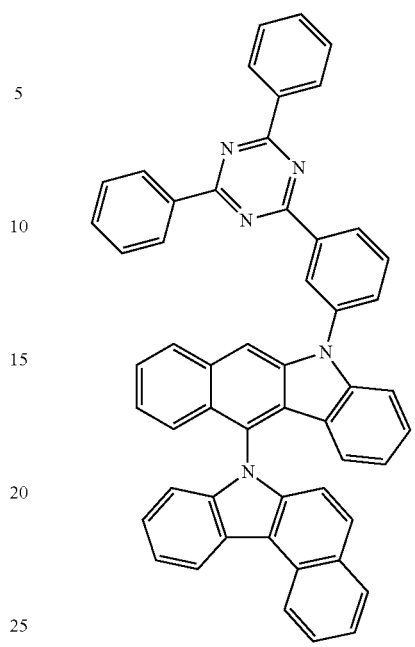
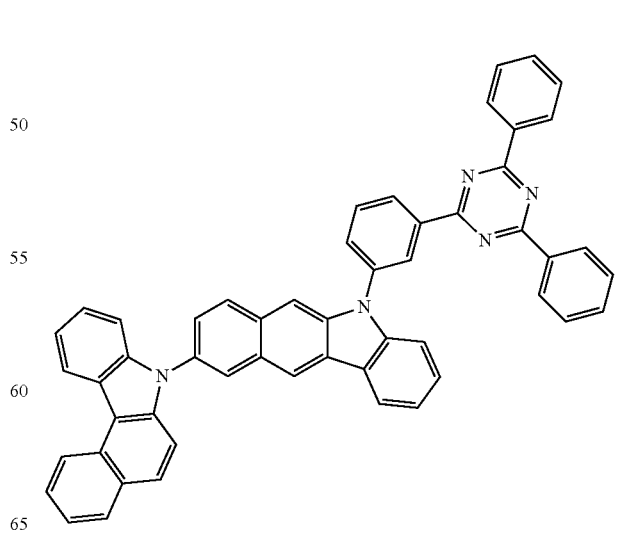

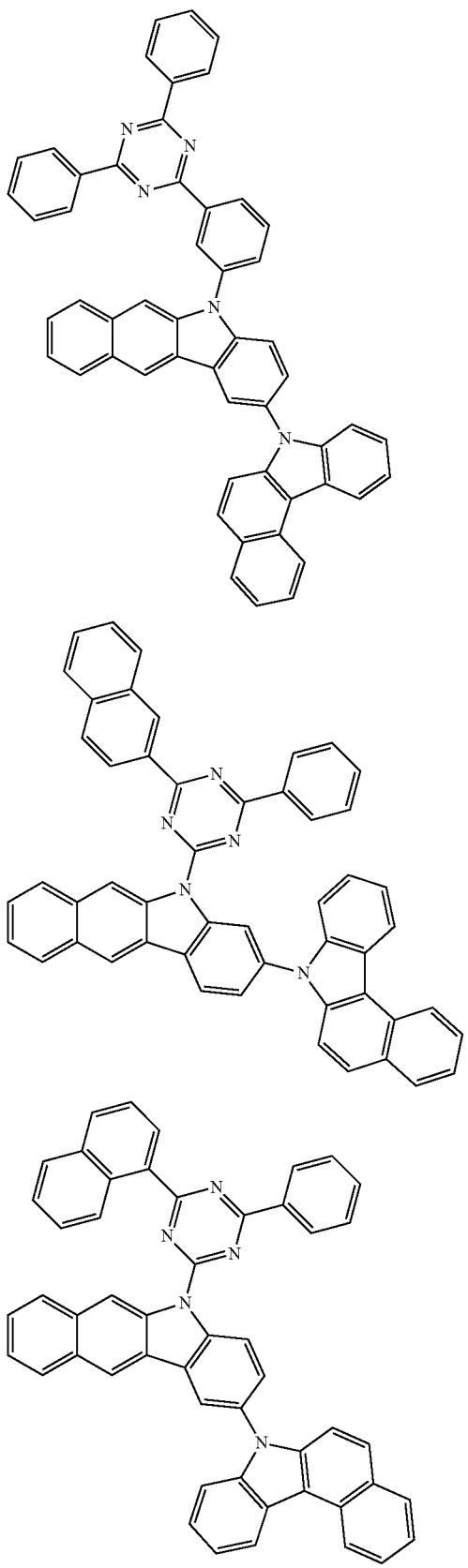
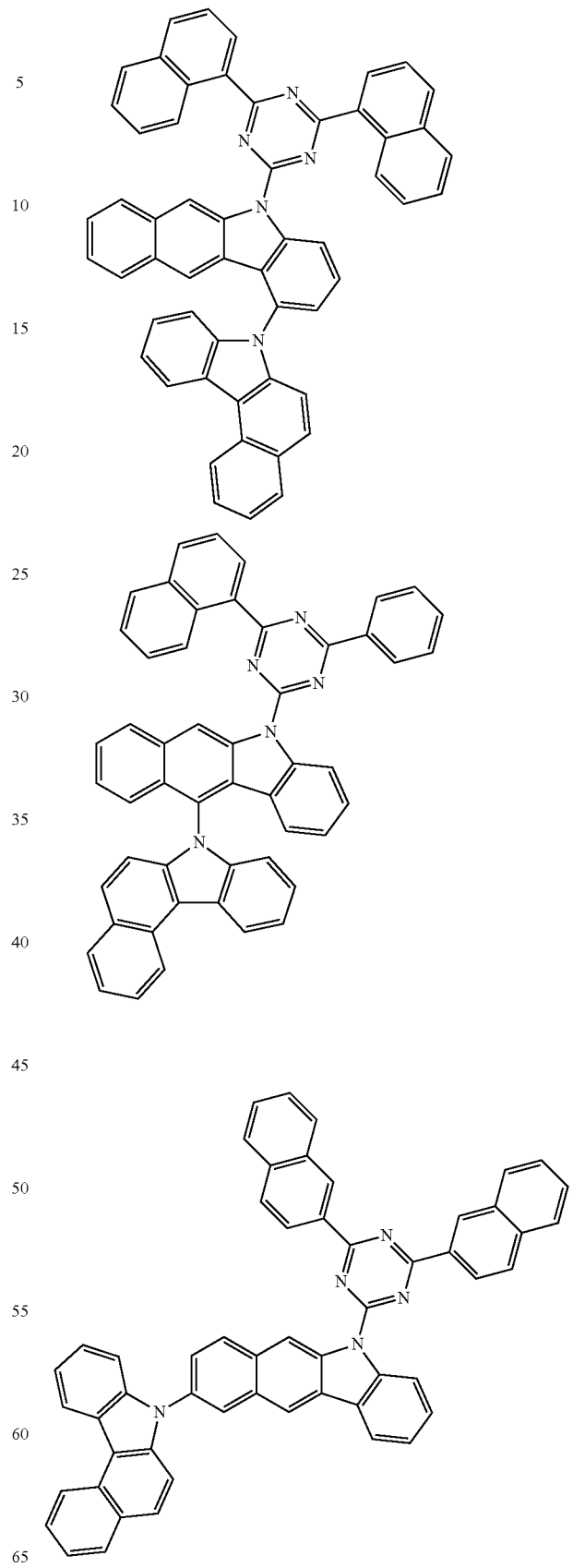

161
-continued
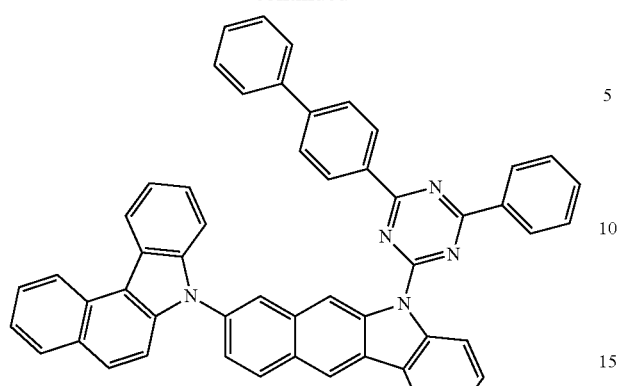
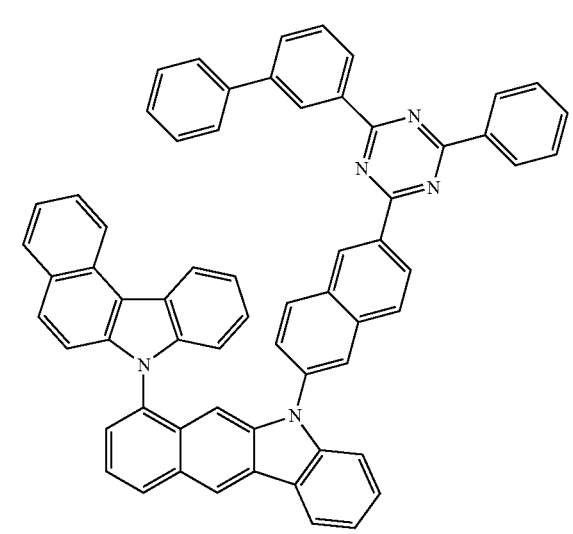
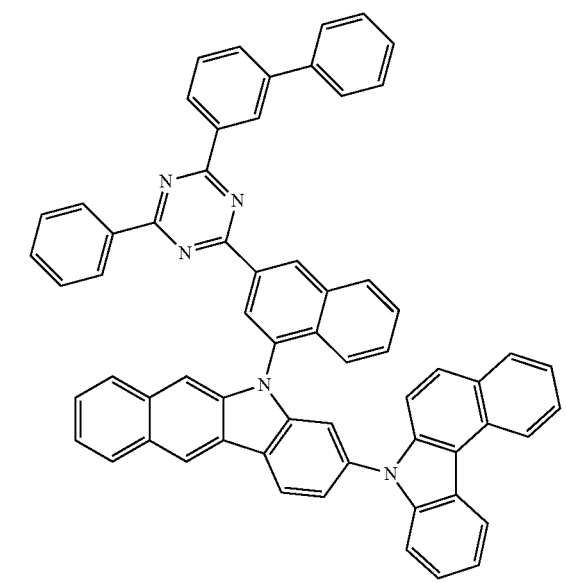
162
-continued
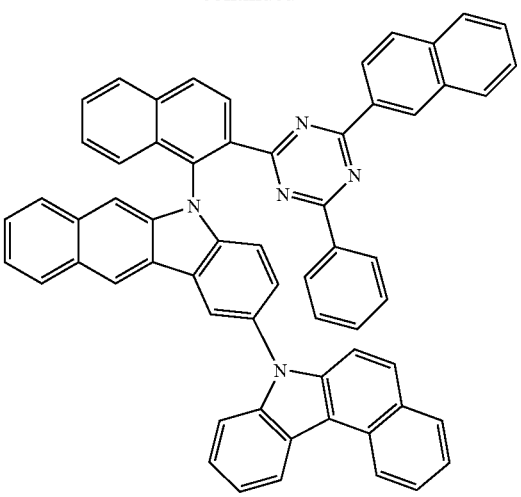
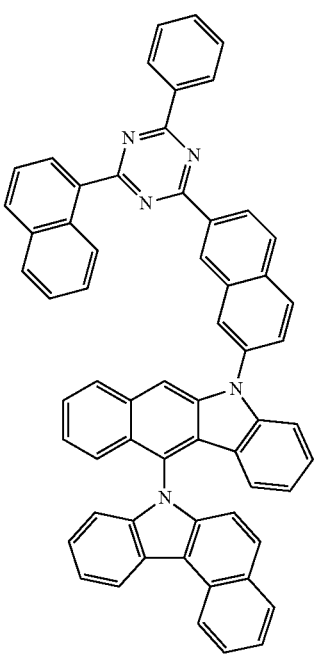
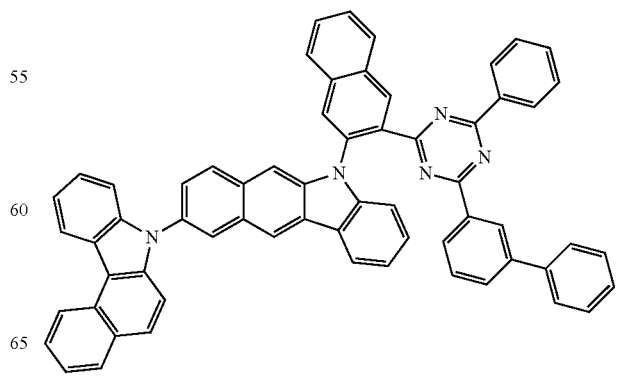

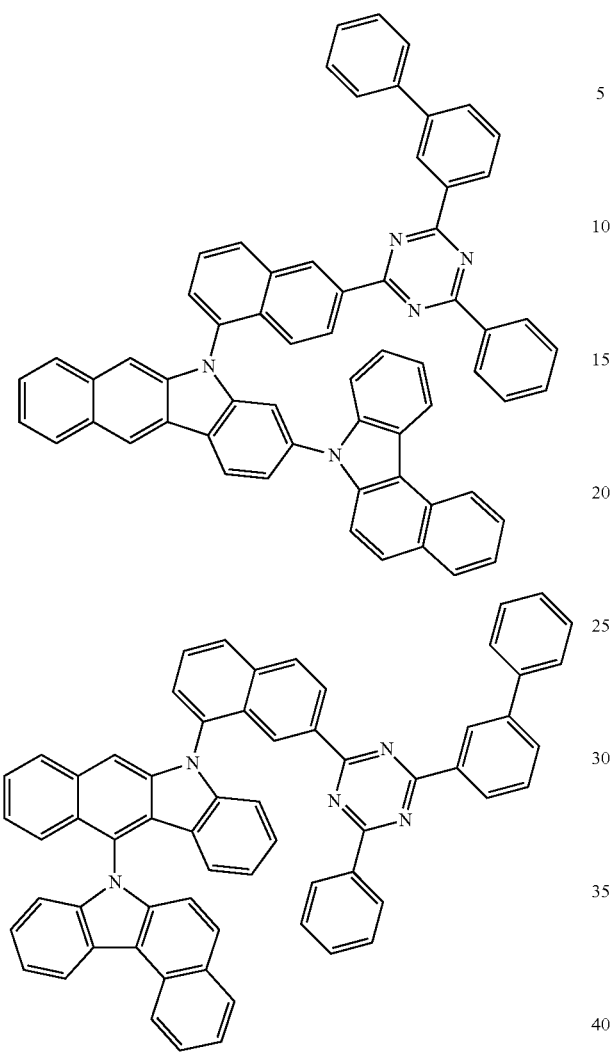
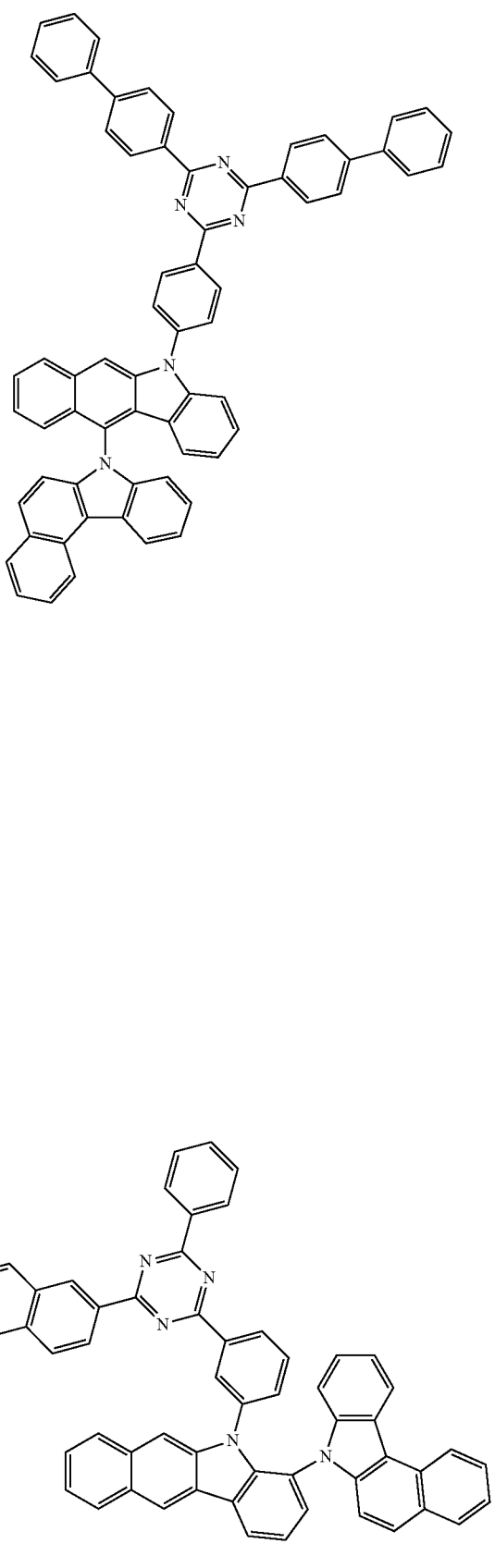

165
-continued
166
-continued
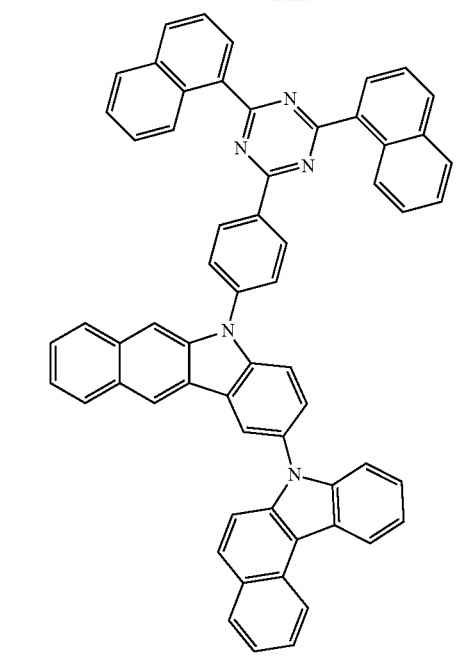
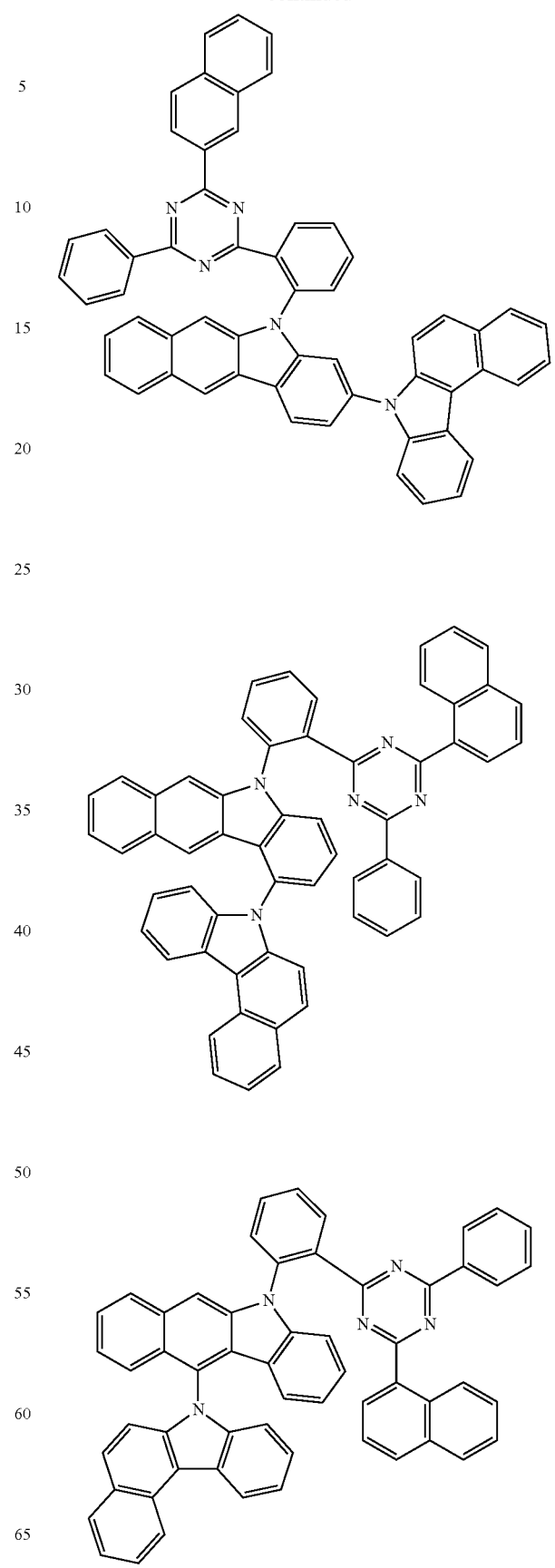

167
-continued
168
-continued
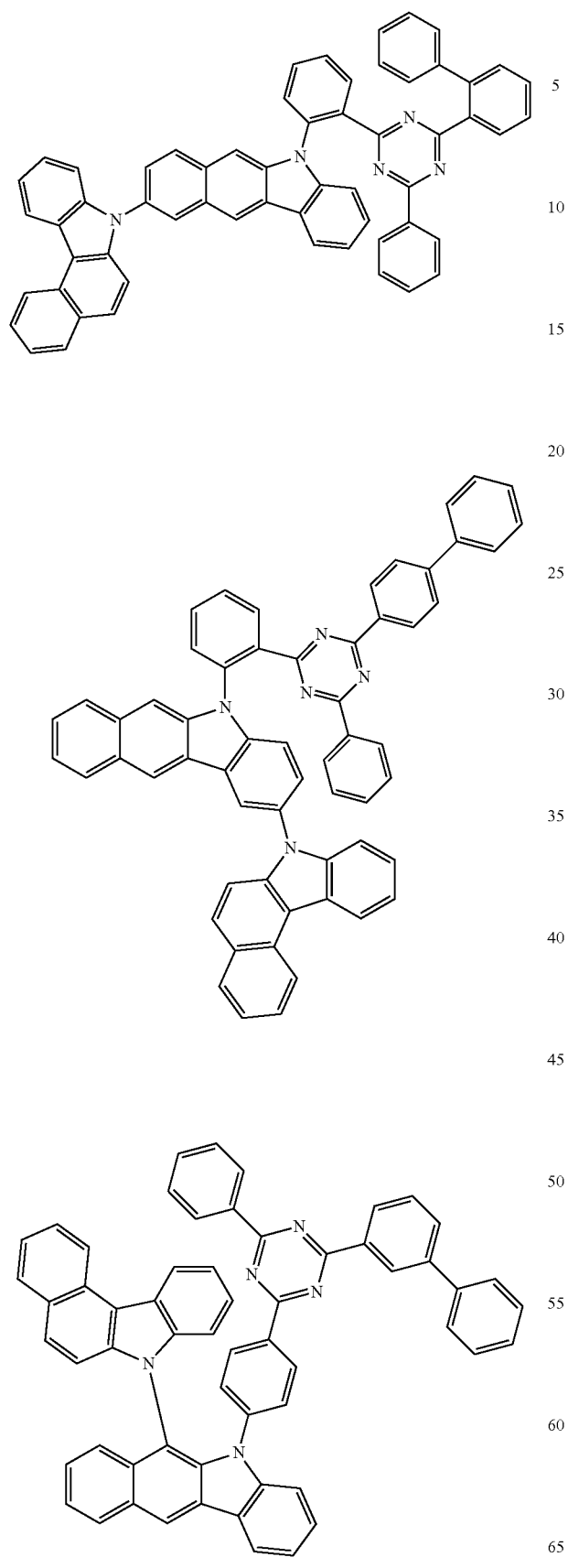
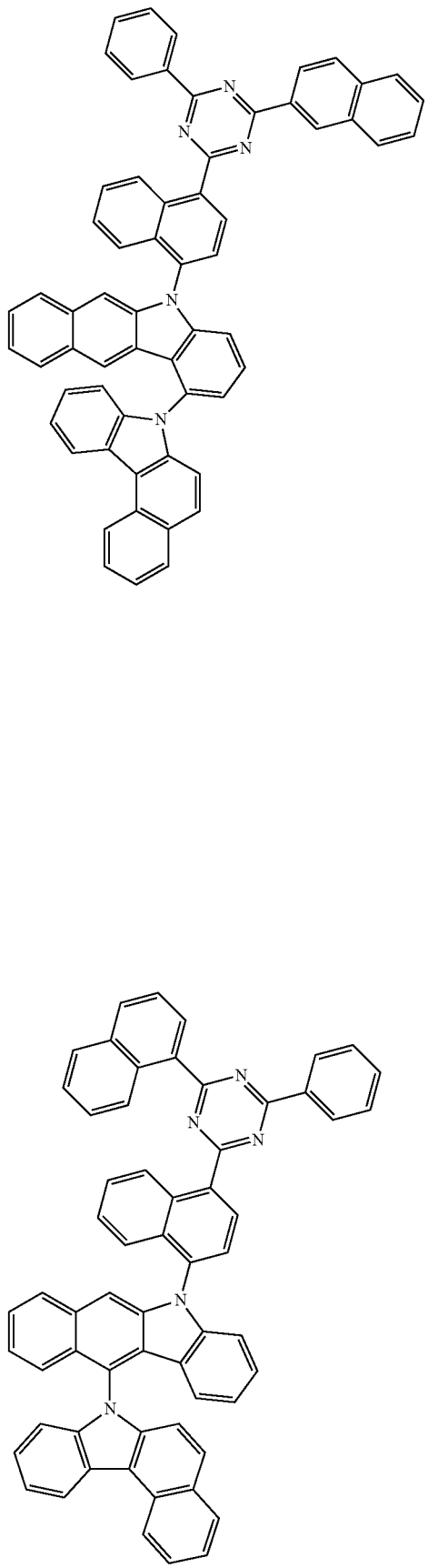

169
-continued
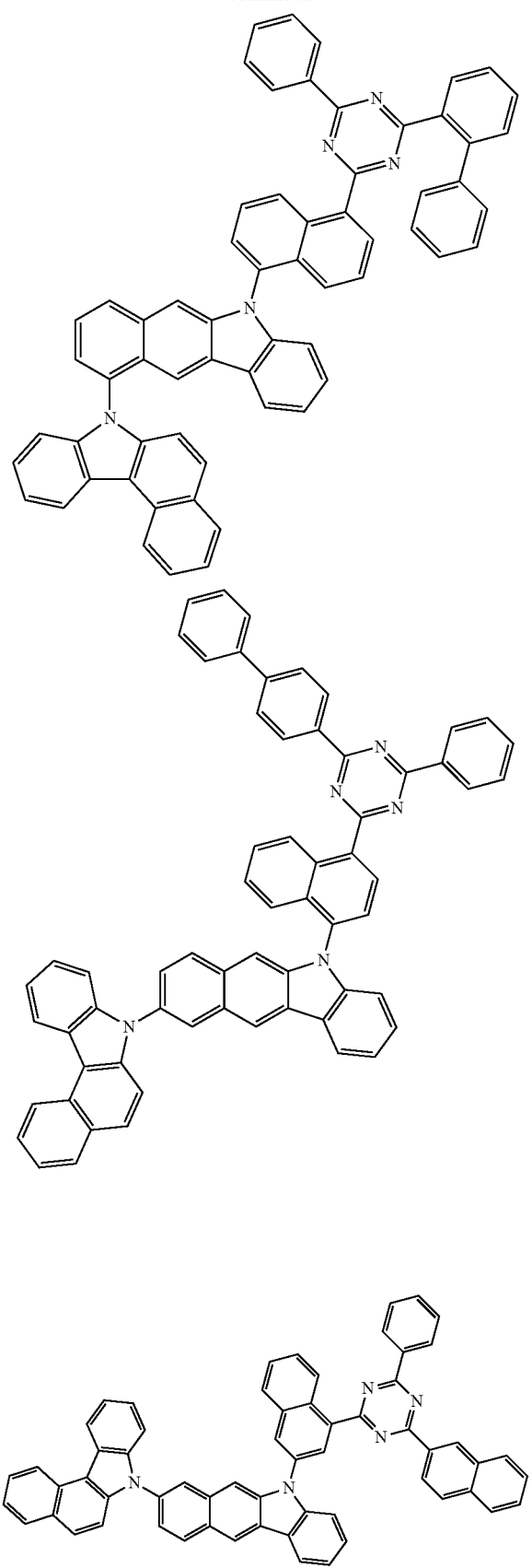
170
-continued
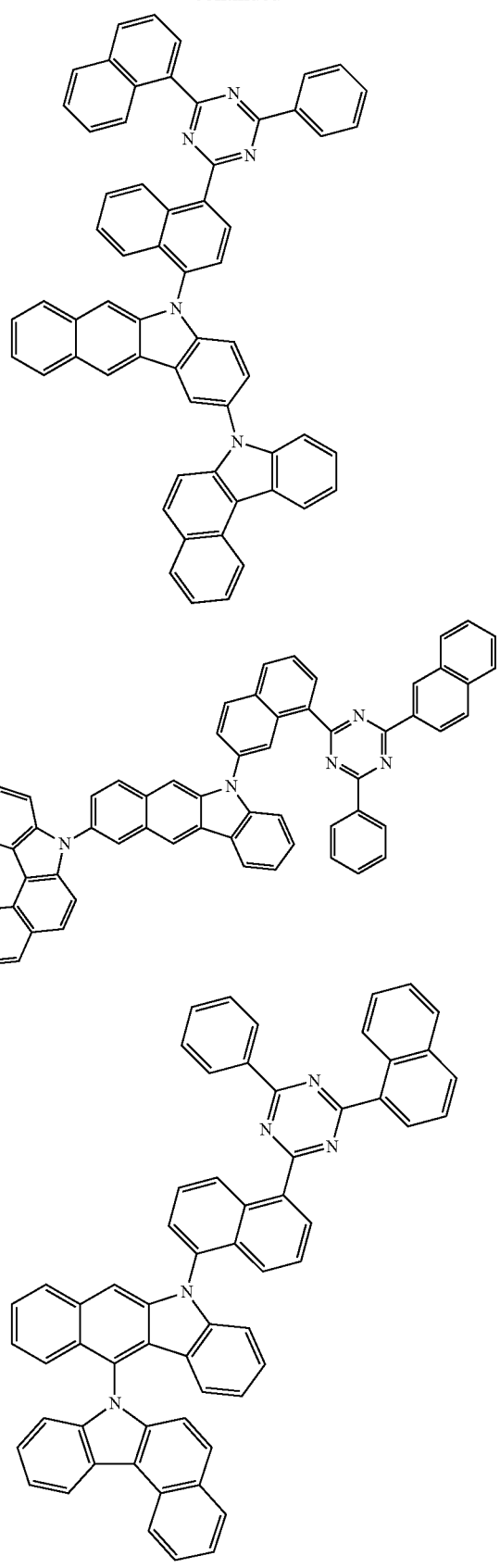

171
-continued
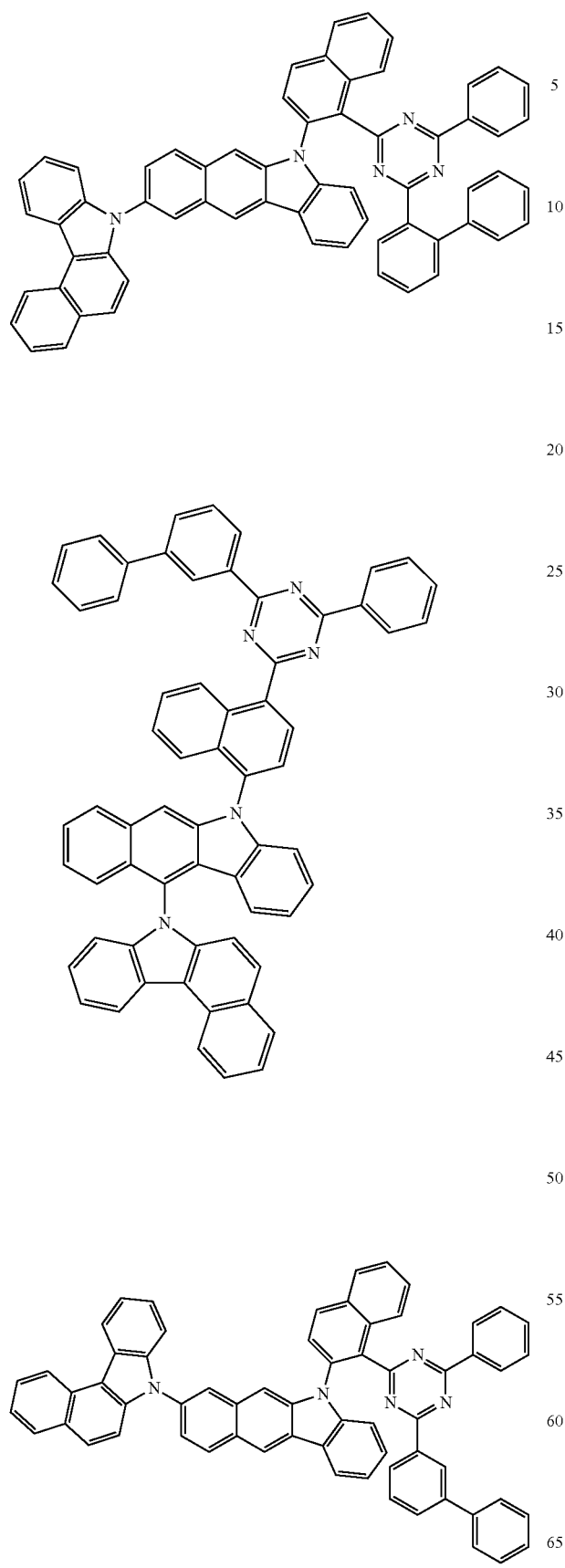
172
-continued
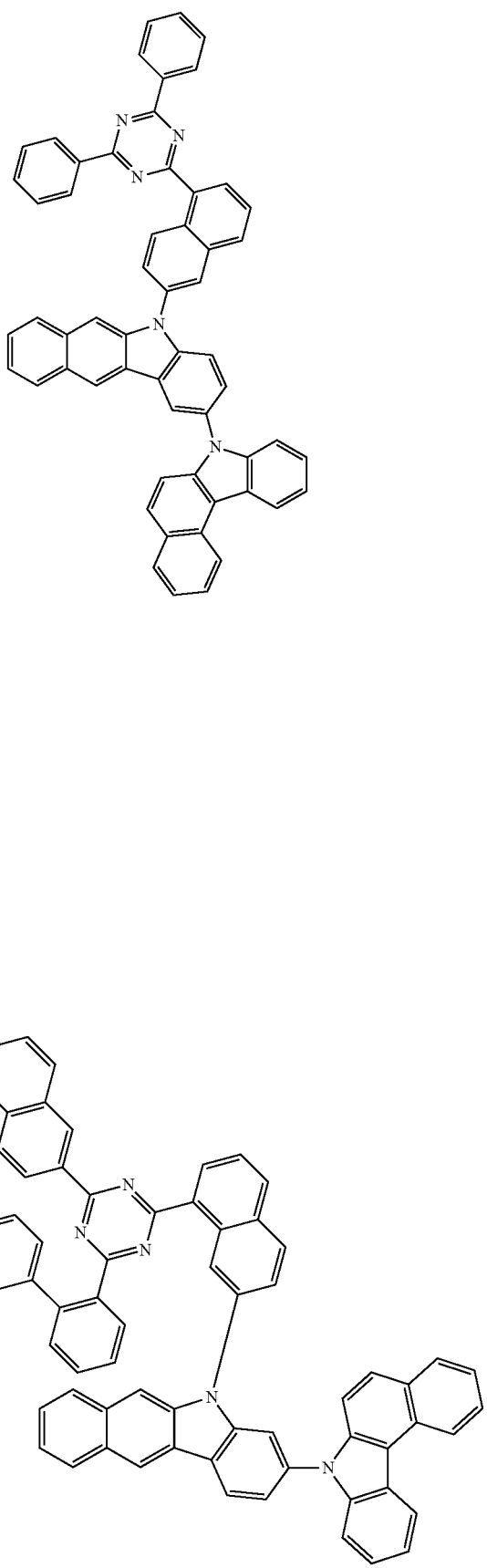

173
-continued
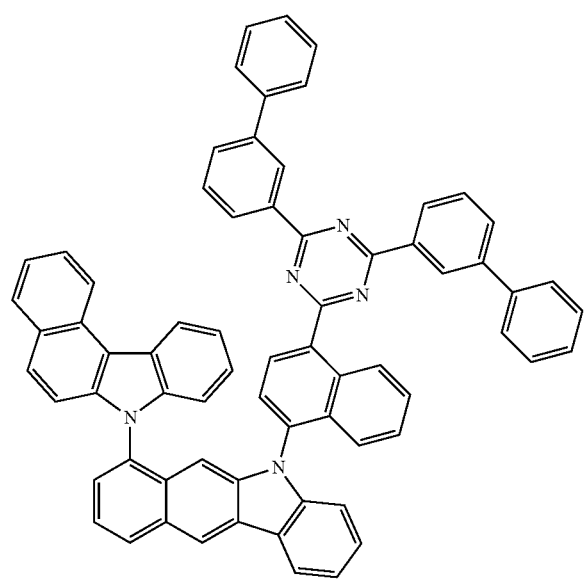
174
-continued
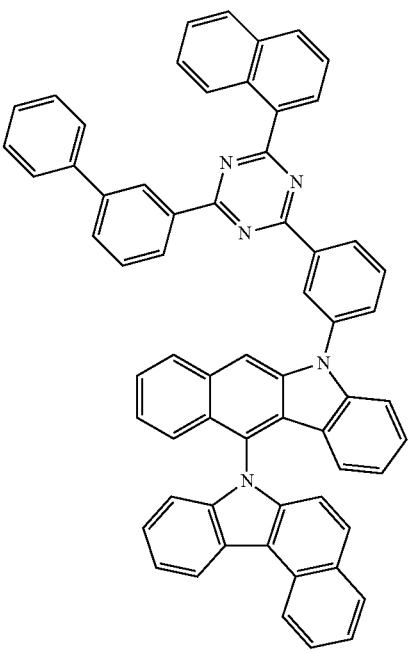
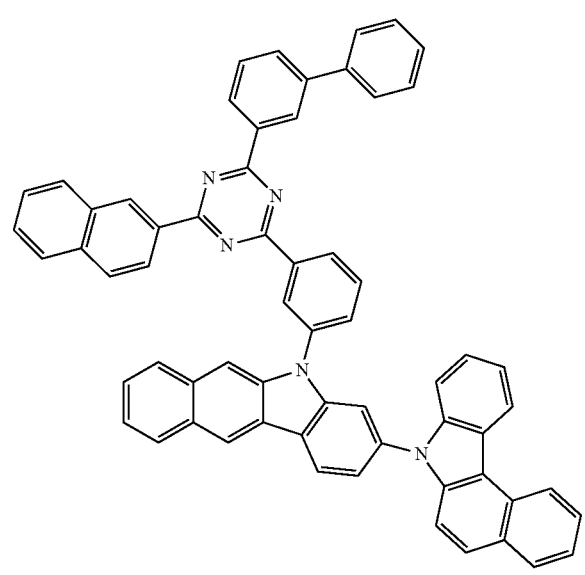

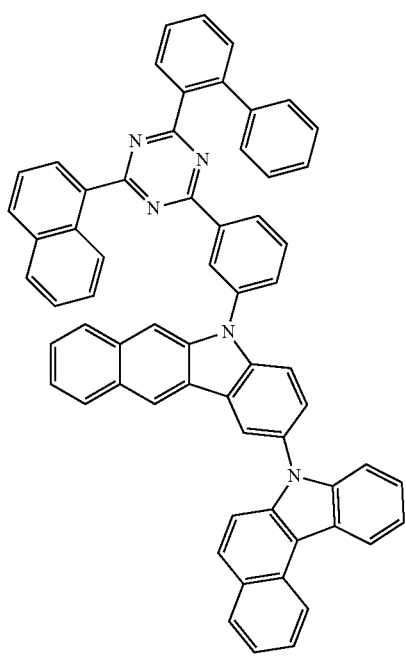
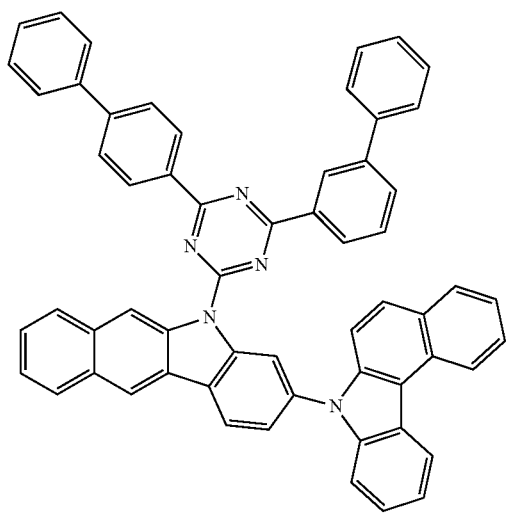
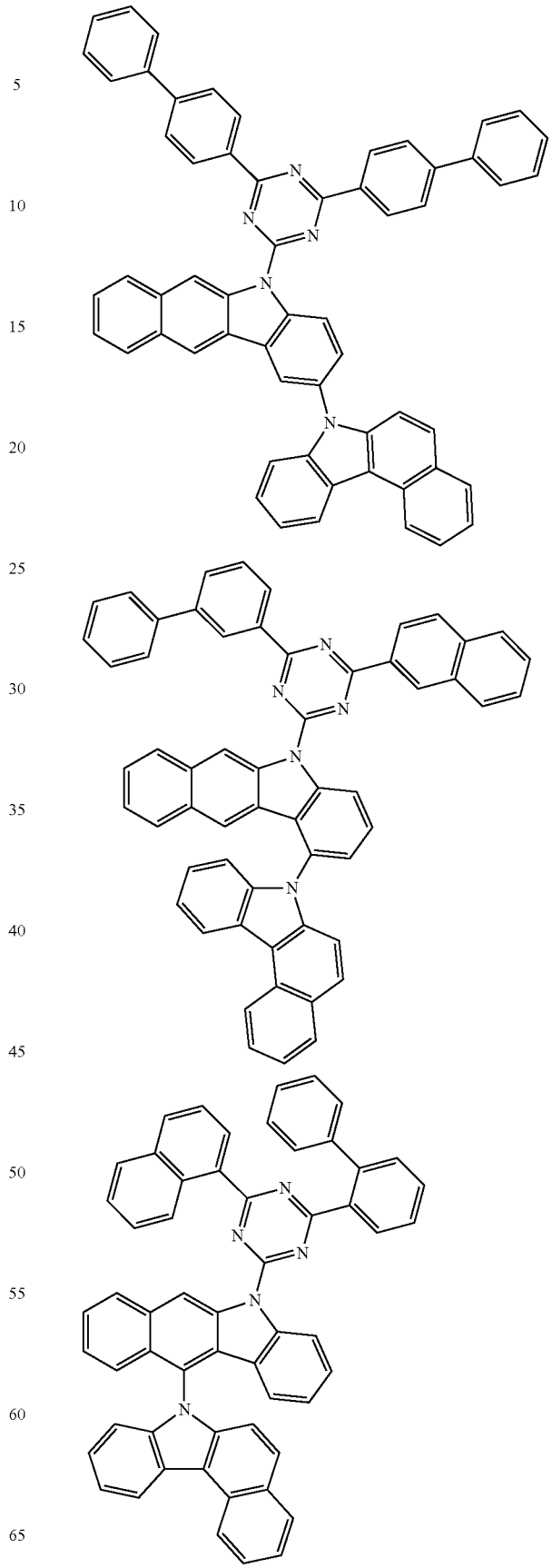

-continued
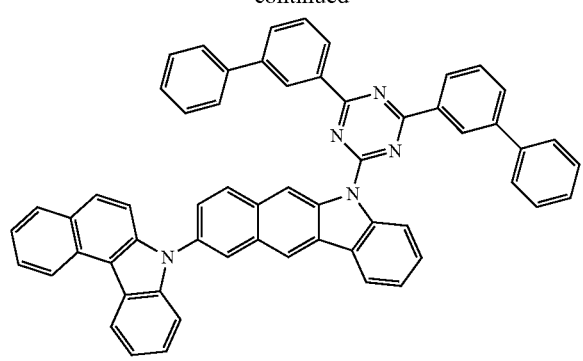
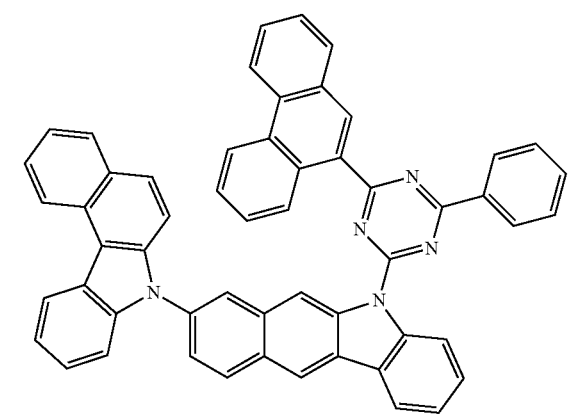
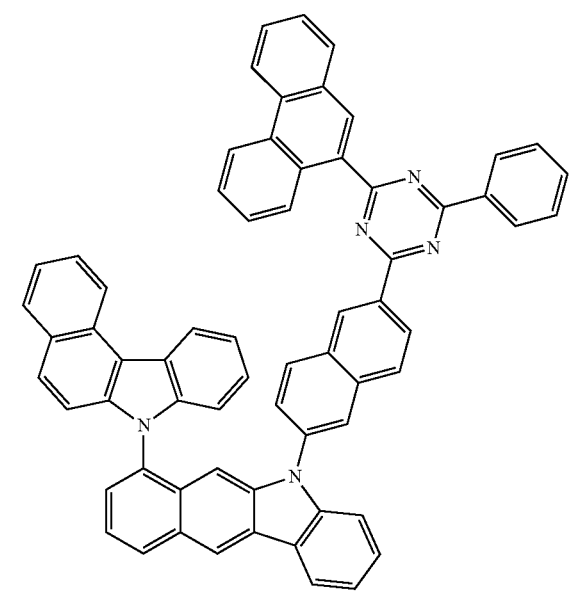
-continued
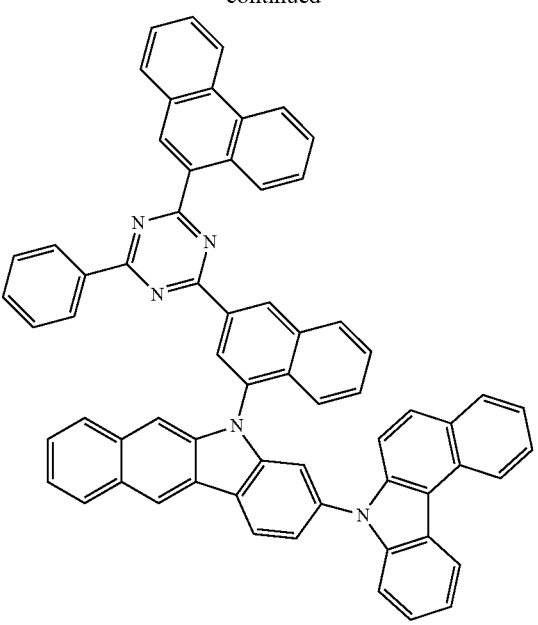
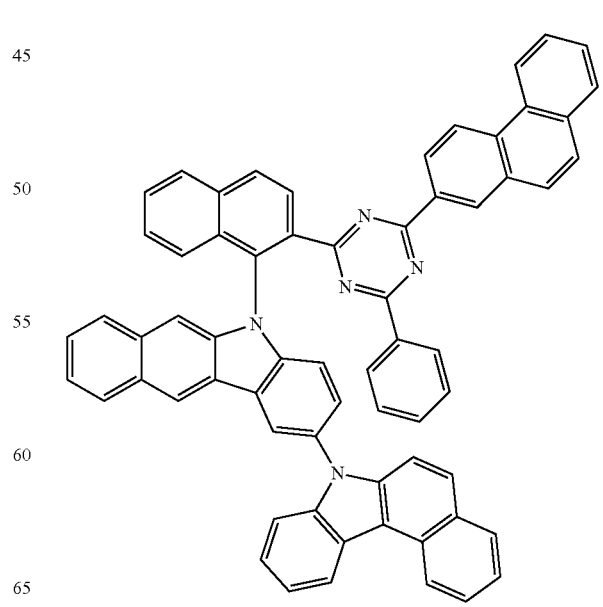

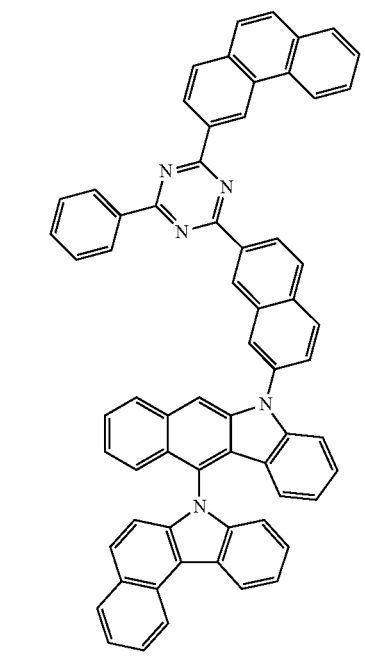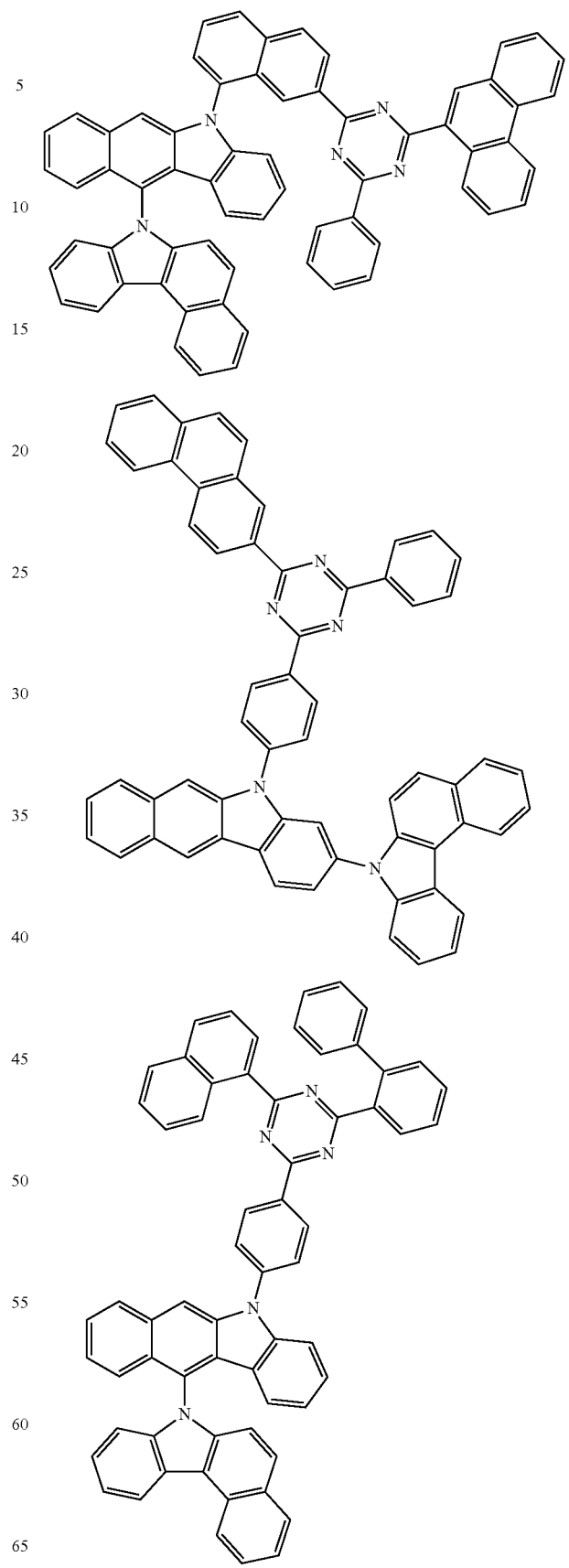

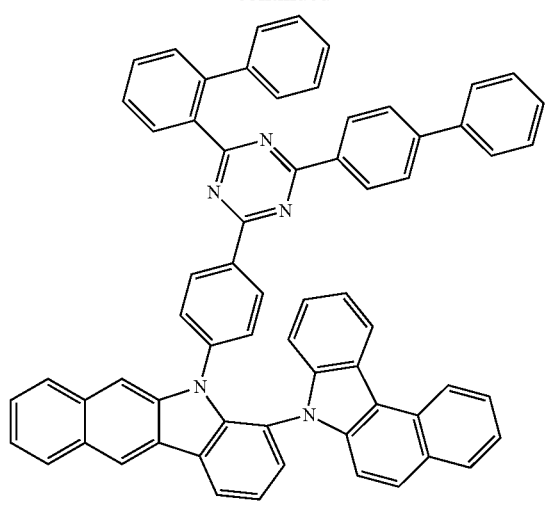
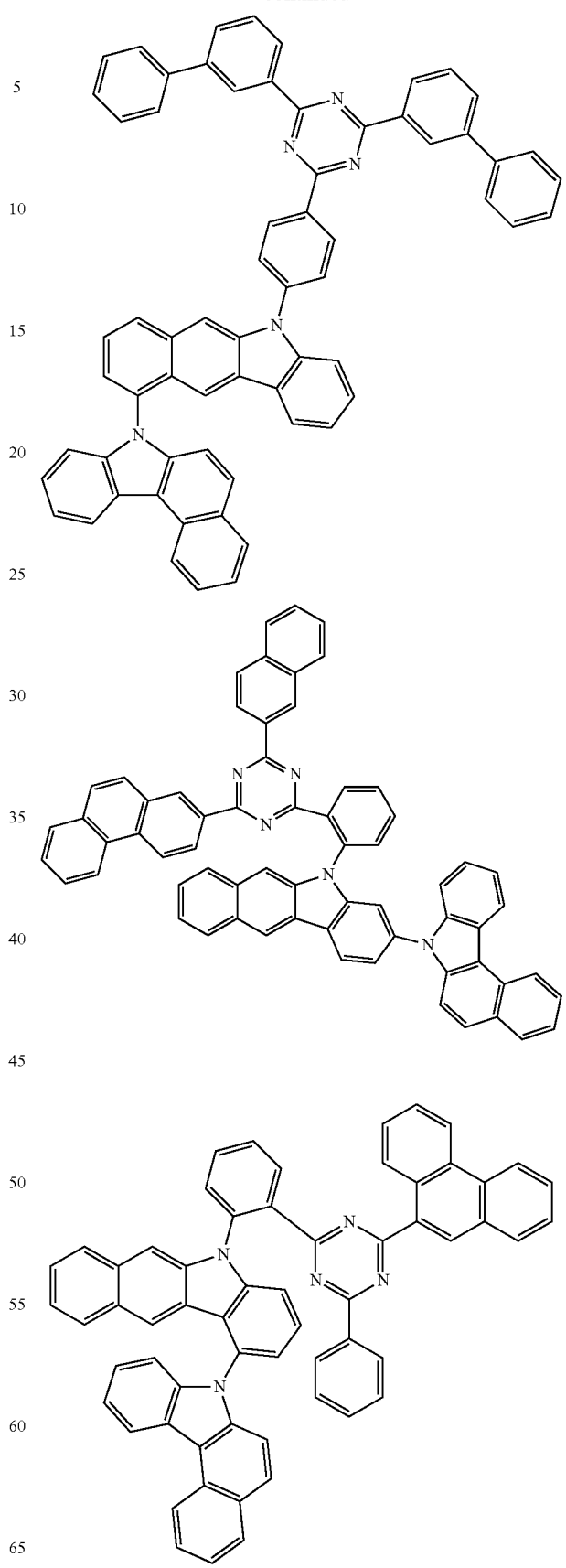

183
-continued
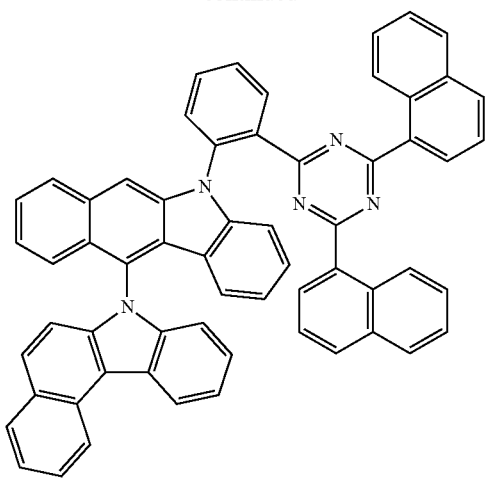
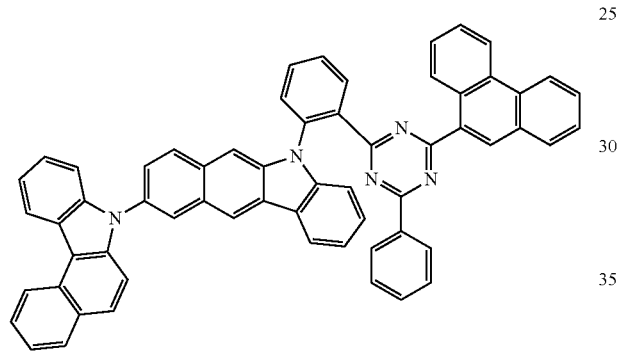
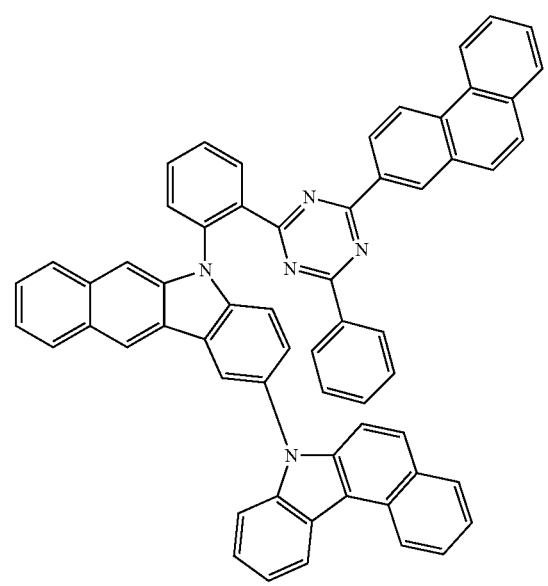
184
-continued
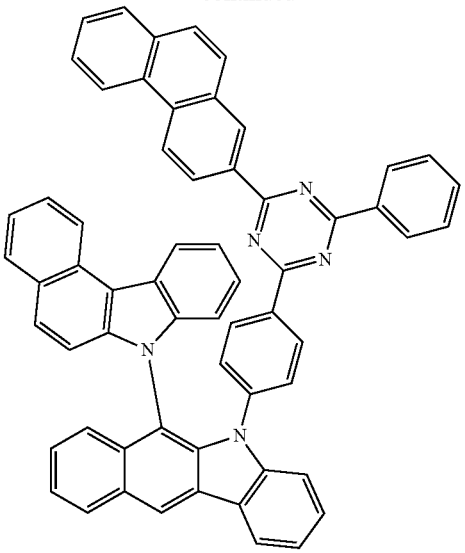
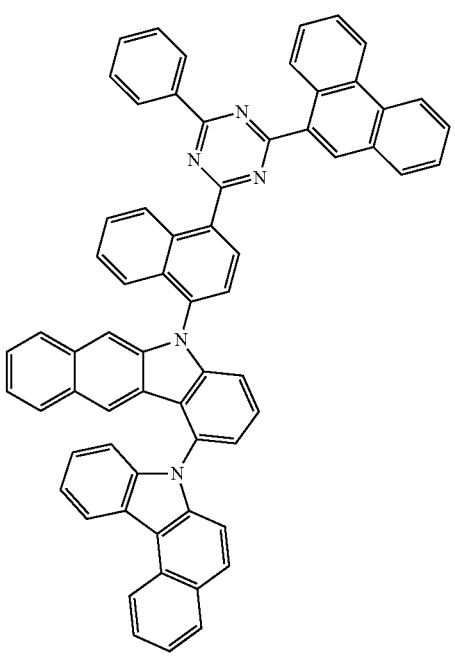

185
-continued
186
-continued
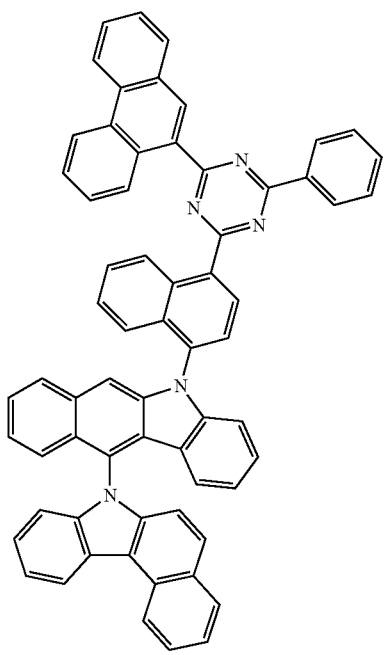
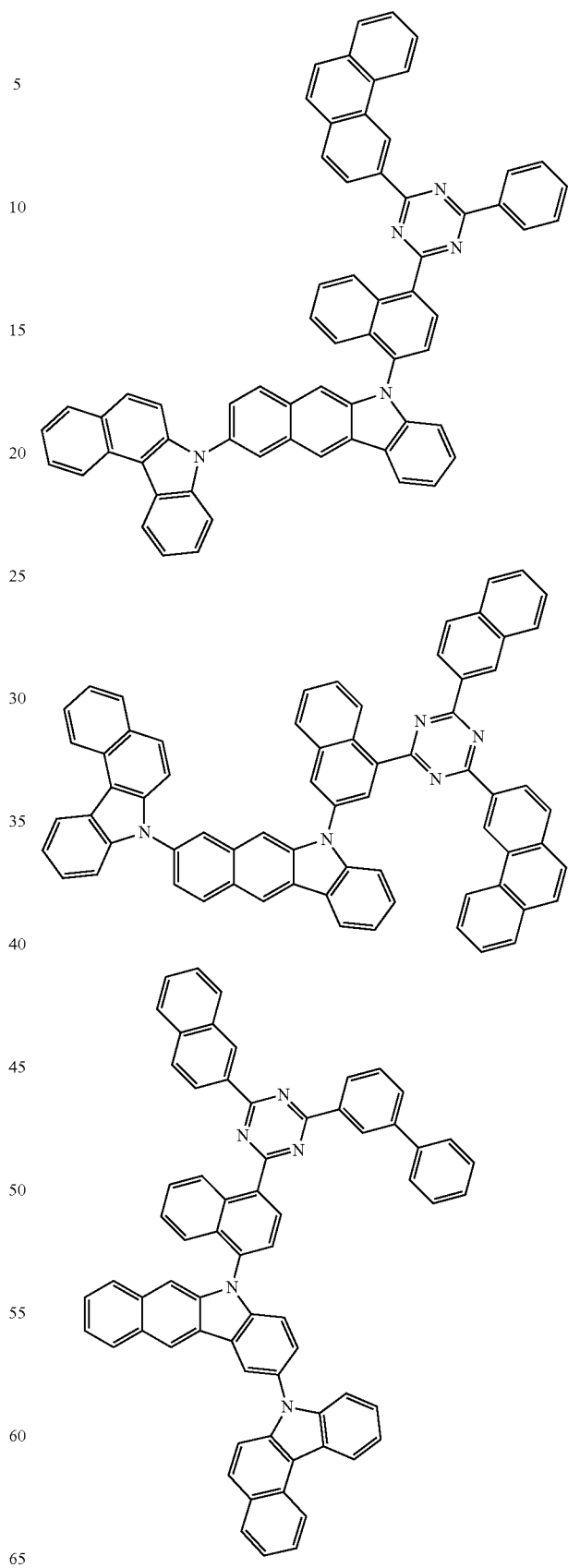

187
-continued
188
-continued
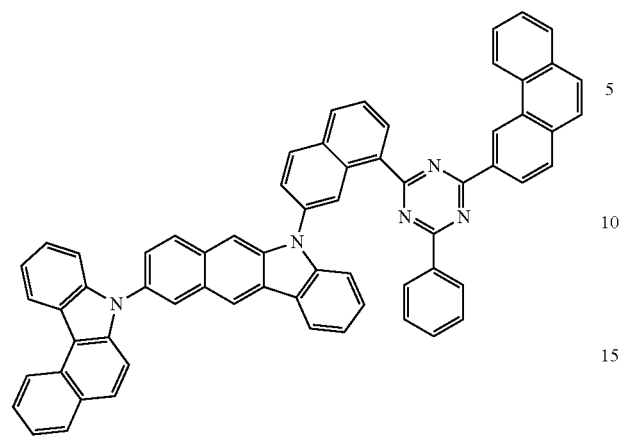
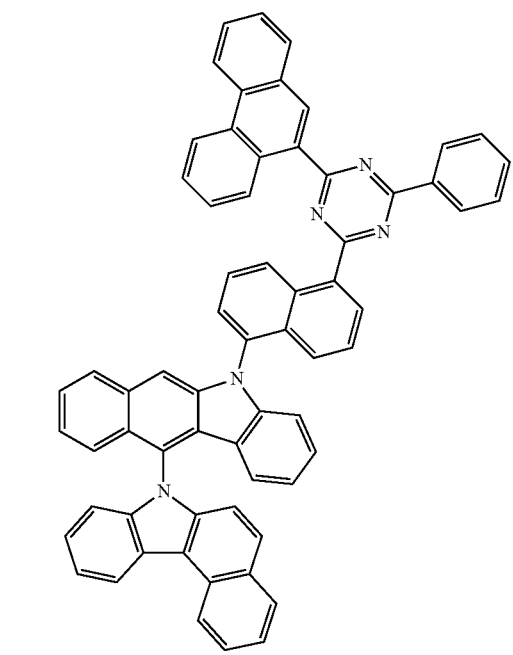
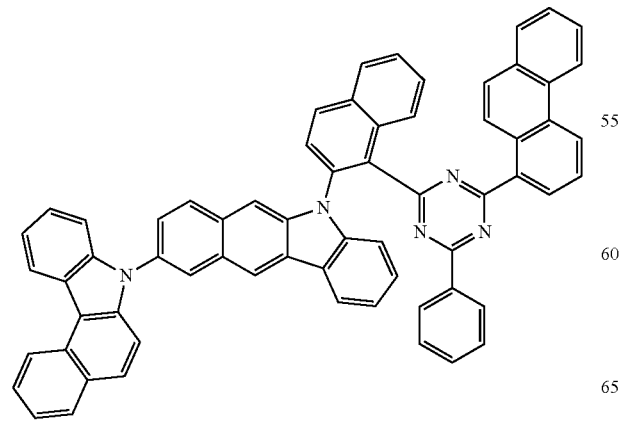
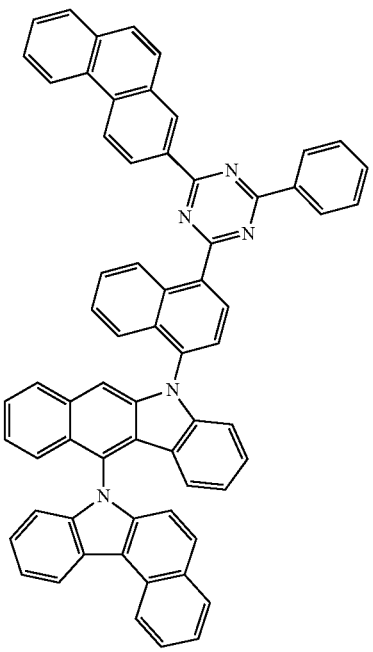
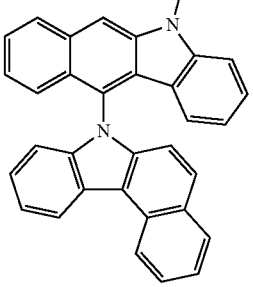
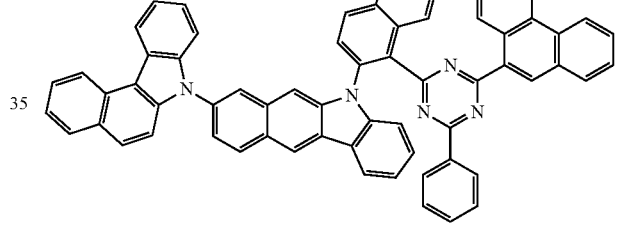
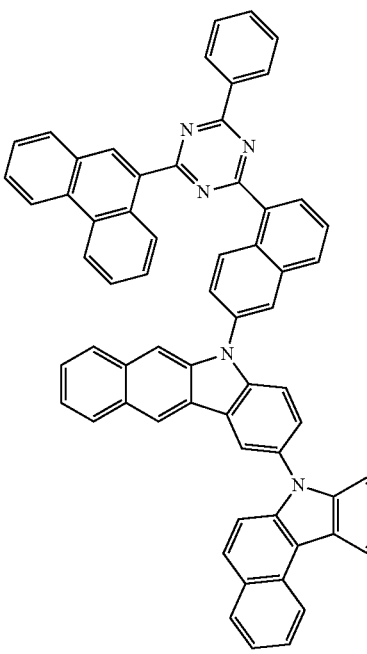

189
-continued
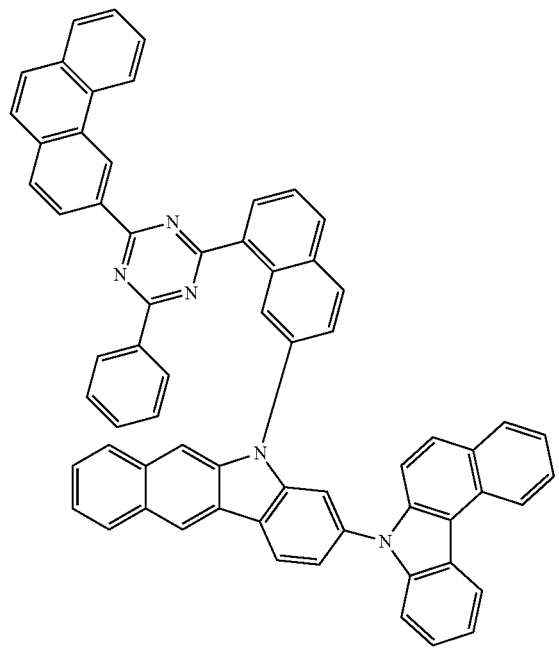
190
-continued
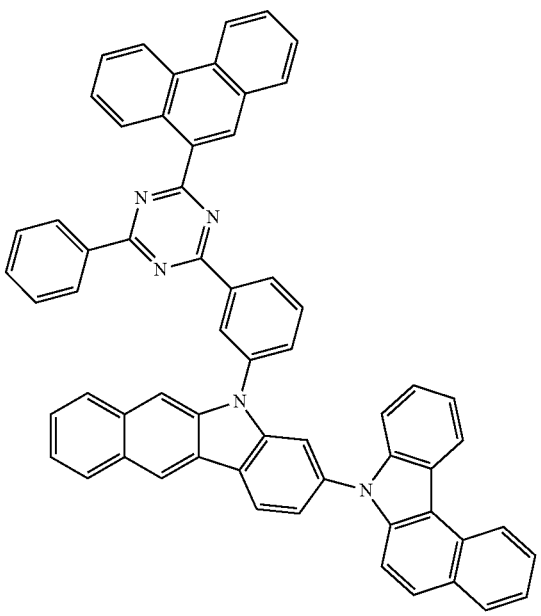
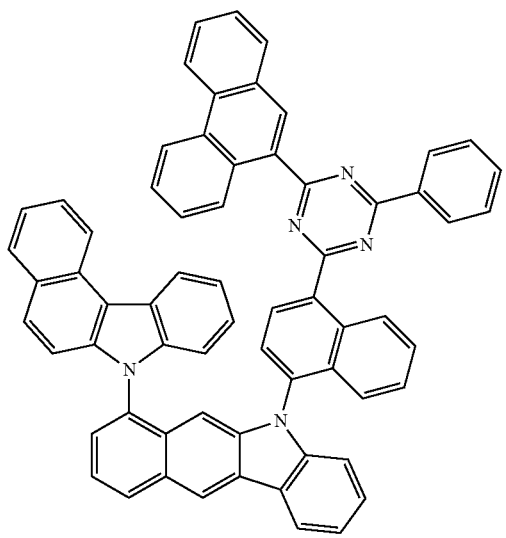
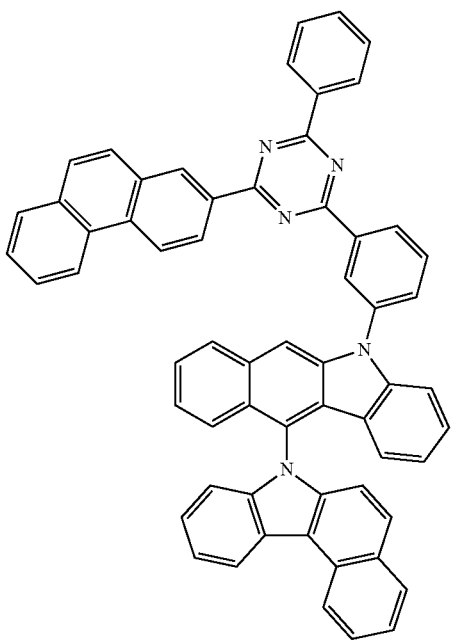

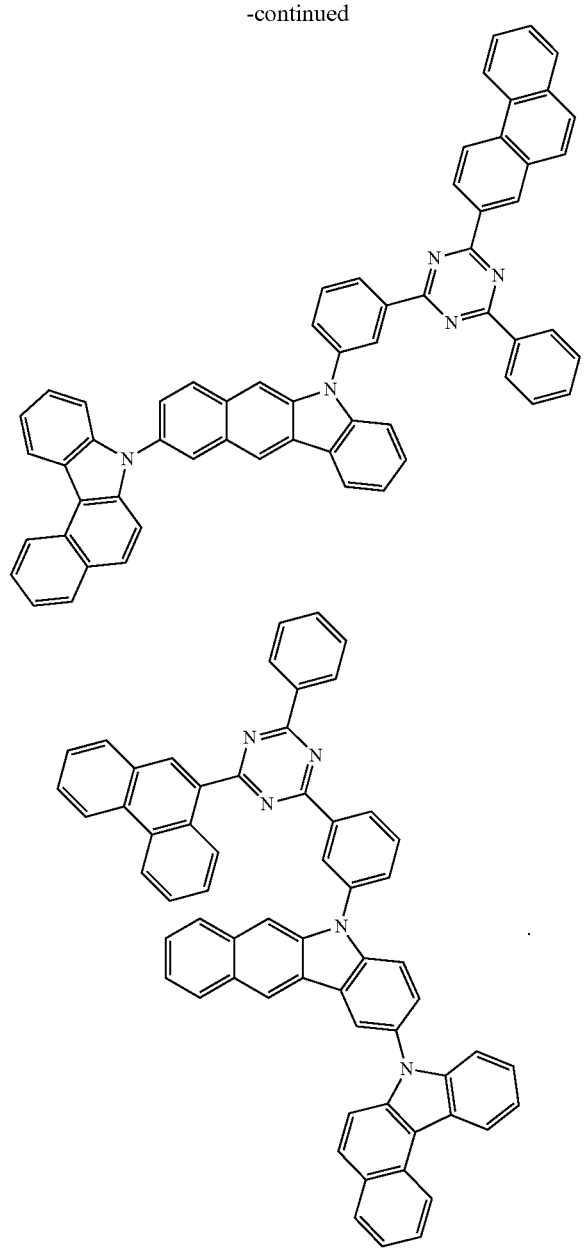

One embodiment of the present specification provides an organic light emitting device comprising a first electrode; a second electrode provided opposite to the first electrode; and one, two or more organic material layers provided between the first electrode and the second electrode, wherein one or more layers of the organic material layers comprise the compound of Chemical Formula 1 described above.

According to one embodiment of the present specification, the organic material layer of the organic light emitting device of the present specification can be formed in a single layer structure, but can also be formed in a multilayer structure in which two or more organic material layers are laminated. For example, the organic light emitting device of the present disclosure can have a structure comprising a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and can include a smaller or a larger number of organic material layers.

For example, the organic light emitting device of the present specification can have structures as illustrated in FIG. 1 to FIG. 4, however, the structure is not limited thereto.

FIG. 1 illustrates a structure of the organic light emitting device in which an anode (2), a light emitting layer (3) and a cathode (4) are consecutively laminated on a substrate (1). FIG. 1 is an exemplary structure of an organic light emitting device according to one embodiment of the present specification, and other organic material layers can be further included. In such a structure, the compound of Chemical Formula 1 can be included in the light emitting layer.

FIG. 2 illustrates a structure of the organic light emitting device in which an anode (2), a hole injection layer (5), a hole transfer layer (6), a light emitting layer (3), an electron transfer layer (7) and a cathode (4) are consecutively laminated on a substrate (1). FIG. 2 is an exemplary structure according to an embodiment of the present specification, and other organic material layers can be further included. Herein, the compound of Chemical Formula 1 can be included in the hole injection layer, the hole transfer layer, the light emitting layer or the electron transfer layer.

FIG. 3 illustrates a structure of the organic light emitting device in which an anode (2), a hole injection layer (5), a hole transfer layer (6), an electron blocking layer (8), a light emitting layer (3), an electron transfer layer (7) and a cathode (4) are consecutively laminated on a substrate (1). FIG. 3 is an exemplary structure according to an embodiment of the present specification, and other organic material layers can be further included. Herein, the compound of Chemical Formula 1 can be included in the hole injection layer, the hole transfer layer, the electron blocking layer, the light emitting layer or the electron transfer layer.

FIG. 4 illustrates a structure of the organic light emitting device in which an anode (2), a hole injection layer (5), a hole transfer layer (6), an electron blocking layer (8), a light emitting layer (3), a hole blocking layer (9), an electron injection and transfer layer (10) and a cathode (4) are consecutively laminated on a substrate (1). Herein, the compound of Chemical Formula 1 can be included in the hole injection layer, the hole transfer layer, the electron blocking layer, the light emitting layer, the hole blocking layer, or the electron injection and transfer layer.

According to one embodiment of the present specification, the organic material layer includes a hole injection layer, a hole transfer layer or an electron blocking layer, and the hole injection layer, the hole transfer layer or the electron blocking layer includes the compound of Chemical Formula 1.

According to one embodiment of the present specification, the organic material layer includes a light emitting layer, and the light emitting layer includes the compound of Chemical Formula 1. In this case, the content of the compound of Chemical Formula 1 is from 50 parts by weight to 100 parts by weight with respect to 100 parts by weight of the light emitting layer.

According to one embodiment of the present specification, the organic material layer comprises a light emitting layer, and the light emitting layer comprises the compound of Chemical Formula 1 as a host of the light emitting layer.

According to one embodiment of the present specification, the organic material layer comprises a light emitting layer, and the light emitting layer comprises the compound of Chemical Formula 1; and a dopant.

According to one embodiment of the present specification, the content of the dopant is from 0.01 parts by weight to 10 parts by weight with respect to 100 parts by weight of the compound of Chemical Formula 1.

According to one embodiment of the present specification, the light emission wavelength of the dopant is not limited, and the dopant can be a phosphorescent dopant or a fluorescent dopant.

According to one embodiment of the present specification, the dopant can be an iridium complex.

According to one embodiment of the present specification, the dopant can be one, two or more types selected from among the following compounds, but is not limited thereto:

Dp-1
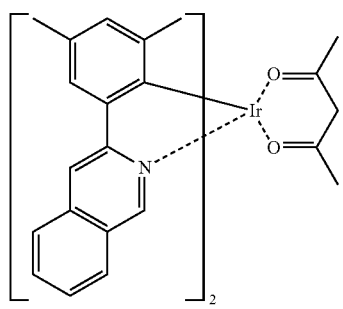

Dp-2
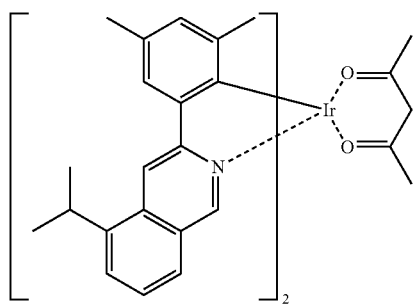

Dp-3
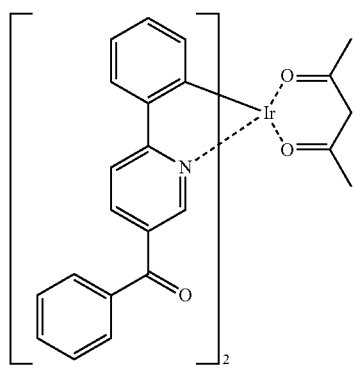

Dp-4
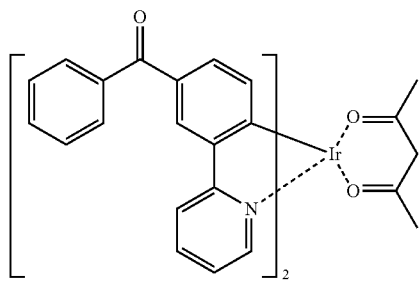

Dp-5
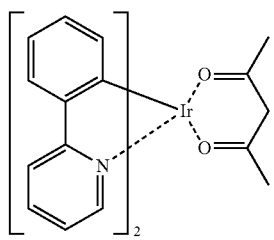

Dp-6
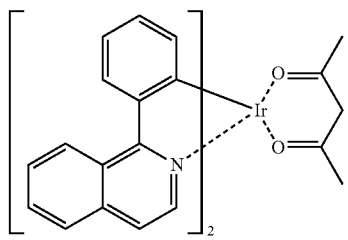

Dp-7
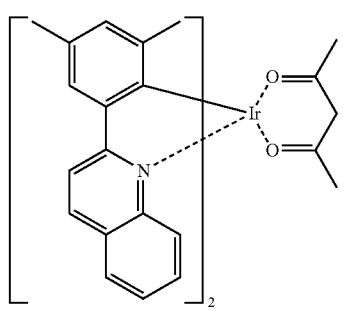

Dp-8
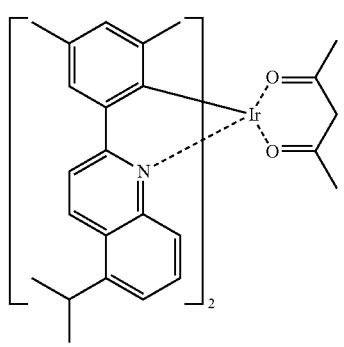

Dp-9
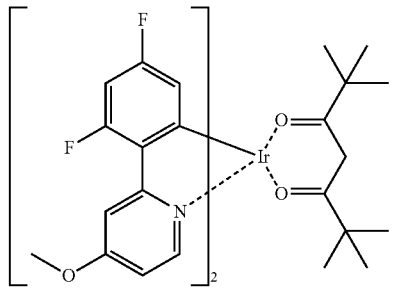

Dp-10
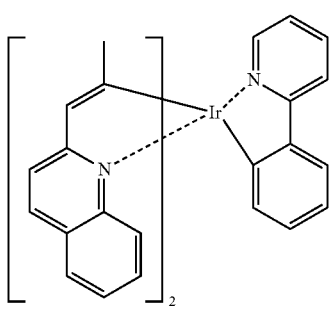
Dp-11
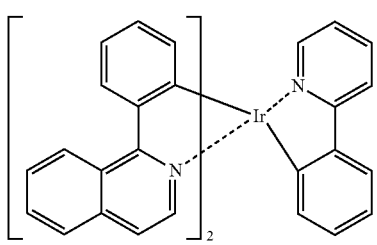
Dp-12
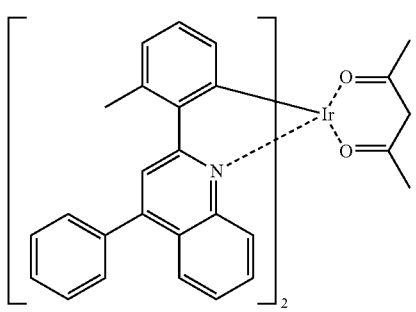
Dp-13
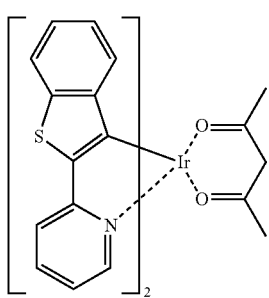
Dp-14
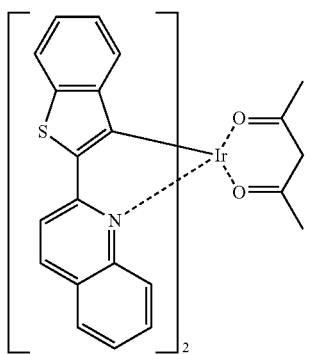
Dp-15
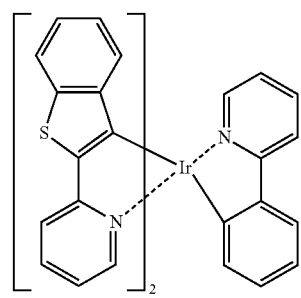
Dp-16
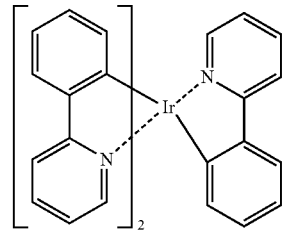
Dp-17
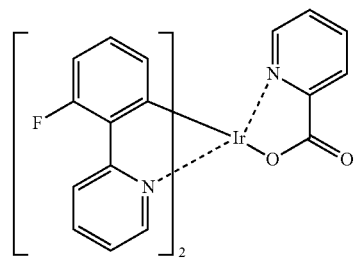
Dp-18
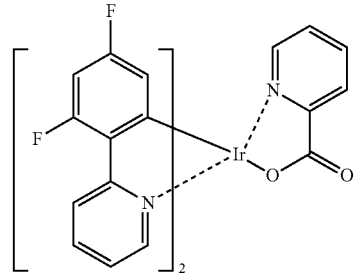
Dp-19
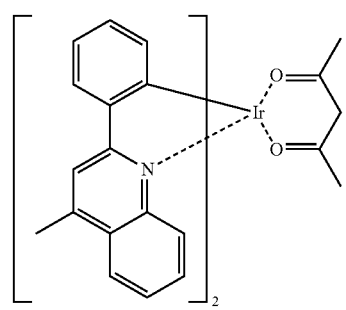

Dp-20 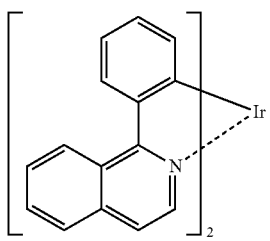
Dp-21 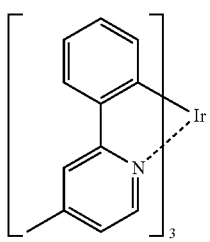
Dp-22 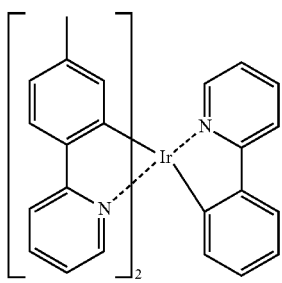
Dp-23 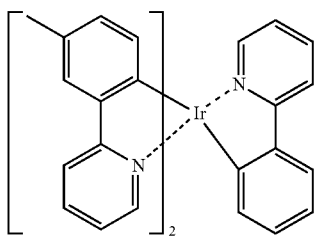
Dp-24 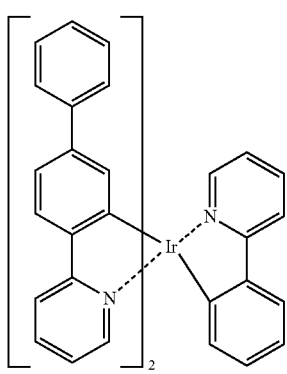
Dp-25 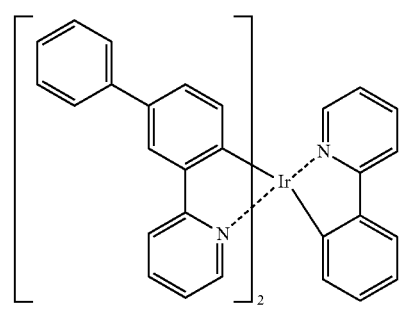
Dp-26 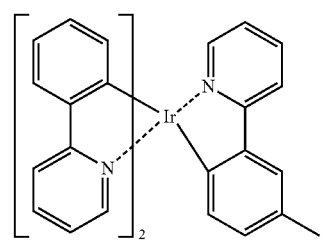
Dp-27 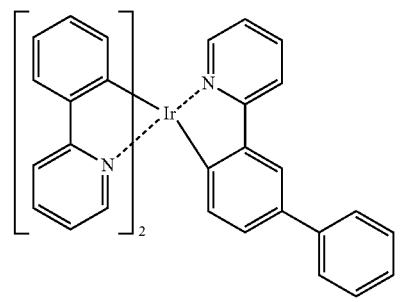
Dp-28 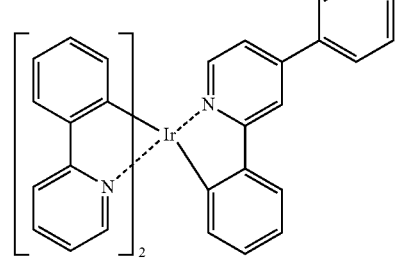
Dp-29 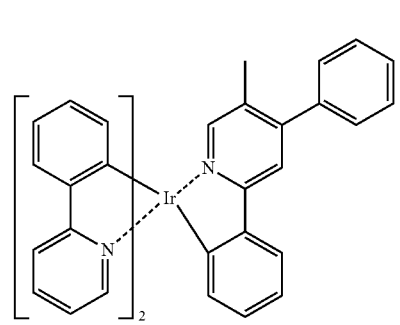

Dp-30 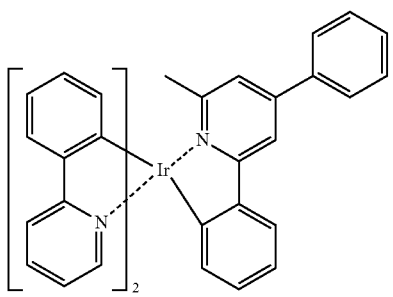
Dp-31 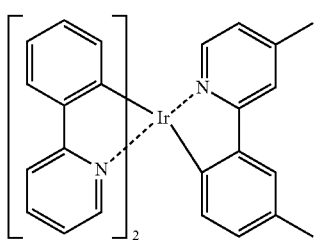
Dp-32 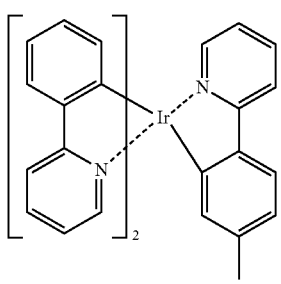
Dp-33 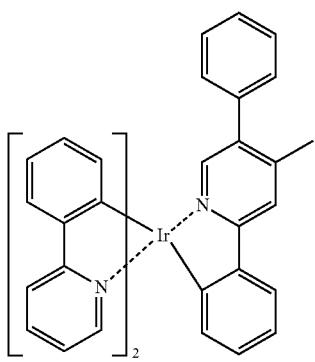
Dp-34 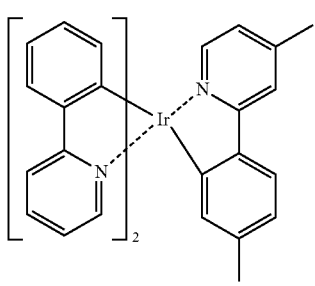
Dp-35 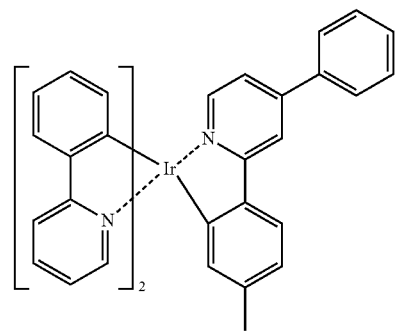
Dp-36 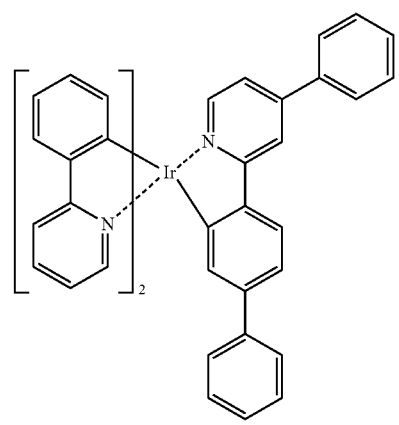
Dp-37 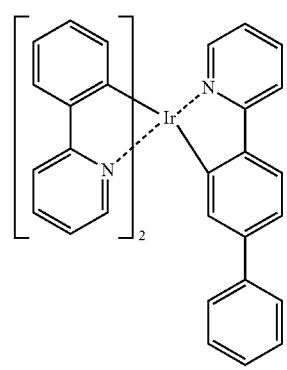
Dp-38 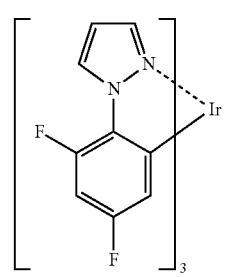

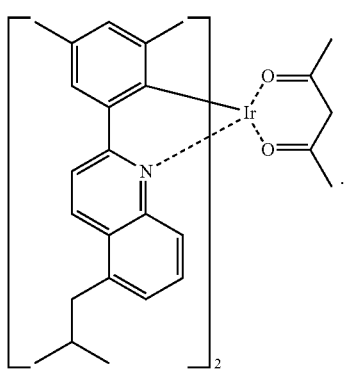

Dp-39

According to one embodiment of the present specification, the organic material layer comprises a hole blocking layer, an electron transfer layer, an electron injection layer, or an electron injection and transfer layer, and the hole blocking layer, the electron transfer layer, the electron injection layer, or the electron injection and transfer layer comprises the compound of Chemical Formula 1.

According to one embodiment of the present specification, the organic material layer can further comprise one or more layers selected form the group consisting of a hole injection layer, a hole transfer layer, an electron blocking layer, a hole blocking layer, an electron transfer layer, and an electron injection layer.

The organic light emitting device of the present specification can be manufactured using materials and methods known in the art, except that one, two or more layers of the organic material layers comprise the compound of the present specification, that is, the compound of Chemical Formula 1.

When the organic light emitting device comprises a plurality of organic material layers, the organic material layers can be formed with the same material or with different materials.

For example, the organic light emitting device of the present specification can be manufactured by consecutively laminating a first electrode, an organic material layer and a second electrode on a substrate. Herein, the organic light emitting device can be manufactured by forming a first electrode on a substrate by depositing a metal, a metal oxide having conductivity, or an alloy thereof using a physical vapor deposition (PVD) method such as a sputtering method or an e-beam evaporation method, forming an organic material layer including a hole injection layer, a hole transfer layer, a light emitting layer and an electron transfer layer thereon, and then depositing a material usable as a second electrode thereon. In addition to this method, the organic light emitting device can be manufactured by consecutively depositing a second electrode material, an organic material layer and a first electrode material on a substrate. In addition, the compound of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, Mg/Al and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The electron blocking layer is a layer preventing excess electrons passing through a light emitting layer from moving toward a hole transfer layer. As the electron blocking material, materials having a lower lowest unoccupied molecular orbital (LUMO) level than the hole transfer layer are preferred, and proper materials can be selected considering energy levels of surrounding layers. In one embodiment, arylamine-based organic materials can be used as the electron blocking layer, however, the electron blocking layer is not limited thereto.

According to one embodiment of the present specification, the hole transfer layer, the hole injection layer, the electron blocking layer, or a hole injection and transfer layer can further include a p-type dopant. As the p-type dopant, those known in the art can be used, and examples thereof can include arylamine-based derivatives, compounds including a cyano group, and the like. The p-type dopant can be included in the electron transfer layer, the electron injection layer, or the electron injection and transfer layer in 0.1% by weight to 75% by weight, and preferably in 30% by weight to 55% by weight.

In one embodiment of the present specification, the hole injection and transfer layer means a layer carrying out hole injection and transfer at the same time. The hole injection and transfer layer can use the materials of the hole injection layer and the hole transfer layer described above.

The light emitting material of the light emitting layer is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes ($Alq_3$); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

In one embodiment of the present specification, the organic material layer can include two or more light emitting layers, and the two or more light emitting layers can be provided horizontally, or provided vertically.

The light emitting layer can include a host material and a dopant material. The host material can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, carbazole derivatives, dibenzofuran derivatives, ladder-type furan compounds, pyrimidine derivatives and the like can be included, however, the host material is not limited thereto.

The dopant material can include aromatic amine derivatives, styrylamine compounds, boron complexes, fluoranthene compounds, metal complexes and the like. The aromatic amine derivative is a fused aromatic ring derivative having a substituted or unsubstituted arylamino group, and arylamino group-including pyrene, anthracene, chrysene, peryflanthene and the like can be included. The styrylamine compound can be a compound in which substituted or unsubstituted arylamine is substituted with at least one arylvinyl group, and one, two or more substituents selected from the group consisting of an aryl group, a silyl group, an alkyl group, a cycloalkyl group and an arylamino group can be substituted or unsubstituted. As the styrylamine compound, styrylamine, styryldiamine, styryltriamine, styryltetramine and the like can be included, however, the styrylamine compound is not limited thereto. As the metal complex, iridium complexes, platinum complexes and the like can be included, however, the metal complex is not limited thereto.

The hole blocking layer performs a role of preventing holes from passing through a light emitting layer and entering a cathode while driving an organic light emitting device. As the hole blocking material, materials having a very low highest occupied molecular orbital (HOMO) level are preferably used. Specific examples of the hole blocking material can include TPBi, BCP, CBP, PBD, PTCBI, BPhen and the like, but are not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including $Alq_3$; organic radical compounds; hydroxyflavon-metal complexes, and the like, but are not limited thereto. The electron transfer layer can be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and as the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxy-quinolinato)copper, bis(8-hydroxyquinolinato)manganese, tris-(8-hydroxyquinolinato)aluminum, tris(2-methyl-8-hydroxy-quinolinato)aluminum, tris(8-hydroxyquinolinato)gallium, bis(10-hydroxybenzo[h]quinolinato)beryllium, bis(10-hydroxy-benzo[h]quinolinato)zinc, bis(2-methyl-8-quinolinato)-chlorogallium, bis(2-methyl-8-quinolinato)(o-cresolato)-gallium, bis(2-methyl-8-quinolinato)(1-naphtholato)aluminum, bis(2-methyl-8-quinolinato)(2-naphtholato)gallium and the like, but is not limited thereto.

In one embodiment of the present specification, the electron injection and transfer layer means a layer carrying out electron injection and transfer at the same time. The electron injection and transfer layer can use the materials of the electron injection layer and the electron transfer layer described above.

According to one embodiment of the present specification, the electron transfer layer; the electron injection layer; the hole blocking layer; or the electron injection and transfer layer can further include an n-type dopant. As the n-type dopant, those known in the art can be used, and for example, alkali metals, alkaline earth metals, alkali metal compounds, alkaline earth metal compounds, alkali metal complexes, alkaline earth metal complexes or the like can be used. As the metal compound, oxides, halides and the like can be used, and the complex can further include an organic ligand. For example, LiQ and the like can be used. The n-type dopant can be included in the electron transfer layer, the electron injection layer, or the electron injection and transfer layer in 0.1% by weight to 75% by weight and preferably in 30% by weight to 55% by weight.

The organic light emitting device according to the present specification can be a top-emission type, a bottom-emission type or a dual-emission type depending on the materials used.

EXAMPLES

A method for preparing the compound of Chemical Formula 1 and a method for manufacturing an organic light emitting device including the same will be specifically described in the following examples. However, the following examples are for illustrative purposes only, and the scope of the present disclosure is not limited thereto.

The compound of the present disclosure can be prepared using, as a representative reaction, a Buchwald-Hartwig coupling reaction, a Heck coupling reaction, a Suzuki coupling reaction or the like.

<Preparation of Compound a>

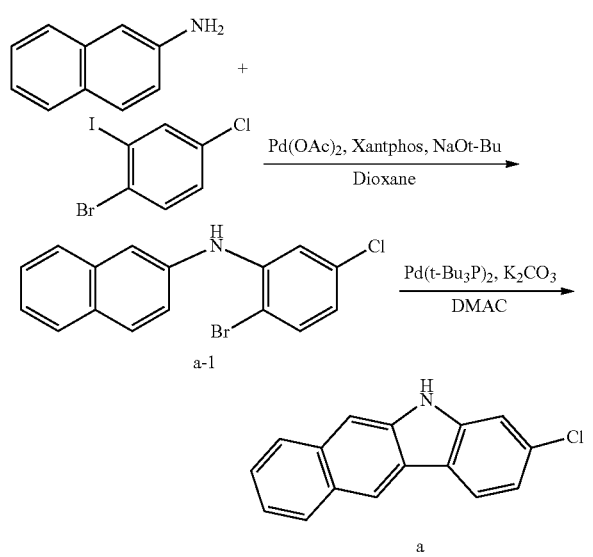

1) Preparation of Compound a-1

Naphthalene-2-amine (200 g, 1.0 eq.), 1-bromo-4-chloro-2-iodobenzene (443.25 g, 1 eq.), NaOt-Bu (201.3 g, 1.5 eq.), Pd(OAc)$_2$ (3.13 g, 0.01 eq.) and Xantphos (8.08 g, 0.01 eq.) were dissolved in 1,4-dioxane (4 L), and stirred under reflux. When the reaction was finished after 3 hours, the solvent was removed under vacuum. After that, the result was completely dissolved in ethyl acetate, washed with water, and then vacuumed again to remove approximately 70% of the solvent. Crystals were precipitated while introducing hexane thereto under reflux again, and the result was cooled and then filtered. This was column chromatographed to obtain Compound a-1 (283.41 g, yield 61%). [M+H]$^+$=333

2) Preparation of Compound a

Pd(t-Bu$_3$P)$_2$ (3.9 g, 0.01 eq.) and potassium carbonate (K$_2$CO$_3$) (211.11 g, 2 eq.) were introduced to Compound a-1 (283.41 g, 1 eq.) in dimethylacetamide (2 L), and the result was stirred under reflux. After 3 hours, the reaction material was poured into water to precipitate crystals, and filtered. The filtered solids were completely dissolved in 1,2-dichlorobenzene, and washed with water, and the product-dissolved solution was vacuum concentrated to precipitate crystals, cooled and then filtered. This was purified using column chromatography to obtain Compound a (3-chloro-5H-benzo[b]carbazole) (74.97 g, yield 39%). [M+H]$^+$=252

<Preparation of Compound b>

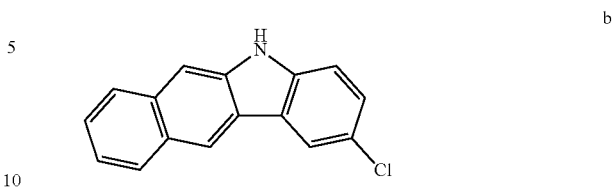

Compound b was synthesized in the same manner as in the preparation of Compound a except that 2-bromo-4-chloro-1-iodobenzene was used instead of 1-bromo-4-chloro-2-iodobenzene.

<Preparation of Compound c>

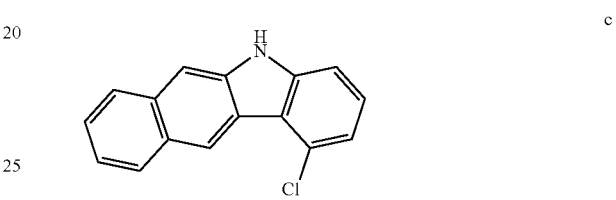

Compound c was synthesized in the same manner as in the preparation of Compound a except that 2-bromo-1-chloro-3-iodobenzene was used instead of 1-bromo-4-chloro-2-iodobenzene.

<Preparation of Compound d>

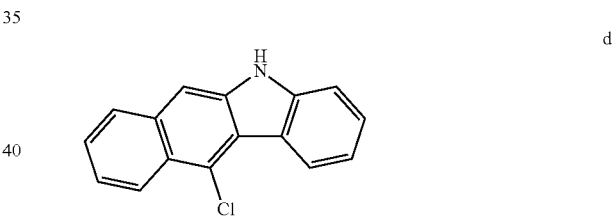

Compound d was synthesized in the same manner as in the preparation of Compound a except that 4-chloronaphthalene-2-amine was used instead of naphthalene-2-amine, and 1-bromo-2-iodobenzene was used instead of 1-bromo-4-chloro-2-iodobenzene.

<Preparation of Compound e>

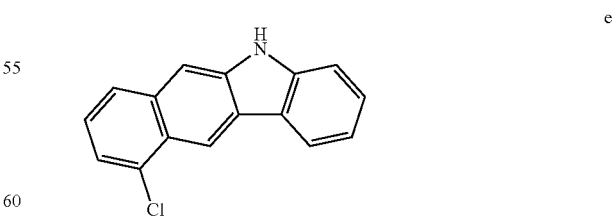

Compound e was synthesized in the same manner as in the preparation of Compound a except that 5-chloronaphthalene-2-amine was used instead of naphthalene-2-amine, and 1-bromo-2-iodobenzene was used instead of 1-bromo-4-chloro-2-iodobenzene.

<Preparation of Compound f>

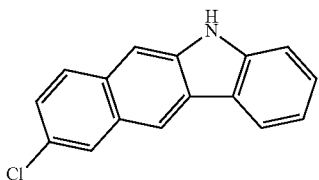

f

Compound f was synthesized in the same manner as in the preparation of Compound a except that 6-chloronaphthalene-2-amine was used instead of naphthalene-2-amine, and 1-bromo-2-iodobenzene was used instead of 1-bromo-4-chloro-2-iodobenzene.

<Preparation of Compound g>

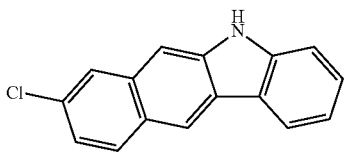

g

Compound g was synthesized in the same manner as in the preparation of Compound a except that 7-chloronaphthalene-2-amine was used instead of naphthalene-2-amine, and 1-bromo-2-iodobenzene was used instead of 1-bromo-4-chloro-4-iodobenzene.

<Preparation of Chemical Formula h>

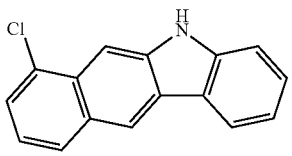

h

Compound h was synthesized in the same manner as in the preparation of Compound a except that 8-chloronaphthalene-2-amine was used instead of naphthalene-2-amine, and 1-bromo-2-iodobenzene was used instead of 1-bromo-4-chloro-2-iodobenzene.

<Preparation of Compound i>

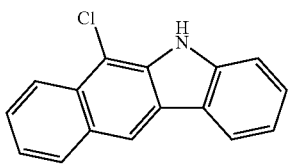

i

Compound i was synthesized in the same manner as in the preparation of Compound a except that 1-chloronaphthalene-2-amine was used instead of naphthalene-2-amine, and 1-bromo-2-iodobenzene was used instead of 1-bromo-4-chloro-2-iodobenzene.

<Preparation of Compound j>

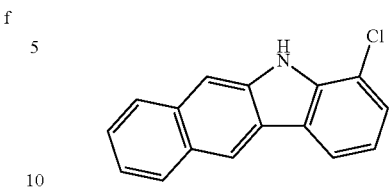

j

Compound j was synthesized in the same manner as in the preparation of Compound a except that 1-bromo-3-chloro-2-iodobenzene was used instead of 1-bromo-4-chloro-2-iodobenzene.

Synthesis Example

Synthesis Example 1

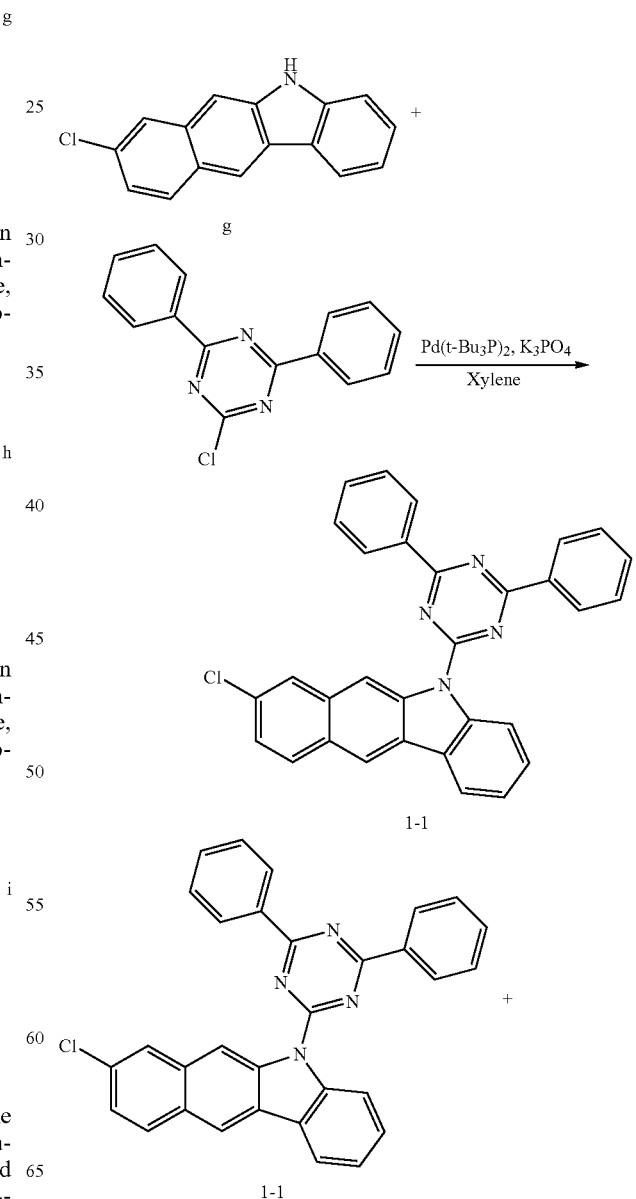

1-1

1-1

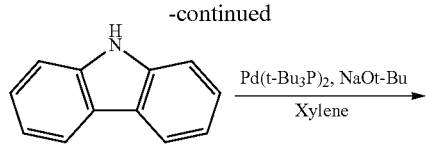

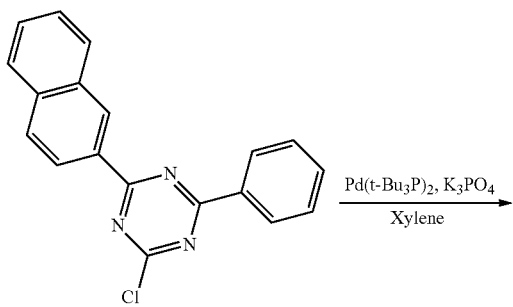

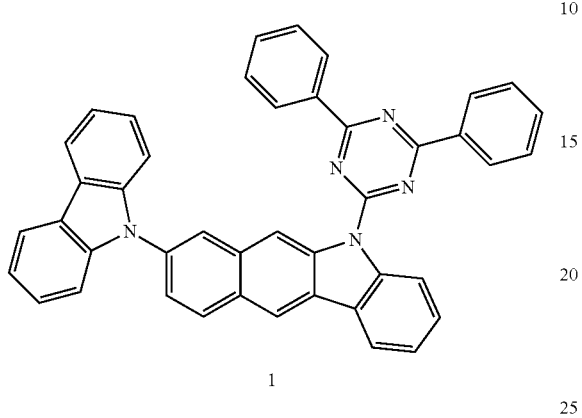

1

Chemical Formula g (10 g, 1 eq.), 2-chloro-4,6-diphenyl-1,3,5-triazine (11.69 g, 1.1 eq.), potassium phosphate tribasic (K$_3$PO$_4$) (16.86 g, 2 eq.) and bis(tri-tert-butylphosphine)palladium(0) (Pd(t-Bu$_3$P)$_2$) (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 1-1 (13.81 g, yield 72%). [M+H]$^+$=483

Compound 1-1 (13.81 g, 1.0 eq.), 9H-carbazole (5.26 g, 1.1 eq.), Pd(t-Bu$_3$P)$_2$ (0.15 g, 0.01 eq.) and NaOt-Bu (5.49 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 1 (11.76 g, yield 67%). [M+H]$^+$=614

Synthesis Example 2

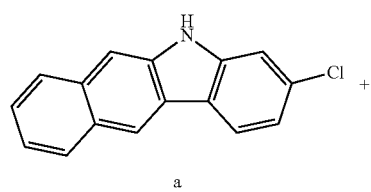

a

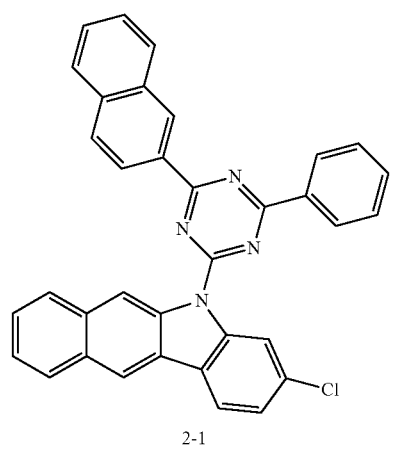

2-1

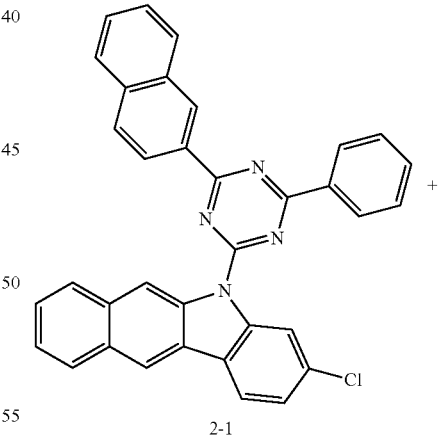

2-1

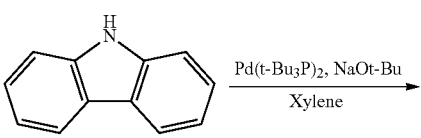

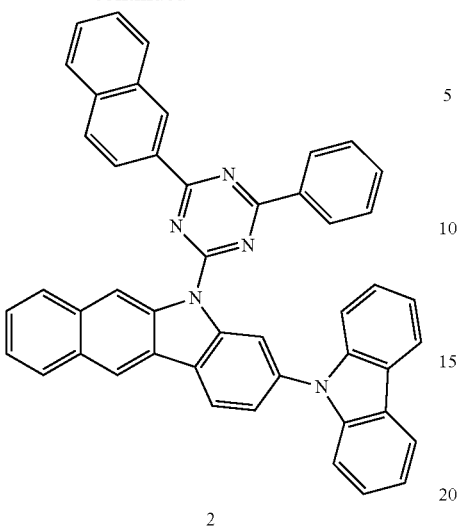

2

Chemical Formula a (10 g, 1.0 eq.), 2-chloro-4-(naphthalen-2-yl)-6-phenyl-1,3,5-triazine (13.88 g, 1.1 eq.), K$_3$PO$_4$ (16.86 g, 2 eq.) and Pd(t-Bu$_3$P)$_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 2-1 (14.82 g, yield 70%). [M+H]$^+$=534

Compound 2-1 (14.82 g, 1 eq.), 9H-carbazole (5.11 g, 1.1 eq.), Pd(t-Bu$_3$P)$_2$ (0.14 g, 0.01 eq.) and NaOt-Bu (5.34 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 2 (11.99 g, yield 65%). [M+H]$^+$=664

Synthesis Example 3

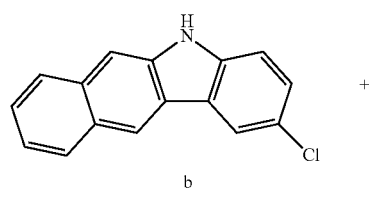

b

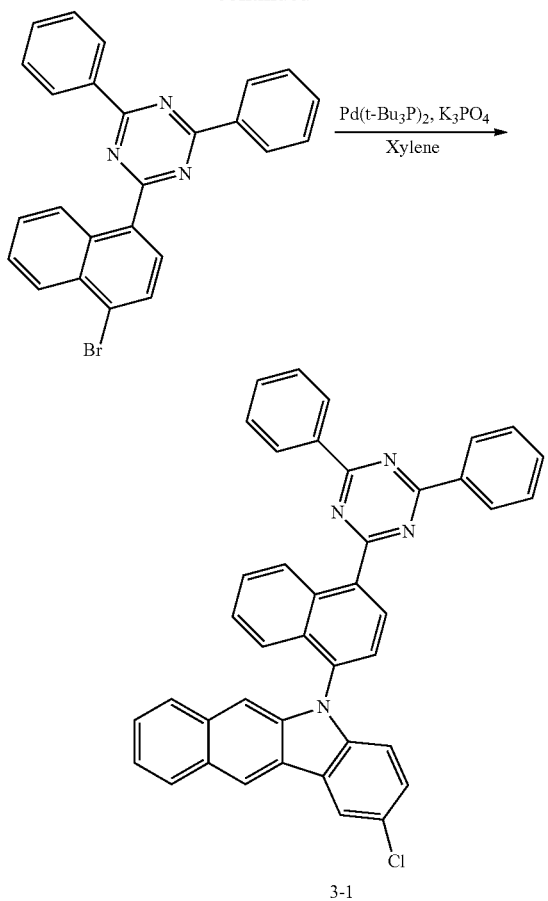

3-1

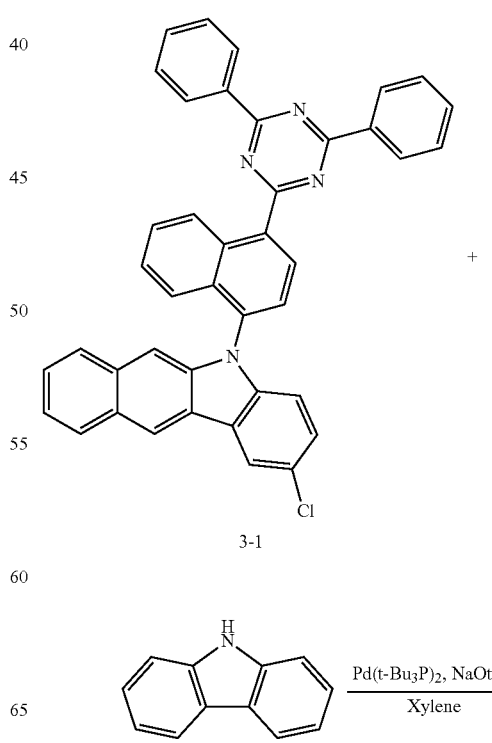

3-1

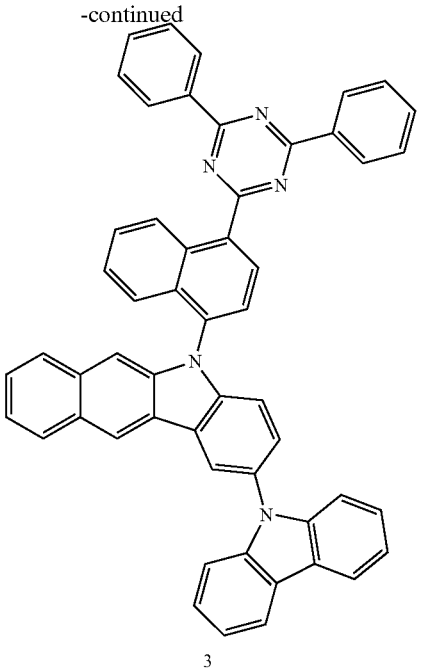

3

Chemical Formula b (10 g, 1 eq.), 2-(4-bromonaphthalen-1-yl)-4,6-diphenyl-1,3,5-triazine (19.15 g, 1.1 eq.), $K_3PO_4$ (16.86 g, 2 eq.) and $Pd(t-Bu_3P)_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 3-1 (18.14 g, yield 75%). $[M+H]^+=610$ Compound 3-1 (18.14 g, 1 eq.), 9H-carbazole (5.48 g, 1.1 eq.), $Pd(t-Bu_3P)_2$ (0.15 g, 0.01 eq.) and NaOt-Bu (5.72 g, 2 eq.) were introduced to xylene (250 ml), and the result was stirred under reflux. When the reaction was finished after 2 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 3 (16.31 g, yield 74%). $[M+H]^+=740$ Synthesis Example 4

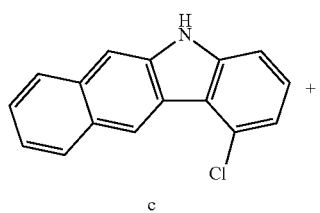

c

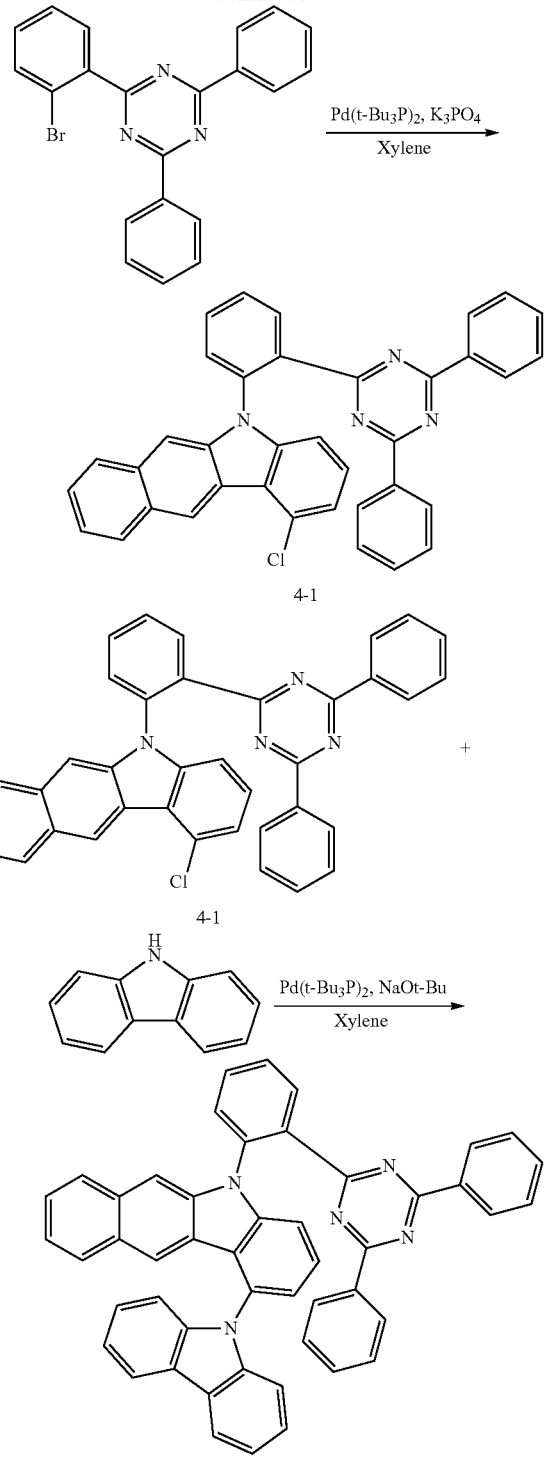

Chemical Formula c (10 g, 1.0 eq.), 2-(2-bromophenyl)-4,6-diphenyl-1,3,5-triazine (16.96 g, 1.1 eq.), $K_3PO_4$ (16.86 g, 2 eq.) and $Pd(t-Bu_3P)_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 4-1 (13.54 g, yield 61%). [M+H]$^+$=600

Compound 4-1 (13.54 g, 1 eq.), 9H-carbazole (4.45 g, 1.1 eq.), Pd(t-Bu$_3$P)$_2$ (0.12 g, 0.01 eq.) and NaOt-Bu (4.65 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 4 (12.03 g, yield 72%). [M+H]$^+$=690

Synthesis Example 5

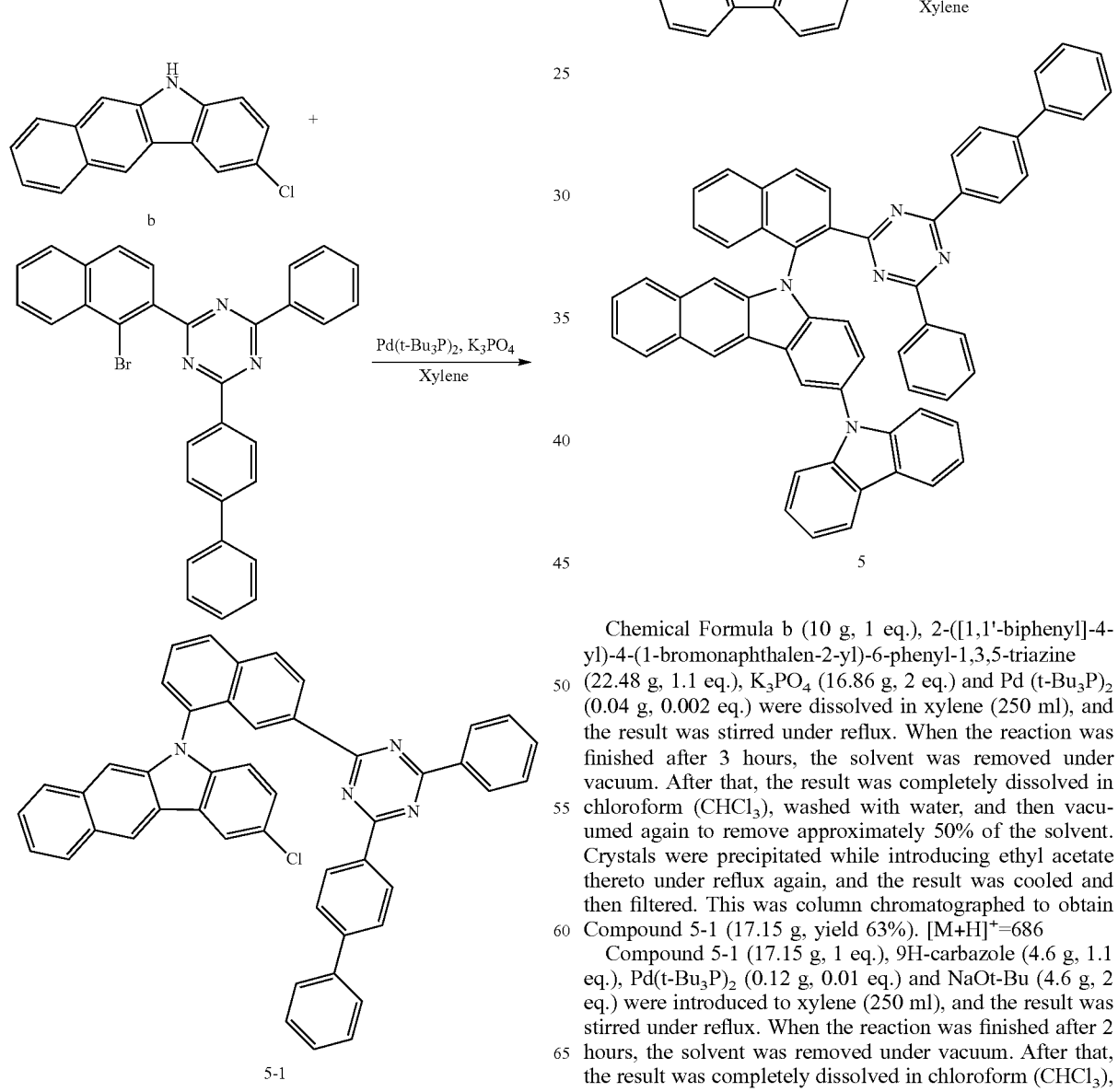

Chemical Formula b (10 g, 1 eq.), 2-([1,1'-biphenyl]-4-yl)-4-(1-bromonaphthalen-2-yl)-6-phenyl-1,3,5-triazine (22.48 g, 1.1 eq.), K$_3$PO$_4$ (16.86 g, 2 eq.) and Pd (t-Bu$_3$P)$_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 5-1 (17.15 g, yield 63%). [M+H]$^+$=686

Compound 5-1 (17.15 g, 1 eq.), 9H-carbazole (4.6 g, 1.1 eq.), Pd(t-Bu$_3$P)$_2$ (0.12 g, 0.01 eq.) and NaOt-Bu (4.6 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 5 (13.68 g, yield 67%). [M+H]$^+$=816

Synthesis Example 6

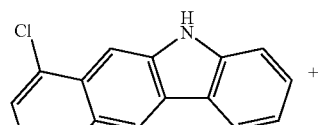

h

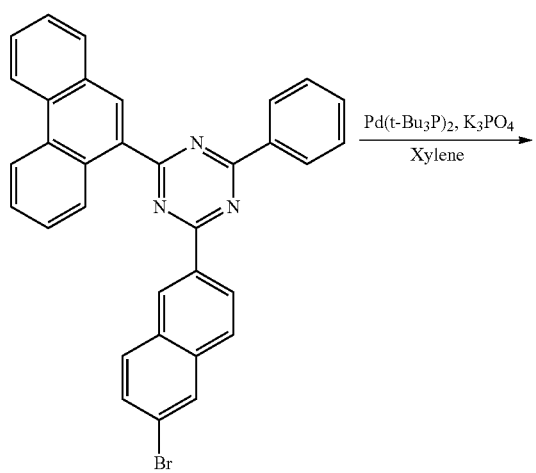

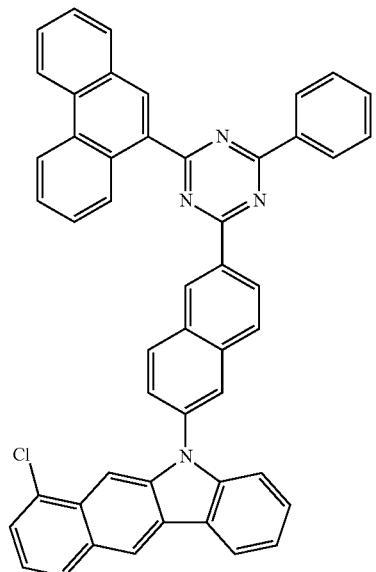

6-1

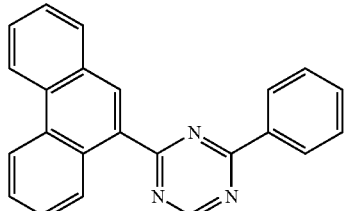

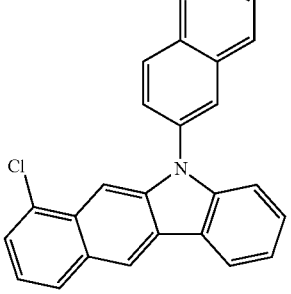

6-1

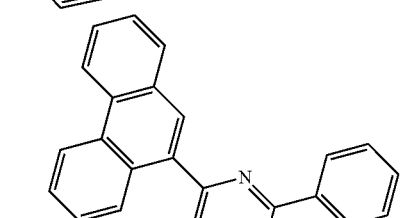

6

Chemical Formula h (10 g, 1 eq.), 2-(6-bromonaphthalen-2-yl)-4-(phenanthren-9-yl)-6-phenyl-1,3,5-triazine (23.53 g, 1.1 eq.), K$_3$PO$_4$ (16.86 g, 2 eq.) and Pd(t-Bu$_3$P)$_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 6-1 (20.85 g, yield 74%). [M+H]$^+$=710

Compound 6-1 (20.85 g, 1 eq.), 9H-carbazole (5.4 g, 1.1 eq.), Pd(t-Bu$_3$P)$_2$ (0.15 g, 0.01 eq.) and NaOt-Bu (5.65 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 6 (15.06 g, yield 61%). [M+H]$^+$=841

Synthesis Example 7

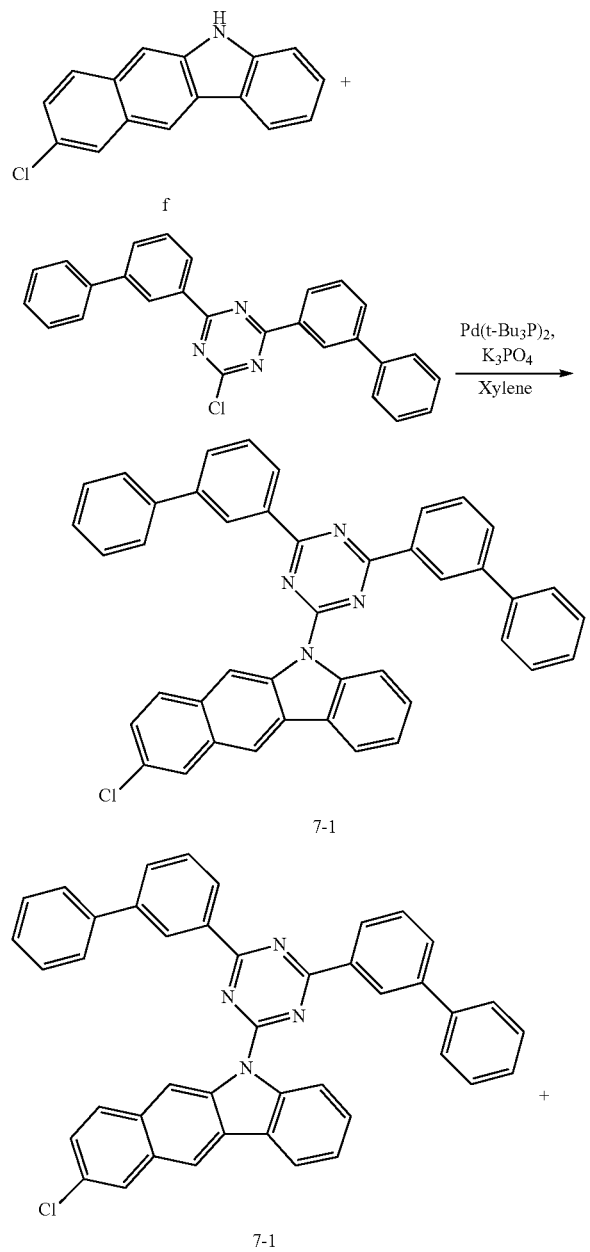

7-1

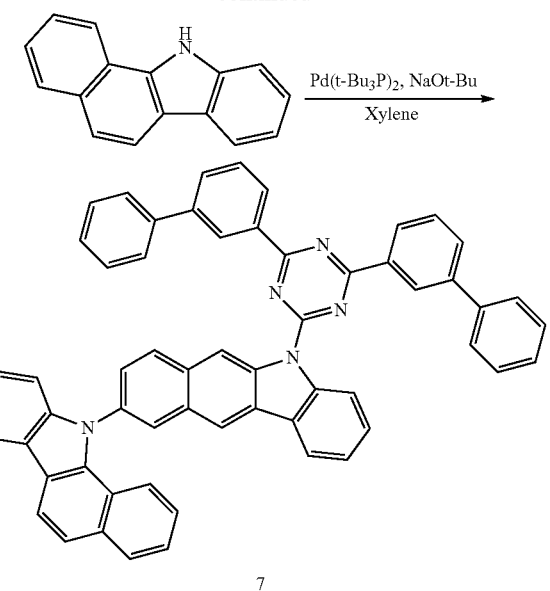

7

Chemical Formula f (10 g, 1 eq.), 2,4-di([1,1'-biphenyl]-3-yl)-6-chloro-1,3,5-triazine (18.35 g, 1.1 eq.), K$_3$PO$_4$ (16.86 g, 2 eq.) and Pd(t-Bu$_3$P)$_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 7-1 (19.43 g, yield 77%). [M+H]$^+$=635.17

Compound 7-1 (19.43 g, 1 eq.), 11H-benzo[a]carbazole (7.31 g, 1.1 eq.), Pd(t-Bu$_3$P)$_2$ (0.16 g, 0.01 eq.) and NaOt-Bu (5.87 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 7 (16.72 g, yield 67%). [M+H]$^+$=816

Synthesis Example 8

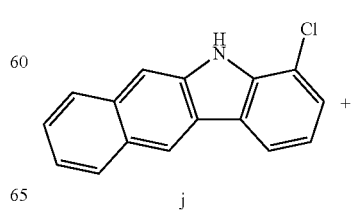

j

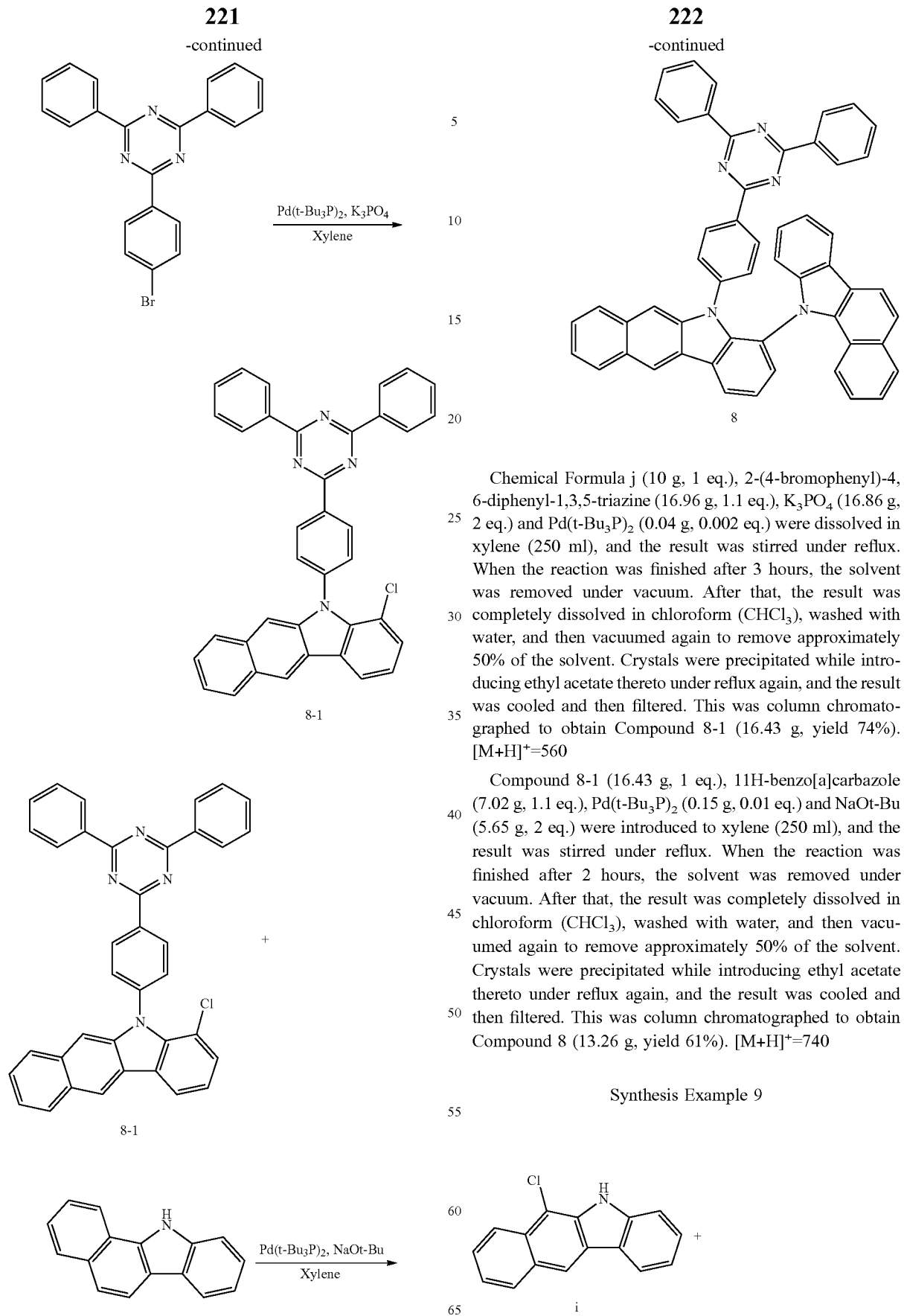

Chemical Formula j (10 g, 1 eq.), 2-(4-bromophenyl)-4,6-diphenyl-1,3,5-triazine (16.96 g, 1.1 eq.), K$_3$PO$_4$ (16.86 g, 2 eq.) and Pd(t-Bu$_3$P)$_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 8-1 (16.43 g, yield 74%). [M+H]$^+$=560

Compound 8-1 (16.43 g, 1 eq.), 11H-benzo[a]carbazole (7.02 g, 1.1 eq.), Pd(t-Bu$_3$P)$_2$ (0.15 g, 0.01 eq.) and NaOt-Bu (5.65 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 8 (13.26 g, yield 61%). [M+H]$^+$=740

Synthesis Example 9

-continued

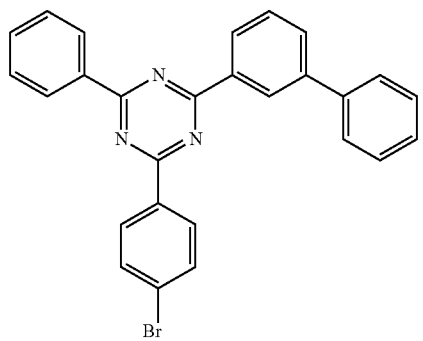

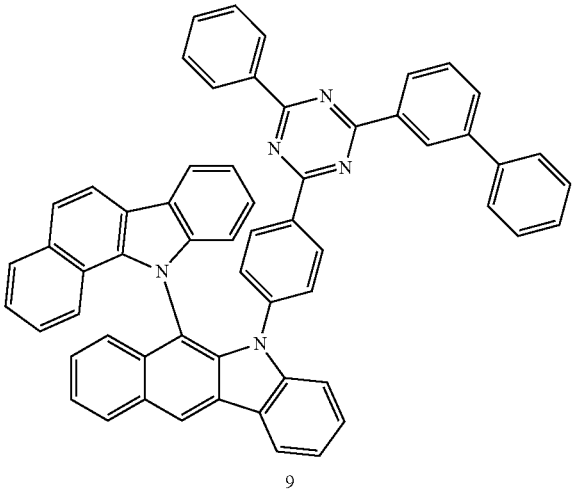

9

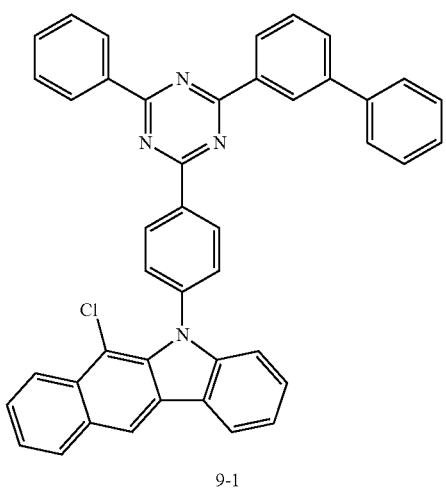

9-1

+

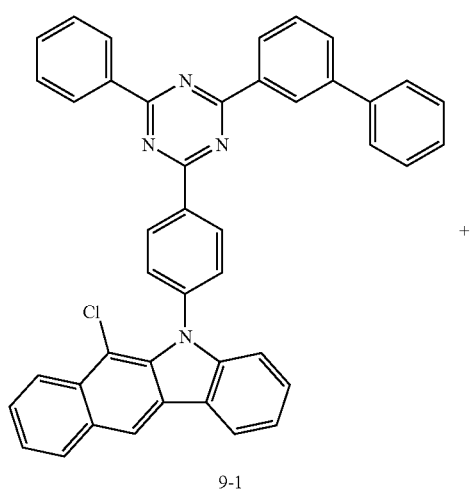

9-1

Chemical Formula i (10 g, 1.0 eq.), 2-([1,1'-biphenyl]-3-yl)-4-(4-bromophenyl)-6-phenyl-1,3,5-triazine (20.29 g, 1.1 eq.), K$_3$PO$_4$ (16.86 g, 2.0 eq.) and Pd(t-Bu$_3$P)$_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 9-1 (18.16 g, yield 72%). [M+H]$^+$=636

Compound 9-1 (18.16 g, 1 eq.), 11H-benzo[a]carbazole (6.83 g, 1.1 eq.), Pd(t-Bu$_3$P)$_2$ (0.14 g, 0.01 eq.) and NaOt-Bu (5.49 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 9 (14.7 g, yield 63%). [M+H]$^+$=816

Synthesis Example 10

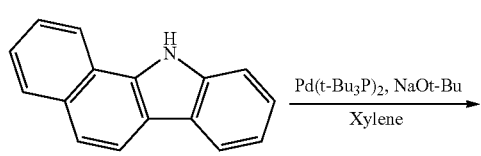

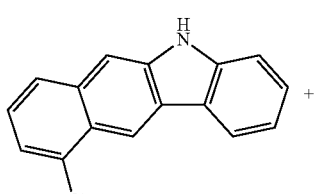

e

+

-continued

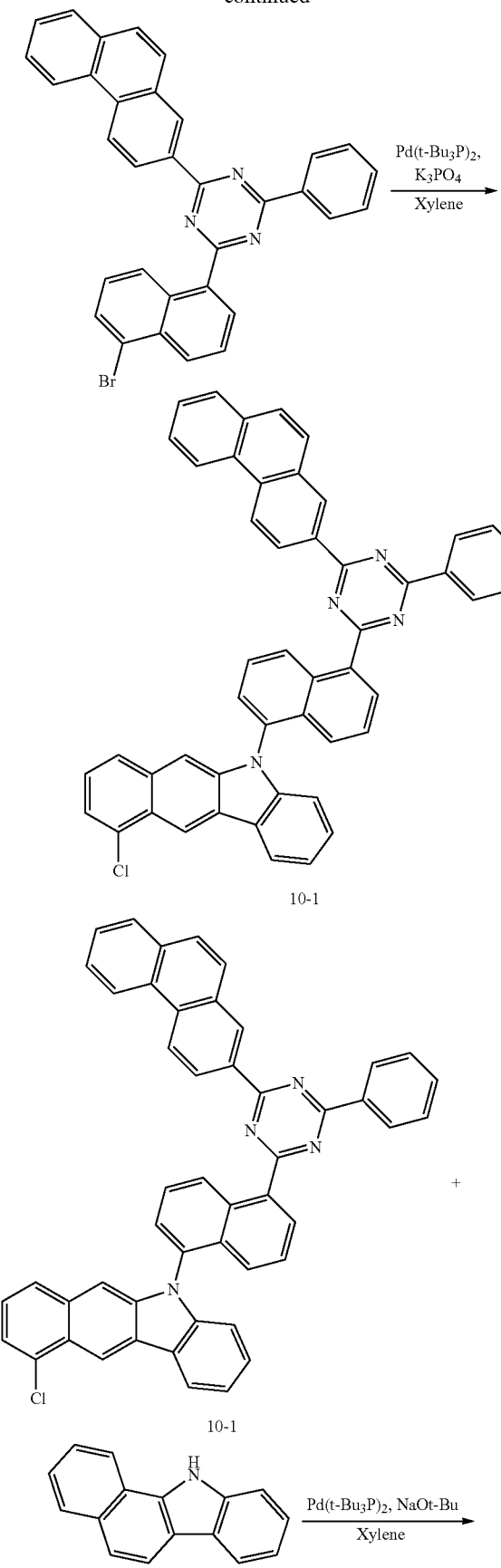

Chemical Formula e (10 g, 1 eq.), 2-(5-bromonaphthalen-1-yl)-4-(phenanthren-2-yl)-6-phenyl-1,3,5-triazine (23.53 g, 1.1 eq.), $K_3PO_4$ (16.86 g, 2 eq.) and $Pd(t-Bu_3P)_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 10-1 (19.72 g, yield 70%). $[M+H]^+=710$ Compound 10-1 (19.72 g, 1 eq.), 11H-benzo[a]carbazole (6.64 g, 1.1 eq.), $Pd(t-Bu_3P)_2$ (0.14 g, 0.01 eq.) and NaOt-Bu (5.34 g, 2 eq.) were introduced to xylene (250 ml), and the result was stirred under reflux. When the reaction was finished after 2 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 10 (16.08 g, yield 65%). $[M+H]^+=891$ Synthesis Example 11

227
-continued

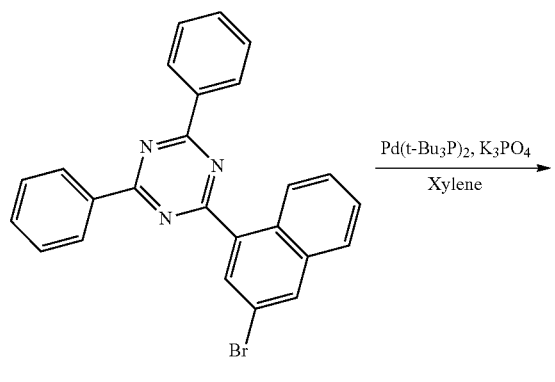

Pd(t-Bu₃P)₂, K₃PO₄
———————————→
Xylene

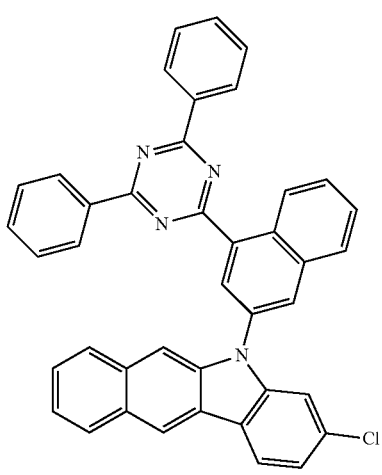

11-1

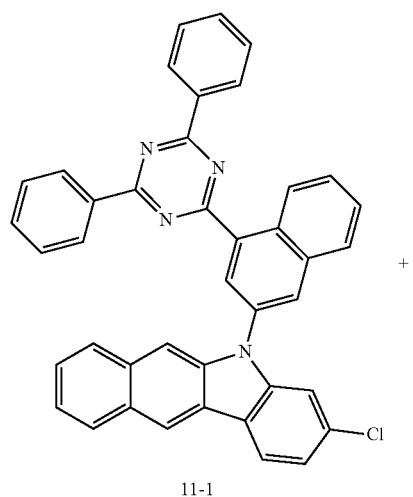

11-1

+

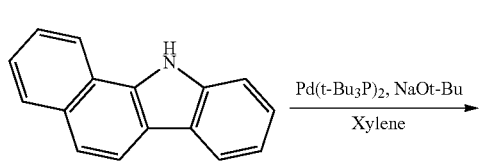

Pd(t-Bu₃P)₂, NaOt-Bu
————————————→
Xylene

228
-continued

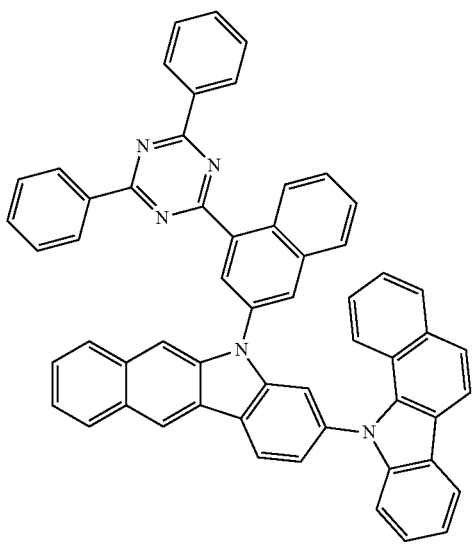

11

Chemical Formula a (10 g, 1 eq.), 2-(3-bromonaphthalen-1-yl)-4,6-diphenyl-1,3,5-triazine (19.15 g, 1.1 eq.), K₃PO₄ (16.86 g, 2 eq.) and Pd(t-Bu₃P)₂ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 11-1 (17.42 g, yield 72%). [M+H]⁺=610

Compound 11-1 (17.42 g, 1 eq.), 11H-benzo[a]carbazole (6.83 g, 1.1 eq.), Pd(t-Bu₃P)₂ (0.14 g, 0.01 eq.) and NaOt-Bu (5.49 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 11 (14.23 g, yield 63%). [M+H]⁺=790

Synthesis Example 12

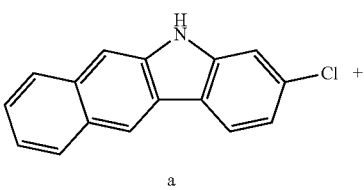

a

-continued

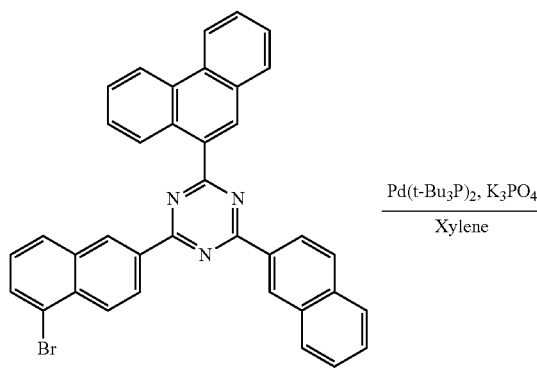

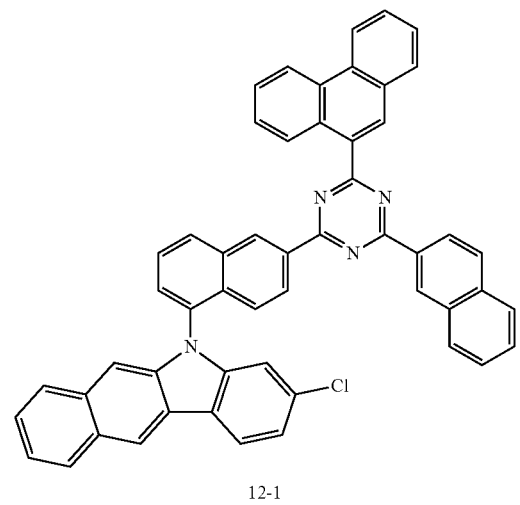

12-1

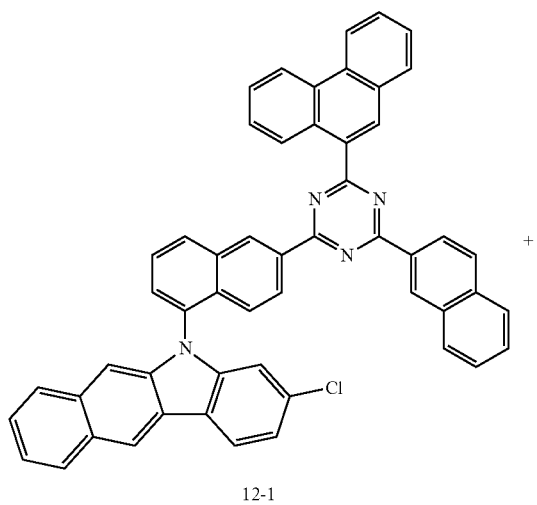

12-1

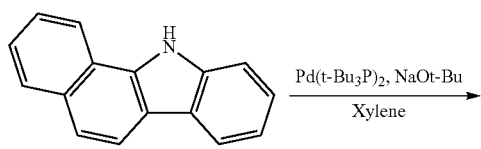

-continued

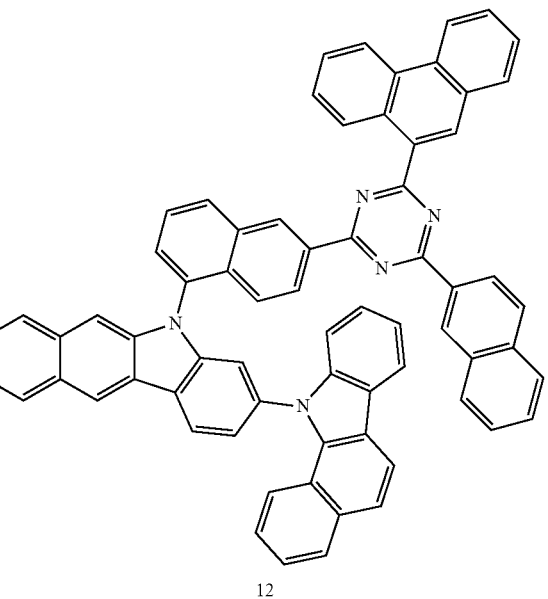

12

Chemical Formula a (10 g, 1 eq.), 2-(5-bromonaphthalen-2-yl)-4-(naphthalen-2-yl)-6-(phenanthren-9-yl)-1,3,5-triazine (25.71 g, 1.1 eq.), K₃PO₄ (16.86 g, 2 eq.) and Pd(t-Bu₃P)₂ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 12-1 (20.21 g, yield 67%). [M+H]⁺=760

Compound 12-1 (20.21 g, 1 eq.), 11H-benzo[a]carbazole (6.36 g, 1.1 eq.), Pd(t-Bu₃P)₂ (0.13 g, 0.01 eq.) and NaOt-Bu (5.11 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 12 (15.01 g, yield 60%). [M+H]⁺=940

Synthesis Example 13

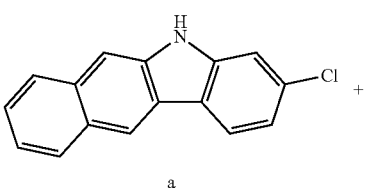

a

231
-continued

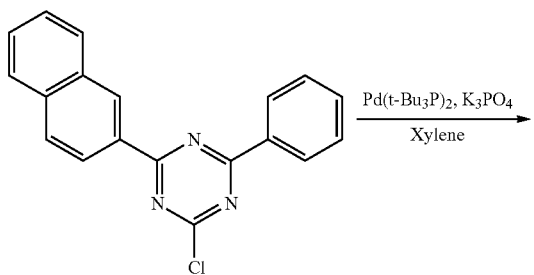

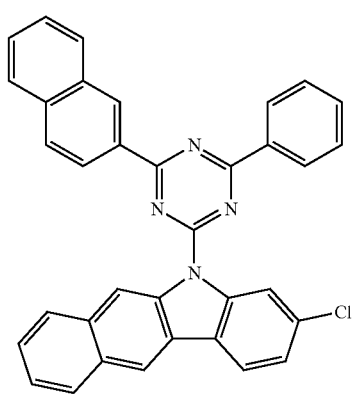
13-1

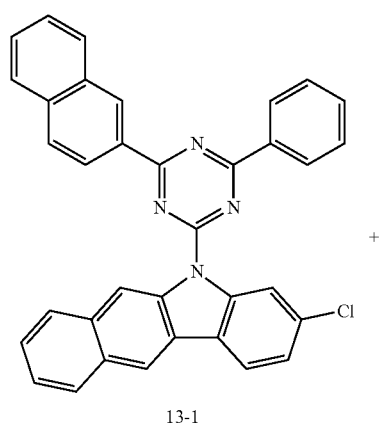
13-1

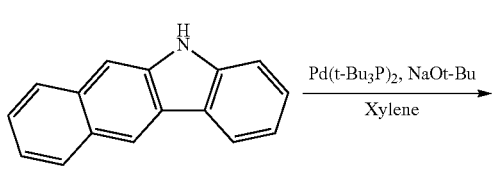

232
-continued

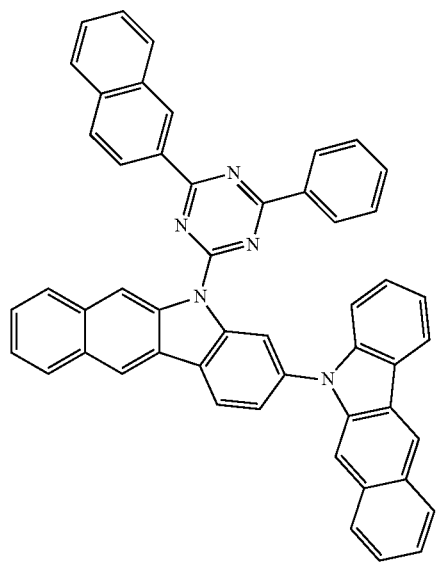
13

Chemical Formula a (10 g, 1 eq.), 2-chloro-4-(naphthalen-2-yl)-6-phenyl-1,3,5-triazine (13.88 g, 1.1 eq.), K₃PO₄ (16.86 g, 2 eq.) and Pd(t-Bu₃P)₂ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 13-1 (16.09 g, yield 76%). [M+H]⁺=534

Compound 13-1 (16.09 g, 1 eq.), 5H-benzo[b]carbazole (7.21 g, 1.1 eq.), Pd(t-Bu₃P)₂ (0.15 g, 0.01 eq.) and NaOt-Bu (5.8 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 13 (14.44 g, yield 67%). [M+H]⁺=714

Synthesis Example 14

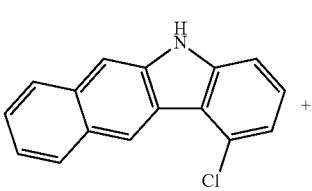
c

-continued

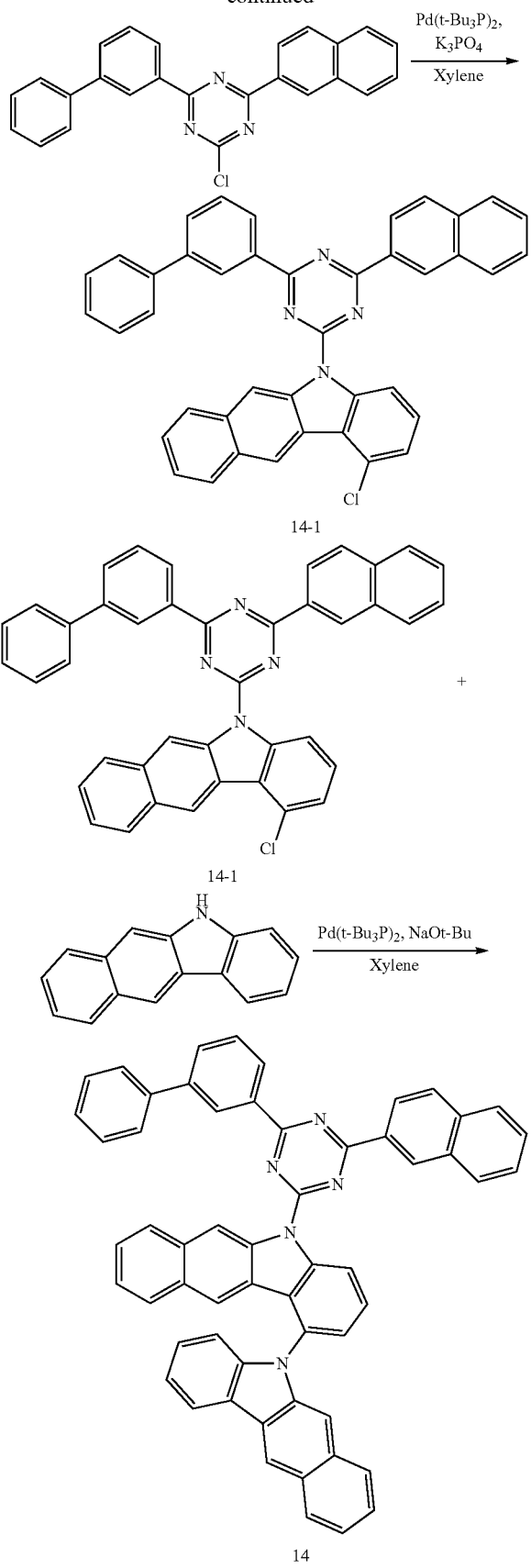

14-1

14

Chemical Formula c (10 g, 1 eq.), 2-([1,1'-biphenyl]-3-yl)-4-chloro-6-(naphthalen-2-yl)-1,3,5-triazine (17.21 g, 1.1 eq.), $K_3PO_4$ (16.86 g, 2 eq.) and $Pd(t-Bu_3P)_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 14-1 (18.14 g, yield 76%). $[M+H]^+=610$ Compound 14-1 (18.14 g, 1 eq.), 5H-benzo[b]carbazole (7.12 g, 1.1 eq.), $Pd(t-Bu_3P)_2$ (0.15 g, 0.01 eq.) and NaOt-Bu (5.72 g, 2 eq.) were introduced to xylene (250 ml), and the result was stirred under reflux. When the reaction was finished after 2 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 14 (16.24 g, yield 69%). $[M+H]^+=790$ Synthesis Example 15

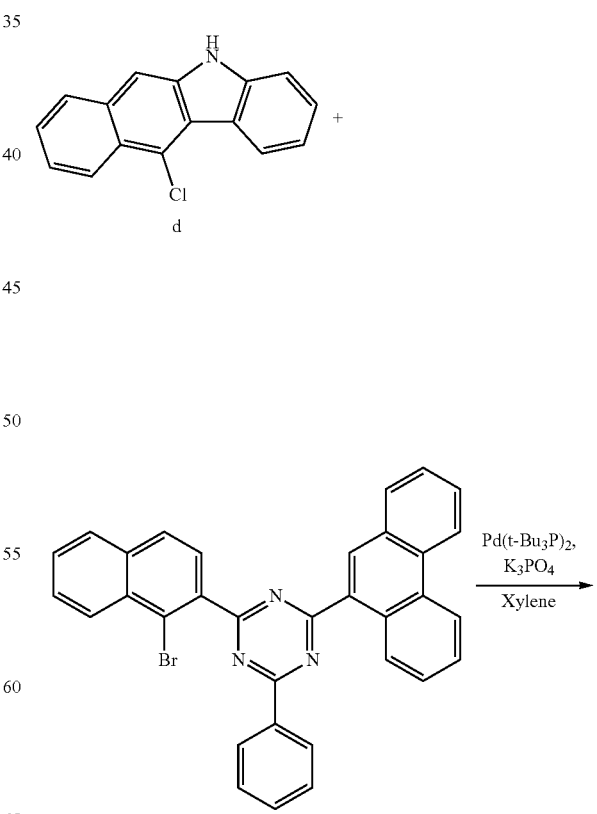

-continued

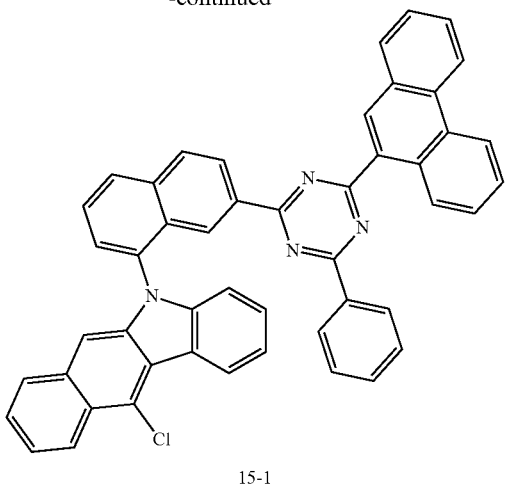

15-1

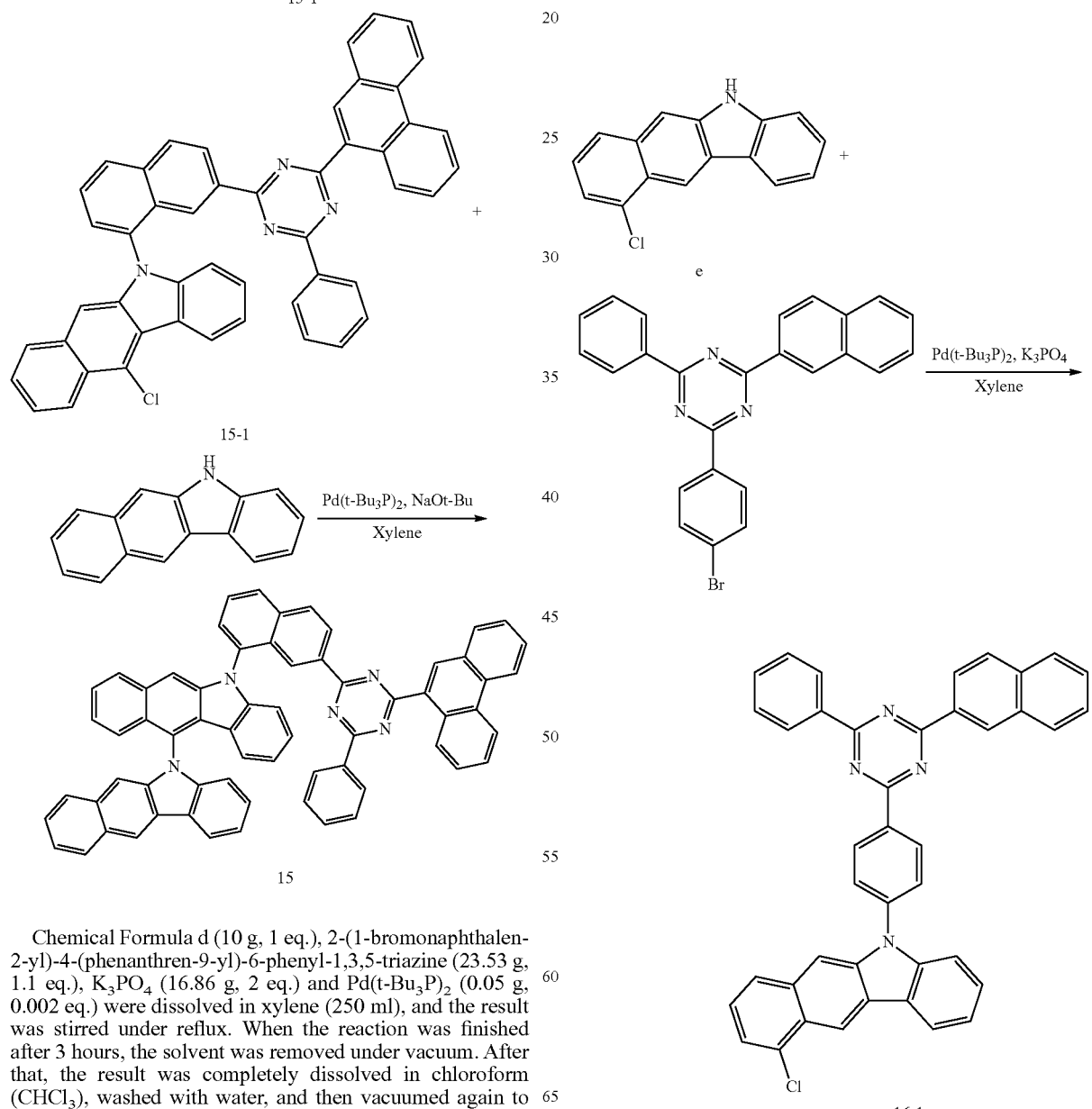

Chemical Formula d (10 g, 1 eq.), 2-(1-bromonaphthalen-2-yl)-4-(phenanthren-9-yl)-6-phenyl-1,3,5-triazine (23.53 g, 1.1 eq.), K₃PO₄ (16.86 g, 2 eq.) and Pd(t-Bu₃P)₂ (0.05 g, 0.002 eq.) were dissolved in xylene (250 ml), and the result was stirred under reflux. When the reaction was finished after 3 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 15-1 (17.18 g, yield 61%). [M+H]⁺=710

Compound 15-1 (17.18 g, 1 eq.), 5H-benzo[b]carbazole (5.79 g, 1.1 eq.), Pd(t-Bu₃P)₂ (0.14 g, 0.01 eq.) and NaOt-Bu (4.65 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 15 (14.45 g, yield 67%). [M+H]⁺=891

Synthesis Example 16

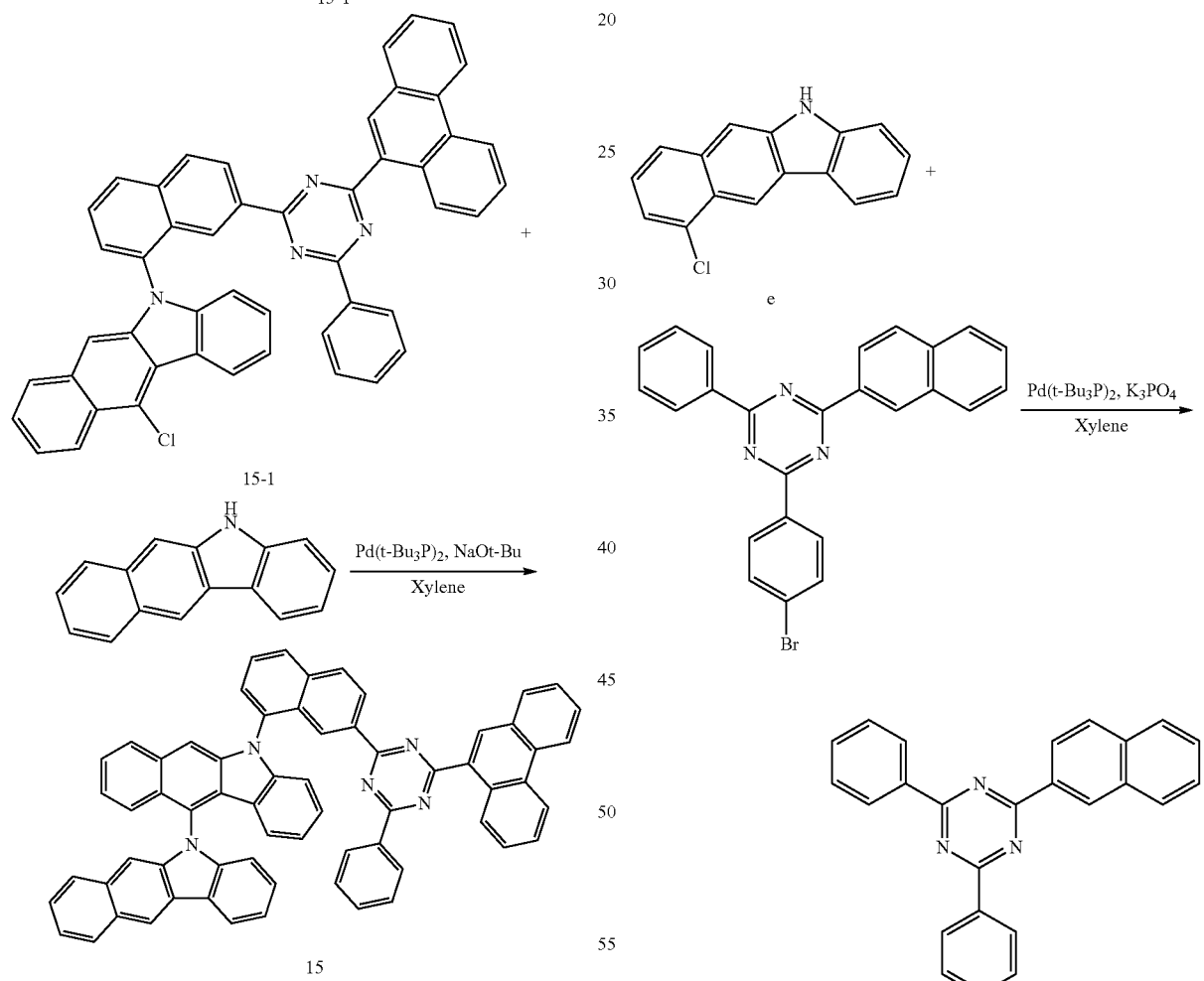

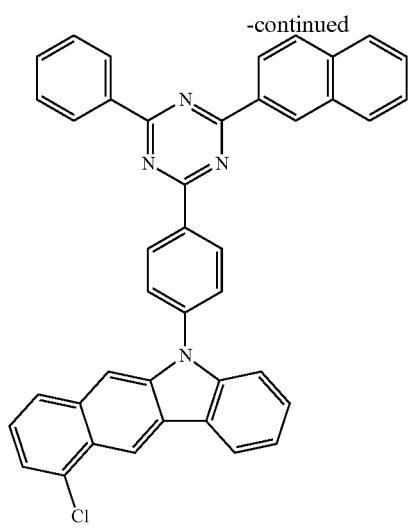
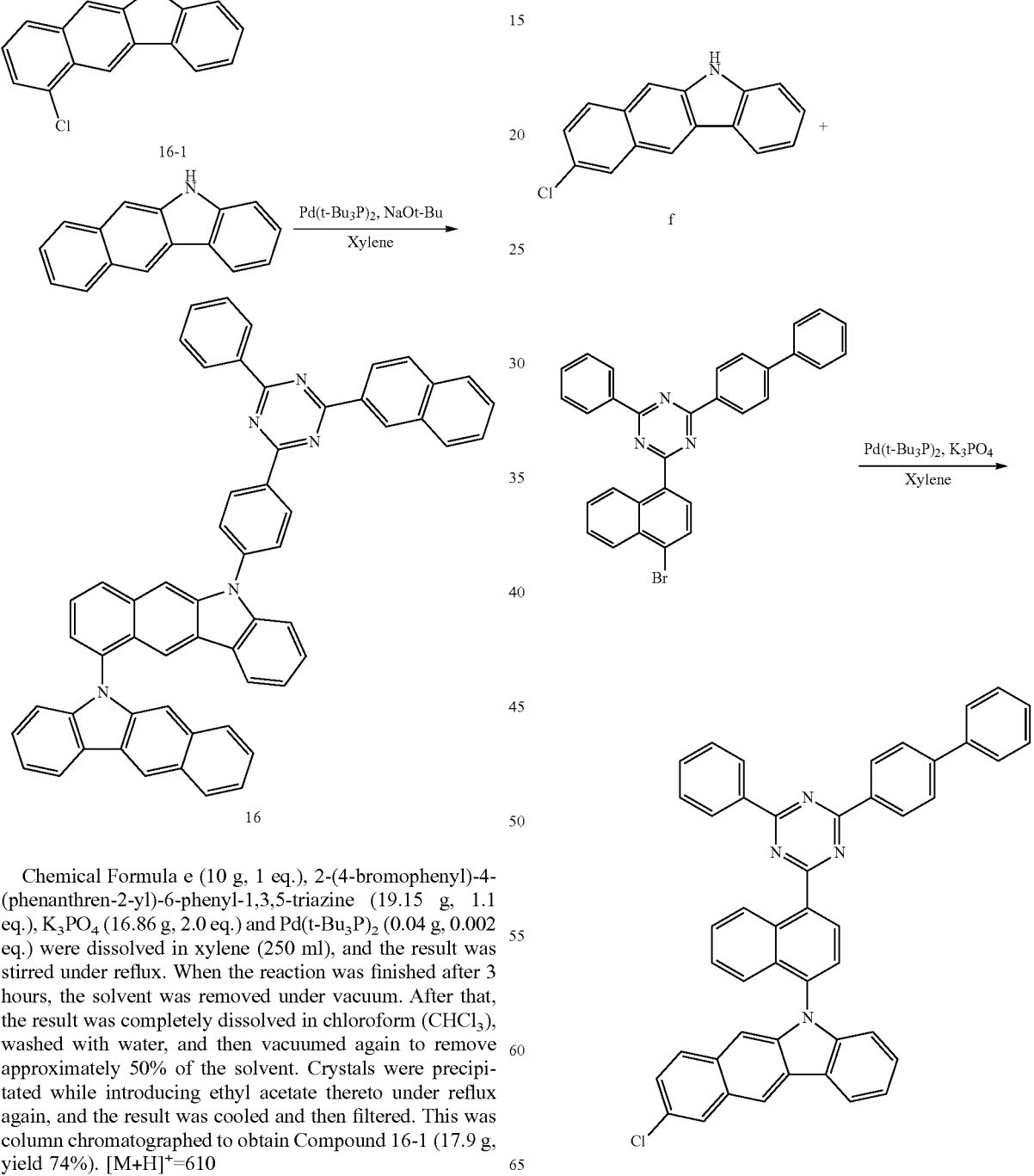

(5.65 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 16 (16.25 g, yield 70%). [M+H]$^+$=790

Synthesis Example 17

Chemical Formula e (10 g, 1 eq.), 2-(4-bromophenyl)-4-(phenanthren-2-yl)-6-phenyl-1,3,5-triazine (19.15 g, 1.1 eq.), K$_3$PO$_4$ (16.86 g, 2.0 eq.) and Pd(t-Bu$_3$P)$_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 16-1 (17.9 g, yield 74%). [M+H]$^+$=610

Compound 16-1 (17.90 g, 1 eq.), 5H-benzo[b]carbazole (7.02 g, 1.1 eq.), Pd(t-Bu$_3$P)$_2$ (0.14 g, 0.01 eq.) and NaOt-Bu

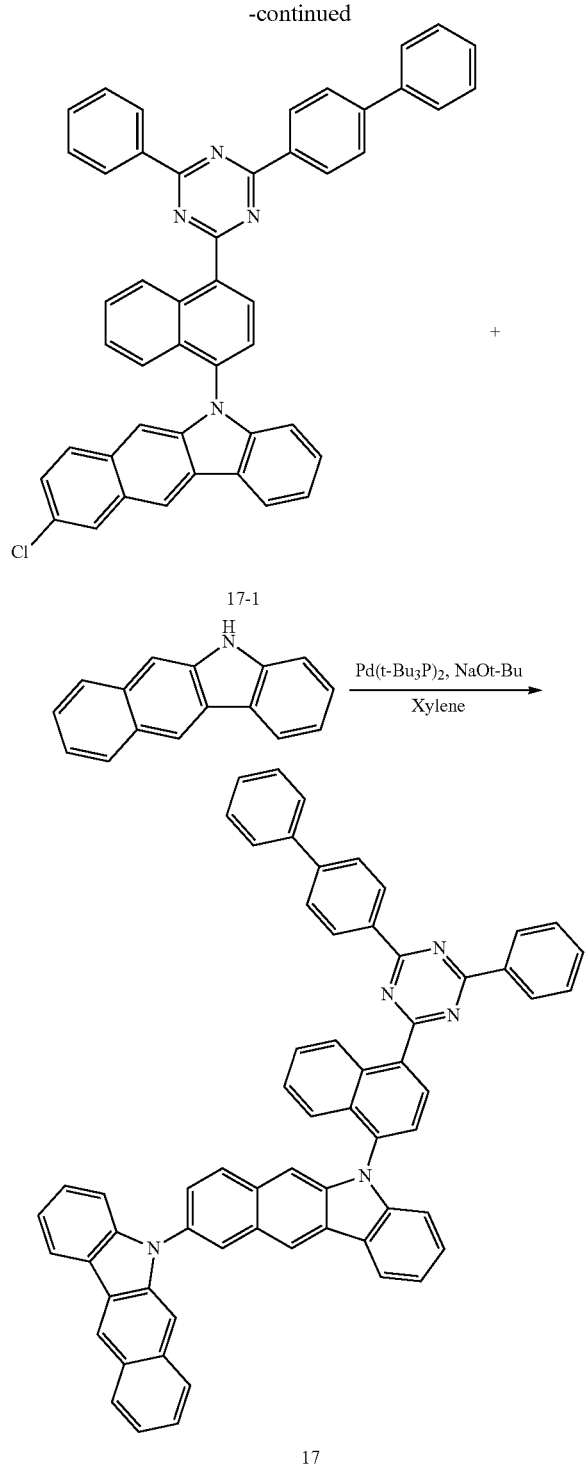

17-1

17

Chemical Formula f (10 g, 1.0 eq.), 2-([1,1'-biphenyl]-4-yl)-4-(4-bromonaphthalen-1-yl)-6-phenyl-1,3,5-triazine (22.48 g, 1.1 eq.), K₃PO₄ (16.86 g, 2.0 eq.) and Pd(t-Bu₃P)₂ (0.05 g, 0.002 eq.) were dissolved in xylene (250 ml), and the result was stirred under reflux. When the reaction was finished after 3 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 17-1 (18.23 g, yield 67%). [M+H]⁺=686

Compound 17-1 (18.23 g, 1 eq.), 5H-benzo[b]carbazole (6.36 g, 1.1 eq.), Pd(t-Bu₃P)₂ (0.14 g, 0.01 eq.) and NaOt-Bu (5.11 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 17 (16.36 g, yield 71%). [M+H]⁺=867

Synthesis Example 18

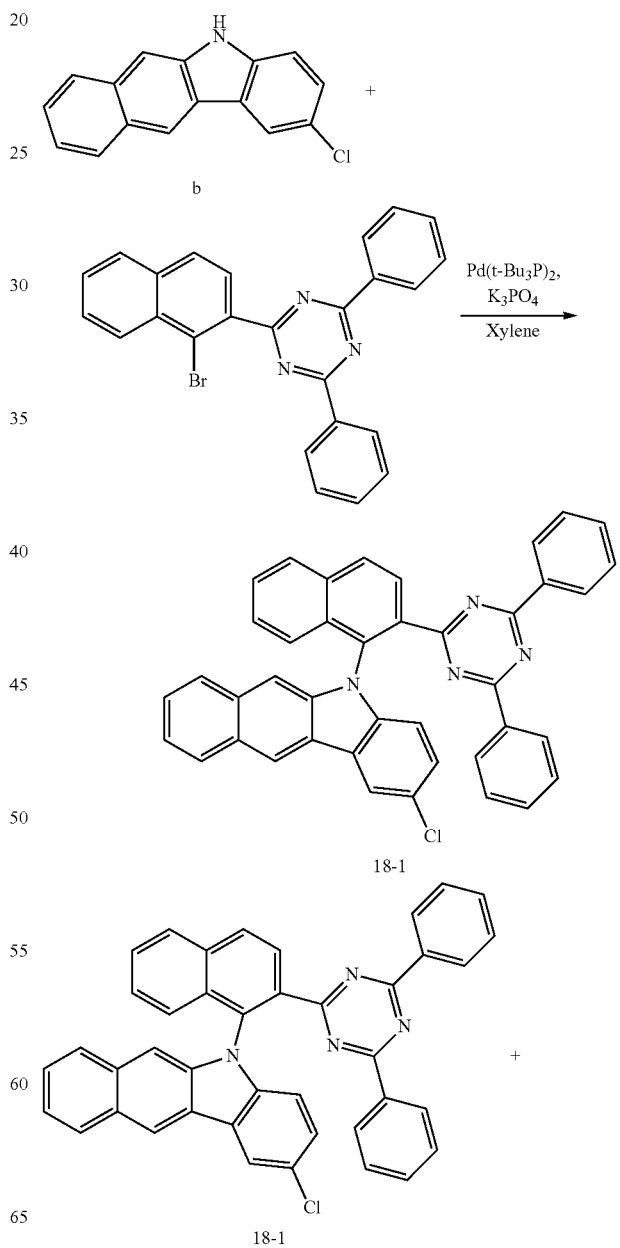

18-1

18-1

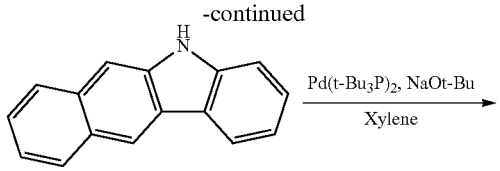

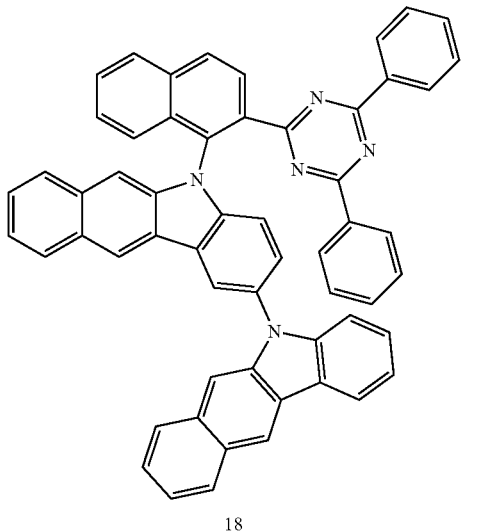 [SMILES: c1ccc(-c2nc(-c3ccccc3)nc(-c3ccc4ccccc4c3-n3c4ccc(-n5c6ccccc6c6cc7ccccc7cc65)cc4c4cc5ccccc5cc43)n2)cc1]

18

Chemical Formula b (10 g, 1 eq.), 2-(1-bromonaphthalen-2-yl)-4,6-diphenyl-1,3,5-triazine (19.15 g, 1.1 eq.), $K_3PO_4$ (16.86 g, 2 eq.) and $Pd(t-Bu_3P)_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 18-1 (14.76 g, yield 61%). $[M+H]^+=610$ Compound 18-1 (14.76 g, 1 eq.), 5H-benzo[b]carbazole (5.79 g, 1.1 eq.), $Pd(t-Bu_3P)_2$ (0.12 g, 0.01 eq.) and NaOt-Bu (4.65 g, 2 eq.) were introduced to xylene (250 ml), and the result was stirred under reflux. When the reaction was finished after 2 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 18 (13.4 g, yield 70%). $[M+H]^+=790$ Synthesis Example 19

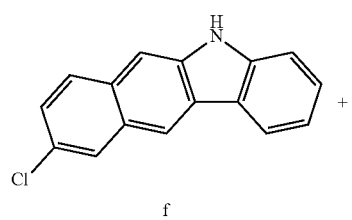

f

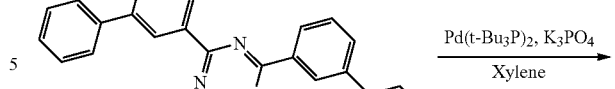

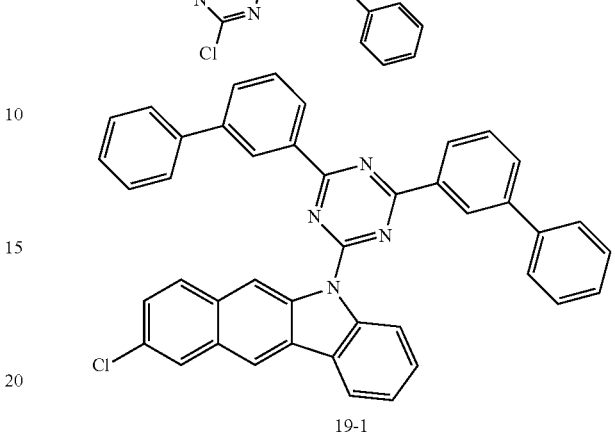

19-1

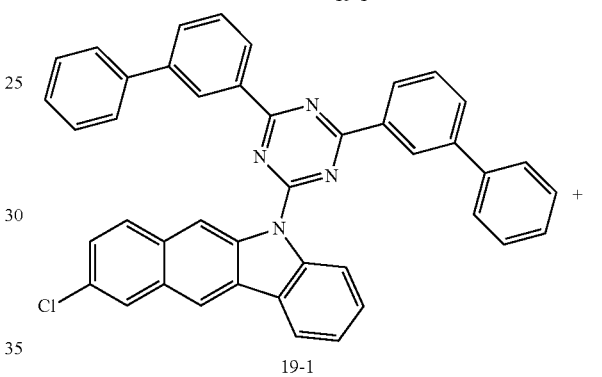

19-1

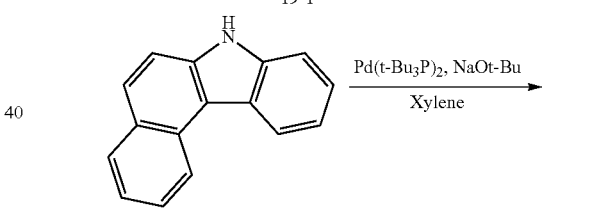

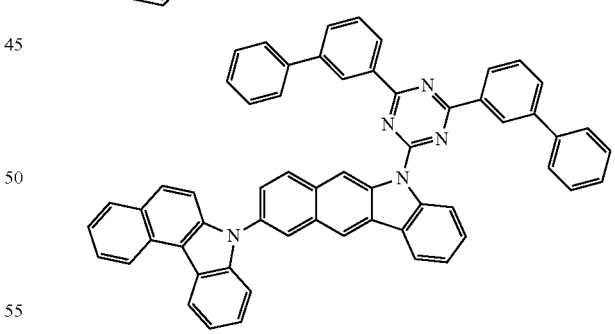

19

Chemical Formula f (10 g, 1.0 eq.), 2,4-di([1,1'-biphenyl]-3-yl)-6-chloro-1,3,5-triazine (18.35 g, 1.1 eq.), $K_3PO_4$ (16.86 g, 2 eq.) and $Pd(t-Bu_3P)_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 19-1 (19.43 g, yield 77%). [M+H]⁺=636

Compound 19-1 (19.43 g, 1 eq.), 7H-benzo[c]carbazole (7.31 g, 1.1 eq.), Pd(t-Bu₃P)₂ (0.54 g, 0.01 eq.) and NaOt-Bu (5.87 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 19 (17.47 g, yield 70%). [M+H]⁺=816

Synthesis Example 20

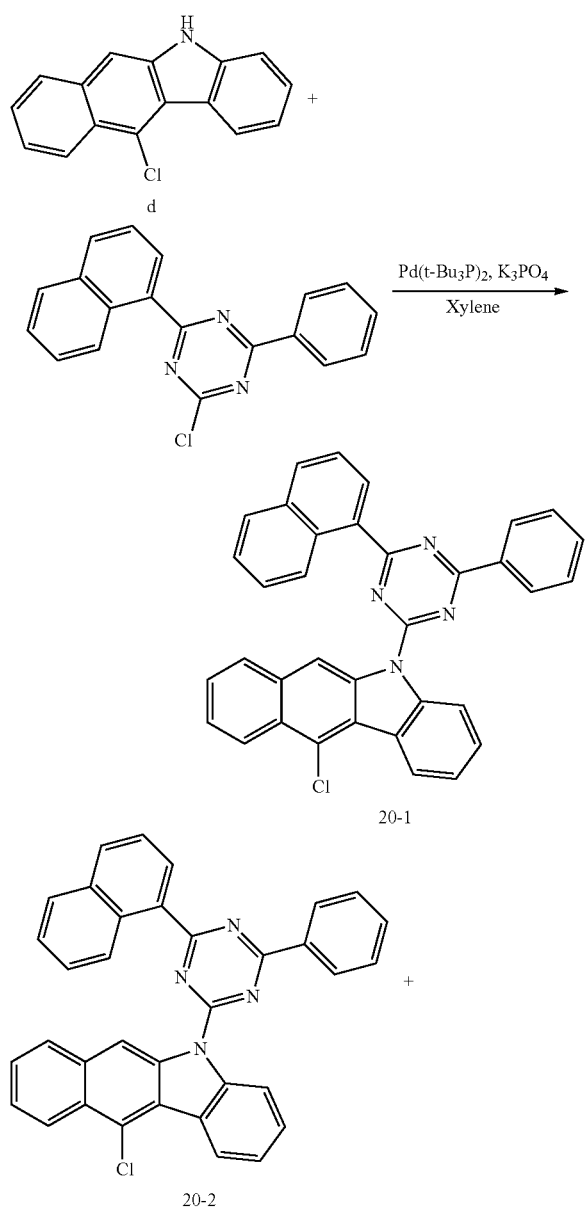

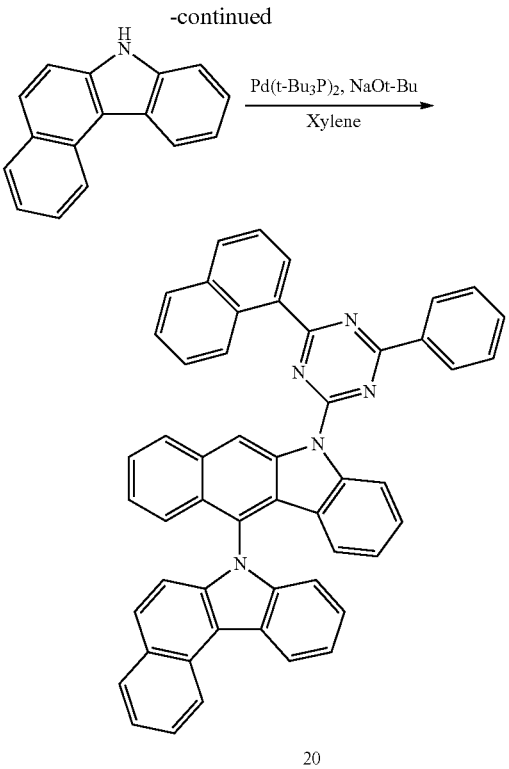

Chemical Formula d (10 g, 1 eq.), 2-chloro-4-(naphthalen-1-yl)-6-phenyl-1,3,5-triazine (13.88 g, 1.1 eq.), K₃PO₄ (16.86 g, 2 eq.) and Pd(t-Bu₃P)₂ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 20-1 (15.88 g, yield 75%). [M+H]⁺=534

Compound 20-1 (15.88 g, 1 eq.), 7H-benzo[c]carbazole (7.12 g, 1.1 eq.), Pd(t-Bu₃P)₂ (0.15 g, 0.01 eq.) and NaOt-Bu (5.72 g, 2 eq.) were introduced to xylene (250 ml), and the result was stirred under reflux. When the reaction was finished after 2 hours, the solvent was removed under vacuum. After that, the result was completely dissolved in chloroform (CHCl₃), washed with water, and then vacuumed again to remove approximately 50% of the solvent. Crystals were precipitated while introducing ethyl acetate thereto under reflux again, and the result was cooled and then filtered. This was column chromatographed to obtain Compound 20 (15.31 g, yield 72%). [M+H]⁺=714

Synthesis Example 21

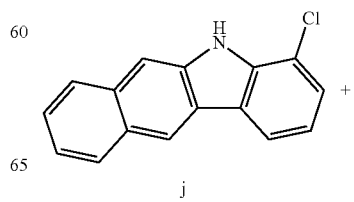

-continued

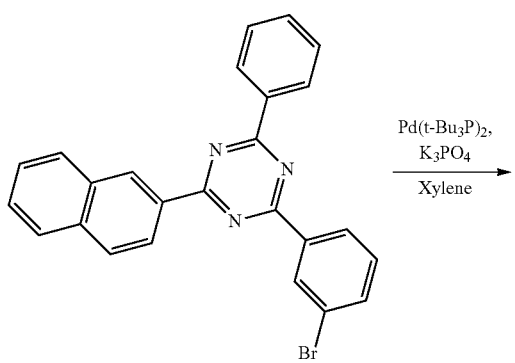

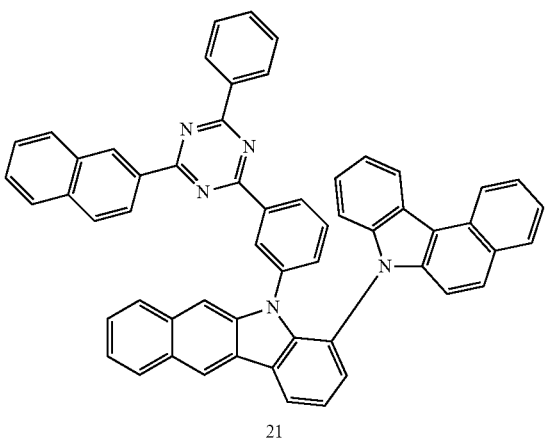

21

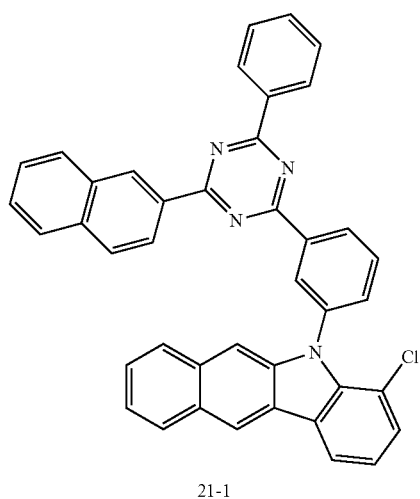

21-1

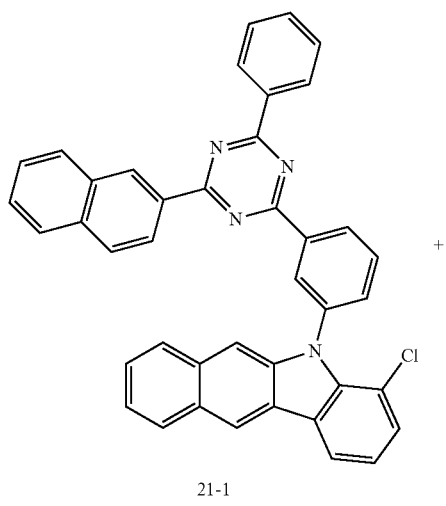

21-1

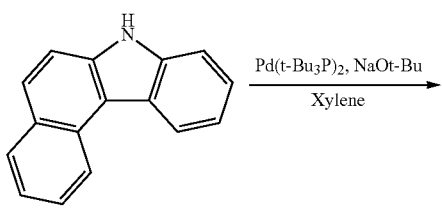

Chemical Formula j (10 g, 1 eq.), 2-(3-bromophenyl)-4-(naphthalen-2-yl)-6-phenyl-1,3,5-triazine (19.11 g, 1.1 eq.), $K_3PO_4$ (16.86 g, 2 eq.) and $Pd(t-Bu_3P)_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 21-1 (16.93 g, yield 70%). $[M+H]^+=610$ Compound 21-1 (16.93 g, 1 eq.), 7H-benzo[c]carbazole (6.64 g, 1.1 eq.), $Pd(t-Bu_3P)_2$ (0.14 g, 0.01 eq.) and NaOt-Bu (5.34 g, 2 eq.) were introduced to xylene (250 ml), and the result was stirred under reflux. When the reaction was finished after 2 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 21 (13.4 g, yield 61%). $[M+H]^+=790$ Synthesis Example 22

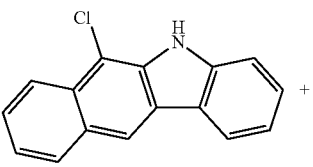

i

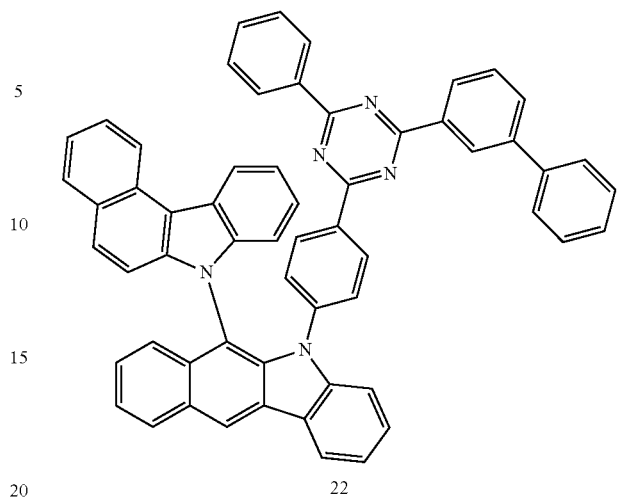

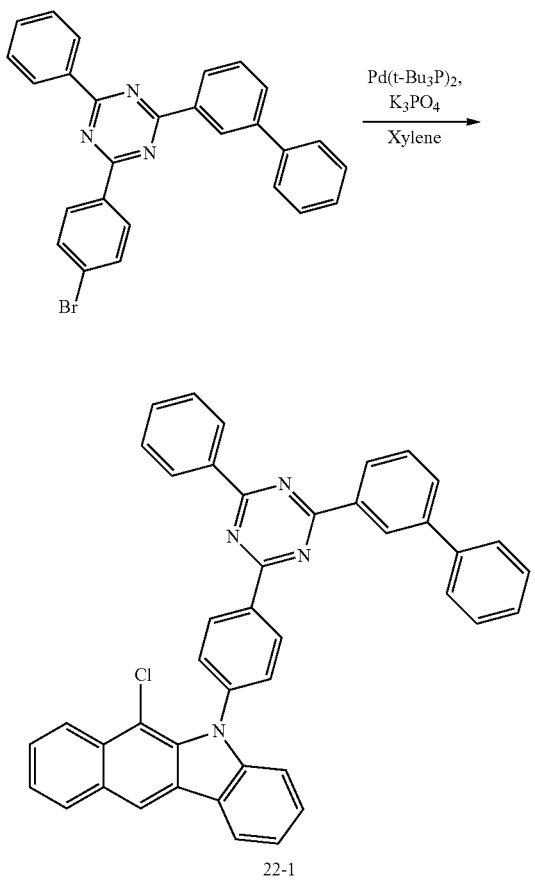

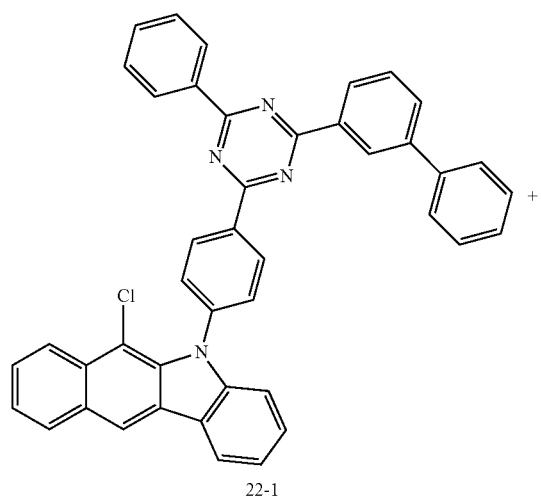

Chemical Formula i (10 g, 1 eq.), 2-([1,1'-biphenyl]-3-yl)-4-(4-bromophenyl)-6-phenyl-1,3,5-triazine (20.29 g, 1.1 eq.), $K_3PO_4$ (16.86 g, 2 eq.) and $Pd(t-Bu_3P)_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 22-1 (16.14 g, yield 64%). $[M+H]^+=636$ Compound 22-1 (16.15 g, 1 eq.), 7H-benzo[c]carbazole (6.07 g, 1.1 eq.), $Pd(t-Bu_3P)_2$ (0.12 g, 0.01 eq.) and NaOt-Bu (4.88 g, 2 eq.) were introduced to xylene (250 ml), and the result was stirred under reflux. When the reaction was finished after 2 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 22 (12.44 g, yield 60%). $[M+H]^+=816$ Synthesis Example 23

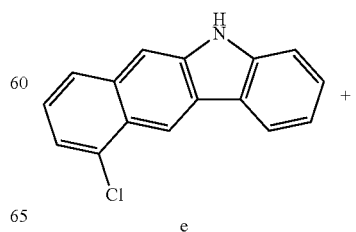

249
-continued

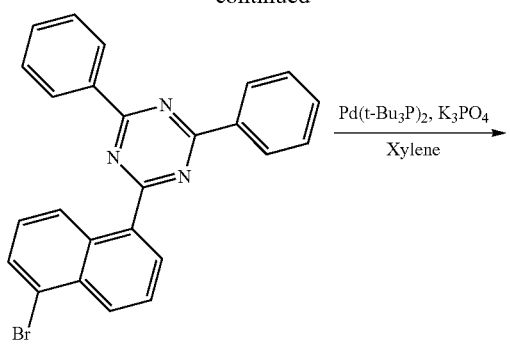

250
-continued

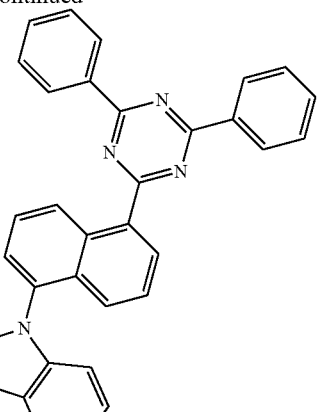

23

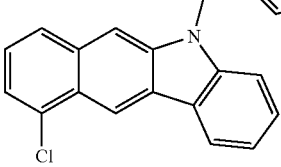

23-1

Chemical Formula e (10 g, 1 eq.), 2-(5-bromonaphthalen-1-yl)-4,6-diphenyl-1,3,5-triazine (19.15 g, 1.1 eq.), K$_3$PO$_4$ (16.86 g, 2 eq.) and Pd(t-Bu$_3$P)$_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 23-1 (16.69 g, yield 69%). [M+H]$^+$=610

Compound 23-1 (16.69 g, 1 eq.), 7H-benzo[c]carbazole (6.55 g, 1.1 eq.), Pd(t-Bu$_3$P)$_2$ (0.14 g, 0.01 eq.) and NaOt-Bu (5.26 g, 2 eq.) were introduced to xylene (250 ml), and the result was stirred under reflux. When the reaction was finished after 2 hours, the solvent was removed under vacuum. After that, the result was completely dissolved in chloroform (CHCl$_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 23 (14.07 g, yield 65%). [M+H]$^+$=790

Synthesis Example 24

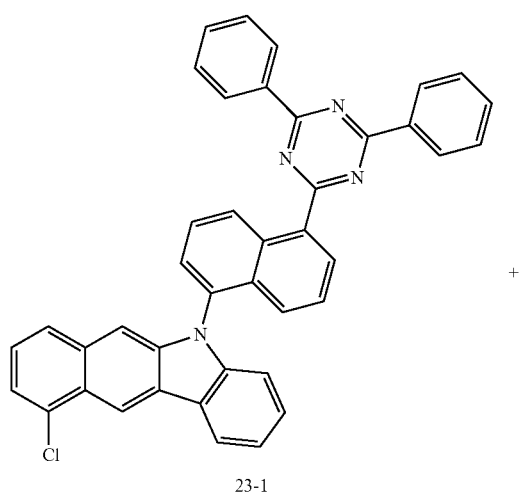

23-1

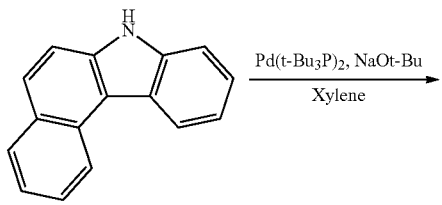

+

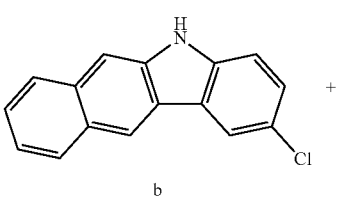

b

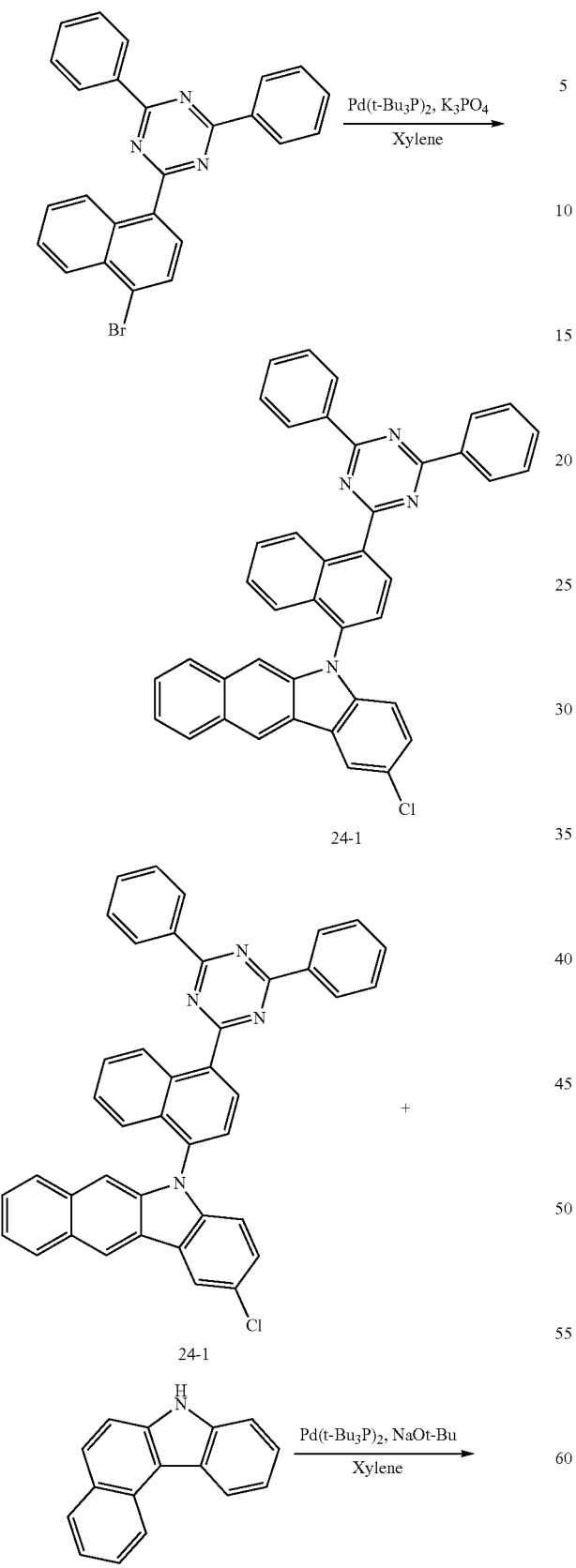

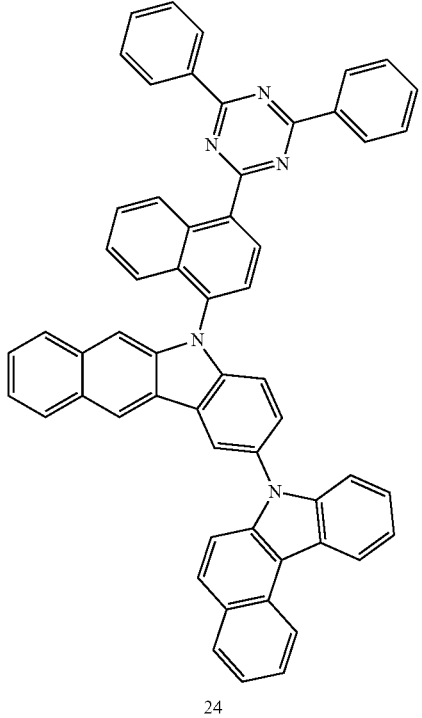

24

Chemical Formula b (10 g, 1 eq.), 2-(4-bromonaphthalen-1-yl)-4,6-diphenyl-1,3,5-triazine (19.15 g, 1.1 eq.), $K_3PO_4$ (16.86 g, 2 eq.) and $Pd(t-Bu_3P)_2$ (0.04 g, 0.002 eq.) were dissolved in xylene (250 ml), and the result was stirred under reflux. When the reaction was finished after 3 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 24-1 (16.21 g, yield 67%). $[M+H]^+$=610

Compound 24-1 (16.21 g, 1 eq.), 7H-benzo[c]carbazole (6.36 g, 1.1 eq.), $Pd(t-Bu_3P)_2$ (0.13 g, 0.01 eq.) and NaOt-Bu (5.11 g, 2 eq.) were introduced to xylene (250 ml), and the result was stirred under reflux. When the reaction was finished after 2 hours, the solvent was removed under vacuum. After that, the result was completely dissolved in chloroform ($CHCl_3$), washed with water, and then vacuumed again to remove approximately 50% of the solvent. Crystals were precipitated while introducing ethyl acetate thereto under reflux again, and the result was cooled and then filtered. This was column chromatographed to obtain Compound 24 (13.24 g, yield 63%). $[M+H]^+$=790

Experimental Example

Comparative Example 1

A glass substrate on which indium tin oxide (ITO) was coated as a thin film to a thickness of 100 nm was placed in distilled water containing dissolved detergent and ultrasonically cleaned. A product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum depositor.

On the transparent ITO electrode prepared as above, the following Compound HI-1 was formed to a thickness of 115 nm as a hole injection layer while p-doping the following Compound A-1 in a concentration of 1.5% weight. On the hole injection layer, a hole transfer layer having film thickness of 80 nm was formed by vacuum depositing the following Compound HT-1. Subsequently, an electron blocking layer was formed on the hole transfer layer by vacuum depositing the following Compound EB-1 to a film thickness of 15 nm. Subsequently, a light emitting layer having a thickness of 40 nm was formed on the electron blocking layer by vacuum depositing the following Compound RH-1 and the following Compound Dp-39 in a weight ratio of 98:2. On the light emitting layer, a hole blocking layer was formed by vacuum depositing the following Compound HB-1 to a film thickness of 3 nm. Subsequently, an electron injection and transfer layer was formed on the hole blocking layer to a thickness of 30 nm by vacuum depositing the following Compound ET-1 and the following Compound LiQ in a weight ratio of 2:1. On the electron injection and transfer layer, a cathode was formed by depositing lithium fluoride (LiF) to a thickness of 1.2 nm and aluminum to a thickness of 100 nm in consecutive order.

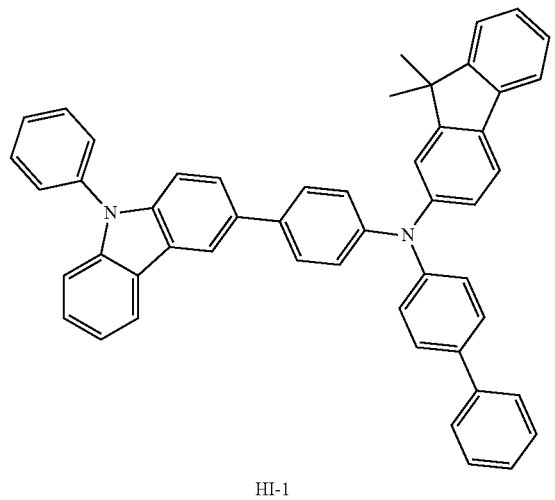

HI-1

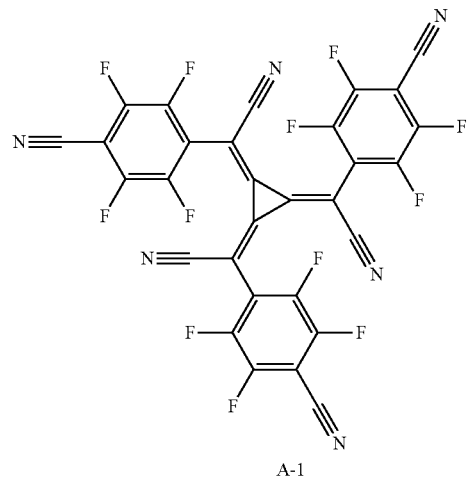

A-1

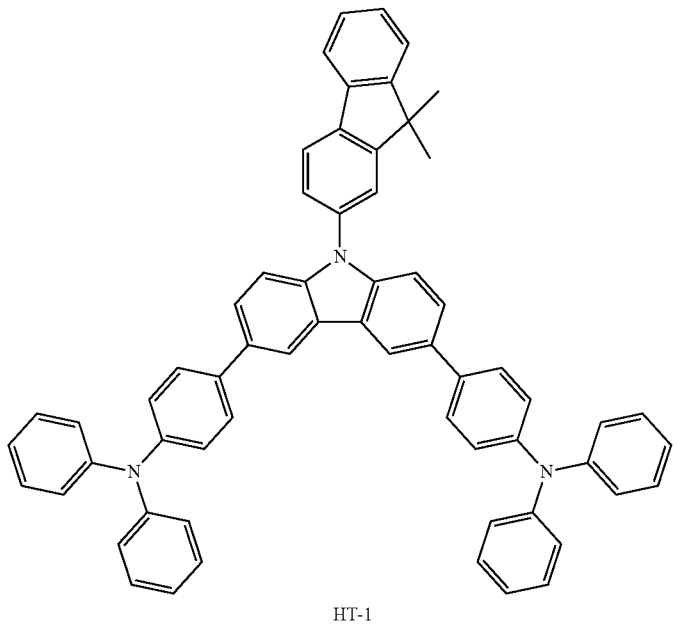

HT-1

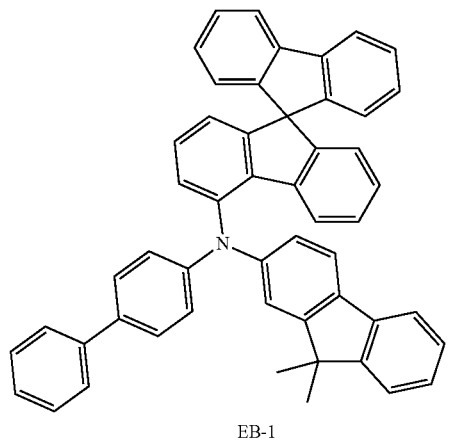

EB-1

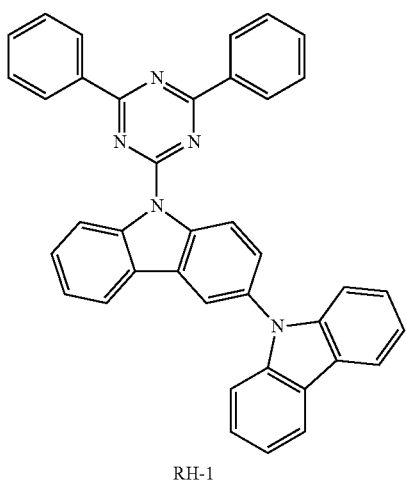

RH-1

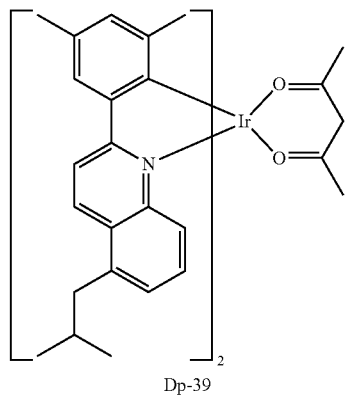

Dp-39

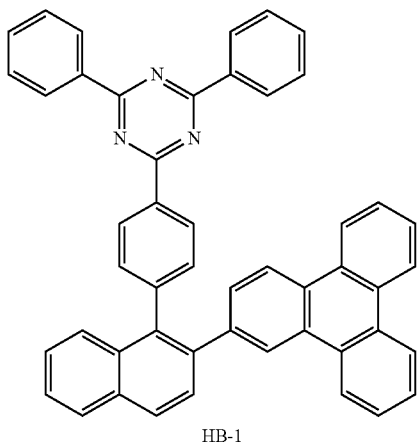

HB-1

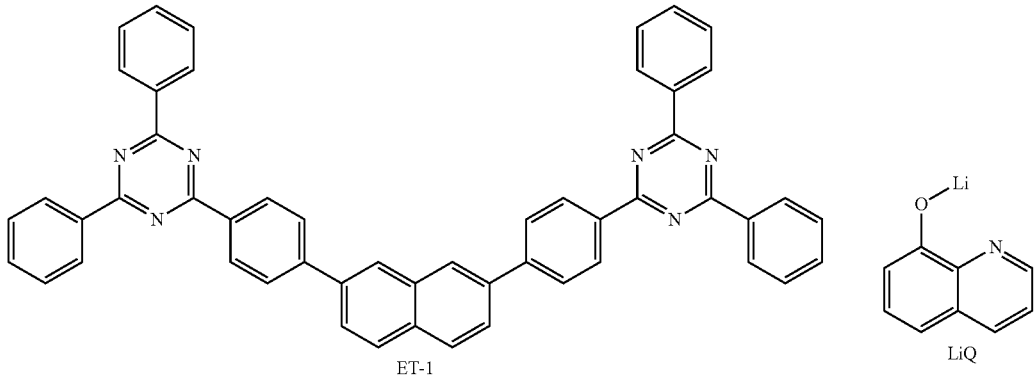

ET-1

LiQ

An organic light emitting device was manufactured by maintaining, in the above-mentioned process, the deposition rates of the organic materials at 0.04 nm/sec to 0.07 nm/sec, the deposition rates of the lithium fluoride and the aluminum of the cathode at 0.03 nm/sec and 0.2 nm/sec, respectively, and the degree of vacuum during the deposition at $2\times10^{-7}$ torr to $5\times10^{-6}$ torr.

Examples 1 to 24 and Comparative Examples 2 to 13

Organic light emitting devices were manufactured in the same manner as in Comparative Example 1 except that compounds described in the following Table 1 were used instead of Compound RH-1.

-continued
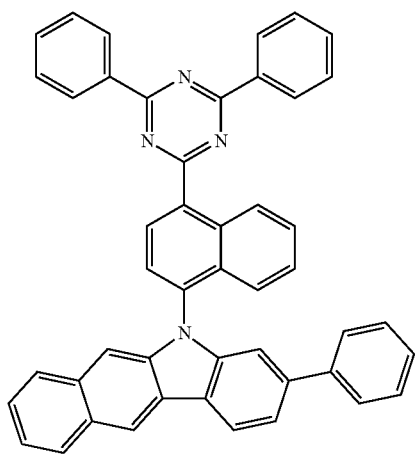
C-1
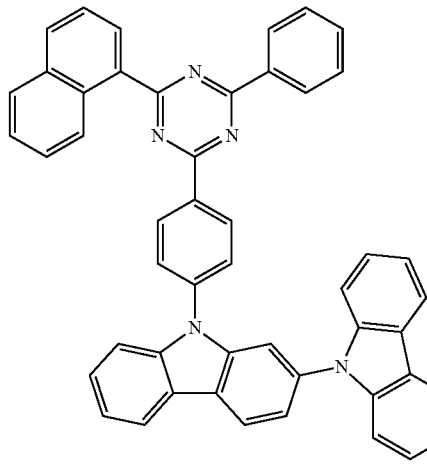
C-4
C-2
C-5
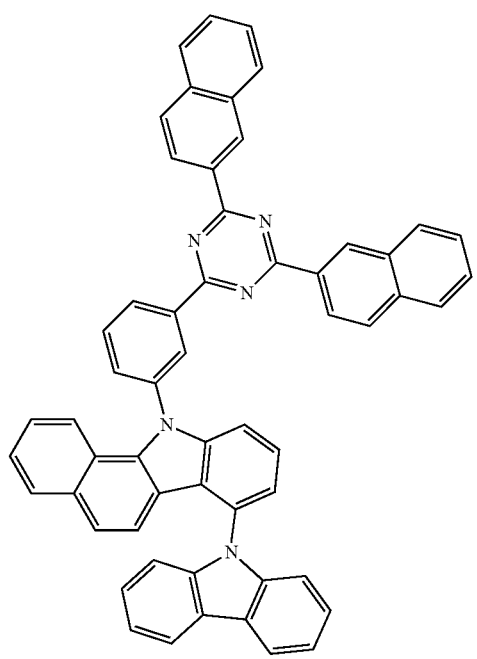
C-3
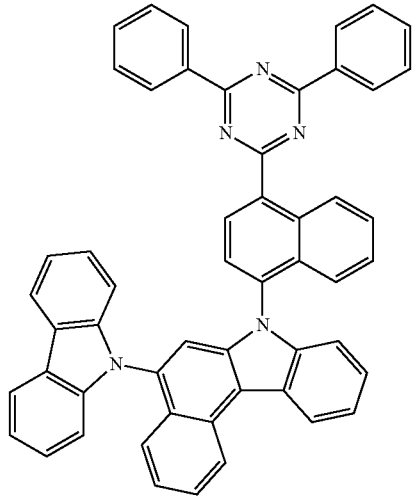
C-6

-continued
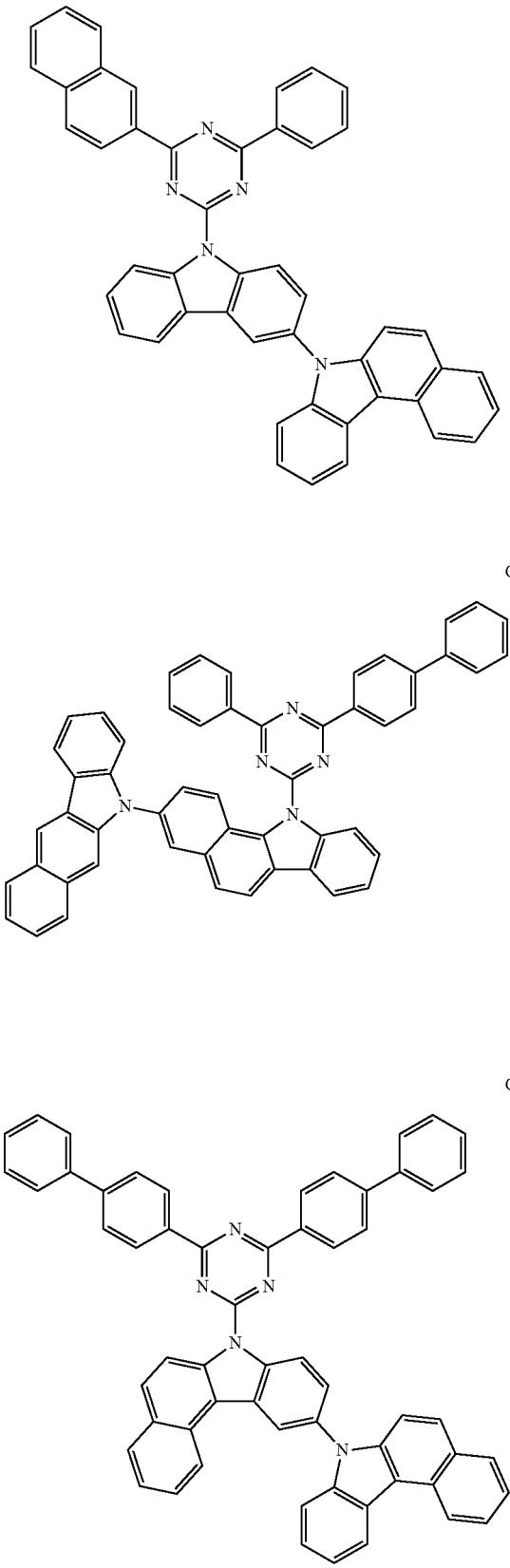
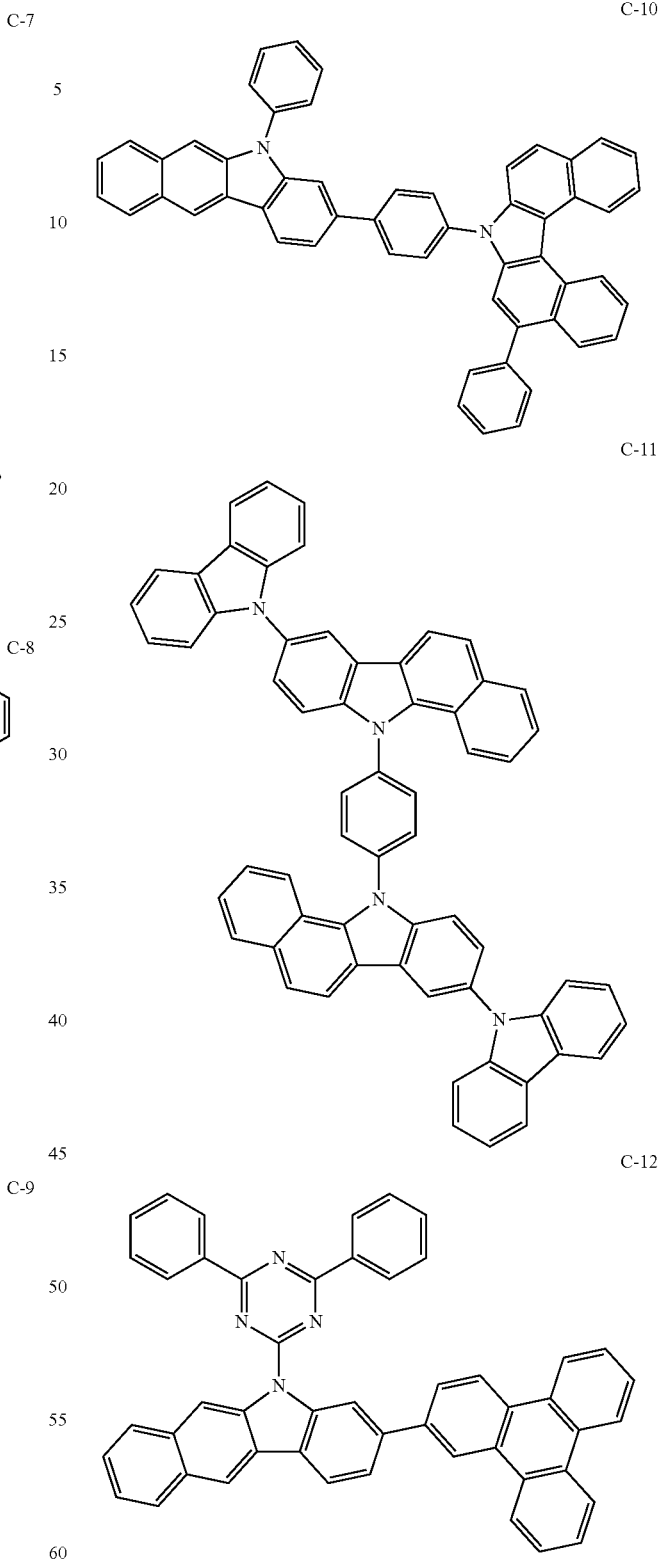
Voltage, efficiency and lifetime obtained when applying a current to each of the organic light emitting devices manufactured in Examples 1 to 24 and Comparative Examples 1 to 13 were measured, and the results are shown in the following Table 1. T95 means time taken for luminance decreasing to 95% from initial luminance (15000 nit).

TABLE 1

| Category | Compound | Driving Voltage (V) | Efficiency (cd/A) | Lifetime T95 (h) | Light Emission Color |
|---|---|---|---|---|---|
| Comparative Example 1 | RH-1 | 4.48 | 30.5 | 132 | Red |
| Example 1 | 1 | 3.93 | 37.5 | 194 | Red |
| Example 2 | 2 | 3.99 | 36.7 | 187 | Red |
| Example 3 | 3 | 4.01 | 34.8 | 287 | Red |
| Example 4 | 4 | 4.11 | 35.7 | 305 | Red |
| Example 5 | 5 | 4.23 | 33.3 | 246 | Red |
| Example 6 | 6 | 4.15 | 35.5 | 203 | Red |
| Example 7 | 7 | 3.87 | 38.4 | 184 | Red |
| Example 8 | 8 | 4.10 | 35.0 | 243 | Red |
| Example 9 | 9 | 4.15 | 34.9 | 237 | Red |
| Example 10 | 10 | 4.07 | 35.3 | 247 | Red |
| Example 11 | 11 | 4.17 | 37.1 | 240 | Red |
| Example 12 | 12 | 4.01 | 36.5 | 264 | Red |
| Example 13 | 13 | 3.81 | 39.1 | 179 | Red |
| Example 14 | 14 | 3.84 | 38.0 | 183 | Red |
| Example 15 | 15 | 4.03 | 34.7 | 259 | Red |
| Example 16 | 16 | 3.97 | 40.5 | 174 | Red |
| Example 17 | 17 | 4.11 | 37.1 | 227 | Red |
| Example 18 | 18 | 4.28 | 35.0 | 241 | Red |
| Example 19 | 19 | 3.85 | 40.3 | 188 | Red |
| Example 20 | 20 | 4.15 | 37.3 | 213 | Red |
| Example 21 | 21 | 3.99 | 36.5 | 294 | Red |
| Example 22 | 22 | 4.24 | 35.0 | 258 | Red |
| Example 23 | 23 | 4.19 | 37.3 | 269 | Red |
| Example 24 | 24 | 4.08 | 36.9 | 227 | Red |
| Comparative Example 2 | C-1 | 4.51 | 31.5 | 73 | Red |
| Comparative Example 3 | C-2 | 4.01 | 34.5 | 51 | Red |
| Comparative Example 4 | C-3 | 4.11 | 34.5 | 79 | Red |
| Comparative Example 5 | C-4 | 4.73 | 29.1 | 45 | Red |
| Comparative Example 6 | C-5 | 4.60 | 30.5 | 52 | Red |
| Comparative Example 7 | C-6 | 4.47 | 32.7 | 120 | Red |
| Comparative Example 8 | C-7 | 4.29 | 29.5 | 57 | Red |
| Comparative Example 9 | C-8 | 4.65 | 27.5 | 41 | Red |
| Comparative Example 10 | C-9 | 4.31 | 32.5 | 64 | Red |
| Comparative Example 11 | C-10 | 4.79 | 13.8 | 27 | Red |
| Comparative Example 12 | C-11 | 4.73 | 15.3 | 29 | Red |
| Comparative Example 13 | C-12 | 4.41 | 32.5 | 69 | Red |

In the red organic light emitting device of Comparative Example 1, Compound RH-1 that has been widely used in the art was used, and Compound EB-1 was used as an electron blocking layer, and RH-1/Dp-39 was used as a red light emitting layer. In Comparative Examples 2 to 13, organic light emitting devices were manufactured using Compounds C-1 to C-12 instead of Compound RH-1.

Based on the results shown in Table 1, it was identified that the devices using the compound of Chemical Formula 1 of the present disclosure as a host of a red light emitting layer had a driving voltage lowered by up to close to 20%, and efficiency increased by 20% or more compared to the devices comprising the materials of the comparative examples as a host of a light emitting layer. This means that energy is more favorably transferred from the compound (host) of Chemical Formula 1 of the present disclosure to the red dopant.

In addition, it was identified from the data in Table 1 that the devices comprising the compound of Chemical Formula 1 of the present disclosure particularly had lifetime properties significantly improved while maintaining high efficiency. This is considered to be due to the fact that, compared to the compounds of the comparative examples, the compound of Chemical Formula 1 of the present disclosure has a higher degree of stability for electrons and holes, and favorably balances electron and hole migration in the red organic light emitting device.

As a result, it was identified that, when using the compound of the present disclosure as a host of a red light emitting layer, driving voltage, light emission efficiency and/or lifetime properties of an organic light emitting device can be improved.

REFERENCE NUMERALS

1: Substrate
2: Anode
3: Light Emitting Layer
4: Cathode
5: Hole Injection Layer
6: Hole Transfer Layer
7: Electron Transfer Layer
8: Electron Blocking Layer
9: Hole Blocking Layer
10: Electron Injection and Transfer Layer

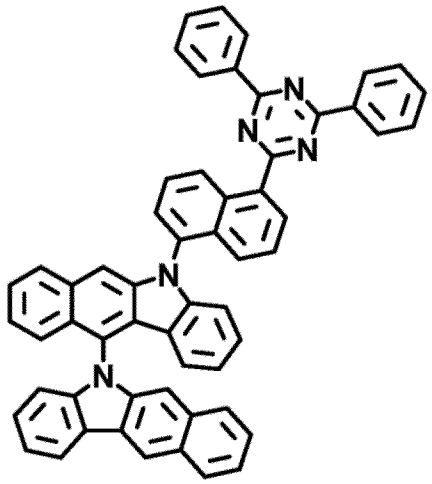

In Claim 3, at Column 386, Lines 22-43, the structure of the compound should be:
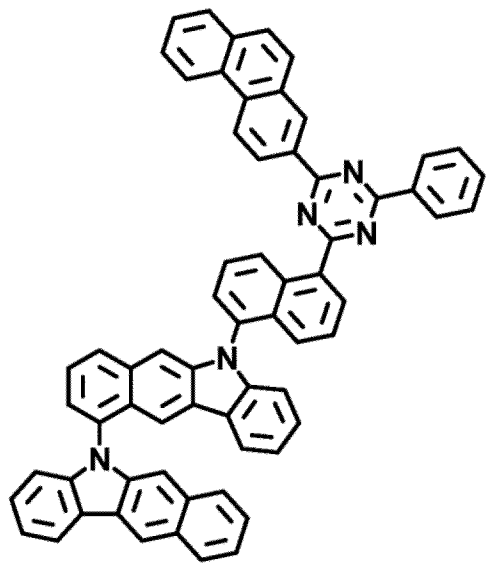
In Claim 3, at Column 388, Lines 25-43, the structure of the compound should be:
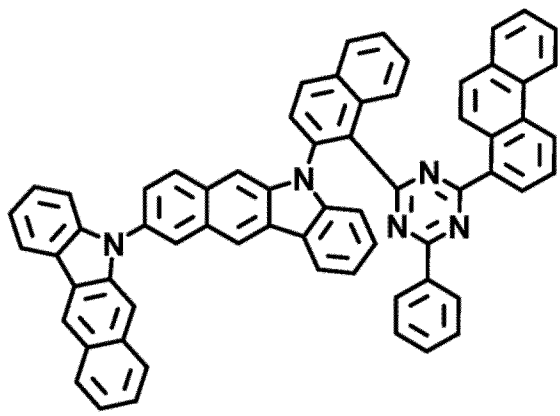

In Claim 3, at Column 401, Lines 33-50, the structure of the compound should be:
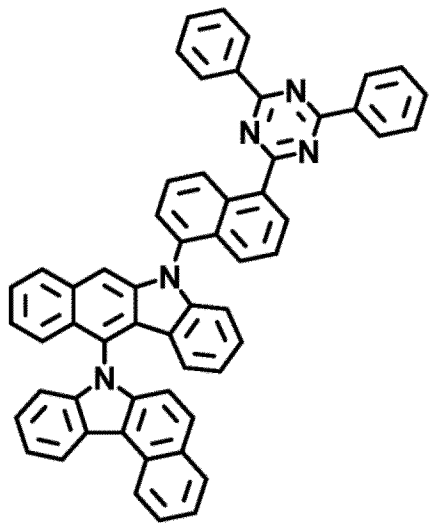
In Claim 3, at Column 415, Lines 20-31, the structure of the compound should be:
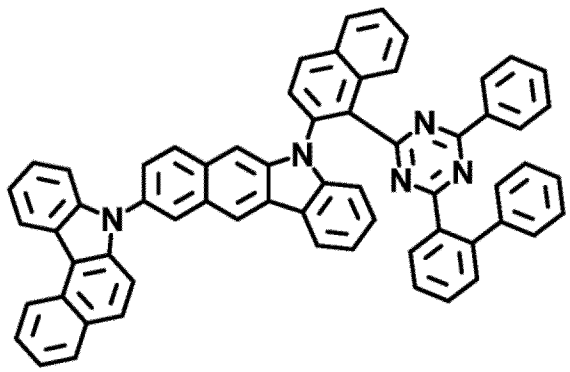
In Claim 3, at Column 415, Lines 55-65, the structure of the compound should be:
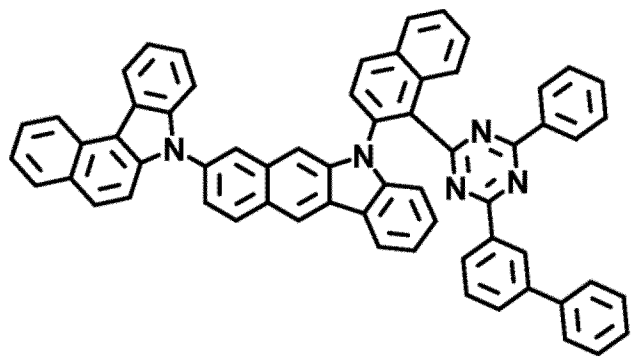

In Claim 3, at Column 426, Lines 24-44, the structure of the compound should be:
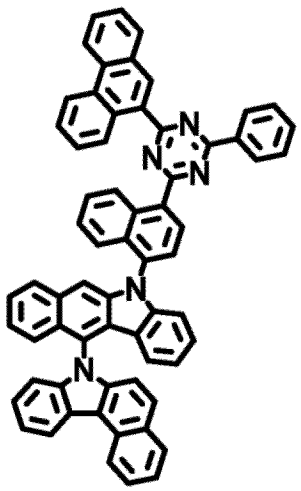
In Claim 3, at Column 429, Lines 5-25 the following structures should be inserted:
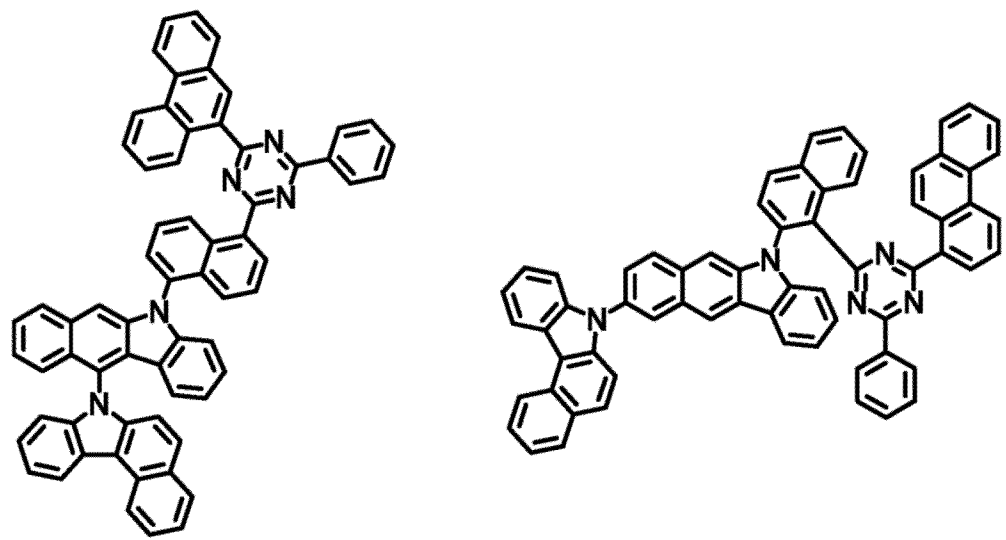
-- --
In Claim 3, at Column 429, Lines 29-39, the structure of the compound should be:
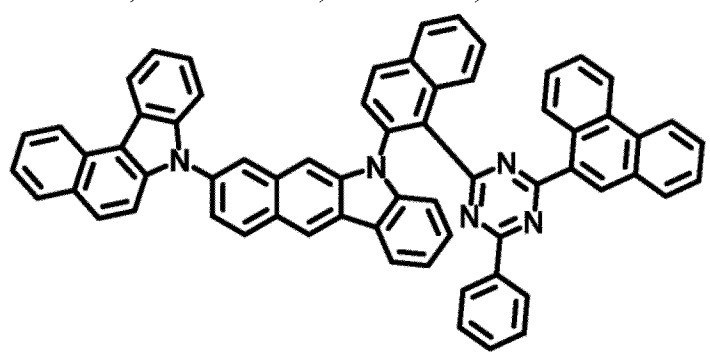

The invention claimed is:
1. A compound of Chemical Formula 1:

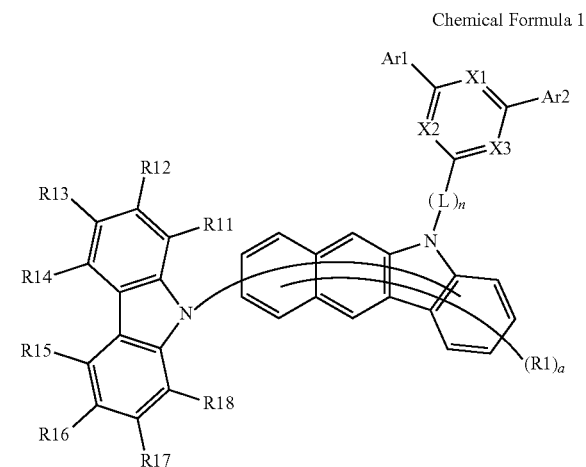

Chemical Formula 1 wherein, in Chemical Formula 1;
X1 is N or CR, X2 is N or CR', and X3 is N or CR";
two or more of X1 to X3 are N;
R, R', R" and R1 are the same as or different from each other, and each independently is hydrogen or deuterium, a is an integer of 0 to 9, and when a is 2 or greater, the R1s are the same as or different from each other;
Ar1 and Ar2 are the same as or different from each other, and each independently is a substituted or unsubstituted aryl group;
L is a direct bond, or a substituted or unsubstituted arylene group, n is an integer of 1 to 3, and when n is 2 or 3, Ls are the same as or different from each other; and
R11 to R18 are the same as or different from each other, and each independently is hydrogen, deuterium, a nitrile group, a substituted or unsubstituted alkyl group, a substituted or unsubstituted cycloalkyl group, a substituted or unsubstituted alkoxy group, a substituted or unsubstituted aryloxy group, a substituted or unsubstituted aryl group, or a substituted or unsubstituted heteroaryl group, or bond to adjacent groups to form a substituted or unsubstituted ring.

2. The compound of claim 1, wherein Chemical Formula 1 is any one of the following Chemical Formulae 2 to 5:

Chemical Formula 2

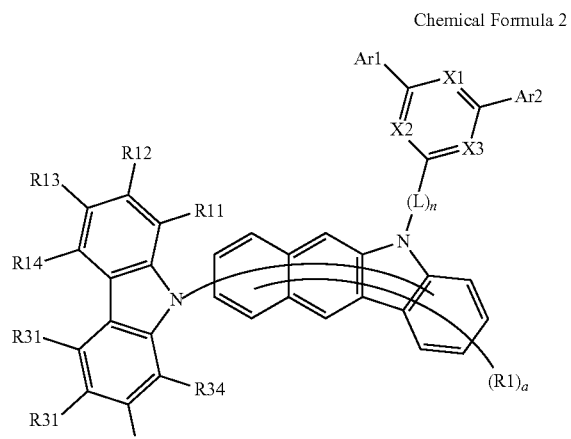

Chemical Formula 3

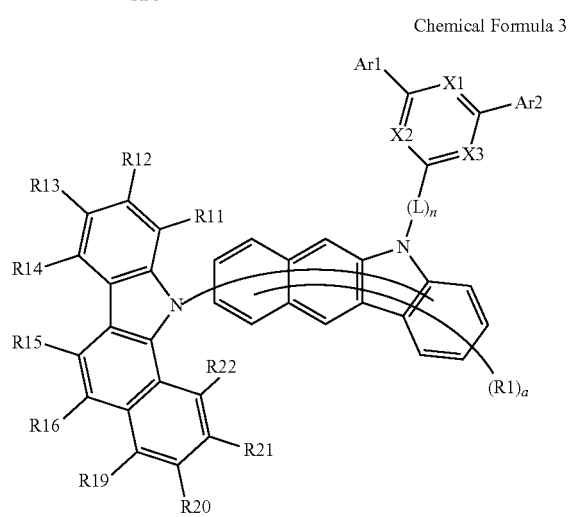

Chemical Formula 4

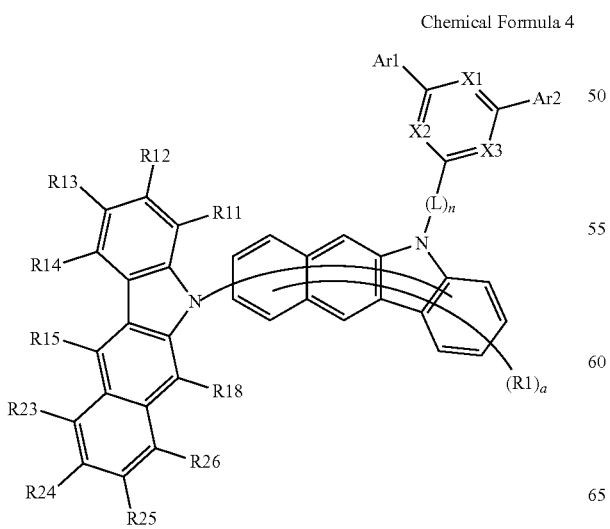

Chemical Formula 5

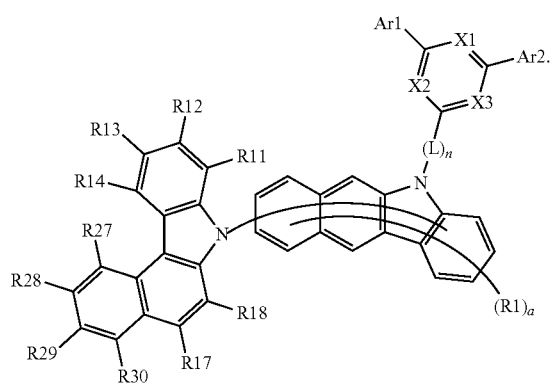

wherein in Chemical Formulae 2 to 5;
R19 to R34 are the same as or different from each other, and each independently is hydrogen, deuterium, a nitrile group a substituted or unsubstituted alkyl group, a substituted or unsubstituted cycloalkyl group a substituted or unsubstituted alkoxy group a substituted or unsubstituted aryloxy group a substituted or unsubstituted aryl group, or a substituted or unsubstituted heteroaryl group; and
the remaining substituents have the same definitions as in claim 1.

3. The compound of claim 1, wherein Chemical Formula 1 is selected from among the following compounds:

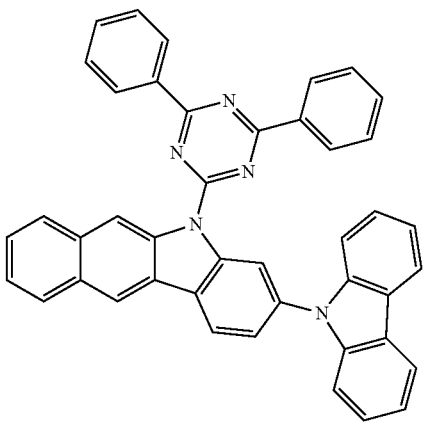

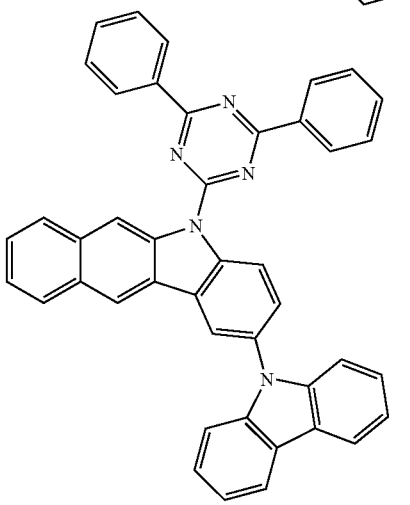

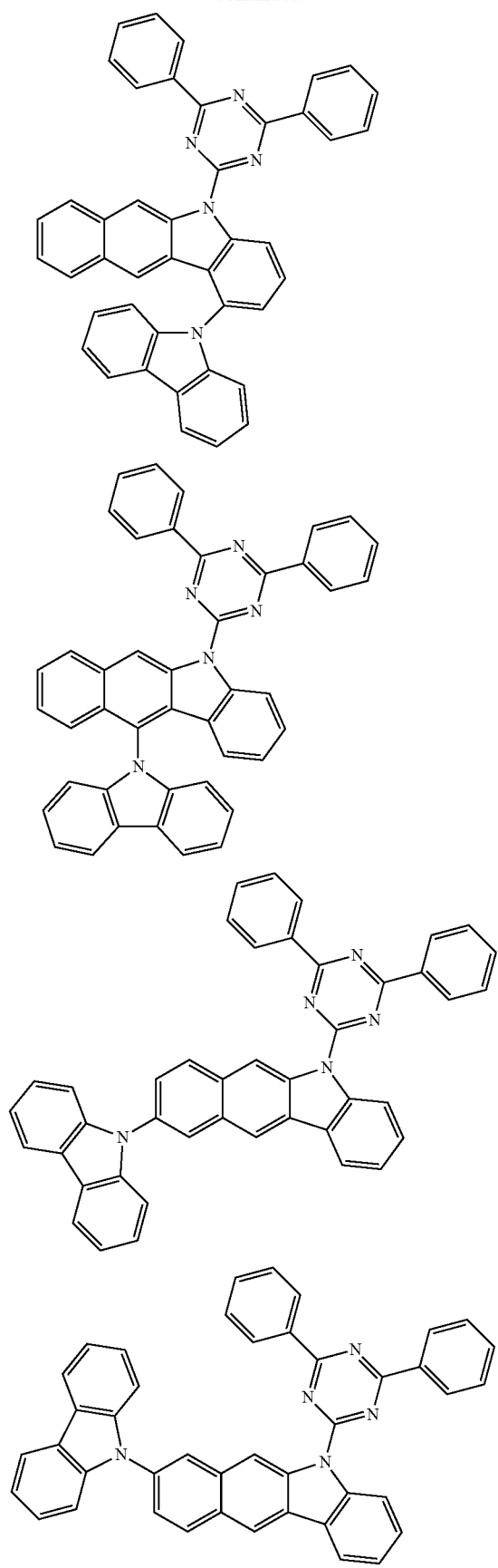
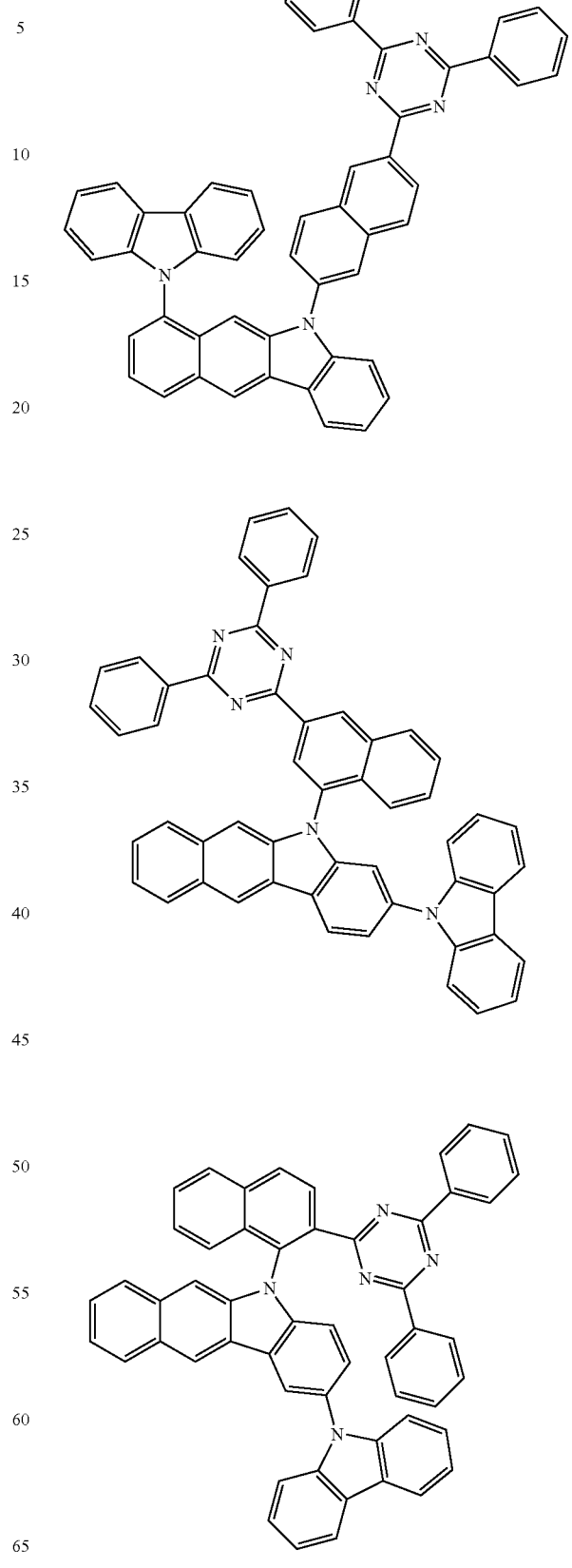

267
-continued
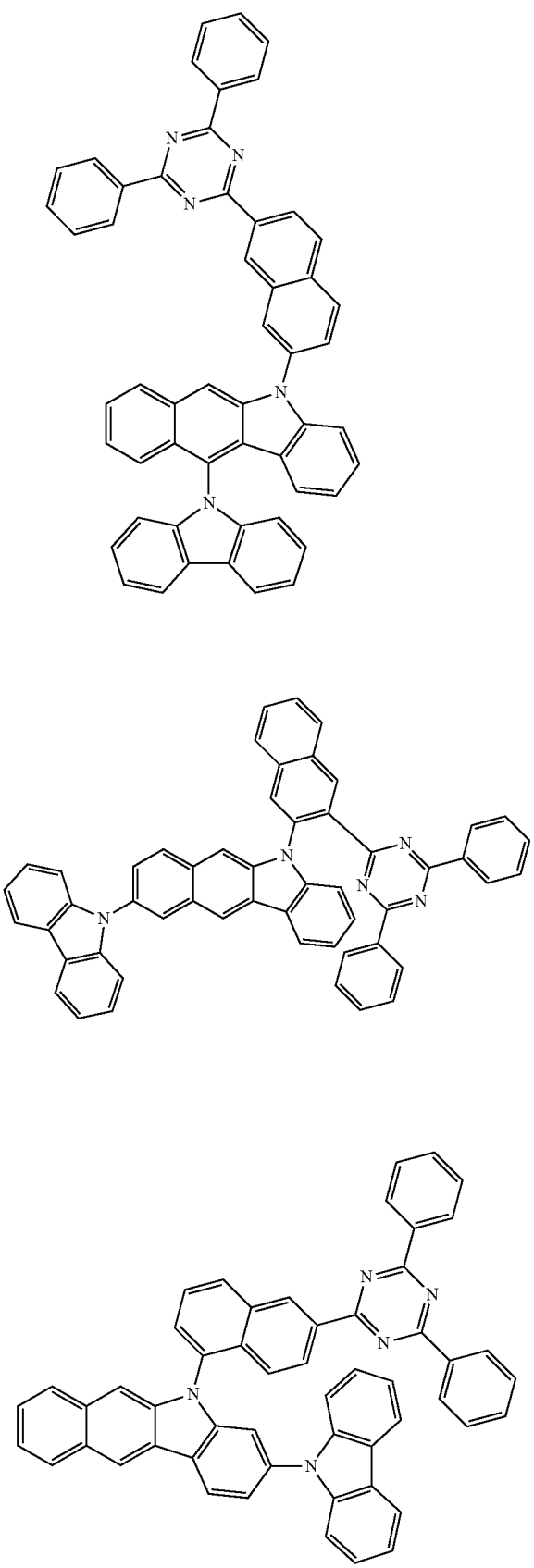
268
-continued
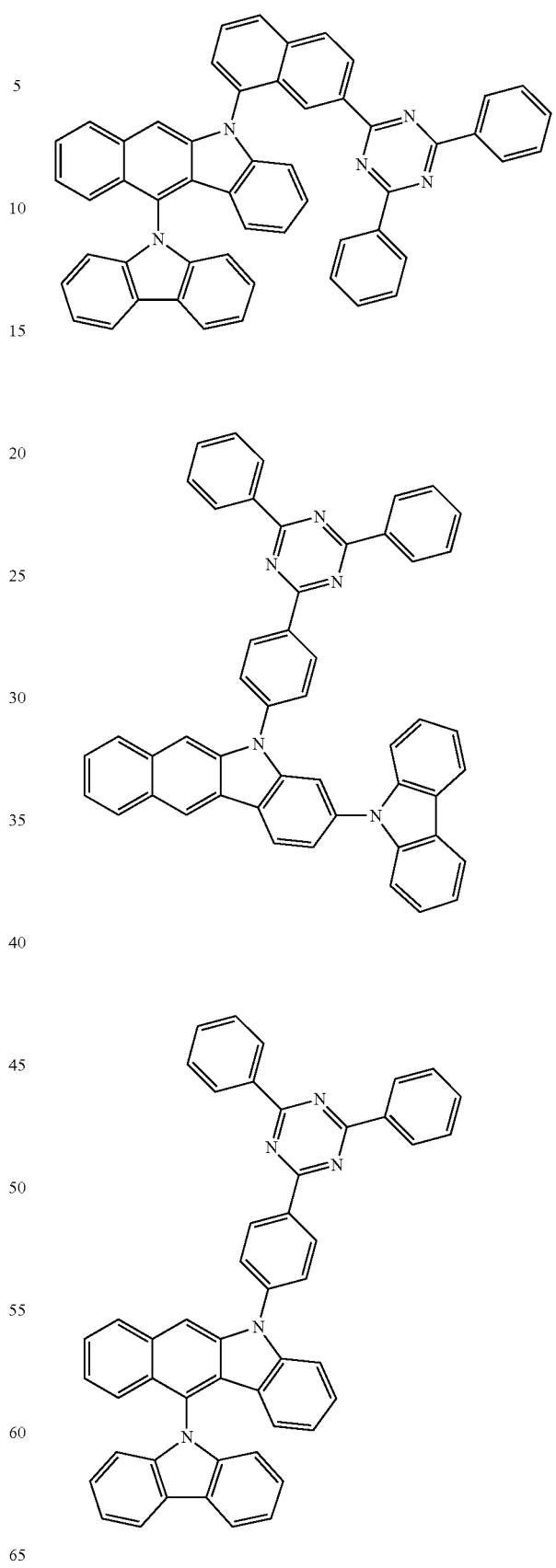

269
-continued
270
-continued
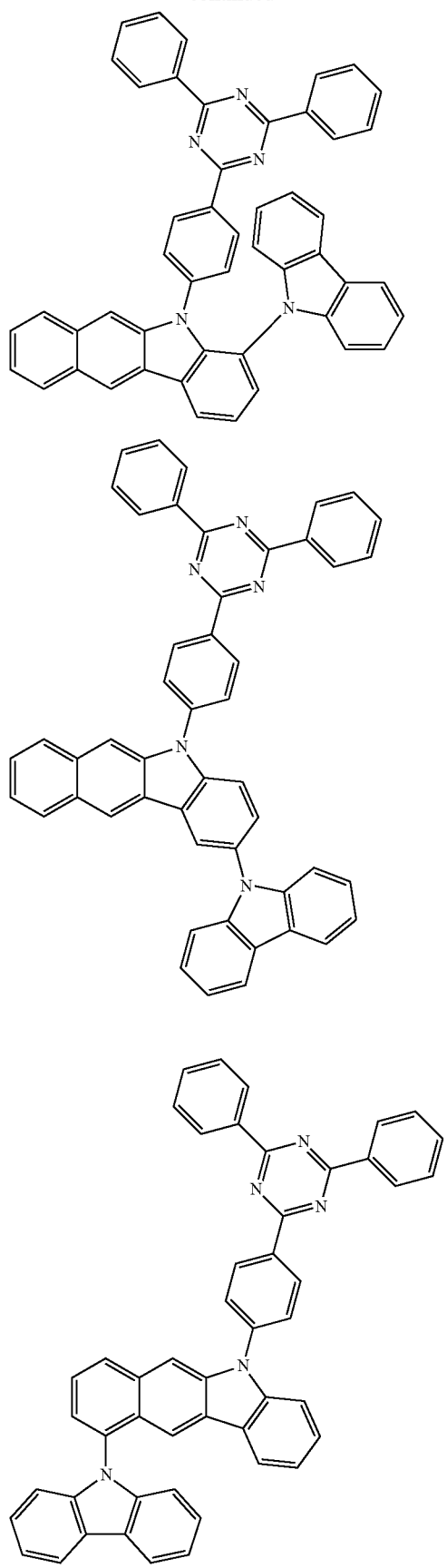
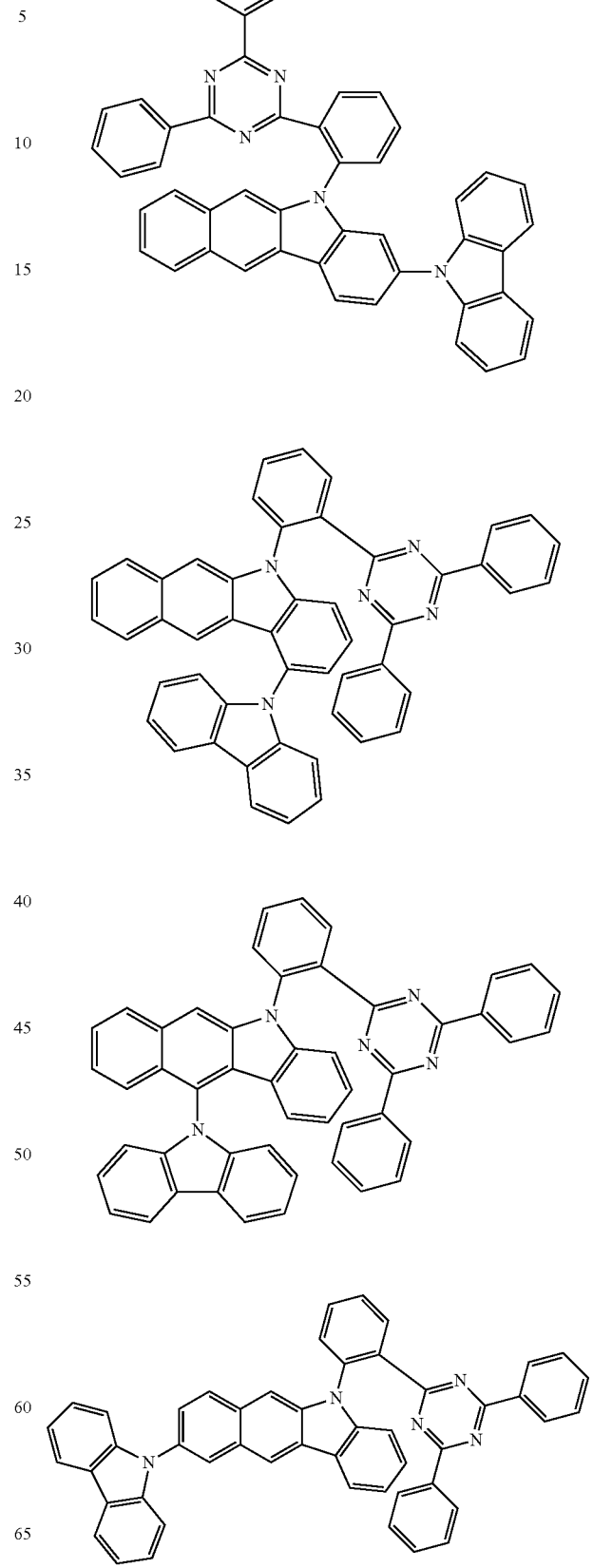

271
-continued
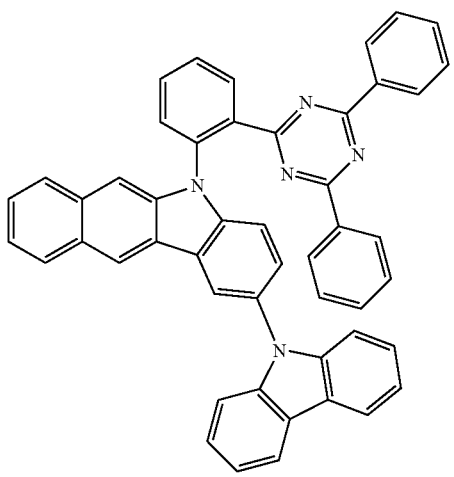
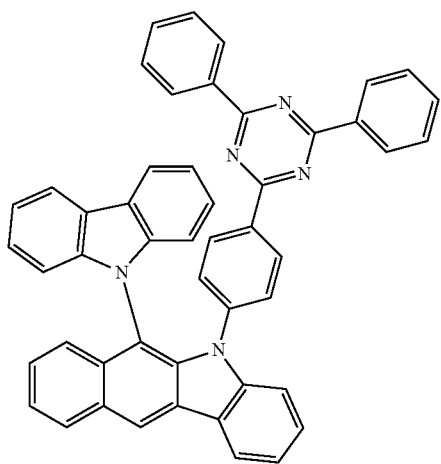
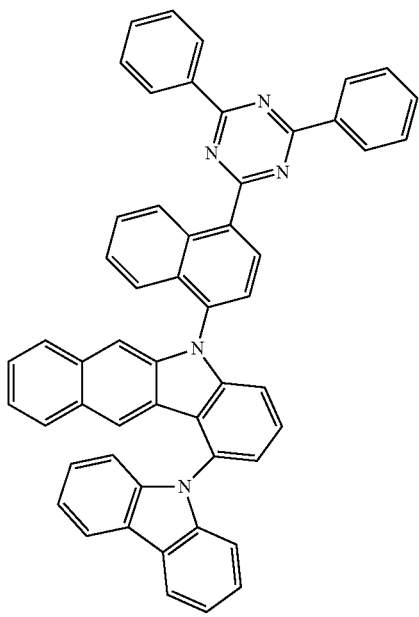
272
-continued
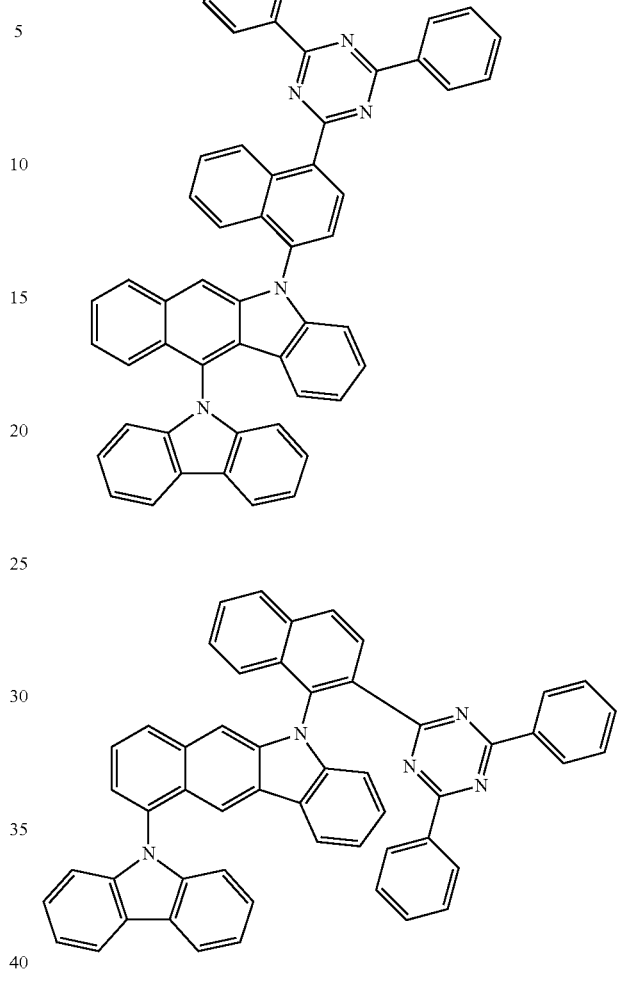
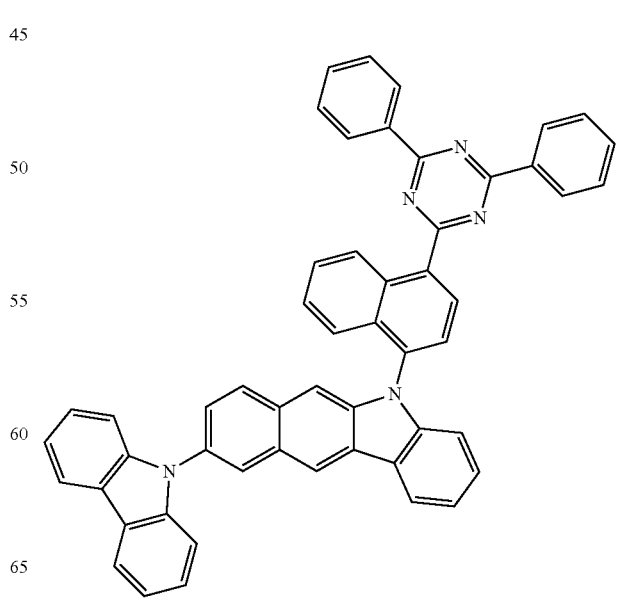

273
-continued
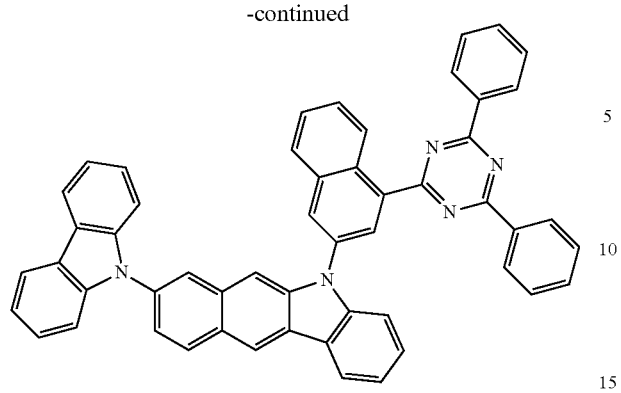
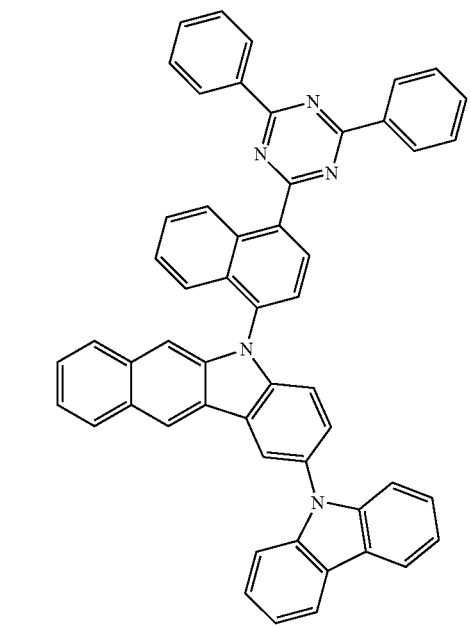
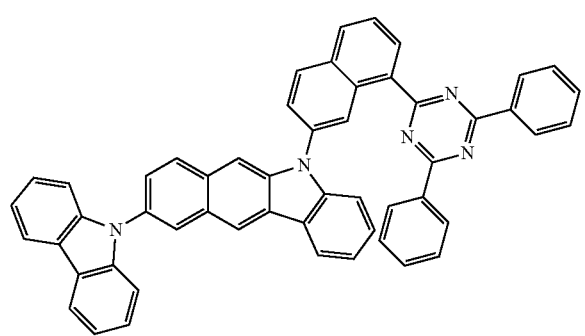
274
-continued
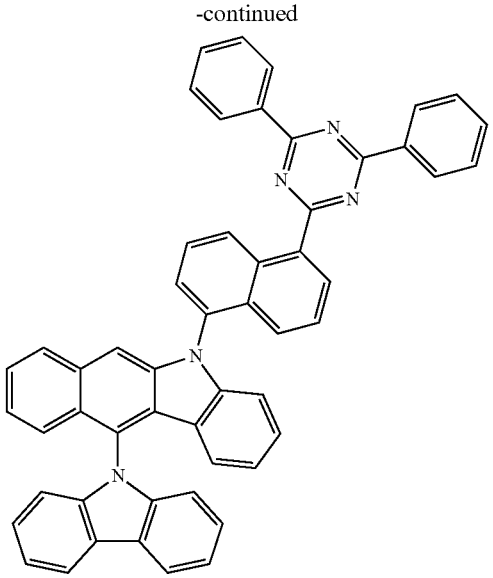
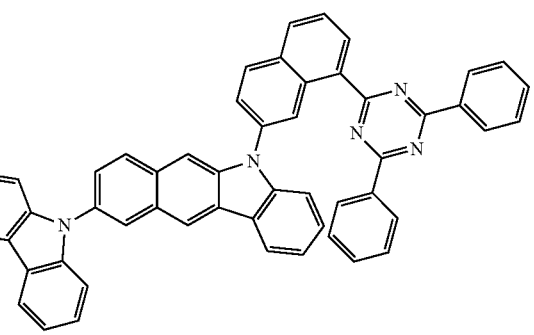
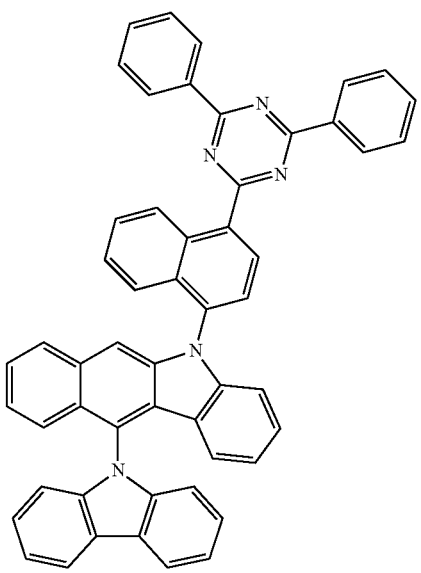

275
-continued
276
-continued
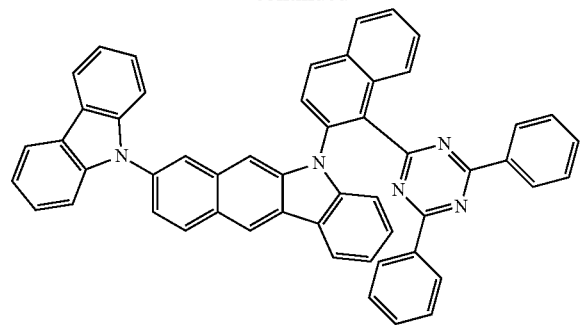
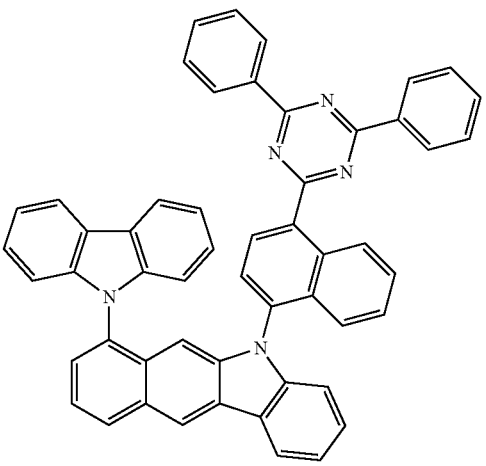
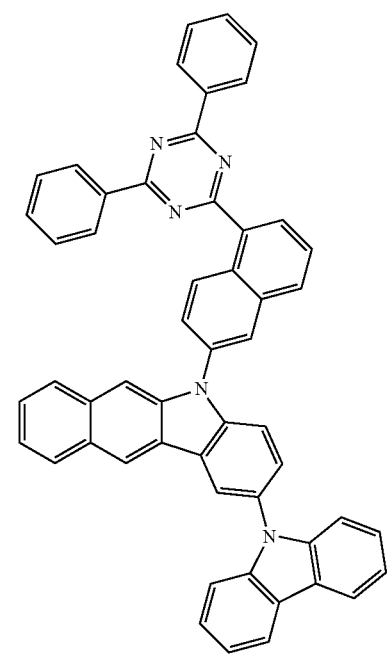
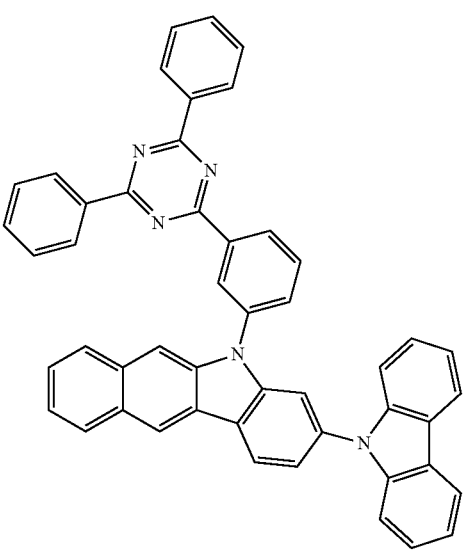
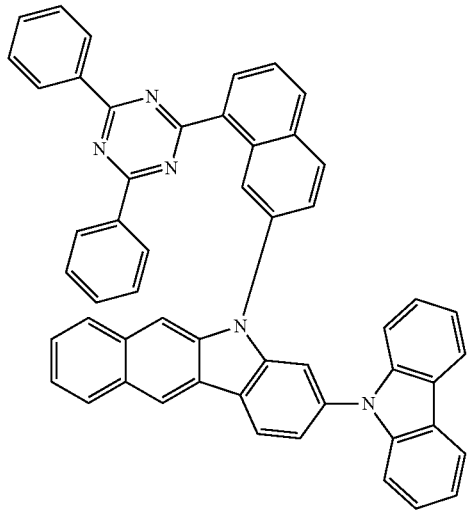
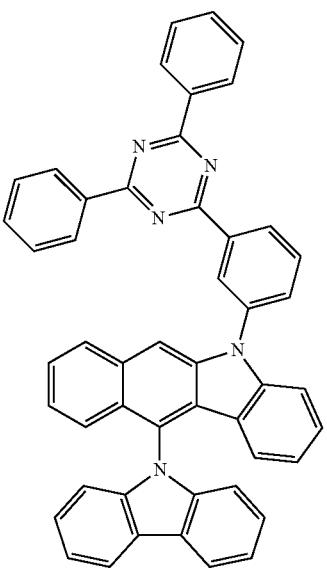

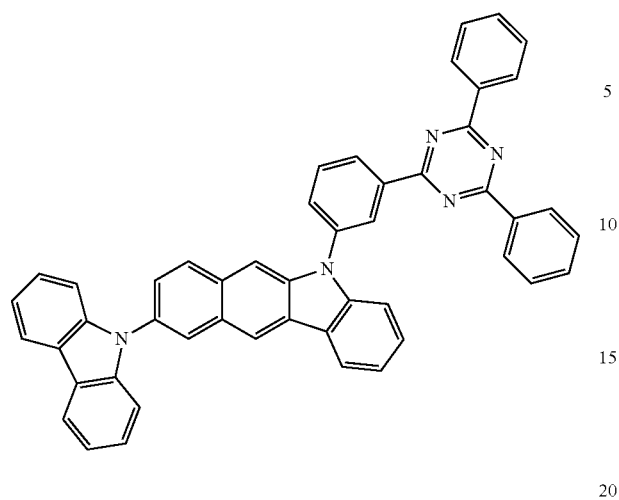
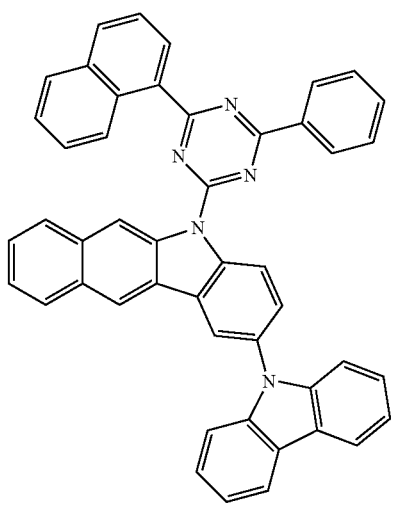
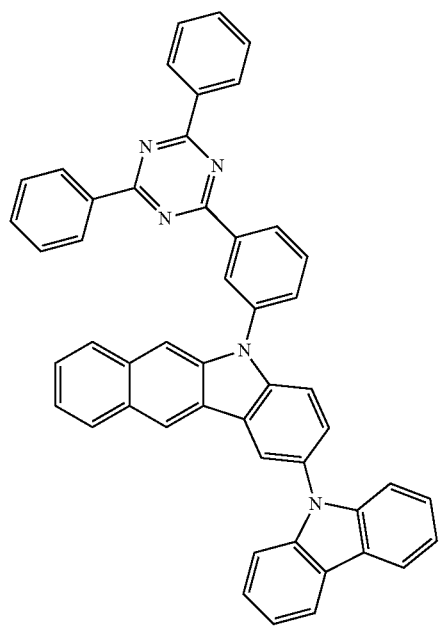
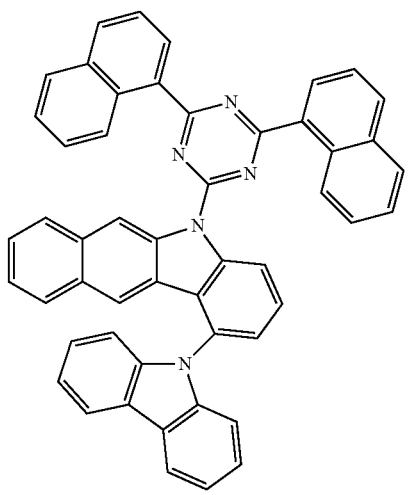
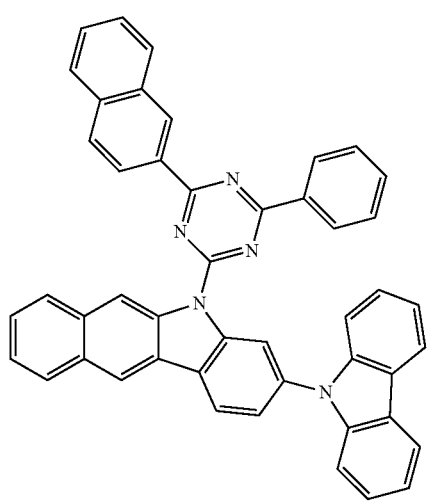
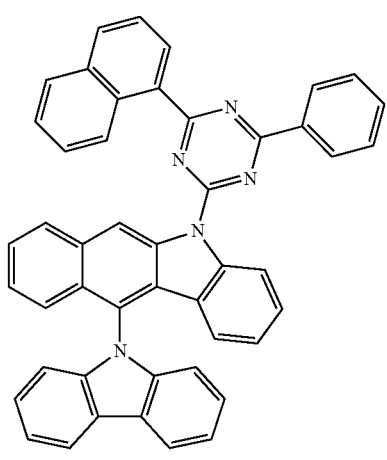

279
-continued
280
-continued
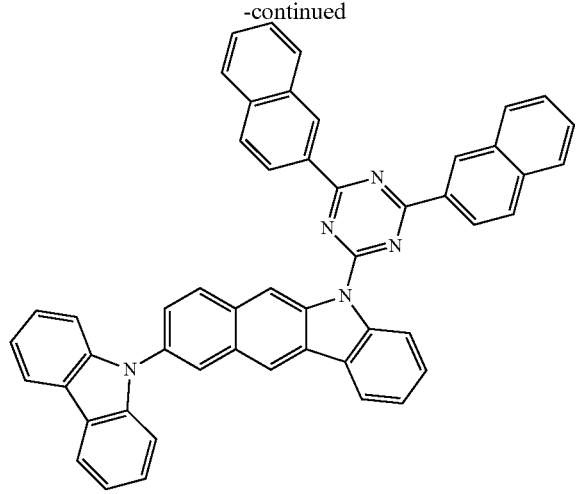
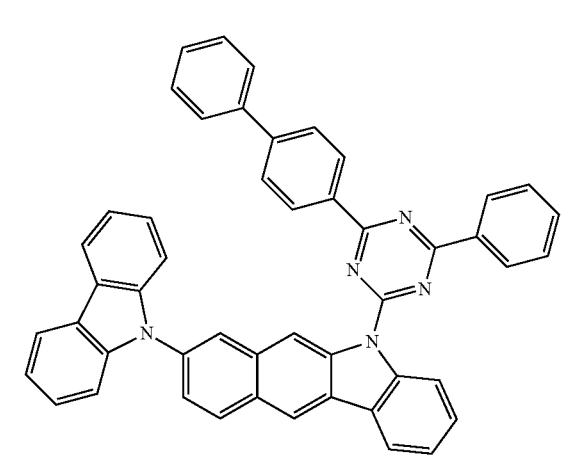
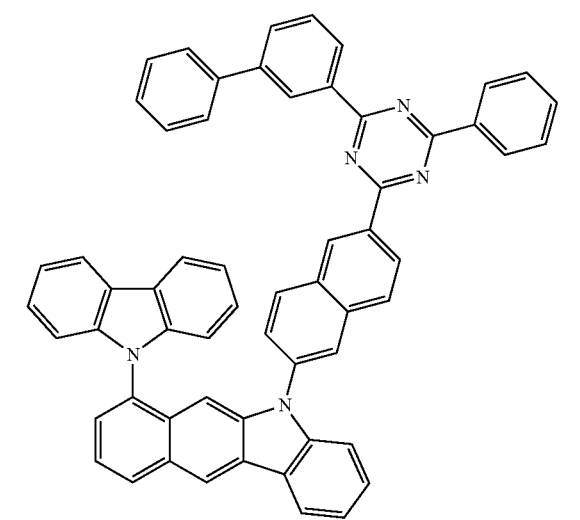
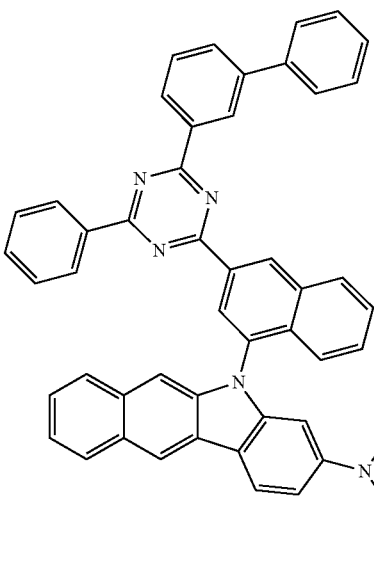
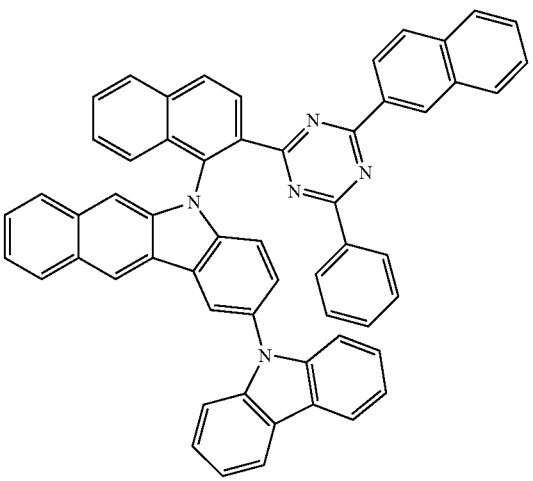
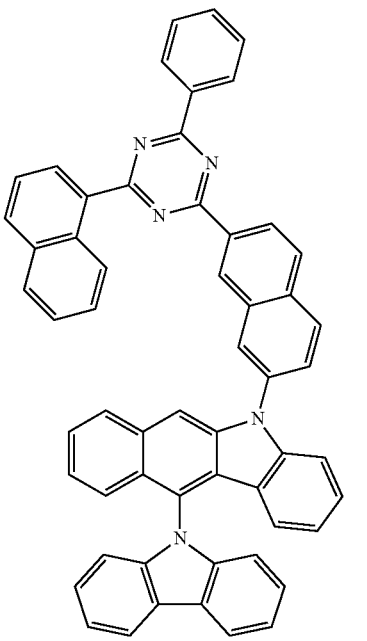

281
-continued
282
-continued
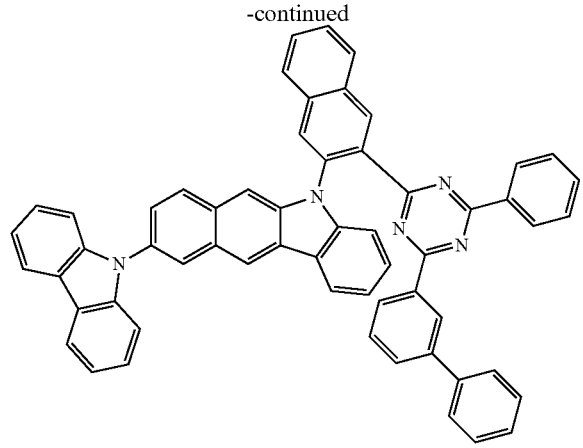
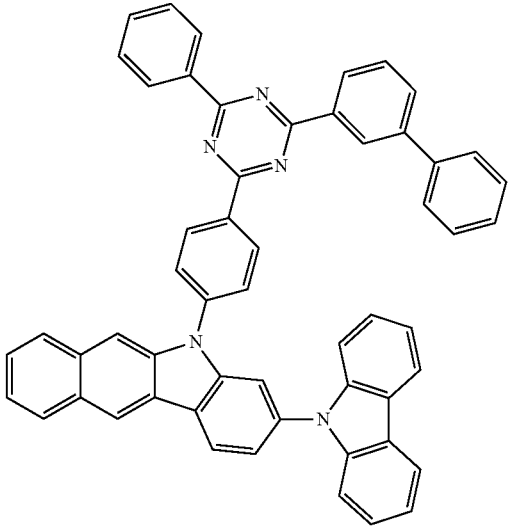

-continued
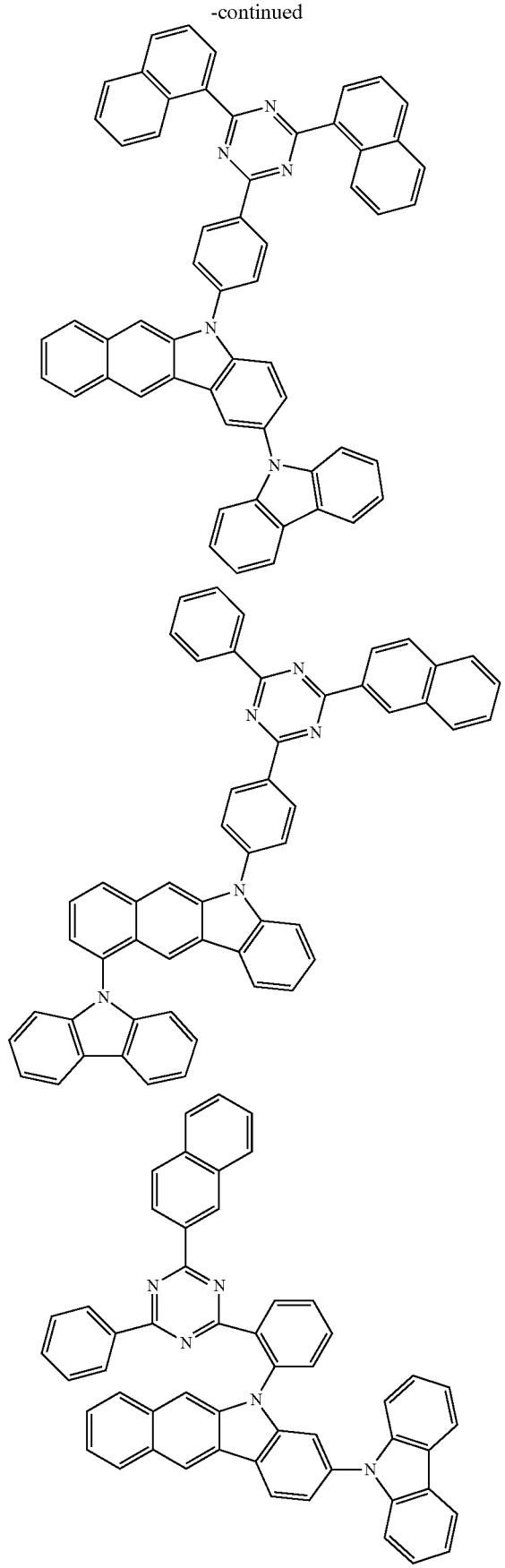
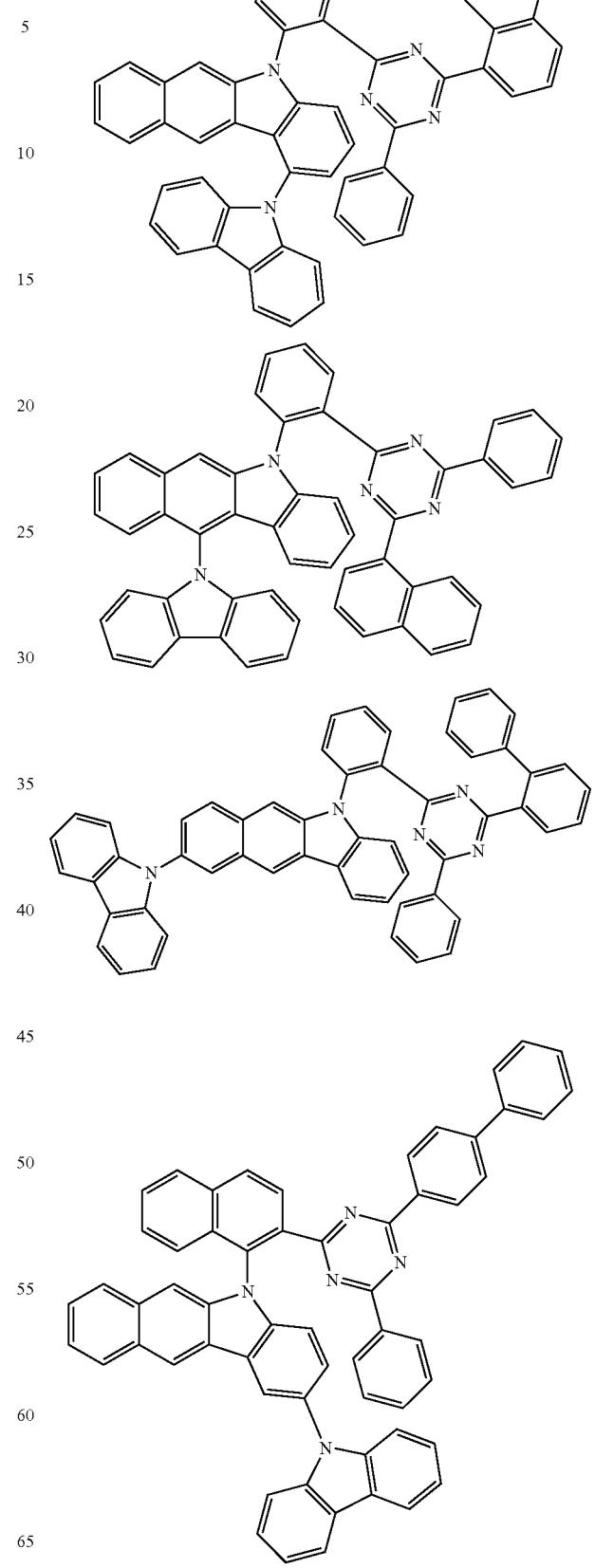

285
-continued
286
-continued
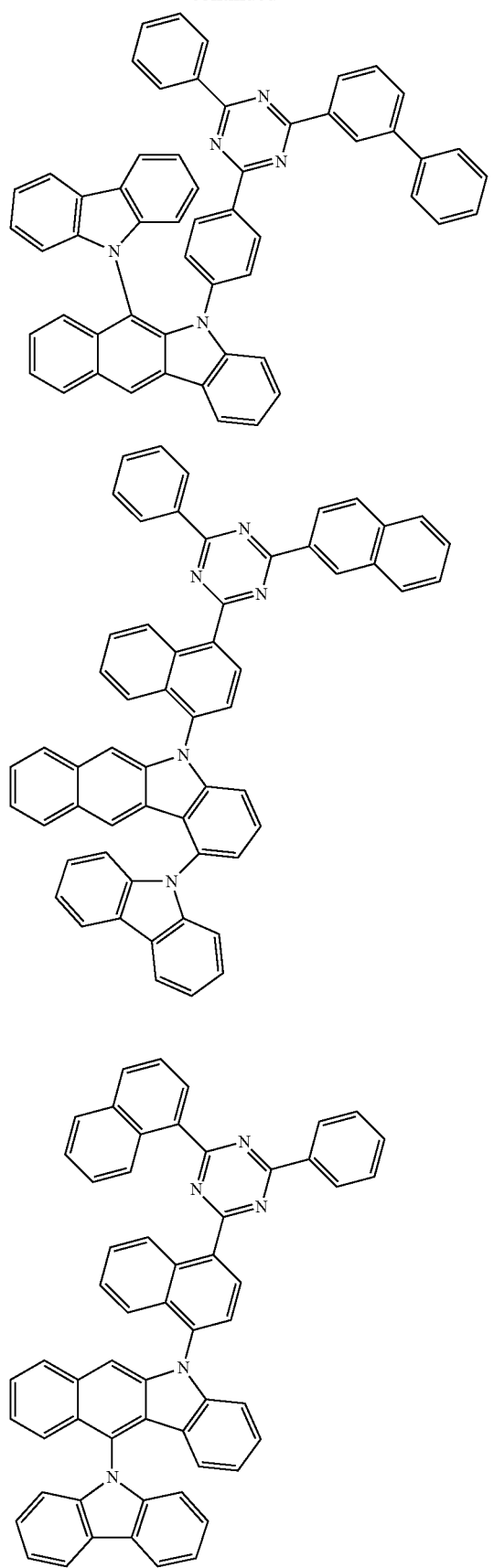
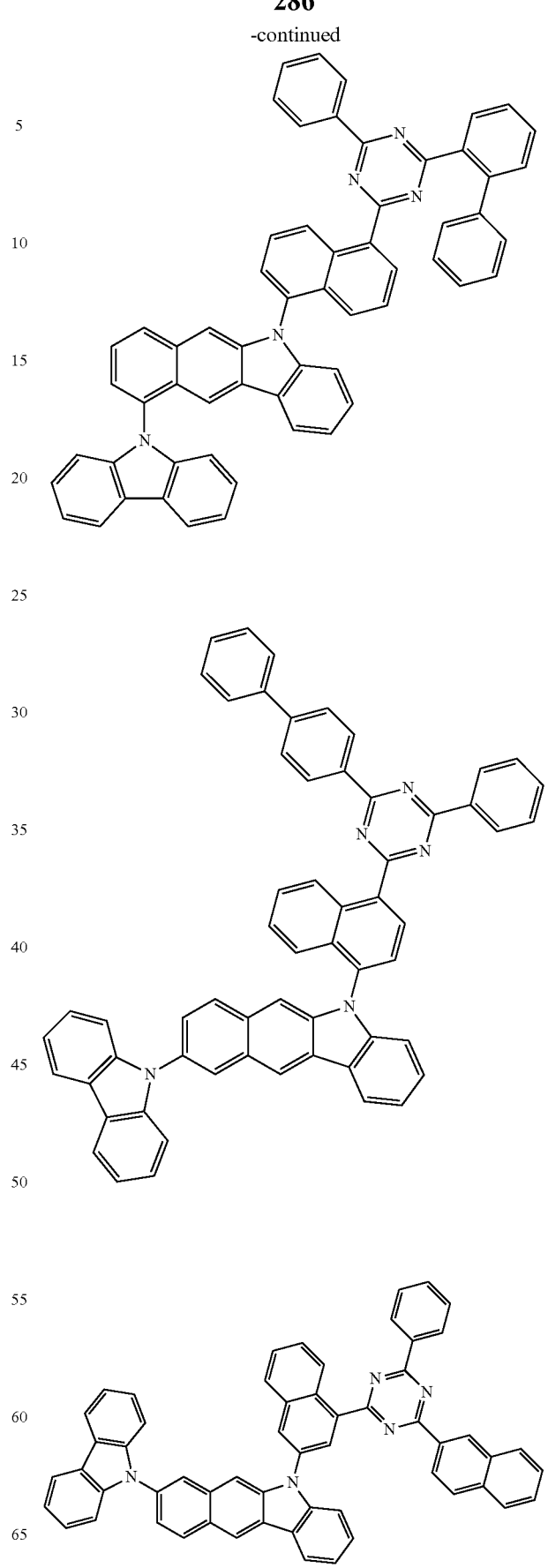

287
-continued
288
-continued
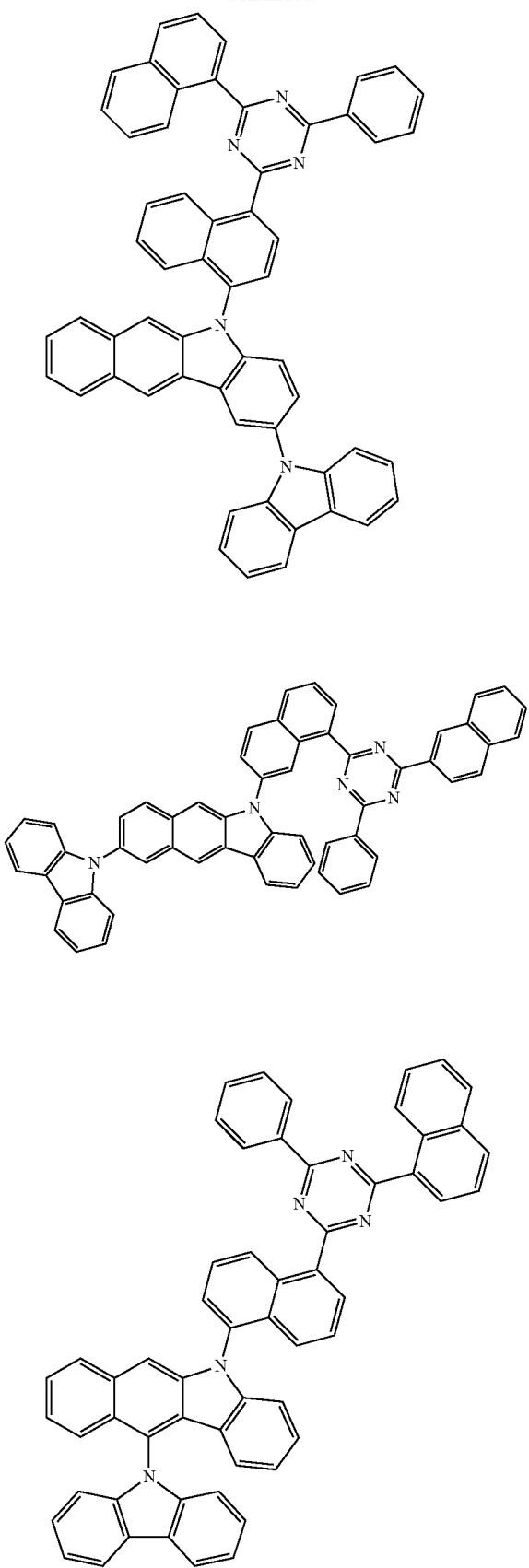
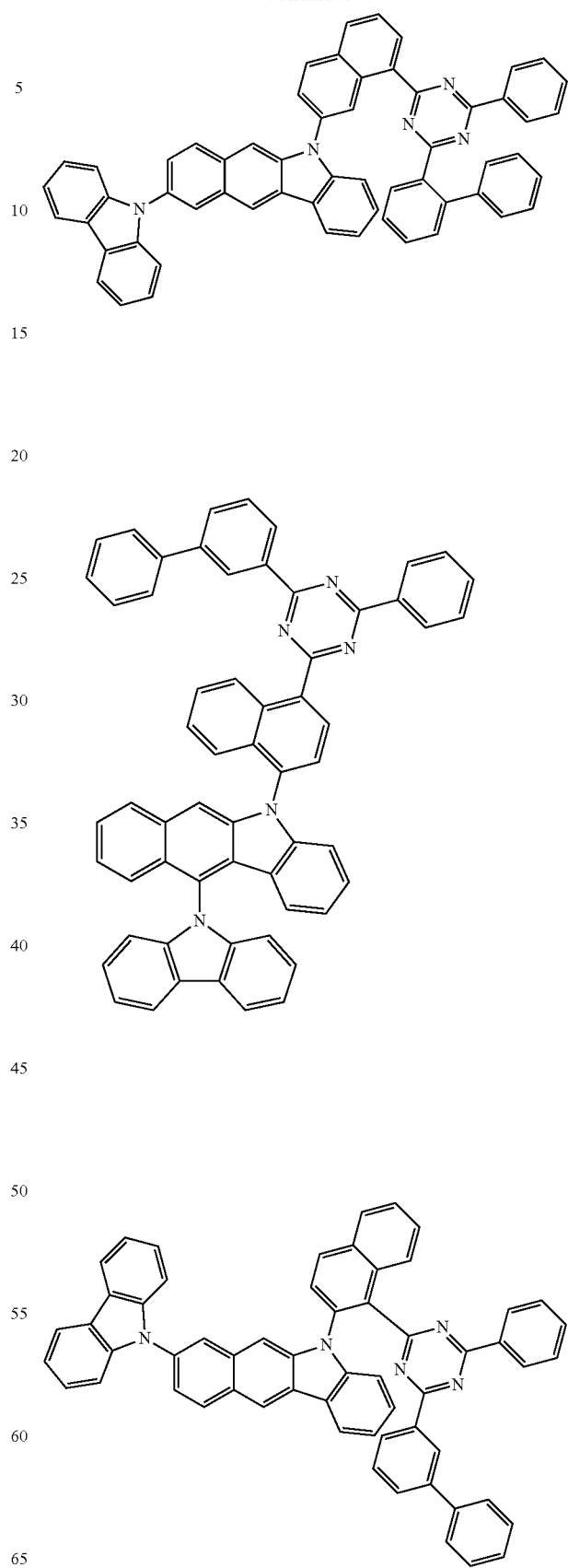

289
-continued
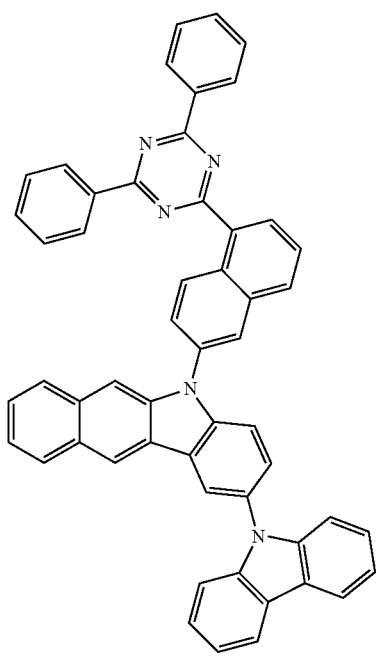
290
-continued
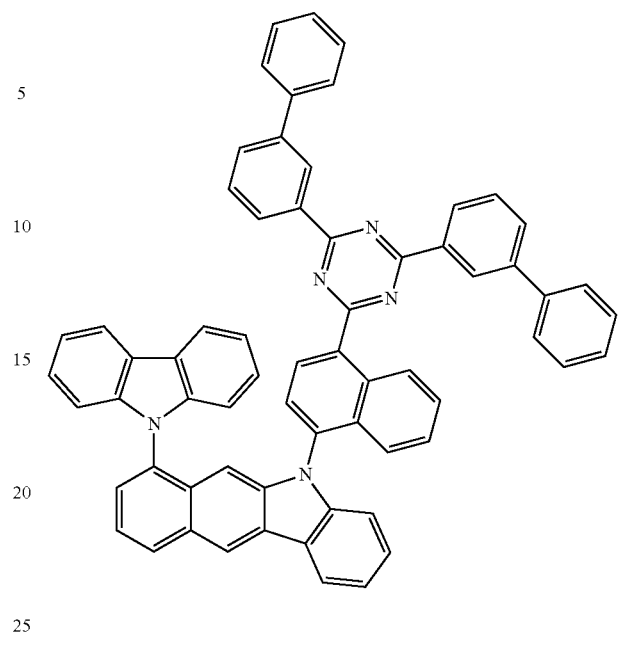
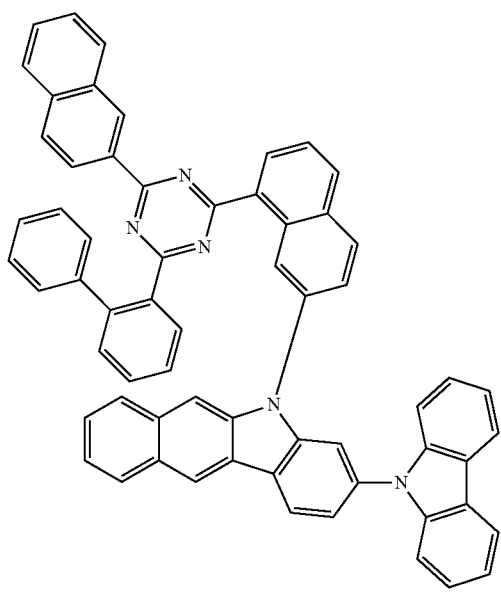
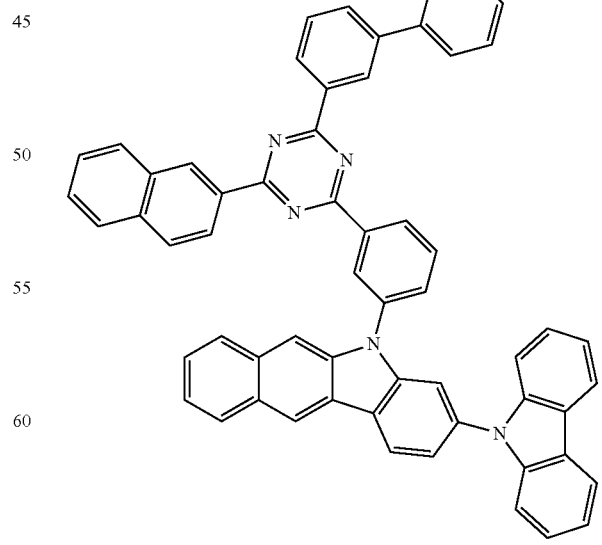

291
-continued
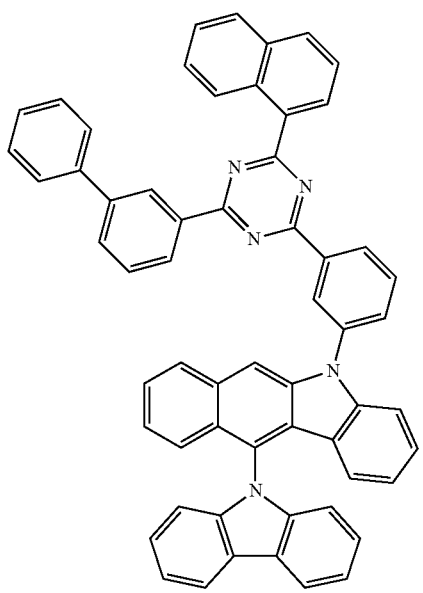
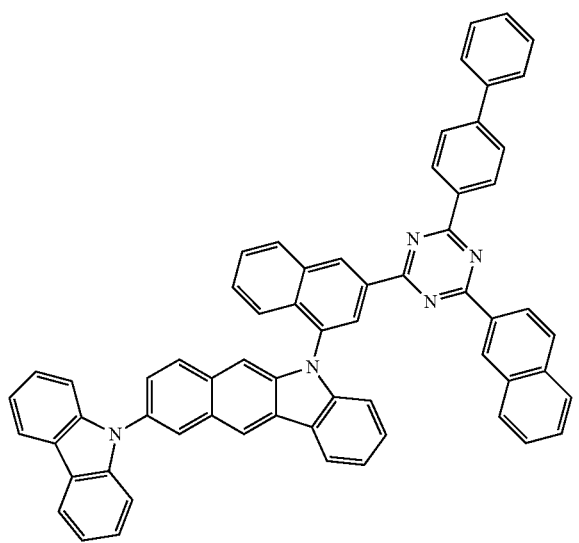
292
-continued
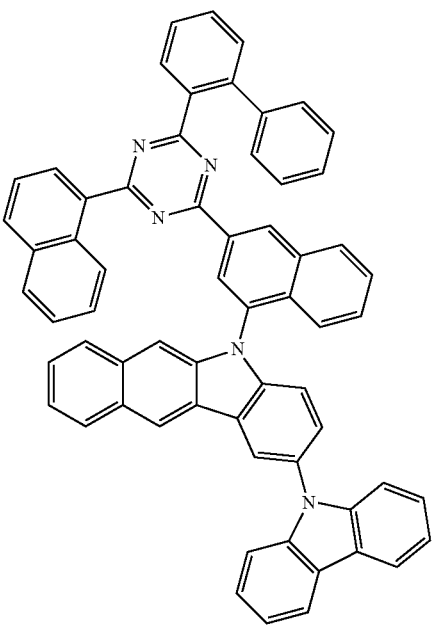
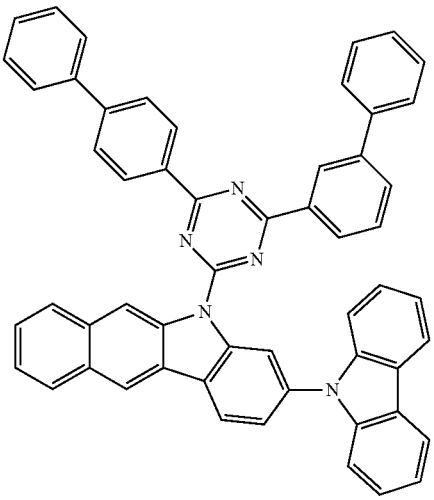
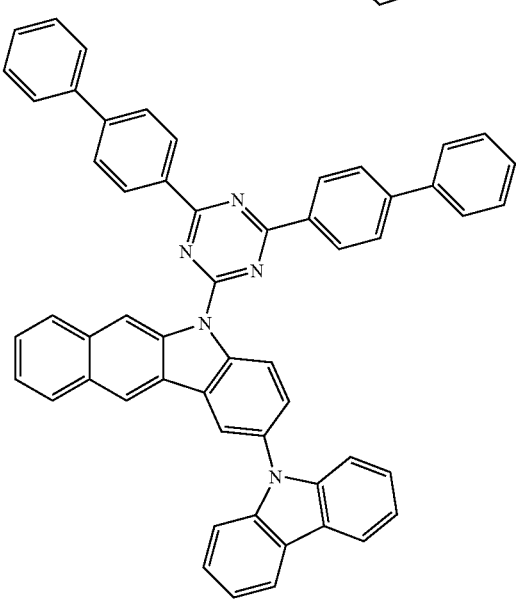

293
-continued
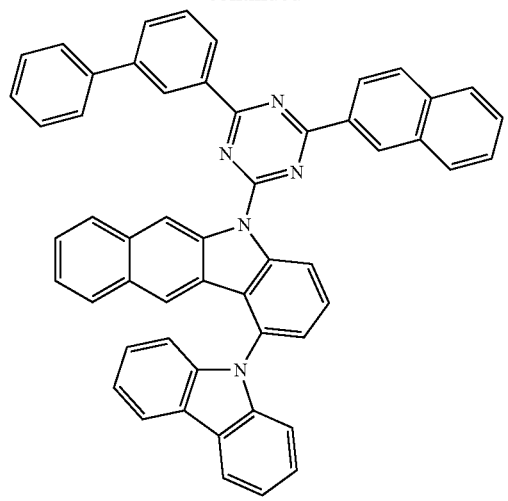
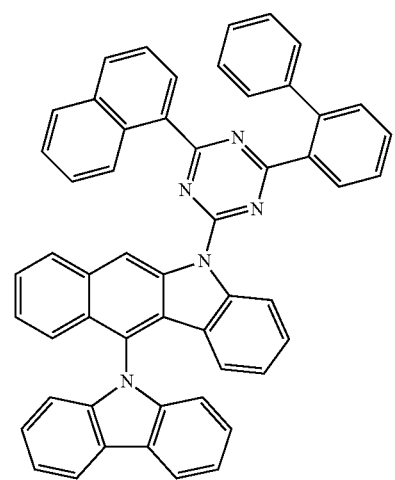
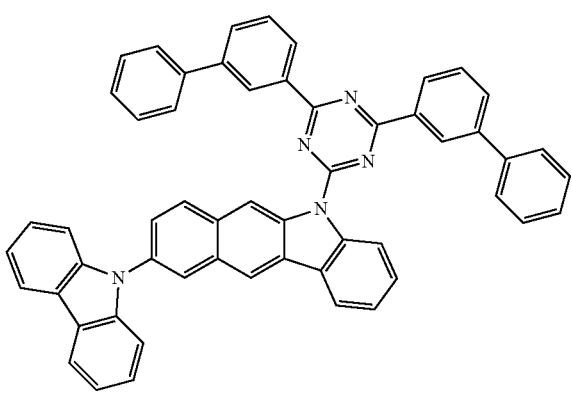
294
-continued
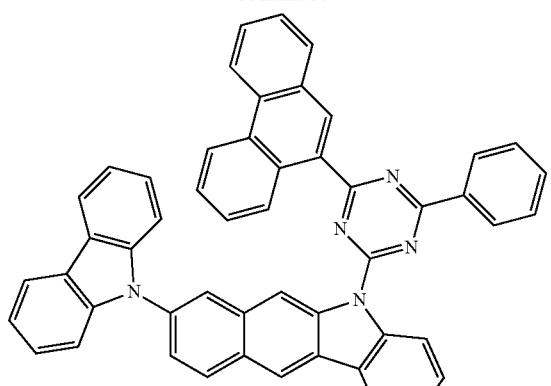
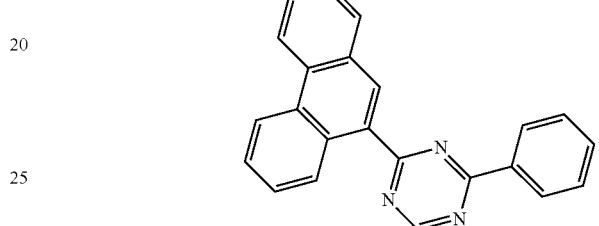
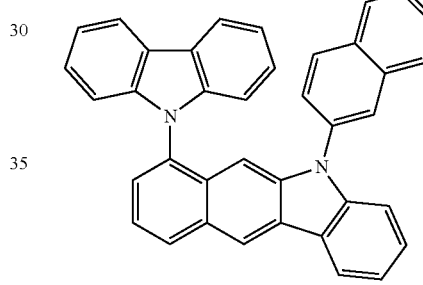
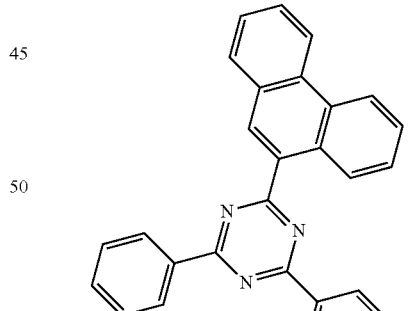
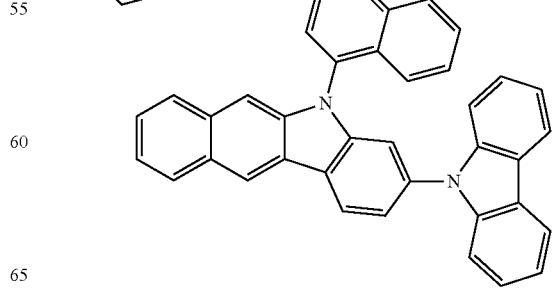

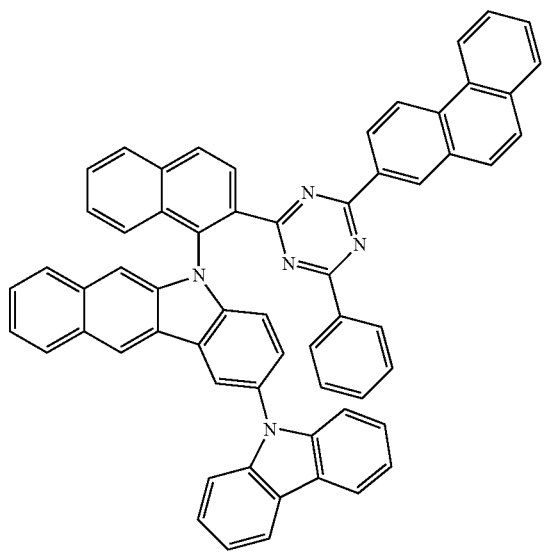
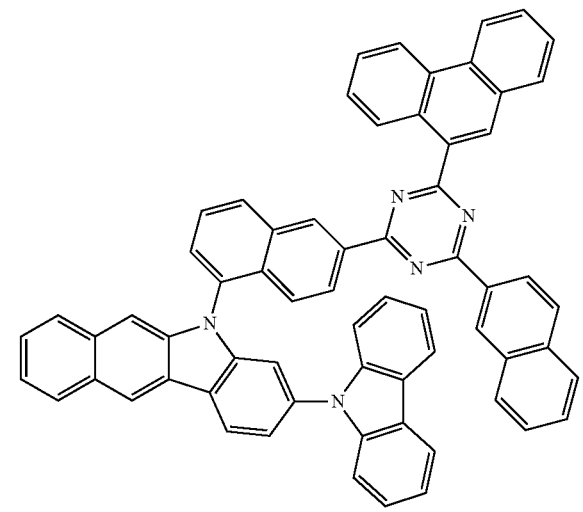
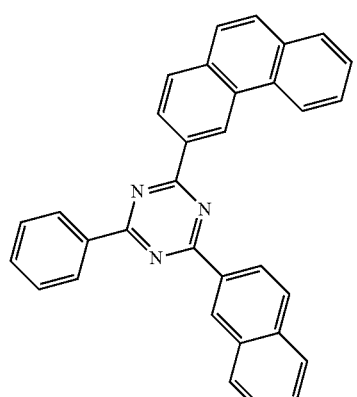
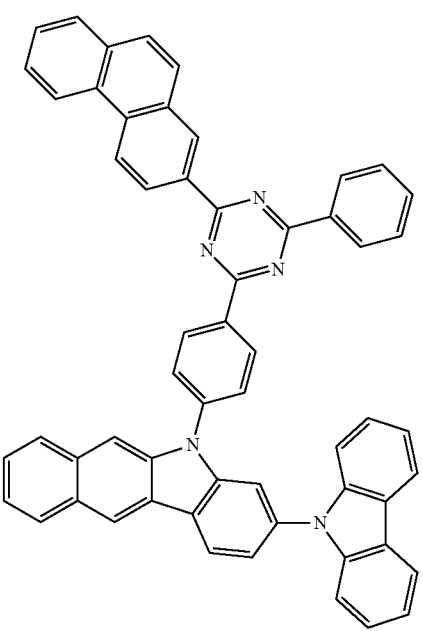
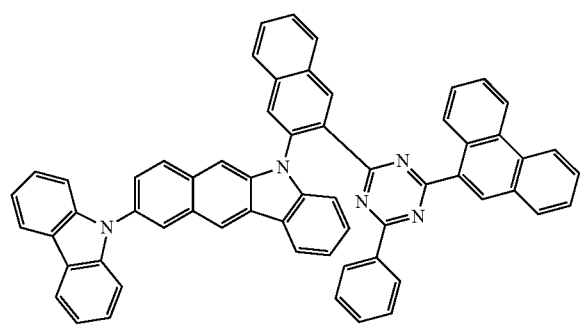
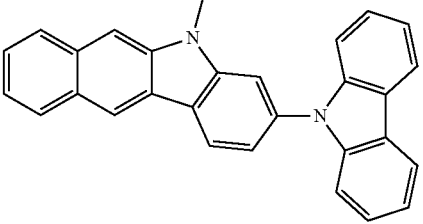

297
-continued
298
-continued
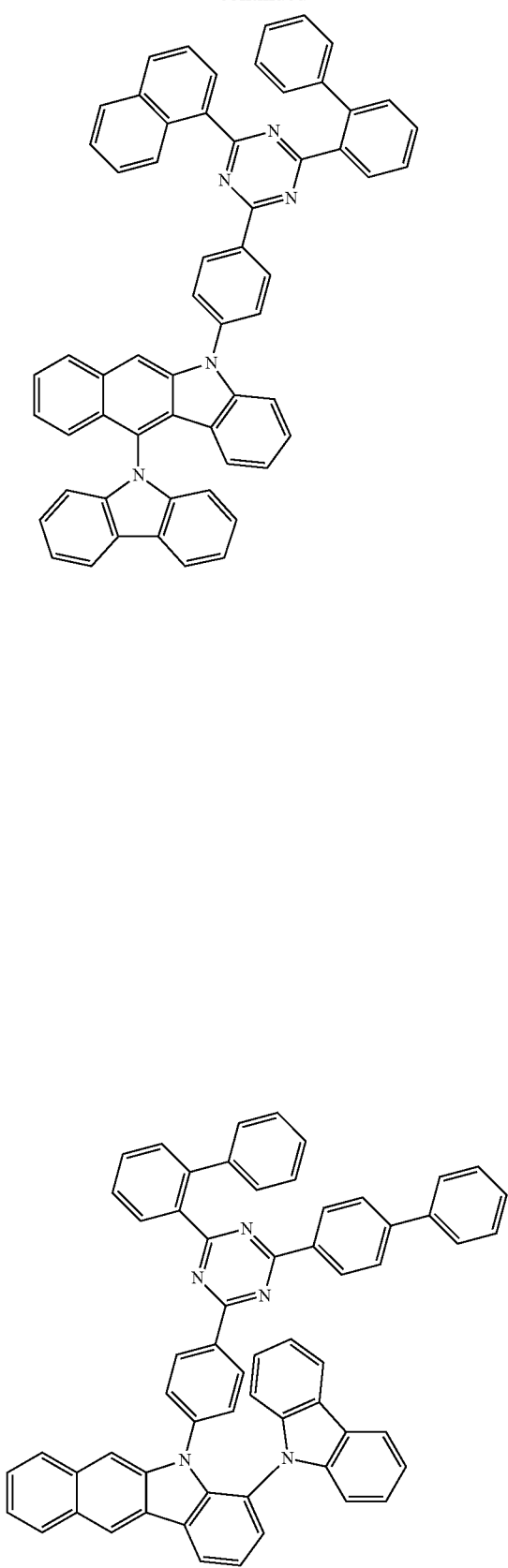
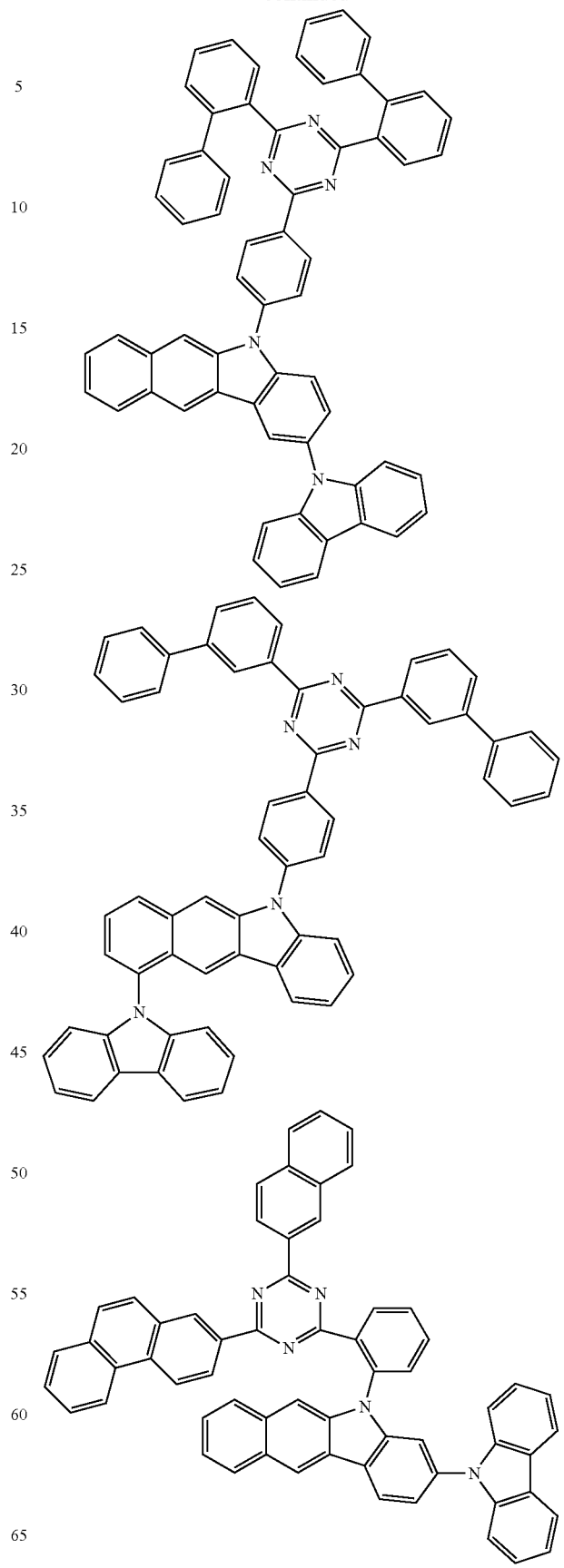

299
-continued
300
-continued
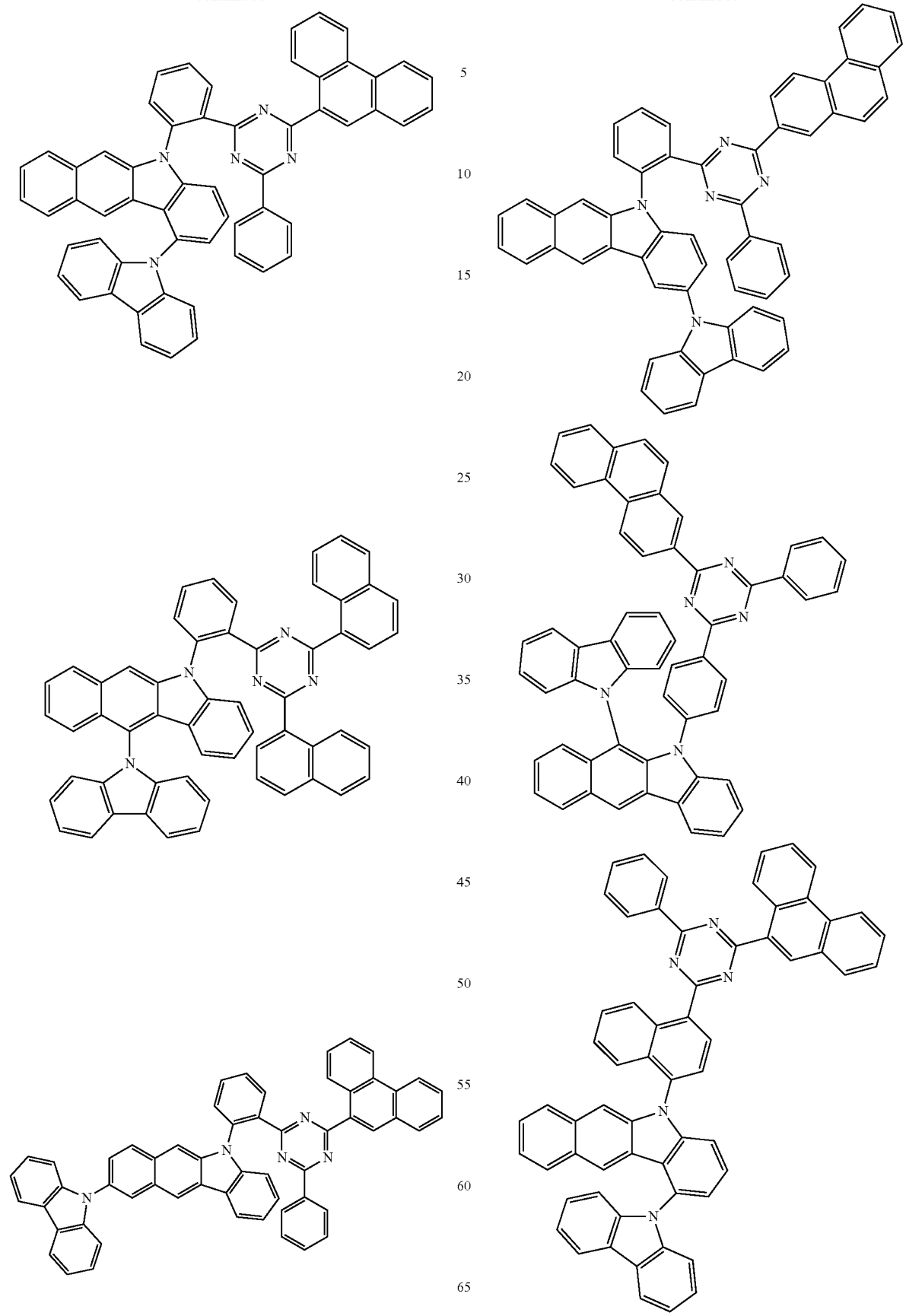

301
-continued
302
-continued
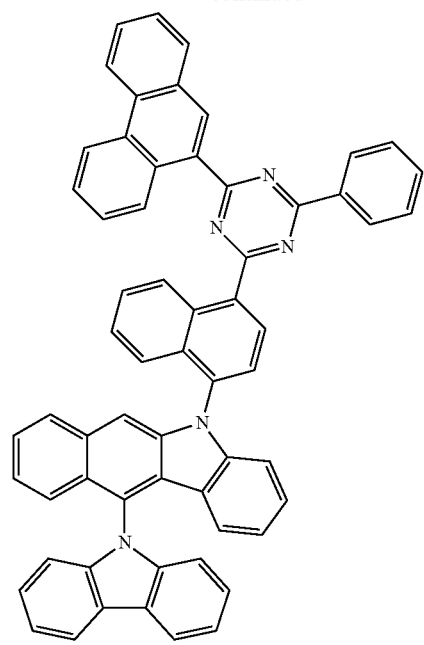
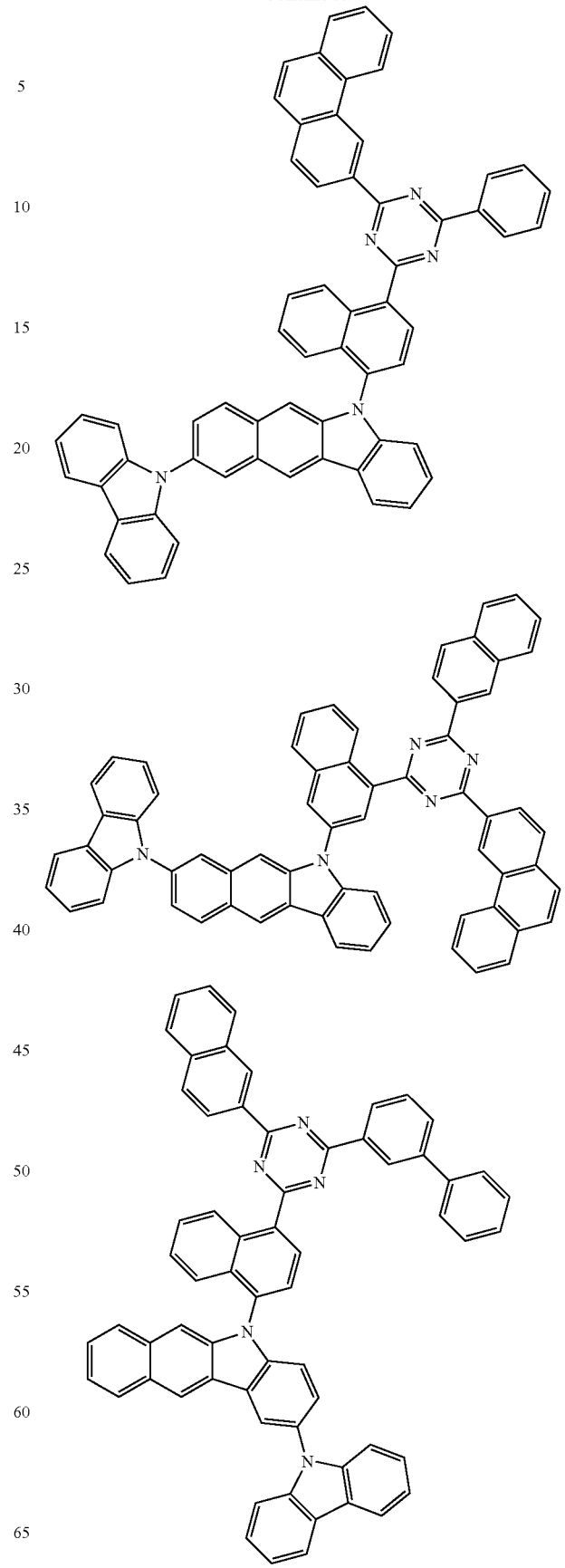

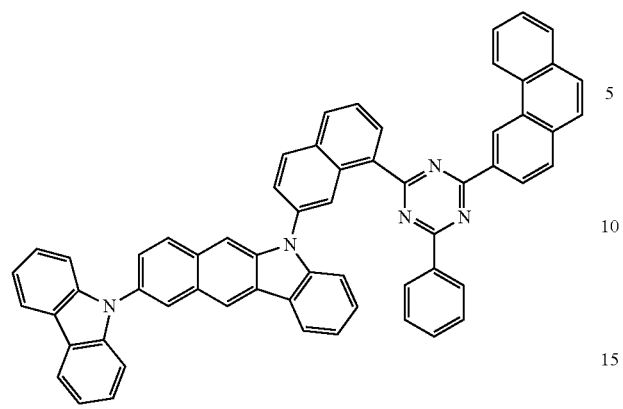
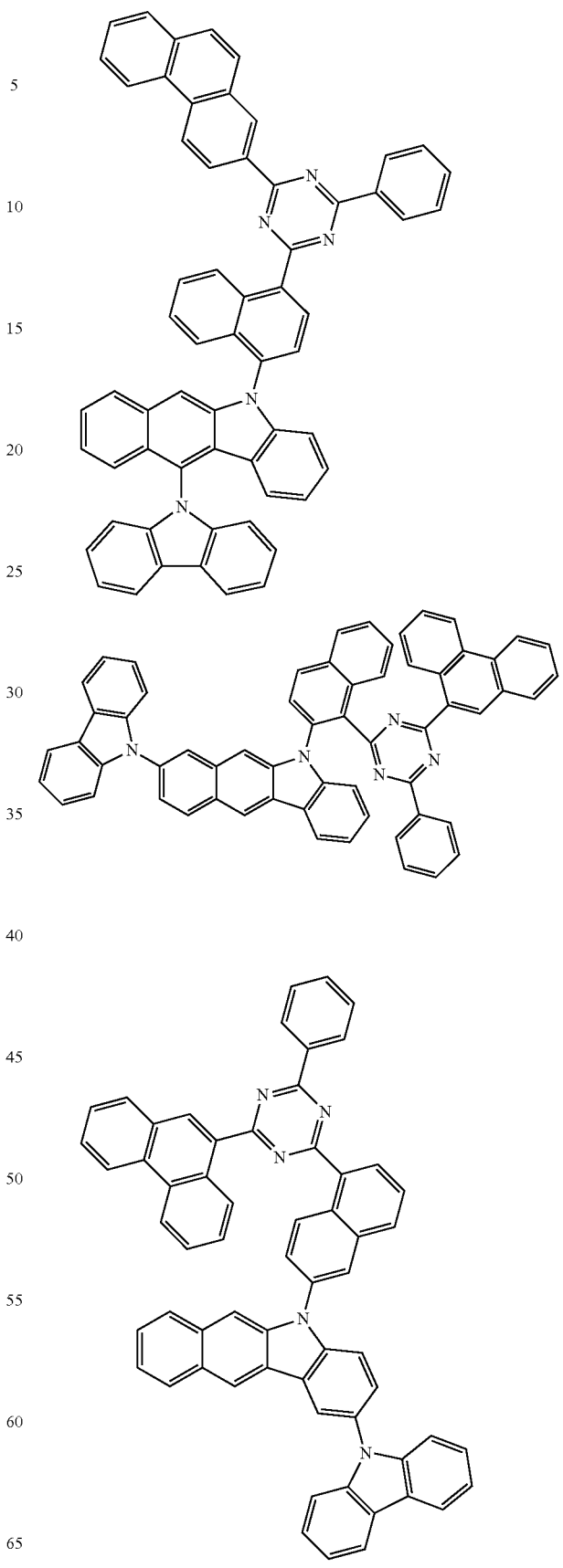

305
-continued
306
-continued
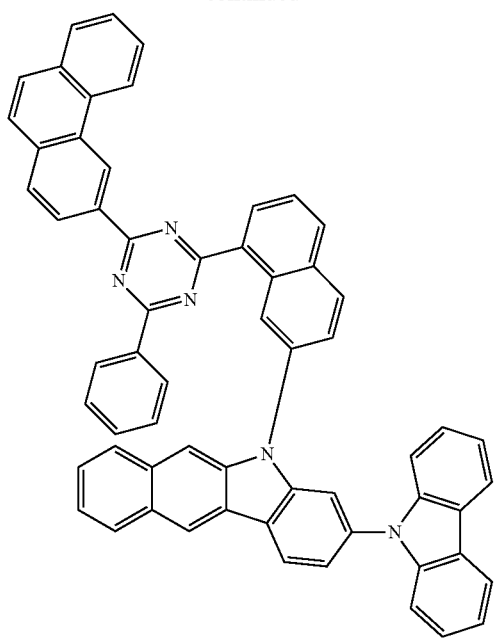
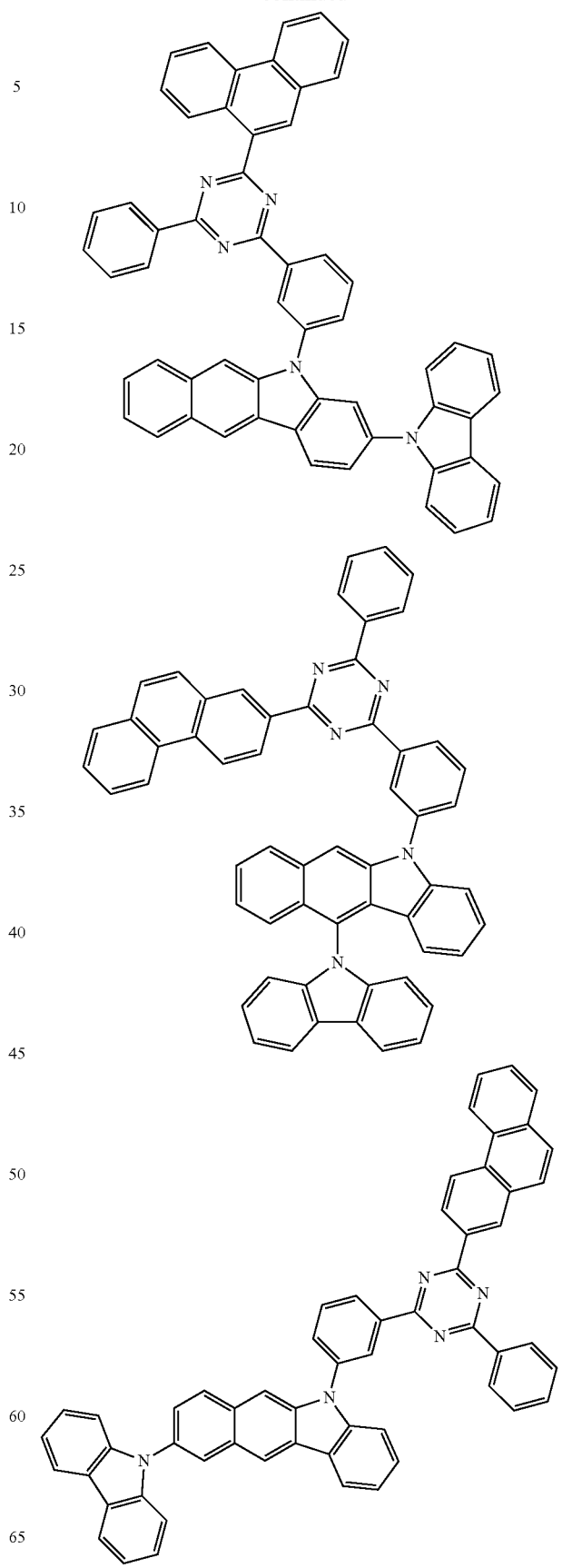

307
-continued
308
-continued
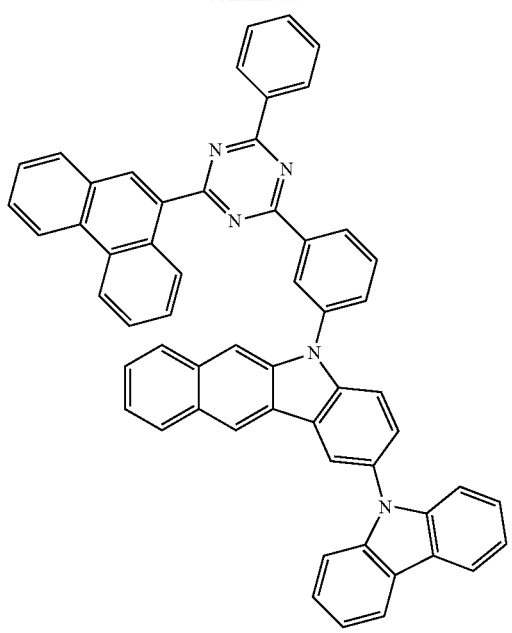
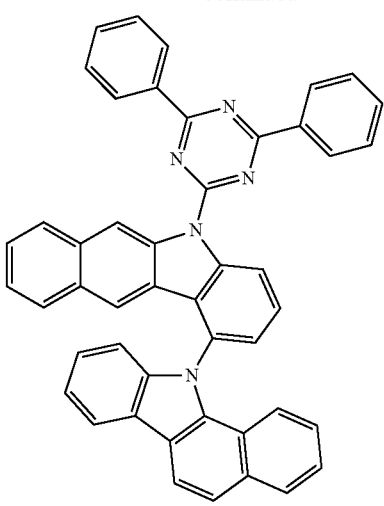

309
-continued
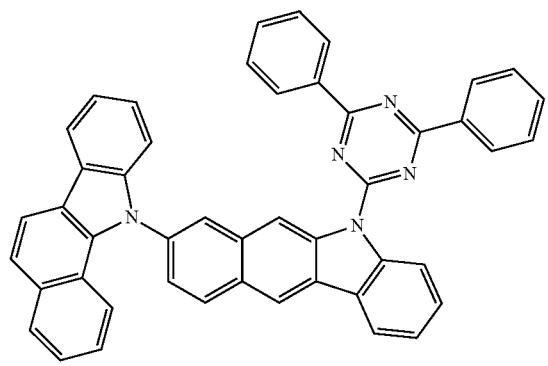
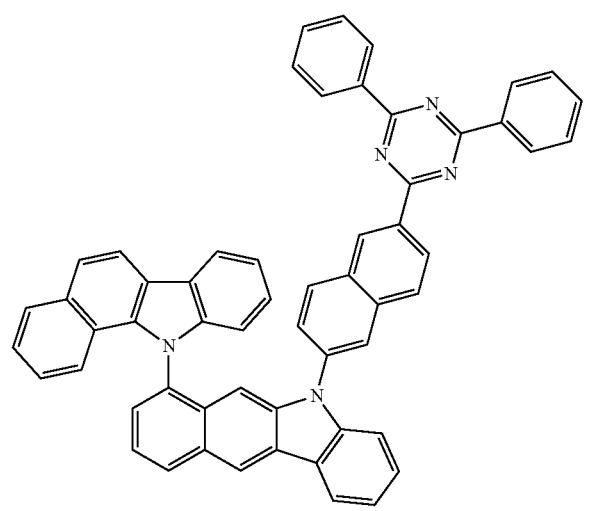
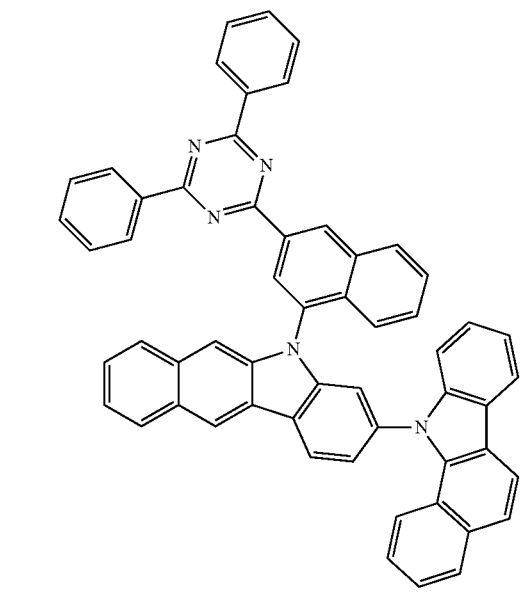
310
-continued
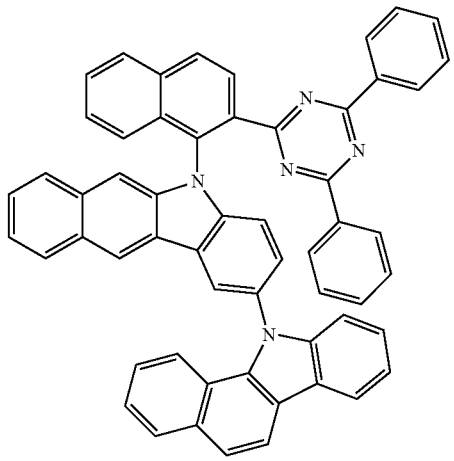
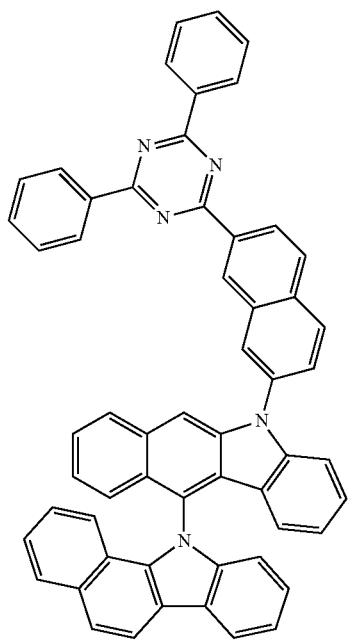
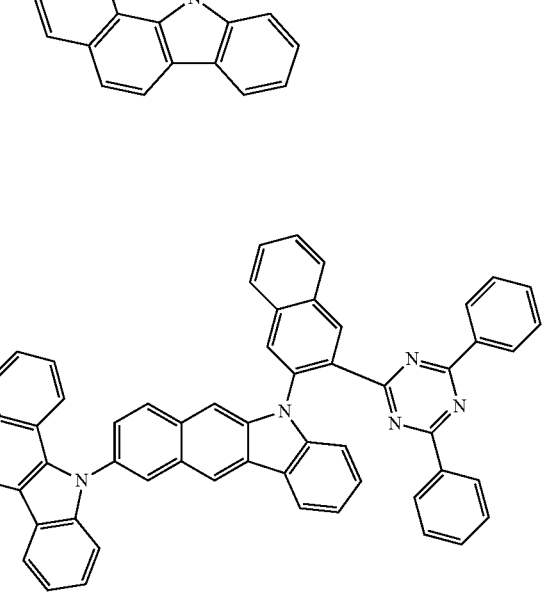

311
-continued
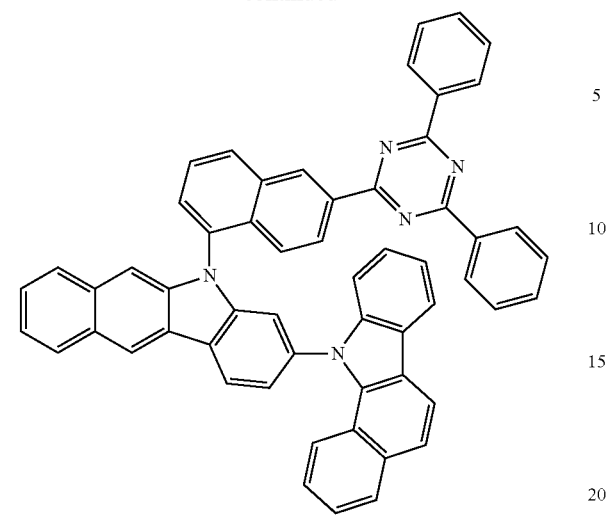
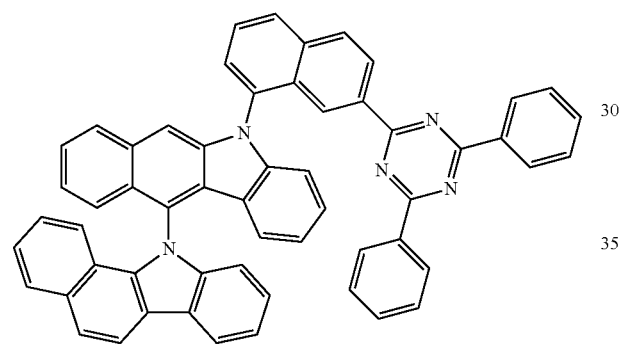
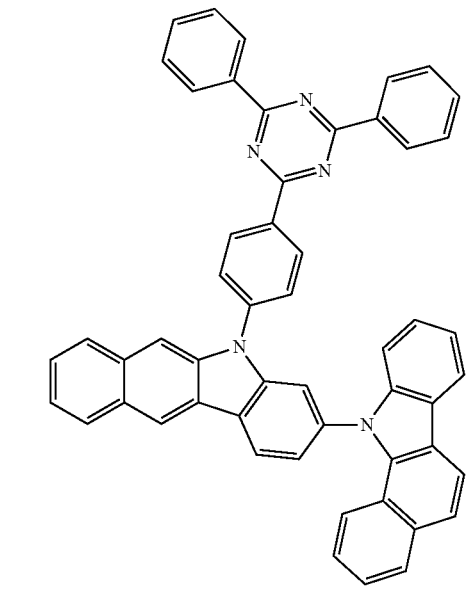
312
-continued
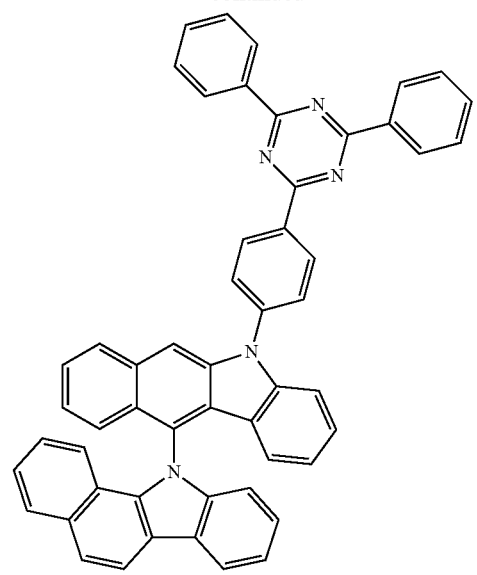
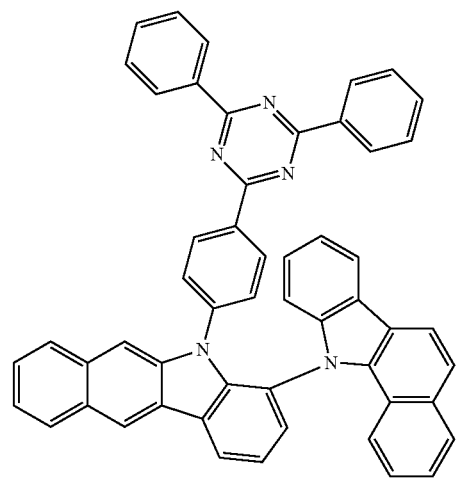
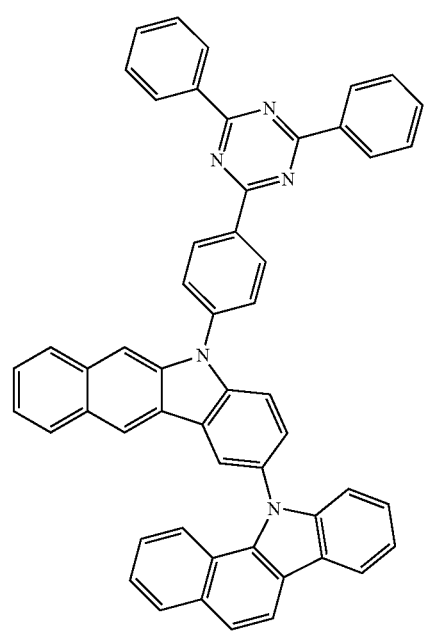

313
-continued
314
-continued
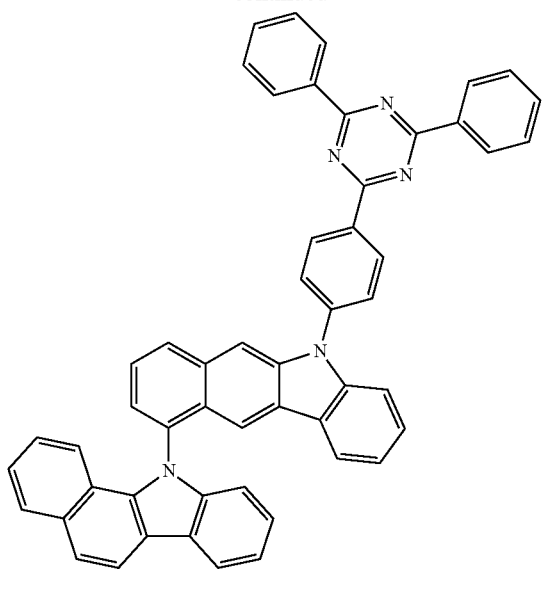
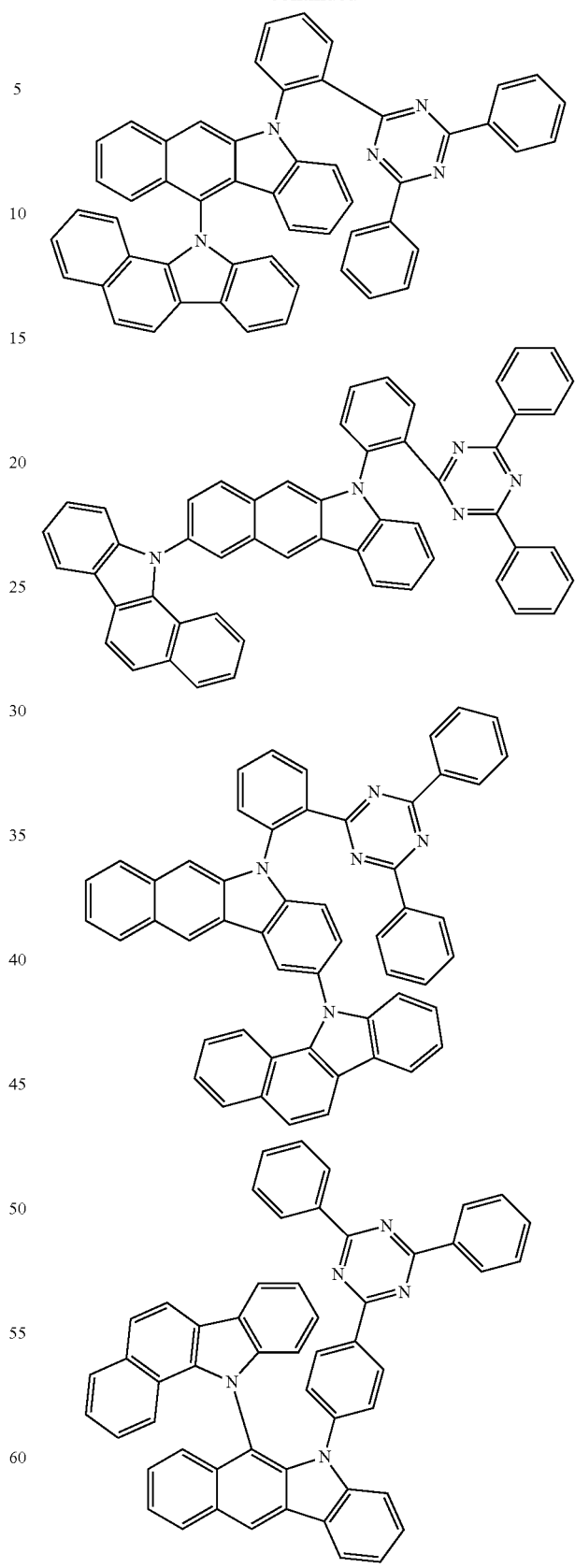

315
-continued
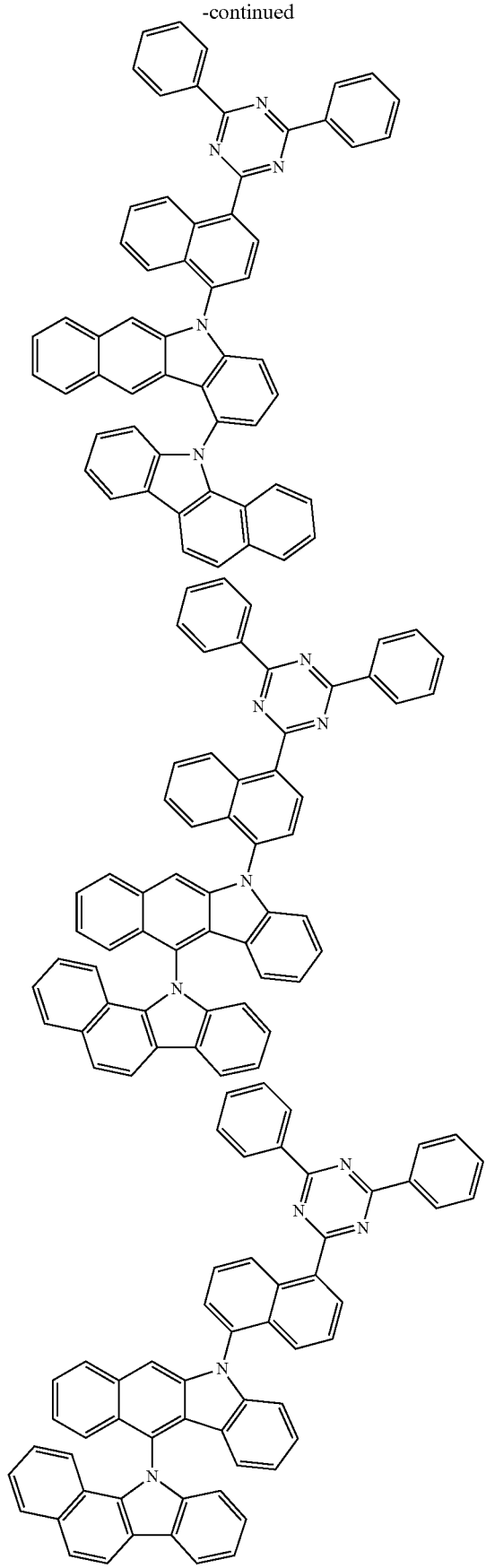
316
-continued
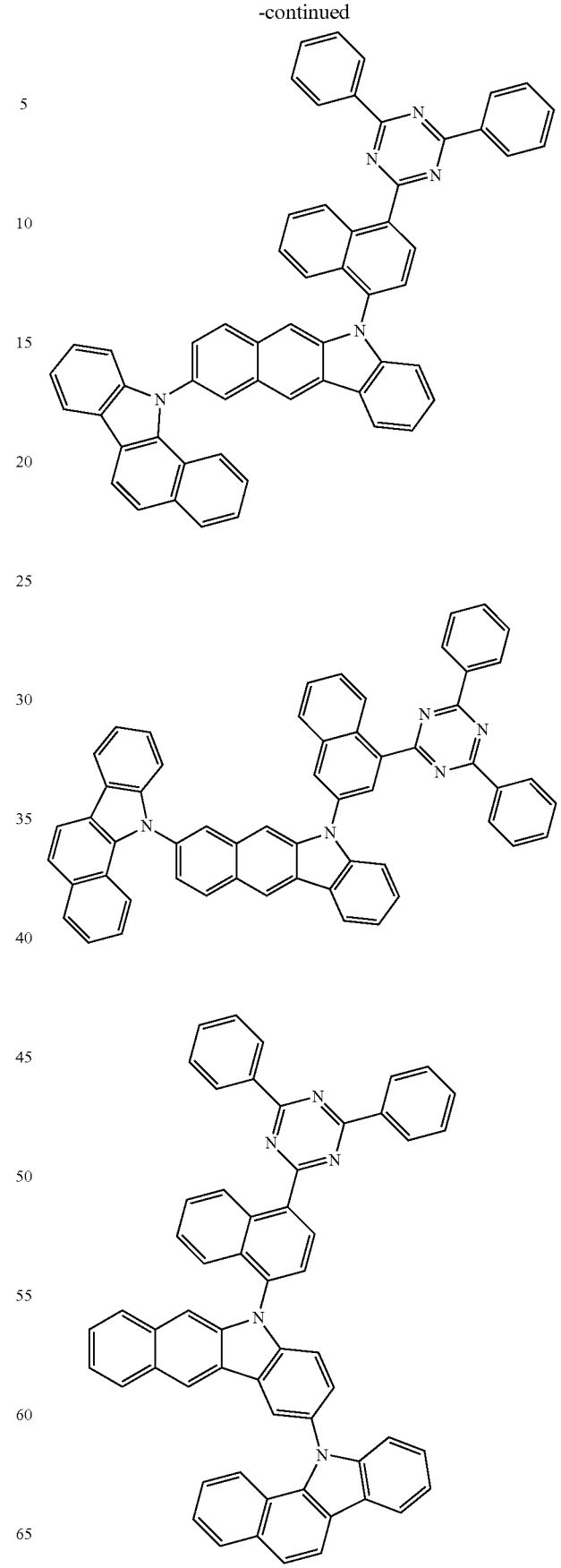

317
-continued
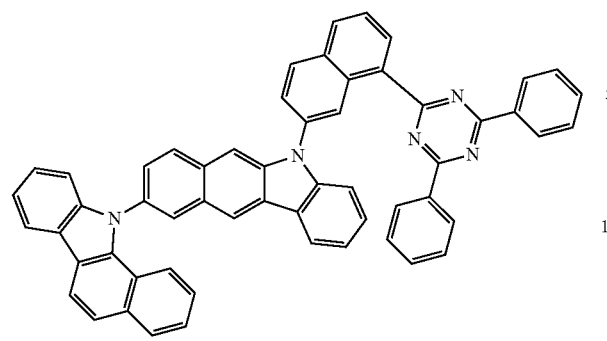
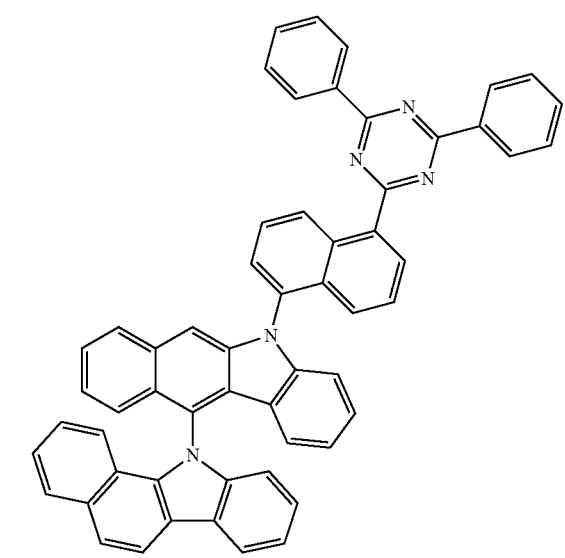
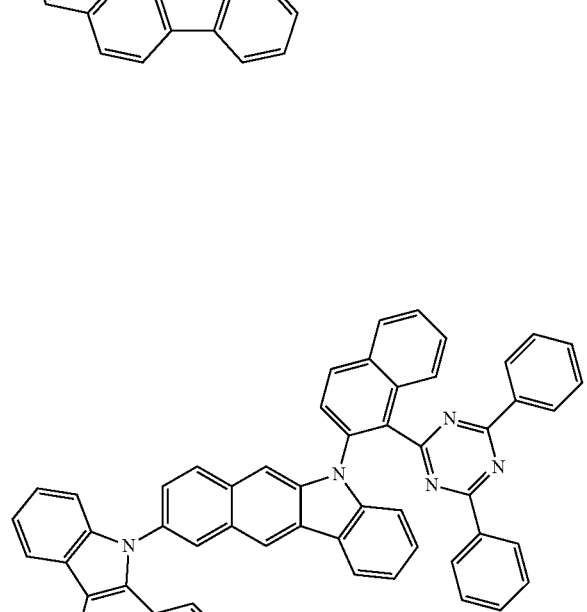
318
-continued
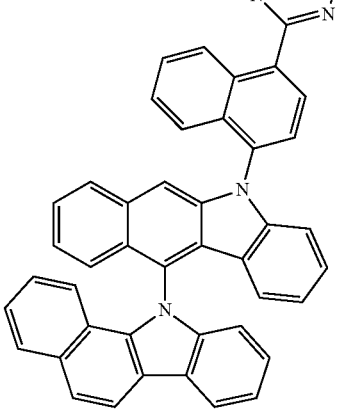
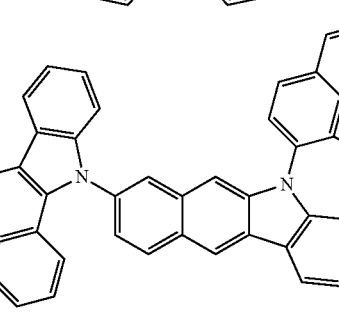
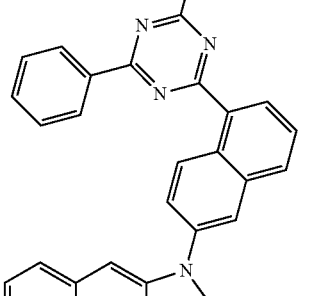

319
-continued
320
-continued
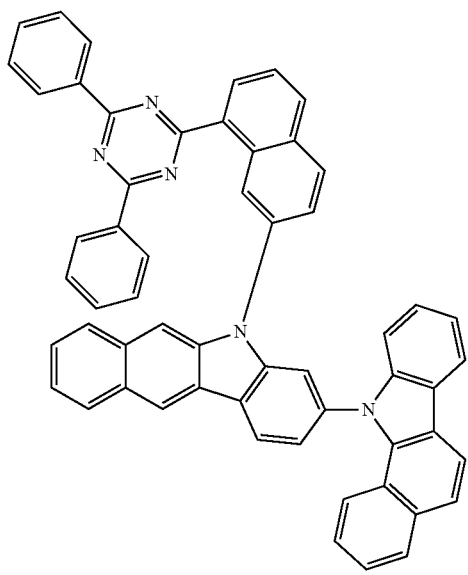
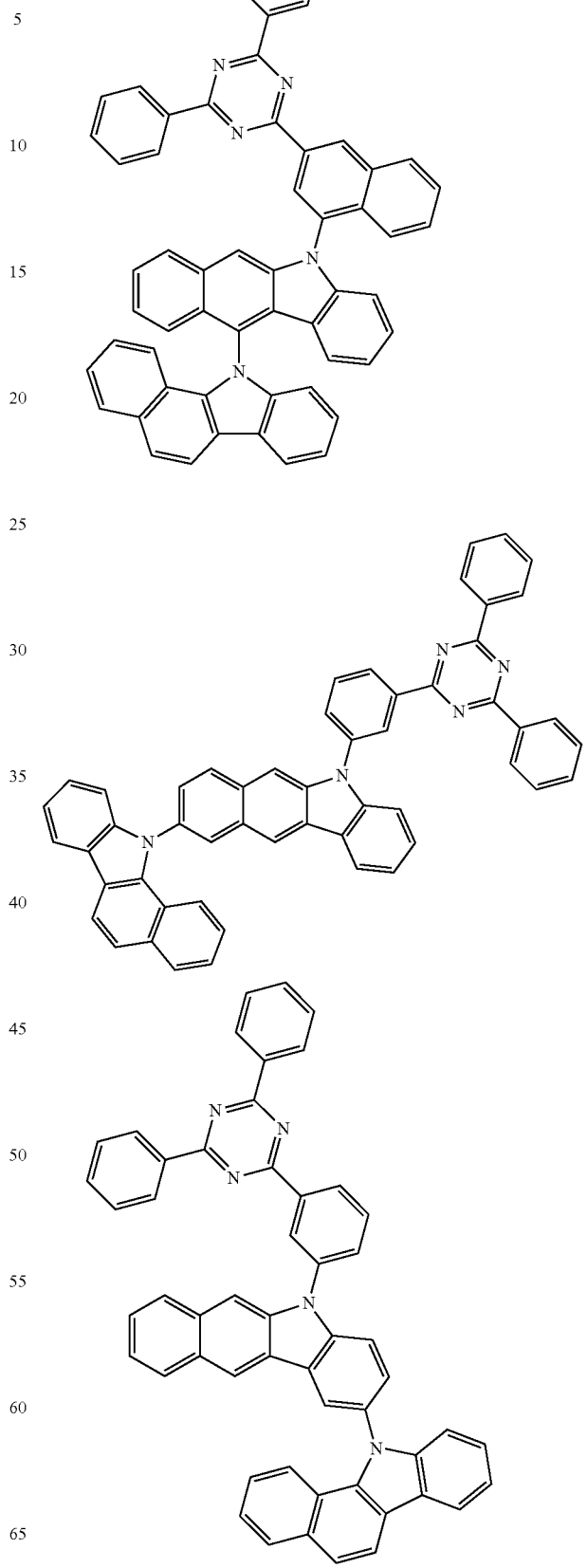

321
-continued
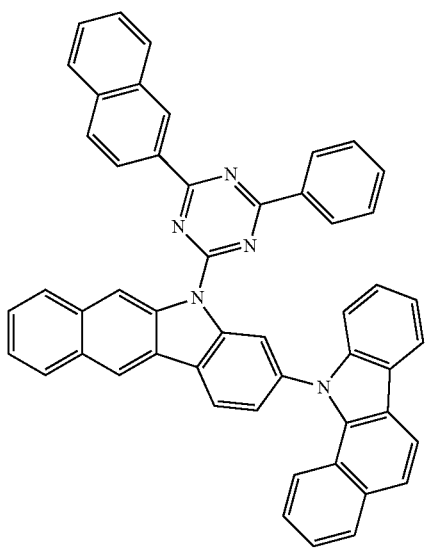
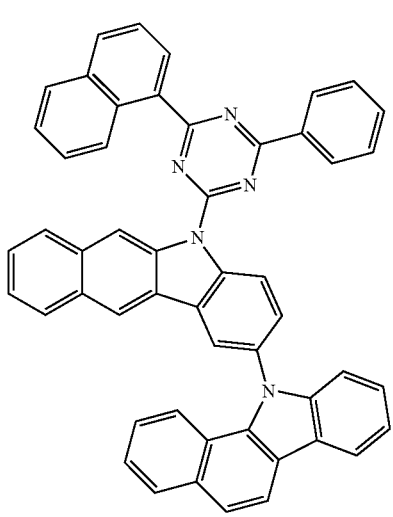
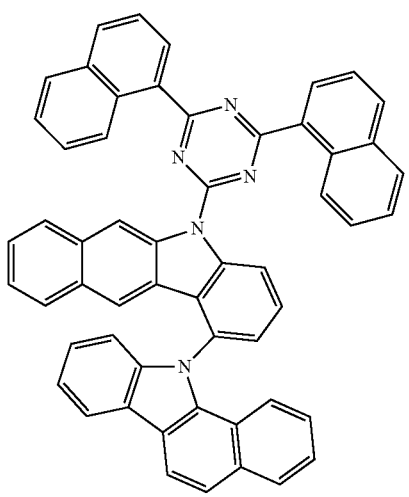
322
-continued
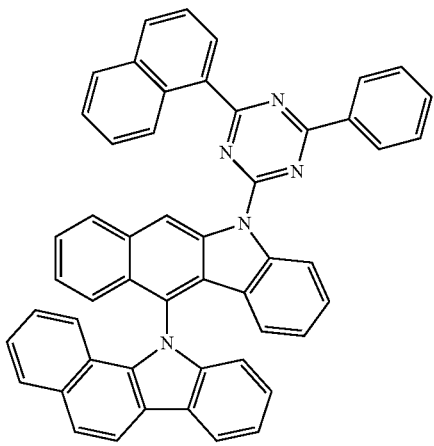
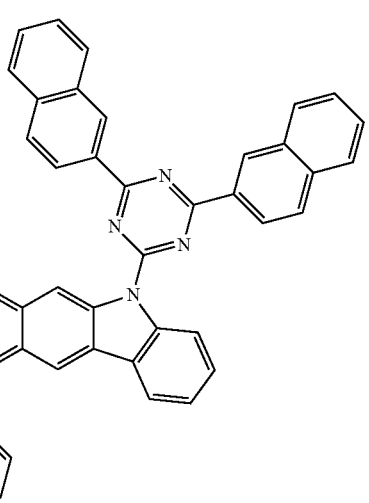
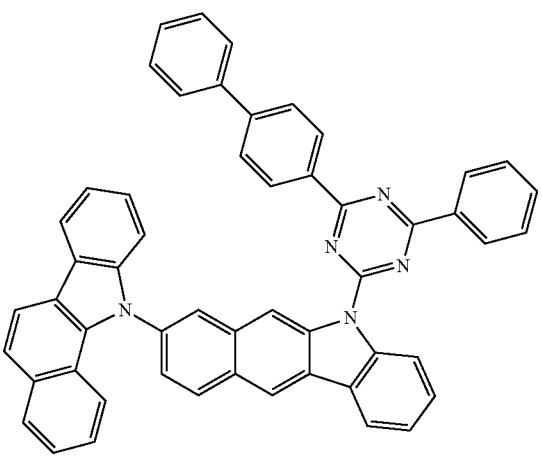

323
-continued
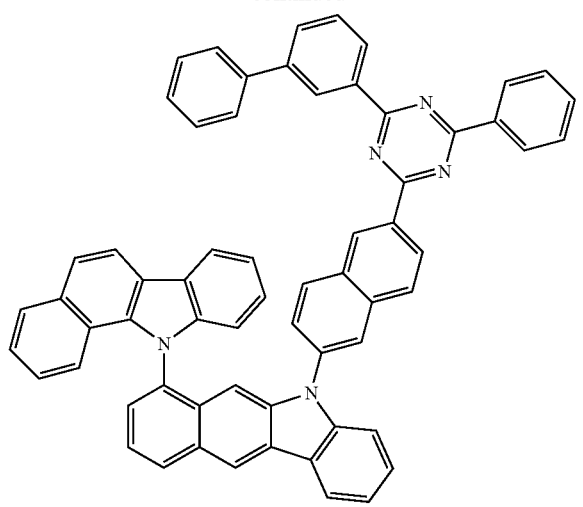
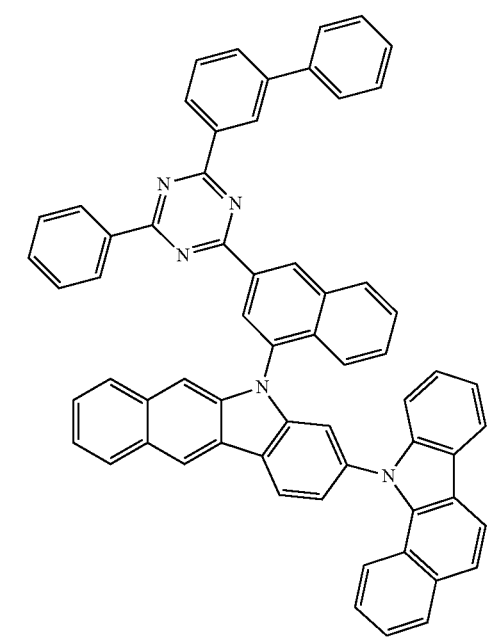
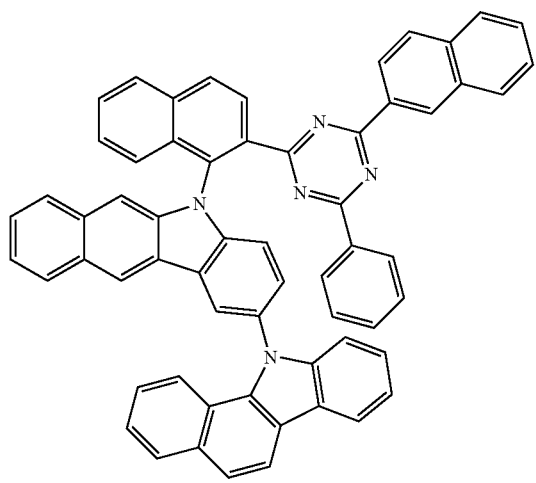
324
-continued
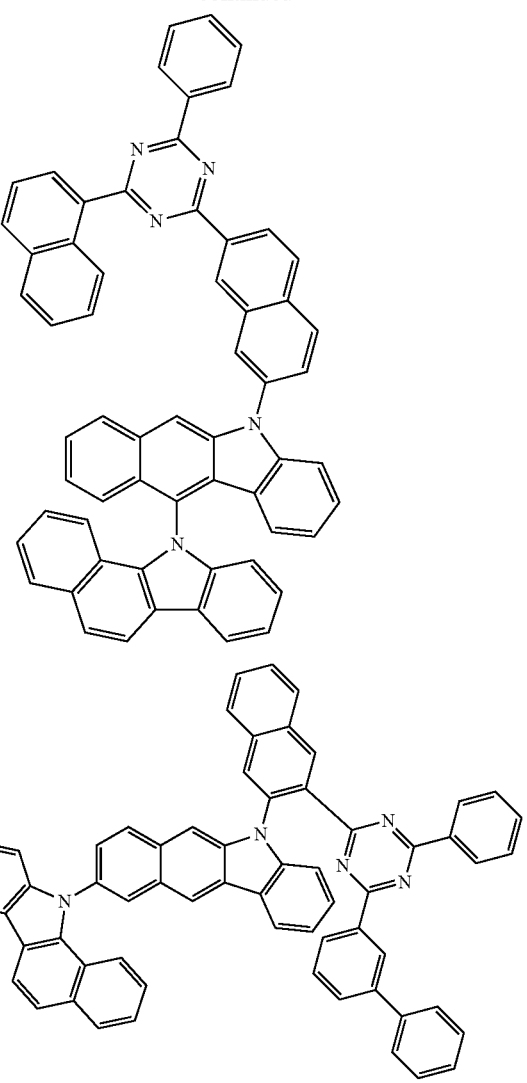
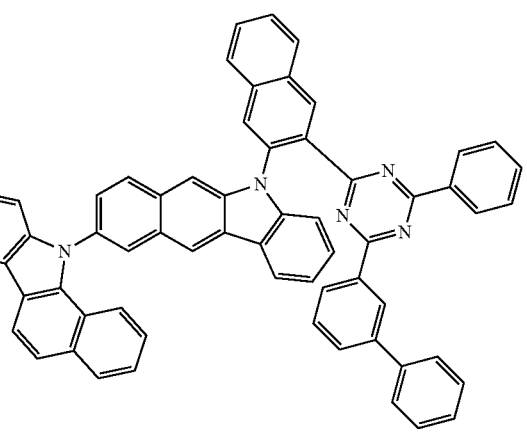
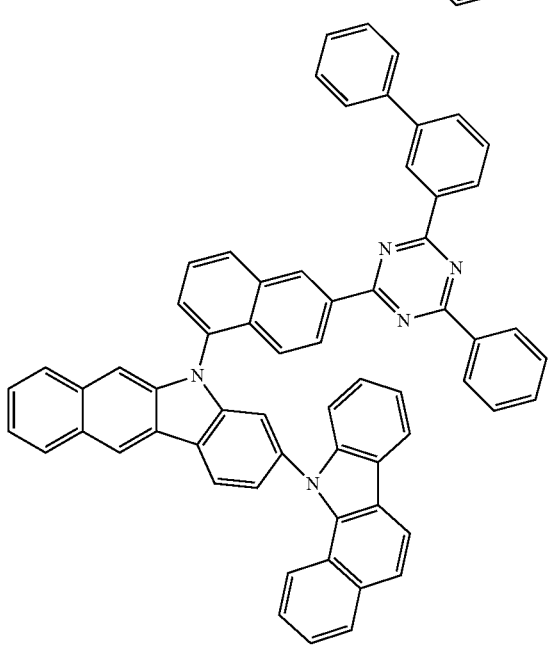

325
-continued
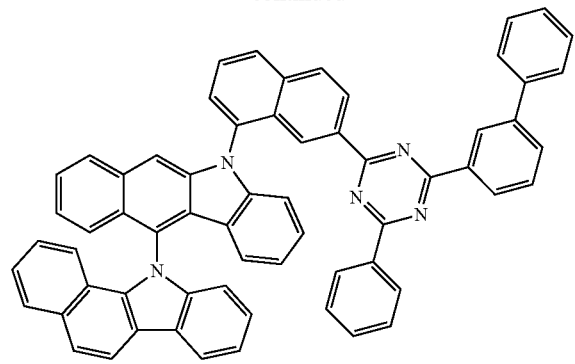
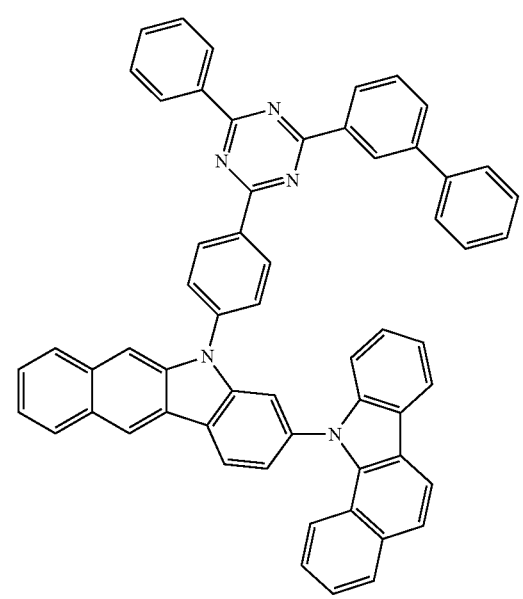
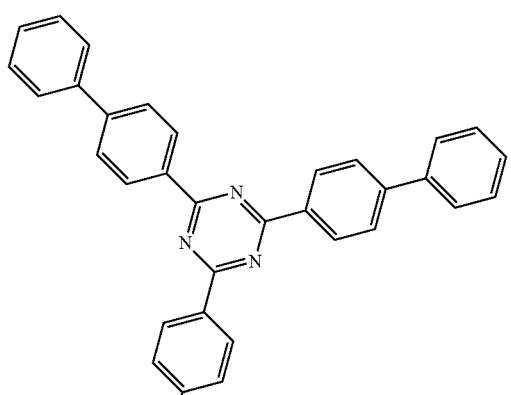
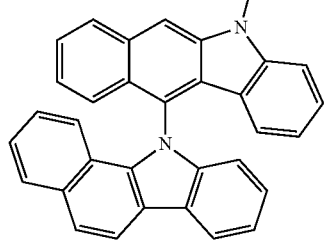
326
-continued
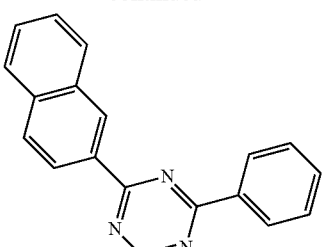
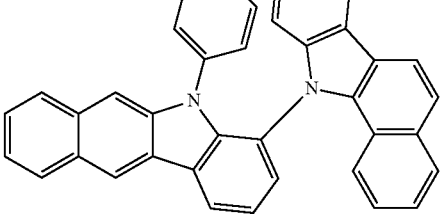
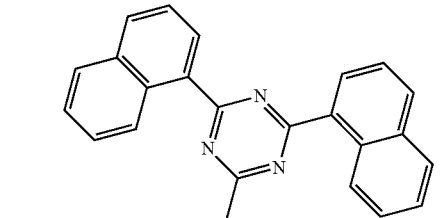
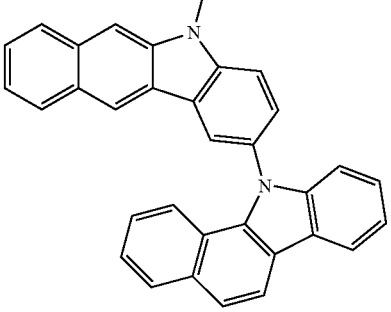
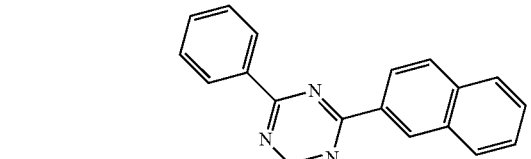
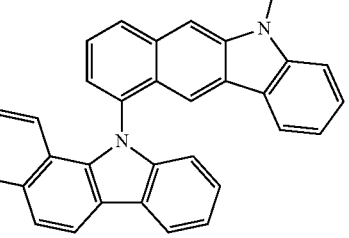

327
-continued
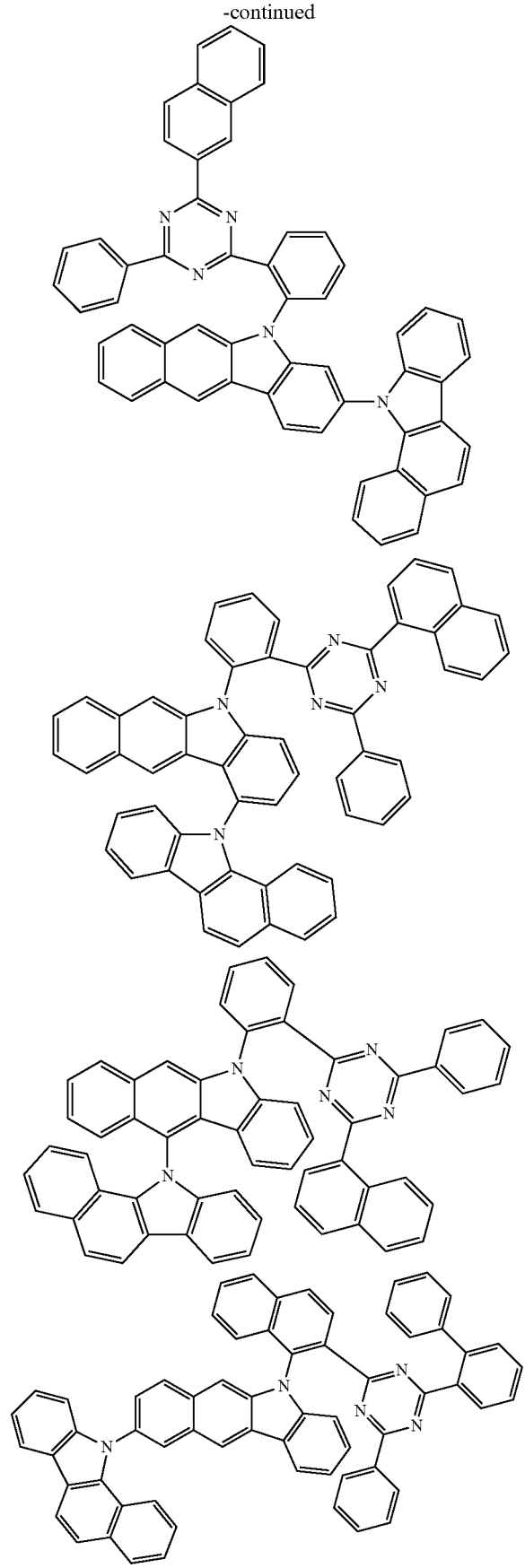
328
-continued
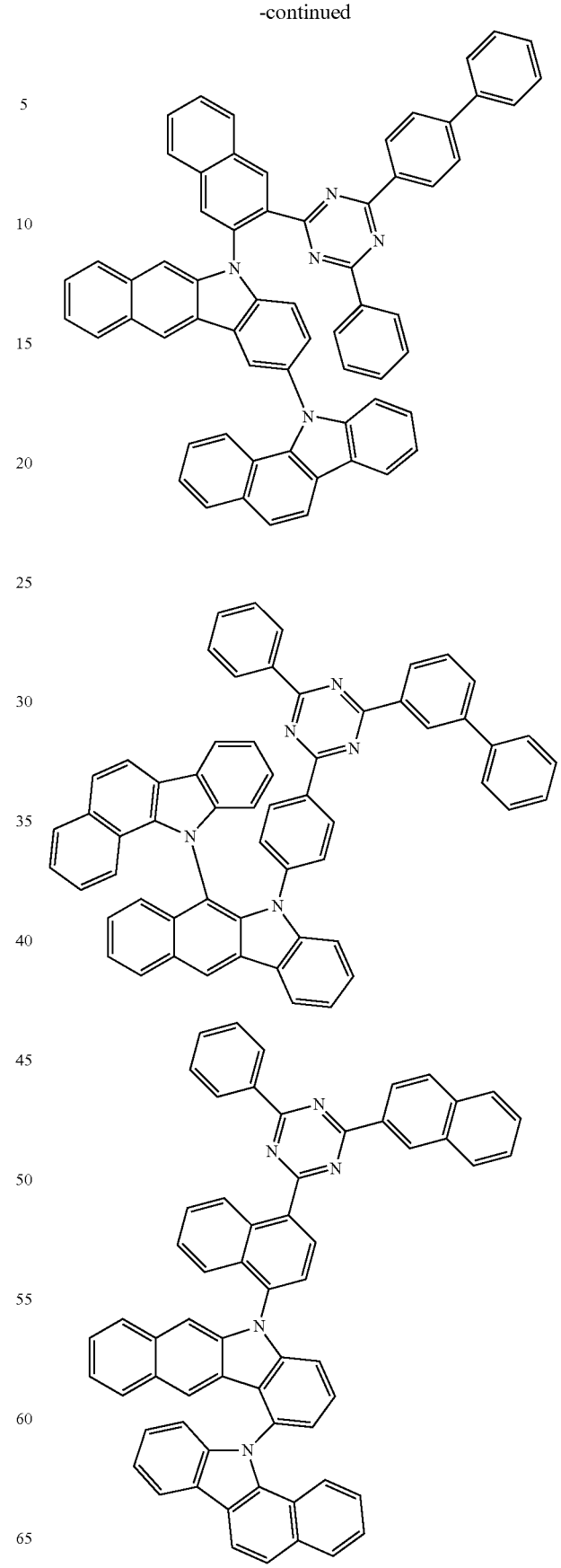

329
-continued
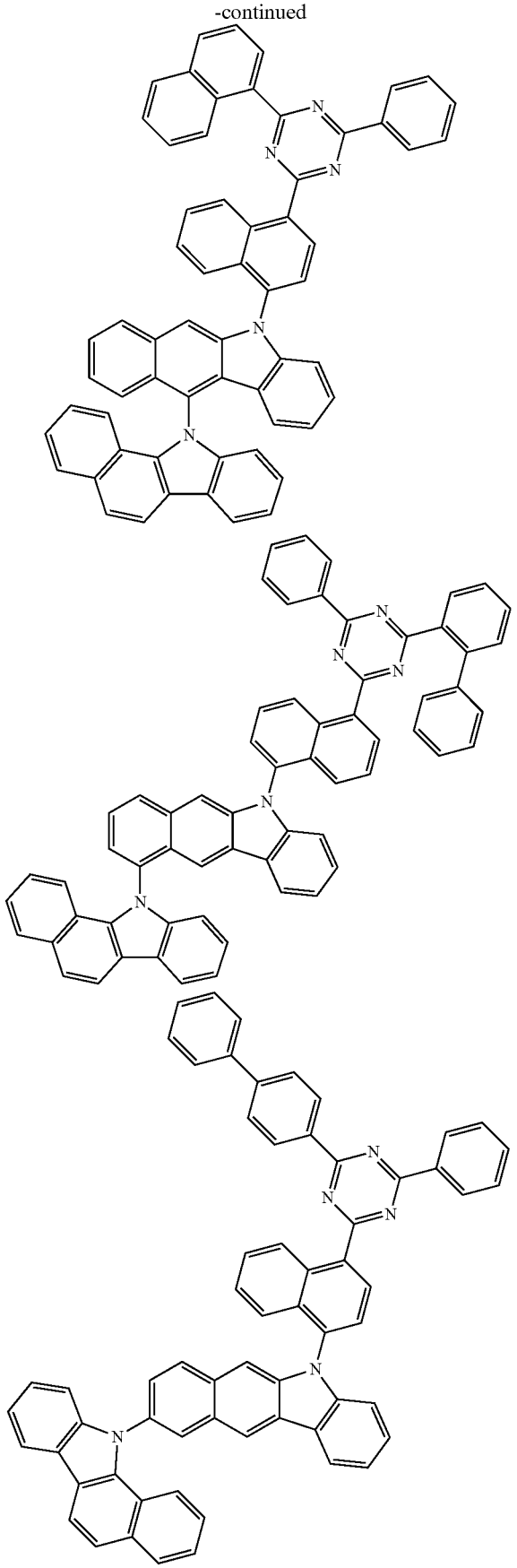
330
-continued
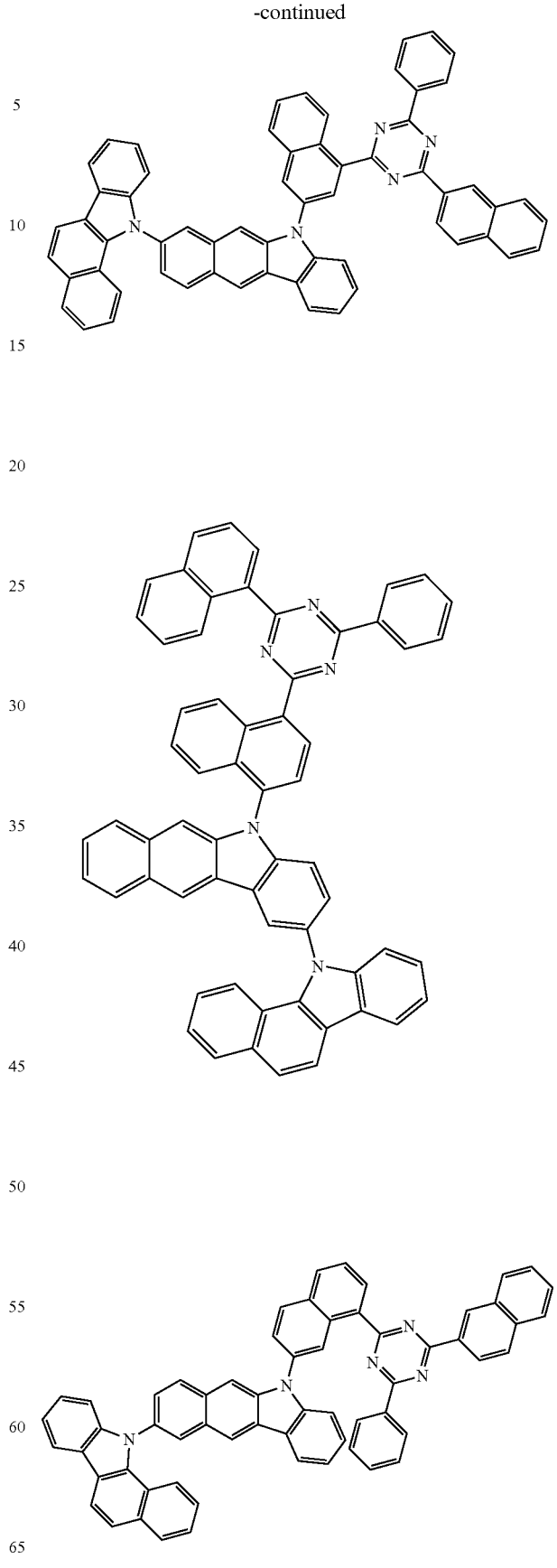

331
-continued
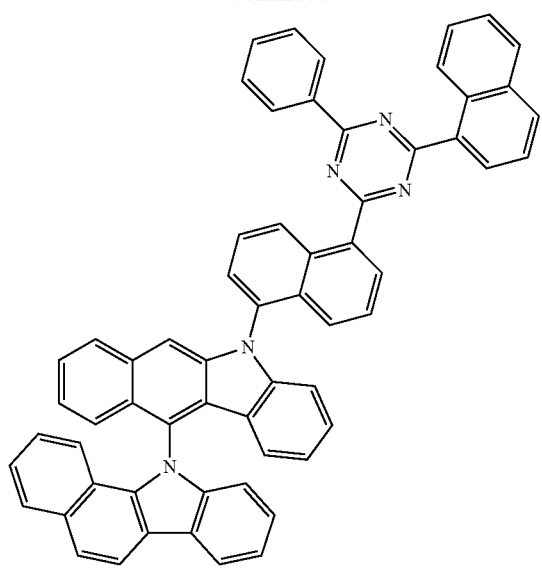
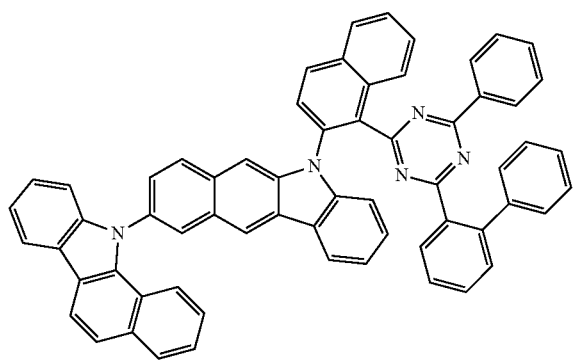
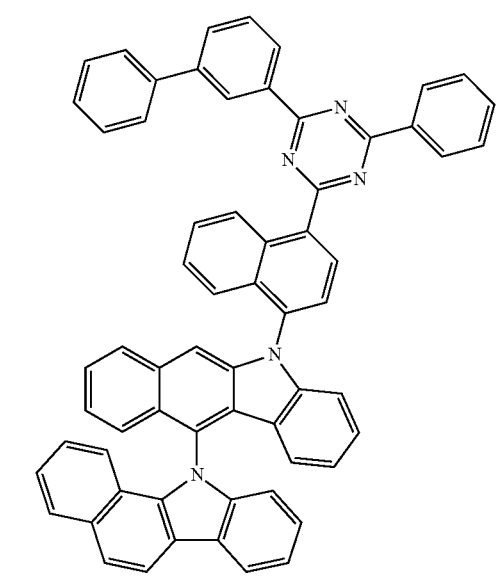
332
-continued
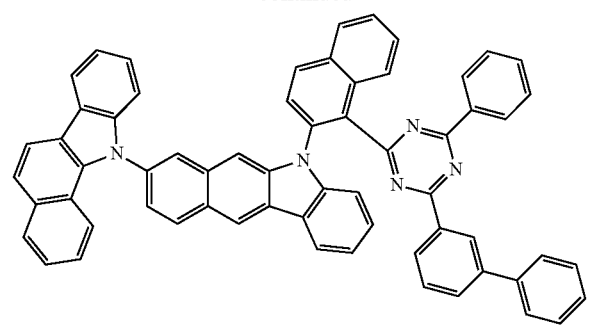
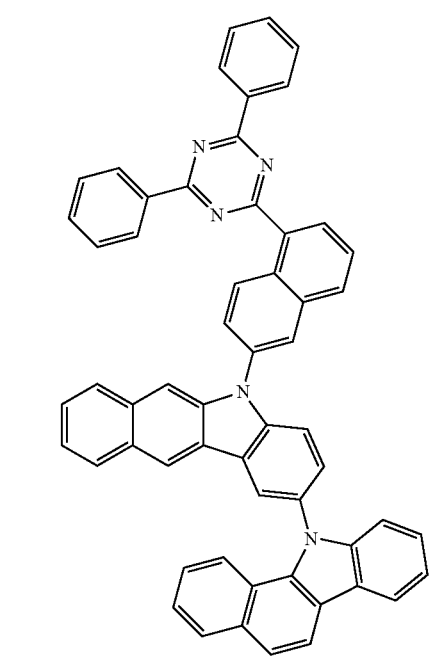
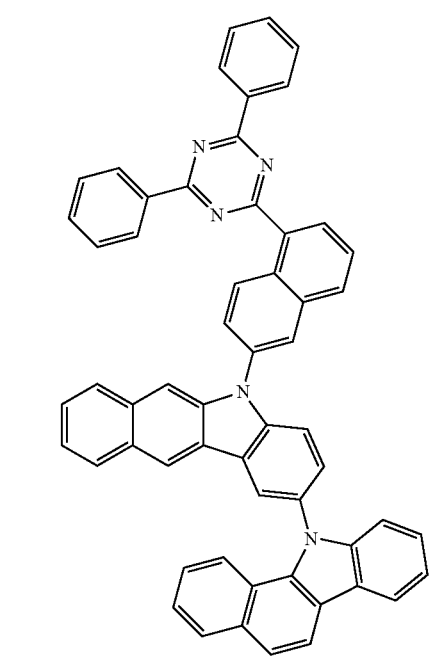
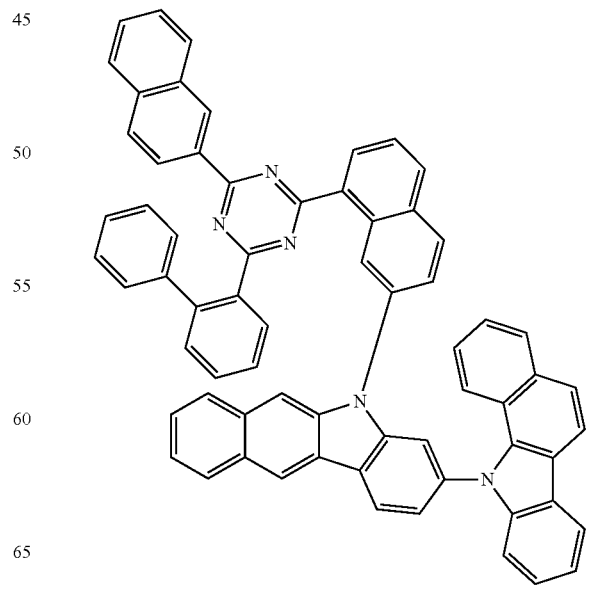

333
-continued
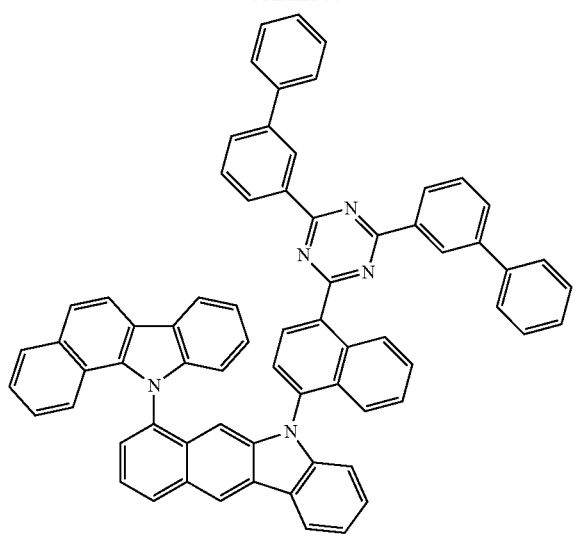
334
-continued
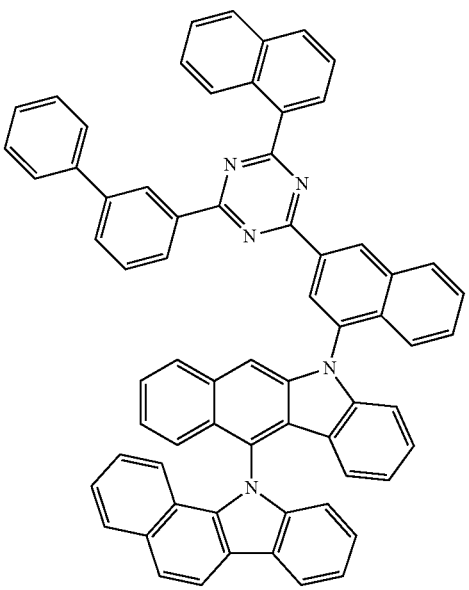
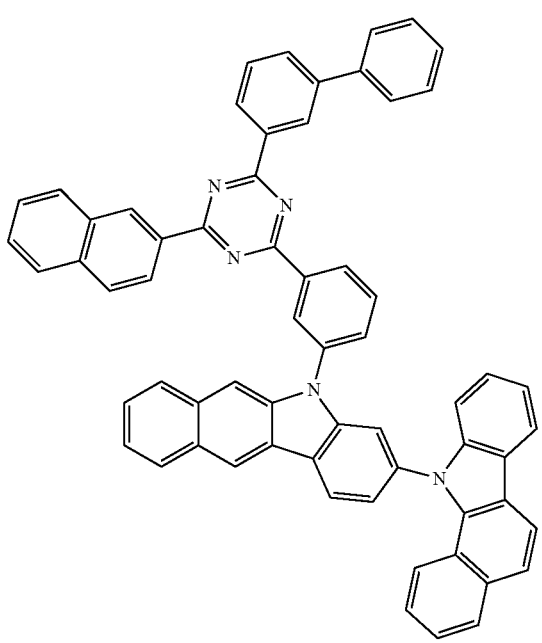

335
-continued
336
-continued
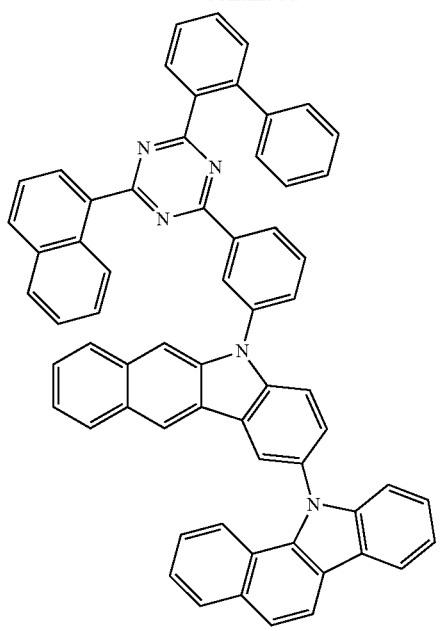
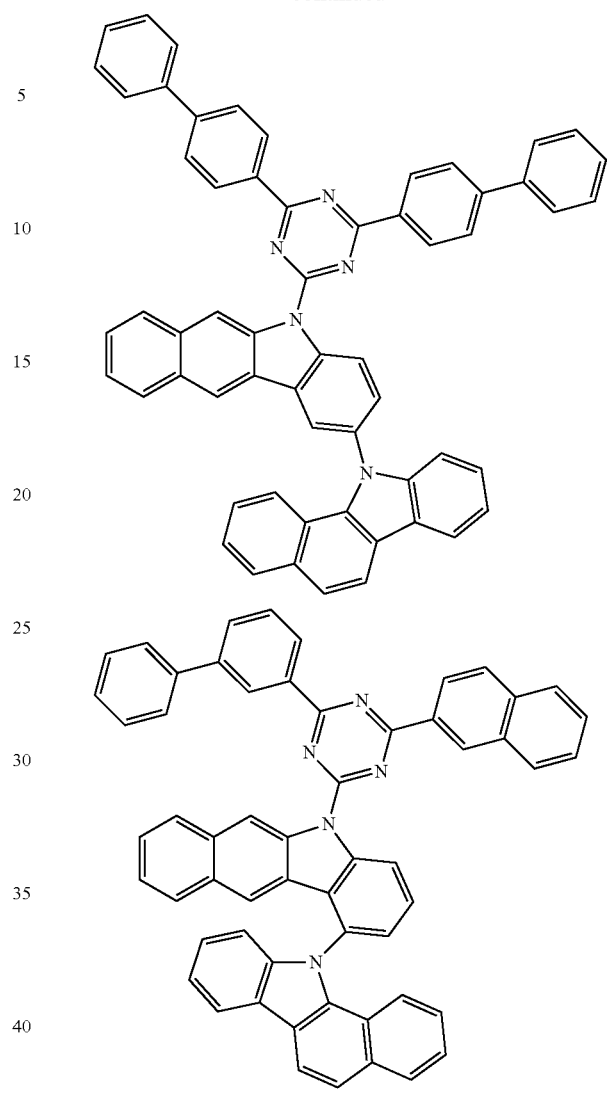
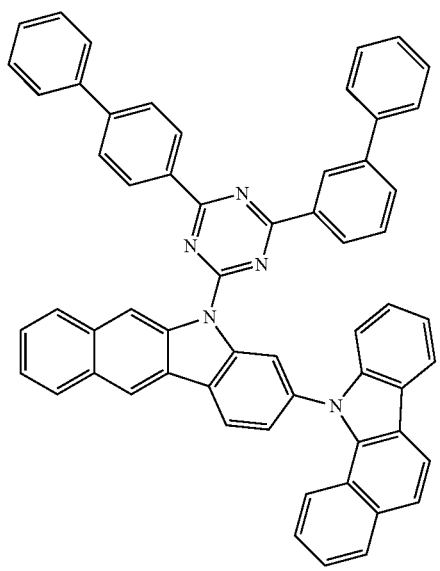
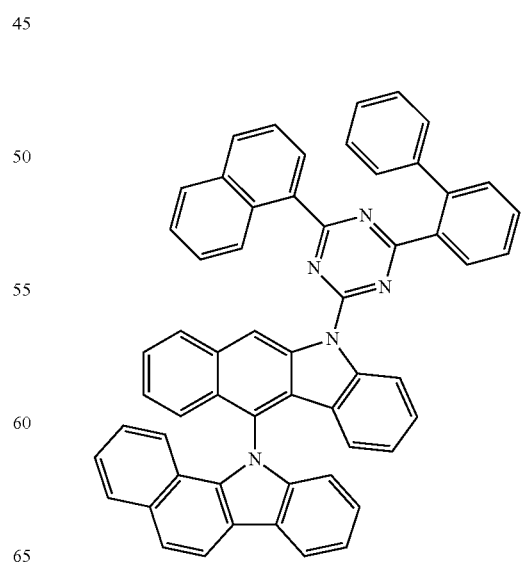

337
-continued
338
-continued
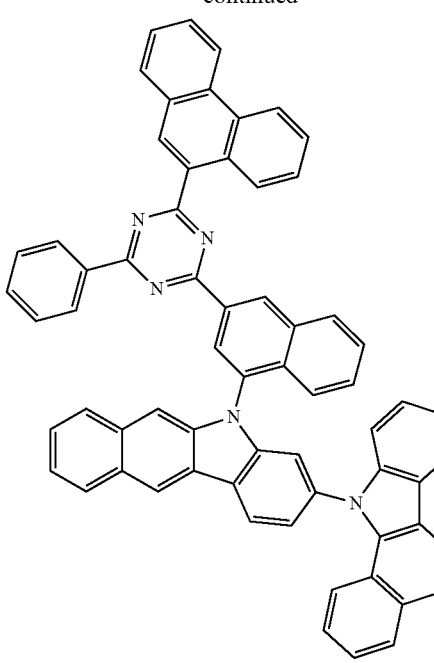
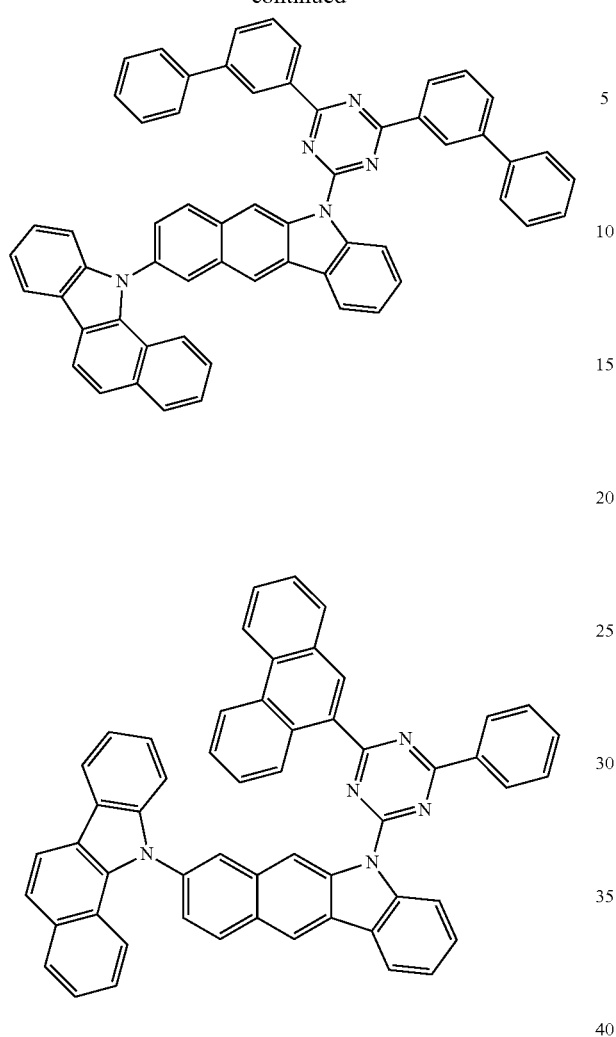
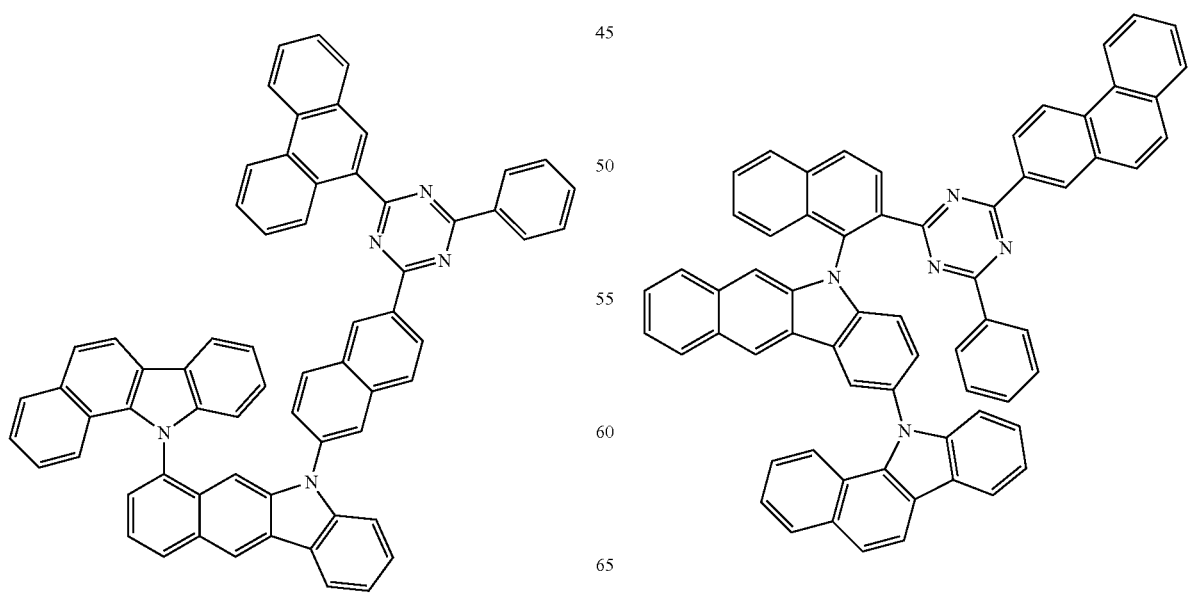

339
-continued
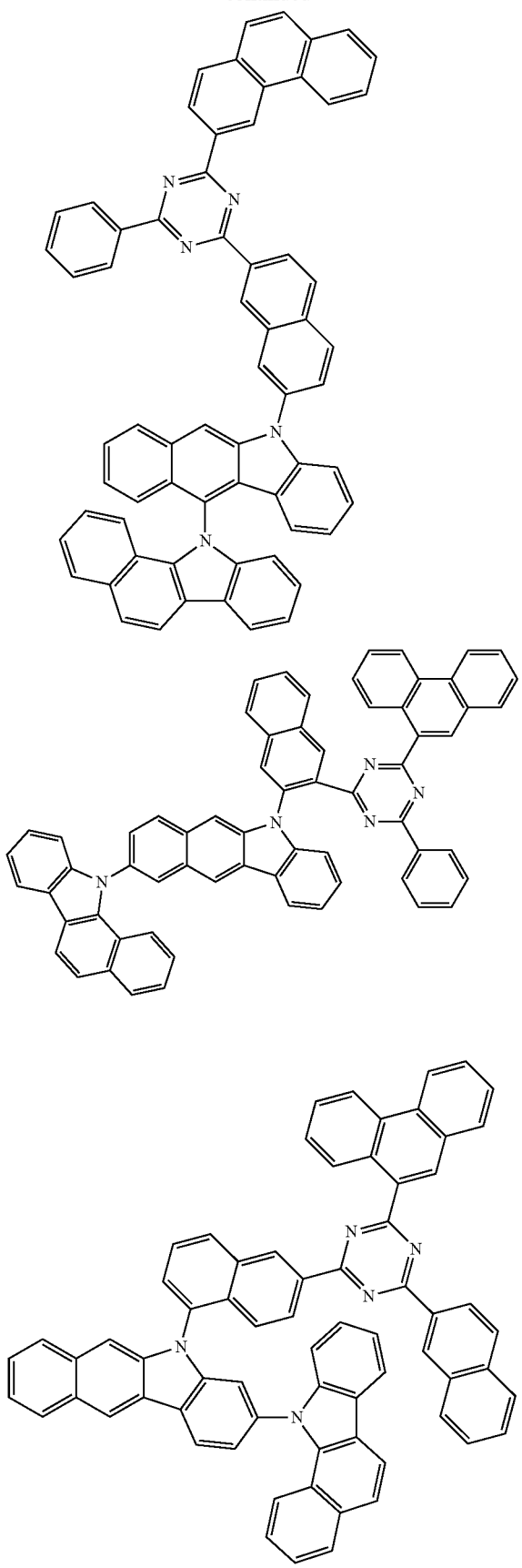
340
-continued
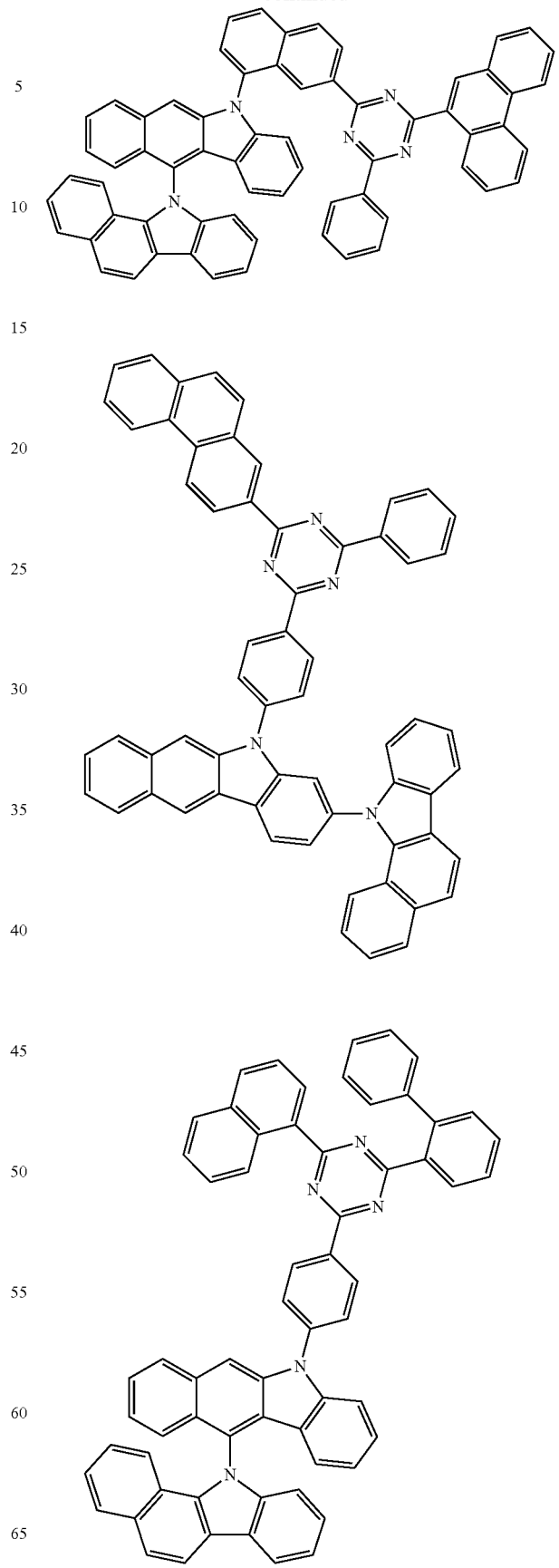

341
-continued
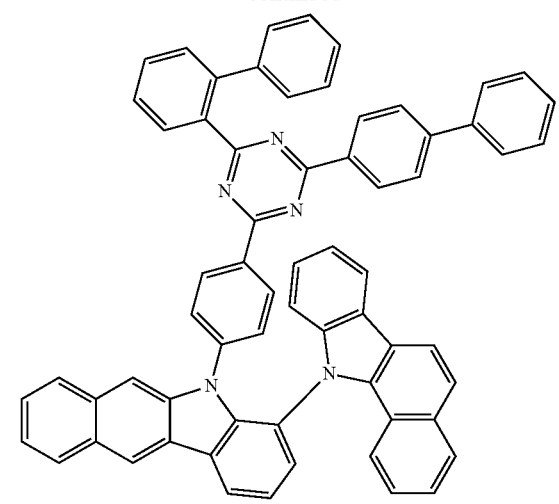
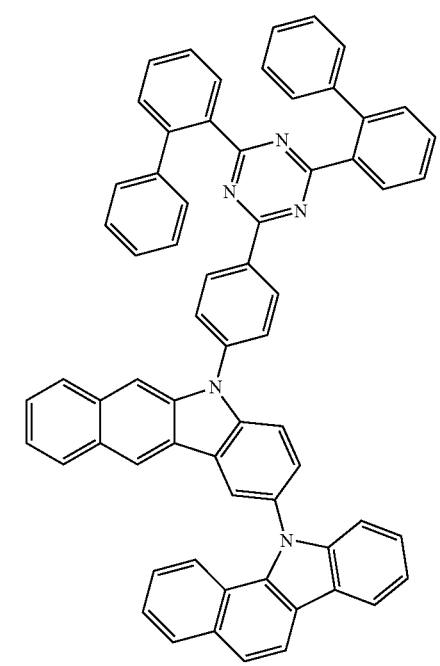
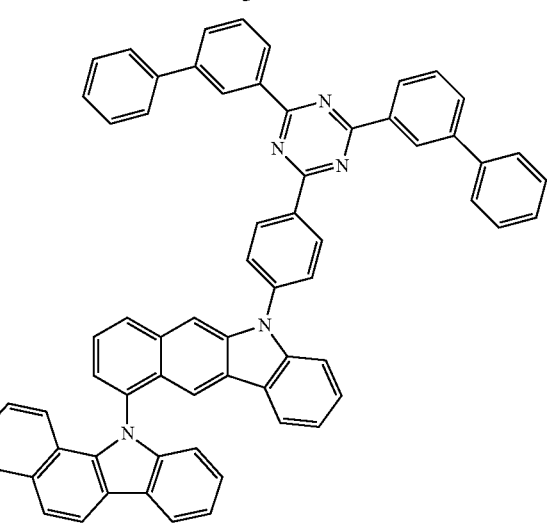
342
-continued
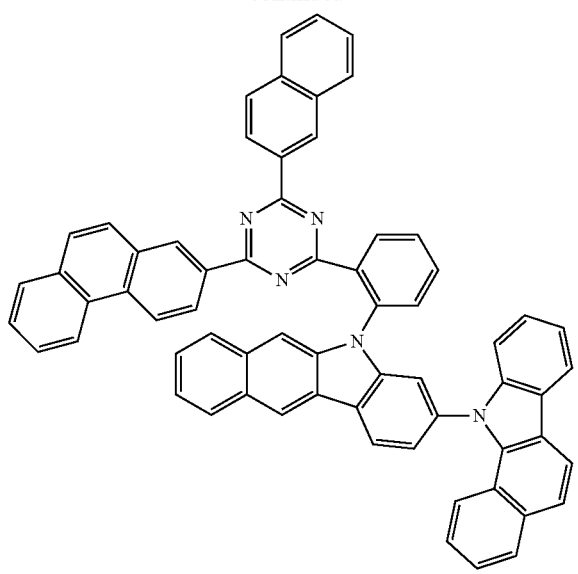
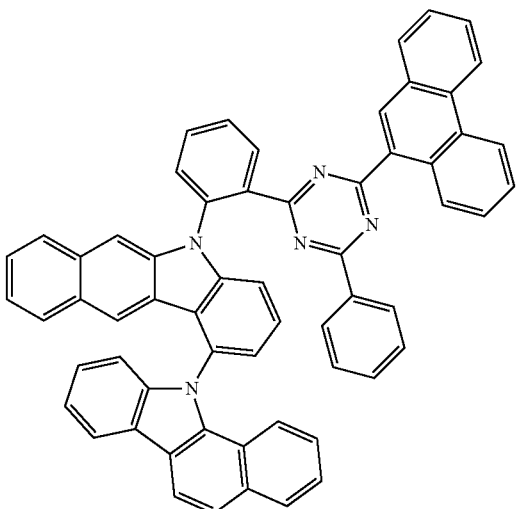
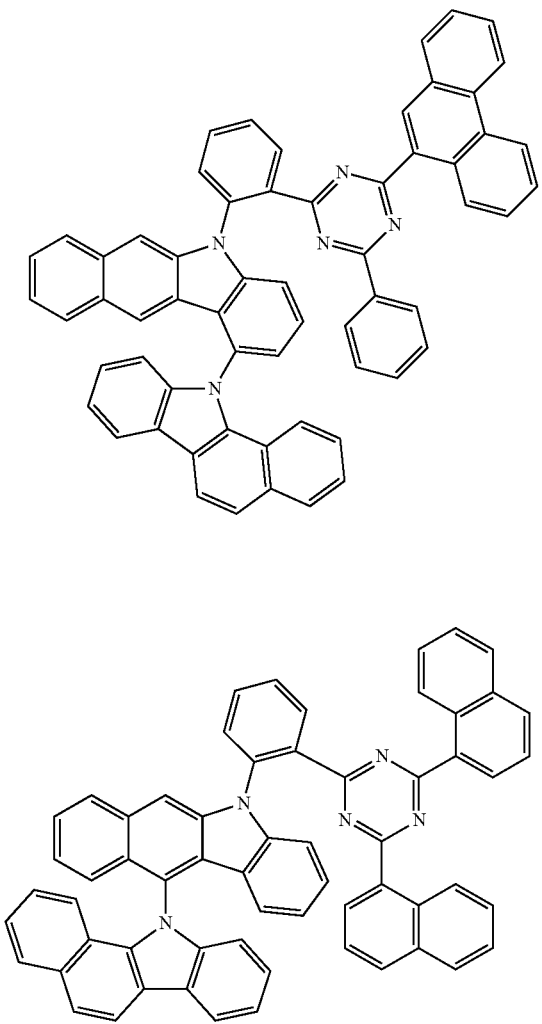

343
-continued
344
-continued
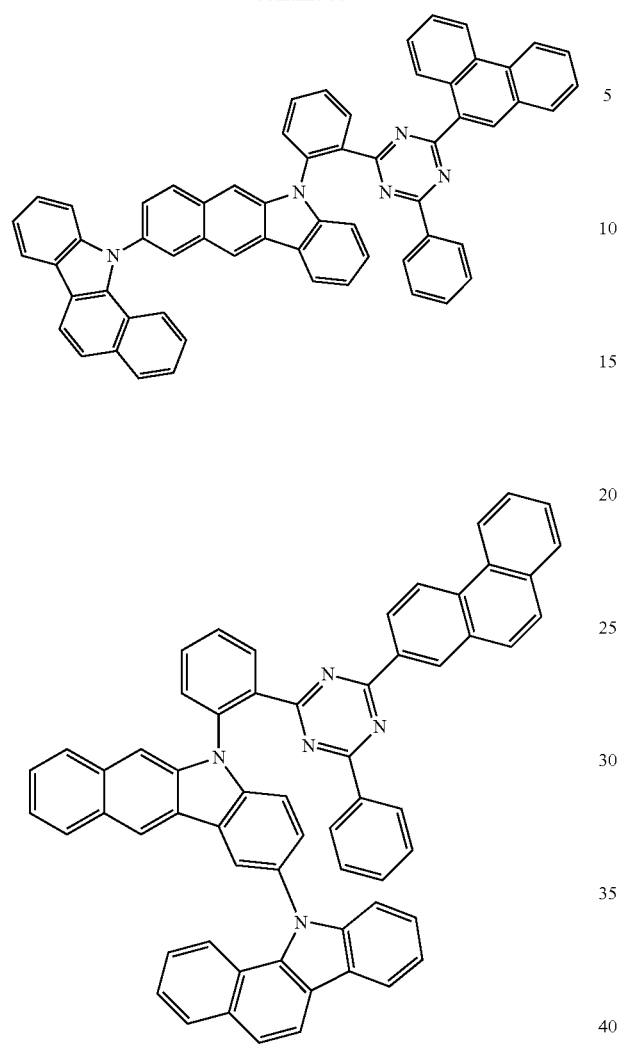
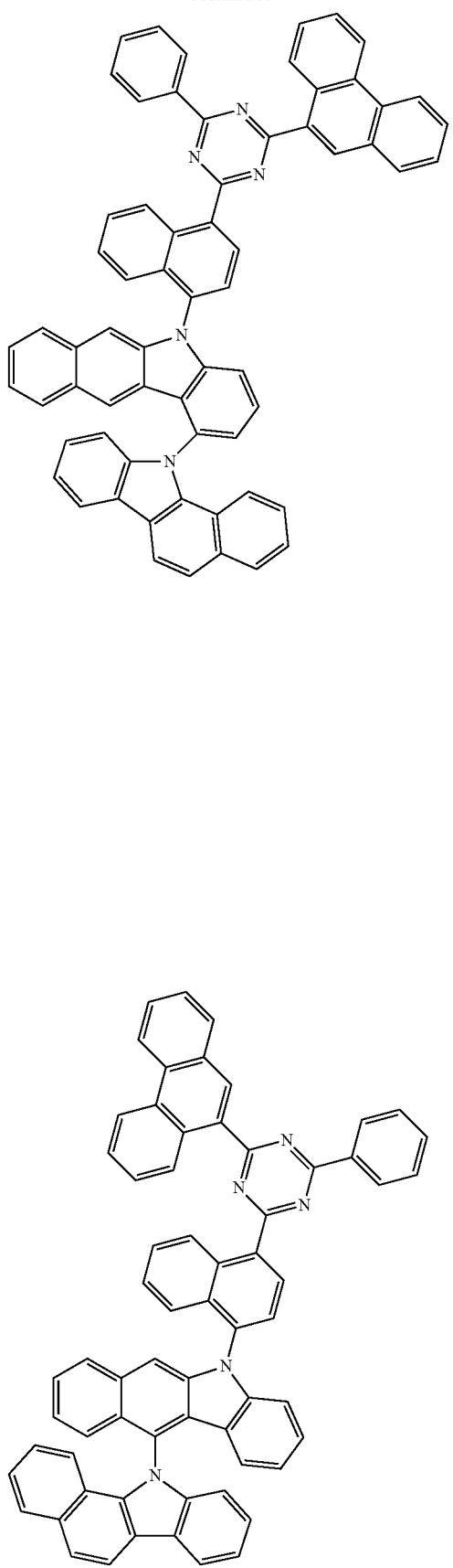

345
-continued
346
-continued
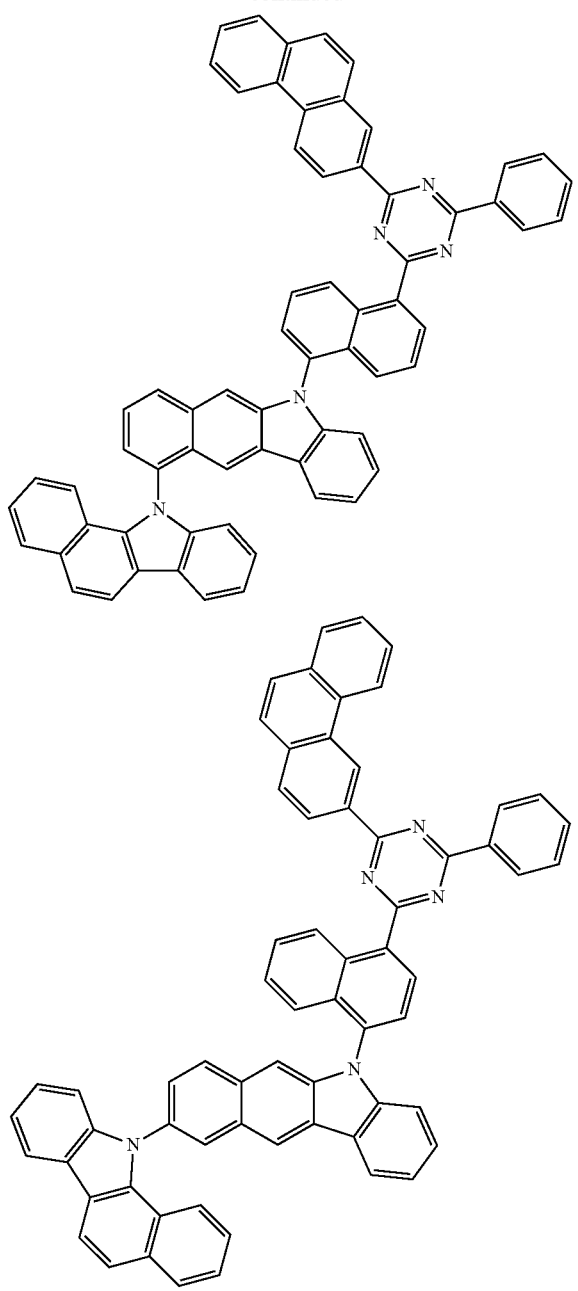
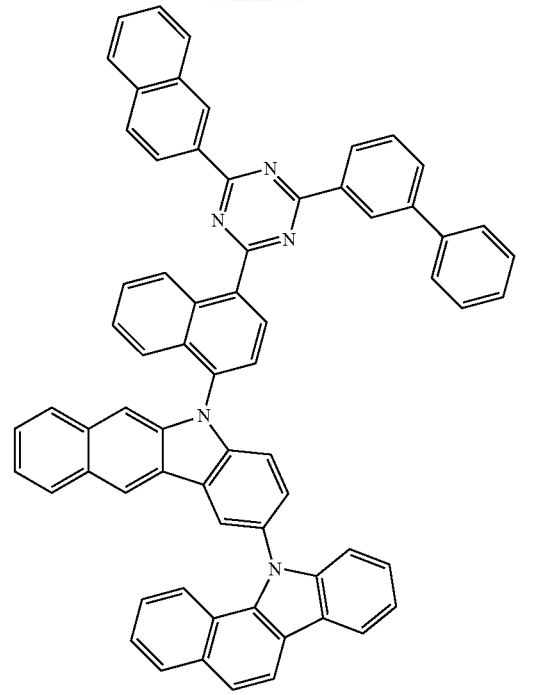
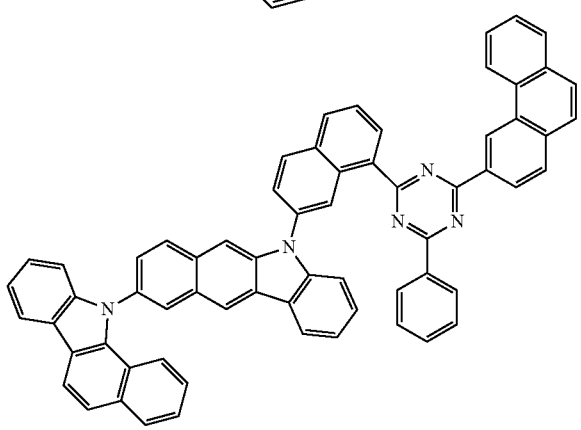
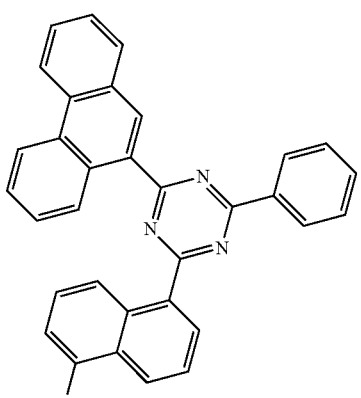
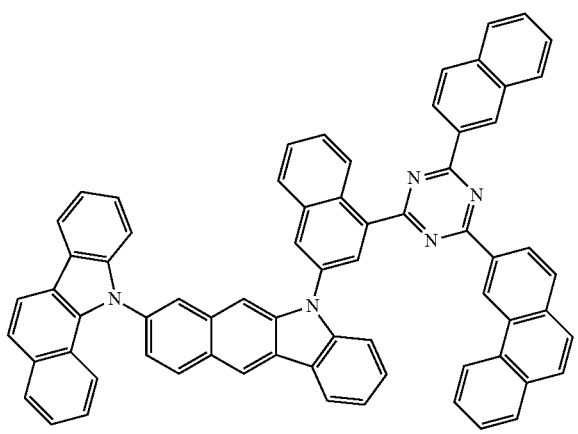
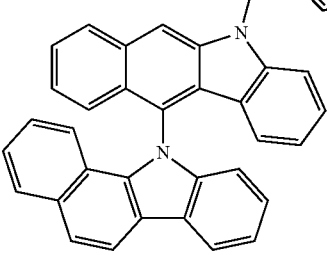

347
-continued
348
-continued
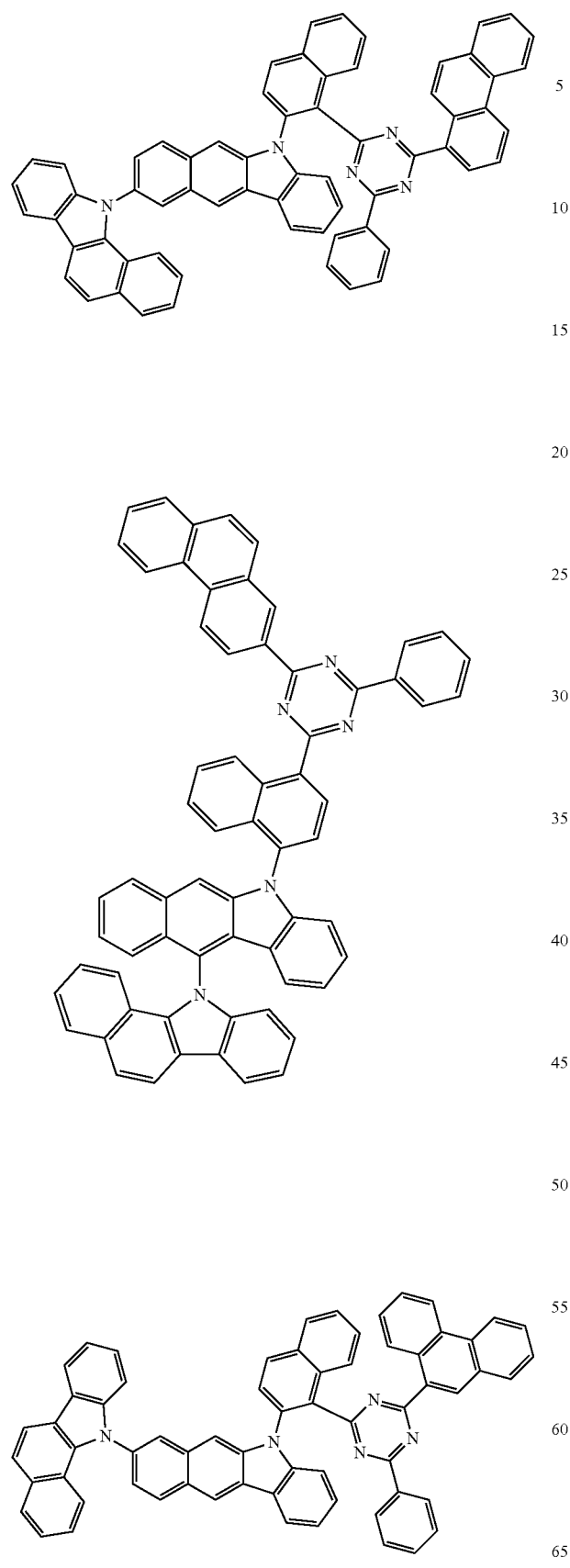
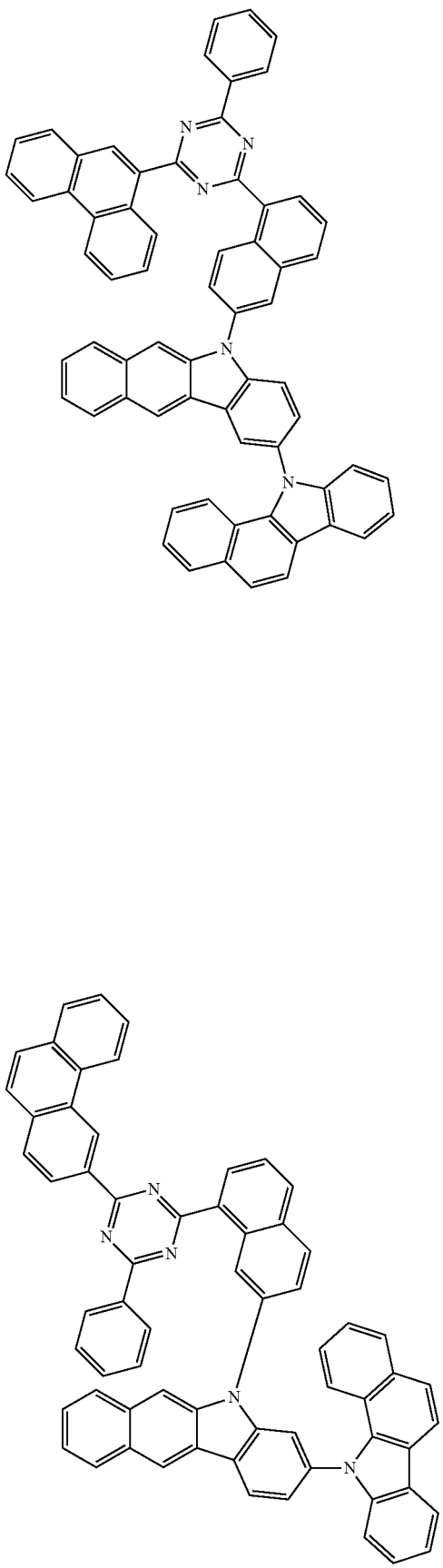

349
-continued
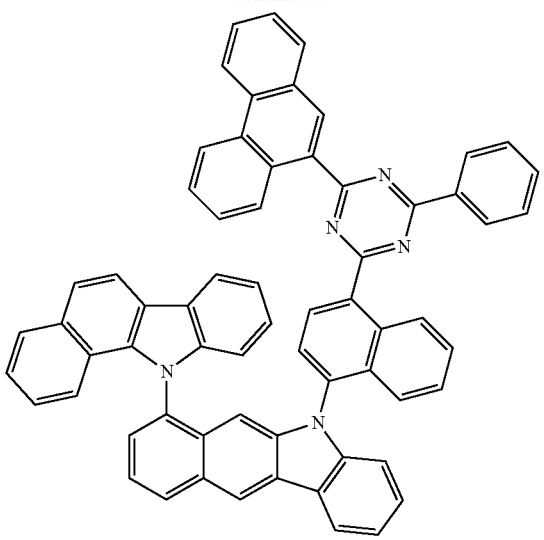
350
-continued
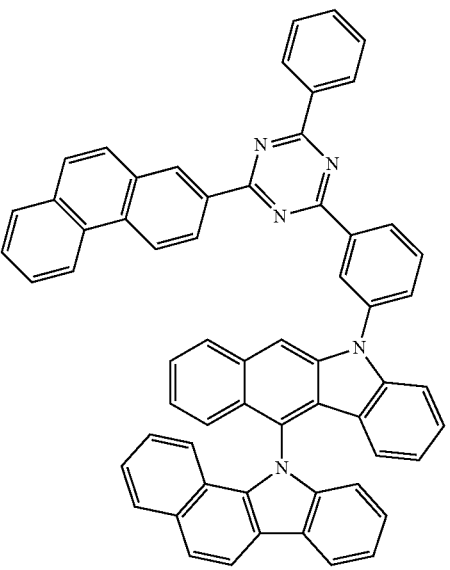
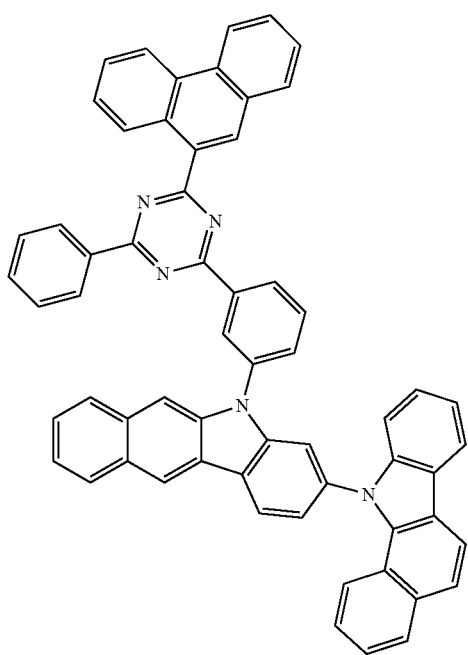
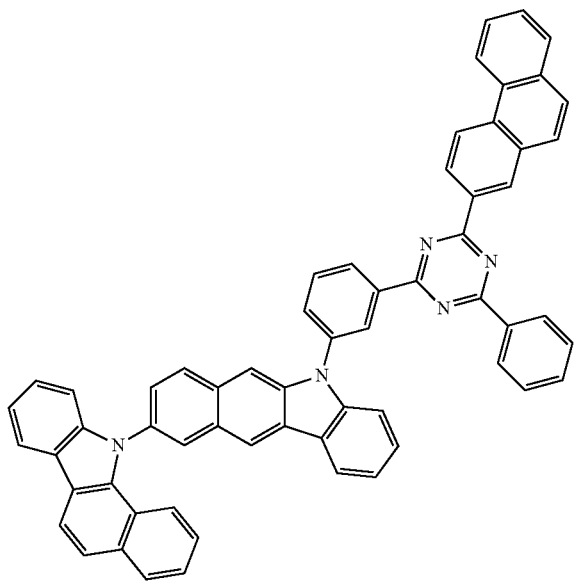

351
-continued
352
-continued
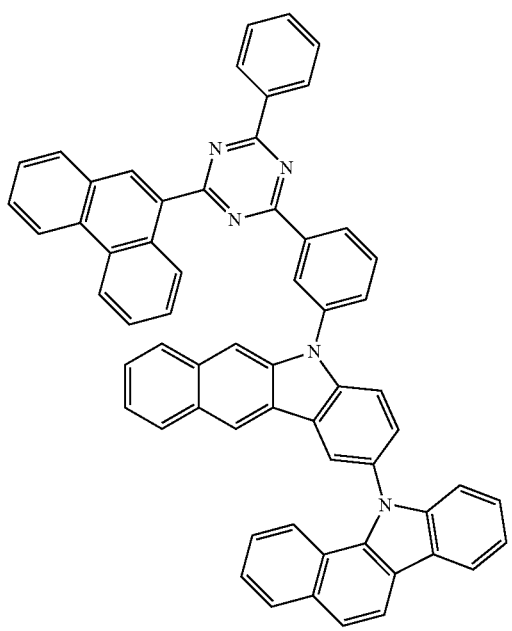 [SMILES: c1ccc(-c2nc(-c3cccc(-n4c5ccc(-n6c7ccccc7c7ccc8ccccc8c76)cc5c5cc6ccccc6cc54)c3)nc(-c3cc4ccccc4c4ccccc34)n2)cc1]
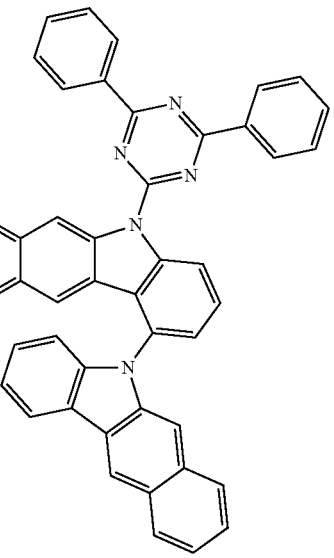
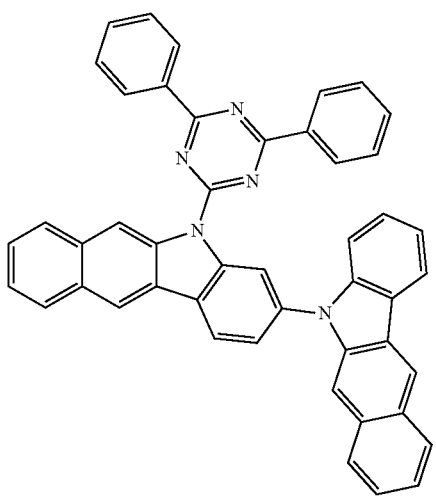
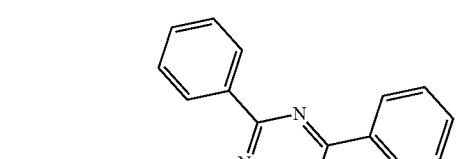
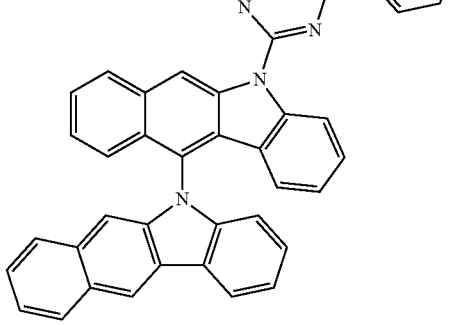
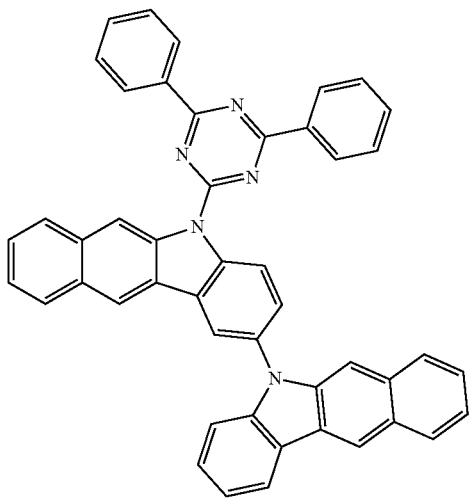
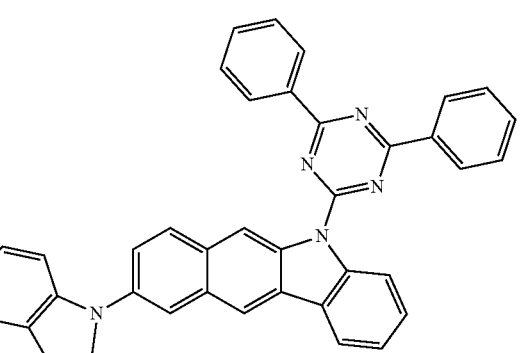

353
-continued
354
-continued
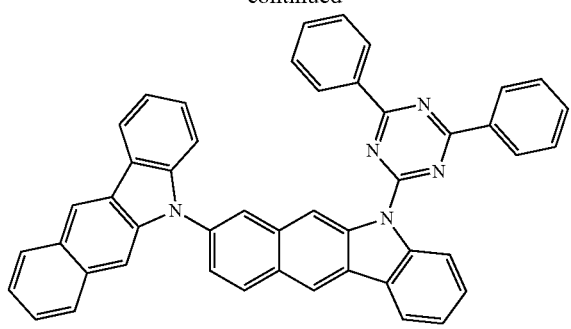
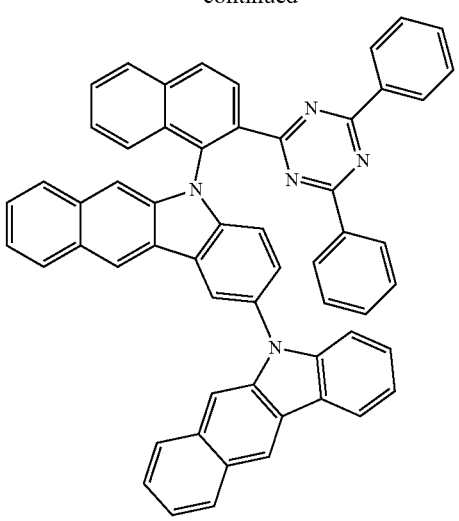
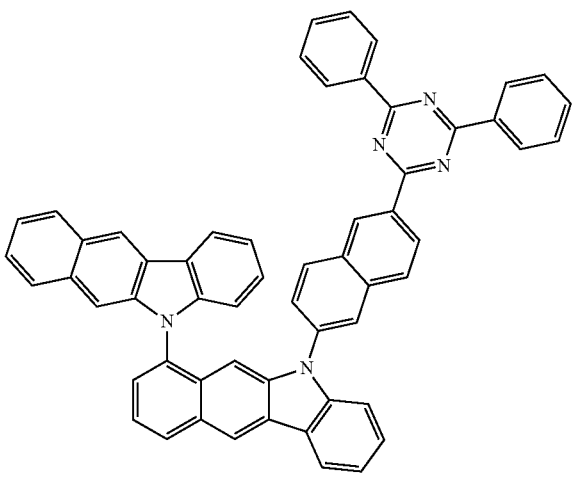
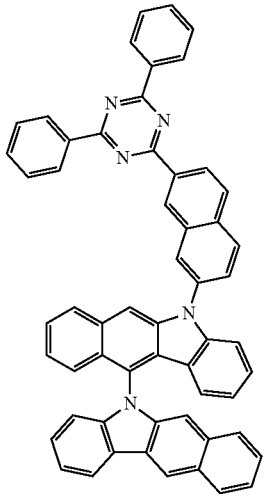
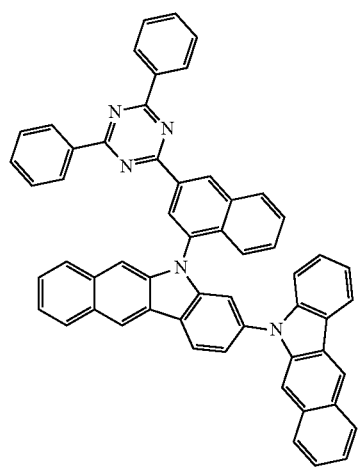
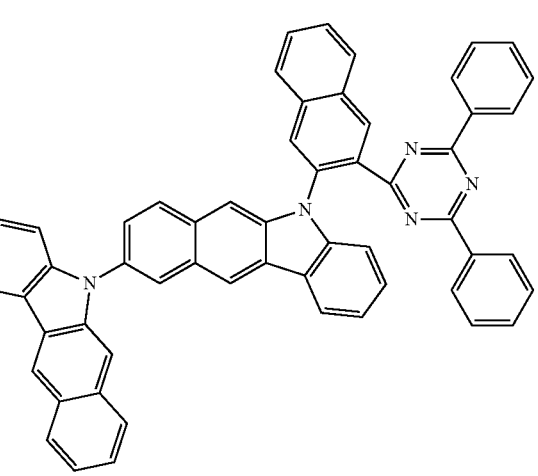

355
-continued
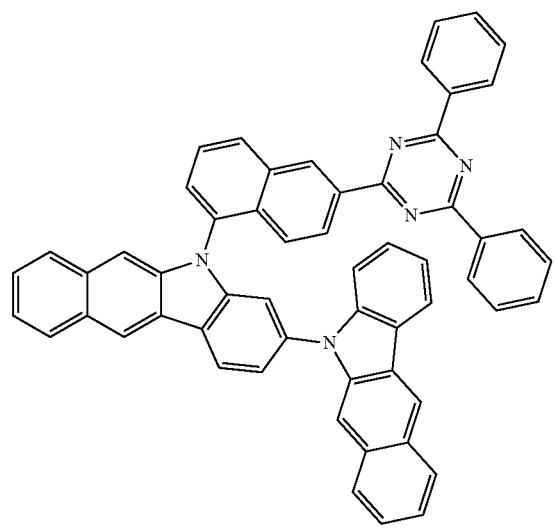
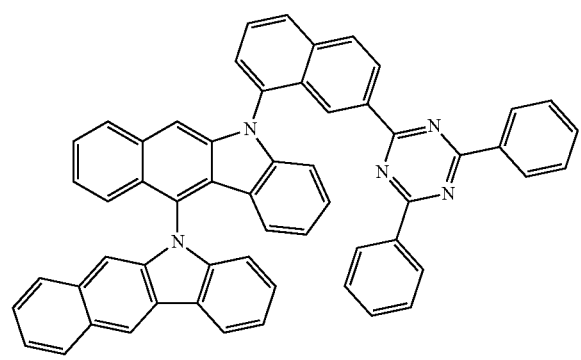
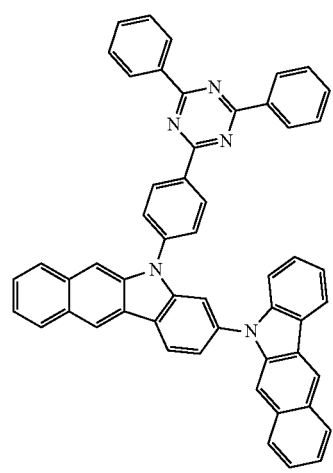
356
-continued
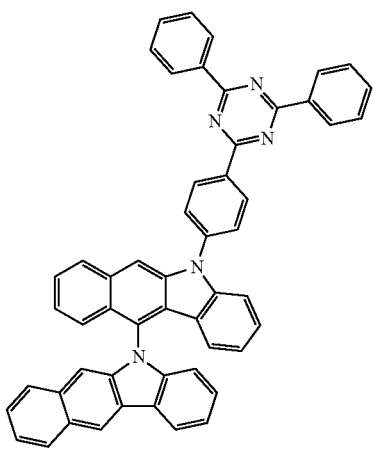
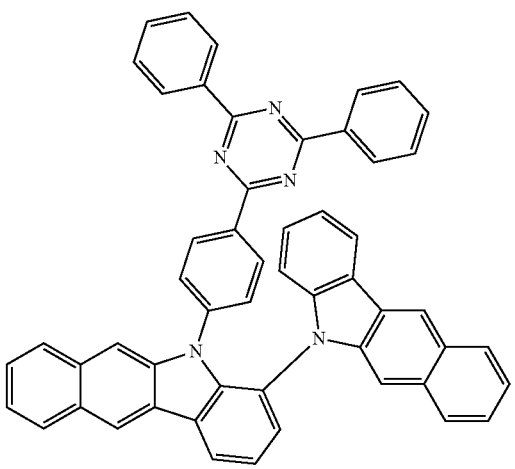
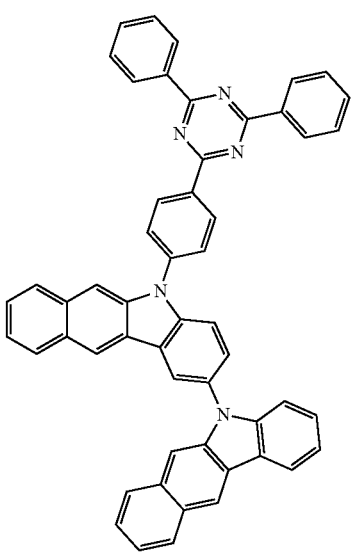

357
-continued
358
-continued
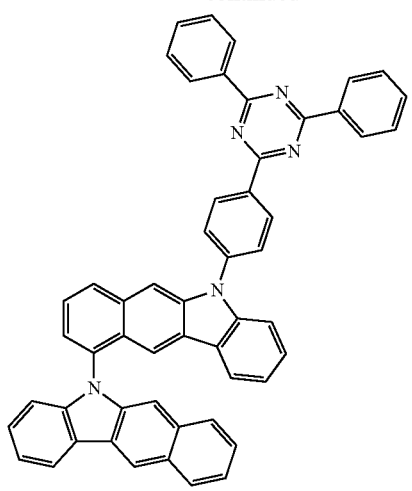
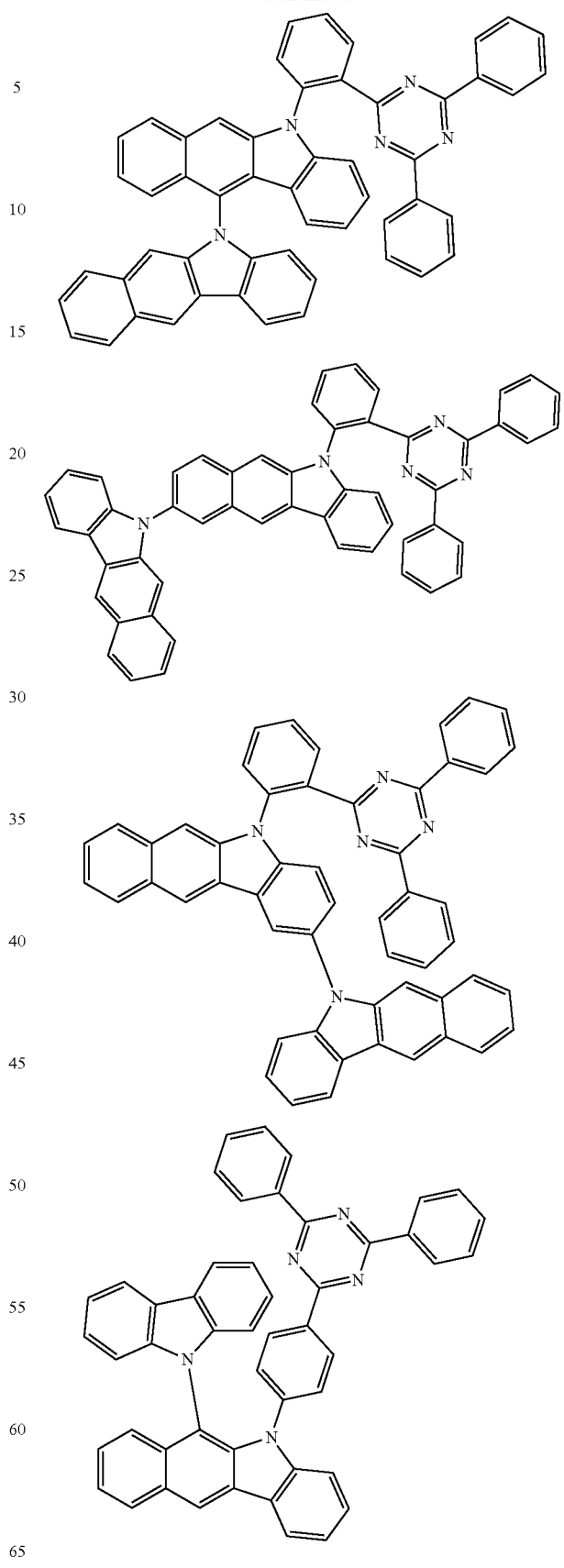

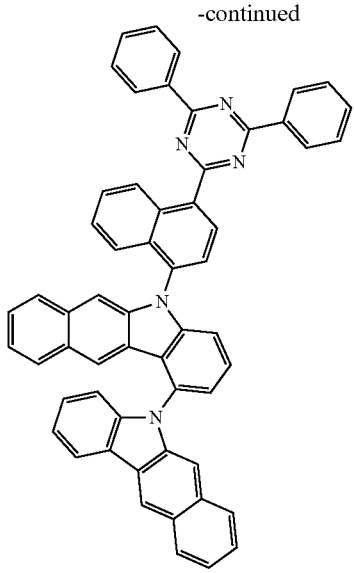
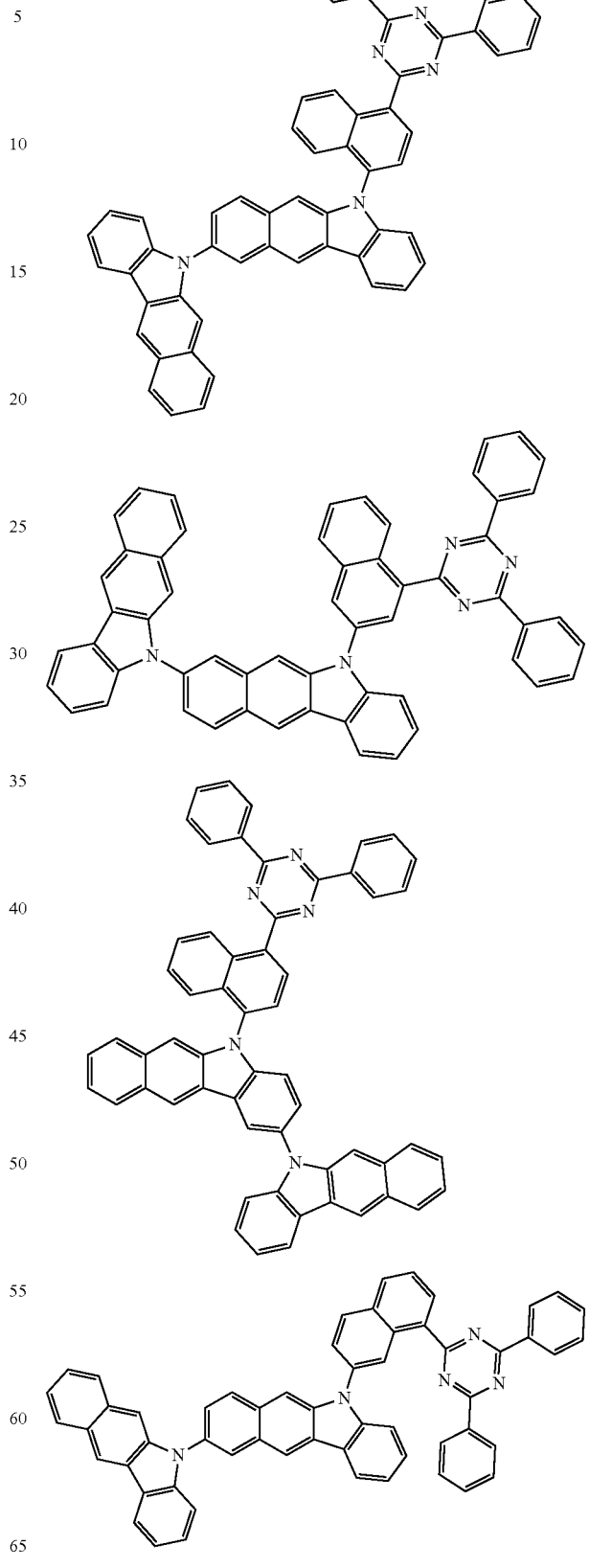

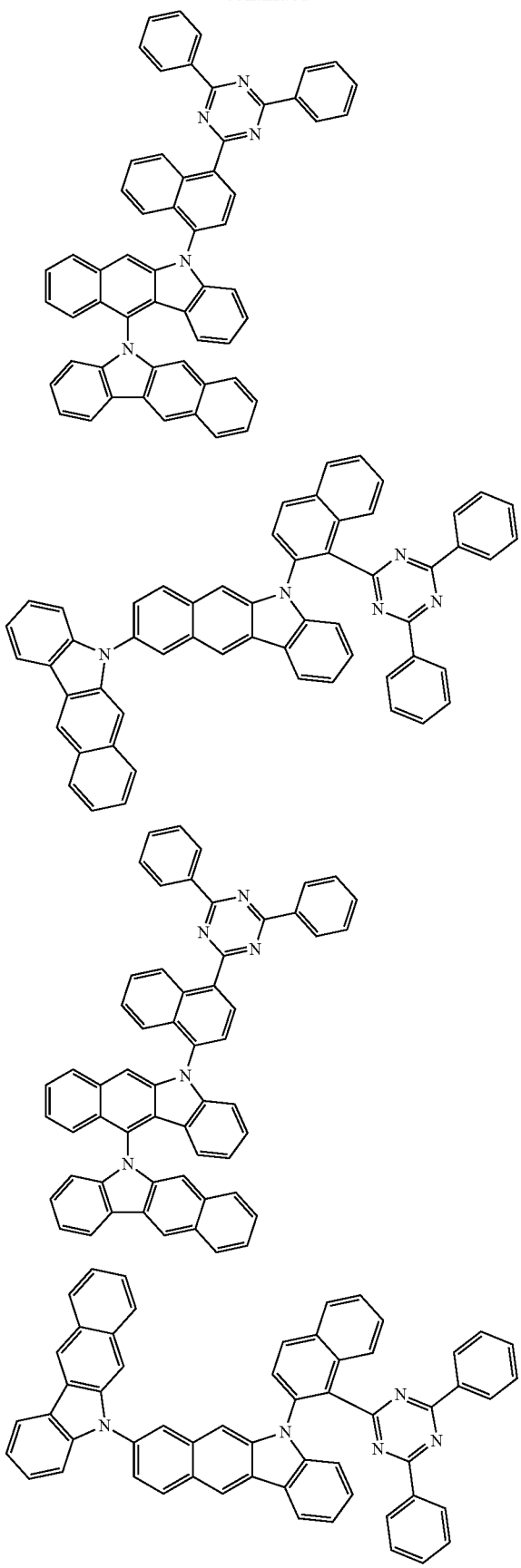

363
-continued
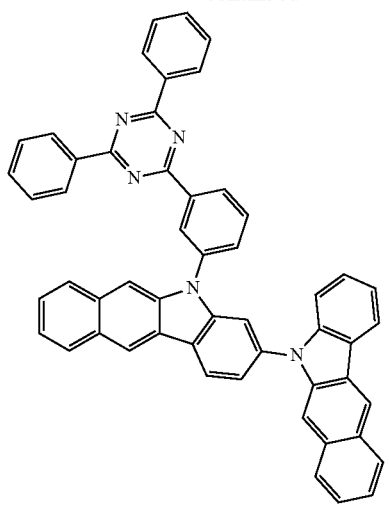
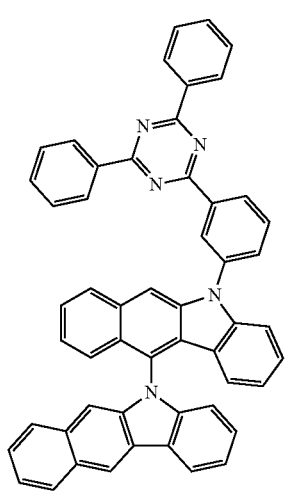
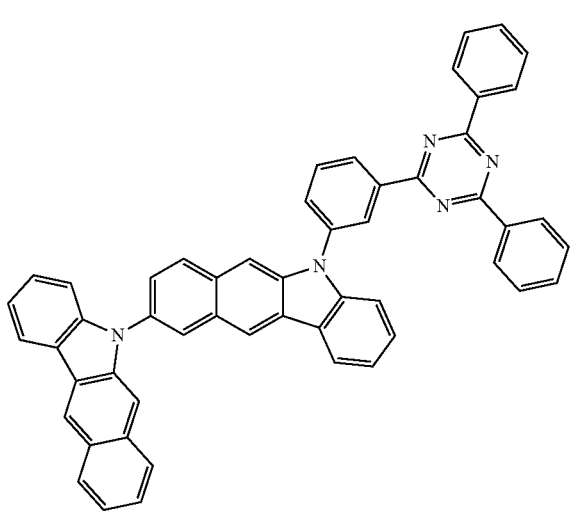
364
-continued
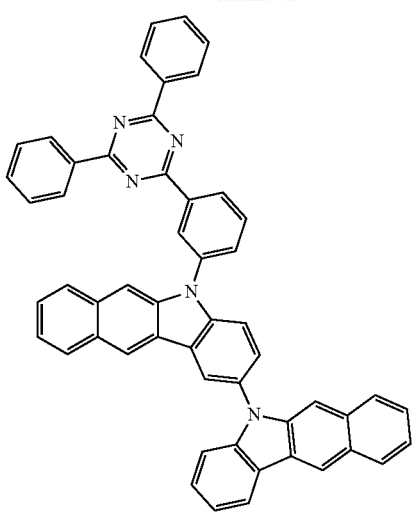
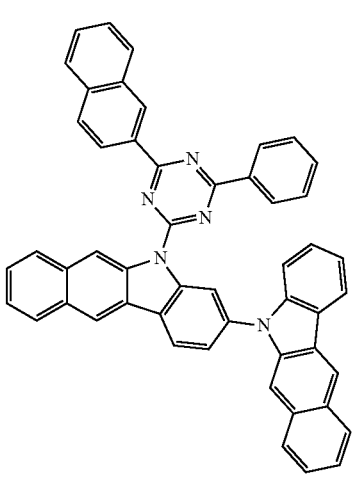
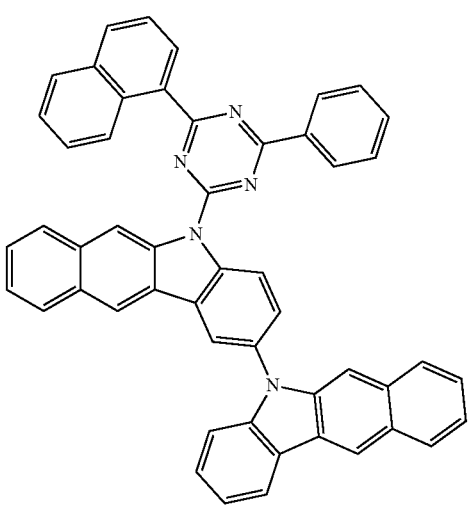

-continued
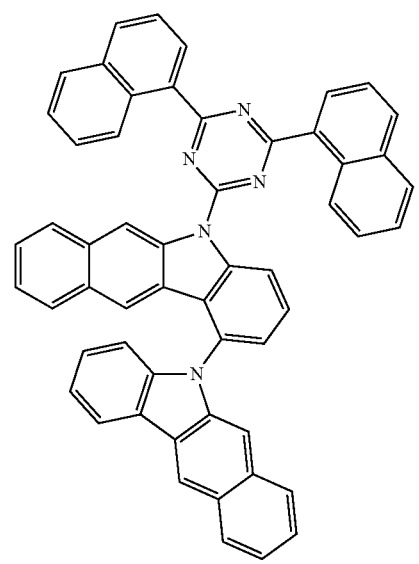
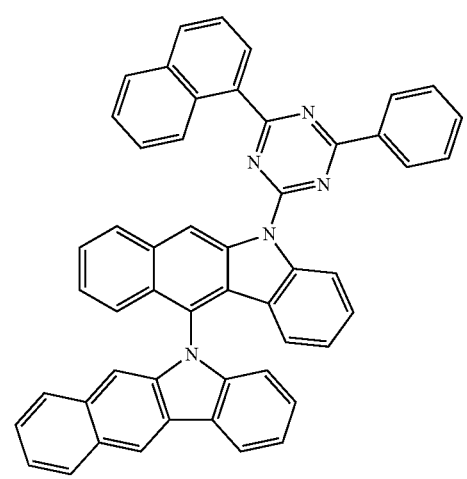
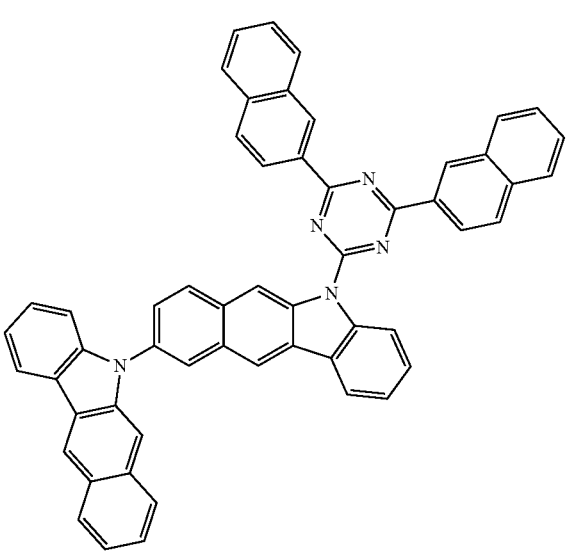
-continued
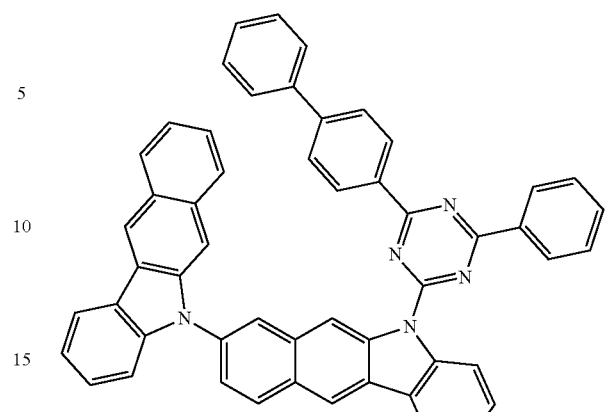
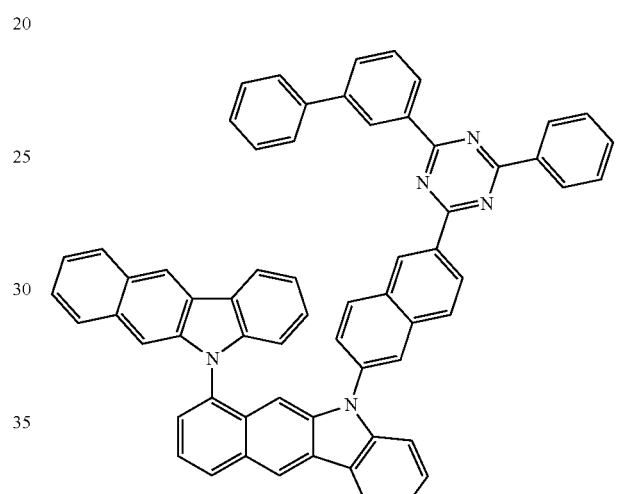
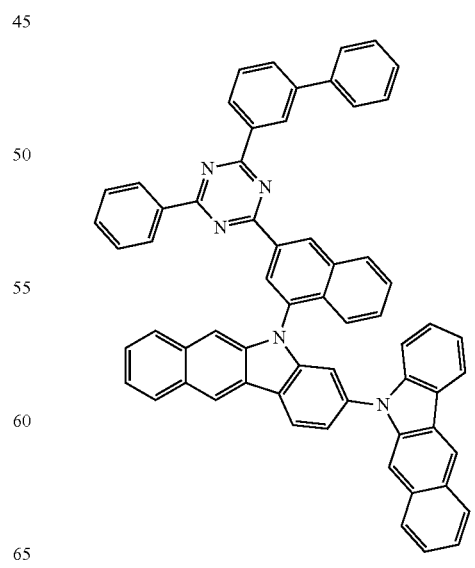

367
-continued
368
-continued
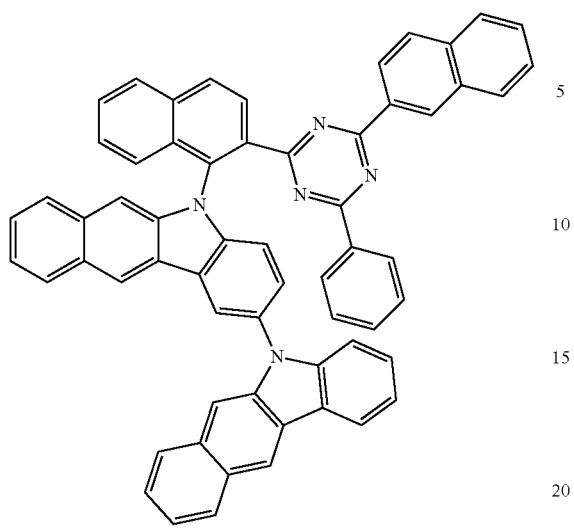
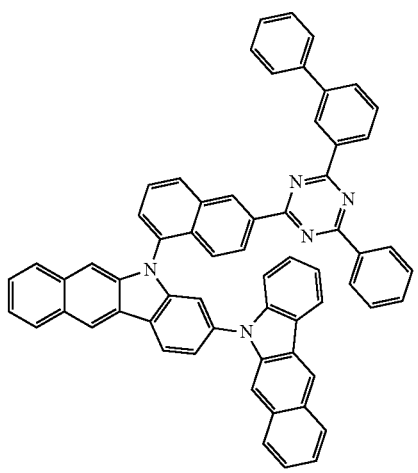
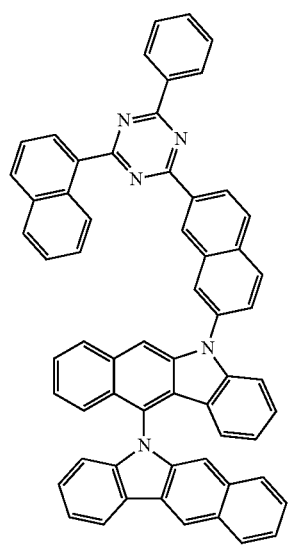
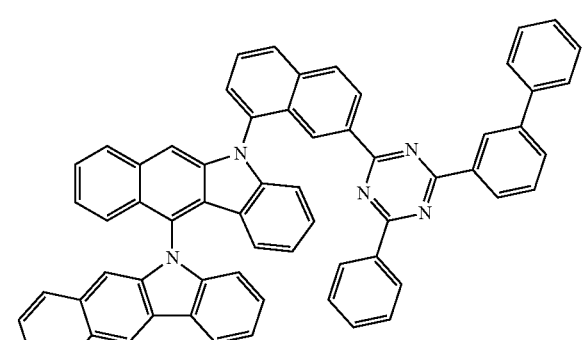
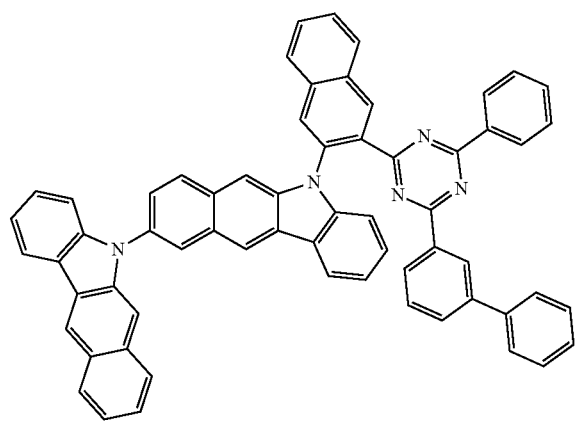
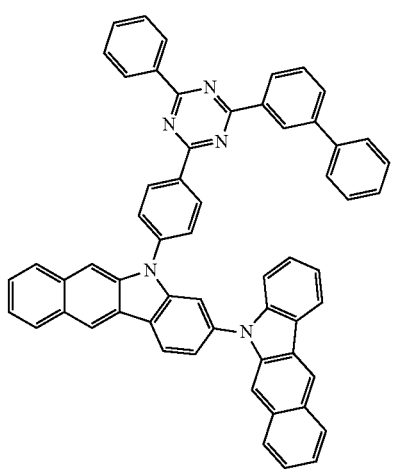

369
-continued
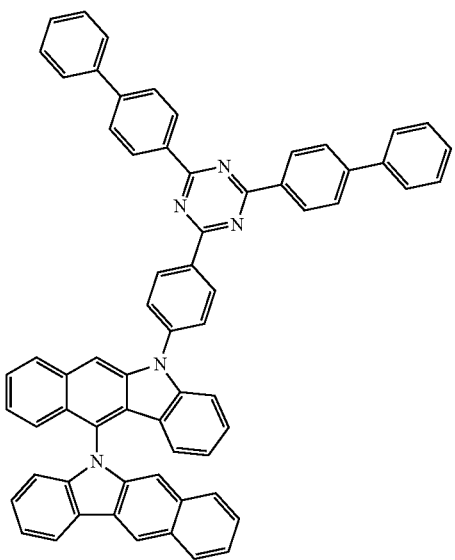
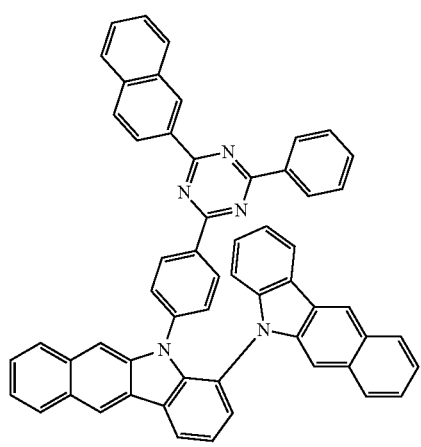
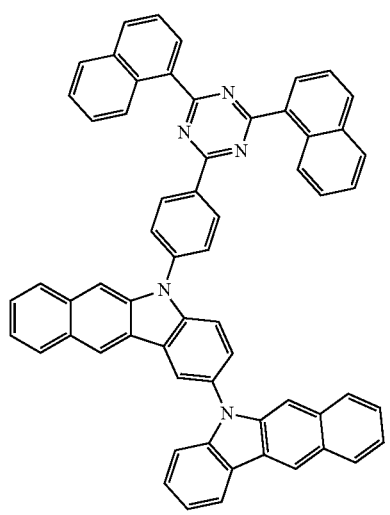
370
-continued
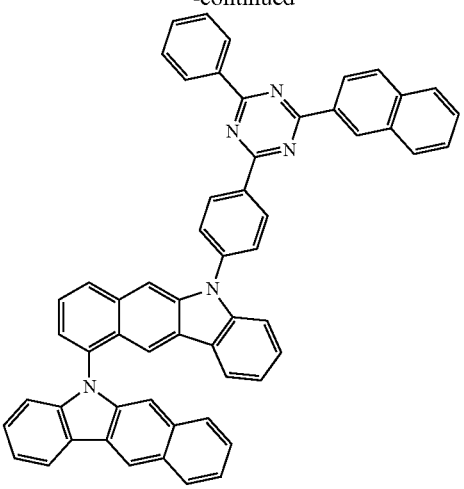
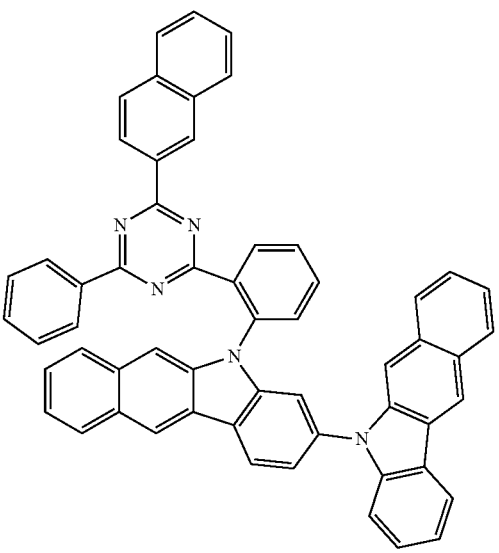
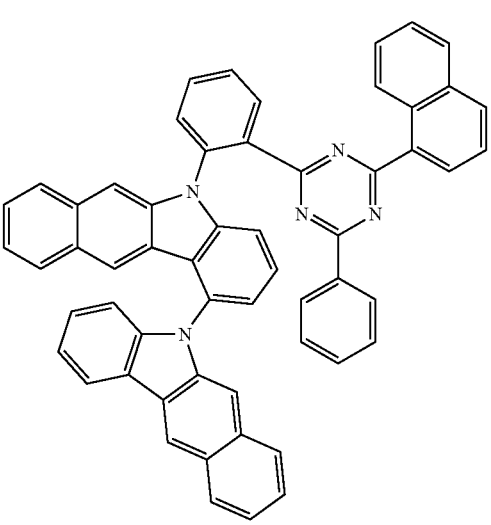

371
-continued
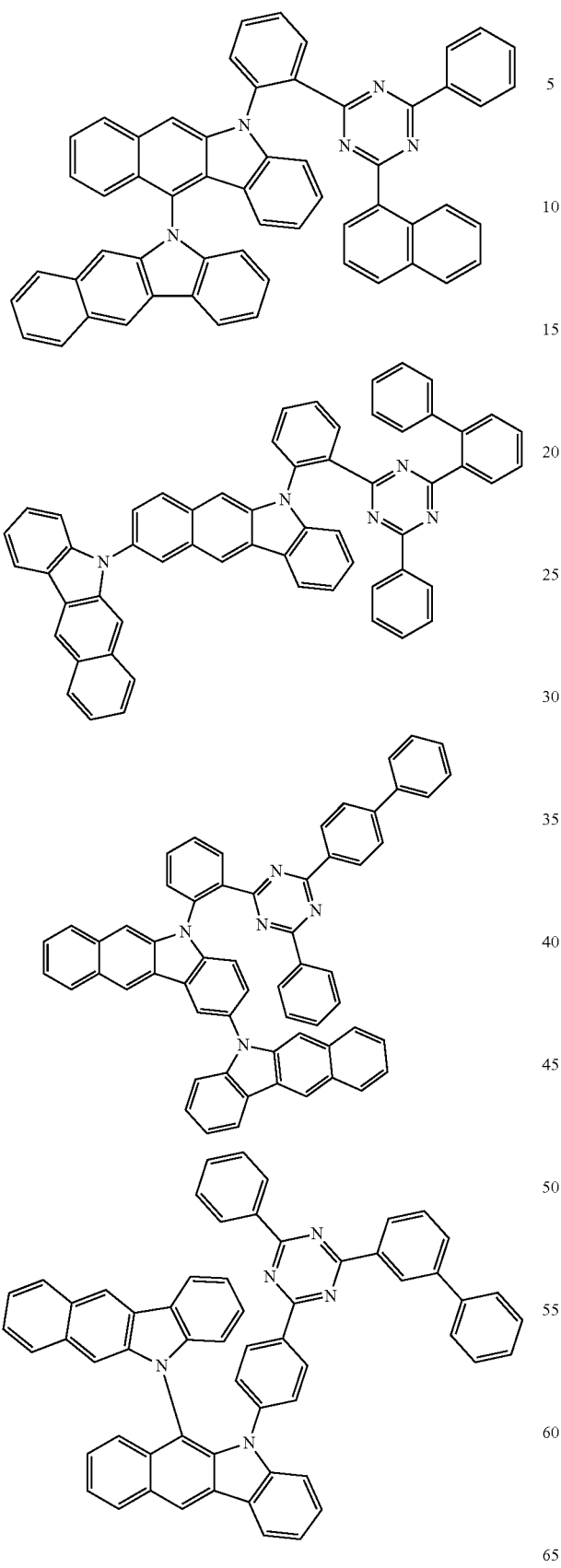
372
-continued
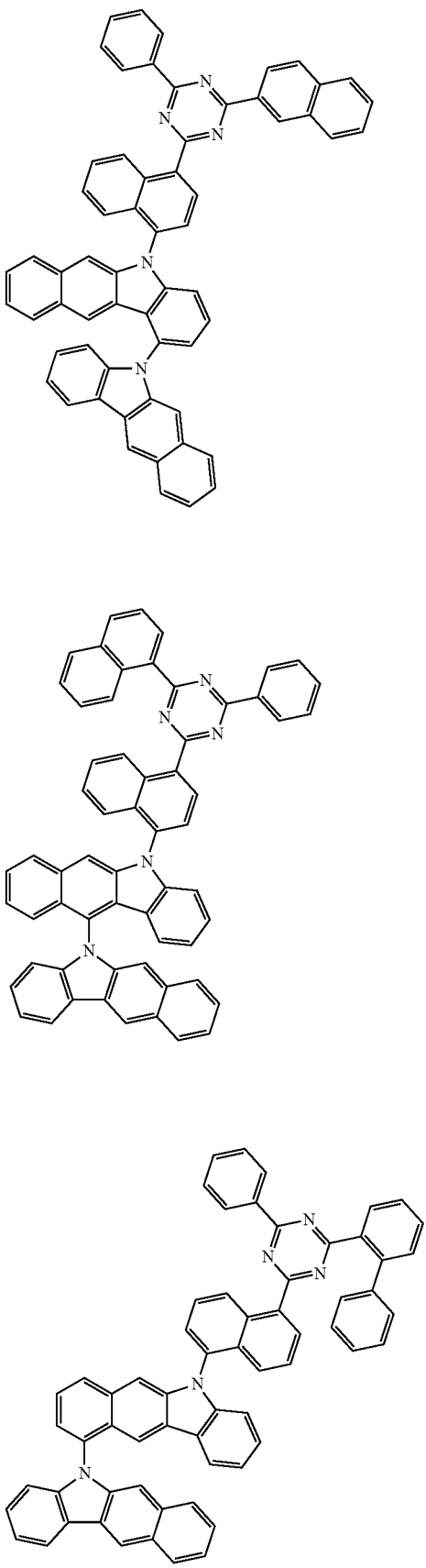

373
-continued
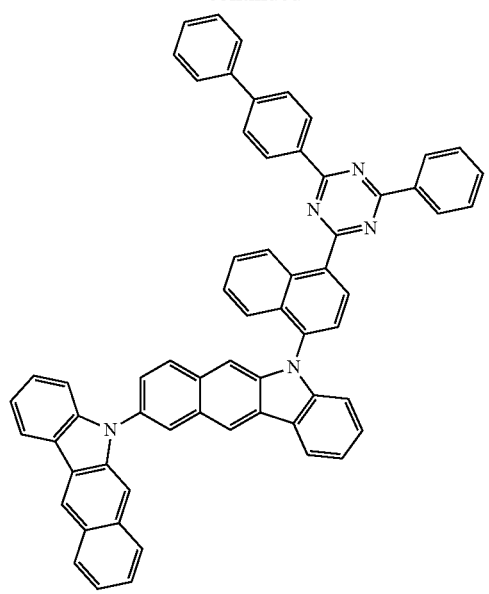
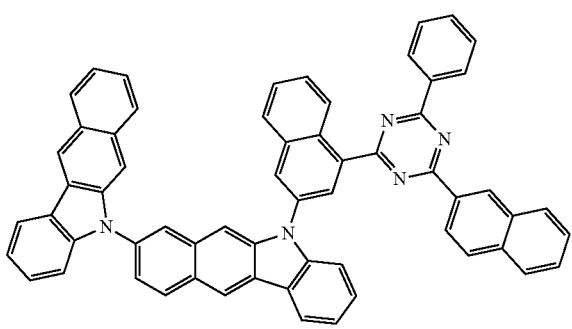
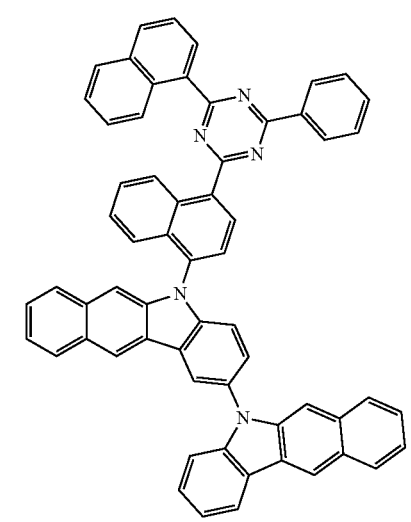
374
-continued
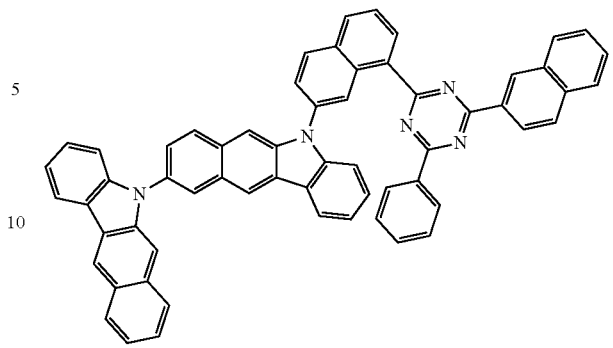
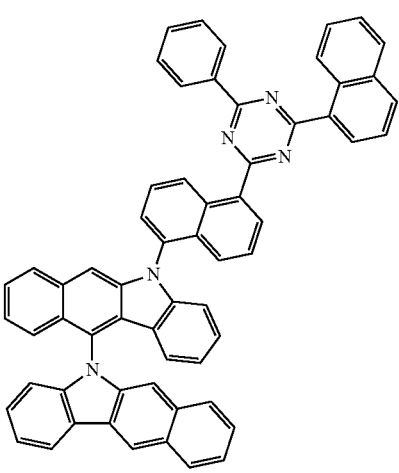
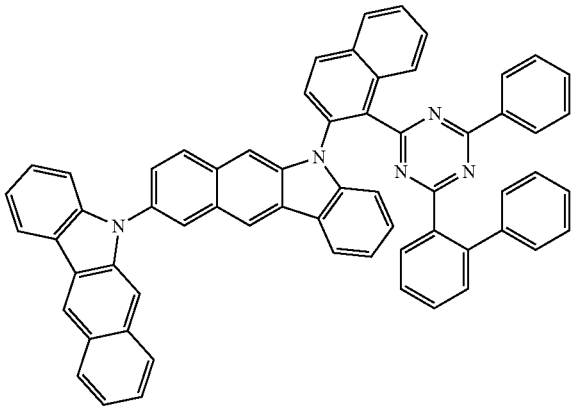

375
-continued
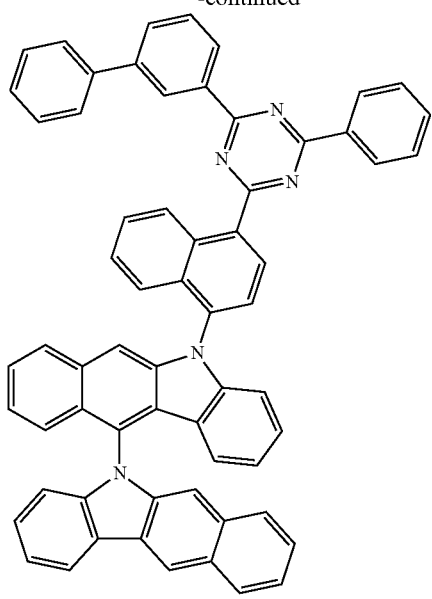
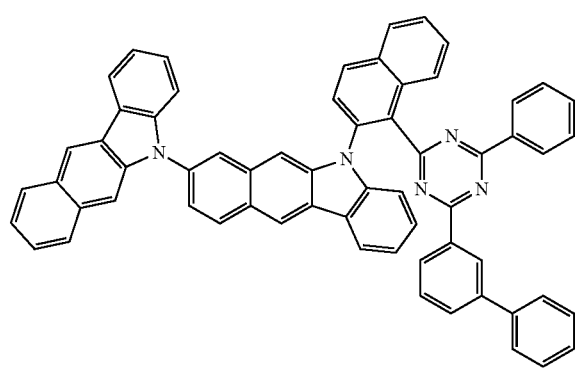
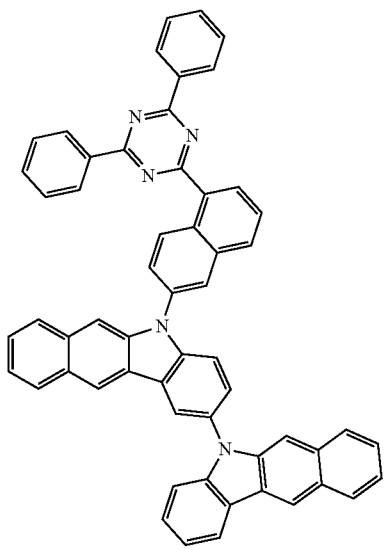
376
-continued
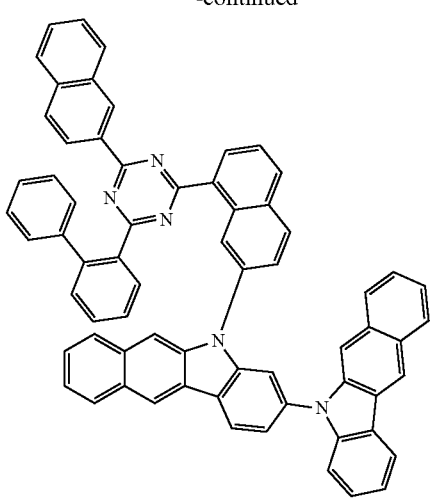
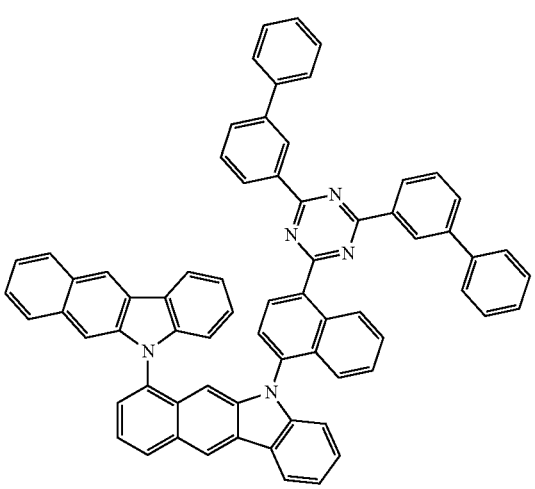
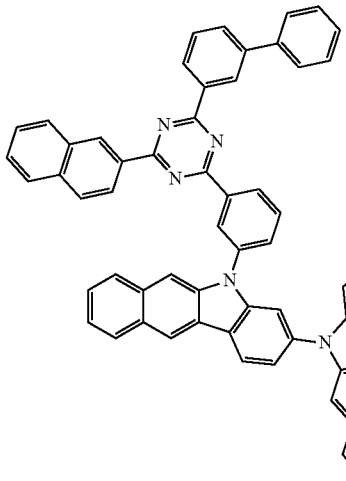

377
-continued
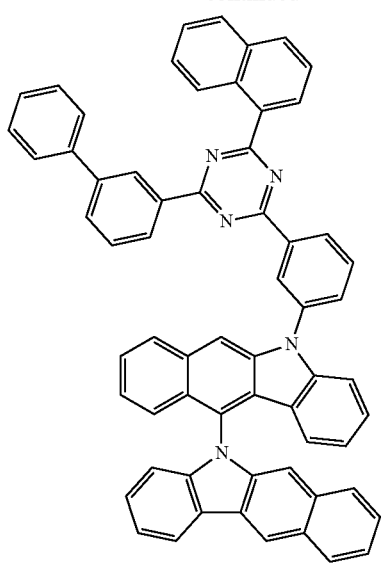
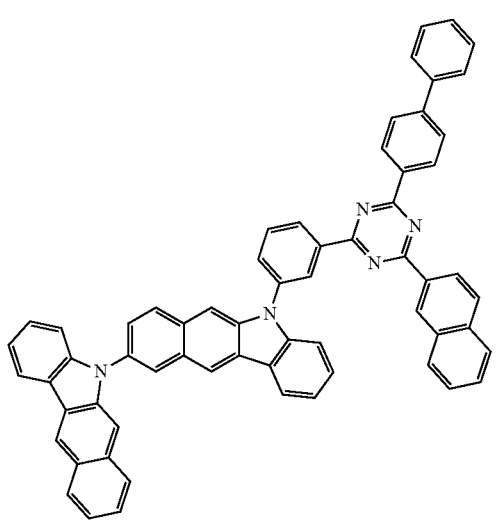
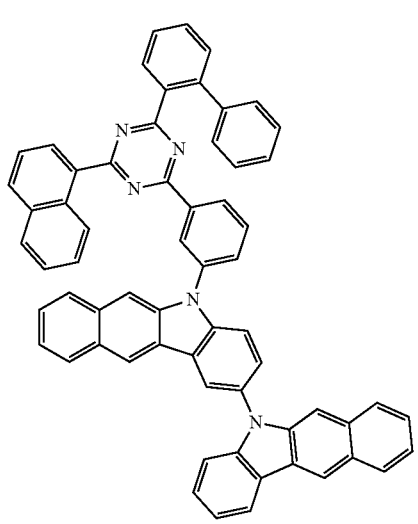
378
-continued
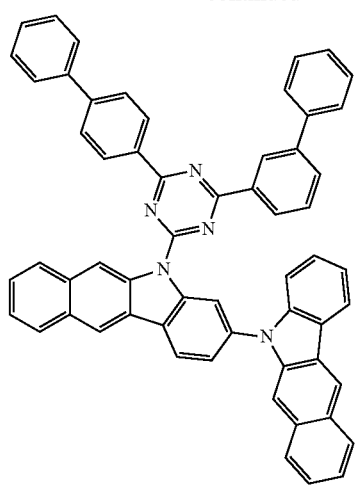
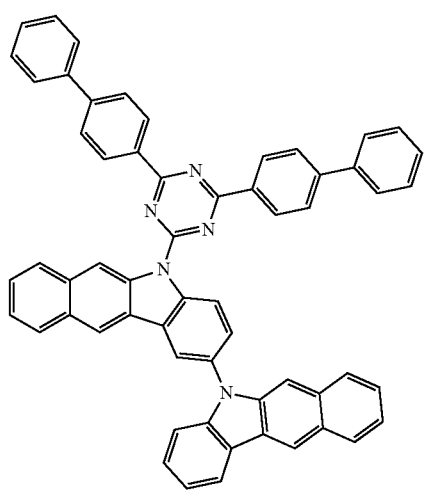
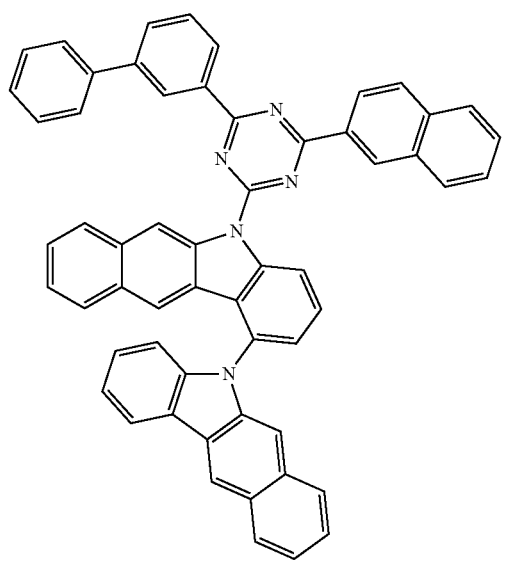

379
-continued
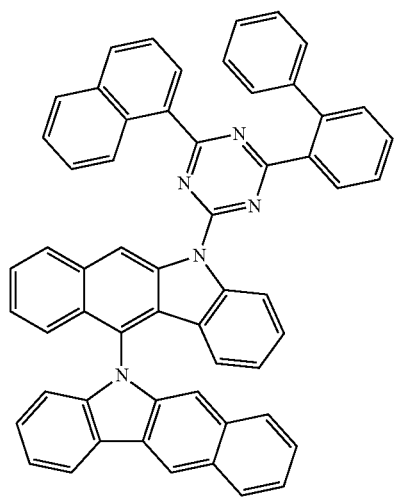
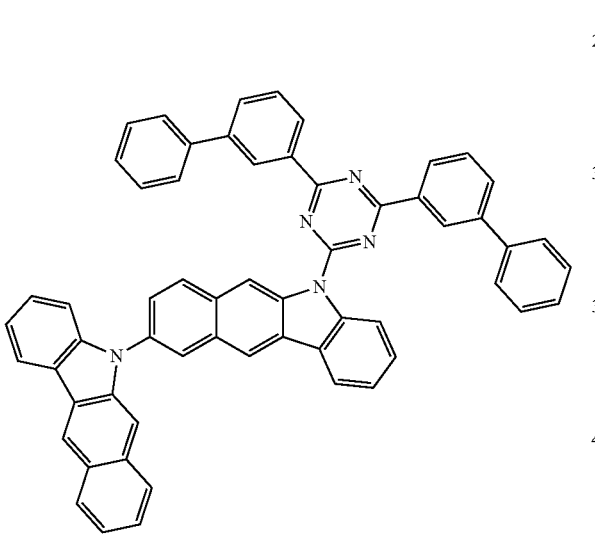
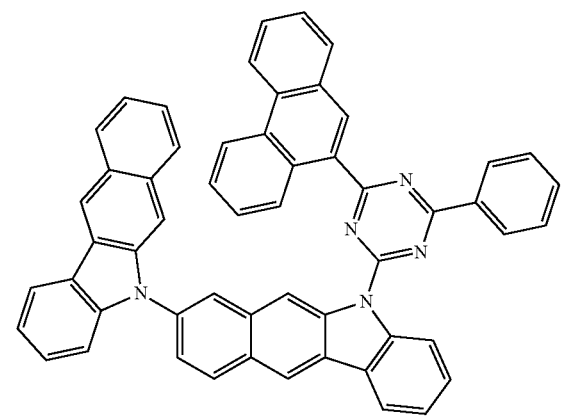
380
-continued
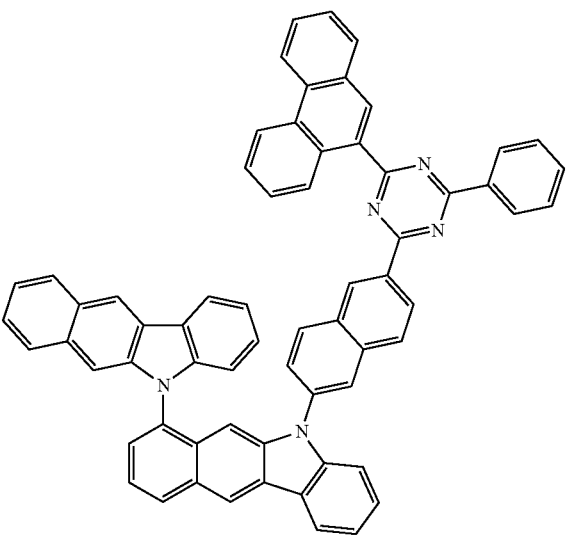
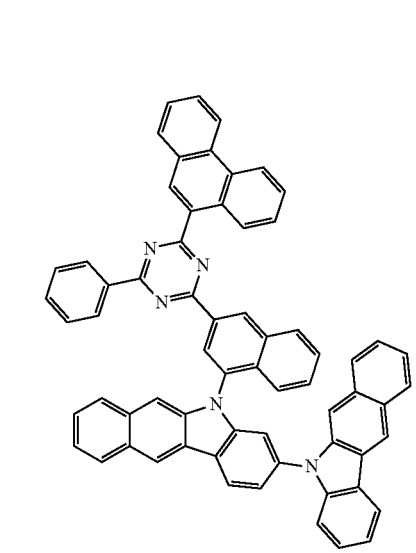
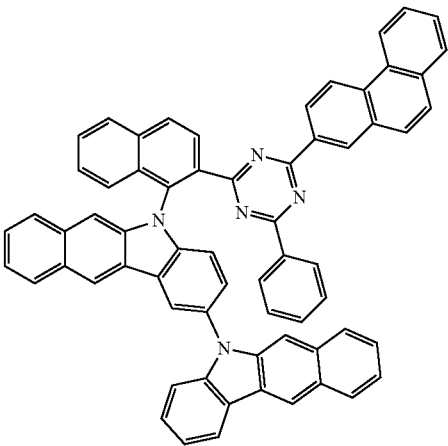

381
-continued
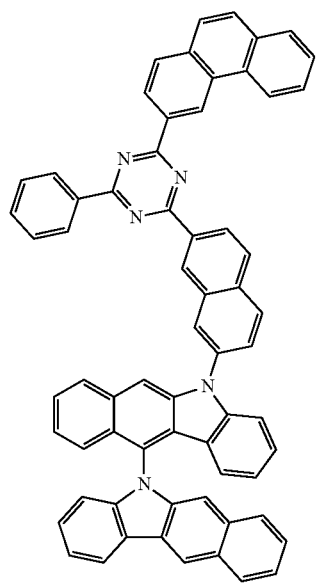
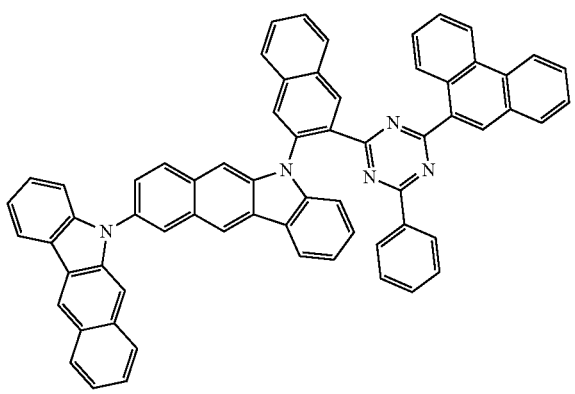
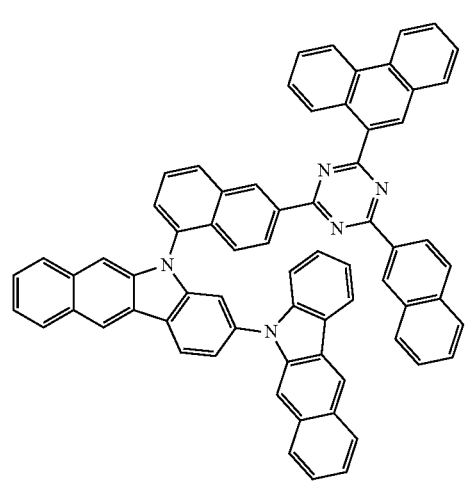
382
-continued
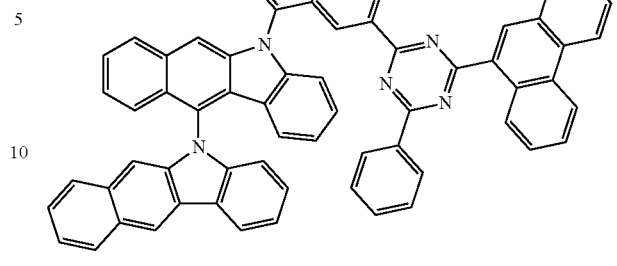
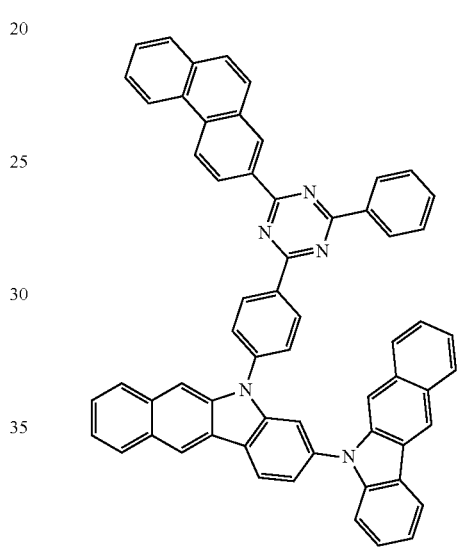
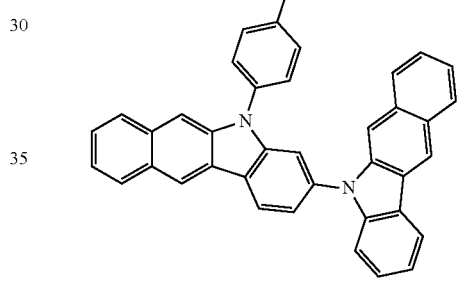
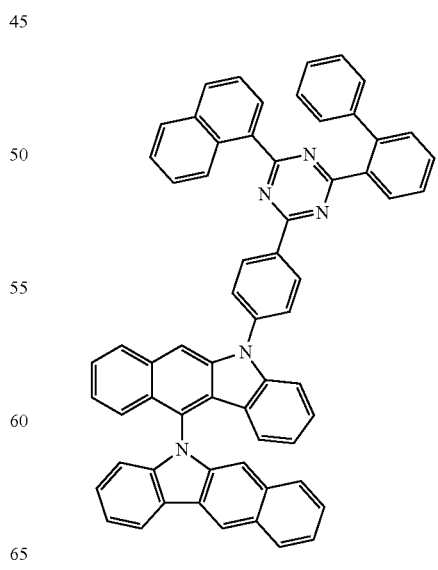

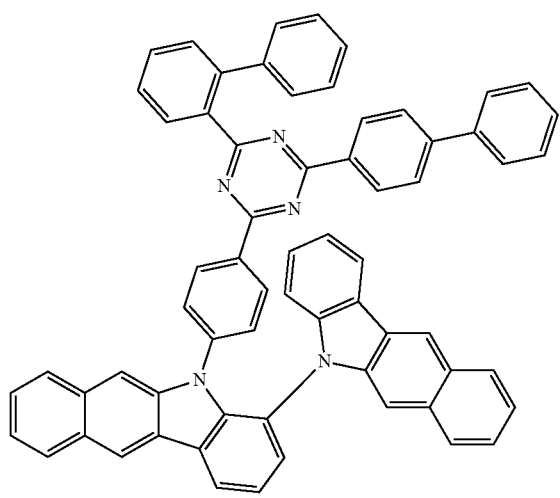
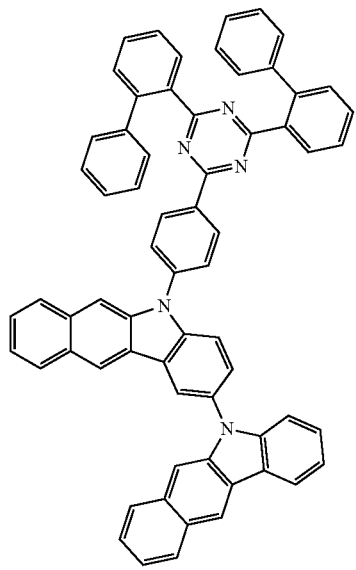
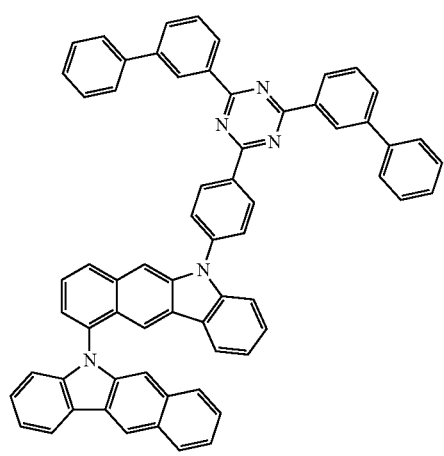
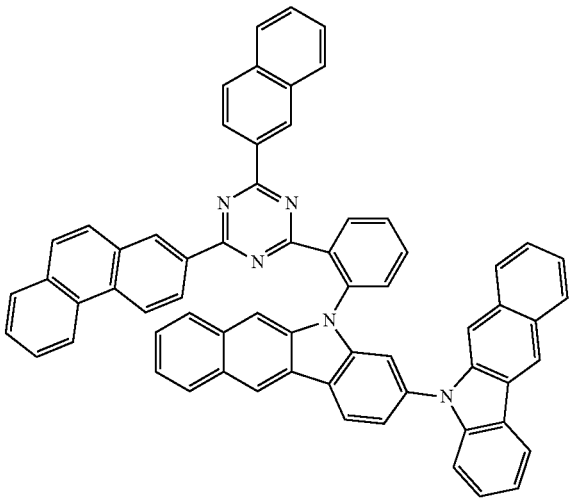
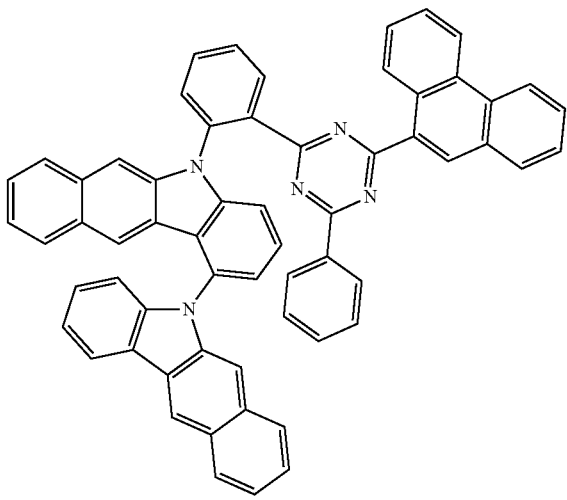
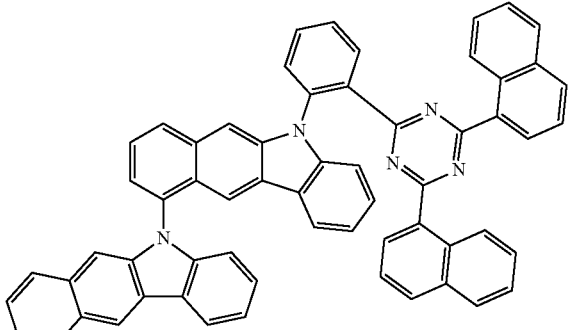
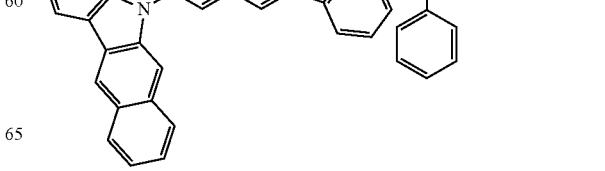

385
-continued
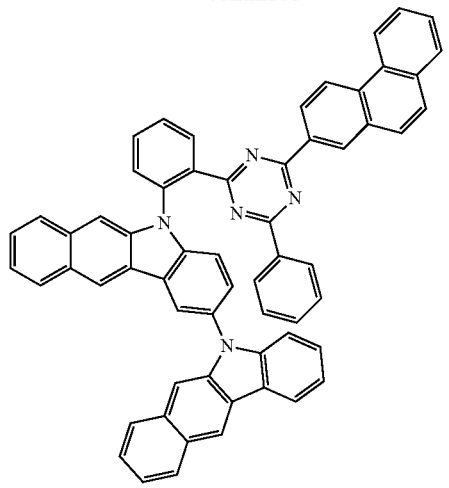
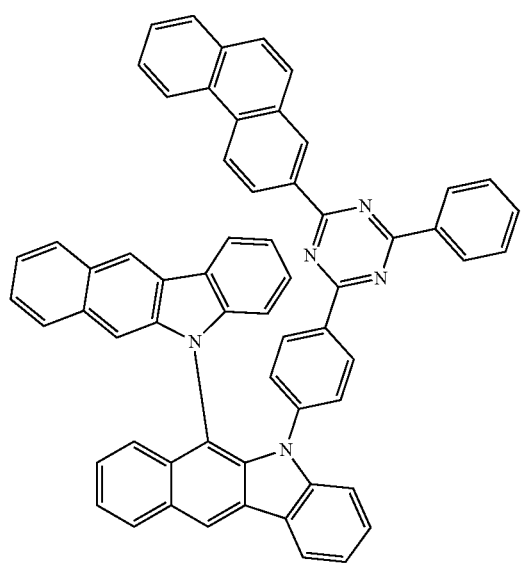
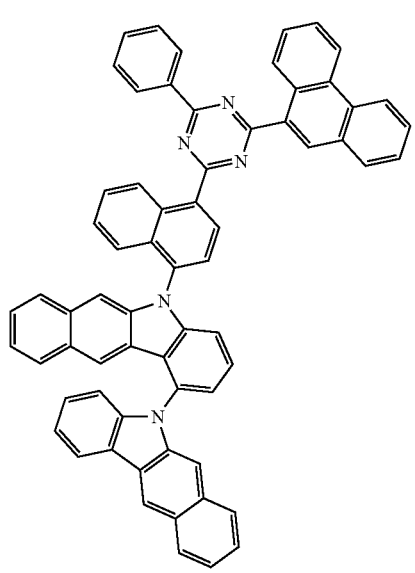
386
-continued
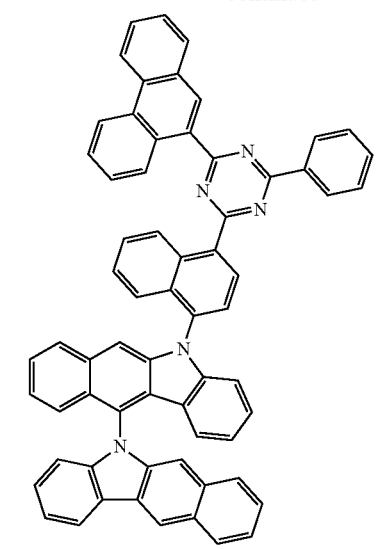
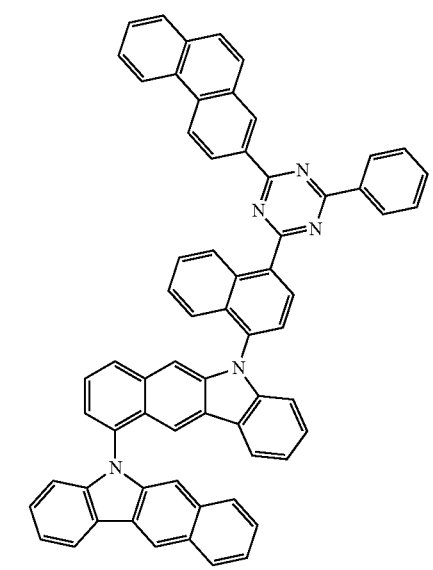
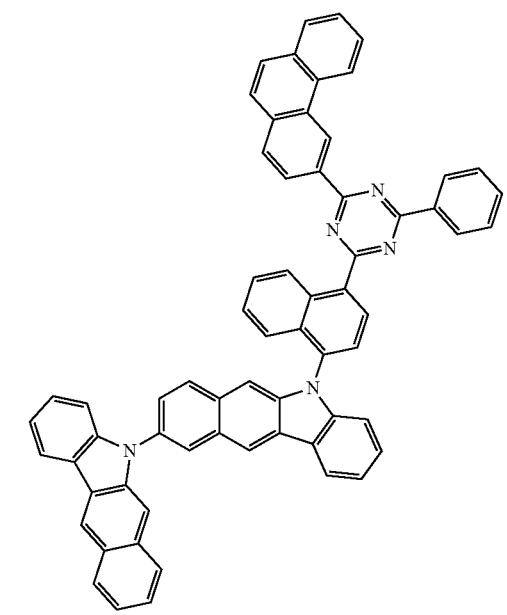

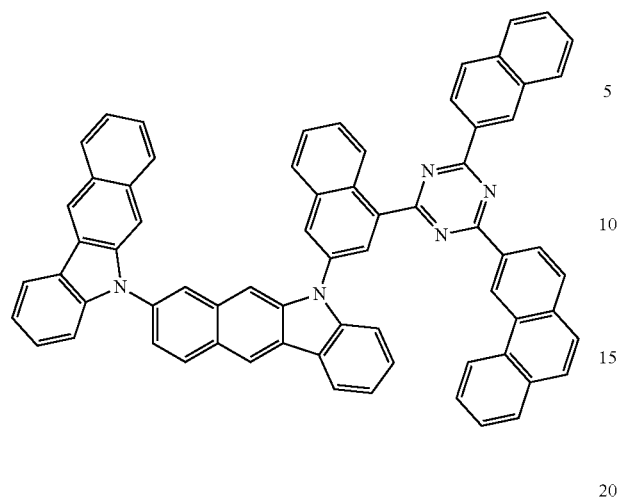
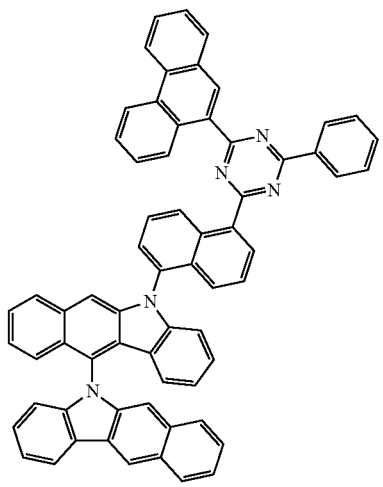
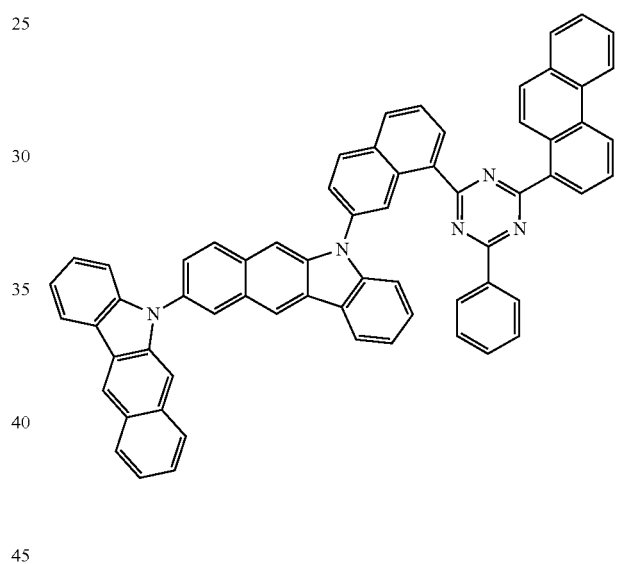
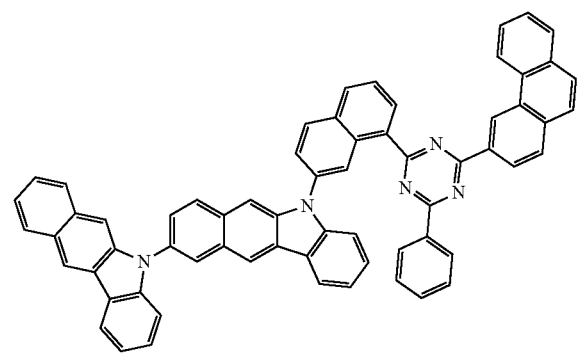
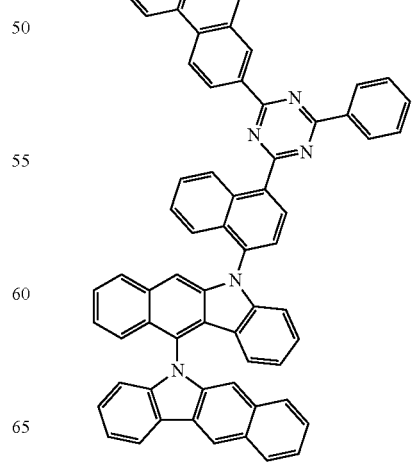

389
-continued
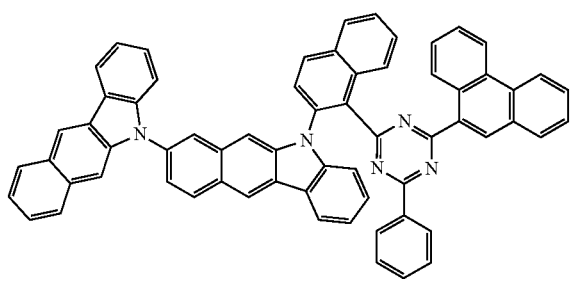
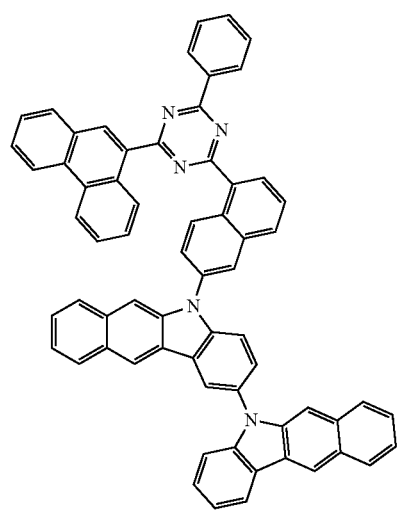
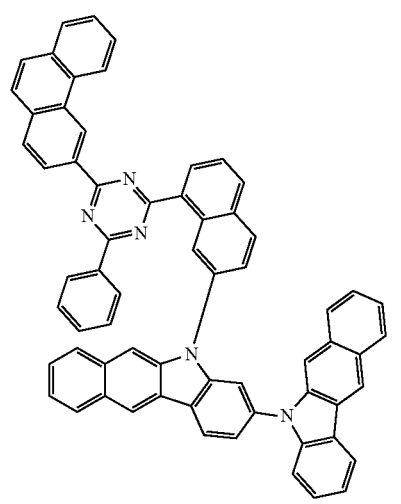
390
-continued
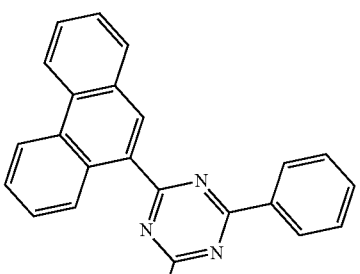
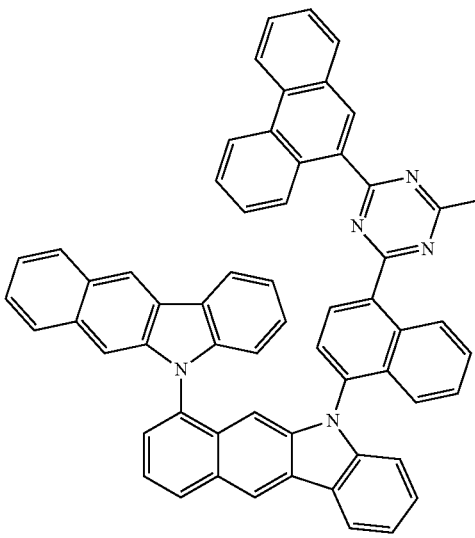
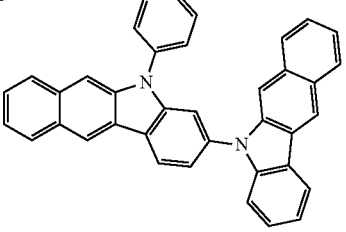
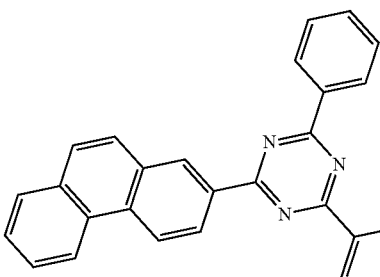
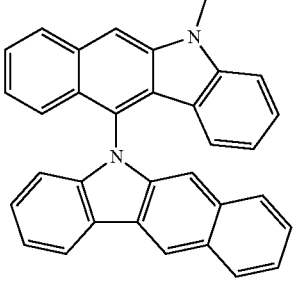

391
-continued
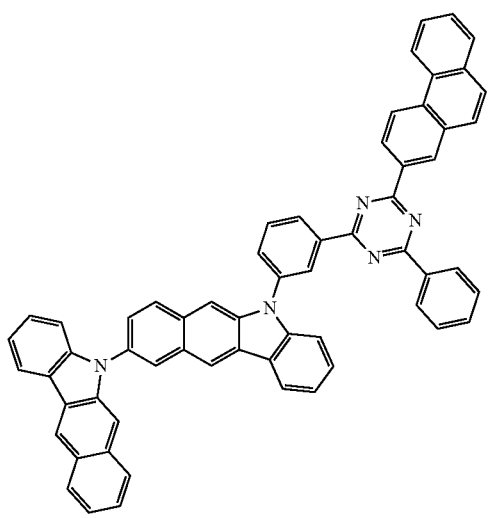
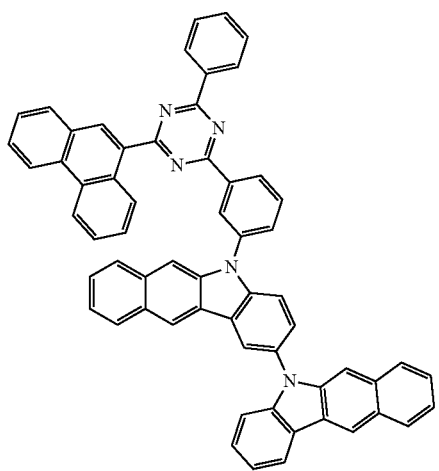
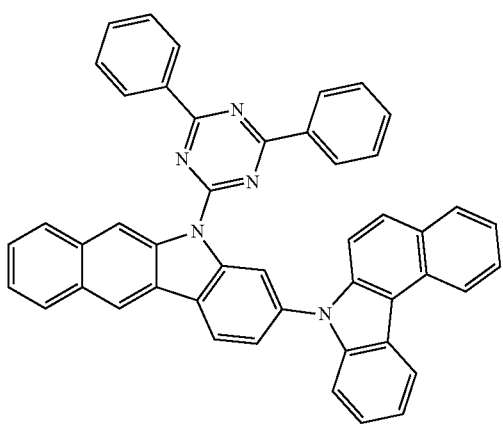
392
-continued
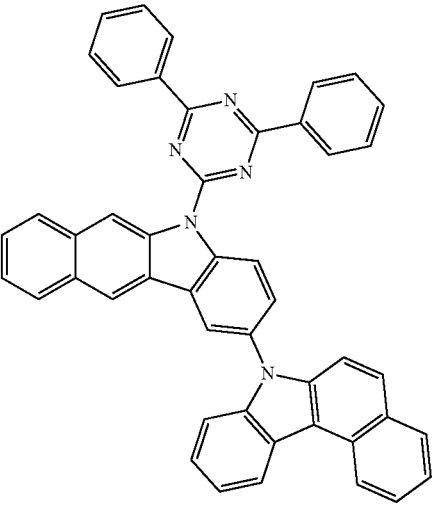
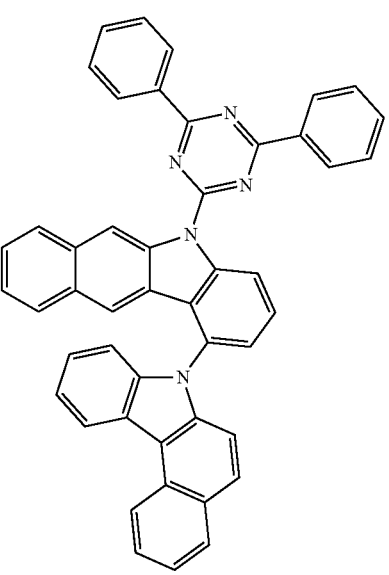
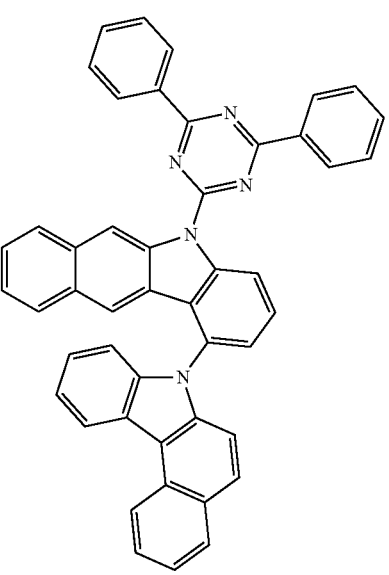

-continued
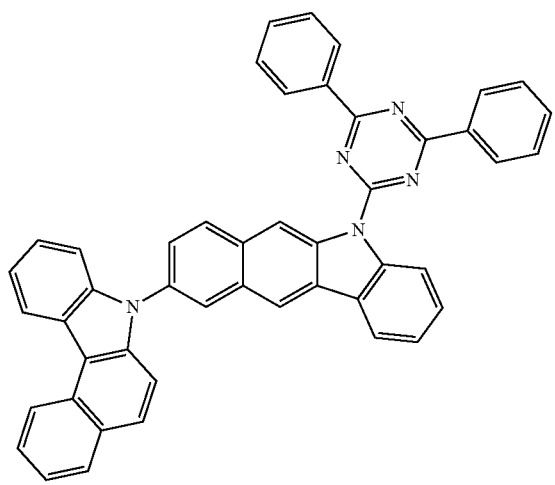
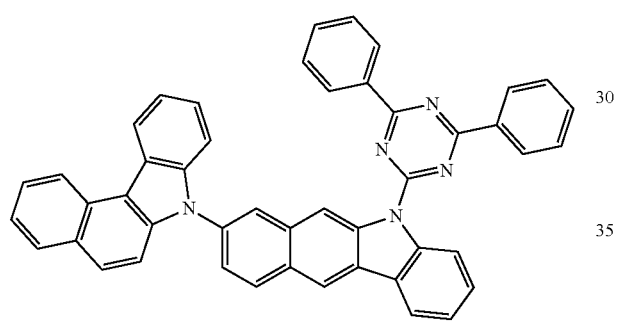
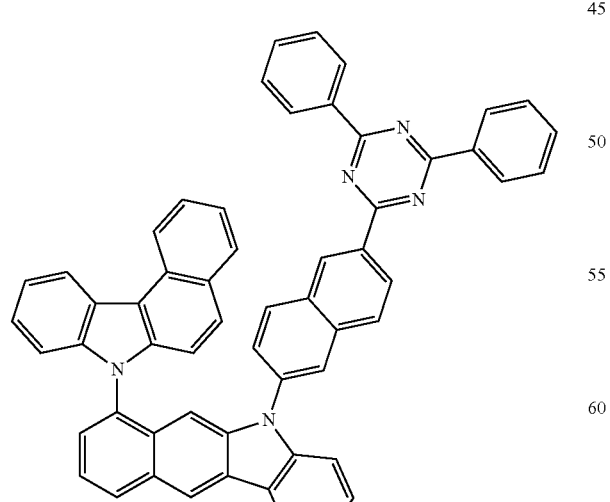
-continued
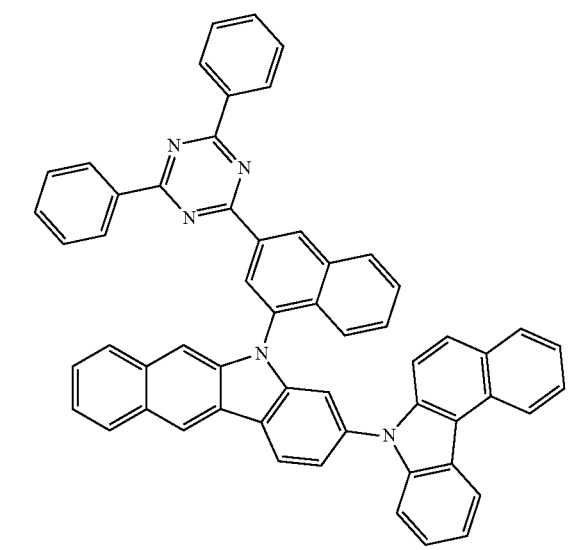
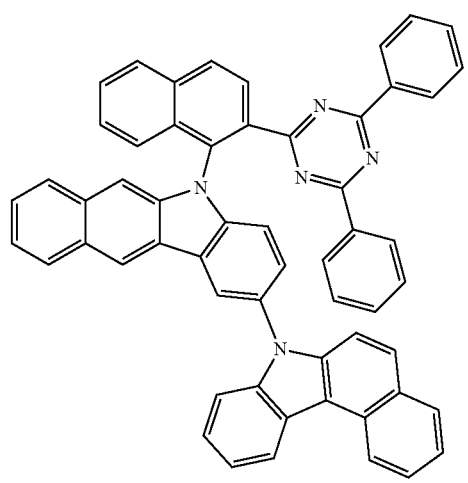
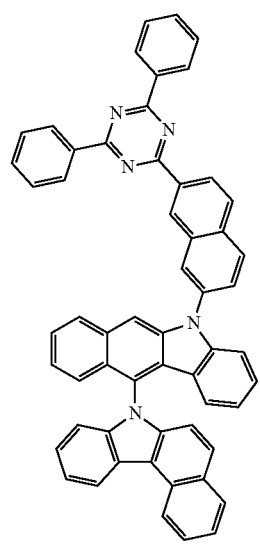

395
-continued
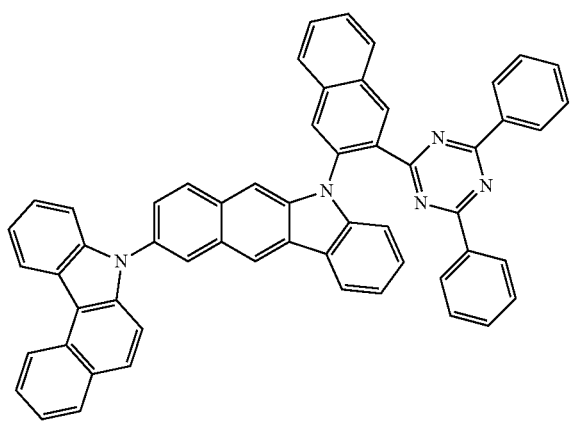
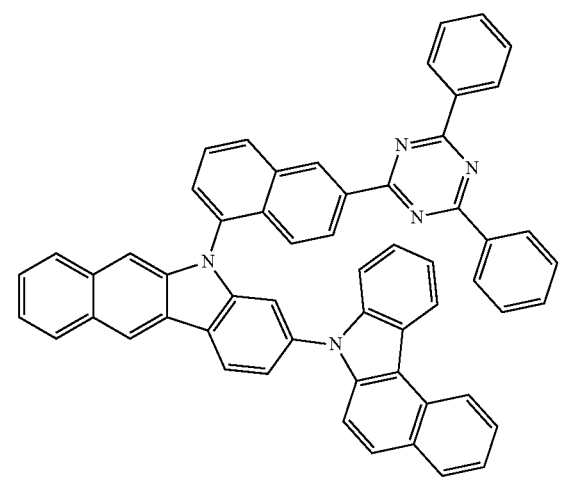
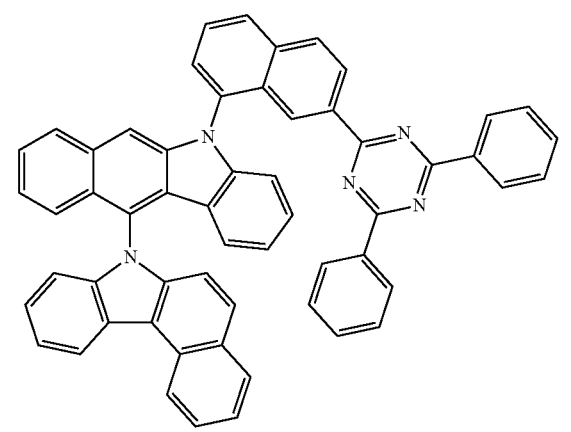
396
-continued
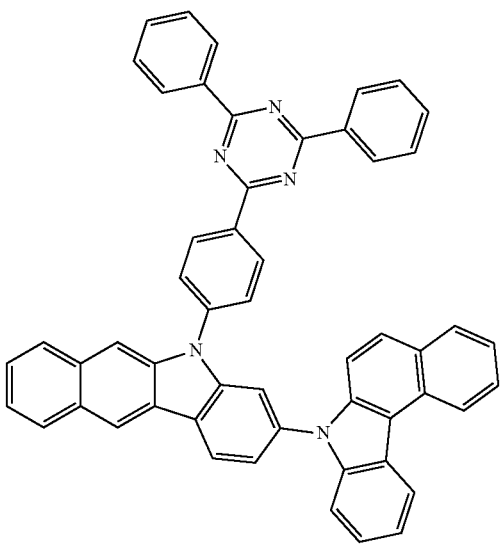
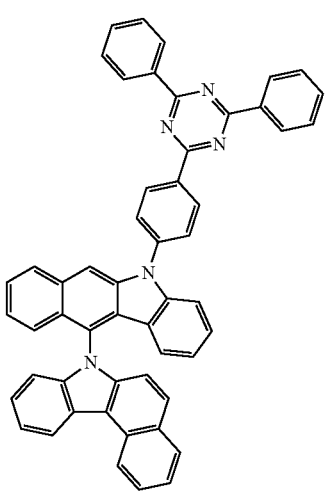
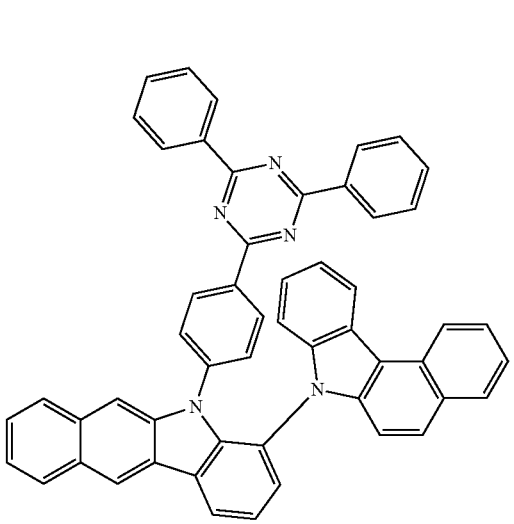

397
-continued
398
-continued
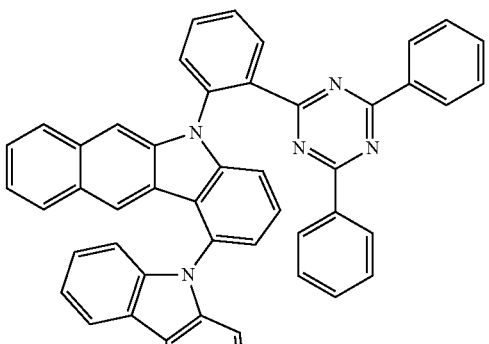
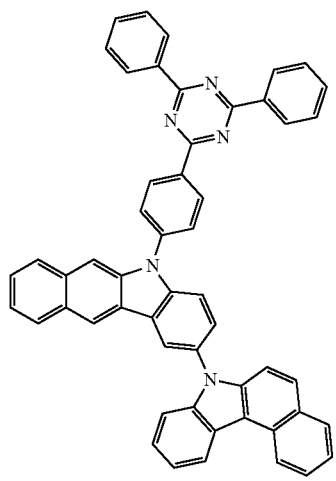
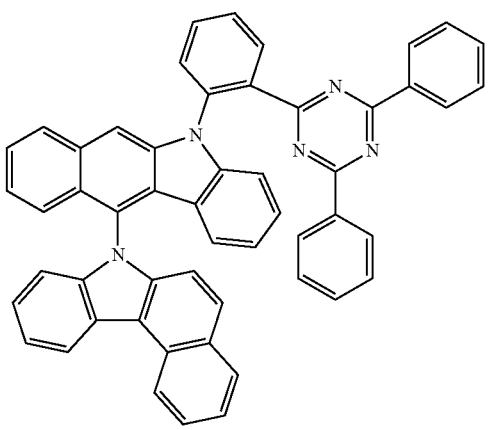
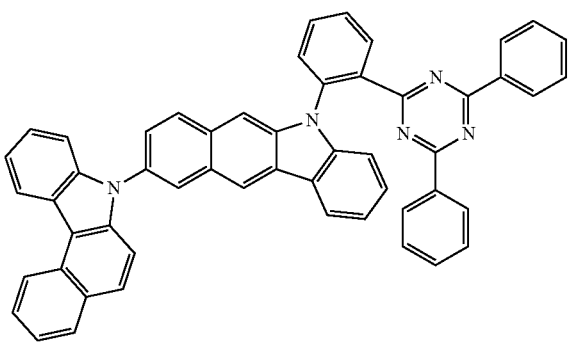
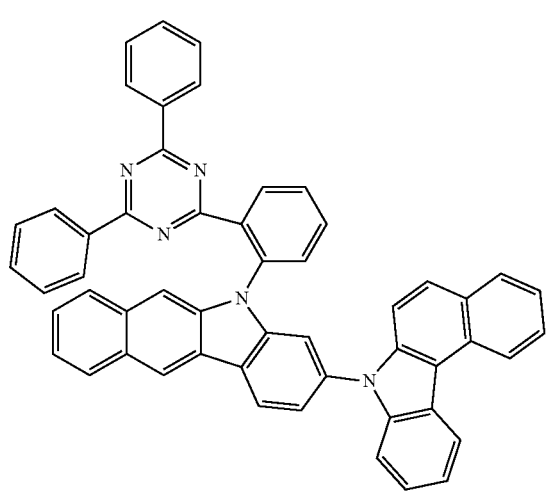

399
-continued
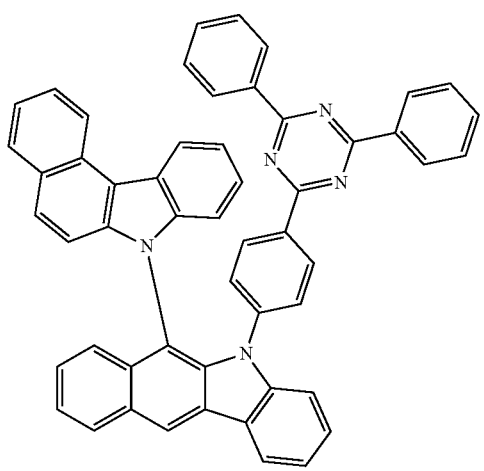
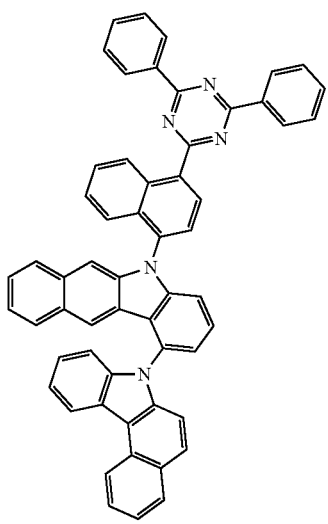
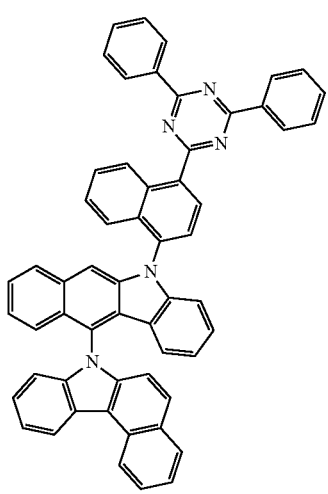
400
-continued
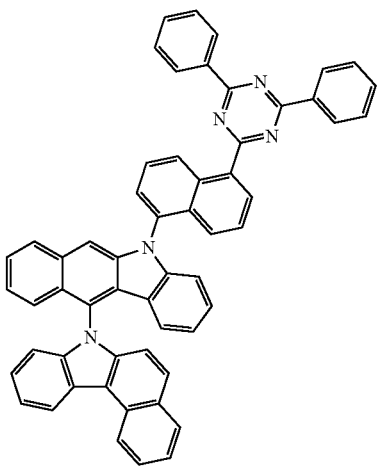
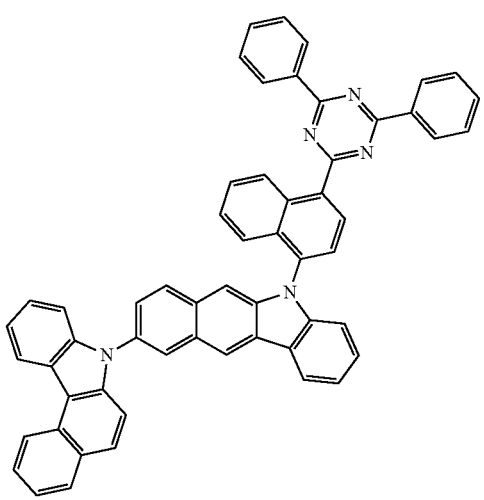
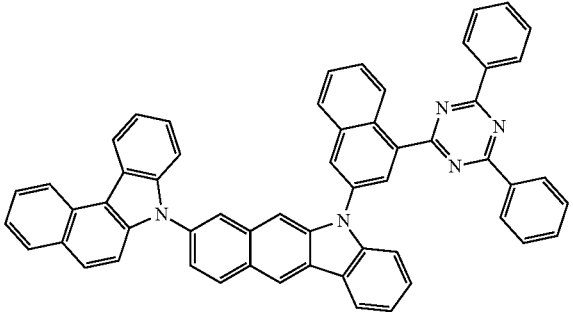

401
-continued
402
-continued
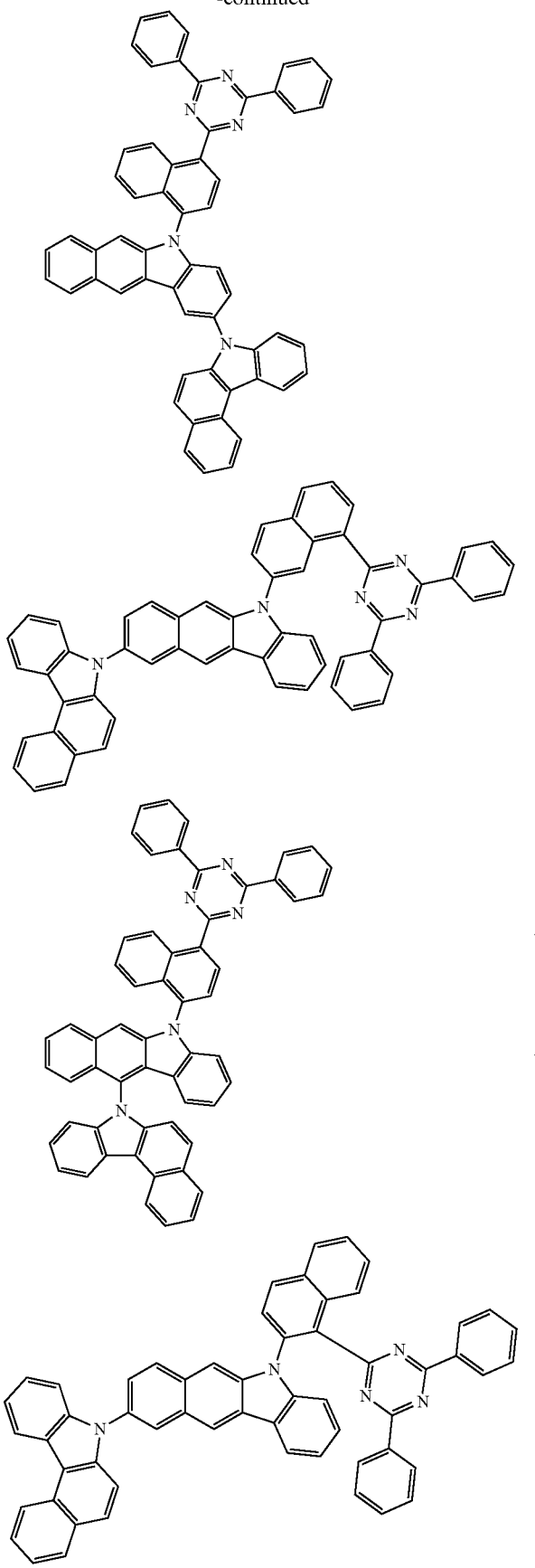
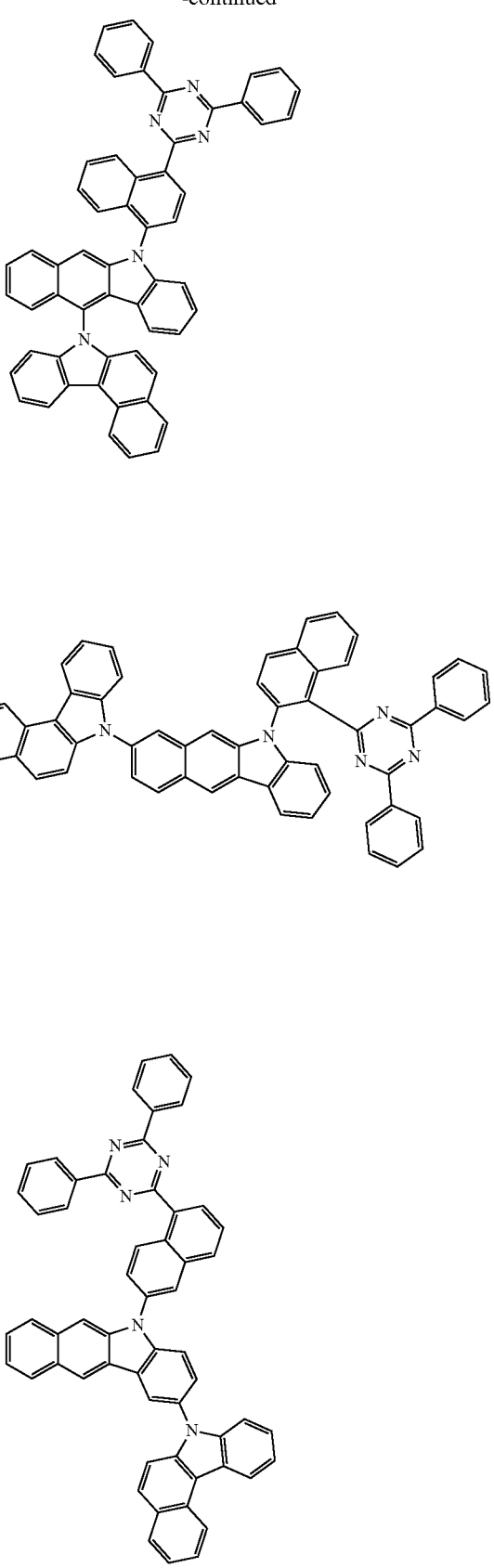

403
-continued
404
-continued
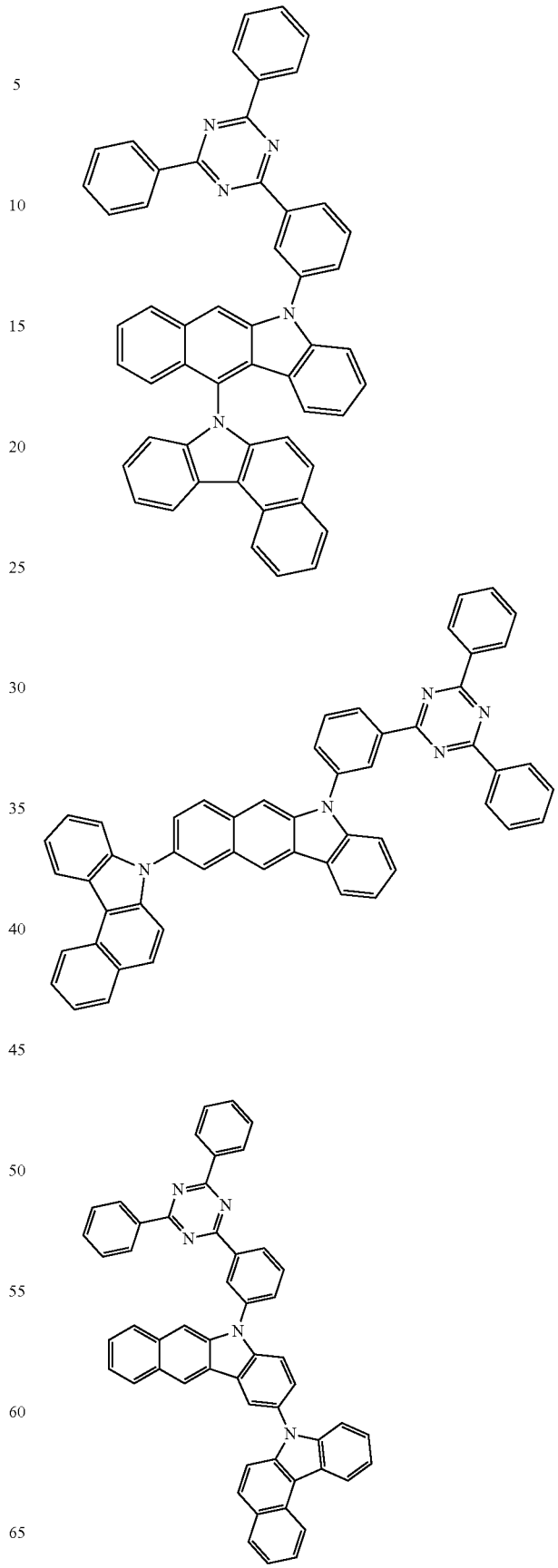

405
-continued
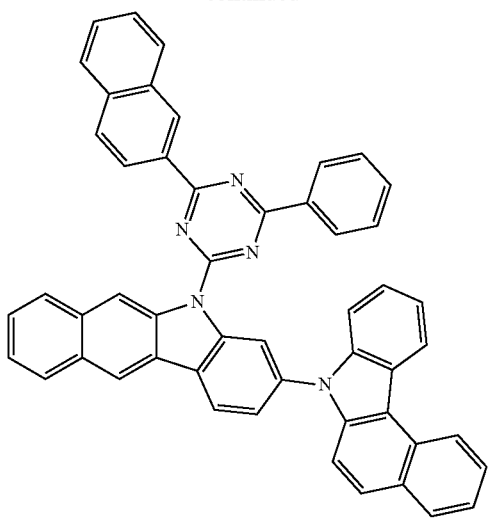
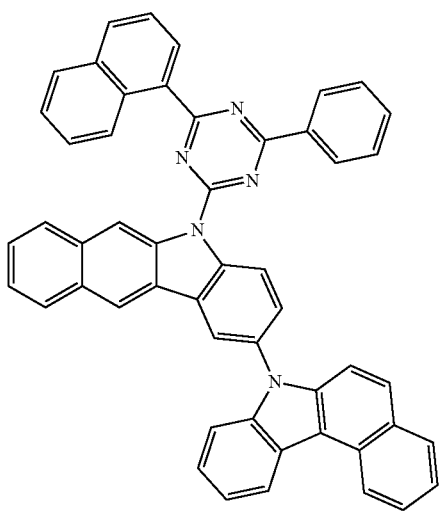
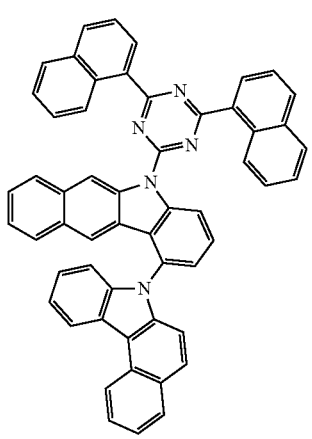
406
-continued
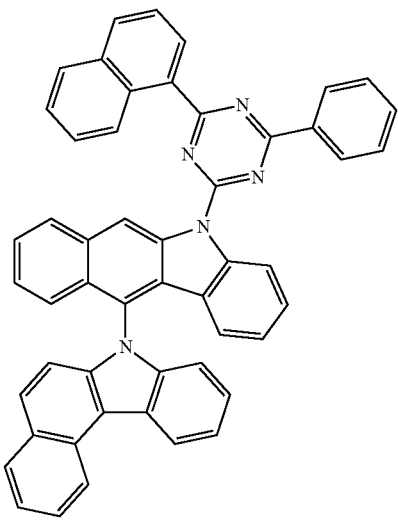
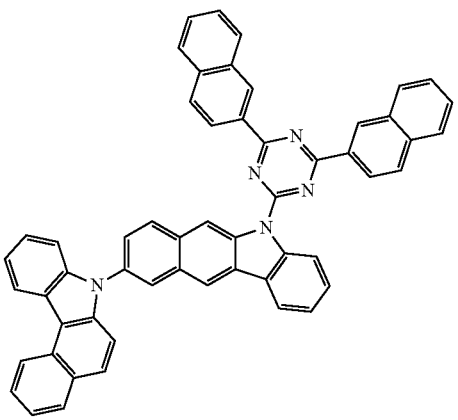
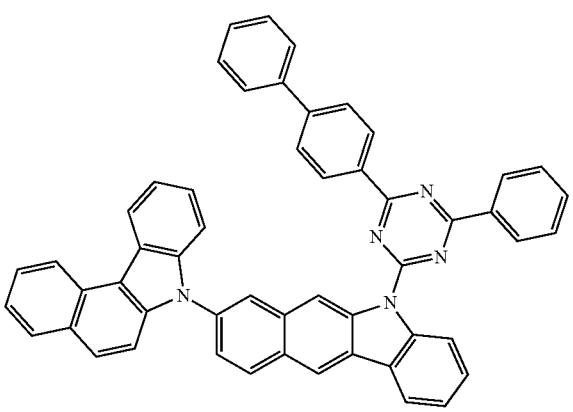

407
-continued
408
-continued
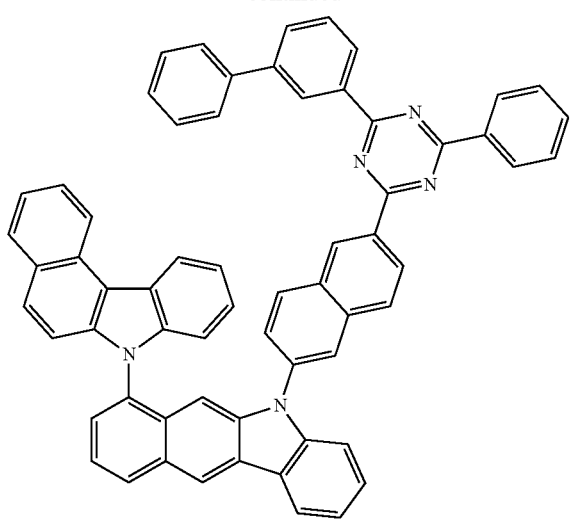
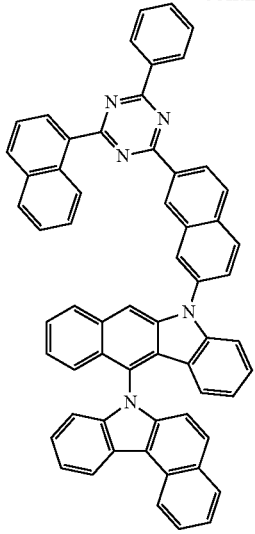
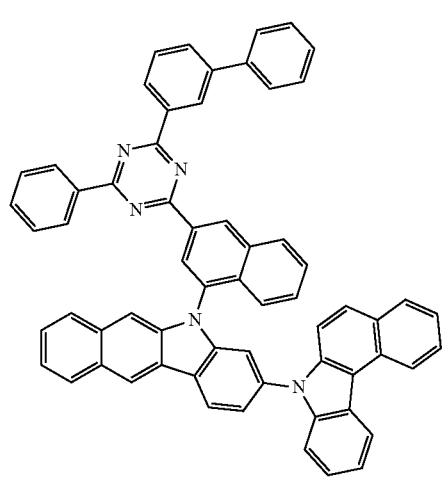
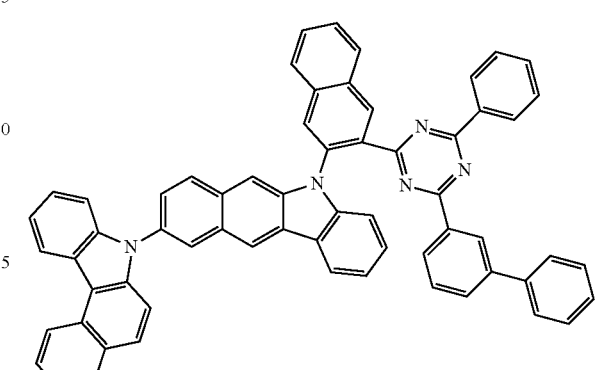
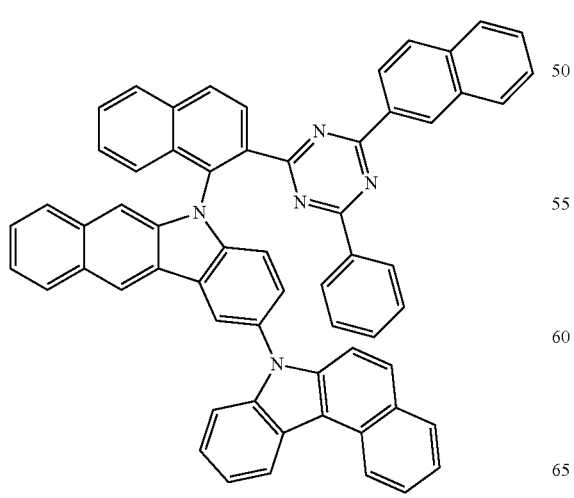
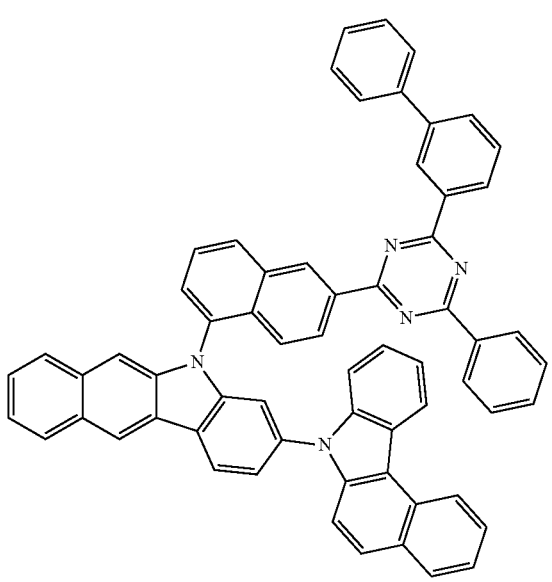

409
-continued
410
-continued
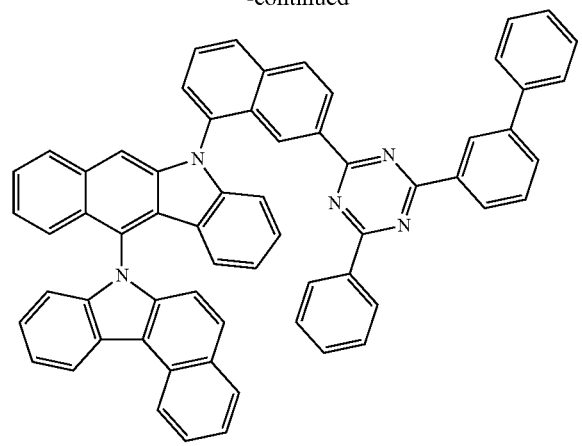
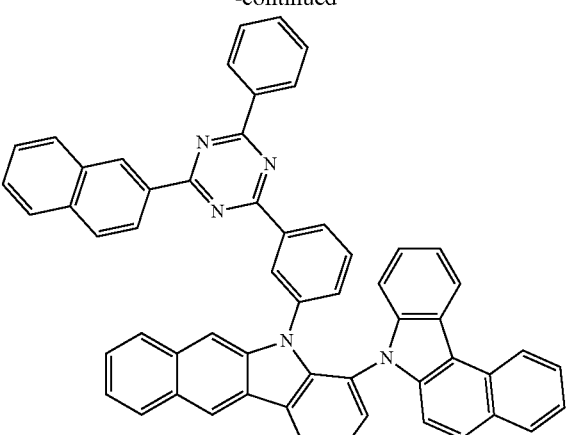
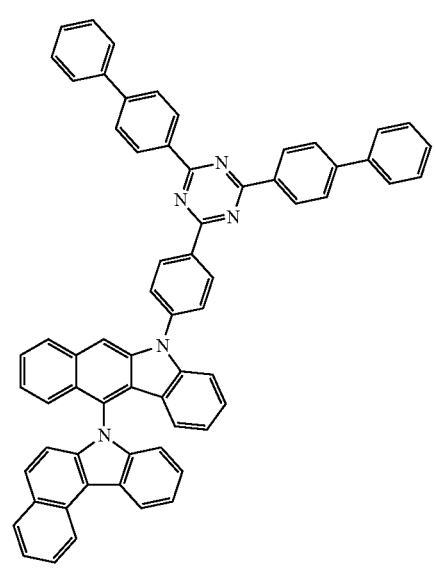
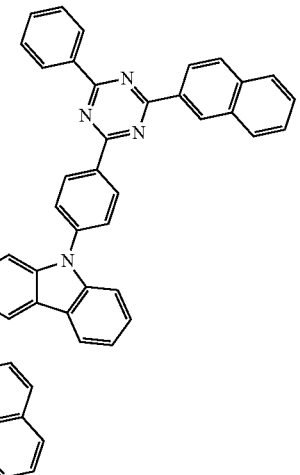

411
-continued
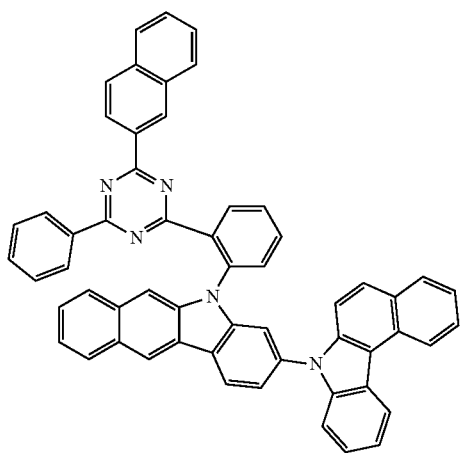
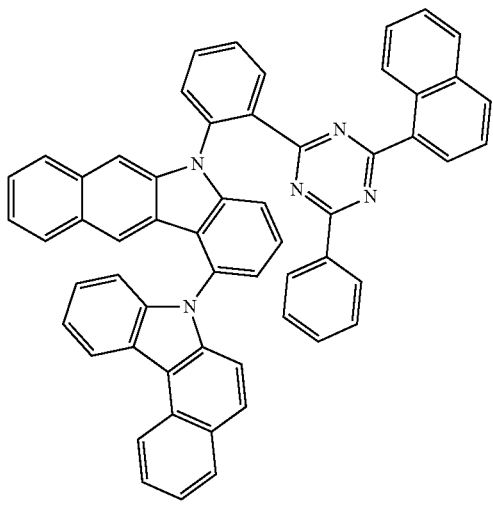
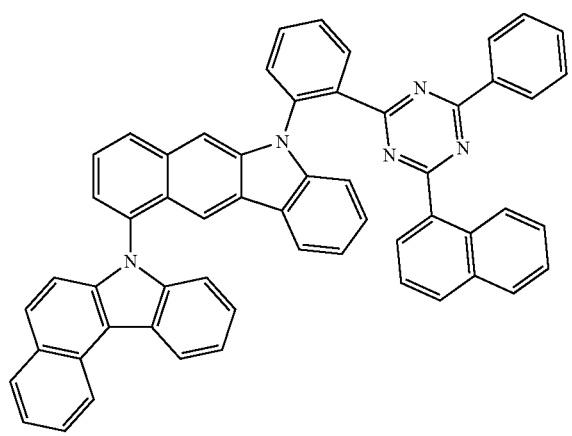
412
-continued
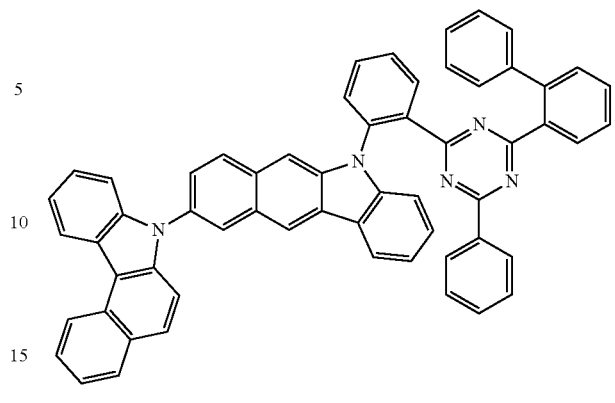
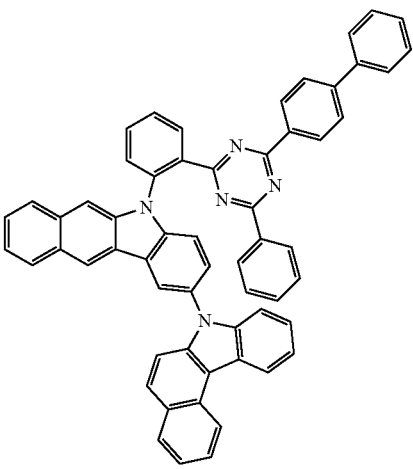
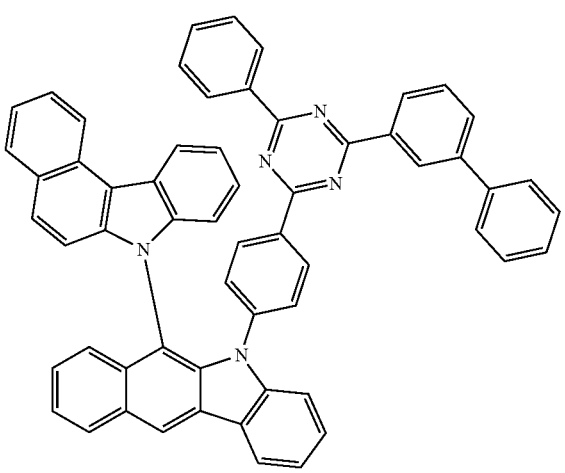

413
-continued
414
-continued
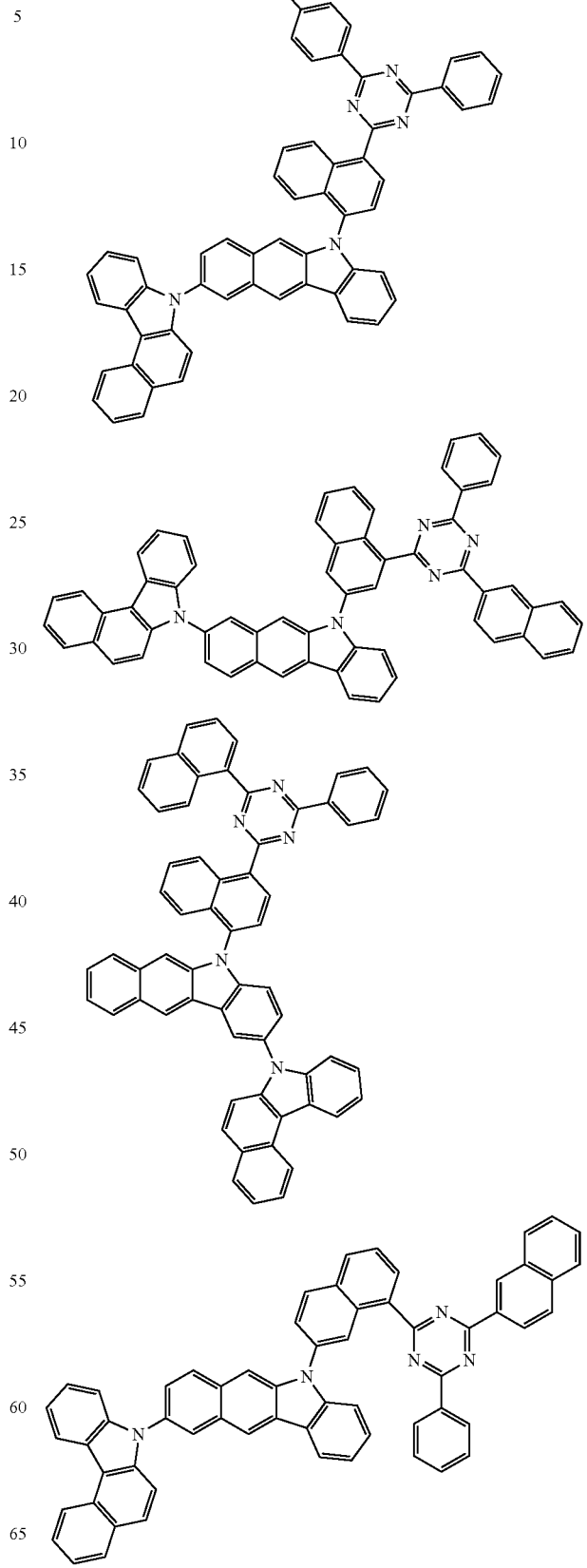

415
-continued
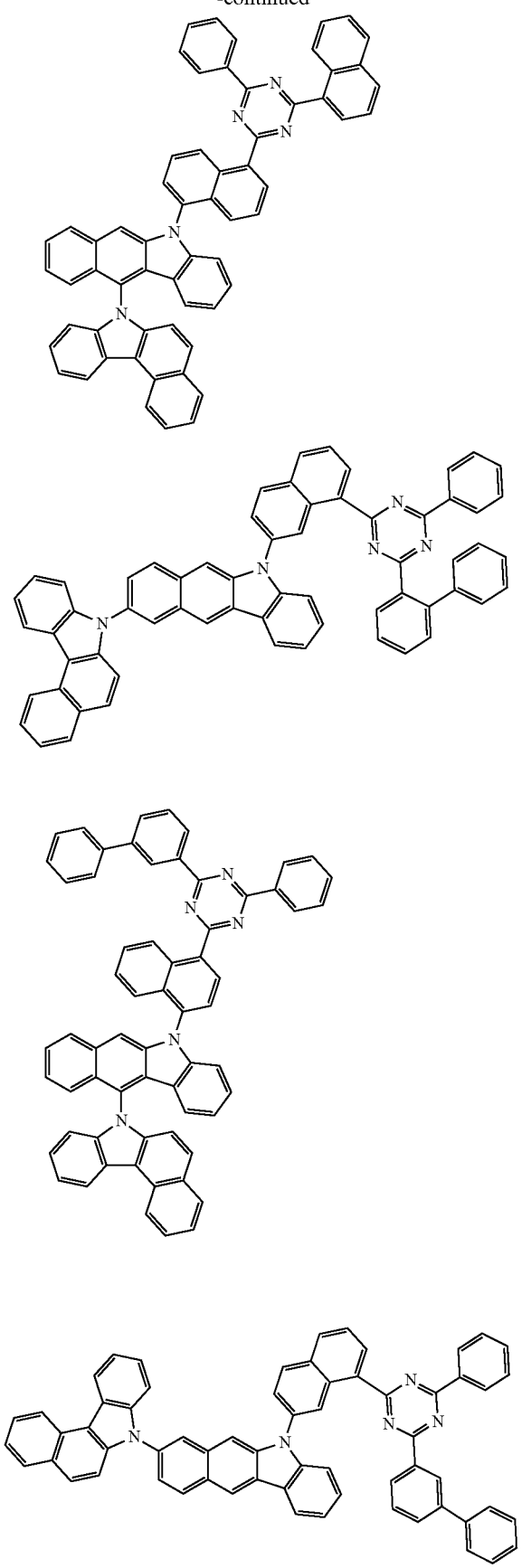
416
-continued
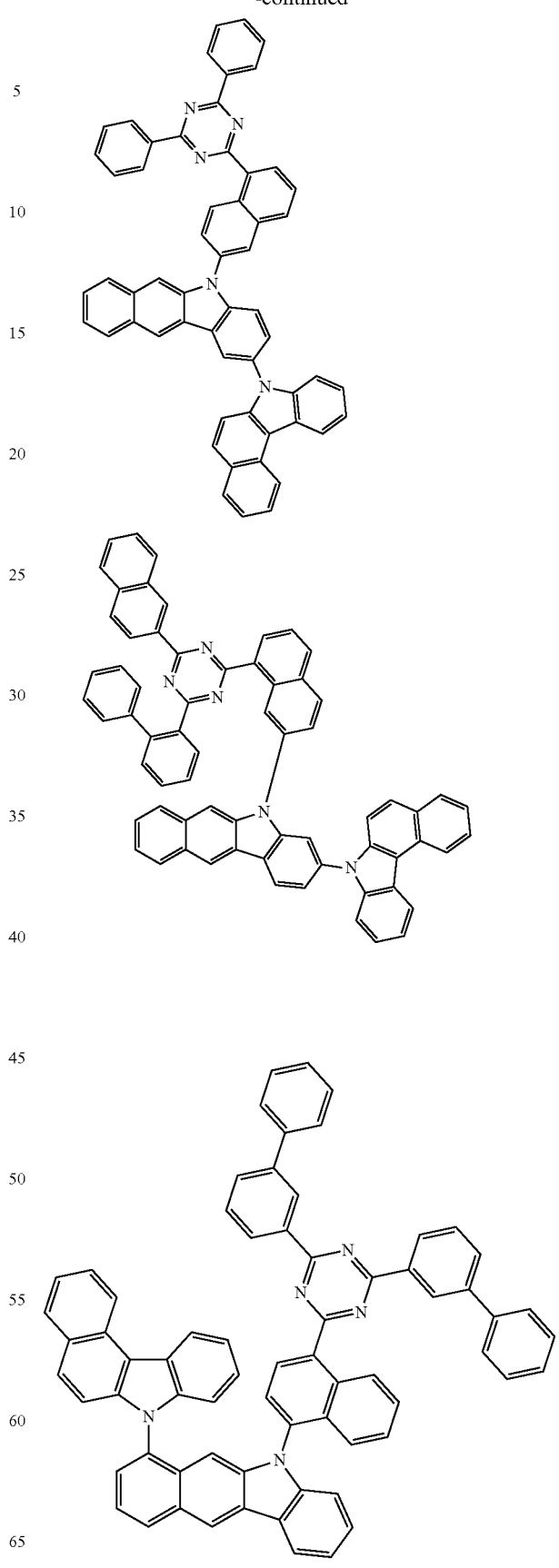

417
-continued
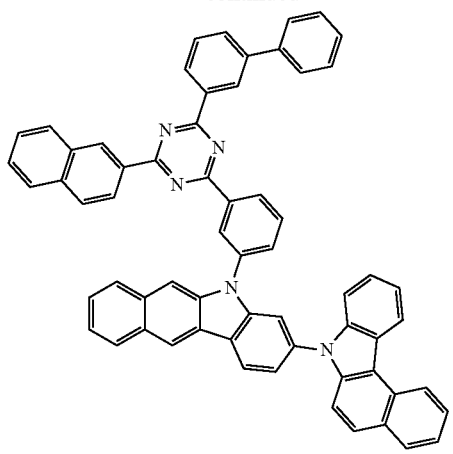
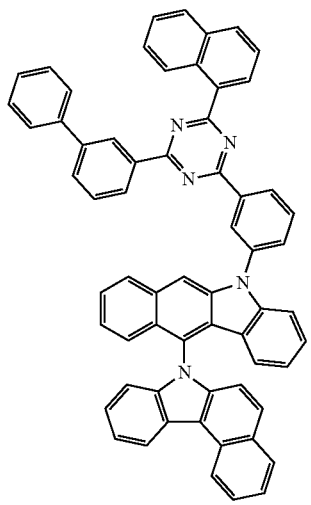
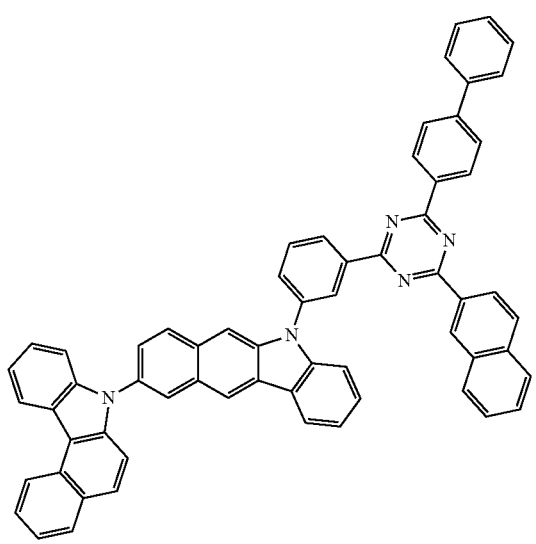
418
-continued
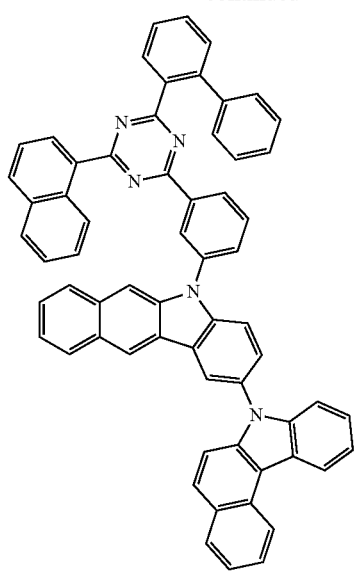
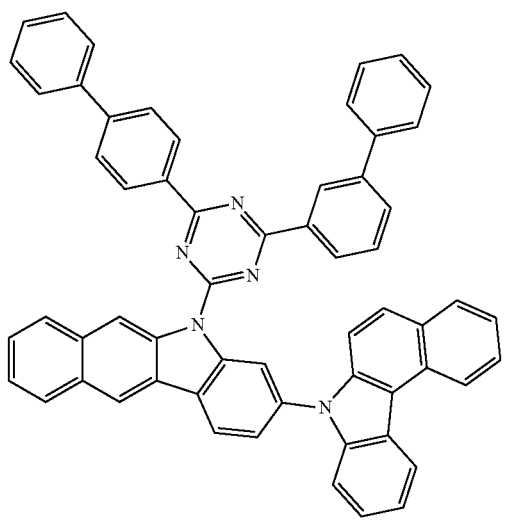
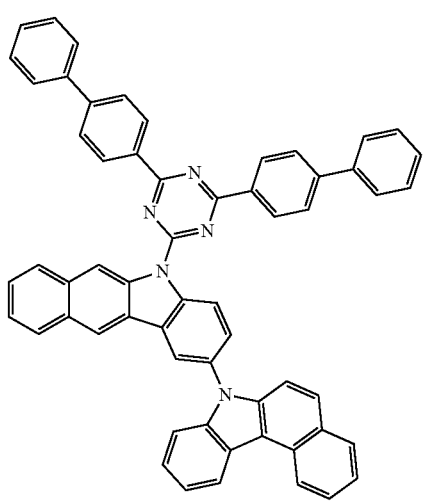

419
-continued
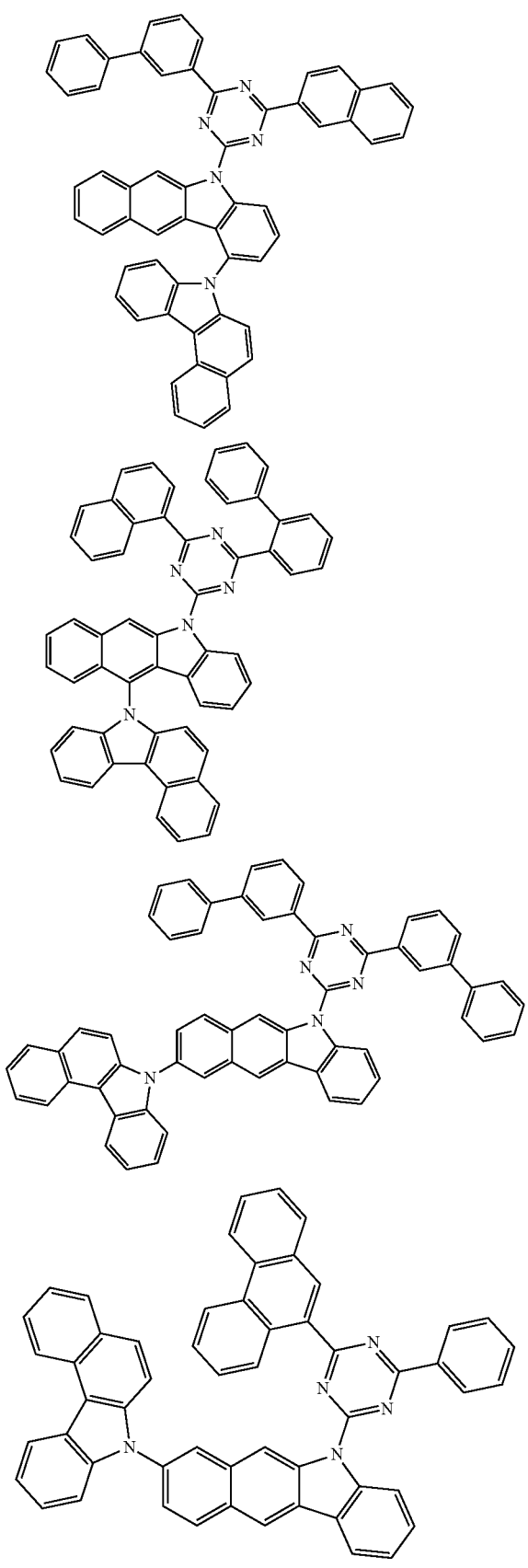
420
-continued
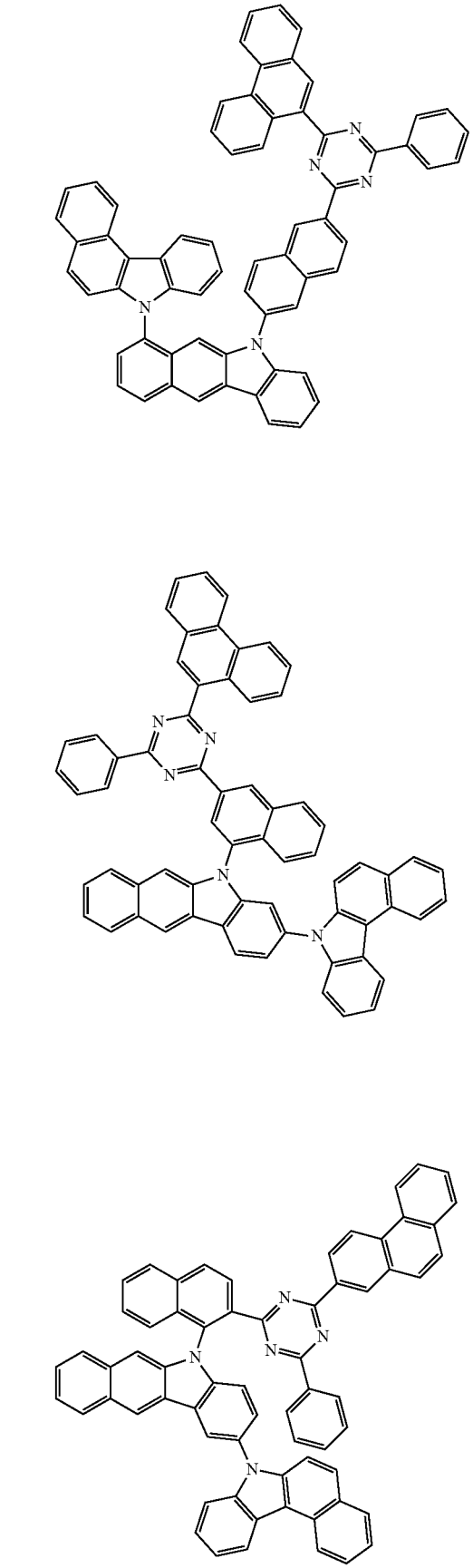

421
-continued
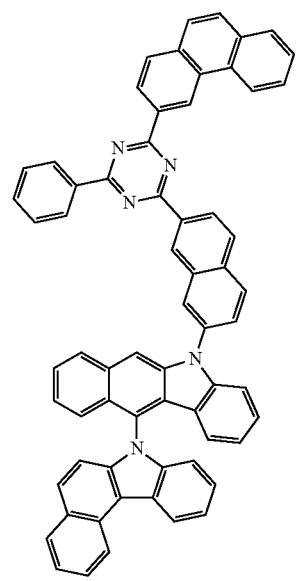
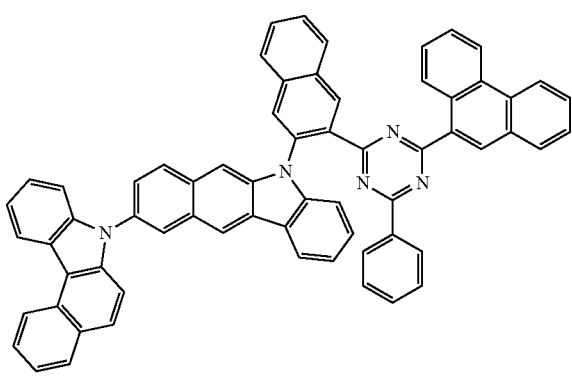
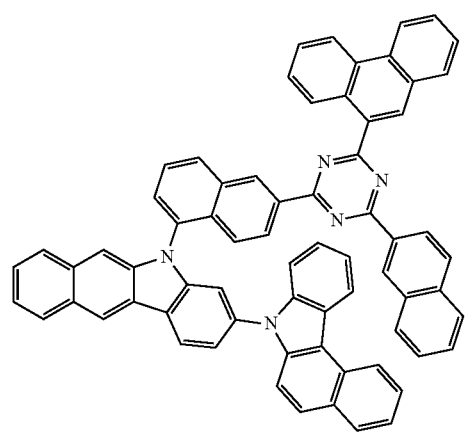
422
-continued
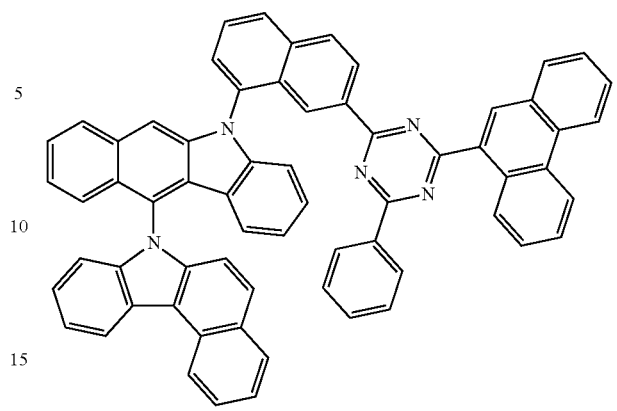
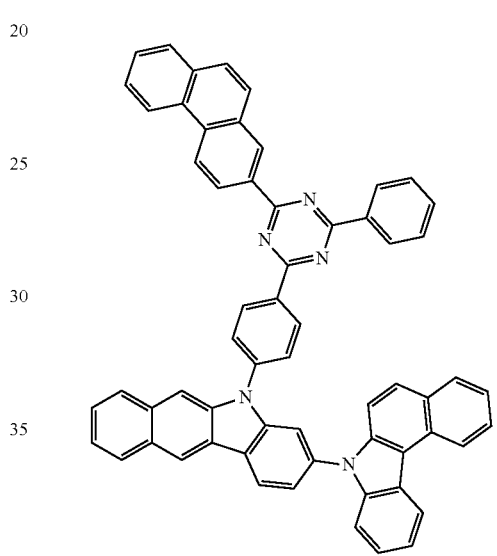
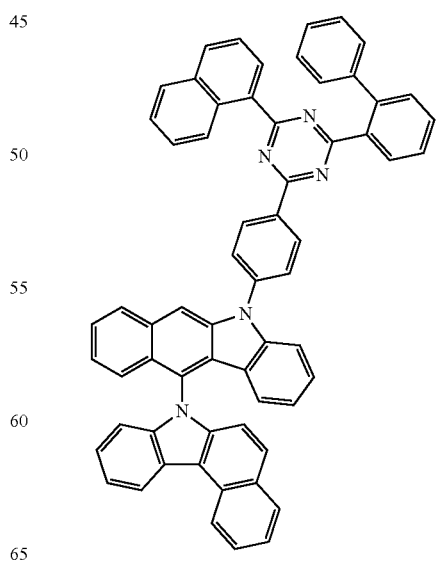

423
-continued
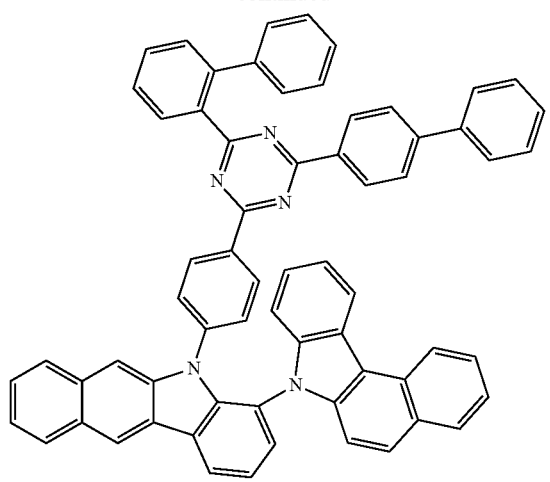
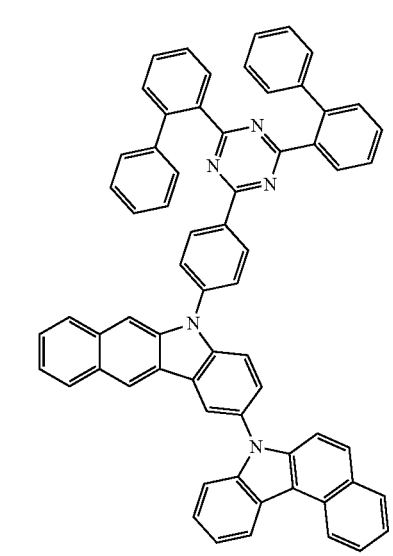
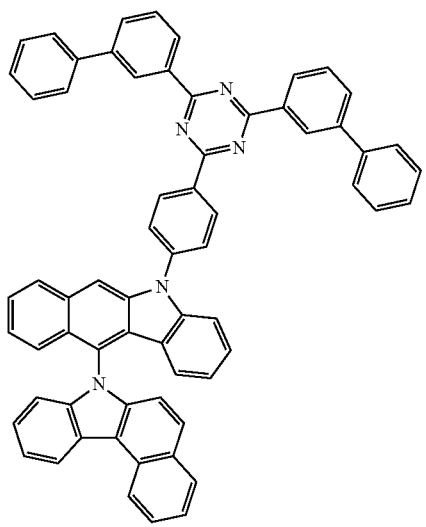
424
-continued
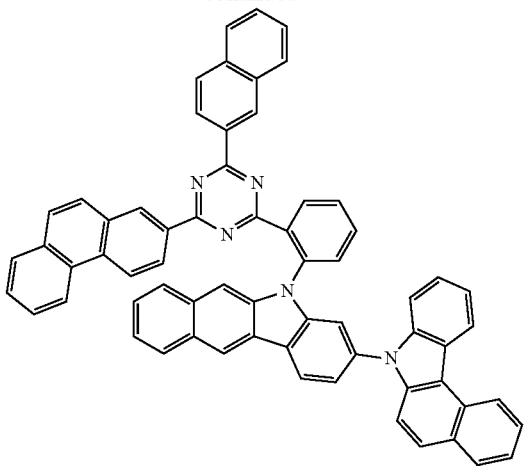
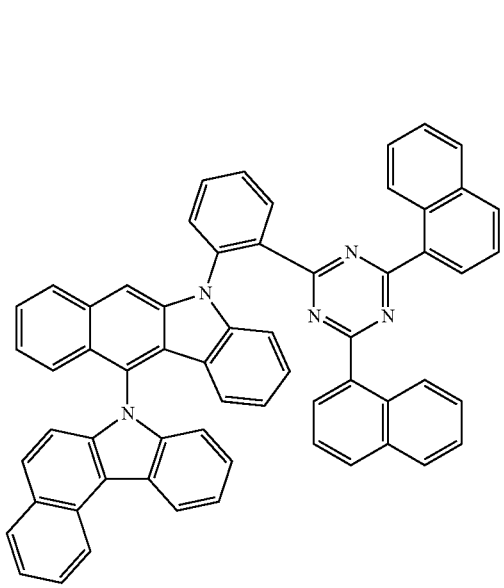

425
-continued
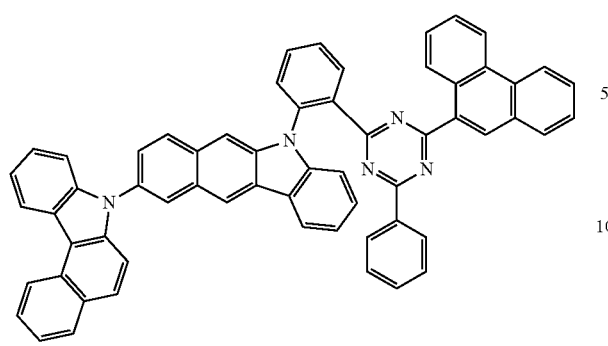
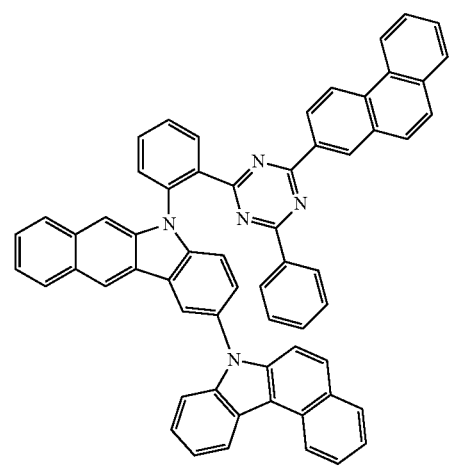
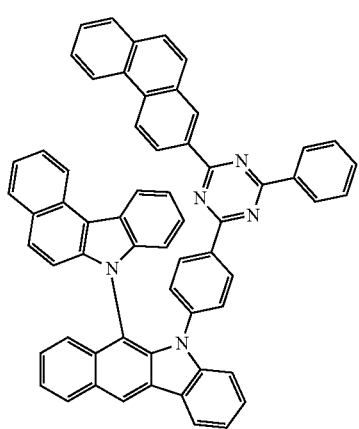
426
-continued
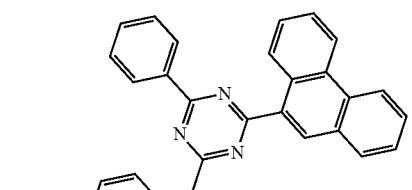
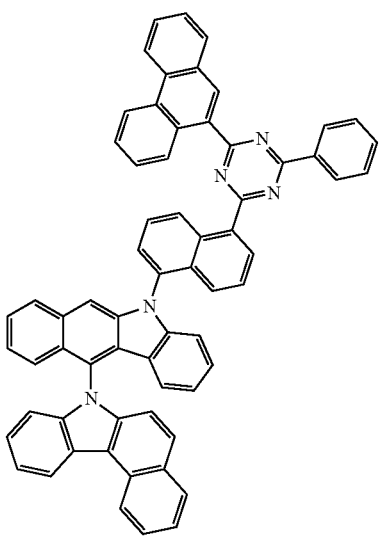
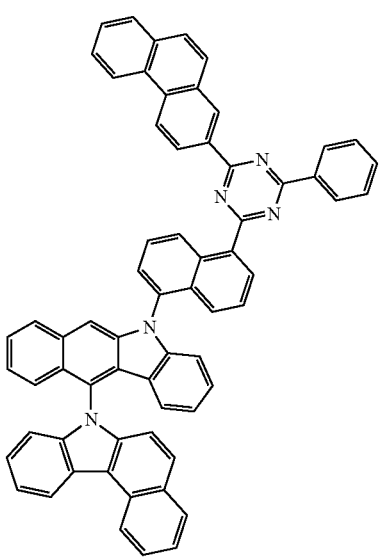

427
-continued
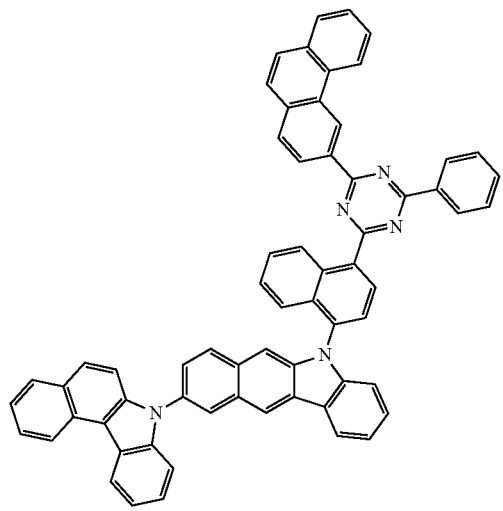
428
-continued
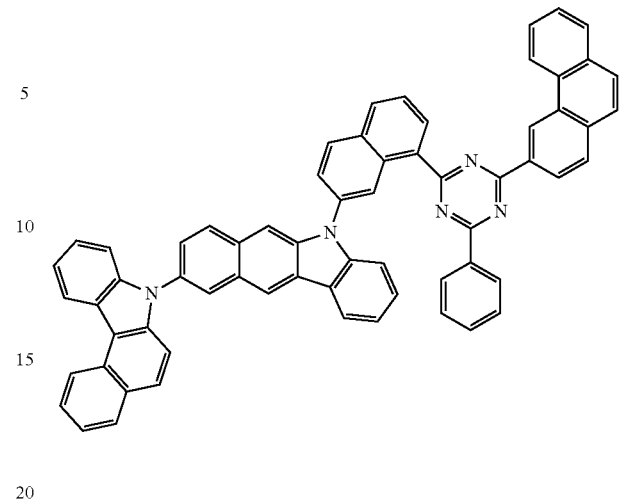
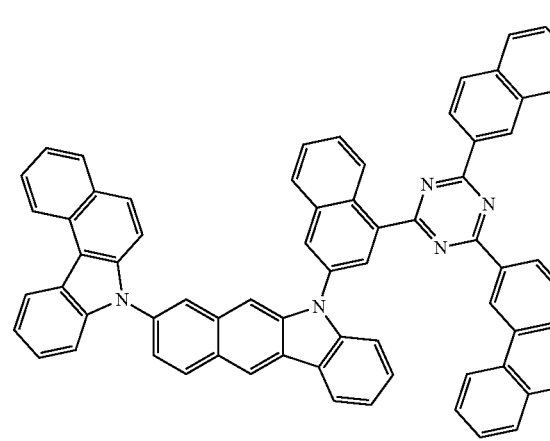
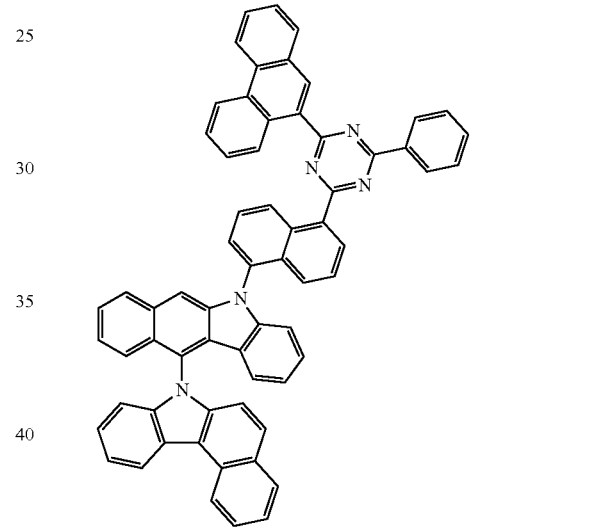
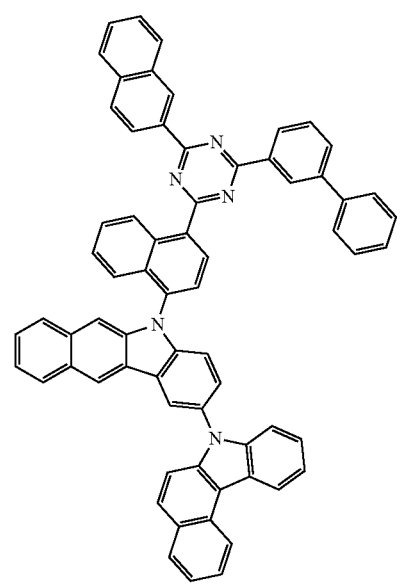
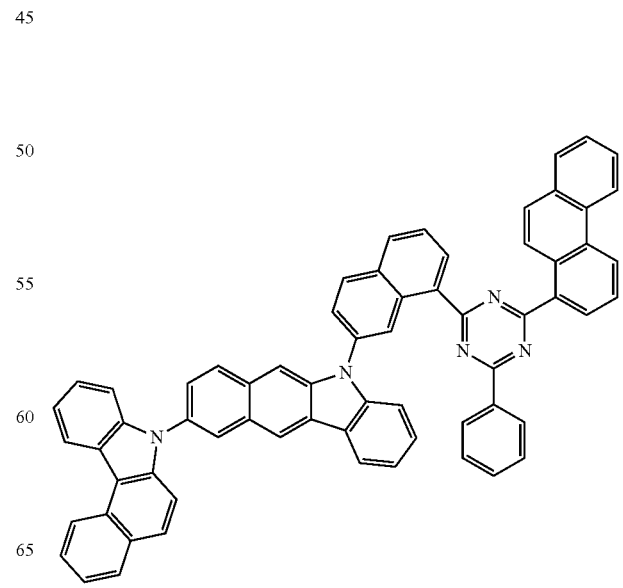

429
-continued
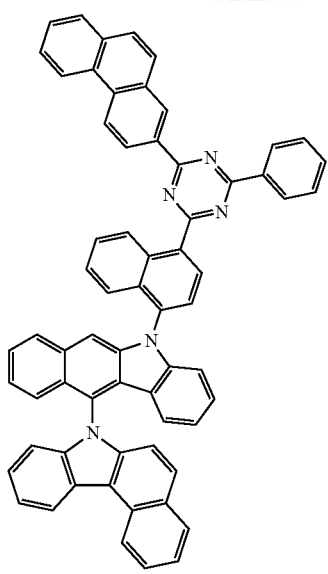
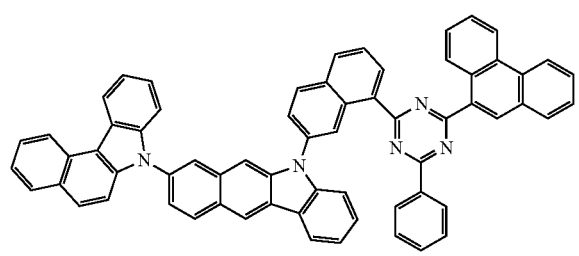
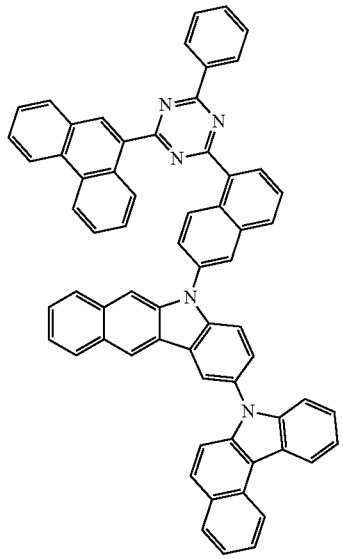
430
-continued
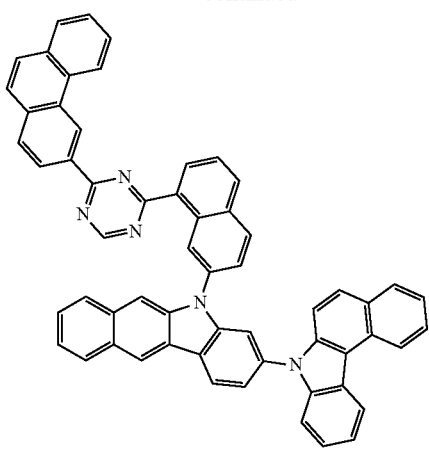
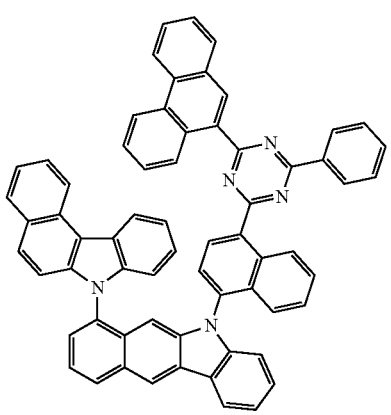
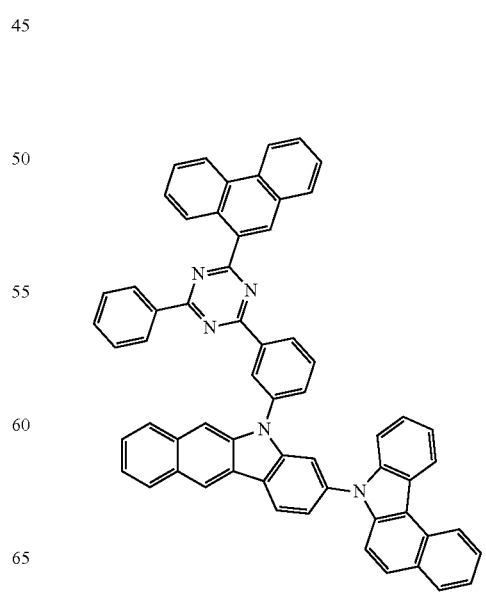

431
-continued

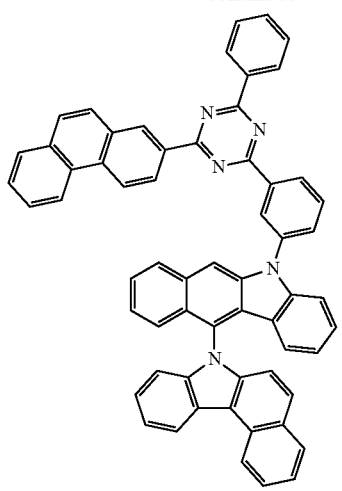

432
-continued

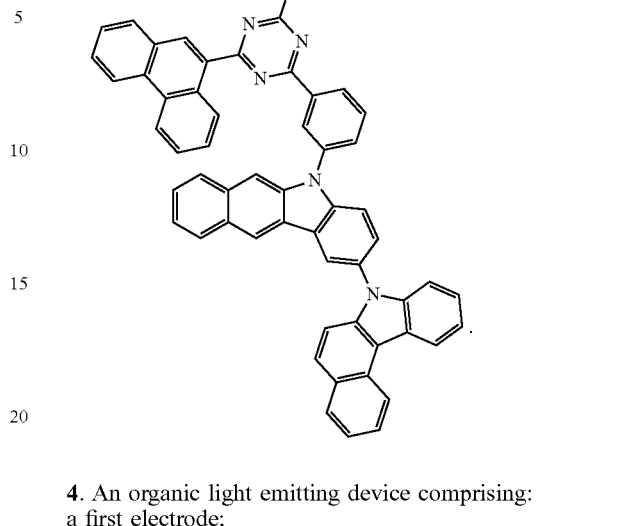

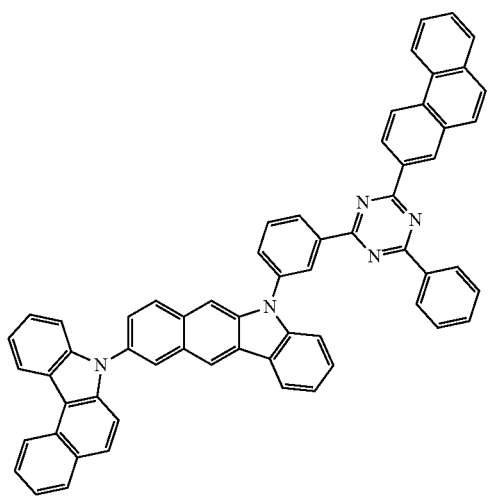

4. An organic light emitting device comprising:
a first electrode;
a second electrode provided opposite to the first electrode; and
one, two or more organic material layers provided between the first electrode and the second electrode,
wherein one or more layers of the organic material layers comprise the compound of claim 1.

5. An organic light emitting device comprising:
a first electrode;
a second electrode provided opposite to the first electrode; and
one, two or more organic material layers provided between the first electrode and the second electrode,
wherein one or more layers of the organic material layers comprise the compound of claim 2.

6. An organic light emitting device comprising:
a first electrode;
a second electrode provided opposite to the first electrode; and
one, two or more organic material layers provided between the first electrode and the second electrode,
wherein one or more layers of the organic material layers comprise the compound of claim 3.

* * * * *

UNITED STATES PATENT AND TRADEMARK OFFICE
CERTIFICATE OF CORRECTION

PATENT NO. : 11,950,505 B2
APPLICATION NO. : 16/981429
DATED : April 2, 2024
INVENTOR(S) : Kim et al.

Page 1 of 5

It is certified that error appears in the above-identified patent and that said Letters Patent is hereby corrected as shown below:

In the Claims

In Claim 2, at Column 263, Lines 10-25, the structure of Chemical Formula 2 should be:

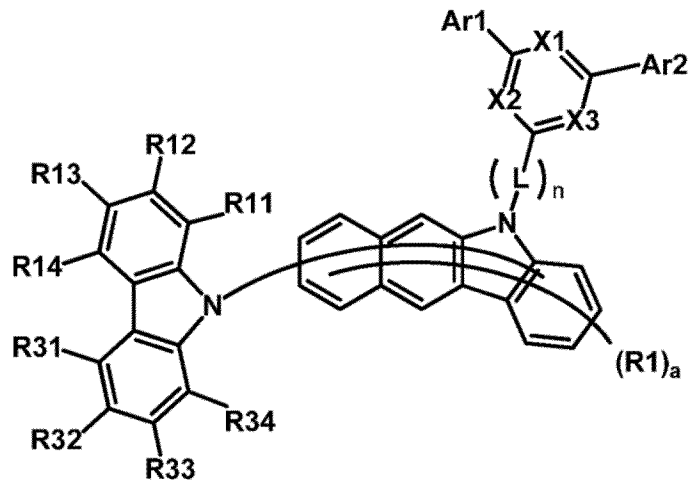

In Claim 2, at Column 264, Lines 3-18, the structure of Chemical Formula 5 should be:

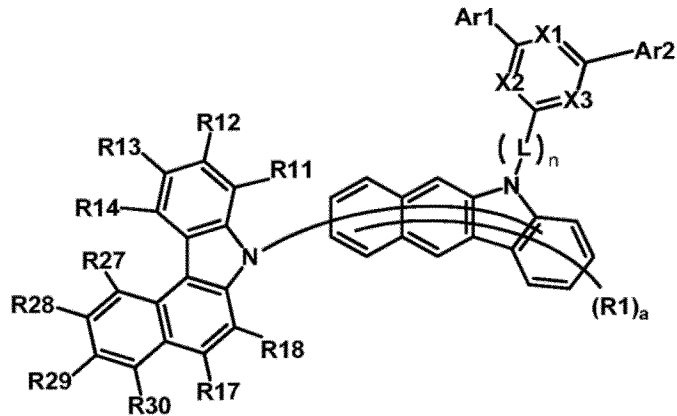

Signed and Sealed this
Twenty-third Day of July, 2024

Katherine Kelly Vidal
*Director of the United States Patent and Trademark Office*

CERTIFICATE OF CORRECTION (continued)
U.S. Pat. No. 11,950,505 B2

In Claim 2, at Column 264, Lines 22-26, the text should read as follows:
–a substituted or unsubstituted cycloalkyl group, a substituted or unsubstituted alkoxy group, a substituted or unsubstituted aryloxy group, a substituted or unsubstituted aryl group, or a substituted or unsubstituted heteroaryl group;–

In Claim 3, at Column 274, Lines 27-39, the structure of the compound should be:

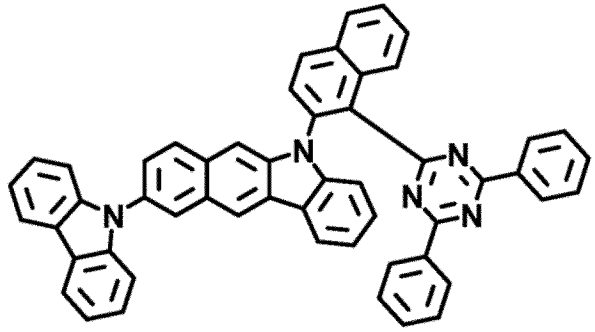

In Claim 3, at Column 361, Lines 1-19, the structure of the compound should be: